United States Patent
Jensen et al.

(10) Patent No.: US 11,649,288 B2
(45) Date of Patent: *May 16, 2023

(54) PHOSPHOLIPID ETHER (PLE) CAR T CELL TUMOR TARGETING (CTCT) AGENTS

(71) Applicant: Seattle Children's Hospital, Seattle, WA (US)

(72) Inventors: Michael C. Jensen, Bainbridge Island, WA (US); James Matthaei, Seattle, WA (US)

(73) Assignee: Seattle Children's Hospital, Seattle, WA (US)

( * ) Notice: Subject to any disclaimer, the term of this patent is extended or adjusted under 35 U.S.C. 154(b) by 83 days.

This patent is subject to a terminal disclaimer.

(21) Appl. No.: 16/480,833

(22) PCT Filed: Feb. 6, 2018

(86) PCT No.: PCT/US2018/017126
§ 371 (c)(1),
(2) Date: Jul. 25, 2019

(87) PCT Pub. No.: WO2018/148224
PCT Pub. Date: Aug. 16, 2018

(65) Prior Publication Data
US 2020/0087399 A1  Mar. 19, 2020

Related U.S. Application Data

(60) Provisional application No. 62/456,027, filed on Feb. 7, 2017.

(51) Int. Cl.
| | |
|---|---|
| A61K 47/54 | (2017.01) |
| A61K 49/00 | (2006.01) |
| C07K 16/28 | (2006.01) |
| C07K 16/08 | (2006.01) |
| C07K 16/12 | (2006.01) |
| C07K 16/30 | (2006.01) |
| C07K 16/32 | (2006.01) |
| A61P 35/00 | (2006.01) |
| G01N 33/569 | (2006.01) |
| A61K 39/00 | (2006.01) |
| C07K 14/725 | (2006.01) |

(52) U.S. Cl.
CPC ........ *C07K 16/2809* (2013.01); *A61K 47/544* (2017.08); *A61P 35/00* (2018.01); *C07K 16/08* (2013.01); *C07K 16/12* (2013.01); *C07K 16/30* (2013.01); *C07K 16/32* (2013.01); *A61K 49/0052* (2013.01); *A61K 2039/5158* (2013.01); *C07K 14/7051* (2013.01); *C07K 2317/622* (2013.01); *C07K 2319/03* (2013.01); *C07K 2319/33* (2013.01)

(58) Field of Classification Search
None
See application file for complete search history.

(56) References Cited

U.S. PATENT DOCUMENTS

| | | |
|---|---|---|
| 5,116,964 A | 5/1992 | Capon et al. |
| 5,202,238 A | 4/1993 | Fell, Jr. et al. |
| 5,216,132 A | 6/1993 | Basi |
| 5,359,046 A | 10/1994 | Capon et al. |
| 5,482,856 A | 1/1996 | Fell, Jr. et al. |
| 5,514,582 A | 5/1996 | Capon et al. |
| 5,525,503 A | 6/1996 | Rudd et al. |
| 5,538,866 A | 7/1996 | Israeli et al. |
| 5,670,148 A | 9/1997 | Sherwin et al. |
| 5,686,281 A | 11/1997 | Roberts |
| 5,712,149 A | 1/1998 | Roberts |
| 5,714,147 A | 2/1998 | Capon et al. |
| 5,741,899 A | 4/1998 | Capon et al. |
| 5,747,292 A | 5/1998 | Greenberg et al. |
| 5,830,755 A | 11/1998 | Nishimura et al. |
| 5,834,256 A | 11/1998 | Finer et al. |
| 5,837,544 A | 11/1998 | Capon et al. |
| 5,843,728 A | 12/1998 | Seed et al. |
| 5,851,828 A | 12/1998 | Seed et al. |
| 5,858,740 A | 1/1999 | Finer et al. |
| 5,906,936 A | 5/1999 | Eshhar et al. |
| 5,912,170 A | 6/1999 | Seed et al. |
| 5,912,172 A | 6/1999 | Eshhar et al. |
| 5,914,109 A | 6/1999 | Zolla-Pazner et al. |
| 5,935,818 A | 8/1999 | Israeli et al. |
| 5,969,102 A | 10/1999 | Bram et al. |
| 6,004,781 A | 12/1999 | Seed |
| 6,004,811 A | 12/1999 | Seed et al. |
| 6,005,004 A | 12/1999 | Katz et al. |
| 6,077,947 A | 6/2000 | Capon et al. |
| 6,083,751 A | 7/2000 | Feldhaus et al. |
| 6,103,521 A | 8/2000 | Capon et al. |
| 6,117,656 A | 9/2000 | Seed |
| 6,132,718 A | 10/2000 | Hansen et al. |
| 6,218,187 B1 | 4/2001 | Finer et al. |
| 6,261,787 B1 | 7/2001 | Davis et al. |
| 6,319,494 B1 | 11/2001 | Capon et al. |

(Continued)

FOREIGN PATENT DOCUMENTS

| | | |
|---|---|---|
| CN | 102775500 | 11/2012 |
| EP | 2 177 230 | 4/2010 |

(Continued)

OTHER PUBLICATIONS

Edwards et al (JMB, 2003, 334: 103-118) (Year: 2003).*

(Continued)

*Primary Examiner* — Michael Szperka
*Assistant Examiner* — Marianne DiBrino
(74) *Attorney, Agent, or Firm* — Knobbe, Martens, Olson & Bear LLP

(57) ABSTRACT

Aspects of the invention described herein relate to synthetic compounds that are useful for targeting and labeling tumor cells so as to facilitate recognition by binding agents including Chimeric Antigen Receptor T cells (CAR T cells), which are administered to a subject by intravenous or locoregional administration. Several compositions and methods of making and using these compositions to treat or inhibit a disease in a subject are contemplated.

20 Claims, 23 Drawing Sheets

(56) References Cited

U.S. PATENT DOCUMENTS

| | | |
|---|---|---|
| 6,392,013 B1 | 5/2002 | Seed et al. |
| 6,406,697 B1 | 6/2002 | Capon et al. |
| 6,407,221 B1 | 6/2002 | Capon et al. |
| 6,410,014 B1 | 6/2002 | Seed et al. |
| 6,410,319 B1 | 6/2002 | Raubitschek et al. |
| 6,432,403 B1 | 8/2002 | Philips |
| 6,521,602 B1 | 2/2003 | Patel et al. |
| 6,524,572 B1 | 2/2003 | Li |
| 6,699,972 B1 | 3/2004 | Roffler et al. |
| 6,753,162 B1 | 6/2004 | Seed et al. |
| 6,759,243 B2 | 7/2004 | Kranz et al. |
| 6,770,749 B2 | 8/2004 | Ellenhorn et al. |
| 6,953,668 B1 | 10/2005 | Israeli et al. |
| 7,037,647 B1 | 5/2006 | Israeli et al. |
| 7,049,136 B2 | 5/2006 | Seed et al. |
| 7,052,906 B1 | 5/2006 | Lawson et al. |
| 7,070,995 B2 | 7/2006 | Jensen |
| 7,105,159 B1 | 9/2006 | Israeli et al. |
| 7,217,421 B1 | 5/2007 | McArthur et al. |
| 7,265,209 B2 | 9/2007 | Jensen |
| 7,320,787 B2 | 1/2008 | Seed et al. |
| 7,348,004 B2 | 3/2008 | Peters et al. |
| 7,354,587 B1 | 4/2008 | Hansen |
| 7,354,762 B2 | 4/2008 | Jensen |
| 7,381,408 B2 | 6/2008 | Mezo et al. |
| 7,404,956 B2 | 7/2008 | Peters et al. |
| 7,435,596 B2 | 10/2008 | Campana et al. |
| 7,446,179 B2 | 11/2008 | Jensen et al. |
| 7,446,190 B2 | 11/2008 | Sadelain |
| 7,446,191 B2 | 11/2008 | Jensen |
| 7,482,005 B2 | 1/2009 | Kim |
| 7,514,537 B2 | 4/2009 | Jensen |
| 7,569,663 B2 | 8/2009 | Tykocinski et al. |
| 7,572,891 B2 | 8/2009 | Belldegrun et al. |
| 7,618,817 B2 | 11/2009 | Campbell |
| 7,632,497 B2 | 12/2009 | Stavenhagen |
| 7,655,461 B2 | 2/2010 | Finn et al. |
| 7,666,424 B2 | 2/2010 | Cheung et al. |
| 7,723,111 B2 | 5/2010 | Hwu et al. |
| 7,741,465 B1 | 6/2010 | Eshhar et al. |
| 7,871,817 B2 | 1/2011 | Voss et al. |
| 7,906,620 B2 | 3/2011 | Elsenbach et al. |
| 7,919,079 B2 | 4/2011 | Simmons et al. |
| 7,939,059 B2 | 5/2011 | Yang et al. |
| 7,994,298 B2 | 8/2011 | Zhang et al. |
| 7,998,736 B2 | 8/2011 | Morgan et al. |
| 8,105,830 B2 | 1/2012 | Weidanz et al. |
| 8,148,154 B2 | 4/2012 | Cheung et al. |
| 8,163,887 B2 | 4/2012 | Hansen |
| 8,211,422 B2 | 7/2012 | Eshhar et al. |
| RE43,586 E | 8/2012 | Israeli et al. |
| 8,252,914 B2 | 8/2012 | Zhang |
| 8,324,353 B2 | 12/2012 | Jensen |
| 8,389,282 B2 | 3/2013 | Sadelain et al. |
| 8,399,645 B2 | 3/2013 | Campana et al. |
| 8,409,577 B2 | 4/2013 | Thompson et al. |
| 8,450,112 B2 | 5/2013 | Li et al. |
| 8,465,743 B2 | 6/2013 | Rosenberg et al. |
| 8,486,911 B2 | 7/2013 | Okada et al. |
| 8,497,118 B2 | 7/2013 | Jensen |
| 8,741,306 B2 | 6/2014 | Belldegrun et al. |
| 8,802,374 B2 | 8/2014 | Jensen |
| 8,809,050 B2 | 8/2014 | Vera et al. |
| 8,822,196 B2 | 9/2014 | Rosenberg et al. |
| 8,822,647 B2 | 9/2014 | Jensen |
| 8,859,229 B2 | 10/2014 | Rabinovich et al. |
| 8,877,199 B2 | 11/2014 | Rader et al. |
| 8,906,682 B2 | 12/2014 | June et al. |
| 8,932,830 B2 | 1/2015 | Peters et al. |
| 8,946,385 B2 | 2/2015 | Kawai |
| 8,956,860 B2 | 2/2015 | Vera et al. |
| 9,023,621 B2 | 5/2015 | Gurney et al. |
| 9,040,669 B2 | 5/2015 | Cheung et al. |
| 9,062,127 B2 | 6/2015 | Voss et al. |
| 9,074,000 B2 | 7/2015 | Scheinberg et al. |
| 9,089,520 B2 | 7/2015 | Brenner |
| 9,101,609 B2 | 8/2015 | Tan et al. |
| 9,133,436 B2 | 9/2015 | Riley et al. |
| 9,156,915 B2 | 10/2015 | Waldman et al. |
| 9,163,258 B2 | 10/2015 | Riddell |
| 9,175,308 B2 | 11/2015 | Shiku et al. |
| 9,211,321 B2 | 12/2015 | Karlsson-Parra et al. |
| 9,212,229 B2 | 12/2015 | Schönfeld et al. |
| 9,220,728 B2 | 12/2015 | Sadelain et al. |
| 9,226,936 B2 | 1/2016 | Hu et al. |
| 9,242,014 B2 | 1/2016 | Kipps et al. |
| 9,266,960 B2 | 2/2016 | Morgan et al. |
| 9,272,002 B2 | 3/2016 | Powell, Jr. et al. |
| 9,273,283 B2 | 3/2016 | Sentman |
| 9,279,008 B2 | 3/2016 | Scholler et al. |
| 9,334,330 B2 | 5/2016 | Birkle et al. |
| 9,345,748 B2 | 5/2016 | Morgan et al. |
| 9,352,036 B2 | 5/2016 | McBride et al. |
| 9,359,447 B2 | 6/2016 | Feldman et al. |
| 9,365,641 B2 | 6/2016 | June et al. |
| 9,393,268 B2 | 7/2016 | Waldman et al. |
| 9,393,292 B2 | 7/2016 | Brenner |
| 9,394,364 B2 | 7/2016 | Ho et al. |
| 9,394,368 B2 | 7/2016 | Brogdon et al. |
| 9,402,888 B2 | 8/2016 | Hildegund et al. |
| 9,408,904 B2 | 8/2016 | Wright et al. |
| 9,409,992 B2 | 8/2016 | Ho et al. |
| 9,409,994 B2 | 8/2016 | Ho et al. |
| 9,416,190 B2 | 8/2016 | Ho et al. |
| 9,422,351 B2 | 8/2016 | Scholler et al. |
| 9,434,935 B2 | 9/2016 | Spencer et al. |
| 9,446,105 B2 | 9/2016 | Powell et al. |
| 9,447,194 B2 | 9/2016 | Jensen |
| 9,453,075 B2 | 9/2016 | Cheung et al. |
| 9,464,140 B2 | 10/2016 | June et al. |
| 9,469,684 B2 | 10/2016 | Finn et al. |
| 9,476,028 B2 | 10/2016 | Karlsson-Parra et al. |
| 9,481,728 B2 | 11/2016 | June et al. |
| 9,487,800 B2 | 11/2016 | Schonfeld et al. |
| 9,492,499 B2 | 11/2016 | Jaynes et al. |
| 9,492,529 B2 | 11/2016 | Karlsson-Parra et al. |
| 9,493,740 B2 | 11/2016 | Brenner et al. |
| 9,499,629 B2 | 11/2016 | June et al. |
| 9,499,855 B2 | 11/2016 | Hyde et al. |
| 9,511,092 B2 | 12/2016 | Campana et al. |
| 9,518,123 B2 | 12/2016 | June et al. |
| 9,522,955 B2 | 12/2016 | Rosenberg et al. |
| 9,540,445 B2 | 1/2017 | June et al. |
| 9,540,448 B2 | 1/2017 | Scheinberg et al. |
| 9,561,291 B2 | 2/2017 | Kovesdi et al. |
| 9,562,087 B2 | 2/2017 | Ring et al. |
| 9,567,399 B1 | 2/2017 | Campbell et al. |
| 9,572,836 B2 | 2/2017 | June et al. |
| 9,572,837 B2 | 2/2017 | Wu |
| 9,573,988 B2 | 2/2017 | Brogdon et al. |
| 9,574,014 B2 | 2/2017 | Williams et al. |
| 9,587,020 B2 | 3/2017 | Wu et al. |
| 9,587,237 B2 | 3/2017 | Hyde et al. |
| 9,597,357 B2 | 3/2017 | Gregory et al. |
| 9,605,049 B2 | 3/2017 | Campana et al. |
| 9,624,292 B2 | 4/2017 | Voss et al. |
| 9,624,306 B2 | 4/2017 | Morgan et al. |
| 9,629,877 B2 | 4/2017 | Cooper et al. |
| 9,636,388 B2 | 5/2017 | Lawman et al. |
| 9,636,416 B2 | 5/2017 | Peters et al. |
| 9,642,906 B2 | 5/2017 | Ramos et al. |
| 9,650,428 B2 | 5/2017 | Sampath et al. |
| 9,657,105 B2 | 5/2017 | Forman et al. |
| 9,662,405 B2 | 5/2017 | Waldman et al. |
| 9,663,756 B1 | 5/2017 | Lipkens et al. |
| 9,663,763 B2 | 5/2017 | Sentman |
| 9,669,058 B2 | 6/2017 | Li et al. |
| 9,670,281 B2 | 6/2017 | Lim et al. |
| 9,676,867 B2 | 6/2017 | Marasco et al. |
| 9,688,740 B2 | 6/2017 | Choi et al. |
| 9,688,760 B2 | 6/2017 | Kufer et al. |
| 9,694,033 B2 | 7/2017 | Yi et al. |
| 9,701,758 B2 | 7/2017 | Cooper et al. |
| 9,708,384 B2 | 7/2017 | Scholler et al. |

(56) References Cited

U.S. PATENT DOCUMENTS

| | | |
|---|---|---|
| 9,714,278 B2 | 7/2017 | June et al. |
| 9,717,745 B2 | 8/2017 | He |
| 9,725,519 B2 | 8/2017 | Masuko et al. |
| 9,733,245 B2 | 8/2017 | Kawai |
| 9,738,726 B2 | 8/2017 | Dimitrov et al. |
| 9,745,368 B2 | 8/2017 | Milone et al. |
| 9,765,142 B2 | 9/2017 | Dimitrov et al. |
| 9,765,156 B2 | 9/2017 | June et al. |
| 9,765,330 B1 | 9/2017 | Niazi et al. |
| 9,765,342 B2 | 9/2017 | Kochenderfer |
| 9,777,061 B2 | 10/2017 | Ebersbach et al. |
| 9,777,064 B2 | 10/2017 | Wang et al. |
| 9,783,591 B2 | 10/2017 | June et al. |
| 9,789,174 B2 | 10/2017 | Karlsson-Parra |
| 9,790,267 B2 | 10/2017 | Kaplan |
| 9,790,278 B2 | 10/2017 | Sentman et al. |
| 9,790,282 B2 | 10/2017 | Orentas et al. |
| 9,790,467 B2 | 10/2017 | Kevlahan et al. |
| 9,796,783 B2 | 10/2017 | Agerstam et al. |
| 9,802,997 B2 | 10/2017 | Mahr et al. |
| 9,803,022 B2 | 10/2017 | Ho et al. |
| 9,808,486 B2 | 11/2017 | Georgiou et al. |
| 9,809,581 B2 | 11/2017 | Chen et al. |
| 9,815,901 B2 | 11/2017 | Brogdon et al. |
| 9,821,011 B1 | 11/2017 | Sentman |
| 9,821,012 B2 | 11/2017 | Wu et al. |
| 9,822,340 B1 | 11/2017 | Sentman |
| 9,828,399 B2 | 11/2017 | Tremblay et al. |
| 9,828,435 B2 | 11/2017 | Evans et al. |
| 9,833,476 B2 | 12/2017 | Zhang et al. |
| 9,833,480 B2 | 12/2017 | Junghans et al. |
| 9,834,545 B2 | 12/2017 | Chen et al. |
| 9,834,590 B2 | 12/2017 | Campana et al. |
| 9,840,548 B2 | 12/2017 | Mahr et al. |
| 9,845,362 B2 | 12/2017 | Mukherjee |
| 9,849,092 B2 | 12/2017 | Peyman |
| 9,855,297 B2 | 1/2018 | Duchateau et al. |
| 9,855,298 B2 | 1/2018 | Bot et al. |
| 9,856,322 B2 | 1/2018 | Campana et al. |
| 9,856,497 B2 | 1/2018 | Qi et al. |
| 9,856,501 B2 | 1/2018 | O'Keefe et al. |
| 9,862,756 B2 | 1/2018 | Mahr et al. |
| 9,862,775 B2 | 1/2018 | Kwon et al. |
| 9,868,774 B2 | 1/2018 | Orentas et al. |
| 9,868,951 B2 | 1/2018 | Hu et al. |
| 9,873,894 B2 | 1/2018 | Conway et al. |
| 9,879,087 B2 | 1/2018 | DeSander et al. |
| 9,885,021 B2 | 2/2018 | Bollard et al. |
| 9,889,160 B2 | 2/2018 | Jantz et al. |
| 9,889,161 B2 | 2/2018 | Jantz et al. |
| 9,890,393 B2 | 2/2018 | Duchateau et al. |
| 2001/0031252 A1 | 10/2001 | Low et al. |
| 2002/0004052 A1 | 1/2002 | Berd et al. |
| 2002/0111474 A1 | 8/2002 | Capon et al. |
| 2003/0175288 A1 | 9/2003 | Itoh |
| 2005/0113564 A1 | 5/2005 | Campana |
| 2006/0155115 A1 | 7/2006 | Jakobsen et al. |
| 2008/0051380 A1 | 2/2008 | Auerbach et al. |
| 2009/0011984 A1 | 1/2009 | Yla-Herttuala et al. |
| 2009/0202501 A1 | 8/2009 | Zhang et al. |
| 2010/0135974 A1 | 6/2010 | Eshhar et al. |
| 2010/0278830 A1 | 11/2010 | Shoemaker et al. |
| 2011/0172254 A1 | 7/2011 | Leamon |
| 2011/0178279 A1 | 7/2011 | Williams et al. |
| 2012/0093842 A1 | 4/2012 | Eshhar et al. |
| 2012/0302466 A1 | 11/2012 | Sentman |
| 2013/0143895 A1 | 6/2013 | McAllister et al. |
| 2013/0156794 A1 | 6/2013 | Eshhar et al. |
| 2013/0287752 A1 | 10/2013 | Davila |
| 2013/0309267 A1 | 11/2013 | Simmons et al. |
| 2013/0309258 A1 | 12/2013 | June et al. |
| 2013/0323834 A1 | 12/2013 | Brenner |
| 2013/0344066 A1 | 12/2013 | Faham et al. |
| 2014/0004132 A1 | 1/2014 | Brenner et al. |
| 2014/0004137 A1 | 1/2014 | Ovaa et al. |
| 2014/0017170 A1 | 1/2014 | Irvine et al. |
| 2014/0120136 A1 | 5/2014 | Katsikis et al. |
| 2014/0134142 A1 | 5/2014 | Smith et al. |
| 2014/0134720 A1 | 5/2014 | Stauss et al. |
| 2014/0227237 A1 | 8/2014 | June et al. |
| 2014/0255363 A1 | 9/2014 | Metelitsa et al. |
| 2014/0271582 A1 | 9/2014 | Forman et al. |
| 2014/0271635 A1 | 9/2014 | Brogdon et al. |
| 2014/0274909 A1 | 9/2014 | Orentas et al. |
| 2014/0286973 A1 | 9/2014 | Powell |
| 2014/0286987 A1 | 9/2014 | Spencer et al. |
| 2014/0308259 A1 | 10/2014 | Scholler et al. |
| 2014/0322183 A1 | 10/2014 | Milone et al. |
| 2014/0322212 A1 | 10/2014 | Brogdon et al. |
| 2014/0322275 A1 | 10/2014 | Brogdon et al. |
| 2014/0378389 A1 | 12/2014 | Robbins et al. |
| 2015/0110760 A1 | 4/2015 | Zhang et al. |
| 2015/0139943 A1 | 5/2015 | Campana et al. |
| 2015/0152181 A1 | 6/2015 | Sentman et al. |
| 2015/0225470 A1 | 8/2015 | Zhang et al. |
| 2015/0238631 A1 | 8/2015 | Kim et al. |
| 2015/0283178 A1 | 10/2015 | June et al. |
| 2015/0307564 A1 | 10/2015 | Young et al. |
| 2015/0307842 A1 | 10/2015 | Sentman |
| 2015/0314014 A1 | 11/2015 | Lauermann |
| 2015/0320799 A1 | 11/2015 | Low et al. |
| 2015/0328292 A1 | 11/2015 | Spencer et al. |
| 2015/0368342 A1 | 12/2015 | Wu et al. |
| 2016/0046700 A1 | 2/2016 | Foster et al. |
| 2016/0046724 A1 | 2/2016 | Brogdon et al. |
| 2016/0051651 A1 | 2/2016 | Brogdon et al. |
| 2016/0058857 A1 | 3/2016 | Spencer et al. |
| 2016/0068601 A1 | 3/2016 | Brogdon et al. |
| 2016/0096892 A1 | 4/2016 | Brogdon et al. |
| 2016/0120907 A1 | 5/2016 | Sentman |
| 2016/0136190 A1 | 5/2016 | Weichert et al. |
| 2016/0151465 A1 | 6/2016 | Slawin et al. |
| 2016/0166613 A1 | 6/2016 | Spencer et al. |
| 2016/0175359 A1 | 6/2016 | Spencer et al. |
| 2016/0340649 A1 | 11/2016 | Brown et al. |
| 2016/0361360 A1 | 12/2016 | Chang et al. |
| 2017/0166877 A1 | 6/2017 | Bayle et al. |
| 2017/0290900 A1 | 10/2017 | Low et al. |
| 2017/0306303 A1 | 10/2017 | Taunton et al. |
| 2017/0340672 A1 | 11/2017 | Wu et al. |
| 2017/0356010 A1 | 12/2017 | Frost et al. |
| 2019/0161531 A1 | 5/2019 | Pule et al. |
| 2019/0209611 A1 | 7/2019 | Eckardt et al. |
| 2019/0224237 A1 | 7/2019 | Jensen et al. |
| 2019/0292517 A1 | 9/2019 | Cheung et al. |
| 2019/0388468 A1 | 12/2019 | Lock et al. |
| 2020/0354477 A1 | 11/2020 | Jensen |
| 2021/0317407 A1 | 10/2021 | Jensen |
| 2022/0257652 A1 | 8/2022 | Jensen |

FOREIGN PATENT DOCUMENTS

| | | |
|---|---|---|
| EP | 2 614 077 | 8/2016 |
| WO | WO 86/04356 | 7/1986 |
| WO | WO 92/10591 | 6/1992 |
| WO | WO 92/15671 | 9/1992 |
| WO | WO 01/091625 | 12/2001 |
| WO | WO 02/088334 | 11/2002 |
| WO | WO 05/084716 | 9/2005 |
| WO | WO 06/029879 | 3/2006 |
| WO | WO 08/057437 | 5/2008 |
| WO | WO 09/091826 | 7/2009 |
| WO | WO 09/117117 | 9/2009 |
| WO | WO 10/025177 | 3/2010 |
| WO | WO 12/054825 | 4/2012 |
| WO | WO 12/082841 | 6/2012 |
| WO | WO 12/138475 | 10/2012 |
| WO | WO 13/039889 | 3/2013 |
| WO | WO 13/177247 | 11/2013 |
| WO | WO 14/011984 | 1/2014 |
| WO | WO 14/031687 | 2/2014 |
| WO | WO 14/043441 | 3/2014 |
| WO | WO 14/055771 | 4/2014 |
| WO | WO 14/068388 | 5/2014 |

(56) References Cited

FOREIGN PATENT DOCUMENTS

| WO | WO 14/100615 | 6/2014 |
|---|---|---|
| WO | WO 14/127261 | 8/2014 |
| WO | WO 15/057834 | 4/2015 |
| WO | WO 15/057852 | 4/2015 |
| WO | WO 16/025322 | 2/2016 |
| WO | WO 16/098078 | 6/2016 |
| WO | WO 16/102965 | 6/2016 |
| WO | WO 16/054520 | 7/2016 |
| WO | WO 16/149665 | 9/2016 |
| WO | WO 16/168766 | 10/2016 |
| WO | WO 2016/168769 A1 | 10/2016 |
| WO | WO 16/201300 | 12/2016 |
| WO | WO 2016/210447 A1 | 12/2016 |
| WO | WO 17/029511 | 2/2017 |
| WO | WO 17/029512 | 2/2017 |
| WO | WO 17/068360 | 4/2017 |
| WO | WO 17/068361 | 4/2017 |
| WO | WO 17/137758 | 8/2017 |
| WO | WO 17/137759 | 8/2017 |
| WO | WO 17/143094 | 8/2017 |
| WO | WO 17/165245 | 9/2017 |
| WO | WO 17/165571 | 9/2017 |
| WO | WO 17/177149 | 10/2017 |
| WO | WO 17/180587 | 10/2017 |
| WO | WO 17/216561 | 12/2017 |
| WO | WO 17/216562 | 12/2017 |
| WO | WO 18/013797 | 1/2018 |
| WO | WO 18/111763 | 6/2018 |
| WO | WO 18/111834 | 6/2018 |
| WO | WO 18/115146 | 6/2018 |
| WO | WO 18/148224 | 8/2018 |
| WO | WO 18/152451 | 8/2018 |
| WO | WO 18/160622 | 9/2018 |
| WO | WO 19/156795 | 8/2019 |

OTHER PUBLICATIONS

Lloyd et al (Protein Engineering, Eng. Design & Selection, 2009, 22(3): 159-168) (Year: 2009).*
Goel et al (J. Immunol., 2004, 173: 7358-7367) (Year: 2004).*
Khan and Salunke (J. Immunol, 2014, 192: 5398-5405) (Year: 2014).*
Poosarla et al (Biotechn. Bioeng., 2017, 114(6): 1331-1342) (Year: 2017).*
Torres and Casadevall (Trend. Immunol., 2008, 29(2): 91-97) (Year: 2008).*
Ramakrishna et al (Expert Opinion on Biological Therapy, 2020, 20(5): 503-516) (Year: 2020).*
Casares et al (Int. J. Mol. Sci., 2019, 20, 2167, pp. 2-30, doi: 10.3390/ijms20092167) (Year: 2019).*
Corn et al (Prog. Lipid Res., 2020, 80: 1-14) (Year: 2020).*
Penn Medicine News (2021, 4 pages) (Year: 2021).*
Alberts et al (Mol. Biol. Cell, 4th Ed. NY, Garland Science, 2002, pp. 1/9-9/9) (Year: 2002).*
Jackson et al (Nature, 2016 13: 370-383) (Year: 2016).*
Zhang et al (Nature Medicine, 2022, 28: 1421-1431) (Year: 2022).*
Haddad et al (Neuro-Oncology Advances, 2021, 3(1): 1-16) (Year: 2021).*
Nolan et al (Cancer Letters, 2020, 474: 53-62) (Year: 2020).*
Abken, H. et al. Chimeric T-Cell Receptors: Highly Specific Tools to Target Cytotoxic T-Lymphocytes to Tumour Cells, Cancer Treatment Reviews (1997); 23:97-112.
Abken, H., et al., Tuning tumor-specific T-cell activation: a matter of costimulation? Trends in Immunology vol. 23 No. 5 May 2002: 240-45.
Abstracts for the 26th Annual Scientific Meeting of the Society for Immunotherapy of Cancer (SITC), J Immunother., vol. 34, No. 9, Nov.-Dec. 2011 (62 PP.).
Airenne et al., Recombinant avidin and avidin-fusion proteins, Biomolecular Engineering16 (1999) 87-92.
Alcover et al., A soluble form of the human CD8 alpha chain expressed in the baculovirus system: Biochemical characterization and binding to MHC Class I, Molecular Immunology, vol. 30, No. 1, pp. 55-67, 1993.
Alexander et al., Indoleamine 2,3-Dioxygenase Expression in Transplanted NOD Islets Prolongs Graft Survival After Adoptive Transfer of Diabetogenic Splenocytes, Diabetes2002, vol. 51 pp. 356-365.
Alonso-Camino et al. CARbodies: Human Antibodies Against Cell Surface Tumor Antigens Selected From Repertoires Displayed on T Ceil Chimeric Antigen Receptors. (2013) Mol Ther Nucl Acids 2, e93 (11 pages).
Altenschmidt, U. et al. Adoptive transfer of in vitro-targeted, activated T lymphocytes results in total tumor regression, J. Immunol. (1997); 159:5509-15.
Altenschmidt, U., et al., Specific cytotoxic T lymphocytes in gene therapy, J. Mol. Med. (1997); 75, 259-266.
Altschul, S. et al., Basic local alignment search tool, J. Mol. Bio., 1990, 215, 403-410.
Altvater, B., et al., 284 (CD244) Signaling by Recombinant Antigen-specific Chimeric Receptors Costimulates Natural Killer Cell Activation to Leukemia and Neuroblastoma Cells, Clin Cancer Res 2009;15(15) Aug. 1, 2009: 4857-66.
Alvarez-Vallina, L. et al., Antigen-specific targeting of CD28-mediated T cell co-stimulation using chimeric single-chain antibody variable fragment-CD28 receptors, Eur. J. Immunol, 1996, 26, 2304-2309.
Amin et al., The Eighth Edition AJCC Cancer Staging Manual: Continuing to Build a Bridge From a Population-Based to a More Personalized Approach to Cancer Staging, CA Cancer J Clin (2017) vol. 67, No. 2, pp. 93-99.
An et al., IgG2m4, an engineered antibody isotype with reduced Fc function, mAbs 2009, Landes Bioscience, 1:6, 572-579.
Ang et al., Generating a Chimeric Antigen Receptor to Redirect T-Cell Specificity after Infusion, Molecular Therapy vol. 19, Supplement 1, May 2011, S137-S138.
Arch, R, et al., 4-1BB and Ox40 are Members of a Tumor Necrosis Factor (TNF)-Nerve Growth Factor Receptor Subfamily That Bind TNF Receptor-Associated Factors and Activate Nuclear Factor kB, Molecular and Cellular Biology (1998); 558-565.
Aruffo. A, et al., Molecular cloning of a CD28 cDNA by a high-efficiency COS cell expression system, Proc. Natl. Acad. Sci. USA (1987); 84: 8573-8577.
Baba et al., N-Linked Carbohydrate on Human Leukocyte Antigen-C and Recognition by Natural Killer Cell Inhibitory Receptors, Human Immunology 61, 1202-1218 (2000).
Barber, et al., Chimeric NKG2D Receptor-Expressing T Cells as an Immunotherapy for Multiple Myeloma, Exp Hematol. (Oct. 2008); 36(10):1318-28.
Barocas et al., A population-based study of renal cell carcinoma and prostate cancer in the same patients, BJU International, (2006) 97(1): 33-36.
Barrett et al., Chimeric Antigen Receptor Therapy for Cancer Annual Review of Medicine vol. 65: 333-347 (2014).
Bauer et al., Activation of NK Cells and T Cells by NKG2D, a Receptor for Stress-Inducible MICA, Science 1999, vol. 285 pp. 727-729.
Bauer, A, et al., Differential signal transduction via T-cell receptor CD3'2, CD3C-,v,and CD3'q2 isoforms, Proc. Natl. Acad. Sci. USA (1991); 88: 3842-3846.
Baum et al. Retrovirus vectors: toward the plentivirus? (2006) Molecular Therapy: The Journal of the American Society of Gene Therapy. 13:1050-1063.
Becker, M. L. B., et al., Expression of a hybrid immunoglobulin-T cell receptor protein in transgenic mice, Cell (1989); 58:911-921.
Bedzyk, WD et al., Active site structure and antigen binding properties of idiotypically cross-reactive anti-fluorescein monoclonal antibodies, J Biol Chem., 1990, 265,133-138.
Bejcek, B, et al., Development and Characterization of Three Recombinant Single Chain Antibody Fragments (scFvs) Directed against the CD19 Antigen1, Cancer Research55, (1995); 2346-2351.

(56) References Cited

OTHER PUBLICATIONS

Berg et al., Section 3.2 Primary Structure: Amino Acids are Linked by Peptide Bonds to Form Polypeptide Chains Biochemistry. 5th Ed. New York. W.H. Freeman; 2002, pp. 1-16.
Berger, C., et al., Analysis of trans gene-specific immune responses that limit the in vivopersistence of adoptively transferred HSV-TK-modified donor T cells after allogeneic hematopoietic cell transplantation. Blood, 2006. 107(6): p. 2294-302.
Bluemel, C., et al., Epitope distance to the target cell membrane and antigen size determine the potency of T cell-mediated lysis by BiTE antibodies specific for a large melanoma surface antigen. Cancer Immunol Immunother (2010); 59(8): 1197-209.
Boder et al., Directed evolution of antibody fragments with monovalent femtomolar antigen-binding affinity, PNAS (Sep. 26, 2000) vol. 97, No. 20, pp. 10701-10705.
Bolhuis, R. L. et al. Preparation for a phase I/II study using autologous gene modified T lymphocytes for treatment of metastatic renal cancer patients., Adv. Exp. Med. Biol. (1998); 451:547-55.
Boomer et al., Cutting Edge: A Double-Mutant Knockin of the CD28 YMNM and PYAP Motifs Reveals a Critical Role for the YMNM Motif in Regulation of T Cell Proliferation andBcl-x L Expression The Journal of Immunology. 2014; 192, pp. 3465-3469.
Boomer, J, et al,. An Enigmatic Tail of CD28 Signaling, Washington University School of Medicine (2010); 1-20.
Boursier et al., Evidence for an Extended Structure of the T-cell Co-receptor CD8α as Deduced from the Hydrodynamic Properties of Soluble Forms of the Extracellular Region*, The Journal of Biological Chemistry 1993, vol. 268, No. 3, Issue of Jan. 25, pp. 2013-2020.
Brennan et al., Carbohydrate Recognition by a Natural Killer Cell Receptor, Ly-49C*, The Journal of Biological Chemistry 1995, vol. 270, No. 17, Issue of Apr. 28, pp. 9691-9694.
Brentjens et al., CD19-targeted T cells rapidly induce molecular remissions in adults with chemotherapy-refractory acute lymphoblastic leukemia. Sci Transl Med. 2013 5(177)ra38 (11 pages).
Brentjens, et al., Eradication of systemic B-cell tumors by genetically targeted human T lymphocytes co-stimulated by CD80 and interleukin-15, Nat. Med. (2003); 9: 279-286.
Bruhns et al., Differential Roles of N- and C-Terminal Immunoreceptor Tyrosine-Based Inhibition Motifs During Inhibition of Cell Activation by Killer Cell Inhibitory Receptors, The Journal of Immunology 1999; 162:3168-3175.
Bukczynski et al., Costimulatory ligand 4-1 BBL (CD137L) as an efficient adjuvant of human antiviral cytotoxic T cell responses, Proc. Natl. Acad. Sci. USA, 2004, 101:1291-1296.
Cambier, et al., Antigen and Fc receptor signaling. The awesome power of the immunoreceptor tyrosine-based activation motif (ITAM), J Immunol. (Oct. 1, 1995):155(7):3281-5.
Camerini, D, et al,. The T cell activation antigen CD27 is a member of the nerve growth factor/tumor necrosis factor receptor gene family, The Journal of Immunology (1991);3165-3169.
Cameron, B.J., et al., Identification of a Titin-Derived HLA-A1-Presented Peptide as a Cross-Reactive Target for Engineered MAGE A3-Directed T Cells, Sci Transl Med (Aug. 7, 2013); 5(197): 197ra103 (11 pages).
Canfield et al., The Binding Affinity of Human IgG for its High Affinity Fc Receptor is Determined by Multiple Amino Acids in the CH2 Domain and is Modulated by the Hinge Region, J. Exp. Med. 1991, vol. 173 pp. 1483-1491.
Cannons et al., 4-1BB ligand induces cell division, sustains survival, and enhances effector function of CD4 and CD8 T cells with similar efficacy, J Immunol. Aug. 2001, 167(3): 1313-1324.
Carlens et al. Ex vivo T lymphocyte expansion for retroviral transduction: influence of serum-free media on variations in cell expansion rates and lymphocyte subset distribution. (2000) Exp Hematol 28(10): 1137-46.
Cartellieri, M. et al., Chimeric antigen receptor-engineered T cells for immunotherapy of cancer, J. Biomedicine and Biotechnology, 2010, Article ID 956304, 13 pages.

Cavalieri et al. Human T lymphocytes transduced by lentiviral vectors in the absence of TCR activation maintain an intact immune competence. (2003) Blood. 102(2): 497-505.
Chalupny et al., T-cell activation molecule 4-1BB binds to extracellular matrix proteins, Proc. Natl. Acad. Sci., USA, 89: 103360-10364 (Nov. 1992).
Chang et al., A Chimeric Receptor with NKG2D Specificity Enhances Natural Killer Cell Activation and Killing of Tumor Cells, Cancer Res 2013;73:1777-1786. Published online Jan. 9, 2013.
Cheadle et al, Chimeric antigen receptors for T-cell based therapy Methods Mol Biol. 2012; 907:645-66.
Chen et al. Fusion protein linkers: property, design and functionality, Adv Drug Deliv Rev. (2013); 65: 1357-1369 (Epub Sep. 29, 2012).
Cho C. Rapid identification of cytokine release syndrome after haploidentical PBSC transplantation and successful therapy with tocilizumab. Bone Marrow Transplant. Dec. 2016;51(12):1620-1621, Epub Sep. 26, 2016.
Cho et al., Macromolecular versus small-molecule therapeutics: drug discovery, development and clinical considerations TIBTECH, vol. 14, May 1996, pp. 153-158.
Cohen et al. Recognition of fresh human tumor by human peripheral blood lymphocytes transduced with a bicistronic retroviral vector encoding a murine anti-p53 TCR (2005) J Immunol. 175:5799-5808.
Colcher, D. et al. In vivo tumor targeting of a recombinant single-chain antigen-binding protein., J. Nat. Cancer Inst. (1990); 82:1191-1197.
Cole et al., The molecular determinants of CD8 co-receptor function, 2012, Immunology,137, 139-148.
Common Terminology Criteria for Adverse Events (CTCAE), National Cancer Institute Common Toxicity Criteria version 4.03 (NCI-CTCAE v4.03 (2010) (196 pages).
Cooper et al. T-cell clones can be rendered specific for CD19: toward the selective augmentation of the graft-versus-B-lineage leukemia effect (2003) Blood. 101(4): 1637-1644.
Cooper et al., Enhanced antilymphoma efficacy of CD19-redirected influenza MP1-specific CTLs by cotransfer of T cells modified to present influenza MP1, Blood 2005, vol. 105 No. 4 pp. 1622-1631.
Cordaro, T. A et al. Tumor size at the time of adoptive transfer determines whether tumor rejection occurs, Eur. J. Immunol. (2000); 30: 1297-1307.
Croft, M., The role of TNF superfamily members in T-cell function and diseases Nature Reviews, Immunology, vol. 9, Apr. 2009, pp. 271-285.
Dall, Peter et al., In vivo cervical cancer growth inhibition by genetically engineered cytotoxic T cells. Cancer Immunol. Immunother. (Jan. 2005); 54(1):51-60.
Darcy, P. K. et al., Expression in cytotoxic T lymphocytes of a single-chain anti-carcinoembryonic antigen antibody. Redirected Fas ligand-mediated lysis of colon carcinoma, Eur. J. Immunol. (1998); 28:1663-72.
Davila M. L. et al: Efficacy and toxicity management of 19-28z CAR T cell therapy in B cell acute lymphoblastic leukemia Sci Transl Med. Feb. 19, 2014;6(224):224-25.
Davila Marco L. et al: CD19-Targeted T Ceils for Hematologic Malignancies Clinical Experience to Date, Cancer Journal, vol. 21, No. 6, Jan. 1, 2015 (Jan. 1, 2015), pp. 470-474.
Debelouchina et al., A molecular engineering toolbox for the structural biologist Quarterly Reviews of Biophysics, 2017, 50, e7, pp. 1-41.
Diefenbach et al., The innate immune response to tumors and its role in the induction of T-cell immunity, Immunological Reviews 2002, vol. 188: 9-21.
Dotti, et al. Design and development of therapies using chimeric antigen receptor-expressing T cells. Immun Rev (Jan. 2014); 257(1): 107-126.
Dubrovska, A., et al., A chemically induced vaccine strategy for prostate cancer, ACS Chem Biol (2011); 6(11): 1223-31.
Duncan et al., Localization of the binding site for the human high-affinity Fc receptor onIg G, Nature 1998 vol. 332 pp. 563-564.

(56) References Cited

OTHER PUBLICATIONS

Ertl, H. C. et al., Considerations for the clinical application of chimeric antigen receptor T cells: observations from a recombinant DNA advisory committee symposium held Jun. 15, 2010, Cancer Res., 2011, 71, 3175-3181.
Eshhar, et al, Design of Cytotoxic T Lymphocytes with Antibody-Type Specificity against Tumor Cells Using Chimeric TcR, Journal of Cellular Biochemistry, Supplement 14B, UCLA Symposia on Molecular & Cellular Biology, Abstracts, 19th Annual Meeting, Jan. 27-Feb. 8, 1990, p. 70.
Eshhar, Z., et al., Functional expression of chimeric receptor genes in human T cells, J. Immunol. Meth. (2001); 248: 67-76.
Fedorov VD, et al., PD-1- and CTLA-4-based inhibitory chimeric antigen receptors (ICARs) divert off-target immunotherapy responses, Sci Transl Med. (Dec. 11, 2013);5(215):215ra172 (12 pages).
Feng et al., Convergence on a Distinctive Assembly Mechanism by Unrelated Families of Activating Immune Receptors, Immunity, vol. 22, 427-438, Apr. 2005.
Feng et al., The Assembly of Diverse Immune Receptors is Focused on a Polar Membrane-Embedded Interaction Site, 2006. PLoS Biol 4(5):e142.
Ferrone, S., et al., How much longer will tumor cells fool the immune system, Immunol. Today (2000); 21: 70-72.
Figini, M, et al., Conversion of murine antibodies to human antibodies and their optimization for ovarian cancer therapy targeted to the folate receptor, Cancer ImmunolImmunother (Apr. 2009);58(4):531-46 (Epub Aug. 15, 2008).
Foell et al., CD137-mediated T cell co-stimulation terminates existing autoimmune disease in SLE-prone NZB/NZW F1 mice., Ann N Y Acad Sci. Apr. 2003; 987:230-5.
Frecha et al. Advances in the field of lentivector-based transduction of T and B lymphocytes for gene therapy (2010) Molecular Therapy: The Journal of the American Society of Gene Therapy. 18:1748-1757.
Frost et al., In Vitro Evaluation of Avidin Antibody Pretargeting Using $^{211}$At-Labeled andBiotinylated Poly-L-Lysine as Effector Molecule*, Cancer 2010, Cancer Therapy With Antibodies and Immunoconjugates, Supplement to Cancer, pp. 1101-1110.
Fujita, K.et al., Prolonged disease-free period in patients with advanced epithelial ovarian cancer after adoptive transfer of tumor-infiltrating lymphocytes. Clin. Cancer Res., 1995, 1, 501-507.
Gargalionis et al, The molecular rationale for Src inhibition in colorectal carcinomas, Int. J.Cancer, 134:2019-2029 (2013).
Gargett, T., et al., GD2-specific CART Cells Undergo Potent Activation and Deletion Following Antigen Encounter but can be Protected From Activation-induced Cell Death by PD-1 Blockade. Mol Ther, 2016. 24(6): p. 1135-49.
Gilboa, E., How tumors escape immune destruction and what we can do about it, Cancer Immunol. Immunother. (1999); 48: 382-385.
Gilham et al., CAR-T cells and solid tumors: tuning T cells to challenge an inveterate foe, Trends in Molecular Medicine (2012); 18(7): 377-384 (Epub May 19, 2012).
Gilham et al., Primary polyclonal human T lymphocytes targeted to carcino-embryonicantigens and neural cell adhesion molecule tumor antigens by CD3zeta-based chimeric immune receptors, J. Immunother, (Mar.-Apr. 2002); 25 (2): 139-151.
Gillies, S.D. et al., Targeting Human Cytotoxic T Lymphocytes to Kill Heterologous Epidermal Growth Factor Receptor-Bearing Tumor Cells, The Journal of Immunology (1991); 146(3): 1067-1071.
Gong, M. C., et al., Prostate-specific membrane antigen (PSMA)-specific monoclonal antibodies in the treatment of prostate and other cancers, Cancer Metastasis Rev. (1999); 18:483-490.
Gonzalez et al., Genetic engineering of cytolytic T lymphocytes for adoptive T-cell therapy of neuroblastoma, The Journal of Gene Medicine (Jun. 2004) vol. 6, Issue 6, 704-711.
Goverman, J. et al., Chimeric immunoglobulin-T cell receptor proteins form functional receptors: implications for T cell receptor complex formation and activation, Cell (1990); 60:929-939.
Greenfield, E. A, Nguyen, K. A & Kuchroo, V. K. CD28/B7 co-stimulation: a review. Crit. Rev. Immunol. 18, 389-41 8 (1998).

Griffiths et al., The Nature of DNA Modern Genetic Analysis. New York: W.H. Freeman; 1999, pp. 1-11.
Grosenbach et al., A recombinant vector expressing transgenes for four T-cell costimulatory molecules (OX40L, B7-1, ICAM-1, LFA-3) induces sustained CD4$^+$ and CD8$^+$ T-cell activation, protection from apoptosis, and enhanced cytokine production, Cellular Immunology 222 (2003) 45-57.
Gross et al., Development and study of chimeric immunoglobulin/T cell receptor molecules as functional receptors that endow T cells with antibody-type specificity, Ph.D. Thesis presented to the Feinberg Graduate School, The Wiezmann Institute of Science, Rehovot, Israel (1990); 1-70.
Gross, G. et al., Endowing T cells with antibody specific using chimeric T cell receptors, Department of Chemical Immunology, FASEB J. (Dec. 1992); 6(15):3370-8.
Gross, G. et al., Expression of immunoglobuling-T-cell receptor chimeric molecules as functional receptors with antibody-type specificity, Proc. Natl. Acad. Sci., 1989, 86, 10024-10028.
Gross, G. et al., Generation of effector T cells expressing chimeric T cell receptor with antibody type-specificity, Transplant. Proc. (1989); 21 (1 Pt 1 ):127-130.
Grupp et al., Chimeric Antigen Receptor-Modified T Cells for Acute Lymphoid Leukemia, N. Engl. J. Med. (Apr. 18, 2013) 368(16):1509-1518.
Grupp Stephan A.: Advances in T-cell therapy for All, Best Practice & Research Clinical Haematology, vol. 27, No. 3-4, Sep. 1, 2014(Sep. 1, 2014), pp. 222-228.
Gruss et al., Tumor Necrosis Factor Ligand Superfamily: Involvement in the Pathology of Malignant Lymphomas Blood, vol. 85, No. 12, Jun. 15, 1995, pp. 3378-3404.
Guinn et al., 4-1BBL Cooperates with B7-1 and B7-2 in Converting a B Cell Lymphoma Cell Line into a Long-Lasting Antitumor Vaccine, The Journal of Immunology162:5003-5010 (1999).
Habib-Agahi,H., Phan,T.T. and Searle,P.F. Co-stimulation with 4-1BB ligand allows extended T-cell proliferation, synergizes with CD80/CD86 and can reactivate anergic T cells Int. Immunol. 19 (12), 1383-1394 (2007).
Hackett et al. A transposon and transposase system for human application (2010) Molecular Therapy: The Journal of the American Society of Gene Therapy. 18:674-683.
Hanson, H. L. et al. Eradication of established tumors by CD8+ T cell adoptive immunotherapy. Immunity 13, 265-276 (2000).
Harper et al., CTLA-4 and CD28 Activated Lymphocyte Molecules are Closely Related in Both Mouse and Human as to Sequence, Message, Expression, Gene Structure, and Chromosomal Location, The Journal of Immunology, vol. 147, 1037-1044, No. 3, Aug. 1, 1991.
Hatakeyama et al., Transmembrane Signaling of Interleukin 2 Receptor, J. Exp. Med. 1987, vol. 166 pp. 362-375.
Haynes et al., Redirecting Mouse CTL Against Colon Carcinoma: Superior Signaling Efficacy of Single-Chain Variable Domain Chimeras Containing TCR-zeta vs Fcepsilon RI-gamma J Immunol 2001; 166:182-187 (Haynes 2001).
Hege et al., Safety, tumor trafficking and immunogenicity of chimeric antigen receptor (CAR)-T cells specific for TAG-72 in colorectal cancer, Journal for Immunotherapy of Cancer 2017, 5:22.
Hege et al., Systemic T Cell-independent Tumor Immunity after Transplantation of Universal Receptor-modified Bone Marrow into SCID Mice, J. Exp. Med. vol. 184 Dec. 1996 pp. 2261-2269.
Herron, J.N., et al., High resolution structures of the 4-4-20 Fab-fluorescein complex in two solvent systems: effects of solvent on structure and antigen-binding affinity. Biophys J, 1994. 67(6): p. 2167-83.
Heuser, et al., T-cell activation by recombinant immunoreceptors: impact of the intracellular signalling domain on the stability of receptor expression and antigen-specific activation of grafted T-cells, Gene Therapy (2003); 10: 1408-1419.
Hombach et al., T cell activation by recombinant FcεRI γ-chain immune receptors: an extracellular spacer domain impairs antigen-dependent T cell activation but not antigen recognition, Gene Therapy (2000) 7, 1067-1075.
Hombach, et al., Adoptive Immunotherapy with Genetically Engineered T Cells: Modification of the IgG1 Fc 'Spacer' Domain in the

(56) References Cited

OTHER PUBLICATIONS

Extracellular Moiety of Chimeric Antigen Receptors Avoids 'Off-Target' Activation and Unintended Initiation of an Innate Immune Response, Gene Ther. (Oct. 2010); 17(10):1206-13.
Honegger et al., A mutation designed to alter crystal packing permits structural analysis of a tight-binding fluorescein-scFv complex, Protein Science (2005) 14(10), 2537-2549.
Huang, J., et al., Modulation by IL-2 of CD70 and CD27 expression on CD8+ T cells: importance for the therapeutic effectiveness of cell transfer immunotherapy J. Immunol. 176(12), 7726-7735 (2006).
Hughes M. S. et al., Transfer of a TCR gene derived from a patient with a marked antitumor response conveys highly active T-cell effector functions. Hum Gene Ther Apr. 2005; 16(4):457-72).
Hunter et al., Inhibition of Fcγ Receptor-Mediated Phagocytosis by a Nonphagocytic FcγReceptor, Blood, vol. 91, No. 5 Mar. 1, 1998: pp. 1762-1768.
Hutchins, B. et al., Site-specific coupling and sterically controlled formation of multimeric antibody fab ftagments with unnatural amino acids, J. Mol. Biol., 2011, 406, 595-603.
Hutloff, A. et al., ICOS is an inducible T-cell costimulator structurally and functionally related to CD28, Nature, 1999, 397, 263-266.
Hwu, et al, The Genetic Modification of T Cells for Cancer Therapy: An Overview of Laboratory and Clinical Trials, Cancer Detection and Prevention (1994); 18(1):43-50.
Imai, C. et al., Chimeric receptors with 4-1BB signaling capacity provoke potent cytotoxicity against acute lymphoblastic leukemia, Leukemia, 2004, 18, 676-684.
Imai, K., et al., Comparing Antibody and Small-Molecule Therapies for Cancer; medscape.com/viewarticle/550008 (26 pages).
Irving, B. A., et al., The cytoplasmic domain of the T cell receptor zeta chain is sufficient to couple to receptor-associated signal transduction pathways' Cell (1991); 64:891-901.
Isakov et al., PKC-theta-mediated signal delivery from the TCR/CD28 surface receptors, Frontiers in Immunology, T Cell Biology, Aug. 2012, vol. 3, Article 273, pp. 1-12.
Janeway et al., Appendix I. Immunologists' Toolbox Immunobiology: The Immune System in Health and Disease. 5th ed. New York: Garland Science; 2001 (101 pages).
Janeway et al., The structure of a typical antibody molecule Immunobiology: The Immune System in Health and Disease. 5th Ed. New York: Garland Science; 2001, pp. 1-11.
Jang, I, et al., Human 4-1BB (CD137) Signals are Mediated by TRAF2 and Activate Nuclear Factor-kB, Biochemical and Biophysical Research Communications (1998);613-620.
Jena et al., Redirecting T-cell specificity by introducing a tumor-specific chimeric antigen Receptor, Blood 2010, vol. 116, No. 7, pp. 1035-1044.
Jensen, M et al. CD20 is a Molecular Target for scFvFc[zeta] Receptor Redirected T Cells: Implications for Cellular Immunotherapy of CD20+ Malignancy, Biology of Blood and Marrow Transplantation (1998); 4:75-83.
Jensen, M. C., et al., Abstract #98: Targeting Pre-B Acute Lymphoblastic Leukemia With T Cell Clones Engineered to Express A CD19-Specific Chimeric Immunoreceptor, Blood (Nov. 16, 2000);96(11):26A.
Jensen, M.C., et al., Antitransgene rejection responses contribute to attenuated persistence of adoptively transferred CD20/CD19-specific chimeric antigen receptor redirected T cells in humans. Biol Blood Marrow Transplant, 2010. 16(9): p. 1245-56.
Jonnalagadda et al., Chimeric Antigen Receptors With Mutated IgG4 Fc Spacer Avoid Fc Receptor Binding and Improve T Cell Persistence and Antitumor Efficacy, Molecular Therapy 2015, vol. 23, No. 4, pp. 757-768.
Jung et al., Improving in vivo folding and stability of a single-chain Fv antibody fragment by loop grafting, Protein Engineering (1997) vol. 10, No. 8, pp. 956-966.
Jung, S. et al., Selection for improved protein stability by phage display, J. Mol. Biol., 1999, 294, 163-180.

Kagoya, Y., et al., Transient stimulation expands superior antitumor T cells for adoptive therapy. JCI Insight, 2017. 2(2): p. e89580 (13 pages).
Kalos et al., T Cells with Chimeric Antigen Receptors Have Potent Antitumor Effects and Can Establish Memory in Patients with Advanced Leukemia, Sci. Transl. Med. (Aug. 10, 2011) 3(95):1-21.
Kandalaft, L. et al., A phase I clinical trial of adoptive transfer of folate receptor-alpha redirected autologous T cells for recurrent ovarian cancer, Journal of Translational Medicine, 2012, 10:157, 10 pages.
Kang, S. et al: Therapeutic uses of anti-interleukin-6 receptor antibody, International Immunology, vol. 27, No. I, Aug. 20, 2014 (Aug. 20, 2014), pp. 21-29.
Karachaliou et al., Common Co-activation of AXL and CDCP1 in *EGFR*-mutation-positive Non-small cell Lung Cancer Associated with Poor Prognosis, EBioMedicine (2017) doi.org/10/1016/j.ebiom.2018.02.001.
Kariv et al., Analysis of the Site of Interaction of CD28 with Its Counterreceptors CD80 and CD86 and Correlation with Function, 157 J. Immunol.29-38 (1996).
Katz et al., Recognition of HLA-Cw4 but Not HLA-Cw6 by the NK Cell Receptor Killer CellIg-Like Receptor Two-Domain Short Tail No. 4, J Immunol 2001; 166:7260-7267.
Kennedy. M. et al., Optical imaging of metastatic tumors using a folate-targeted fluorescent probe, J. Biomed. Opt., 2003, 8, 636-641.
Kim et al. Redirection of Genetically Engineered CAR-T Cells Using Bifunctional Small Molecules, Journal of the American Chemical Society (Feb. 18, 2015) vol. 137, No. 8, pp. 2832-2835, with 8 page supporting document.
Kim et al., NMR Structural Studies of Interactions of a Small, Nonpeptidyl Tpo Mimic with the Thrombopoietin Receptor Extracellular Juxtamembrane and Transmembrane Domains, J Biol Chem (2007) 282(19):14253-14261.
Kim et al., Protein conjugation with genetically encoded unnatural amino acids. Curr OpinChem Biol (2013); 17:412-419 (Epub May 9, 2013).
Kim et al., Therapeutic Potential of 4-1BB (CD137) as a Regulator for Effector $CD8^+$ T Cells, Journal of Hematotherapy & Stem Cell Research (2001) 10:441-449.
Kintzing et al., Emerging Strategies for Developing Next-Generation Protein Therapeutics for Cancer Treatment Trends in Pharmacological Sciences, vol. 37, No. 12, Dec. 2016, pp. 993-1008.
Klotz et al., Macromolecule-Small Molecule Interactions. Strong Binding by Intramolecularly Cross-Linked Polylysine Biochemistry. vol. 10, No. 6, Mar. 16, 1971, pp. 923-926.
Kochenderfer et al., Construction and pre-clinical evaluation of an anti-CD19 chimeric antigen receptor, Journal of Immunotherapy (2009); 32(7): 689-702.
Kochenderfer et al., Treating B-cell cancer with T cells expressing anti-CD19chimeric antigen receptors 2013, Nature Reviews Clinical Oncology, 10, 267-276 (2013).
Kochenderfer, J. et al., Eradication of B-lineage cells and regression of lymphoma in a patient treated with autologous T cells genetically engineered to recognize CD19, Blood, 2010, 116, 4099-4102.
Kochenderfer, J. et al., B-cell depletion and remissions of malignancy along with cytokine-associated toxicity in a clinical trial of anti-CD19 chimeric-antigen-receptor-transduced T cells, Blood, 2012, 119, 2709-2720.
Kolmar, H. et al., Alternative binding proteins: biological activity and therapeutic potential of cystine-knot miniproteins, The FEBS Journal, 2008, 275, 26684-26690.
Kranz et al., Partial elucidation of an anti-hapten repertoire in BALB/c mice: comparative characterization of several monoclonal antiFLuorescyl antibodies, Mol Immunol (1981) 18(10), 889-898.
Krause, A., et al., Genetic approaches to sustain the function of tumor-specific T-lymphocytes, Mol. Ther. (2000); 1 (S260): 713.
Kularatne, S.A. et al., Prostate-specific membrane antigen targeted imaging and therapy of prostate cancer using a PSMA inhibitor as a homing ligand, Mol. Pharm., 2009, 6,780-789.
Kuwana, Y. et al., Expression of chimeric receptor composed of immunoglobulin-derived V regions and T-cell receptor-derived C regions, Biochem. Biophys. Res. Comm. (1987); 149:960-968.

(56) References Cited

OTHER PUBLICATIONS

Kwon, B, et al., cDNA sequences of two inducible T-cell genes, cDNA sequences of two inducible T-cell genes (1989); 86: 1963-1967.
Kwon, B, et al., Expression Characteristics of Two Potential T Cell Mediator Genes, Cellular Immunology (1989); 414-422.
Lafage-Pochitaloff M, Costello R, Couez D, Simonetti J, Mannoni P, Mawas C, Olive D. Human CD28 and CTLA-4 Ig superfamily genes are located on chromosome 2 at bands q33-q34 Immunogenetics 1190;31(3):198-201.
Lamers et al., Immune responses to transgene and retroviral vector in patients treated with ex vivo-engineered T cells, Blood (2011) 117(1): 72-82.
Lamers, C. et al., Treatment of Metastatic Renal Cell Carcinoma With Autologous T-Lymphocytes Genetically Retargeted Against Carbonic Anhydrase IX: First Clinical Experience, J. Clin. Oncol., 2006, 24, e20-22.
Laroche et al., Characterization of a Recombinant Single-chain Molecule Comprising the Variable Domains of a Monoclonal Antibody Specific for Human Fibrin Fragment D-dimer*, The Journal of Biological Chemistry 1991, vol. 266, No. 25, issue of Sep. 5, pp. 16343-16349.
Latza, U. et al., The human OX40 homolog: cDNA structure, expression and chromosomal assignment of the ACT35 antigen, Eur. J. Immunol., 1994, 24, 677-683.
Lee D. W. et al: Current concepts in the diagnosis and management of cytokine release syndrome Blood. Jul. 10, 2014;124(2):188-95. doi: 10.1182/blood-2014-05-552729. Epub May 29, 2014, with errata.
Lee, D, et al., 4-1BB Signaling Activates the T Cell Factor 1 Effector/b-Catenin Pathway with Delayed Kinetics via ERK Signaling and Delayed PI3K/AKT Activation to Promote the Proliferation of CD8+ T Cells, PLOS One (2013); 8: 1-11.
Liebowitz, D. N., Lee, K. P. & June, C. H. Co-stimulatory approaches to adoptive immunotherapy. Curr. Opin. Oncol. 10, 533-541 (1998).
Lin et al., Transglutaminase-catalyzed site-specific conjugation of small-molecule probes to proteins in vitro and on the surface of living cells, J. Am. Chem. Soc. (2006);128:4542-4543.
Linenberger, CD33-directed therapy with gemtuzumab ozogamicin in acute myeloid leukemia: progress in understanding cytotoxicity and potential mechanisms of drug resistance, Leukemia (2005) 19, 176-182.
Liou et al., A chimeric mouse-human antibody that retains specificity for HIV gp 120 and mediates the lysis of HIV-infected cells, J Immunol 1989; 143: 3967-3975.
Lodish et al., Hierarchical Structure of Proteins Molecular Cell Biology. 4th Ed. New York: W.H. Freeman; 2000. pp. 1-25.
Long, A.H., et al., 4-IBB costimulation ameliorates T cell exhaustion induced by tonic signaling of chimeric antigen receptors. Nat Med, 2015. 21(6): p. 581-90.
Love et al., ITAM-mediated Signaling by the T-Cell Antigen Receptor, Cold Spring Harb Perspect Biol 2010;2:a002485.
Lowin-Kropf et al., Cytoskeletal Polarization of T Cells is Regulated by an Immunoreceptor Tyrosine-based Activation Motif-dependent Mechanism, The Journal of Cell Biology 1998, vol. 140, No. 4, pp. 861-871.
Lu, Y. et al., Folate-targeted dinitrophenyl hapten immunotherapy: effect of linker chemistry on antitumor activity and allergic potential, Mol. Pharm., 2007, 695-706.
Lu, Y. et al., Preclinical pharmacokinetics, tissue distribution, and antitumor activity of a folate-hapten conjugate-targeted immunotherapy in hapten-immunized mice, Molecular Cancer Therapeutics, 2006, 5, 3258-3267.
Lueders et al., The Long Terminal Repeat of an Endogenous Intracisternal A—Particle Gene Functions as a Promoter When Introduced into Eucaryotic Cells by Transfection Molecular and Cellular Biology, vol. 4, No. 10, Oct. 1984, pp. 2128-2135.
Lustgarten, J., et al., Specific Elimination of IgE Production Using T Cell Lines Expressing Chimeric T Cell Receptor Genes, European Journal of Immunology (1995); 25(10):2985-2991.
Ma et al., Versatile strategy for controlling the specificity and activity of engineered T cells, Proc. Nat. Acad. Sci. U.S.A (Jan. 12, 2016) vol. 113, No. 4, pp. 450-458.
Ma, J. et al., Versatile strategy for controlling the specificity and activity of engineered T cells, Proc. Natl. Acad. Sci., 2016, 113, E450-458.
Ma, Q. et al., Carcinoembryonic antigen-immunoglobulin Fc fusion protein (CEA-Fc) for identification and activation of anti-CEA immunoglobulin-T-cell receptor-modified T cells, representative of a new class of Ig fusion proteins, Cancer Gene Therapy (2004); 11: 297-306.
Ma, Q., et al., Genetically engineered T cells as adoptive immunotherapy of cancer, Cancer Chemother Biol Response Modif (2002); 20: 315-41.
Maeda et al., Tumor vascular permeability and the EPR effect in macromolecular therapeutics: a review, Journal of Controlled Release 65 (2000), pp. 271-284 (14 pages).
Maher, et al., Human T-lymphocyte cytotoxicity and proliferation directed by a single chimeric TCRzeta/CD28 receptor, Nature Biotechnology (2002); 20: 70-75.
Marincola, F. M., et al., Escape of human solid tumors from T cell recognition: molecular mechanisms and functional significance, Adv. Immunol. (2000); 74: 181-273.
Maude Shannon L. et al. Chimeric Antigen Receptor T Cells for Sustained Remissions in Leukemia N Engl J Med. Oct. 16, 2014;371(16):1507-17.
Maude Shannon L. et al. Managing Cytokine Release Syndrome Associated With Novel T Cell-Engaging Therapies Cancer J. Mar.-Apr. 2014;20(2):119-22.
Maus et al., Ex vivo expansion of polyclonal and antigen-specific cytotoxic T lymphocytes by artificial APCs expressing ligands for the T-cell receptor, CD28 and 4-1BB, Nature Biotechnology, Nature Publishing Group, New York, NY, US, vol. 20, No. 2, Feb. 1, 2002, pp. 143-148.
Maus, M.V., et al., T cells expressing chimeric antigen receptors can cause anaphylaxis in humans. Cancer Immunol Res, 2013. 1(1): p. 26-31.
McGuinness RP, et al., Anti-tumor activity of human T cells expressing the CC49-zeta chimeric immune receptor, Hum Gene Ther. (Jan. 20, 1999); 10(2):165-73.
Medstrand et al., Long Terminal Repeats are Used as Alternative Promoters for the Endothelin B Receptor and Apolipoprotein C—I Genes in Humans, The Journal of Biological Chemistry, vol. 276, No. 3, Issue of Jan. 19, pp. 1896-1903, 2001.
Melero, I, et al., Amplification of tumor immunity by gene transfer of the co-stimulatory 4-1BB ligand: synergy with the CD28 co-stimulatory pathway, Bristol-Myers Squibb Pharmaceutical Research Institute (1998); 1116-1121.
Melief, C. J. et al., Strategies for immunotherapy of cancer, Adv. Immunol. (2000); 75:235-282.
Mooney et al., Concise Review: Neural Stem Cell-Mediated Targeted Cancer Therapies Stem Cells Translational Medicine, 2018, pp. 740-747.
Moore et al., Characterisation of salmon and trout CD8α and CD8β, Molecular Immunology 42 (2005) 1225-1234.
Moretta et al., Activating Receptors and Coreceptors Involved in Human Natural Killer Cell-Mediated Cytolysis, Annu. Rev. Immunol. 2001. 19:197-223.
Morgan RA, et al., Cancer regression in patients after transfer of genetically engineered lymphocytes, Science (Oct. 6, 2006); 314(5796): 126-9.
Morrison, C, CAR-T Field Booms as Next-Generation Platforms Attract Big Players, Nature Biotechnology (Jun. 2015); 33: 571-72.
Muller T, et al., Expression of a CD20-specific chimeric antigen receptor enhances cytotoxic activity of NK cells and overcomes NK-resistance of lymphoma and leukemia cells, Cancer Immunol. Immunother. (2008); 57: 411-423.
Mungra et al., Targeted human cytolytic fusion proteins at the cutting edge: harnessing the apoptosis-inducing properties of human enzymes for the selective elimination of tumor cells Oncotarget, vol. 10, No. 8, 2019, pp. 897-915.

(56) References Cited

OTHER PUBLICATIONS

Munn et al., Role of Low-Affinity Fc Receptors in Antibody-dependent Tumor Cell Phagocytosis by Human Monocyte-derived Macrophages, Cancer Research 51, 1117-1123, Feb. 15, 1991.
Nam, K, et al., Cross-Linking of 4-1BB Activates TCR-Signaling Pathways in CD8 T Lymphocytes1, The Journal of Immunology; 1898-1905.
National Cancer Institute. CAR T-Cell Therapy: Engineering Patients' Immune Cells to Treat their Cancers, Cancer Research Updates, Updated: Oct. 16, 2014; 5 pages; retrieved Nov. 17, 2014 cancer. gov/cancertopics/research-updates/2013/CAR-T-Cells.
Nelson, Aaron L., Antibody fragments, mAbs 2010, Landes Bioscience, vol. 2, Issue 1, pp. 77-83.
Nieba, L. et al., Disrupting the hydrophobic patches at the antibody variable/constant domain interface: improved in vivo folding and physical characterization of an engineered scFv fragment, Protein Eng., 1997, 10, 435-444.
Oelke et al., Ex vivo induction and expansion of antigen-specific cytotoxic T cells by HLA-Ig-coated artificial antigen-presenting cells, Nature Medicine (2003); 9(5):619-624.
Oelsner, S., et al., Continuously expanding CAR NK-92 cells display selective cytotoxicity against B-cell leukemia and lymphoma, Cytotherapy, 2017; 19: 235-249.
Okazaki et al., PD-1 immunoreceptor inhibits B cell receptor mediated signaling by recruiting src homology2-domain-containing tyrosine phosphatase 2 to phosphotyrosine, PNAS Nov. 20, 2001, vol. 98, No. 24, 13866-13871.
Orr, B. et al., Rapid method for measuring ScFv thermal stability by yeast surface display, Biotechnol Prog., 2003. 19, 631-638.
Pages et al., Two Distinct Intracytoplasmic Regions of the T-cell Adhesion Molecule CD28 Participate in Phosphatidylinositol 3-Kinase Association The Journal of Biological Chemistry, vol. 271, No. 16, Apr. 19, 1996, pp. 9403-9409.
Paillard, F. Immunotherapy with T cells bearing chimeric antitumor receptors, Hum. Gene Ther. (1999); 10: 151-153.
Paillasse, M, et al., Insights into the Cholecystokinin 2 Receptor Binding Site and Processes of Activation, The American Society for Pharmacology and Experimental Therapeutics (2006); 70:1935-1945.
Pameijer, C.R., et al., Conversion of a tumor-binding peptide identified by phage display to a functional chimeric T cell antigen receptor, Cancer Gene Ther., 2007, 14, 91-07.
Park et al., Treating cancer with genetically engineered T cells Trends Biotechnol. Nov. 29, 2011(11): 550-557.
Parkhurst et al. Characterization of genetically modified T-cell receptors that recognize the CEA:691-699 peptide in the context of HLA-A2.1 on human colorectal cancer cells (2009) Clin Cancer Res. Jan. 1, 2009;15(1):169-80.
Patel Jaina M et al: Cancer CARtography: charting out a new approach to cancer immunotherapy, Immunotherapy. 2014;6(6):675-8.
Pollock et al., Inducible T cell antigen 4-1BB. Analysis of expression and function, J Immunol 1993; 150:771-781.
Porter DL, et al. Chimeric antigen receptor T cells persist and induce sustained remissions in relapsed refractory chronic lymphocytic leukemia. Science translational medicine. 2015;7(303):303-39. doi: 10. I 126/scitranslmed.aac5415. PubMed PMID:26333935.
Porter, D.L. et al., Chimeric antigen receptor-modified T cells in chronic lymphoid leukemia, N. Engl. J. Med., 2011, 365, 725-733.
Prasad et al., T-cell antigen CD28 interacts with the lipid kinase phosphatidylinositol3-kinase by a cytoplasmic Tyr(P)-Met-Xaa-Met motif, Proc. Natl. Acad. Sci. USA, vol. 91, pp. 2834-2838, Mar. 1994.
Product brochure for the Engineered Autologous Cell Therapy (eACT™) Platform, available from Kite Pharma, retrieved Oct. 25, 2015 from kitepharma.com/c/products/eact.php.
Pule et al., Artificial T-cell receptors, Cytotherapy (2003) 5(3):211-226.
Pule et al., Virus-specific T cells engineered to coexpress tumor-specific receptors: persistence and antitumor activity in individuals with neuroblastoma, Nat. Med. (2008); 14: 1264-1270.
Qin et al., Incorporation of a hinge domain improves the expansion of chimeric antigen receptor T cells, Journal of Hematology & Oncology (2017) 10:68.
Rai et al., Expression systems for production of heterologous proteins, Current Science2001, vol. 80, No. 9, pp. 1121-1128.
Recent patent applications in chimeric antigen receptors, Nature Biotechnology 32(3): 239 (2014).
Reddy et al., Elimination of Fc Receptor-Dependent Effector Functions of a Modified IgG4Monoclonal Antibody to Human CD4, J Immunol 2000; 164: 1925-1933.
Redmond et al., The role of OX40-mediated co-stimulation in T cell activation and survival, Crit. Rev. Immunol. 2009, 29(3): 187-201.
Reichert. J. Day 1, Emerging Disruptive Technologies and Cutting-Edge Analytical Techniques, MAbs, 2009, 1, 190-209.
Restifo et al., Adoptive immunotherapy for cancer: harnessing the T cell response, Nat. Rev. Immunol. (Mar. 22, 2012) 12(4):269-281.
Reubi, Jean Claude, Peptide Receptors as Molecular Targets for Cancer Diagnosis and Therapy, Endocrine Reviews 24(4): 389-427.
Riha et al., CD28 co-signaling in the adaptive immune response Self/Nonself 1:3, 231-240: Jul./Aug./Sep. 2010.
Riley et al., The CD28 family: a T-cell rheostat for therapeutic control of T-cell activation, Blood, Jan. 1, 2005, vol. 105, No. 1, pp. 13-21.
Riviere, I., Gallardo, H. F., Hagani, A B. & Sadelain, M. Retroviral-mediated gene transfer in primary murine and human T-lymphocytes. Mol. Biotechnol. 15, 133-142 (2000).
Roberts et al., Chemistry for peptide and protein PEGylation, Advanced Drug Delivery Reviews (2002); 54:459-476.
Rodgers, D. et al., Switch-mediated activation and retargeting of CAR-T cells for B-cell malignancies, Proc. Natl. Acad. Sci., 2016, 113, E459-468.
Romeo, C. at al., Sequence requirements for induction of cytolysis by the T cell antigen/Fc receptor zeta chain, Cell (1992); 68:889-897.
Romeo, C., et al., Cellular immunity to HIV activated by CD4 fused to T cell or Fc receptor polypeptides, Cell (1991); 64:1037-1046.
Rosenberg Cell transfer immunotherapy for metastatic solid cancer—what clinicians need to know (2011) Nat Rev Clin Oncol. 8(10):577-85).
Rosenberg et al. Adoptive cell transfer: a clinical path to effective cancer immunotherapy. Nat Rev Cancer. Apr. 2008; 8(4):299-308.
Rosenberg, S. A. et al., Adoptive cell therapy for the treatment of patients with metastatic melanoma, Current Opinion in Immunology, 2009, 21, 233-240.
Rotz Seth J. et al. Severe cytokine release syndrome in a patient receivingPD-1-directed therapy Pediatr Blood Cancer. Dec. 2017;64(12). Epub May 24, 2017 (4 pages).
Rueckert S, et al., A monoclonal antibody as an effective therapeutic agent in breast cancer: trastuzumab Expert Opin Biol Ther. Jun. 2005;5(6):853-66.
Sadelain et al., Targeting Tumours with Genetically Enhanced T Lymphocytes, Nat Rev Cancer (Jan. 2003); 3(1): 35-45.
Sadelain, et al., The promise and potential pitfalls of chimeric antigen receptors, Current Opinion in Immunology (2009); 21: 215-223.
Sadelain, M. et al., The basic principles of chimeric antigen receptor design, Cancer Discov., 2013, 3, 388-398.
Saoulli, C, et al., CD28-independent, TRAF2-dependent Costimulation of Resting T Cells by 4-1BB Ligand, Master of Science Thesis, Department of Immunology University of Toronto (1998), 77 pp.
Saraswat et al., DNA as Therapeutics; an Update, Indian J Pharm Sci. Sep.-Oct. 2009;71(5): 488-498.
Scholler, J., et al., Decade-long safety and function of retroviral-modified chimeric antigen receptor T cells, Sci Transl Med (May 2, 2012); 4(132): 132ra53 (7 pages).
Schonfeld, K, et al., Selective Inhibition of Tumor Growth by Clonal NK Cells Expressing an Erb82/HER2-Specific Chimeric Antigen Receptor, Mol. Ther., vol. 23 No. 2, 330-338 Feb. 2015.
Schreiber, S.L., Organic synthesis toward small-molecule probes and drugs PNAS, vol. 108, No. 17, Apr. 26, 2011, pp. 6699-6702.

(56) References Cited

OTHER PUBLICATIONS

Schwesinger et al., Unbinding forces of single antibody-antigen complexes correlate with their thermal dissociation rates, PNAS (2000) 97(18), 9972-9977.
Scott, D., et al., Immunogenicity of biotinylated hapten-avidin complexes, Mol Immunol(1984); 21(11):1055-60.
Sega, E. et al., Tumor detection using folate receptor-targeted imaging agents, Cancer Metastasis Rev., 2008, 27, 655-664.
Sentman Challenges of creating effective chimeric antigen receptors for cancer therapy Immunotherapy. Aug. 2013;5(8):783-5.
Serghides et al., Evaluation of OX40 Ligand as a Costimulator of Human Antiviral Memory CD8 T Cell Responses: Comparison with B7.1 and 4-1BBL, The Journal of Immunology 175:6368-6377 (2005).
Shields et al., High Resolution Mapping of the Binding Site on Human IgG1 for FcγRI, FcγRII, FcγRIII, and FcRn and Design of IgG1 Variants with Improved Binding to the FcγR*, The Journal of Biological Chemistry 2001, vol. 276, No. 9, Issue of Mar. 2, pp. 6591-6604.
Shirasu, N. et al., Construction and Molecular Characterization of Human Chimeric T-Cell Antigen Receptors Specific for Carcinoembryonic Antigen, Anticancer Research (2010); 30:2731-2738.
Sobota et al., Binding of IgG-Opsonized Particles to FcγR is an Active Stage of Phagocytosis That Involves Receptor Clustering and Phosphorylation, The Journal of Immunology 2005; 175:4450-4457.
Stancovski et al., Targeting of T Lymphocytes to Neu/HER2-Expresslng Cells Using Chimeric Single Chain Fv Receptors, J. Immunol. (1993); 151(11):6577-6582.
Stein et al., The Cytoplasmic Domain of CD28 is both Necessary and Sufficient for Costimulation of Interleukin-2 Secretion and Association with Phosphatidylinositol3'-Kinase, Molecular and Cellular Biology, (May 1994) 14(5): 3392-3402.
Stephan et al., T cell-encoded CD80 and 4-1BBL induce auto- and transcostimulation, resulting in potent tumor rejection, Nature Medicine (Dec. 2007); 13(12): 1440-1449.
Stevens et al., Generation of Tumor-Specific CTLs from Melanoma Patients by Using Peripheral Blood Stimulated with Allogeneic Melanoma Tumor Cell Lines, J. Immunol(1995); 154:762-771.
Suhoski, M.M., et al., Engineering artificial antigen-presenting cells to express a diverse array of co-stimulatory molecules. Mol Ther, 2007. 15(5): p. 981-8.
Swanson et al., The coordination of signaling during Fc receptor-mediated phagocytosis, Journal of Leukocyte Biology, vol. 76, Dec. 2004, pp. 1093-1103.
Tam et al., Functional, Biophysical, and Structural Characterization of Human IgG1 andIgG4 Fc Variants with Ablated Immune Functionality, *Antibodies* 2017, 6, 12.
Tamada et al. Redirecting Gene-Modified T Cells toward Various Cancer Types Using Tagged Antibodies, Clinical Cancer Research (Oct. 2, 2012) vol. 18, iss. 23, pp. 6436-6445, with correction.
Tanaka, Toshio et al. Immunotherapeutic implications of IL-6 blockade for cytokine storm. immunotherapy. Jul. 2016;8(8):959-70.
Teachey D. T. et al. Cytokine release syndrome after blinatumomab treatment related to abnormal macrophage activation and ameliorated with cytokine-directed therapy Blood. Jun. 27, 2013;121(26):5164-7. doi: 10.1182/blood-2013-02-485623. Epub May 15, 2013.
Themeli, M., et al., Generation of tumor-targeted human T lymphocytes from induced pluripotent stem cells for cancer therapy, Nat Biotechnol (2013); 31(10):928-33 (Epub Aug. 11, 2013).
Tsukahara et al. CD19 target-engineered T-cells accumulate at tumor lesions in human B-cell lymphoma xenograft mouse models (2013) Biochem Biophys Res Commun 438(1): 84-9. Epub Jul. 17, 2013.
Turatti, F., et al., Redirected activity of human antitumor chimeric immune receptors is governed by antigen and receptor expression levels and affinity of interaction, J Immunother (2007); 30(7): 684-93.
Turtle et al., Engineered T cells for anti-cancer therapy Curr. Opin. Immunol., Oct. 2012; 24(5): 633-39. Epub Jul. 18, 2012.
Uherek, C, et al., Chimeric antigen receptors for the retargeting of cytotoxic effector cells, J. Hematother. Stem Cell Res. (2001); 10: 523-534.
UniProtKB—P01732 (CD8A_HUMAN). T-cell surface glycoprotein CD8 alpha chain; 11pages; retrieved on May 13, 2016 from uniprot.org/uniprot/P01732.
UniProtKB—P20963 (CD3Z_HUMAN). T-cell surface glycoprotein CD3 zeta chain; 12pages; retrieved on May 13, 2016 from uniprot.org/uniprot/P20963.
UniProtKB—Q07011 (TNR9_HUMAN). Tumor necrosis factor receptor superfamily member 9; 14 pages; retrieved on May 13, 2016 from uniprot.org/uniprot/Q07011.
Urba, W.J. et al., Redirecting T cells, New Engl. J. Med., 2011, 365, 754-757.
Urbanska et al., A Universal Strategy for Adoptive Immunotherapy of Cancer through Use of a Novel T-cell Antigen Receptor, Cancer Research (2012) 72(7): 1844-1852.
Urbanska, K., et al., A Universal Immune Receptor Expressed by T Celis for the Targeting of Diverse and Multiple Tumor Associated Antigens IN Abstracts for the 26th Annual Scientific Meeting of the Society for Immunotherapy of Cancer (SITC), J Immunother, vol. 34, No. 9, Nov.-Dec. 2011 (62 pages), p. 381.
Uttenthal, B.J., et al., Challenges in T cell receptor gene therapy. J Gene Med (Jun. 2012): 14(6): 386-99.
Van Blitterswijk et al., Anticancer mechanisms and clinical application of alkylphopholipids, Biochimica et Biophysica Acta (2013) 1831(3):663-674.
Van Dam, G. et al., Intraoperative tumor-specific fluorescence imaging in ovarian cancer by folate receptor-α targeting: first in-human results, Nature Medicine, 2011, 17, 1315-1319.
Van der Luit et al., A new class of anticancer alkylphospholipids uses lipid rafts as membrane gateways to induce apoptosis in lymphoma cells, Mol Cancer Ther (2007) 6(8):2337-2345.
Van Rhijn et al., Nov. 30, 2015, Human autoreactive T cells recognize CD1b and phospholipids, Proceedings of the National Academy of Sciences 113(2):380-385.
Vaughan et al., Human antibodies with sub-nanomolar affinitis isolate from a large non-immunized phage display library, Nature Biotechnology (1996) vol. 14(3), pp. 309-314.
Verdine et al., The Challenge of Drugging Undruggable Targets in Cancer: Lessons Learned from Targeting BCL-2 Family Members Clin. Cancer Res. vol. 13, No. 24, Dec. 15, 2007, pp. 7264-7270.
Verhoeyen et al. Lentiviral vector gene transfer into human T cells (2009) Methods Mol Biol. 506: 97-114.
Wang et al. Phenotypic and functional attributes of lentivirus-modified CD19-specific human CD8+ central memory T cells manufactured at clinical scale (2012) J lmmunother.35(9):689-701.
Wang et al., Current status and perspectives of chimeric antigen receptor modified T cells for cancer treatment, Protein Cell 2017, 8(12):896-925.
Wayua, C. et al., Evaluation of a Cholecystokinin 2 Receptor-Targeted Near-Infrared Dye for Fluorescence-Guided Surgery of Cancer, Molecular Pharmaceutics, 2014, 11,468-476.
Weijtens, M. E. et al., Single chain Ig/gamma gene-redirected human T lymphocytes produce cytokines, specifically lyse tumor cells, and recycle lytic capacity., J. Immunol.(Jul. 15, 1996); 157(2):836-43.
Weissman et al., Molecular cloning and chromosomal localization of the human T-cell receptor zeta chain: Distinction from the molecular CD3 complex Proc. Natl. Acad. Sci. vol. 85, Dec. 1988, pp. 9709-9713.
Weissman et al., Role of the zeta chain in the expression of the T cell antigen receptor: genetic reconstitution studies The EMBO Journal, vol. 8, No. 12, 1989, pp. 3651-3656.
Wesolowski, J, et al., Single domain antibodies: promising experimental and therapeutic tools in infection and immunity, Med Microbiol Immunol (2009) 198:157-174.
Wilkie et al., Retargeting of Human T Cells to Tumor-Associated MUC1: The Evolution of a Chimeric Antigen Receptor, The Journal of Immunology Apr. 2008, pp. 4901-4909.

(56) References Cited

OTHER PUBLICATIONS

Wilson, et al. DAP12 and KAP10 (DAP10)-novel transmembrane adapter proteins of the CD3zeta family, Immunol Res. (2000); 22(1):21-42.

Wu et al., Remote control of therapeutic T cells through a small molecule-gated chimeric receptor, Science (2015) vol. 350, Issue 6258, pp. 293 and aab4077-aab4077.

Wu et al., Adoptive T-cell therapy using an A tumor-infiltrating lymphocytes for metastatic melanoma: current status and future outlook Cancer, Mar. 18, 2012(2): 160-75.

Wu, et al., An activating immunoreceptor complex formed by NKG2D and DAP10, Science (1999): 285:730-732.

Xu et al., Cytokine release syndrome in cancer immunotherapy with chimeric antigen receptor engineered T cells Cancer Lett. Feb. 28, 2014;343(2):172-8. Epub Oct. 16, 2013.

Xu, X.J., et al., Efficacy and safety of adoptive immunotherapy using anti-CD 19 chimeric antigen receptor transduced T-cells: a systematic review of phase I clinical trials, LeukLymphoma (2013); 54(2): 255-60 (Published online: Sep. 8, 2012).

Yee, C., et al., Prospects for Adoptive T Cell Therapy, Current Opinion in Immunology (1997): 9(5):702-708.

Zhang et al., Phase I Escalating-Dose Trial of CAR-T Therapy Targeting CEA+ Metastatic Colorectal Cancers, Molecular Therapy (2017), 25(5): 1248-1258.

Zhang, H., et al., 4-IBB is superior to CD28 costimulation for generating CD8+ cytotoxic lymphocytes for adoptive immunotherapy. J Immunol, 2007. 179(7): p. 4910-8.

Zhao, Y. et al., A herceptin-based chimeric antigen receptor with modified signaling domains leads to enhanced survival of transduced T lymphocytes and antitumor activity, J. Immunol, 2009, 183, 5563-5574.

Zheng et al., Arming Tumor-Reactive T Cells with Costimulator B7-1 Enhances Therapeutic Efficacy of the T Cells, Cancer Research, 2006, vol. 66, No. 13, pp. 6793-6799.

Zhong, et al., Integrated CD28 and 4-1BB Signals Strongly Potentiate CD8+ T Cell Mediated Eradication of Metastatic Prostate Cancer, Molecular Therapy (Jan. 1, 2006); 13: p. S103, Abstract.

Ma, Jennifer S.Y. et al., "Versatile strategy for controlling the specificity and activity of engineered T cells" PNAS, Jan. 2016, pp. 450-458, vol. 113, Issue 4.

International Search Report for PCT/US2018/017126 dated Jul. 11, 2018.

Altschul et al., "Local Alignment Statistics, [27] Multiple Alignment and Phylogenetic Trees," Methods in Enzymology (1996) 266:460-480.

Berger et al., Feb. 2015, Safety of targeting ROR1 in primates with chimeric antigen receptor modified T cells, Cancer Immunology Research, 3(2):206-216.

Cheng et al., Mar. 26, 2004, Hapten-directed targeting to single-chain antibody receptors, Cancer Gene Therapy, 11(5):380-388.

Chothia et al., Dec. 1989, Conformations of immunoglobulin hypervariable regions, Nature, 342:877-883.

Deng et al., 2019, Antitumor activity of NKG2D CAR-T cells against human colorectal cancer cells in vitro and in vivo, Am J. Cancer Res, 9(5):945-958.

Hudecek et al. Jun. 15, 2013, Receptor affinity and extracellular domain modifications affect tumor recognition by ROR1-specific chimeric antigen receptor T-cells. Clin Cancer Res. 19(12):3153-3164.

Johnson et al., 2000, Kabat database and its applications: 30 years after the first variability plot, Nucleic Acids Res., 28(1): 214-218.

Kabat et al., 1991, Sequences of Proteins of Immunological Interest, 5th Ed. Public Health Service, National Institutes of Health, Bethesda, Md. (TOC).

Kunik et al., Jun. 6, 2012, Paratome: an online tool for systematic identification of antigen-binding regions in antibodies based on sequence or structure, Nucl Acids Res. 40:W521-W524.

Lee et al., Jan. 15, 2019, Use of a single CAR T cell and several bispecific adapters facilitates eradication of multiple antigenically different solid tumors, Cancer Research, 79(2):387-396.

Lefranc et al., 2003, IMGT unique numbering for immunoglobulin and T cell receptor variable domains and Ig superfamily V-like domains, Dev Comp Immunol. 27:55-77.

Li et al., Jan. 2020, CAIZ-specific CAR-T cells and sunitinib show synergistic effects against metastatic renal cancer models, J Immunother, 43(1):16-28.

Makabe et al., Jan. 11, 2008, Thermodynamic consequences of mutations in Vernier zone residues of a humanized anti-human epidermal growth factor receptor murine antibody, 528, Journal of Biological Chemistry, 283(2):1156-1166.

Martin et al., Dec. 1989, Modeling antibody hypervariable loops: a combined algorithm, Proc Natl Acad Sci (USA), 86:9268-9272.

Samudrala et al., 1999, Ab Initio Protein Structure Prediction Using a Combined Hierarchical Approach, Proteins, Structure, Function and Genetics Suppl., 3:194-198.

Sun et al., Jan. 2018, Immunotherapy with CAR-Modified T cells: toxicities and overcoming strategies, Journal of Immunology Research, 2018:1-10.

Zarour, Reversing T-cell dysfunction and exhaustion in cancer, Clinical Cancer Research, 22(8):1856-1864.

Fang et al., Jul. 17, 2013, Lipid-insertion enables targeting functionalization of erythrocyte membrane-cloaked nanoparticles, Nanoscale, 5(19):8884-8888.

\* cited by examiner

Y = O or NH

■ DAPI, an nuclear stain
■ FL-PLE
■ antiFL-Alexa647 Antibody

PHOSPHOLIPID ETHER (PLE) CAR T CELL TUMOR TARGETING (CTCT) AGENTS

CROSS REFERENCE TO RELATED APPLICATIONS

This application is a U.S. National Phase Application of PCT International Application Number PCT/US2018/017126 filed on Feb. 6, 2018, designating the United States of America and published in the English language, which is an International Application of and claims the benefit of priority to U.S. Provisional Application No. 62/456,027, filed on Feb. 7, 2017. The disclosures of the above-referenced applications are hereby expressly incorporated by reference in their entireties

FIELD OF THE INVENTION

The alternatives described herein pertain to synthetic compounds that are designed to target and selectively decorate tumor cell membranes so as to facilitate recognition by binding agents. In some alternatives, the synthetic compounds have recognition moieties that interact with specific Chimeric Antigen Receptor T cells (CAR T cells), in which both the synthetic compounds and the CAR T cells are administered to a subject by intravenous or locoregional administration. Accordingly, several compositions and methods of making and using these compositions to treat or inhibit disease in a subject are contemplated.

BACKGROUND

The adoptive transfer of human T lymphocytes that are engineered by gene transfer to express chimeric antigen receptors (CARs) specific for surface molecules expressed on tumor cells has the potential to effectively treat cancer. Chimeric receptors are synthetic receptors that include an extracellular ligand binding domain, most commonly a single chain variable fragment of a monoclonal antibody (scFv) linked to intracellular signaling components, most commonly CD3 alone or combined with one or more costimulatory domains. Much of the research in the design of chimeric receptors has focused on defining scFvs and other ligand binding elements that target malignant cells without causing serious toxicity to essential normal tissues, and on defining the optimal composition of intracellular signaling modules to activate T cell effector functions. There remains a need for a CAR T cell-mediated therapy that is selective for specific targets and which minimizes adverse side effects.

SUMMARY

In a first aspect, a complex comprising a chimeric antigen receptor (CAR) or a T cell receptor (TCR) is provided, wherein the CAR or TCR is joined to a lipid, wherein the lipid comprises a target moiety and the CAR is joined to said lipid through an interaction with said target moiety. In some alternatives, the lipid comprises a polar head group and a hydrophobic group. In some alternatives, the hydrophobic group is a carbon chain or a fatty acid such as an aliphatic chain. In some alternatives, the carbon chain or fatty acid is saturated or unsaturated. In some alternatives, the hydrophobic group comprises an alkyl, alkenyl or alkynyl group. In some alternatives, the hydrophobic group comprises a terpenoid lipid such as a steroid or cholesterol or it comprises an aromatic ring. In some alternatives, the hydrophobic group comprises an ether linkage, wherein the ether linkage is between the polar head group and the aliphatic chain. In some alternatives, the lipid is a phospholipid ether. In some alternatives, the polar head comprises a choline, a phosphatidylcholine, sphingomyelin, phosphoethanolamine group, an oligosaccharide residue, a sugar residue, phosphatidyl serine or phosphatidyl inositol. In some alternatives, the sugar is a glycerol. In some alternatives, the target moiety is a hapten, poly(his) tag, Strep-tag, FLAG-tag, V5-tag, Myc-tag, HA-tag, NE-tag, biotin, digoxigenin, dinitrophenol or fluorescein. In some alternatives, the hapten, which is a target moiety, comprises Alexa Fluor 405, Cascade Blue, Alexa Fluor 488, BODIPY, Dansyl chloride, Oregon Green, Lucifer yellow, Rhodamine, Tetramethylrhodamine, Nitrotyrosine, digoxigenin, 2,4-Dichlorophenoxyacetic acid, Atrazine (2-Chloro-4-(ethylamino)-6-(isopropylamino)-s-triazine), Nicotine (3-(1-Methyl-2-pyrrolidyl) pyridine, Black Leaf), Morphine (morph, Morphine Sulfate), 2,4-DINITROCHLOROBENZENE (1-Chloro-2, 4-dinitrobenzene; DNCB; Dinitrochlorobenzene), 4-chloro-6-(ethylamino)-1,3,5-triazine-2-(6-aminohexanecarboxylic acid), Structurally related s-triazines (Modifications: H/Cl/C6 R1=NH2- R2=—Cl R3=—NH—(CH2)5-COOH; iPr/Cl/nBu R1=(CH3)2-CH—NH— R2=—Cl R3=—NH—(CH2) 3-(CH3)), Ametryn (2-Ethylamino-4-isopropylamino-6-methylthio-1,3,5-triazine), Deethylatrazine (DEA) (Structurally related s-triazines), Deisopropylatrazine (DIA) (Structurally related s-triazines), Deethyldeisopropylatrazine (DEDIA) (Structurally related s-triazines), Deethyldeisopropylatrazine (DEDIA) (Structurally related s-triazines), HydroxyAtrazine (HA) (Structurally related s-triazines), DeisopropylHydroxyAtrazine (DIHA) (Structurally related s-triazines), DeethylDeisopropylHydroxyAtrazine (DE-DIHA) (Structurally related s-triazines), Simazine (Structurally related s-triazines), Desmetryne (Structurally related s-triazines), Prometryne (Structurally related s-triazines), 2-hydroxyatrazine (atrazine derivative), 2-hydroxypropazine (structurally related s-triazine), 2-hydroxysimazine, N-(4-Amine-6-hydroxy-[1,3,5]triazin-2-yl)-4-aminobutanoic Acid (Modification: R1=NH2 R2=NH(CH2)3COOH R3=OH), SulcoFuron, 5-chloro-2-{4-chloro-2-[3-(3,4-dichlorophenyl)ureido]phenoxy}benzenesulfonic acid, Fluco-Furon (1,3-bis(4-chloro-α,α,α-trifluoro-m-tolyl)urea), Agatharesinol, Sequirin C, Sugiresinol, Hydroxysugiresinol, Hinokiresinol, Coniferyl alcohol, Cinnamyl alcohol, p-Coumaric acid, Cinnamic acid, p-Coumaric acid, Cinnamic acid, Hinokinin, Guaiacylglycerol-beta-guaiacyl ether, Morphine-3-glucuronide (M3G), Codeine, Nor-Codeine, 6-Monoacetylmorphine, (+) Methamphetamine, Ceftazidime, Phenobarbital, p-hydroxyPhenobarbital, p-aminophenobarbital, Cyclobarbital, 3'-Ketocyclobarbital, 3'-Hydroxycyclobarbital, Secobarbital, Barbital, Metharbital, Barbituric acid, Thiopental, Thiobarbituric acid, Primidone, Glutethimide, Pentobarbital, Heroin, Diacetylmorphine, Levallorphan, L-11-Allyl-1,2,3,9,10,10a-hexahydro-4H-10,4a-iminoethanophenanthren-6-ol, Pethidine (Demerol; Dolantin; Meperidine; Ethyl 1-methyl-4-phenylpiperidine-4-carboxylate; Isonipecaine), Methamphetamine, d-Desoxyephedrine; Methedrine; Tolpropamine; Pratalgin; Pragman. Benzoylecgonine, 3-Carboxymethylmorphine, Cocaine, 5-benzimidazolecarboxylic acid, ABA (4-acetyl benzoic acid), Dexamethasone, Flumethasone, 6alpha, 9 alpha-difluoro-11 beta, 17,21-trihydroxy-16 alpha-methylpregna-1,4-diene-3, 20-dione, 9 alpha-fluoro-11 beta,17,21-trihydroxy-16 beta-methylpregna-1,4-diene-3,20-dione, 9-alpha-fluoroprednisolone, Desoxymethasone, Triamcinolone, 9 alpha-fluoro-11 beta,16 alpha, 17,21-tetrahydroxypregna-1,4-diene-3,20-dione, Fluocortolone, 6 alpha-fluoro-11 beta,21-dihydroxypregna-1,4-diene-3,20-dione, Cortisol, 11 beta, 17,21-trihydroxypregna-4-ene-3,20-dione, Prednisone, 17,21-dihydroxypregn-4-ene-3,11,20-trione, Methylprednisolone, 11 beta, 17,21-trihydroxy-6 alpha-methylpregna-1,4-diene-3,20-dione, Triamcinolone hexacetonide, 21-(3,3-dimethyl-1-oxobutoxy)-9 alpha-fluoro-11-hydroxy-16,17-[(1-methylethylidene) bis(oxy)]pregna-1,4-diene-3,20-dione, Carbofuran, 2,3-dihydro-2,2-dimethyl-7-benzofuranyl methylcarbamate, BFNP (3-[[(2,3-dihydro-2,2-dimethyl-7-benzofuranyloxy)carbonyl]amino]propanoic acid), Carbofuran derivative, 2,3-dihydro-2,2-dimethyl-7-benzofuranol, Bendiocarb, Carbaryl, Methiocarb, Propoxur, Aldicarb, Methomyl, Benalaxyl, methyl N-(phenylacetyl)-N-(2,6-xylyl)-DL-alaninate, Bn-Ba (4-[2-(N-phenylacetyl-N-2,6-xylylamino)propionamido] butyric acid), Bn-COOH (4-[2-(N-phenylacetyl-N-2,6-xylyl-DL-alanine), Benalaxyl derivative, Furalaxyl, Metalaxyl, Acetochlor, Dimetachlor, Metolachlor, 2-chloro-6'-ethyl-N-(2-methoxy-1-methylethyl)acet-o-toluidine, Diethathyl-ethyl, Benzoylprop-ethyl, Benzoylprop-ethyl, 2,4,5-Trichlorophenoxyacetic acid, 2-chloro-6'-ethyl-N-(2-methoxy-1-methylethyl)acet-o-toluidine, Diethathyl-ethyl, Benzoylprop-ethyl, Propachlor, Propachlor, 2,4,5-Trichlorophenoxyacetic acid, 2,4,5,T; Weedone, 2,4-Dichlorophenoxybutyric acid (2,4-DB), 2,4-DB; Butanoic acid, 4-(2,4-dichlorophenoxy)-; Butoxone; Embutone, MCPA, 2-Methyl-4-chlorophenoxyacetic acid; Metaxon, Dichlorprop (2,4-DP), 1-[(2-chloro)phenylsulfonyl]monoamidosuccinic acid, Chlorsulfuron, chlorbromuron, amidosulfuron, chlortoluron, isoproturon, diuron, Linuron O-Methyl-O-(4-nitrophenyl)-N-(4-carboxybutyl)-phosphoramidothioate Parathion-methyl, O,O-dimethyl O-4-nitrophenyl phosphorothioate; Methaphos; Wolfatox; Dimethylparathion; Metacide, Parathion-ethyl, DIETHYL P-NITROPHENYL THIOPHOSPHATE; O,O-DIETHYL O—(P-NITROPHENYL) PHOSPHOROTHIOATE; Fenitrothion, O,O-dimetyl O-4-nitro-m-tolyl phosphorothioate, Fenthion, O,O-dimethyl O-4-methylthio-m-tolyl phosphorothioate, Bromophos, O-4-bromo-2,5-dichlorophenyl O,O-dimethyl phosphorothioate, chlorpyrifos-methyl, O,O-dimethyl O-3,5,6-trichloro-2-pyridyl phosphorothioate, Oxidized parathion-methyl, Paraoxon, phosphoric acid, O,O-diethyl O-(4-nitrophenyl) ester, Diazinon, O,O-diethyl O-2-isopropyl-6-methylpyrimidin-4-yl phosphorothioate, Azinphos-methyl, pirimiphos-methyl, O-2-diethylamino-6-methylpyrimidin-4-yl O,O-dimethyl phosphorothioate, Methidathion, S-2,3-dihydro-5-methoxy-2-oxo-1,3,4-thiadiazol-3-ylmethyl O,O-dimethyl phosphorodithioate, Dimethylchlorothiophosphate, 4-NITROPHENOL, p-nitrophenol, Phenolic derivative (Modification On benzene ring; R1=OH R2=NO2 R3=H R4-CH2COOH R5=H R6=H); 2-Nitrophenol, o-Nitrophenol, 3-Nitrophenol, m-nitrophenol, 2,4-Dinitrophenol, 3,4-Dinitrophenol, 2,5-Dinitrophenol, 2,4-Dinitro-6-methylphenol, 2,3,6-trinitrophenol, 2-Chlorophenol, 4-Chloro-3-methylphenol, Fenitroxon, 3-Methyl-4-nitrophenol, Nonylphenol, HOM(3-[2-hydroxy-5nitro benzylthio] propionic acid, Phenol, Delor 103, Polychlorinated Biphenyls, Delor 104, Polychlorinated Biphenyls, Delor 105, Polychlorinated Biphenyls, Delor 106, 4,4'-Dichlorobiphenyl, PCB congeners, 2,4,4'-Trichlorobiphenyl, PCB congeners, 2,4'-Bichlorobiphenyl, PCB congeners, 2,2'-Dichlorobiphenyl, PCB congeners, 2,4,5-Trichlorobiphenyl, PCB congeners, 3,3',4,4'-Tetrachlorobiphenyl, PCB congeners, PCB congeners, 2,2',4,4',5,5'-Hexachlorobiphenyl, 2-(5-Carboxypentanoylamino)-4,4'-dichlorobiphenyl, Biphenyl derivative, 4-chlorophenoxyacetic acid, 2-Chlorophenoxyacetic acid, DDT,1,1,1-trichloro-2, 2-bis-(p-chlorophenyl)ethane, DDE, 1,1-dichloro-2, 2-bis(p-chlorophenyl)ethylene, p-Chlorophenol, 4-Chlorophenol, m-Chlorophenol 3,4-Dichlorophenol, 3,5-Dichlorophenol, 2,3,4-Trichlorophenol, 2,3,5-Trichlorophenol, 3-methylindole, 3-methylindole Derivatives, 4-(3-methylindol-5-yloxy)butanoic acid, 4-(3-methylindol-5-yloxy)butanoic acid, 3-methylindole Derivatives, 6-[n-3-methylindol-5-yloxy carbonyl)amino]hexanoic acid, 6-[n-3-methylindol-5-yloxy carbonyl)amino]hexanoic acid, 3-methylindole Derivatives, 2-[4-(3-methylindol-6-yl)but-1-ylthio]acetic acid, 2-[4-(3-methylindol-6-yl)but-1-ylthio]acetic acid, 3-methylindole Derivatives, 4-(3-methylindol-6-yl-4-oxo)butanoic acid, 4-(3-methylindol-6-yl-4-oxo)butanoic acid, 3-methylindole Derivatives, 6-(3-methylindol-7-yloxy) hexanoic acid, 6-(3-methylindol-7-yloxy)hexanoic acid, Indole, Indole-3-Carboxylic acid, Indole Derivative-Indole-3-Acetic acid, Indole-3-Acetic acid, Indole Derivative-Indole-3-Propionic acid, Indole-3-Propionic acid, Indole Derivative-Indole-3-Carbinol, Indole-3-Carbinol, Tryptophan, Tryptamine, 5-Methoxyindole-3-carboxaldehyde, 5-Methoxytryptamine, 5-Methoxyindole, 6-Methoxyindole, 7-Methoxyindole,EB1089(Seocalcitol),EB1089(Seocalcitol) Derivative, (22E,24E)-Des-A,B-24-homo-26,27-dimethyl-8-[(E)-N-(2-carboxyethyl)-carbamoylmethylidene]-cholesta-22,24-dien-25-ol, 1 alpha-25-dihydroxyvitamin D3, 25(OH)D3,25-hydroxyvitamin D3,24R,25(OH)2D3, 24R,25-dihydroxyvitamin D3, Vitamin D2, ergocalciferol, Vitamin D3, cholecalciferol,EB1446,EB1436,EB1445, EB1470, DeethylHydroxyAtrazine (DEHA) (Structurally related s-triazines), Irgarol 1051, Flourescein Isothiocyanate, FITC, Metanephrine, NorMetanephrine, Propazine, Terbutylazine, Terbuthylazine, 6-chloro-N-(1,1-dimethylethyl)-N'-ethyl-1,3,5-triazine-2,4-diamine, (Structurally related s-triazines), Ametryn (2-Ethylamino-4-isopropylamino-6-methylthio-1,3,5-triazine (Modification iPr/SCH3/Et R1=(CH3)2-CH—NH— R2=—SCH3 R3=—NH—CH2-CH3, Irgarol, Cyanazine (Modification R1=Cl R2=NHCH2CH3 R3=NHCCN(CH3)2), OH-Terbutylazine, Terbutylazine-2OH, Hydroxytriazine (EQ-0027), Deisopropylatrazine (Structurally related S-triazine), Desethylterbutylazine (Structurally related S-triazine), Desethyl-deisopropylatrazine (Structurally related S-triazine), Atraton, Terbutryn (Structurally related s-triazines), Atrazine derivative (Modification R1=—NHCH(CH3)2 R2=—S(CH2) 2COOH R3=—NHC2H5), Cyanuric chloride, Trifluralin, (Structurally related s-triazines) tBu/C4/SCH3 (Modification R1=—NH—C—(CH3)3 R2=—NH(CH2)3COOH R3=—SCH3), Sulphamethazine, (Structurally related s-triazines) 6-[[[4-Chloro-6-(methylamino)]-1,3,5-triazin-2-yl] amino]hexanoic Acid (Modification Me/Cl/C6 R1=—NHCH3 R2=—Cl R3=—NH(CH2)5COOH), (Structurally related s-triazines) Procyazine (Modification R1=—Cl R2=—NHcyclopropyl R3=—NHCCN(CH3)2), (Structurally related s-triazines), Prometon (Modification R1=—OCH3 R2=—NHCH(CH3)2 R3=—NHCH(CH3)2); (Structurally related s-triazines) Atrazine Mercapturic Acid (AM) (Modification R1=—SCH2CH(NHAc)COOH R2=—NHCH2CH3 R3=—NHCH(CH3)2), (Structurally related s-triazines), desethyl atrazine mercapturic acid (desethyl AM) (Modification R1=—NAcCys R2=—NH2 R3=—NHCH(CH3)2), (Structurally related s-triazines), deisopropyl atrazine mercapturic acid (deisopropyl AM) (Modification R1=—NAcCys R2=—NHCH2CH3 R3=—NH2), (Structurally related s-triazines), didealkylated atrazine mercapturic acid (didealkylated AM) (Modification R1=—NAcCys R2=—NH2 R3=—NH2), (Structurally related s-triazines), simazine mercapturate (Modification R1=

—NAcCys R2=—NHCH2CH3 R3=—NHCH2CH3), (Structurally related s-triazines) (Modification R1=—S(CH2)2COOH R2=—NHCH2CH3 R3=—NHCH2CH3), (Structurally related s-triazines) (Modification R1=—Cl R2=—NHCH(CH3)2 R3=—NH(CH2)2COOH), (Structurally related s-triazines) (Modification R1=—Cl R2=—NHCH2CH3 R3=—NH(CH2)2COOH), (Structurally related s-triazines), atrazine mercapturic acid methyl ester (AM methyl ester) (Modification R1=—NAcCysME R2=—NHCH2CH3 R3=—NHCH(CH3)2), N-acetylcysteine, S-benzyl mercapturate, (Structurally related s-triazines), simetryn (Modification R1=—SCH3 R2=—NHCH2CH3 R3=—NHCH2CH3), Metribuzin, 4-amino-6-tert-butyl-4,5-dihydro-3-methylthio-1,2,4-triazin-5-one, Sulpha Drugs, N4-acetyl-sulphamethazine (Modification N4-acetyl-sulphamethazine), Sulpha Drugs, Sulphathiazole, Sulphathiazole, Sulphamerazine, Sulphamerazine, Sulphaquinoxaline, Sulphaquinoxaline Sulphachlorpyridazine, Sulphachlorpyridazine, Sulphapyridine, Sulphadimethoxine, Sulphadimethoxine, Sulphamethoxazole, Sulphamethoxazole, Sulphisoxazole, Sulphisoxazole, Sulphamethizole, Sulphamethizole, Sulphanilamide, Sulphanilamide, Sulphaguanidine, Sulphaguanidine, Sulphadiazine, Sulphadiazine, Sulphamethoxypyridazine, Sulphamethoxypyridazine, Pentachlorophenoxypropionic acid, Pentachlorophenol, PCP, 2,3,5,6-Tetrachlorophenol, 1,2,4,5 Tetrachlorobenzene, 2,4,6 Trichlorophenol, 2-Methoxy-3,5,6-trichloropyridine, 1,3,5 Trichlorobenzene, 1,3 Dichlorobenzene, 2,4,5-Trichlorophenol, 2,6-Dichlorophenol, 3,5,6-Trichloro-2-pyridinoxyacetic acid, 3,5,6-Trichloro-2-Pyridinol, TCP, 2,4-Dichlorophenol, 2,5-Dichlorophenol, DNC, 4,4'-dinitrocarbanilide, (Structurally related s-triazines), Dichloroatrazine, (Structurally related s-triazines), Dichlorosimazine, 1-((6-chloropyridin-3-yl)methyl)imidazolidin-2-imin, Pyridine Derivative, 6-chloropyridine-3-carboxylic acid, Nicotinic acid, Pyridine Derivative, N-((6-chloropyridin-3-yl)methyl)-N-methylacetamide, (6-chloropyridin-3-yl)-N-methylmethanamine, (6-chloropyridin-3-yl)methanol, Imidacloprid, 1-(6-chloro-3-pyridylmethyl)-N-nitroimidazolidin-2-ylideneamine, Acetamiprid, (E)-N1-[(6-chloro-3-pyridyl)methyl]-N2-cyano-N1-methylacetamidine, Nitenpyram, Deltamethrin, 1(R)-cis-alpha (S)-3-(2,2-dibromoethenyl)-2,2-dimethylcyclopropane carboxylic acid cyano(3-phenoxyphenyl)methyl ester, DON, deoxynivalenol, DON derivative, 15-AcDON (15-acetyldeoxynivalenol), DON derivative, 3-AcDON (3-acetyldeoxynivalenol), DON derivative, 3,15-DiacDON (3,15-diacetyldeoxynivalenol), DON derivative, 3,7,15-TriacDON (3,7,15-Triacetyldeoxynivalenol), NIV (nivalenol), nivalenol, NIV Derivative, 4-AcNIV (fusarenon X), Flutolanil, alpha,alpha,alpha-trifluoro-3'-isopropoxy-o-toluanilide, Mepronil, Mebenil, Benodanil, 24,25(OH)2D3, (24R)-24,25-dihydroxyvitamin D3, 24S,25(OH)2D3, 24S,25-dihydroxyvitamin D3, 25R,26(OH)2D3, 25R,26-dihydroxyvitamin D3, 25S,26(OH)2D3, 25S,26-dihydroxyvitamin D3, 1,24,25(OH)3D3, 1,24,25-trihydroxyvitamin D3, 1,25-lactone, (23S,25R)-1,25(OH)2 D3 26,23-lactone, 24,25(OH)2-7-DHC, 24,25(OH)2-7-dehydrocholesterol, 25(OH)D3 3S, 25(OH)D3 3-sulfate, 24,25(OH)2D3-Hemiglutarate Derivative, 11 alpha-hemiglutaryloxy-(24R)-24,25-dihydroxyvitamin D3, 24,25(OH)2D3-Hemiglutarate Derivative, (24R)-24,25-dihydroxyvitaminD3-3-hemiglutarate, 24R,25(OH)2D2, 24S,25(OH)2D2, 25(OH)D2, 1,24(OH)2D3, 2,3,6-Trichlorophenol, Tetrachlorohydroquinone, Pentachloroaniline, Pentachlorobenzene, 2,3-Dinitrotoluene, 4-Dinitrotoluene, 2,4,5-Trichloronitrobenzene, 3-(3-Hydroxy-2,4,6-trichlorophenyl)-propanoic acid, 2,3,4,6-Tetrachlorophenol, 2,4,6-Trichloroanisol, 2,4,6-TCA, Pentabromophenol, PBP, 2,4,6-Tribromophenol, 2,4,6-TBP, 2-Bromo-4-Chlorophenol, 2-B-4-CP 2,4-Dibromophenol, 2,4-DBP, 2,6-Dibromophenol, 2,6-DBP, 4-Bromophenol, 4-BP, Furosemide, Ampicillin, Amoxicillin, 6-amino-penicillanic acid (6-APA), Azlocillin, Bacampicillin, Carbenicillin, Epicillin, Cloxacillin, Dicloxacillin, Metampicillin, Methicillin, Moxalactam, Oxacillin, Penicillin G, benzyl penicillin, Penicillin V, phenoxy methyl penicillin, Pheneticillin, Piperacillin, Ticarcillin, Ampicillin hydrolyzed, Penicillin G hydrolyzed, 3-phenoxybenzoic acid (3-PBAc) Chlorpyrifos, Chlorpyrifos derivatives, HClo1, Synthesized directly from chlorpyrifos technical grade by substitution of the chlorine in position 6 by a 3-mercaptopropanoic acid spacer arm, Chlorpyrifos derivatives, HTCP (Modification HTCP of TCP metabolite was prepared from HClo1 by hydrolysis of the thiophosphate ester), Zeatin Riboside (trans isomer), Zeatin (trans isomer), N6-(2-isopentenyl)-adenosine, IPA, N6-(2-isopentenyl)-adenine, 2-iP, Benzyladenine, Kinetin, monuron, monolinuron, fenuron, neburon, propanil, propham, chloropropham, 4-chloroaniline, Methyl Urea Derivative, 1-(3-Carboxypropyl)-3-(4-chlorophenyl)-1-methylurea, Methyl Urea Derivative, 1-(5-Carboxypentyl)-3-(4-chlorophenyl)-1-methylurea, metobromuron, Sennoside B, SB, Sennoside B possessed a erythro configuration between C-10 and C-10', Sennoside A (Modification Sennoside A possessed a threo configuration between C-10 and C-10'), Rhein, Emodin, Aloe-emodin, Barbaloin, 1,4 Dihydroxyanthraquinone, Rhaponticin, Galic acid, Vanillic acid, Caffeic acid, Homogentisic acid, Esculin, Cinnamtannin B1, Baicalin, Naringin hydrate, Wogonin, Wogonin 7-o-beta-glucuronide, Curcumin, delta1-Tetrahydrocannabinolic acid, delta1-Tetrahydrocannabinol, (+−)-cis-4-Aminopermethrin, 3-(4-Aminophenoxy)benzyl(+−)-cis-3-(2,2-dichloroethenyl)-2,2-dimethylcyclopropanecarboxylate, Permethrin, trans-Permethrin, cis-Permethrin, Cypermethrin, Phenothrin, Resmethrin, Cyfluthrin, trans-Permethrin acid Esfenvalerate, Fluvalinate, Fenpropathrin, cis-permethrin acid, 4-Phenoxybenzoyl alcohol, Diuron Derivative, 1-(3-Carboxypropyl)-3-(3,4-dichlorophenyl)-1-methylurea, Siduron, Terbuthiuron, Barban, acid trifluralin, 2,6-dinitro-N-propyl-N-(2-carboxyethyl)-4-(trifluoromethyl)benzenamine, TR-13, 2-ethyl-7-nitro-1-propyl-5-(trifluoromethyl)-1H-benzimidazole, benefin, 2,6-dinitro-N-butyl-N-ethyl-4-(trifluoromethyl)benzenamine, TR-2, 2,6-dinitro-N-propyl-4-(trifluoromethyl)benzenamine, ethalfluaralin, 2,6-dinitro-N-ethyl-N-(2-methyl-2-propenyl)-4-(trifluoromethyl) benzenamine, TR-40, N-(2,6-dinitro-4-(trifluoromethyl) phenyl)-N-propylpropanamide, TR-15, 2-ethyl-4-nitro-6-(trifluoromethyl)-1H-benzimidazole, TR-3, 2,6-dinitro-4-(trifluoromethyl)benzenamine, TR-6, 3-nitro-5-(trifluoromethyl)-1,2-benzenediamine, TR-9, 5-(trifluoromethyl)-1,2,3-benzenetriamine, TR-21, 4-(dipropylamino)-3,5-dinitrobenzoic acid, TR-36M, 3-methoxy-2,6-dinitro-N,N-dipropyl-4-(trifluoromethyl)benzenamine, oryzalin, 3,5-dinitro-4-(dipropylamino)benzenesulfonamide, pendimethalin, 2,6-dinitro-N-(1-ethylpropyl)-3,4-dimethylbenzenamine, penta galloyl glucose, Pyrene Pyrene-1-carboxaldehyde, Phenanthrene, Benzo(a)pyrene, 3,4-Benzopyrene, Anthracene, 3,4-Benzopyrene, Acenaphthene, Fluorene, Chrysene, 1,2-Benzphenanthrene, Benzo[g,h,i]perylene, Benzo[e]pyrene, Acenaphthylene, Fluoranthene, Benzo(j,k)fluorene, Indeno-1,2,3-cd-pyrene, 1,10-(1,2-Phenylene)pyrene, Benzo[a]anthracene, 1,2-Benzanthracene, Benzo(k)fluoranthene, Naphthalene, Benzo[a]fluoranthene, Dibenzo[ah]anthracene, 1,2:5,6-Dibenzanthracene, 2,3-Diaminonaphthalene, 2,6-Dinitroaniline, 17-beta-estradiol (ED), estra-1,3,5(10)-triene-3,17-beta-diol, Trifluralin derivative, 2,6-dinitro-4-tri-fluoromethylaniline, Trifluralin derivative, N-(2,6-dinitro-4-trifluoromethylphenyl)-6-aminohexanoic acid, Trifluralin derivative, N-(2,6-dinitro-4-trifluoromethylphenyl)-N-methyl-6-aminohexanoic acid, Trifluralin derivative, N-(2,6-dinitro-4-trifluoromethylphenyl)-N-propyl-6-aminohexanoic acid, Trifluralin derivative, N-(2,6-dinitro-4-trifluoromethylphenyl)-6-aminohexanoic acid methyl ester, Trifluralin derivative, N-(2,6-dinitro-4-trifluoromethylphenyl)-6-aminohexanoic acid tert-butyl ester, Benfluralin, Ethalfluralin, Trifluralin derivative, 2,6-Dinitro-4-trifluoromethylphenol, Isopropalin, Aniline, 2-Hydroxybenzotrifluoride, N-propyl-6-aminohexanoic acid, N-methyl-6-aminohexanoic acid, MHPG Derivatives, D-MHPG (D-3-methoxy-4-hydroxyphenylglycol), MHPG Derivatives, L-MHPG (L-3-methoxy-4-hydroxyphenylglycol), MHPG Derivatives, DL-MHPG (DL-3-methoxy-4-hydroxyphenylglycol), Isomeric mixture of D-MHPG and L-MHPG forms, MHPG Derivatives, DL-MHPG-SO4 (DL-3-methoxy-4-hydroxyphenylglycol-sulfate) Modification can include Isomeric mixture of D-MHPG-SO4 and L-MHPG-SO4 forms, Serotonin, 5-HT, 5-hydroxydopamine (5-4HDA), 3,4-dihydroxyphenylglycol (DOPEG), Dopamine, 4-(2-aminoethyl)pyrocatechol; 3-hydroxytyramine; 3,4-dihydroxyphenethylamine; L-3,4-dihydroxyphenylalanine, L-DOPA, Vanillomandelic acid, DL-VMA, Homovanillic acid, Norepinephrine, DL-NE, D-Epinephrine, D-E, 3-methoxytyramine, MTA, 3-methoxytyrosine, MTyr, 3,4-dihydroxymandelic acid, DL-DOMA, 3,4-dihydroxyphenyl acetic acid, DOPAC, L-Phenylalanine, Tyramine, p-tyramine; 4-(2-Aminoethyl)phenol, D-Mandelic acid, Homocatechol, Octopamine, DL-Octopamine, Azinphos-Ethyl, S-(3,4-dihydro-4-oxobenzo[d]-[1,2,3]-triazin-3-ylmethyl) O,O-diethyl phosphorodithioate, Phosmet, O,O-dimethyl S-phthalimidomethyl phosphorodithioate, Folpet, N-[(Trichloromethyl)thio]phthalimide, Tetramethrin, (1-Cyclohexene-1,2-dicarboximido)methyl-2,2-dimethyl-3-(2-methylpropenyl)-cyclopropanecarboxylate, N-(bromomethyl)phthalimide, N-(Chloromethyl)benzazimide, 6-(N-phthalimidoylmethylthio)hexanoic acid (MFH), Bromacil, 5-bromo-3-sec-butyl-6-methyluracil, Bromacil Derivative, 5-bromo-6-(hydroxymethyl)-3-(1-methylpropyl)-2,4(1H,3H)-pyrimidineone, Bromacil Derivative, 5-bromo-3-(2-methylpropyl-6-methyl-2,4(1H,3H)-pyrimidinedione, Metabolite of Bromacil, Bromacil Derivative, 3-hydroxy-1-methylpropyl-6-methyl-2,4(1H,3H)-pyrimidinedione (Modification Bromacil Metabolite), Bromacil Derivative, 6-methyl-3-(1-methylpropyl)-2,4(1H,3H)-pyrimidinedione (Modification Bromacil Metabolite), Terbacil Derivative, [5-chloro-3-(1,1-dimethylethyl)-6-(hydroxymethyl)-2,4 (1H,3H)-pyrimidinedione, Terbacil, 3-tert-butyl-5-chloro-6-methyluracil, Bromacil Derivative, Ethyl-5-(5-Bromo-6-methyl-3-(1-methylpropyl)-2,4(1H,3H)-pyrimidinedione-1-yl)hexanoate, Bromacil Derivative alkylated at N-1, Bromacil Derivative 5-(5-Bromo-6-methyl-3-(1-methylpropyl)-2,4(1H,3H)-pyrimidinedione-1-yl)hexanoic Acid (Modification Bromacil Derivative alkylated at N-1), Bromacil Derivative, -Bromo-6-(Bromomethyl-3-(1-methylpropyl)-2,4(1H,3H)-pyrimidinedione (Modification Bromacil Derivative substituted at the 6-methyl position), Bromacil Derivative-[5-Bromo-3-(1-methylpropyl)-2,4(1H, 3H)-pyrimidinedione-6-yl]-2-carboxylpropanoic Acid (Modification Bromacil Derivative substituted at the 6-methyl position), 3-[5-Bromo-3-(1-methylpropyl)-2,4 (1H,3H)-pyrimidinedione-6-yl]propanoic Acid (Modification Bromacil Derivative substituted at the 6-methyl position), Bromacil Derivative 5-Bromo-1,6-dimethyl-3-(1-methylpropyl)-2,4(1H,3H)-pyrimidinedione, Bromacil Derivative 5-Bromo-1-butyl-6-methyl-3-(1-methylpropyl)-2,4(1H,3H)-pyrimidinedione, Butachlor, N-butoxymethyl-2-chloro-2',6'-diethylacetanilide, Amidochlor, N-[(acetylamino)methyl]-2-chloro-N-(2,6-diethylpenyl)acetamide, Nicarbazin, N,N'-bis(4-nitrophenyl)-compound with 4,6-dimethyl-2(1H)-pyrimidinone (Modification (DNC+HDP)), 2-hydroxy-4,6-dimethylpyrimidine, HDP, Imazalil, [1-(beta-allyloxy-2,4-dichlorophenethyl)imidazole], Imazalil Derivative, EIT-0073 (Modification Have a —O(CH2)5-COOH group instead of original —OCH2CH═CH2 group of imazalil), Penconazole, (RS)-1-(2,4-dichloro-β-propylphenethyl)-1H-1,2,4-triazole, Hexaconazole, (RS)-2-(2,4-dichlorophenyl)-1-(1H-1,2,4-triazol-1-yl)hexan-2-ol, Propiconazole, cis-trans-1-[2-(2,4-dichlorophenyl)-4-propyl-1,3-dioxolan-2-ylmethyl]-1H-1,2,4-triazole, Diclobutrazol, 2RS,3RS)-1-(2,4-dichlorophenyl)-4,4-dimethyl-2-(1H-1,2, 4-triazol-1-yl)pentan-3-ol, Triflumizole, (E)-4-chloro-α,α, α-trifluoro-N-(1-imidazol-1-yl-2-propoxyethylidene)-o-toluidine, Imazalil Derivative, EIT-0183, Imazalil Derivative, EIT-0180, Imazalil Derivative, EIT-0111, Imazalil Derivative, EIT-0158, Imazalil Derivative, K-240, Chlorothalonil, tetrachloroisophthalonitrile Modification On benzene Ring R1=CN R2=Cl R3=CN R4=Cl R5=Cl R6=Cl), Chlorothalonil Derivative-2,4,5,6-tetrachloro-3-cyanobenzamide (Modification On benzene Ring R1=CONH2 R2=Cl R3=CN R4=Cl R5=Cl R6=Cl), Chlorothalonil Derivative-2,5,6-trichloro-4-hydroxyisophthalonitrile (Modification On benzene Ring R1=CN R2=Cl R3=CN R4=OH R5=Cl R6=Cl), 3-carbamyl-2,4,5-trichlorobenzoic acid (Modification On benzene Ring R1=CONH2 R2=Cl R3=COOH R4=H R5=Cl R6=Cl), Pentachloronitrobenzene (Modification On benzene Ring R1=NO2 R2=Cl R3=Cl R4=Cl R5=Cl R6=Cl), Benzene hexachloride, Hexachlorobenzene, BHC, Lindane (Modification On benzene Ring R1=Cl R2=Cl R3=Cl R4=Cl R5=Cl R6=Cl), 2,4,5,6-tetrachlorophenol (Modification On benzene Ring R1=OH R2=Cl R3=H R4=Cl R5=Cl R6=Cl), Carbaryl Derivative, Ethylcarbamate (Modification R1=OCONHCH2CH3 R3=H), 1-Naphthol, 1-naphthaleneacetamide, -(1-naphthyl) acetamide, Carbaryl Derivative, 1-Methylcarbonate (Modification R1=OCOOCH3 R2=H, Carbaryl Derivative, 1-Ethylcarbonate (Modification R1=OCOOCH2CH3 R2=H), Carbaryl Derivative 2-Ethylcarbonate (Modification R1=H R2=OCOOCH2CH3, Carbaryl Derivative, 1-Ethylthiocarbonate (Modification R1=OCOSCH2CH3 R2=H), Carbaryl Derivative, 2-Ethylthiocarbonate (Modification R1=H R2=OCOSCH2CH3), Naptalam, N-1-naphthylphthalamic acid, Carbaryl Derivative, 3-hydroxycarbaryl (Modification R1=OCONHCH3 R2=H R3=OH R4=H R5=H), Carbaryl Derivative 4-hydroxycarbaryl (Modification R1=OCONHCH3 R2=H R3=H R4=OH R5=H), Carbaryl Derivative 5-hydroxycarbaryl (Modification R1=OCONHCH3 R2=H R3=H R4=H R5=OH), Carbaryl Derivative, 1-(5-Carboxypentyl)-3-(1-naphthyl)urea (Modification R1=NHCONH(CH2)5COOH R2=H), (Structurally related s-triazines)-Aziprotryn, 4-azido-N-isopropyl-6-methylthio-1,3,5-triazin-2-ylamine (Modification R1=—SCH3 R2=—N3 R3=—CH(CH3)2), (Structurally related s-triazines), 2-(ethylamino)-4-(methylthio)-6-aminotriazine (Modification R1=—SCH3 R2=—NH—C2H5 R3=—NH2), (Structurally related s-triazines)-2-amino-4-(methylthio)-6-(isopropylamino)triazine (Modification R1=—SCH3 R2=—NH2 R3=—NH—CH(CH3)2), (Structurally related s-triazines)-2-amino-4-methoxy-6-(isopropylamino) triazine (Modification R1=—OCH3 R2=—NH2

R3=—NH—CH(CH3)2), TCP Derivative (3,5,6-trichloro-2-pyridinol Derivative), 3-(3,5-dichloro-6-hydroxy-2-pyridyl)thiopropanoic Acid, p-nitrosuccinanilic acid (PNA-S), PNA-S, PNA-C, p-nitro-cis-1,2-cyclohexanedicarboxanilic acid, Nitroaniline Derivative, 2-nitroaniline, o-Nitroaniline, Nitroaniline Derivative-3-nitroaniline, m-Nitroaniline, Nitroaniline Derivative-4-nitroaniline, p-Nitroaniline, Aeromatic Alcohols, 4-nitrobenzyl alcohol, Aeromatic Alcohols-4-nitrophenethyl alcohol, Aeromatic Alcohols 2-nitrobenzyl alcohol, Aeromatic Alcohols, 3-nitrobenzyl alcohol, Urea Derivative-1-benzyl-3-(4-nitrophenyl)urea, Urea Derivative-1-(3-chlorophenyl)-3-(2-methoxy-5-nitrophenyl)urea, Urea Derivative-1-(3-chlorophenyl)-3-(4-methoxy-3-nitrophenyl)urea, Urea Derivative-1-(4-chlorophenyl)-3-(4-nitrophenyl)urea, Urea Derivative-(2-fluorophenyl)-3-(2-mehtoxy-4-nitrophenyl) urea, 1-(3-mehtoxyphenyl)-3-(3-nitrophenyl)urea, Carbofuran Derivative m Carbofuran-phenol, Carbofuran-hydroxy, Carbofuran-keto, Carbosulfan, 3-dihydro-2,2-dimethylbenzofuran-7-yl (dibutylaminothio) methylcarbamate, Benfuracarb, N-[2,3-dihydro-2,2-dimethylbenzofuran-7-yloxycarbonyl(methyl)aminothio]-N-isopropyl-β-alaninate, Furathiocarb, 2,3-dihydro-2,2-dimethyl-7-benzofuranyl 2,4-dimethyl-5-oxo-6-oxa-3-thia-2,4-diazadecanoate, Carbofuran Derivative, 4-[[(2,3-Dihydro-2,2-dimethyl-7-benzofuranyloxy)carbonyl]-amino]butanoic Acid (BFNB) (Modification n=3 X=CH2), Endrin, nendrin, (1R,4S,4aS,5S,6S,7R,8R,8aR)-1,2,3,4,10,10-hexachloro-1,4,4a,5,6,7,8,8a-octahydro-6,7-epoxy-1,4:5,8-dimethanonaphthalene, Heptachlor, 1,4,5,6,7,8,8-heptachloro-3a,4,7,7a-tetrahydro-4,7-, Chlordane, 1,2,4,5,6,7,8,8-octachloro-2,3,3a,4,7,7a-hexahydro-4,7-methanoindene, Endosulfan (Modification isomer mix of alpha and beta forms), Endosulfan (Modification alpha isomeric form), Endosulfan (Modification beta isomeric form), Endosulfan Derivative, Endosulfan sulfate (Modification sulfate form), Endosulfan Derivative, Endosulfan diol, Diol metabolite of endosulfan, Endosulfan Derivative, Endosulfan ether (Modification ether metabolite of endosulfan), Endosulfan Derivative, hydroxy ether, hydroxy ether metabolite of endosulfan, Endosulfan Derivative, Endosulfan lactone (Modification lactone metabolite of endosulfan), Aldrin, Dieldrin, Fenvalerate isomers Modification 1S,2R isomer R: Ph), Fenvalerate isomers (Modification 1R,2S isomer R: Ph), Fenvalerate isomers (Modification 1R,2R isomer R: Ph), Fenvalerate isomers (Modification 1S,2R/S isomer R: Ph), Fenvalerate isomers (Modification 1R,2R/S isomer R: Ph), Fenvalerate isomers, fenvalerate (Modification 1R/S, 2R/S isomer R: Ph), Thiabendazole, 2-(thiazol-4-yl)benzimidazole, Thiabendazole Derivative, 5-hydroxythiabendazole (Modification 5-OH-TBZ), Thiabendazole Derivative, 5-NH2-TBZ, Thiabendazole Derivative, methyl benzimidazole carbamate, Albendazole, Mebendazole, Fenbendazole, Thiabendazole Derivative, 2-succinamidothiabendazole, Thiabendazole Derivative, 2-succinamidothiabendazole, Cambendazole, Fenvalerate Haptens, Cyano[3-(4-aminophenoxy)phenyl]methyl (S)-4-Chloro-alpha-(1-methylethyl)benzeneacetate (4-Aminoesfenvalerate), Fenvalerate Haptens, Benzyl 4-[3-[Cyano[(S)-2-(4-chlorophenyl)-3-methyl-1-oxobutanoxy]methyl]phenoxy]benzenepropanoate, Fenvalerate Haptens, Benzyl 3-[Cyano[(S)-2-(4-chlorophenyl)-3-methyl-1-oxobutanoxy]methyl]phenoxyacetate, Fenvalerate Haptens, 3-[Cyano[(S)-2-(4-chlorophenyl)-3-methyl-1-oxobutanoxy]methyl]phenoxyacetic Acid, Fenvalerate Haptens, Benzyl 6-[Cyano[(S)-2-(4-chlorophenyl)-3-methyl-1-oxobutanoxy]methyl]phenoxy] hexanoate, Fenvalerate Haptens, 6-[3-[Cyano[(S)-2-(4-chlorophenyl)-3-methyl-1-oxobutanoxy]methyl]phenoxy] hexanoic Acid Fenvalerate Haptens, 4-[3-[Cyano[(S)-2-(4-chlorophenyl)-3-methyl-1-oxobutanoxy]methyl]phenoxy] benzenepropanoic Acid, (S)-fenvalerate Acid, (Structurally related s-triazines), atrazine mercapturate Modification R1=—SCH2CH(NHCOCH3)COOH R2=—NHCH2CH3 R3=—NHCH(CH3)2, Fenthion Hapten, -Methyl O-[3-methyl-4-(methylthio)phenyl] N-(3-carboxypropyl)phosphoramidothioate Modification referred as Hapten B, Fenthion Derivative, Oxidized Fenthion, Fenthion Derivative, Oxidized oxidized Fenthion, pirimiphos-ethyl, 4-(Methylthio)-m-cresol, Chlorpyrifos Derivative, Chlorpyrifos-oxon, Fenchlorphos, O,O-dimethyl O-2,4,5-trichlorophenyl phosphorothioate, Trichloronate, O-Ethyl O-2,4,5-trichlorophenyl ethyl-phosphonothioate, Dichlofenthion, O-2,4-dichlorophenyl O,O-diethyl phosphorothioate, Parathion, O,O-diethyl O-4-nitrophenyl phosphorothioate; Thiophos, Chlorpyrifos Derivative Modification Synthesis of AR1 is described, Chlorpyrifos Derivative, O-Ethyl O-(3,5,6-Trichloro-2-pyridyl)O-(3-Carboxypropyl)Phosphorothioate; (PO), Chlorpyrifos Derivative-O-Ethyl O-(3,5,6-Trichloro-2-pyridyl)N-(5-Carboxyethyl) Phosphoramidothioate; (PN1) (Modification Amide linkage of thiophosphate reagents), Chlorpyrifos Derivative, O-Ethyl O-(3,5,6-Trichloro-2-pyridyl)N-(2-Carboxyethyl) Phosphoramidothioate; (PN1) (Modification Amide linkage of suitable thiophosphate reagents), Triadimefon, (RS)-1-(4-chlorophenoxy)-3,3-dimethyl-1-(1H-1,2,4-triazol-1-yl)butan-2-one, GR151004, (4-[[5-[3-[2-(dimethylamino)ethyl]]-5-benzofuranyl]-3-pyridinyl]acetyl]morpholine dihydrochloride, Diflubenzuron, 1-(4-chlorophenyl)-3-(2,6-difluorobenzoyl)urea, (Structurally related s-triazines)-SprAAT (Modification R1=SCH2CH2COOH R2=NH2 R3=NH2), (Structurally related s-triazines), SBeAAT (Modification R1=S(C6H4)COOH R2=NH2 R3=NH2), (Structurally related s-triazines), SAAT (Modification R1=SH R2=NH2 R3=NH2), (Structurally related s-triazines), CDAT (Modification R1=Cl R2=NH[C(O)CH3] R3=NH2), (Structurally related s-triazines)-CDET (Modification R1=Cl R2=NH[C(O)CH3] R3=NH(CH2CH3), (Structurally related s-triazines)-CDIT (Modification R1=Cl R2=NH[C(O)CH3] R3=NH(CH(CH3)2)), (Structurally related s-triazines), CDDT (Modification R1=Cl R2=NH[C(O)CH3] R3=NH[C(O)CH3]), (Structurally related s-triazines)-ammeline, OAAT (Modification R1=OH R2=NH2 R3=NH2), (Structurally related s-triazines)-ammelide, OOAT (Modification R1=OH R2=OH R3=NH2), (Structurally related s-triazines)-cyanuric acid, OOOT (Modification R1=OH R2=OH R3=OH), (Structurally related s-triazines), melamine, AAAT (Modification R1=NH2 R2=NH2 R3=NH2), Structurally related s-triazines-N-isoropylammeline, OIAT (Modification R1=OH R2=NH[CH(CH3)2] R3=NH2, Structurally related s-triazines-N-ethylammeline, OEAT (Modification R1=OH R2=NHCH2CH3 R3=NH2), Structurally related s-triazines, N-ethylammelide, OOET (Modification R1=OH R2=OH R3=NHCH2CH3), Structurally related s-triazines-cyromazine, CyPAAT (Modification R1=NH(C3H5) R2=NH2 R3=NH2), Structurally related s-triazines-diamino-s-triazine, HAAT (Modification R1=H R2=NH2 R3=NH2), PCB congeners, 2,5,3',4'-tetrachlorobiphenyl (Modification IUPAC no.: 70), PCB congeners 2,4,5,3',4'-pentachlorobiphenyl (Modification IUPAC no.: 118), PCB congeners-2,2',5,5'-tetrachlorobiphenyl (Modification IUPAC no.: 52), PCB congeners, 6-[3,3',4'-Trichlorobiphenyl-4-yl)oxy]hexanoic Acid, Metolazone, Brand Names: Mykrox; Zaroxolyn, Furfuryl benzoate, DDT Metabolites, DDA, Paraquat, 1,1'-dimethyl-4,4'-bipyridinium ion, Diethylcarbamazine, THP, 2,4,6-triphenyl-N-(4-hydroxyphenyl)-pyridinium, o-DNCP, -dinitrocarboxyphenol, PCB congeners, 3-chlorobiphenylol (Modification IUPAC No. 2), PCB congeners, 3,4'-dichlorobiphenyl (Modification IUPAC No. 13), PCB congeners, 3,5-dichlorobiphenyl (Modification IUPAC No. 14), PCB congeners, 3,4,5,3',4'-pentachlorobiphenyl (Modification IUPAC No. 126), 2,3,3',4'-tetrachlorobiphenyl (Modification IUPAC No. 56), 2',3,4,5-tetrachlorobiphenyl (Modification IUPAC No. 76), 3,3',5,5'-tetrachlorobiphenyl (Modification IUPAC No. 80), 2,4,5,2',5'-pentachlorobiphenyl (Modification IUPAC No. 101), 2,3,3',4,4'-pentachlorobiphenyl (Modification IUPAC No. 105), 2,3,6,3',4'-pentachlorobiphenyl (Modification IUPAC No. 110), 3,3',4,5,5'-pentachlorobiphenyl (Modification IUPAC No. 127), 3,4,5,3',4',5'-hexachlorobiphenyl (Modification IUPAC No. 169), 2,3,3',4,4',5-hexachlorobiphenyl (Modification IUPAC No. 156), 3,4,3',4'-tetrabromobiphenyl, 3,4,5,3',4',5'-hexabromobiphenyl, 2,4,5,2',4',5'-hexabromobiphenyl, Dibenzofurans and Dioxins, 2,3,7,8-tetrachlorobenzofuran, 2,3,7,8-tetrachlorodibenzo-p-dioxin, 3,4',5-trichloro-4-biphenylol, 3,3',5,5'-tetrachloro-4,4'-biphenyldiol, 3,4,3',4'-tetrachlorodiphenyl ether, 1-2-dichlorobenzene, 1,4-dichlorobenzene, 1,2,4-trichlorobenzene, 3,4-dichloroaniline, DDT Metabolites, 4,4'-DDT, 4,4'-DDD Retronecine, 3,4-dichlorobiphenyl Modification IUPAC No. 12, 3,4,3'-trichlorobiphenyl (Modification IUPAC No. 35), PCB Congeners, 3,4,4'-trichlorobiphenyl (Modification IUPAC No. 37), 3,4,3',5-tetrachlorobiphenyl (Modification IUPAC No. 78), 3,4,3',5'-tetrachlorobiphenyl (Modification IUPAC No. 79), 3,4,4',5-tetrachlorobiphenyl (Modification IUPAC No. 81), DDT Metabolites, p,p'-DDT (Modification p,p'-dichlorodiphenyltrichloroethane), o,p'-DDT Modification o,p'-dichlorodiphenyltrichloroethane, p,p'-DDE Modification p,p'-DDE, o,p'-DDE Modification o,p'-DDE, p,p'-DDD Modification p,p'-DDD, o,p'-DDD Modification o,p'-DDD, Dicofol, 4,4-dichloro-a-(trichloromethyl)benzhydrol, Cyprazine, 6-chloro-N-cyclopropyl-N-(1-methylethyl)-1,3,5-triazine-2,4-diamine, Structurally related s-triazines, Dipropetryn, 6-(ethylthio)-N,N'-bis(1-methylethyl)-1,3,5-triazine-2,4-diamine, Trietazine, 6-chloro-N,N,N'-triethyl-1,3,5-triazine-2,4-diamine, 6-Hydroxyatrazine, hexazinone, 3-cyclohexyl-6-dimethylamino-1-methyl-1,3,5-triazine-2,4 (1H,3H)-dione, TNT, 2,4,6-Trinitrotoluene, Tetraconazole (M14360), 1-[2-(2,4-dichlorophenyl)-3-(1,1,2,2-tetrafluoroethoxy)propyl]-1H-1,2,4-triazole, DTP, 2-(2,4-dichlorophenyl)-3-(1H-1,2,4-triazol-1-yl)propanol, Imazalyl, fenarimol, (RS)-2,4'-dichloro-α-(pyrimidin-5-yl)benzhydryl alcohol, Lupanine metabolites, (+)-lupanine (Modification R=H), Lupanine metabolites, (+)-13-hydroxylupanine (Modification R=OH), Lupanine metabolites, hemisuccinate ester of (+)-13-hydroxylupanine (Modification R=OCO—(CH2)2.COOH), Lupanine metabolites, cis-hexahydrophthalate ester of (+)-13-hydroxylupanine (Modification R=OCO.C6H10.COOH), Lupanine metabolites, alpha-isolupanine, Lupanine metabolites, -hydroxylupanine, Sparteine, Cysteine, multiflorine, epilupinine, (Structurally related s-triazines), CYANAZINE ACID Modification R1=Cl R2=NHCH2CH3 R3=NHCCOOH(CH3)2, Structurally related s-triazines Modification R1=Cl R2=NHCH2CH3 R3=NH(CH2)3COOH, Structurally related s-triazines (Modification R1=Cl R2=NHCH2CH3 R3=NHCH2COOH), (Structurally related s-triazines) (Modification R1=Cl R2=NHCH2CH3 R3=NH(CH2)4COOH), norflurazon, 4-chloro-5-(methylamino)-2-[3-(trifluoromethyl)phenyl]-3(2H)-pyridazinone, norflurazon derivative, desmethyl-norflurazon, metflurazon, -chloro-5-(dimethylamino)-2-[(3-trifluoromethyl)phenyl]-3(2H)-pyridazinone, Pyrazon, Chloridazon, 5-amino-4-chloro-2-phenyl-3(2H)-pyridazinone (active ingradient), dichlorophenyl-pyridazone, (Structurally related s-triazines) azidoatrazine (Modification R1=N3 R2=NHCH(CH3)2 R3=NHCH2CH3), ALACHLOR 2-chloro-2',6'-diethyl-N-methoxymethylacetanilide, trichothecolone (Modification R1=H R2=OH R3=H R4=O R5=H), DON derivative, acetyl-T-2, DON derivative, T-2 tetrol tetraacetate, Chlorpyrifos derivatives, mono-dechloro-CP, Bromophos derivative, Bromophos-methyl, Bromophos derivative, Bromophos-ethyl dicapthon, -2-chloro-4-nitrophenyl O,O-dimethyl phosphorothioate, tetrachlorvinphos, (Z)-2-chloro-1-(2,4,5-trichlorophenyl)vinyl dimethyl phosphate, triclopyr, 3,5,6-trichloro-2-pyridyloxyacetic acid, picloram, 4-amino-3,5,6-trichloropyridine-2-carboxylic acid, Formononetin, Biochanin A, 5, 7-dihydroxy-4'-methoxyisoflavone (Modification It is the 4'-methyl ether of genistein), equol, (7-hydroxy-3-(4'-hydroxyphenyl)-chroman, 2'methoxyformononetin, Daidzein, 7-hydroxy-3-(4-hydroxyphenyl)-4H-1-benzopyran-4-one, geninstein, quercetin, 3,3',4',5,7-Pentahydroxyflavone; 3,5,7,3',4'-Pentahydroxyflavone; matheucinol, coumestrol (Structurally related s-triazines), Hydroxysimazine (Modification R1=OHR2=NHCH2CH3R3=NHCH2CH3, angustifoline, Alodan, 1-Methyl-4-phenyl-4-carboethoxypiperidine hydrochloride, Zearalenone, RAL, F-2 Toxin, Fenpropimorph, (RS)-cis-4-[3-(4-tert-butylphenyl)-2-methylpropyl]-2,6-dimethylmorpholine, Tridemorph, 2,6-dimethyl-4-tridecylmorpholine, 2,6-dimethylmorpholine, Amorolfine, Fenpropidine, (RS)-1-[3-(4-tert-butylphenyl)-2-methylpropyl]piperidine, (Structurally related s-triazines) (Modification R1=Cl R2=Cl R3=NHCH2CH3, (Structurally related s-triazines) Modification R1=Cl R2=Cl R3=NHCH(CH3)2, (Structurally related s-triazines) Modification R1=Cl R2=NHCH2CH3 R3=NH(CH2)5COOH, (Structurally related s-triazines) Modification R1=Cl R2=NHCH(CH3)2 R3=NHCH2COOH, (Structurally related s-triazines) (Modification R1=Cl R2=NHCH(CH3)2 R3=NH(CH2)5COOH), Structurally related s-triazines, cyanazine amide (Modification R1=Cl R2=NHCH2CH3 R3=NHCCONH2(CH3)2), hydroxycyanazine acid (Modification R1=OH R2=NHCH2CH3 R3=NHCCOOH(CH3)2), deethylsimazine (Modification R1=Cl R2=NH2 R3=NHCH2CH3), Albendazole sulfoxide, [5-(propylthionyl)-1H-benzimidazol-2-yl]-, methylester, Albendazole sulfone, 5(6)-alkylbenzimidazoles, 2-amino-5-(propylthio)benzimidazole, 5(6)-alkylbenzimidazoles, 2-amino-5-(propylsulfonyl) benzimidazole, oxibendazole, 5-propoxy-benzimidazole-2-methyl carbamate, 5(6)-arylbenzimidazoles, fenbendazole sulfone (Modification sulfone metabolite of fenbendazole), 5(6)-arylbenzimidazoles, 4'-hydroxyfenbendazole, 5(6)-arylbenzimidazoles, oxfendazole (Modification Oxfendazole is the sulfoxide metabolite of fenbendazole), 5(6)-arylbenzimidazoles, flubendazole, benzimidazole Metabolites, 2-aminobenzimidazole, benzimidazole Metabolites, 5-aminobenzimidazole, benzimidazole Metabolites, 2-acetylbenzimidazole, Benzophenone, Diphenylmethanone; phenyl ketone; Diphenyl ketone; Benzoylbenzene, Benzaldehyde, benzoic aldehyde, 4-Bromo-2,5-dichlorophenol, Acephate, O,S-dimethyl acetylphosphoramidothioate, methamidophos, O,S-dimethyl phosphoramidothioate, Dichlorvos, 2,2-dichlorovinyl dimethyl phosphate, Phenthoate, S-α-ethoxycarbonylbenzyl O,O-dimethyl phosphorodithioate, EPN, Ethyl p-nitrophenyl thionobenzenephosphonate, Bioresmethrin, -benzyl-3-furylmethyl (1R,3R)-2,2-dimethyl-3-(2-methylprop-1-enyl) cyclopropanecarboxylate (Modification The unresolved isomeric mixture of this substance has the ISO common name resmethrin), flufenoxuron, 1-[4-(2-chloro-α,α,α-trifluoro-p-tolyloxy)-2-fluorophenyl]-3-(2,6-difluorobenzoyl) urea, Amitrole, 1H-1,2,4-triazol-3-ylamine, molinate, S-ethyl azepane-1-carbothioate, molinate derivative (Modification S-2-carboxyethyl hexahydroazepine-1-carbothioate), molinate derivative (Modification S-5-carboxypentyl hexahydroazepine-1-carbothioate) molinate derivative (Modification molinate sulfone), molinate derivative (Modification S-(p-aminobenzyl) hexahydroazepine-1-carbothioate), molinate derivative (Modification S-2-(p-aminophenyl) ethyl hexahydroazepine-1-carbothioate), hexamethylenimine, thiobencarb (Bolero), butylate (Sutan), EPTC (Eptam), cycloate (Roneet), pebulate (Tillam), vernolate (Vernam), Aflatoxin M1, AFM1 (Modification AFM1), Aflatoxin B1, AFB1 (Modification AFB1), Aflatoxin G1, AFG1 (Modification AFG1), Aflatoxin M2, AFM2 (Modification AFM2), Aflatoxin B2, AFB2 (Modification AFB2), Aflatoxin G2, AFG2 (Modification AFG2), Aflatoxin B2alpha, AFB2alpha (Modification AFB2alpha), Aflatoxin G2alpha, AFG2alpha (Modification AFG2alpha), KB-6806, 6-amino-5-chloro-1-isopropyl-2-(4-methyl-1-piperazinyl) (Modification R1=NH2 R2=CH(CH3)2 R3=CH3), KB-6806 (Benzimidazole) Derivatives Modification R1=NH2 R2=CH2CH(CH3)2 R3=CH3, Hapten Name KB-6806 (Benzimidazole) Derivatives (Modification R1=NH2 R2=CH(CH2CH3)2 R3=CH3), KB-6806 (Benzimidazole) Derivatives (Modification R1=NHCOCH3 R2=CH(CH3)2 R3=CH3), KB-6806 (Benzimidazole) Derivatives (Modification R1=H R2=CH(CH3)2 R3=CH3), KB-6806 (Benzimidazole) Derivatives (Modification R1=NH2 R2=CH(CH3)2 R3=CH3), KB-6806 (Benzimidazole) Derivatives Modification R1=NH2 R2=CH(CH3)2 R3==N(—>O) CH3 (N-OXIDE), KB-6806 (Benzimidazole) Derivatives Modification R1=NH2 R2=CH(CH3)2 R3=H, KB-6806 (Benzimidazole) Derivatives Modification R1=NH2 R2=CH2CH3 R3=CH3, Aminoparaoxon, phosphoric acid, O,O-diethyl O-(4-aminophenyl) ester, Methylparathion, phosphorothioic acid, O,O-dimethyl O-(4-nitrophenyl) ester, Diethyl phenylphosphate, phenylphosphonic acid, O,O-diethyl ester, Diethyl phosphate, ethylphosphonic acid, O,O-diethyl ester, p-Nitrophenyl phosphate, phosphonic acid, O-(4-nitrophenyl)ester, Phorate, phosphorodithioic acid, O,O-diethyl S-[(ethylthio) methyl] ester, Ethion, bis(phosphorodithioic acid), S,S'-methylene O,O,O',O'-tetraethyl ester, Carbophenthion, phosphorodithioic acid, O,O-diethyl S-[[(4-chlorophenyl) thio]methyl] ester, Disulfoton, phosphorodithioic acid, O,O-diethyl S-[(2-ethylthio)ethyl] ester, TS, N-[4-(Carboxymethyl)-2-thiazolyl)sulfanilamide, NS, N-(4-Nitrophenyl) sulfanilamide, Sulfamoxole, Sulfacetamide, DNP-SL, Spin labelled dinitrophenyl (Modification The synthesis of DNP-SL has been described by Balakrishnan et al (1982) formula can be found in Anglister et al. (1984)), beta ecdysone, Benzimidazole Derivative, 5(6)-[Carboxypentyl)thio]-2-(methoxycarbonyl)amino]-benzimidazole, 2-hydroxybiphenyl HBP, Atrazine Caproic acid, Lysophosphatidic acid (LPA), 1-acyl-2-hydroxy-sn-glycero-3-phosphate), berberine, Palmatine, 9-Acetylberberine, Corydaline, Coptisine, Berberrubine, 8-Oxoberberine, Papaverine, Berberine Derivative, 9-O-carboxymethyl berberine, phencyclidine, 1-(1-phenylcyclohexyl)piperidine, Methoxychlor, Endosulfan Derivative, 4-Oxobutanoic Acid,4-(4,5,6,7,8,8-Hexachloro-3a,4,7,7a-tetrahydro-4,7-methano-1H-indenyl-1-oxy), Endosulfan Derivative, 4-oxybutanoic Acid,4-(1,3,4, 5,6,7,8-Octachloro-3a,4,7,7a-tetrahydro-4,7-methanoindanyl-2-oxy, Endosulfan Derivative (Modification Hemisuccinate of Endosulfan diol), Triazole Derivatives, 5-(3-Hydroxypropyl)-3-amino-2H-1,2,4-triazole, Triazole Derivatives, 5-(3-Hydroxypropyl)-3-(2-nitrophenylsulfenyl)amino-2H-1,2,4-triazole, Triazole Derivatives, 3-Amino-5-[(3-succinyloxy)propyl]-2H-1,2,4-triazole, Triazole Derivatives, 3-amino-1,2,4-triazole-5-thiol, Triazole Derivatives, 3-[(2-nitrophenylsulfenyl) amino-2H-1,2,4-triazole-5-thiol, Triazole Derivatives, 2H-1,2,4-triazole-5-thiol, Triazole Derivatives, 4-methyl-1, 2,4-triazole-3-thiol, Triazole Derivatives (1,2,4-triazol-2-yl) acetic acid, 1,2,4-triazole, 4-nitrophenyl 4'-carboxymethylphenyl phosphate, Triazole Derivative, 4-amino-1,2,4-triazole, Triazole Derivative, 3-acetamido-1H-1,2,4-triazole, Triazole Derivative, 3-amino-1,2,4-triazole-5-carboxylic acid hemihydrate, Triazole Derivative, 2-(4-chlorophenyl)-2-(1,2,4-triazol-1-yl)-methylhexanoic acid, succinic acid, Imidazole, L-histidine, L-glutamic acid, Permethrin derivative, 3-phenoxybenzyl 2,2-dimethylcyclopropane-1,3-dicarboxylate, 3-phenoxybenzaldehyde, flucythrinate, Chrysanthemic acid, 2,4-Dinitrophenyl, DNP, Thiram Haptens, Disodium 4-[Carbodithioato(methyl)-amino]butanoate, Thiram Haptens 5,11-Dimethyl-6,10-dithioxo-7,9-dithia-5,11-diazadodecanoic Acid, Thiram Haptens, 2-{[(Dimethylamino)carbothioyl]sulfanyl}ethanoic Acid, Thiram Haptens, 4-{[(Dimethylamino)carbothioyl] sulfanyl}butanoic Acid, Thiram Haptens, 6-{[(Dimethylamino)carbothioyl]sulfanyl}hexanoic Acid, Thiram Haptens, 11-{[(Dimethylamino)carbothioyl] sulfanyl}undecanoic Acid, Thiram Haptens, 2-{[(Dimethylamino)carbothioyl] sulfanyl}ethanoic Acid, Thiram, Tetramethylthiurammonosulfide, Tetraethylthiuram disulfide, Dimethyldithiocarbamic acid sodium salt, Dimethyldithiocarbamic acid zinc salt, Diethyldithiocarbamic acid sodium salt, N,N,N',N'-tetramethylthiourea, Nabam, Zineb, Maneb, Ethylenethiourea, Chlorpyrifos hapten, O,O Diethyl O-[3,5-Dichloro-6-[(2-carboxyethyl)thio]-2-pyridyl] Phosphorothioate, 2-Succinamidobenzimidazole, Methyl 2-Benzimidazolecarbamate, MBC, Benzimidazole, 2-benzimidazolylurea, succinamide, Ethyl carbamate, Urea, N-methylurea, N,N'-dimethylurea, Brevetoxin PbTx-3, Organophosphorous Haptens, O,O-Diethyl O-(5-carboxy-2-fluorophenyl) phosphorothioate, Chlorpyrifos-ethyl, Anandamide hapten, N-Arachidonyl-7-amino-6-hydroxy-heptanoic acid, Anandamide, Arachidonic acid, Docosatetraenoyl ethanolamide, Dihomo-gamma-linolenyl ethanolamide, 2-Arachidonyl glycerol, 2-Arachidonyl glycerol ether, Stearoyl ethanolamide, Heptadecanoyl ethanolamide, Prostaglandin E1, 3-hydroxy-2-(3-hydroxy-1-octenyl)-5-oxocyclopentaneheptanoic acid; alprostadil; PGE1, Prostaglandin D2, PGD2, Prostaglandin A2, PGA2, Prostaglandin B2, PGB2, Prostaglandin F2 alpha, 7-[3,5-dihydroxy-2-(3-hydroxy-1-octenyl)cyclopentyl]-5-heptenoic acid; dinoprost; PGF2alpha, Prostaglandin F1 alpha, PGF1alpha, 6-keto-Prostaglandin F1 alpha, 6-keto-PGF1alpha, 13,14-Dihydro-15-keto-Prostaglandin E2, 13,14-Dihydro-15-keto-PGE2, 13,14-Dihydro-15-keto-Prostaglandin F2alpha, 14-Dihydro-15-keto-PGF2alpha, 5alpha,7alpha-Dihydroxy-11-ketotetranorpostane-1,16-dioic acid, 15-keto-PGF2alpha, TXB2, Prostaglandin E2,7-[3-hydroxy-2-(3-hydroxy-1-octenyl)-5-oxocyclopentyl]-5-heptenoic acid; dinoprostone; PGE2, hCG-alpha-(59-92)-peptide (34 residues), Paraquat Derivative, Paraquat hexanoate (PQ-h), Monoquat, Diquat, 9,10-dihydro-8a,10a-diazoniaphenanthrene, MPTP, 1-methyl-4-phenyl-1,2,5,6-tetrahydropyridine, 1,2-Naphthoquinone, N-Acetyl-S-(1,2-dihydroxy-4-naphthyl)cysteine, N-Acetyl-S-(1,4-dihydroxy-2-naphthyl)cysteine, N-Acetyl-S-(1,2-dihydroxy-1-hydroxy- 1-naphthyl)cysteine, 2-Chloro-2'.6'-diethylacetanilide (CDA) Hapten, 2-[2-Chloro-(2'-6'-diethyl)acetanilido]ethanoic Acid, 2-Chloro-2'.6'-diethylacetanilide (CDA) Hapten, 2-[2-Chloro-(2-6'-diethyl)acetanilido]butanoic Acid, 2-Chloro-2'.6'-diethylacetanilide (CDA) Hapten, 5-(4-Chloroacetamido-3,5-diethyl)phenoxypentanoic Acid, CDA, 2-Chloro-2'.6'-diethylacetanilide, HDA, 2-Hydroxy-2'.6'-diethylacetanilide, 2,6-diethyl-aniline, Hydroxyalachlor, Alachlor ESA, Alachlor ethanesulfonic acid, Isoproturon Hapten, 3-(4-Isopropylphenyl)-1-carboxypropyl-1-methyl urea, chlorotoluron, 3-(3-chloro-p-tolyl)-1,1-dimethylurea, Metoxuron, 3-(3-chloro-4-methoxyphenyl)-1,1-dimethylurea, metamitron, 4-amino-4,5-dihydro-3-methyl-6-phenyl-1,2,4-triazin-5-one, mecoprop, (RS)-2-(4-chloro-o-tolyloxy) propionic acid, propyzamide, 3,5-dichloro-N-(1,1-dimethylpropynyl)benzamide, Paraquat dichloride, MCPB, 4-(4-chloro-o-tolyloxy)butyric acid, Chlortoluron Hapten, N-(3-Chloro-4-methylphenyl)-N-methyl-N-carboxypropyl Urea, Metsulfuron, Methyl 2-[3-(4-methoxy-6-methyl-1,3,5-triazin-2-yl)ureidosulphonyl]benzoate, Captopril Haptens, Captopril-4-(Maleimidomethyl)-cyclohexane Carboxylic Acid (MCC), Captopril Haptens, Captopril Disulfide Modification, Mercaptoethanol-MCC, Mercaptoethanol-4-(Maleimidomethyl)-cyclohexane Carboxylic Acid Modification, Captopril Haptens, Captopril without MCC, Aculeatiside A, Aculeatiside B, Solamargine, Solasonine, solanine-S; purapurine, Solasodine, Khasianine, Tomatine, lycopersicin, Tomatidine, 3-O-beta-D-Glucopyranosyl-solasodine, O-alpha-L-Rhamnosyl-1(1→2)-3-O-beta-D-glucopyranosyl-solasodine, 3-O-beta-D-Galacopyranosyl-solasidine, O-beta-D-Glucopyranosyl-1(1→3)-3-O-beta-D-galacopyranosyl-solasodine, 12-Hydroxysolamargine, 12-Hydroxysolasonine, Isoanguivine, Solaverine I, Solaverine II, Xylosyl-beta-solamargine, alpha-Solanine, alpha-Chaconine, Dioscine, Indole Derivatives, beta-Indole Acetic Acid, 2-Bromo-4,6-dinitroaniline, 2-Chloro-4,6-dinitroaniline, Tetryl, 2,4,6-trinitrophenyl-n-methylnitramine, nitramine, tetralite, tetril, 2-Amino-4,6-dinitrotoluene, 2,4-Dinitroaniline, 3,5-Dinitroaniline, 2-Amino-4,6-dinitrobenzoic acid, Disperse Blue 79, N-[5-[bis[2-(acetyloxy)ethyl]amino]-2-[(2-bromo-4,6-dinitrophenyl) azo]-4-ethoxyphenyl]acetamide, 1,3-Dinitrobenzene, 2,6-Dinitrotoluene, 4-Amino-2,6-dinitrotoluene, 1,3,5-Trinitrobenzene, Nicergoline, Ethylmorphine, 8-Didehydro-4,5-epoxy-3-ethoxy-17-methylmorphinan-6-ol, Dihydromorphine, Dihydrocodeine, dihydromorphinone, Hydromorphone, Dihydrocodeinone, Hydrocodone, Naltrexone, N-cyclopropylmethyl-14-hydroxydihydromorphinone, Dextromethorphan, (±)-3-Methoxy-17-methylmorphinan, Homatropine, Endorphins Modification Derivative Type: b-Endorphin, Met-enkephalin, DALEA, D-Ala(2)-D-Leu(5)-enkephalinamide, Vincristine, 22-Oxovincaleukoblastine, leurocristine; VCR; LCR, OCT, 22-Oxacalcitriol, OCT-3-HG, 22-oxacalcitriol-3-Hemiglutarate, 24(OH)OCT, 24(OH)-22-oxacalcitriol, 1,20(OH)2-hexanor-D3, Synephrine, Epinephrine, 4-[(1R)-1-Hydroxy-2-(methylamino)ethyl]-1,2-benzenediol, Phenylephrine, Dopamine Derivative, 6-hydroxy dopamine, Tyramine derivative, 3-methoxy tyramine, Phenethylamine, Benzeneethanamine; PEA, m-tyramine, o-tyramine, dimethoxyphenethylamine, Thymidine glycol monophosphate, 5,6-Dihydroxythymidine monophosphate, Thymidine monophosphate, Thymidine glycol, Thymine glycol, 5,6-Dihydrothymidine, Thymidine, Thymine, 5-methyluracil; 2,4-dihydroxy-5-methylpyrimidine, AMP, Adenosine mono phosphate, CMP, Cytidine mono phosphate, Carbamazepine, 5-carbamoyl-5H-dibenz[b,f]azepine, Neopterin isomers, D-erythro-Neopterin, Neopterin isomers, L-erythro-Neopterin, Neopterin isomers, D-threo-Neopterin, Biopterin isomers, L-erythro-Biopterin, Biopterin isomers, D-erythro-Biopterin, Biopterin isomers, L-threo-Biopterin, Biopterin isomers, D-threo-Biopterin, Pterin-6-Carboxylic Acid, C7H5NiO3, Pterin, Thromboxane B2, (5Z,9alpha,13E,15S)-9,11,15-trihydroxythromboxa-5,13-dien-1-oic acid, 15 Ketoprostaglandin F2alpha, Fumonisin B1, macrofusine; FBI, Thyroliberin, TRH; thyrotropin-releasing factor; thyrotropin releasing hormone; TRF; protirelin; lopremone, Thyroliberin-OH, TRH-OH, Diketopiperazine, cyclo (H-P), TRH analogues, Methylated TRH, TRH analogues, TRH elongated peptides, TRH-Gly, TRH elongated peptides, TRH-Gly-Lys-Arg, TRH elongated peptides, TRH-Gly-Lys-Arg-Ala, TRH elongated peptides, P7 (Modification Q-H-P-G-L-R-F), TRH elongated peptides, P10 (Modification S-L-R-Q-H-P-G-L-R-F), TRH elongated peptides, Ps5 Modification pro-TRH[178-199], TRH elongated peptides, TRH-Ps5 (Modification pro-TRH[172-199]), Hypothalmic peptide, LHRH, Cyanoginosin-LA, Cyanoginosin-LB, Cyanoginosin-LR, Cyanoginosin-LY, Cyanoginosin-AY, Cyanoginosin-FR, Cyanoginosin-YR, Ne-acetyllysine-containing peptide, Gly-Lys (Ac)-e-aminocaproic acid (Aca)-Cys, Benzoic Acid, Benzenecarboxylic acid; phenylformic acid; dracylic acid, m-hydroxybenzoic acid, 3-hydroxybenzoic acid, o-methoxybenzoic acid, 2-methoxybenzoic acid, o-toluic acid, 2-Methylbenzoic acid, o-chlorobenzoic acid, 2-chlorobenzoic acid, o-aminobenzoic acid, 2-aminobenzoic acid, thiosalicylic acid, 2-Mercaptobenzoic acid; o-sulfhydrylbenzoic acid, Salicylamide, 2-Hydroxybenzamide, Saligenin, saligenol; o-hydroxybenzyl alcohol; Salicyl alcohol, 2-cyanophenol, 2-hydroxyphenyl acetic acid, p-hydroxybenzoic acid, p-aminobenzoic acid, 4-Aminobenzoic acid; vitamin Bx; bacterial vitamin H1, p-toluic acid, p-methylamino benzoic acid, p-chlorosalicylic acid, 4-chloro-2-hydroxybenzoic acid, 2,4-dihydroxybenzoic acid, beta-Resorcylic Acid; 2,4-dihydroxybenzenecarboxylic acid; BRA, 4-aminosalicylic acid, 4-Amino-2-hydroxybenzoic acid; p-aminosalicylic acid, Gentisic Acid, 2,5-dihydroxybenzoic acid; 5-hydroxysalicylic acid, Picolinic acid, o-Pyridinecarboxylic acid; 2-Pyridinecarboxylic acid, picolinic acid N-oxide, 3-hydroxypicolinic acid, 2-hydroxynicotinic acid, 7-methylguanine, N2-Carboxymethyl-N7-methylguanine, 2-(7-methyl-6-oxo-6,7-dihydro-1H-purin-2-ylamino)acetic acid, 7-methylxanthine, 7-methyluric acid, 7-methyladenine, Guanine, 2-Amino-1,7-dihydro-6H-purin-6-one; 2-aminohypoxanthine, Adenine, 6-aminopurine; 6-amino-1H-purine; 6-amino-3H-purine; 6-amino-9H-purine, 7-(2-Carboxyethyl)guanine, 7-CEGua, 7-Ethylguanine, 2-amino-7-ethyl-1H-purin-6(7H)-one, 7-(2,3-Dihydroxypropyl) guanine, 2-amino-7-(2,3-dihydroxypropyl)-1H-purin-6 (7H)-one, 7-(2-Hydroxyethyl)guanine, 2-amino-7-(2-hydroxyethyl)-1H-purin-6(7H)-one, 7-(2-[(2-Hydroxyethyl) amino]ethyl)-guanine, 2-amino-7-(2-(2-hydroxyethylamino)ethyl)-1H-purin-6(7H)-one, 7-Carboxymethylguanine, or 2-(2-amino-6-oxo-1,6-dihydropurin-7-yl)acetic acid. In some alternatives, the CAR or T cell receptor comprises a fragment specific for the hapten, wherein the CAR or TCR comprises 14G8, Anti 3-methylindole antibodies, 3F12, Anti 3-methylindole antibodies, 4A1G, Anti 3-methylindole antibodies, 8F2, Anti 3-methylindole antibodies, 8H1, Anti 3-methylindole antibodies, Anit-Fumonisin B1 antibodies, Anti-1,2-Naphthoquinone-antibodies, Anti-15-Acetyldeoxynivalenol antibodies, Anti-(2-(2,4-dichlorophenyl)-3(1H-1,2,4-triazol-1-yl)propanol) Antibodies (Anti-DTP antibodies), Anti-22-oxacalcitriol antibodies (As-1, 2 and 3), Anti-(24,25(OH)2D3) Antibodies (Ab11), Anti-(24,25(OH)2D3) Antibodies (Ab3), Anti-(24,25(OH)2D3) Antibodies (Ab3-4), Anti-2,4,5-Trichlorophenoxyacetic acid antibodies, Anti (2,4,5-Trichlorphenoxyacetic acid) Antibodies, Anti-(2,4,6-Trichlorophenol) Antibodies, Anti-(2,4,6-Trichlorophenol) Antibodies, Anti 2,4,6-Trinitrotoluene (TNT) Antibodies, Anti-2,4-Dichlorophenoxyacetic acid (MAb's B5/C3, E2/B5, E2/G2, F6/C10, and F6/E5), Anti (2,4-Dichlorphenoxyacetic acid) Antibodies, Anti-2-hydroxybiphenyl-antibodies, Anti-(3,5,6-trichloro-2-pyridinol) Antibodies (LIB-MC2, LIB-MC3), Anti (3,5,6-trichloro-2-pyridinol) antibodies (LIB-MC2 MAb), Anti-3-Acetyldeoxynivalenol(3-AcDON) Antibodies, Anti-3-phenoxybenzoic acid (3-PBAc)-Antibodies, Anti-4-Nitrophenol antibodies, anti-4-nitrophenyl 4'-carboxymethylphenyl phosphate antibodies, Anti-7-(Carboxyethyl)guanine(7-CEGua) antibodies (group specific for 7-meGua), Anti-7-methylguanine(7-MEGua) antibodies, Anti-ABA antibodies, Anti Acephate antibodies (Antiserum 8377), Anti-acetyllysine antibodies (mAbs AL3D5, AL11, AKL3H6, AKL5C1), Anti Aculaetiside-A antibody, Anti Aflatoxin M1(AFM1)antibodies (mAbs A1, N12, R16, FF32), Anti-agatharesinol Antibody, Anti-agatharesinol Antibody, Anti Amidochlorantibodies, Anti-Amitrole antibodies (anti 1a-BSA antibodies), Anti ampicillin Antibodies (AMPI I 1D1 and AMPI II 3B5), Anti-anandamide antibodies (9C11.C9C, 30G8.E6C, 7D2.E2b, 13C2 MAbs), Anti atrazine antibodies, Anti-atrazine antibodies, Anti-Atrazine antibodies, Anti Atrazine Antibodies, Anti-Atrazine Antibodies, Anti-Atrazine Antibodies, Anti-Atrazine Antibodies (4063-21-1 MAb cell line mAb and scAbs), Anti-Atrazine Antibodies (4D8 and 6C8 scAb), Anti Atrazine Antibodies (C193), Anti Atrazine Antibodies (In Rabbit/Sheep), Anti Atrazine Antibodies (K4E7), Anti Atrazine Antibodies (MAb: AM7B2.1), Anti Atrazine Antibodies (ScAb), Anti Atrazine Mercapturic acid antibodies, Anti (Azinphos methyl) Antibodies (MAB's LIB-MFH14, LIB-MFH110), Anti benalaxyl antibody, Anti benzimidazolecarboxylic acid, Anti benzimidazoles antibody (Ab 587), Anti-Benzo[a]pyrene antibodies, Anti Benzo(a)pyrene antibodies (10C10 and 4D5 MAbs), Anti-(Benzoylphenylurea)-Antibodies (mainly against Diflubenzuron), Anti-berberine Antibodies, Anti-beta Indole Acetic Acid Antibodies, Anti-Biopterin (L-erythro form) Antibodies, Anti-Brevetoxin PbTx-3-Antibodies, Anti Bromacil Antibodies, Anti-Bromophos Antibodies, Anti-Bromophos ethyl Antibodies, Anti Butachlor antibodies, Anti-Captopril-MCC Antibodies, Anti-Carbamazepine (CBZ)-Antibodies, Anti Carbaryl Antibodies, Anti Carbaryl Antibodies (LIB-CNH32, LIB-CNH33, LIB-CNH36, LIB-CNH37, LIB-CNH45, LIB-CNA38), Anti-Carbaryl Antibodies (LIB/CNH-3.6 MAb), Anti Carbofuran Antibodies (LIB-BFNB-52, LIB-BFNB-62, LIB-BFNB-67), Anti Carbofuran Antibodies (LIB-BFNP21), Anti-CDA-antibodies, Anti-CDA-antibodies (anti-2-[2-Chloro-(2'-6'-diethyl)acetanilido]butanoic Acid), Anti-CDA-antibodies (anti-2-[2-Chloro-(2'-6'-diethyl)acetanilido]ethanoic Acid), Anti-CDA-antibodies (anti-5-(4-Chloroacetamido-3,5-diethyl)phenoxypentanoic Acid), anti-ceftazidime antibody, Anti-(chlorodiamino-s-triazine) Antibodies (Anti-CAAT) (PAb1-8), Anti Chlorothalonil Antibodies, Anti-Chlorpyrifos antibodies, Anti-Chlorpyrifos Antibodies, Anti-Chlorpyrifos Antibodies (LIB-AR1.1, LIB-AR1.4 Mabs), Anti-Chlorpyrifos Antibodies (LIB-C4), Anti (chlorpyrifos) antibodies (LIB-C4 MAb), Anti-Chlorpyrifos Antibodies (LIB-PN1 Mabs), Anti-Chlorpyrifos Antibodies (LIB-PN2 Mabs), Anti-Chlorpyrifos Antibodies (LIB-PO Mabs), Anti-chlorsulfuron antibodies, Anti-Chlorsulfuron antibodies, Anti Chlortoluron Antibodies (Antiserum), Anti-Cyanoginosin-LA antibodies (mAbs 2B2-2, 2B2-7, 2B2-8, 2B2-9, 2B2-10, 2B5-5, 2B5-8, 2B5-14, 2B5-15, 2B5-23), Anti (D-3-methoxy-4-hydroxyphenylglycol) antibodies, Anti-DDA antibodies, Anti DDT antibodies (PAbs and MAbs), Anti-DDT Mabs (LIB1-11, LIB5-21, LIB5-25, LIB5-28, LIB5-212, LIB5-51, LIB5-52, LIB5-53), Anti-DEC Antibodies (Anti diethylcarbamazine Antibodies), Anti DEHA antibodies, Anti-(Delor 103) antibodies, Anti-Deltamethrin Antibodies, Anti Deltamethrin Antibodies (Del 01 to Del 12 MAbs and PAbs), Anti-deoxynivalenol (DON) Antibodies, Anti-Deoxynivalenol (DON) Antibodies, Anti Dexamethasone Antibody, Anti Dexamethasone Antibody, Anti-Dinitrophenyl (DNP)-antibodies, Anti dinitrophenyl spin labeled antibodies (AN01-AN12), Anti Diuron Antoboides (MAb's: 21, 60, 195, 202, 275, 481, 488, 520), Anti-D-MHPG Antibodies, Anti DNC antibodies, Anti-EB1089 antibodies, Anti-ecdysone antibodies, Anti-endosulfan antibodies, Anti-Endosulfan Antibodies, Anti Esfenvalerate antibodies (Ab7588), Anti estradiol antibodies, Anti-Fenitrothion antibodies (pAbs and mAbs), Anti-Fenpropimorph antibodies, Anti Fenthion Antibodies, Anti-Fenthion Antibodies, Anti FITC antibodies (B13-DEI), Anti-Flucofuron antibodies (F2A8/1/A4B3), Anti-flufenoxuron antibodies, and Anti-(Benzoylphenylurea)-Antibodies, Anti-Formononetin Antibodies, Anti-Furosemide antibodies (Furo-26, Furo37, furo-72, Furo 73 Mabs), Anti-GR151004 Antibodies, Anti-hCG-alpha-peptide Antibodies (FA36, Anti hydroxyatrazine antibodies (HYB-283-2), Anti-Hydroxysimazine Antibodies, Anti Imazalil Antibodies MoAb's (9C1-1-1, 9C5-1-1, 9C6-1-1, 9C8-1-1, 9C9-1-1, 9C12-1-1, 9C14-1-1, 9C16-1-1, 9C18-1-1, 9C19-1-1, 9E1-1, 9G2-1), Anti Irgarol Antibodies, Anti Isopentenyl adenosine antibodies, Anti Isoproturon Antibodies, Anti-KB-6806 antiserum, Anti-(+)lupanine antibodies, Anti Lysophosphatidic (LPA) acid, Anti M3G Ab1 and Ab2, Anti M3G Ab1 and Ab2, Anti-MBC antibodies (Anti-2-succinamidobenzimidazole antiserum), Anti Metanephrine antibodies, anti (+)methamphetamine antibodies, Anti-Methiocarb Antibodies (LIB-MXNB31, LIB-MXNB-33, LIB-MXNH14 and LIB-MXNH-15 MAbs), Anti Metolachlor antibodies, Anti-Metolachlor Antibodies, Anti-Metolachlor Antibodies (MAb 4082-25-4), Anti Molinate Antibodies, Anti monuron antibodies, Anti-morphine-3-glucuronide (E3 scFv antibody), Anti morphine antibodies, Anti-Morphine Antibodies, Anti-Morphine Antibodies (mAbs 8.2.1, 33.2.9, 35.4.12, 39.3.9, 44.4.1, 76.7F.16, 83.3.10, 115.1.3, 124.2.2, 131.5.13, 158.1.3, 180.2.4), Anti-Neopterin (D-erythro form) Antibodies, Anti-Nicarbazin Antibodies (Nic 6, Nic 7, Nic 8, and Nic 9), Anti Nicergoline Antibodies (Nic-1, Nic-2, Nic-3 & BNA-1, BNA-3), Anti-norflurazon antibodies, Anti NorMetanephrine antibodies, Anti (o-DNCP) Antibodies, Anti-P10 antibodies (TRH elongated peptide), Anti-Paraoxon Antibodies (BD1 and CE3), Anti Paraquat antibodies, Anti-Paraquat antibodies, anti Parathion-methyl antibodies, Anti PCB Antibodies (against 3,3',4,4'-tetrachlorobiphenyl) MAb S2B1, Anti pentachlorophenol antibodies, Anti Pentachlorophenol antibodies, Anti-Pentachlorophenol antibodies, Anti permethrin antibodies (Mabs Py-1, Py-3 and Py-4), Anti-Phencyclidine Antibodies (Mab 6B5 Fab), Anti-phenobarbital antibodies, Anti-phenobarbital antibodies, Anti-(p.p'-DDT)-Antibodies (LIB-DDT-35 and LIB-DDT5-52), Anti permethrin antibodies (Ab549), Anti Propoxur antibodies (LIB-PRNP15, LIB-PRNP21, LIB-PRNB21, LIB-PRNB33), Anti-Prostaglandin E2-antibodies, Anti-p-tyramine antibodies, Anti pyrene antibodies, Anti retronecine antibodies, Anti-Retronecine Antibodies, Anti salicylate antibodies, Anti Sennoside A antibodies (MAb 6G8), Anti Sennoside B antibodies (MAb's: 7H12, 5G6, 5C7), Anti Simizine antibodies, Anti Sulfonamides antibodies (Anti-TS), Anti-Sulocfuron antibodies (S2B5/1/C3), Anti sulphamethazine antibodies (21C7), Anti-synephrine antibodies, Anti-Thiabendazole antibodies (Antibody 300), Anti-Thiabendazole antibodies (Antibody 430 and 448), Anti-Thiram-Antibodies, Anti-THP antibodies (7S and 19S), Anti-Thromboxane B2 Antibodies, Anti-thymidine glycol monophosphate antibodies (mAb 2.6F.6B.6C), Anti-Thyroliberin (TRH) antibodies, Anti TNT antibodies (AB1 and AB2 antiserum), Anti Triadimefon Antibodies, Anti-triazine antibodies (AM1B5.1), Anti-triazine antibodies (AM5C5.3), Anti-triazine antibodies (AM5D1.2), Anti-triazine antibodies (AM7B2.1), Anti-triazine antibodies (SA5A1.1), Anti-Triazine serum (anti-ametryne), Anti-Triazine serum (anti-atrazine), Anti-Triazine serum (anti-simazine), Anti-Triazine serum (anti-simetryne), Anti Trifluralin Antibodies, Anti Trifluralin Antibodies, Anti Vincristine Antibodies, Anti-Zearalenone Antibodies, Anti Zeatin riboside antibodies, E2 G2 and E4 C2, Fab Fragment K411B derived from MAb K4E7 (isotype IgG2b with k light chain), LIB-BFNP23 Mab, MAb's H-7 and H-9 (against O,O-diethyl OP pesticides), MoAb 33A7-1-1, MoAb 33B8-1-1, MoAb 33C3-1-1, MoAb 3C10-1-1 and MoAb 3E17-1-1, MoAb 45D6-5-1, MoAb 45E6-1-1, MoAb 45-1-1, Mutant (GlnL89Glu) in Fab Fragment K411B derived from MAb K4E7 (isotype IgG2b with k light chain), Mutant (GlnL89Glu/ValH37Ile/GluL3Val) in Fab Fragment K411B derived from MAb K4E7 (isotype IgG2b with k light chain), Mutant (GlnL89Glu/ValH37Ile/GluL3Val) in Fab Fragment K411B derived from MAb K4E7 (isotype IgG2b with k light chain), Mutant (GlnL89Glu/ValH37Ile) in Fab Fragment K411B derived from MAb K4E7 (isotype IgG2b with k light chain), Mutant (GlnL89Glu/ValH37Ile) in Fab Fragment K411B derived from MAb K4E7 (isotype IgG2b with k light chain), Mutant (GluH50Gln) in Fab Fragment K411B derived from MAb K4E7 (isotype IgG2b with k light chain), Mutant (GluH50X) in Fab Fragment K411B derived from MAb K4E7 (isotype IgG2b with k light chain), Mutant (GlyH100aAla) in Fab Fragment K411B derived from MAb K4E7 (isotype IgG2b with k light chain), Mutant (GlyH100aSer) in Fab Fragment K411B derived from MAb K4E7 (isotype IgG2b with k light chain), Mutant (HisH95Phe) in Fab Fragment K411B derived from MAb K4E7 (isotype IgG2b with k light chain), Mutant (HisH95Tyr) in Fab Fragment K411B derived from MAb K4E7 (isotype IgG2b with k light chain), Mutant (PheL32Leu) in Fab Fragment K411B derived from MAb K4E7 (isotype IgG2b with k light chain), Mutant (TrpH33Phe,Tyr,Leu) in Fab Fragment K411B derived from MAb K4E7 (isotype IgG2b with k light chain), Mutant (Tryl96Phe) in Fab Fragment K411B derived from MAb K4E7 (isotype IgG2b with k light chain), Mutant (TryL96Phe) in Fab Fragment K411B derived from MAb K4E7 (isotype IgG2b with k light chain), Mutant (ValH37Ile) in Fab Fragment K411B derived from MAb K4E7 (isotype IgG2b with k light chain), Mutant (ValH37Ile) in Fab Fragment K411B derived from MAb K4E7 (isotype IgG2b with k light chain), P6A7 MAb, PNAS2 6/3 56(1)-1-5-1, PNAS2 6/3 56(1)-1-5-2, PNAS2 6/3 56(1)-1-10-4, PNAS2 6/3 56(1)-1-10-5 and PNAS2 6/3 56(1)-3-1-5, Alexa Fluor 405/Cascade Blue dye antibody, Alexa Fluor 488 dye antibody, BODIPY FL dye antibody, Dansyl antibody, Fluorescein/Oregon Green dye antibody, Lucifer yellow dye antibody, Tetramethylrhodamine and Rhodamine Red dye antibody, Texas Red and Texas Red-X dye antibody, Biotin antibody, Dinitrophenyl antibody and/or Nitrotyrosine antibody or any portion thereof of the aforementioned haptens. In some alternatives, the hydrophobic group comprises a carbon alkyl chain, wherein the carbon alkyl chain comprises at least 8, 9, 10, 11, 12, 13, 14, 15, 16, 17, 18, 19, 20, 21 or 22 carbons or any number that is within a range defined by any two aforementioned values. In some alternatives, the carbon alkyl chain comprises 8-22 carbons, such as 8-12, 12-14, 14-16, or 16-22 carbons. In some alternatives, the polar-head group comprises phosphocholine, a piperidine moiety or a trimethylarseno-ethylphosphate moiety. In some alternatives, the lipid further comprises a spacer that separates the target moiety from the polar head group. In some alternatives, the spacer comprises a PEG spacer, a Hapten (2×) spacer, a Hapten (3×) spacer, a Hapten (4×) spacer, a Hapten (5×) spacer, or an alkane chain. In some alternatives, the spacer comprises poly(carboxybetaine), peptides, polyglycidols, polyethylene, Polyanhydrides, Polyphosphoesters, Polycaprolactone or Poly(ethylene oxide). In some alternatives, the PEG spacer comprises 1, 2, 3, 4, 5, 6, 7, 8, 9, 10, 11, 12, 13, 14, 15, 16, 17, 18, 19, 20 or 21 PEG molecules, or any amount of PEG molecules that is within a range defined by any two aforementioned values. In some alternatives, the CAR or TCR is expressed by a cell or a T cell. In some alternatives, the CAR or TCR is on the surface of a cell or a T cell. In some alternatives, the cell is a precursor T cell. In some alternatives, the precursor T cell is a hematopoietic stem cell. In some alternatives, the cell is a CD8+ T cytotoxic lymphocyte cell selected from the group consisting of naïve CD8+ T cells, central memory CD8+ T cells, effector memory CD8+ T cells and bulk CD8+ T cells. In some alternatives, the cell is a CD4+ T helper lymphocyte cell that is selected from the group consisting of naïve CD4+ T cells, central memory CD4+ T cells, effector memory CD4+ T cells, and bulk CD4+ T cells. In some alternatives, the lipid is intercalated in a lipid bilayer of a target cell, such as a cancer cell. In some alternatives, the target cell is a tumor cell. In some alternatives, the target cell is an immune cell. In some alternatives, the immune cell is a T cell or a B cell. In some alternatives, the target cell exists in a tumor microenvironment.

In a second aspect, a cell comprising a chimeric antigen receptor (CAR) or T cell receptor (TCR) is provided, wherein the CAR or TCR is bound to a lipid, wherein the lipid comprises a target moiety and the cell comprising the CAR is bound to the target moiety of the lipid. In some alternatives, the lipid comprises a polar head group and a hydrophobic group. In some alternatives, the hydrophobic group is a carbon chain or a fatty acid such as an aliphatic chain. In some alternatives, the carbon chain or fatty acid is saturated or unsaturated. In some alternatives, the hydrophobic group comprises an alkyl, alkenyl or alkynyl group. In some alternatives, the hydrophobic group comprises a terpenoid lipid such as a steroid or cholesterol or it comprises an aromatic ring. In some alternatives, the hydrophobic group comprises an ether linkage, wherein the ether linkage is between the polar head group and the aliphatic chain. In some alternatives, the lipid is a phospholipid ether. In some alternatives, the polar head comprises a choline, a phosphatidylcholine, sphingomyelin, phosphoethanolamine group, an oligosaccharide residue, a sugar residue, phosphatidyl serine or phosphatidyl inositol. In some alternatives, the sugar is a glycerol. In some alternatives, the target moiety is a hapten, poly(his) tag, Strep-tag, FLAG-tag, V5-tag, Myc-tag, HA-tag, NE-tag, biotin, digoxigenin, dinitrophenol or fluorescein. In some alternatives, the hydrophobic group comprises a carbon alkyl chain, wherein the carbon alkyl chain comprises at least 8, 9, 10, 11, 12, 13, 14, 15, 16, 17, 18, 19, 20, 21 or 22 carbons or any number that is within a range defined by any two aforementioned values. In some alternatives, the carbon alkyl chain comprises 8-22 carbons, such as 8-12, 12-14, 14-16, or 16-22 carbons. In some alternatives, the polar-head group comprises phosphocholine, a piperidine moiety or a trimethylarseno-ethyl-phosphate moiety. In some alternatives, the lipid further comprises a spacer group that separates the target moiety from the polar head group. In some alternatives, the spacer comprises a PEG spacer, a Hapten (2×) spacer, a Hapten (3×) spacer, a Hapten (4×) spacer, a Hapten (5×) spacer, or an alkane chain. In some alternatives, the PEG spacer comprises 1, 2, 3, 4, 5, 6, 7, 8, 9, 10, 11, 12, 13, 14, 15, 16, 17, 18, 19, 20 or 21 PEG molecules, or any amount of PEG molecules that is within a range defined by any two aforementioned values. In some alternatives, the cell is a precursor T cell. In some alternatives, the precursor T cell is a hematopoietic stem cell. In some alternatives, the cell is a CD8+ T cytotoxic lymphocyte cell selected from the group consisting of naïve CD8+ T cells, central memory CD8+ T cells, effector memory CD8+ T cells and bulk CD8+ T cells. In some alternatives, the cell is a CD4+ T helper lymphocyte cell that is selected from the group consisting of naïve CD4+ T cells, central memory CD4+ T cells, effector memory CD4+ T cells, and bulk CD4+ T cells. In some alternatives, the lipid is intercalated in a lipid bilayer of a target cell, such as a cancer cell. In some alternatives, the target cell is a tumor cell. In some alternatives, the target cell is an immune cell. In some alternatives, the immune cell is a T cell or a B cell. In some alternatives, the target cell exists in a tumor microenvironment. In some alternatives, the hapten, which is a target moiety, comprises Alexa Fluor 405, Cascade Blue, Alexa Fluor 488, BODIPY, Dansyl chloride, Oregon Green, Lucifer yellow, Rhodamine, Tetramethylrhodamine, Nitrotyrosine, digoxigenin, 2,4-Dichlorophenoxyacetic acid, Atrazine (2-Chloro-4-(ethylamino)-6-(isopropylamino)-s-triazine), Nicotine (3-(1-Methyl-2-pyrrolidyl)pyridine, Black Leaf), Morphine (morph, Morphine Sulfate), 2,4-DINITROCHLOROBENZENE (1-Chloro-2,4-dinitrobenzene; DNCB; Dinitrochlorobenzene), 4-chloro-6-(ethylamino)-1,3,5-triazine-2-(6-aminohexanecarboxylic acid), Structurally related s-triazines (Modifications: H/Cl/C6 R1=NH2- R2=—Cl R3=—NH—(CH2)5-COOH; iPr/Cl/nBu R1=(CH3)2-CH—NH— R2=—Cl R3=—NH—(CH2) 3-(CH3)), Ametryn (2-Ethylamino-4-isopropylamino-6-methylthio-1,3,5-triazine), Deethylatrazine (DEA) (Structurally related s-triazines), Deisopropylatrazine (DIA) (Structurally related s-triazines), Deethyldeisopropylatrazine (DEDIA) (Structurally related s-triazines), Deethyldeisopropylatrazine (DEDIA) (Structurally related s-triazines), HydroxyAtrazine (HA) (Structurally related s-triazines), DeisopropylHydroxyAtrazine (DIHA) (Structurally related s-triazines), DeethylDeisopropylHydroxyAtrazine (DE-DIHA) (Structurally related s-triazines), Simazine (Structurally related s-triazines), Desmetryne (Structurally related s-triazines), Prometryne (Structurally related s-triazines), 2-hydroxyatrazine (atrazine derivative), 2-hydroxypropazine (structurally related s-triazine), 2-hydroxysimazine, N-(4-Amine-6-hydroxy-[1,3,5]triazin-2-yl)-4-aminobutanoic Acid (Modification: R1=NH2 R2=NH(CH2)3COOH R3=OH), SulcoFuron, 5-chloro-2-{4-chloro-2-[3-(3,4-dichlorophenyl)ureido]phenoxy}benzenesulfonic acid, Fluco-Furon (1,3-bis(4-chloro-α,α,α-trifluoro-m-tolyl)urea), Agatharesinol, Sequirin C, Sugiresinol, Hydroxysugiresinol, Hinokiresinol, Coniferyl alcohol, Cinnamyl alcohol, p-Coumaric acid, Cinnamic acid, p-Coumaric acid, Cinnamic acid, Hinokinin, Guaiacylglycerol-beta-guaiacyl ether, Morphine-3-glucuronide (M3G), Codeine, Nor-Codeine, 6-Mono-acetylmorphine, (+) Methamphetamine, Ceftazidime, Phenobarbital, p-hydroxyPhenobarbital, p-aminophenobarbital, Cyclobarbital, 3'-Ketocyclobarbital, 3'-Hydroxycyclobarbital, Secobarbital, Barbital, Metharbital, Barbituric acid, Thiopental, Thiobarbituric acid, Primidone, Glutethimide, Pentobarbital, Heroin, Diacetylmorphine, Levallorphan, L-11-Allyl-1,2,3,9,10,10a-hexahydro-4H-10,4a-iminoethanophenanthren-6-ol, Pethidine (Demerol; Dolantin; Meperidine; Ethyl 1-methyl-4-phenylpiperidine-4-carboxylate; Isonipecaine), Methamphetamine, d-Desoxyephedrine; Methedrine; Tolpropamine; Pratalgin; Pragman. Benzoylecgonine, 3-Carboxymethylmorphine, Cocaine, 5-benzimidazolecarboxylic acid, ABA (4-acetyl benzoic acid), Dexamethasone, Flumethasone, 6alpha, 9 alpha-difluoro-11 beta, 17,21-trihydroxy-16 alpha-methylpregna-1,4-diene-3,20-dione, 9 alpha-fluoro-11 beta,17,21-trihydroxy-16 beta-methylpregna-1,4-diene-3,20-dione, 9-alpha-fluroprednisolone, Desoxymethasone, Triamcinolone, 9 alpha-fluoro-11 beta,16 alpha, 17,21-tetrahydroxypregna-1,4-diene-3,20-dione, Fluocortolone, 6 alpha-fluoro-11 beta,21-dihydroxy-pregna-1,4-diene-3,20-dione, Cortisol, 11 beta, 17,21-trihydroxypregna-4-ene-3,20-dione, Prednisone, 17,21-dihydroxypregn-4-ene-3,11,20-trione, Methylprednisolone, 11 beta, 17,21-trihydroxy-6 alpha-methylpregna-1,4-diene-3,20-dione, Triamcinolone hexacetonide, 21-(3,3-dimethyl-1-oxobutoxy)-9 alpha-fluoro-11-hydroxy-16,17-[(1-methylethylidene) bis(oxy)]pregna-1,4-diene-3,20-dione, Carbofuran, 2,3-dihydro-2,2-dimethyl-7-benzofuranyl methylcarbamate, BFNP (3-[[(2,3-dihydro-2,2-dimethyl-7-benzofuranyloxy)carbonyl]amino]propanoic acid), Carbofuran derivative, 2,3-dihydro-2,2-dimethyl-7-benzofuranol, Bendiocarb, Carbaryl, Methiocarb, Propoxur, Aldicarb, Methomyl, Benalaxyl, methyl N-(phenylacetyl)-N-(2,6-xylyl)-DL-alaninate, Bn-Ba (4-[2-(N-phenylacetyl-N-2,6-xylylamino)propionamido] butyric acid), Bn-COOH (4-[2-(N-phenylacetyl-N-2,6-xylyl-DL-alanine), Benalaxyl derivative, Furalaxyl, Metalaxyl, Acetochlor, Dimetachlor, Metolachlor, 2-chloro-6'-ethyl-N-(2-methoxy-1-methylethyl)acet-o-toluidine, Diethathyl-ethyl, Benzoylprop-ethyl, Benzoylprop-ethyl, 2,4,5-Trichlorophenoxyacetic acid, 2-chloro-6'-ethyl-N-(2-methoxy-1-methylethyl)acet-o-toluidine, Diethathyl-ethyl, Benzoylprop-ethyl, Propachlor, Propachlor, 2,4,5-Trichlorophenoxyacetic acid, 2,4,5,T; Weedone, 2,4-Dichlorophenoxybutyric acid (2,4-DB), 2,4-DB; Butanoic acid, 4-(2,4-dichlorophenoxy)-; Butoxone; Embutone, MCPA, 2-Methyl-4-chlorophenoxyacetic acid; Metaxon, Dichlorprop (2,4-DP), 1-[(2-chloro)phenylsulfonyl]monoamidosuccinic acid, Chlorsulfuron, chlorbromuron, amidosulfuron, chlortoluron, isoproturon, diuron, Linuron O-Methyl-O-(4-nitrophenyl)-N-(4-carboxybutyl)-phosphoramidothioate Parathion-methyl, O,O-dimethyl O-4-nitrophenyl phosphorothioate; Methaphos; Wolfatox; Dimethylparathion; Metacide, Parathion-ethyl, DIETHYL P-NITROPHENYL THIOPHOSPHATE; O,O-DIETHYL O—(P-NITROPHENYL) PHOSPHOROTHIOATE; Fenitrothion, O,O-dimetyl O-4-nitro-m-tolyl phosphorothioate, Fenthion, O,O-dimethyl O-4-methylthio-m-tolyl phosphorothioate, Bromophos, O-4-bromo-2,5-dichlorophenyl O,O-dimethyl phosphorothioate, chlorpyrifos-methyl, O,O-dimethyl O-3,5,6-trichloro-2-pyridyl phosphorothioate, Oxidized parathion-methyl, Paraoxon, phosphoric acid, O,O-diethyl O-(4-nitrophenyl) ester, Diazinon, O,O-diethyl O-2-isopropyl-6-methylpyrimidin-4-yl phosphorothioate, Azinphos-methyl, pirimiphos-methyl, O-2-diethylamino-6- methylpyrimidin-4-yl O,O-dimethyl phosphorothioate, Methidathion, S-2,3-dihydro-5-methoxy-2-oxo-1,3,4-thiadiazol-3-ylmethyl O,O-dimethyl phosphorodithioate, Dimethylchlorothiophosphate, 4-NITROPHENOL, p-nitrophenol, Phenolic derivative (Modification On benzene ring; R1=OH R2=NO2 R3=H R4-CH2COOH R5=H R6=H); 2-Nitrophenol, o-Nitrophenol, 3-Nitrophenol, m-nitrophenol, 2,4-Dinitrophenol, 3,4-Dinitrophenol, 2,5-Dinitrophenol, 2,4-Dinitro-6-methylphenol, 2,3,6-trinitrophenol, 2-Chlorophenol, 4-Chloro-3-methylphenol, Fenitroxon, 3-Methyl-4-nitrophenol, Nonylphenol, HOM(3-[2-hydroxy-5nitro benzylthio] propionic acid, Phenol, Delor 103, Polychlorinated Biphenyls, Delor 104, Polychlorinated Biphenyls, Delor 105, Polychlorinated Biphenyls, Delor 106, 4,4'-Dichlorobiphenyl, PCB congeners, 2,4,4'-Trichlorobiphenyl, PCB congeners, 2,4'-Bichlorobiphenyl, PCB congeners, 2,2'-Dichlorobiphenyl, PCB congeners, 2,4,5-Trichlorobiphenyl, PCB congeners, 3,3',4,4'-Tetrachlorobiphenyl, PCB congeners, PCB congeners, 2,2',4,4',5,5'-Hexachlorobiphenyl, 2-(5-Carboxypentanoylamino)-4,4'-dichlorobiphenyl, Biphenyl derivative, 4-chlorophenoxyacetic acid, 2-Chlorophenoxyacetic acid, DDT,1,1,1-trichloro-2, 2-bis-(p-chlorophenyl)ethane, DDE, 1,1-dichloro-2, 2-bis(p-chlorophenyl)ethylene, p-Chlorophenol, 4-Chlorophenol, m-Chlorophenol 3,4-Dichlorophenol, 3,5-Dichlorophenol, 2,3,4-Trichlorophenol, 2,3,5-Trichlorophenol, 3-methylindole, 3-methylindole Derivatives, 4-(3-methylindol-5-yloxy)butanoic acid, 4-(3-methylindol-5-yloxy)butanoic acid, 3-methylindole Derivatives, 6-[n-3-methylindol-5-yloxy carbonyl)amino]hexanoic acid, 6-[n-3-methylindol-5-yloxy carbonyl)amino]hexanoic acid, 3-methylindole Derivatives, 2-[4-(3-methylindol-6-yl)but-1-ylthio]acetic acid, 2-[4-(3-methylindol-6-yl)but-1-ylthio]acetic acid, 3-methylindole Derivatives, 4-(3-methylindol-6-yl-4-oxo) butanoic acid, 4-(3-methylindol-6-yl-4-oxo)butanoic acid, 3-methylindole Derivatives, 6-(3-methylindol-7-yloxy) hexanoic acid, 6-(3-methylindol-7-yloxy)hexanoic acid, Indole, Indole-3-Carboxylic acid, Indole Derivative-Indole-3-Acetic acid, Indole-3-Acetic acid, Indole Derivative-Indole-3-Propionic acid, Indole-3-Propionic acid, Indole Derivative-Indole-3-Carbinol, Indole-3-Carbinol, Tryptophan, Tryptamine, 5-Methoxyindole-3-carboxaldehyde, 5-Methoxytryptamine, 5-Methoxyindole, 6-Methoxyindole, 7-Methoxyindole,EB1089(Seocalcitol),EB1089(Seocalcitol) Derivative, (22E,24E)-Des-A,B-24-homo-26,27-dimethyl-8-[(E)-N-(2-carboxyethyl)-carbamoylmethylidene]-cholesta-22,24-dien-25-ol, 1 alpha-25-dihydroxyvitamin D3, 25(OH)D3,25-hydroxyvitamin D3,24R,25(OH)2D3, 24R,25-dihydroxyvitamin D3, Vitamin D2, ergocalciferol, Vitamin D3, cholecalciferol,EB1446,EB1436,EB1445, EB1470, DeethylHydroxyAtrazine (DEHA) (Structurally related s-triazines), Irgarol 1051, Flourescein Isothiocyanate, FITC, Metanephrine, NorMetanephrine, Propazine, Terbutylazine, Terbuthylazine, 6-chloro-N-(1,1-dimethylethyl)-N'-ethyl-1,3,5-triazine-2,4-diamine, (Structurally related s-triazines), Ametryn (2-Ethylamino-4-isopropylamino-6-methylthio-1,3,5-triazine (Modification iPr/SCH3/Et R1=(CH3)2-CH—NH— R2=—SCH3 R3=—NH—CH2-CH3, Irgarol, Cyanazine (Modification R1=Cl R2=NHCH2CH3 R3=NHCCN(CH3)2), OH-Terbutylazine, Terbutylazine-2OH, Hydroxytriazine (EQ-0027), Deisopropylatrazine (Structurally related S-triazine), Desethylterbutylazine (Structurally related S-triazine), Desethyl-deisopropylatrazine (Structurally related S-triazine), Atraton, Terbutryn (Structurally related s-triazines), Atrazine derivative (Modification R1=—NHCH(CH3)2 R2=—S(CH2) 2COOH R3=—NHC2H5), Cyanuric chloride, Trifluralin, (Structurally related s-triazines) tBu/C4/SCH3 (Modification R1=—NH—C—(CH3)3 R2=—NH(CH2)3COOH R3=—SCH3), Sulphamethazine, (Structurally related s-triazines) 6-[[[4-Chloro-6-(methylamino)]-1,3,5-triazin-2-yl] amino]hexanoic Acid (Modification Me/Cl/C6 R1=—NHCH3 R2=—Cl R3=—NH(CH2)5COOH), (Structurally related s-triazines) Procyazine (Modification R1=—Cl R2=—NHcyclopropyl R3=—NHCCN(CH3)2), (Structurally related s-triazines), Prometon (Modification R1=—OCH3 R2=—NHCH(CH3)2 R3=—NHCH(CH3)2); (Structurally related s-triazines) Atrazine Mercapturic Acid (AM) (Modification R1=—SCH2CH(NHAc)COOH R2=—NHCH2CH3 R3=—NHCH(CH3)2), (Structurally related s-triazines), desethyl atrazine mercapturic acid (desethyl AM) (Modification R1=—NAcCys R2=—NH2 R3=—NHCH(CH3)2), (Structurally related s-triazines), deisopropyl atrazine mercapturic acid (deisopropyl AM) (Modification R1=—NAcCys R2=—NHCH2CH3 R3=—NH2), (Structurally related s-triazines), didealkylated atrazine mercapturic acid (didealkylated AM) (Modification R1=—NAcCys R2=—NH2 R3=—NH2), (Structurally related s-triazines), simazine mercapturate (Modification R1=—NAcCys R2=—NHCH2CH3 R3=—NHCH2CH3), (Structurally related s-triazines) (Modification R1=—S(CH2)2COOH R2=—NHCH2CH3 R3=—NHCH2CH3), (Structurally related s-triazines) (Modification R1=—Cl R2=—NHCH(CH3)2 R3=—NH(CH2) 2COOH), (Structurally related s-triazines) (Modification R1=—Cl R2=—NHCH2CH3 R3=—NH(CH2)2COOH), (Structurally related s-triazines), atrazine mercapturic acid methyl ester (AM methyl ester) (Modification R1=—NAcCysME R2=—NHCH2CH3 R3=—NHCH(CH3)2), N-acetylcysteine, S-benzyl mercapturate, (Structurally related s-triazines), simetryn (Modification R1=—SCH3 R2=—NHCH2CH3 R3=—NHCH2CH3), Metribuzin, 4-amino-6-tert-butyl-4,5-dihydro-3-methylthio-1,2,4-triazin-5-one, Sulpha Drugs, N4-acetyl-sulphamethazine (Modification N4-acetyl-sulphamethazine), Sulpha Drugs, Sulphathiazole, Sulphathiazole, Sulphamerazine, Sulphamerazine, Sulphaquinoxaline, Sulphaquinoxaline Sulphachlorpyridazine, Sulphachlorpyridazine, Sulphapyridine, Sulphadimethoxine, Sulphadimethoxine, Sulphamethoxazole, Sulphamethoxazole, Sulphisoxazole, Sulphisoxazole, Sulphamethizole, Sulphamethizole, Sulphanilamide, Sulphanilamide, Sulphaguanidine, Sulphaguanidine, Sulphadiazine, Sulphadiazine, Sulphamethoxypyridazine, Sulphamethoxypyridazine, Pentachlorophenoxypropionic acid, Pentachlorophenol, PCP, 2,3,5,6-Tetrachlorophenol, 1,2,4,5 Tetrachlorobenzene, 2,4,6 Trichlorophenol, 2-Methoxy-3,5,6-trichloropyridine, 1,3,5 Trichlorobenzene, 1,3 Dichlorobenzene, 2,4,5-Trichlorophenol, 2,6-Dichlorophenol, 3,5,6-Trichloro-2-pyridinoxyacetic acid, 3,5,6-Trichloro-2-Pyridinol, TCP, 2,4-Dichlorophenol, 2,5-Dichlorophenol, DNC, 4,4'-dinitrocarbanilide, (Structurally related s-triazines), Dichloroatrazine, (Structurally related s-triazines), Dichlorosimazine, 1-((6-chloropyridin-3-yl) methyl)imidazolidin-2-imin, Pyridine Derivative, 6-chloropyridine-3-carboxylic acid, Nicotinic acid, Pyridine Derivative, N-((6-chloropyridin-3-yl)methyl)-N-methylacetamide, (6-chloropyridin-3-yl)-N-methylmethanamine, (6-chloropyridin-3-yl)methanol, Imidacloprid, 1-(6-chloro-3-pyridylmethyl)-N-nitroimidazolidin-2-ylideneamine, Acetamiprid, (E)-N1-[(6-chloro-3-pyridyl)methyl]-N2-cyano-N1-methylacetamidine, Nitenpyram, Deltamethrin, 1(R)-cis-alpha (S)-3-(2,2-dibromoethenyl)-2,2-dimethylcyclopropane carboxylic acid cyano(3-phenoxyphenyl)methyl ester, DON, deoxynivalenol, DON derivative, 15-AcDON (15-acetyldeoxynivalenol), DON derivative, 3-AcDON (3-acetyldeoxynivalenol), DON derivative, 3,15-DiacDON (3,15-diacetyldeoxynivalenol), DON derivative, 3,7,15-TriacDON (3,7,15-Triacetyldeoxynivalenol), NIV (nivalenol), nivalenol, NIV Derivative, 4-AcNIV (fusarenon X), Flutolanil, alpha,alpha,alpha-trifluoro-3'-isopropoxy-o-toluanilide, Mepronil, Mebenil, Benodanil, 24,25(OH)2D3, (24R)-24,25-dihydroxyvitamin D3, 24S,25(OH)2D3, 24S,25-dihydroxyvitamin D3, 25R,26(OH)2D3, 25R,26-dihydroxyvitamin D3, 25S,26(OH)2D3, 25S,26-dihydroxyvitamin D3, 1,24,25(OH)3D3, 1,24,25-trihydroxyvitamin D3, 1,25-lactone, (23S,25R)-1,25(OH)2 D3 26,23-lactone, 24,25(OH)2-7-DHC, 24,25(OH)2-7-dehydrocholesterol, 25(OH)D3 3S, 25(OH)D3 3-sulfate, 24,25(OH)2D3-Hemiglutarate Derivative, 11 alpha-hemiglutaryloxy-(24R)-24,25-dihydroxyvitamin D3, 24,25(OH)2D3-Hemiglutarate Derivative, (24R)-24,25-dihydroxyvitaminD3-3-hemiglutarate, 24R,25(OH)2D2, 24S,25(OH)2D2, 25(OH)D2, 1,24(OH)2D3, 2,3,6-Trichlorophenol, Tetrachlorohydroquinone, Pentachloroaniline, Pentachlorobenzene, 2,3-Dinitrotoluene, 4-Dinitrotoluene, 2,4,5-Trichloronitrobenzene, 3-(3-Hydroxy-2,4,6-trichlorophenyl)-propanoic acid, 2,3,4,6-Tetrachlorophenol, 2,4,6-Trichloroanisol, 2,4,6-TCA, Pentabromophenol, PBP, 2,4,6-Tribromophenol, 2,4,6-TBP, 2-Bromo-4-Chlorophenol, 2-B-4-CP 2,4-Dibromophenol, 2,4-DBP, 2,6-Dibromophenol, 2,6-DBP, 4-Bromophenol, 4-BP, Furosemide, Ampicillin, Amoxicillin, 6-amino-penicillanic acid (6-APA), Azlocillin, Bacampicillin, Carbenicillin, Epicillin, Cloxacillin, Dicloxacillin, Metampicillin, Methicillin, Moxalactam, Oxacillin, Penicillin G, benzyl penicillin, Penicillin V, phenoxy methyl penicillin, Pheneticillin, Piperacillin, Ticarcillin, Ampicillin hydrolyzed, Penicillin G hydrolyzed, 3-phenoxybenzoic acid (3-PBAc) Chlorpyrifos, Chlorpyrifos derivatives, HClo1, Synthesized directly from chlorpyrifos technical grade by substitution of the chlorine in position 6 by a 3-mercaptopropanoic acid spacer arm, Chlorpyrifos derivatives, HTCP (Modification HTCP of TCP metabolite was prepared from HClo1 by hydrolysis of the thiophosphate ester), Zeatin Riboside (trans isomer), Zeatin (trans isomer), N6-(2-isopentenyl)-adenosine, IPA, N6-(2-isopentenyl)-adenine, 2-iP, Benzyladenine, Kinetin, monuron, monolinuron, fenuron, neburon, propanil, propham, chloropropham, 4-chloroaniline, Methyl Urea Derivative, 1-(3-Carboxypropyl)-3-(4-chlorophenyl)-1-methylurea, Methyl Urea Derivative, 1-(5-Carboxypentyl)-3-(4-chlorophenyl)-1-methylurea, metobromuron, Sennoside B, SB, Sennoside B possessed a erythro configuration between C-10 and C-10', Sennoside A (Modification Sennoside A possessed a threo configuration between C-10 and C-10'), Rhein, Emodin, Aloe-emodin, Barbaloin, 1,4 Dihydroxyanthraquinone, Rhaponticin, Galic acid, Vanillic acid, Caffeic acid, Homogentisic acid, Esculin, Cinnamtannin B1, Baicalin, Naringin hydrate, Wogonin, Wogonin 7-o-beta-glucuronide, Curcumin, delta1-Tetrahydrocannabinolic acid, delta1-Tetrahydrocannabinol, (+−)-cis-4-Aminopermethrin, 3-(4-Aminophenoxy)benzyl(+−)-cis-3-(2,2-dichloroethenyl)-2,2-dimethylcyclopropanecarboxylate, Permethrin, trans-Permethrin, cis-Permethrin, Cypermethrin, Phenothrin, Resmethrin, Cyfluthrin, trans-Permethrin acid Esfenvalerate, Fluvalinate, Fenpropathrin, cis-permethrin acid, 4-Phenoxybenzoyl alcohol, Diuron Derivative, 1-(3-Carboxypropyl)-3-(3,4-dichlorophenyl)-1-methylurea, Siduron, Terbuthiuron, Barban, acid trifluralin, 2,6-dinitro-N-propyl-N-(2-carboxyethyl)-4-(trifluoromethyl)benzenamine, TR-13, 2-ethyl-7-nitro-1-propyl-5-(trifluoromethyl)-1H-benzimidazole, benefin, 2,6-dinitro-N-butyl-N-ethyl-4-(trifluoromethyl)benzenamine, TR-2, 2,6-dinitro-N-propyl-4-(trifluoromethyl)benzenamine, ethalfluaralin, 2,6-dinitro-N-ethyl-N-(2-methyl-2-propenyl)-4-(trifluoromethyl) benzenamine, TR-40, N-(2,6-dinitro-4-(trifluoromethyl) phenyl)-N-propylpropanamide, TR-15, 2-ethyl-4-nitro-6-(trifluoromethyl)-1H-benzimidazole, TR-3, 2,6-dinitro-4-(trifluoromethyl)benzenamine, TR-6, 3-nitro-5-(trifluoromethyl)-1,2-benzenediamine, TR-9, 5-(trifluoromethyl)-1,2,3-benzenetriamine, TR-21, 4-(dipropylamino)-3,5-dinitrobenzoic acid, TR-36M, 3-methoxy-2,6-dinitro-N,N-dipropyl-4-(trifluoromethyl)benzenamine, oryzalin, 3,5-dinitro-4-(dipropylamino)benzenesulfonamide, pendimethalin, 2,6-dinitro-N-(1-ethylpropyl)-3,4-dimethylbenzenamine, penta galloyl glucose, Pyrene Pyrene-1-carboxaldehyde, Phenanthrene, Benzo(a)pyrene, 3,4-Benzopyrene, Anthracene, 3,4-Benzopyrene, Acenaphthene, Fluorene, Chrysene, 1,2-Benzphenanthrene, Benzo[g,h,i]perylene, Benzo[e]pyrene, Acenaphthylene, Fluoranthene, Benzo(j,k)fluorene, Indeno-1,2,3-cd-pyrene, 1,10-(1,2-Phenylene)pyrene, Benzo[a]anthracene, 1,2-Benzanthracene, Benzo(k)fluoranthene, Naphthalene, Benzo[a]fluoranthene, Dibenzo[ah]anthracene, 1,2:5,6-Dibenzanthracene, 2,3-Diaminonaphthalene, 2,6-Dinitroaniline, 17-beta-estradiol (ED), estra-1,3,5(10)-triene-3,17-beta-diol, Trifluralin derivative, 2,6-dinitro-4-tri-fluoromethylaniline, Trifluralin derivative, N-(2,6-dinitro-4-trifluoromethylphenyl)-6-aminohexanoic acid, Trifluralin derivative, N-(2,6-dinitro-4-trifluoromethylphenyl)-N-methyl-6-aminohexanoic acid, Trifluralin derivative, N-(2,6-dinitro-4-trifluoromethylphenyl)-N-propyl-6-aminohexanoic acid, Trifluralin derivative, N-(2,6-dinitro-4-trifluoromethylphenyl)-6-aminohexanoic acid methyl ester, Trifluralin derivative, N-(2,6-dinitro-4-trifluoromethylphenyl)-6-aminohexanoic acid tert-butyl ester, Benfluralin, Ethalfluralin, Trifluralin derivative, 2,6-Dinitro-4-trifluoromethylphenol, Isopropalin, Aniline, 2-Hydroxybenzotrifluoride, N-propyl-6-aminohexanoic acid, N-methyl-6-aminohexanoic acid, MHPG Derivatives, D-MHPG (D-3-methoxy-4-hydroxyphenylglycol), MHPG Derivatives, L-MHPG (L-3-methoxy-4-hydroxyphenylglycol), MHPG Derivatives, DL-MHPG (DL-3-methoxy-4-hydroxyphenylglycol), Isomeric mixture of D-MHPG and L-MHPG forms, MHPG Derivatives, DL-MHPG-SO4 (DL-3-methoxy-4-hydroxyphenylglycol-sulfate) Modification can include Isomeric mixture of D-MHPG-SO4 and L-MHPG-SO4 forms, Serotonin, 5-HT, 5-hydroxydopamine (5-4HDA), 3,4-dihydroxyphenylglycol (DOPEG), Dopamine, 4-(2-aminoethyl)pyrocatechol; 3-hydroxytyramine; 3,4-dihydroxyphenethylamine; L-3,4-dihydroxyphenylalanine, L-DOPA, Vanillomandelic acid, DL-VMA, Homovanillic acid, Norepinephrine, DL-NE, D-Epinephrine, D-E, 3-methoxytyramine, MTA, 3-methoxytyrosine, MTyr, 3,4-dihydroxymandelic acid, DL-DOMA, 3,4-dihydroxyphenyl acetic acid, DOPAC, L-Phenylalanine, Tyramine, p-tyramine; 4-(2-Aminoethyl)phenol, D-Mandelic acid, Homocatechol, Octopamine, DL-Octopamine, Azinphos-Ethyl, S-(3,4-dihydro-4-oxobenzo[d]-[1,2,3]-triazin-3-ylmethyl) O,O-diethyl phosphorodithioate, Phosmet, O,O-dimethyl S-phthalimidomethyl phosphorodithioate, Folpet, N-[(Trichloromethyl)thio]phthalimide, Tetramethrin, (1-Cyclohexene-1,2-dicarboximido)methyl-2,2-dimethyl-3-(2-methylpropenyl)-cyclopropanecarboxylate, N-(bromomethyl)phthalimide, N-(Chloromethyl)benzazimide, 6-(N-phthalimidoylmethylthio)hexanoic acid (MFH), Bromacil, 5-bromo-3-sec-butyl-6-methyluracil, Bromacil Derivative, 5-bromo-6-(hydroxymethyl)-3-(1-methylpropyl)-2,4(1H, 3H)-pyrimidineone, Bromacil Derivative, 5-bromo-3-(2-methylpropyl-6-methyl-2,4(1H,3H)-pyrimidinedione, Metabolite of Bromacil, Bromacil Derivative, 3-hydroxy-1-methylpropyl-6-methyl-2,4(1H,3H)-pyrimidinedione (Modification Bromacil Metabolite), Bromacil Derivative, 6-methyl-3-(1-methylpropyl)-2,4(1H,3H)-pyrimidinedione (Modification Bromacil Metabolite), Terbacil Derivative, [5-chloro-3-(1,1-dimethylethyl)-6-(hydroxymethyl)-2,4 (1H,3H)-pyrimidinedione, Terbacil, 3-tert-butyl-5-chloro-6-methyluracil, Bromacil Derivative, Ethyl-5-(5-Bromo-6-methyl-3-(1-methylpropyl)-2,4(1H,3H)-pyrimidinedione-1-yl)hexanoate, Bromacil Derivative alkylated at N-1, Bromacil Derivative 5-(5-Bromo-6-methyl-3-(1-methylpropyl)-2,4(1H,3H)-pyrimidinedione-1-yl)hexanoic Acid (Modification Bromacil Derivative alkylated at N-1), Bromacil Derivative, -Bromo-6-(Bromomethyl-3-(1-methylpropyl)-2,4(1H,3H)-pyrimidinedione (Modification Bromacil Derivative substituted at the 6-methyl position), Bromacil Derivative-[5-Bromo-3-(1-methylpropyl)-2,4(1H,3H)-pyrimidinedione-6-yl]-2-carboxylpropanoic Acid (Modification Bromacil Derivative substituted at the 6-methyl position), 3-[5-Bromo-3-(1-methylpropyl)-2,4 (1H,3H)-pyrimidinedione-6-yl]propanoic Acid (Modification Bromacil Derivative substituted at the 6-methyl position), Bromacil Derivative 5-Bromo-1,6-dimethyl-3-(1-methylpropyl)-2,4(1H,3H)-pyrimidinedione, Bromacil Derivative 5-Bromo-1-butyl-6-methyl-3-(1-methylpropyl)-2,4(1H,3H)-pyrimidinedione, Butachlor, N-butoxymethyl-2-chloro-2′,6′-diethylacetanilide, Amidochlor, N-[(acetylamino)methyl]-2-chloro-N-(2,6-diethylpenyl)acetamide, Nicarbazin, N,N′-bis(4-nitrophenyl)-compound with 4,6-dimethyl-2(1H)-pyrimidinone (Modification (DNC+HDP)), 2-hydroxy-4,6-dimethylpyrimidine, HDP, Imazalil, [1-(beta-allyloxy-2,4-dichlorophenethyl)imidazole], Imazalil Derivative, EIT-0073 (Modification Have a —O(CH2)5-COOH group instead of original —OCH2CH—CH2 group of imazalil), Penconazole, (RS)-1-(2,4-dichloro-β-propylphenethyl)-1H-1,2,4-triazole, Hexaconazole, (RS)-2-(2,4-dichlorophenyl)-1-(1H-1,2,4-triazol-1-yl)hexan-2-ol, Propiconazole, cis-trans-1-[2-(2,4-dichlorophenyl)-4-propyl-1,3-dioxolan-2-ylmethyl]-1H-1,2,4-triazole, Diclobutrazol, 2RS,3RS)-1-(2,4-dichlorophenyl)-4,4-dimethyl-2-(1H-1,2,4-triazol-1-yl)pentan-3-ol, Triflumizole, (E)-4-chloro-α,α,α-trifluoro-N-(1-imidazol-1-yl-2-propoxyethylidene)-o-toluidine, Imazalil Derivative, EIT-0183, Imazalil Derivative, EIT-0180, Imazalil Derivative, EIT-0111, Imazalil Derivative, EIT-0158, Imazalil Derivative, K-240, Chlorothalonil, tetrachloroisophthalonitrile Modification On benzene Ring R1=CN R2=Cl R3=CN R4=Cl R5=Cl R6=Cl), Chlorothalonil Derivative-2,4,5,6-tetrachloro-3-cyanobenzamide (Modification On benzene Ring R1=CONH2 R2=Cl R3=CN R4=Cl R5=Cl R6=Cl), Chlorothalonil Derivative-2,5,6-trichloro-4-hydroxyisophthalonitrile (Modification On benzene Ring R1=CN R2=Cl R3=CN R4=OH R5=Cl R6=Cl), 3-carbamyl-2,4,5-trichlorobenzoic acid (Modification On benzene Ring R1=CONH2 R2=Cl R3=COOH R4=H R5=Cl R6=Cl), Pentachloronitrobenzene (Modification On benzene Ring R1=NO2 R2=Cl R3=Cl R4=Cl R5=Cl R6=Cl), Benzene hexachloride, Hexachlorobenzene, BHC, Lindane (Modification On benzene Ring R1=Cl R2=Cl R3=Cl R4=Cl R5=Cl R6=Cl), 2,4,5,6-tetrachlorophenol (Modification On benzene Ring R1=OH R2=Cl R3=H R4=Cl R5=Cl R6=Cl), Carbaryl Derivative, Ethylcarbamate (Modification R1=OCONHCH2CH3 R3=H), 1-Naphthol, 1-naphthaleneacetamide, -(1-naphthyl)acetamide, Carbaryl Derivative, 1-Methylcarbonate (Modification R1=OCOOCH3 R2=H, Carbaryl Derivative, 1-Ethylcarbonate (Modification R1=OCOOCH2CH3 R2=H), Carbaryl Derivative 2-Ethylcarbonate (Modification R1=H R2=OCOOCH2CH3, Carbaryl Derivative, 1-Ethylthiocarbonate (Modification R1=OCOSCH2CH3 R2=H), Carbaryl Derivative, 2-Ethylthiocarbonate (Modification R1=H R2=OCOSCH2CH3), Naptalam, N-1-naphthylphthalamic acid, Carbaryl Derivative, 3-hydroxycarbaryl (Modification R1=OCONHCH3 R2=H R3=OH R4=H R5=H), Carbaryl Derivative 4-hydroxycarbaryl (Modification R1=OCONHCH3 R2=H R3=H R4=OH R5=H), Carbaryl Derivative 5-hydroxycarbaryl (Modification R1=OCONHCH3 R2=H R3=H R4=H R5=OH), Carbaryl Derivative, 1-(5-Carboxypentyl)-3-(1-naphthyl)urea (Modification R1=NHCONH(CH2)5COOH R2=H), (Structurally related s-triazines)-Aziprotryn, 4-azido-N-isopropyl-6-methylthio-1,3,5-triazin-2-ylamine (Modification R1= —SCH3 R2=—N3 R3=—CH(CH3)2), (Structurally related s-triazines), 2-(ethylamino)-4-(methylthio)-6-aminotriazine (Modification R1=—SCH3 R2=—NH—C2H5 R3= —NH2), (Structurally related s-triazines)-2-amino-4-(methylthio)-6-(isopropylamino)triazine (Modification R1= —SCH3 R2=—NH2 R3=—NH—CH(CH3)2), (Structurally related s-triazines)-2-amino-4-methoxy-6-(isopropylamino) triazine (Modification R1=—OCH3 R2=—NH2 R3= —NH—CH(CH3)2), TCP Derivative (3,5,6-trichloro-2-pyridinol Derivative), 3-(3,5-dichloro-6-hydroxy-2-pyridyl) thiopropanoic Acid, p-nitrosuccinanilic acid (PNA-S), PNA-S, PNA-C, p-nitro-cis-1,2-cyclohexanedicarboxanilic acid, Nitroaniline Derivative, 2-nitroaniline, o-Nitroaniline, Nitroaniline Derivative-3-nitroaniline, m-Nitroaniline, Nitroaniline Derivative-4-nitroaniline, p-Nitroaniline, Aeromatic Alcohols, 4-nitrobenzyl alcohol, Aeromatic Alcohols-4-nitrophenethyl alcohol, Aeromatic Alcohols 2-nitrobenzyl alcohol, Aeromatic Alcohols, 3-nitrobenzyl alcohol, Urea Derivative-1-benzyl-3-(4-nitrophenyl)urea, Urea Derivative-1-(3-chlorophenyl)-3-(2-methoxy-5-nitrophenyl)urea, Urea Derivative-1-(3-chlorophenyl)-3-(4-methoxy-3-nitrophenyl)urea, Urea Derivative-1-(4-chlorophenyl)-3-(4-nitrophenyl)urea, Urea Derivative-(2-fluorophenyl)-3-(2-mehtoxy-4-nitrophenyl)urea, 1-(3-mehtoxyphenyl)-3-(3-nitrophenyl)urea, Carbofuran Derivative m Carbofuranphenol, Carbofuran-hydroxy, Carbofuran-keto, Carbosulfan, 3-dihydro-2,2-dimethylbenzofuran-7-yl (dibutylaminothio)methylcarbamate, Benfuracarb, N-[2,3-dihydro-2,2-dimethylbenzofuran-7-yloxycarbonyl(methyl)aminothio]-N-isopropyl-β-alaninate, Furathiocarb, 2,3-dihydro-2,2-dimethyl-7-benzofuranyl 2,4-dimethyl-5-oxo-6-oxa-3-thia-2,4-diazadecanoate, Carbofuran Derivative, 4-[[(2,3-Dihydro-2,2-dimethyl-7-benzofuranyloxy)carbonyl]-amino]butanoic Acid (BFNB) (Modification n=3 X=CH2), Endrin, nendrin, (1R,4S,4aS,5S,6S,7R,8R,8aR)-1,2,3,4,10,10-hexachloro-1,4,4a,5,6,7,8,8a-octahydro-6,7-epoxy-1,4:5,8-dimethanonaphthalene, Heptachlor, 1,4,5,6,7,8,8-heptachloro-3a,4,7,7a-tetrahydro-4,7-, Chlordane, 1,2,4,5,6,7,8,8-octachloro-2,3,3a,4,7,7a-hexahydro-4,7-methanoindene, Endosulfan (Modification isomer mix of alpha and beta forms), Endosulfan (Modification alpha isomeric form), Endosulfan (Modification beta isomeric form), Endosulfan Derivative, Endosulfan sulfate (Modification sulfate form), Endosulfan Derivative, Endosulfan diol, Diol metabolite of endosulfan, Endosulfan Derivative, Endosulfan ether (Modification ether metabolite of endosulfan), Endosulfan Derivative, hydroxy ether, hydroxy ether metabolite of endosulfan, Endosulfan Derivative, Endosulfan lactone (Modification lactone metabolite of endosulfan), Aldrin, Dieldrin, Fenvalerate isomers Modification 1S,2R isomer R: Ph), Fenvalerate isomers (Modification 1R,2S isomer R: Ph), Fenvalerate isomers (Modification 1R,2R isomer R: Ph), Fenvalerate isomers (Modification 1S,2R/S isomer R: Ph), Fenvalerate isomers (Modification 1R,2R/S isomer R: Ph), Fenvalerate isomers, fenvalerate (Modification 1R/S,2R/S isomer R: Ph), Thiabendazole, 2-(thiazol-4-yl)benzimidazole, Thiabendazole Derivative, 5-hydroxythiabendazole (Modification 5-OH-TBZ), Thiabendazole Derivative, 5-NH2-TBZ), Thiabendazole Derivative, methyl benzimidazole carbamate, Albendazole, Mebendazole, Fenbendazole, Thiabendazole Derivative, 2-succinamidothiabendazole, Thiabendazole Derivative, 2-succinamidothiabendazole, Cambendazole, Fenvalerate Haptens, Cyano[3-(4-aminophenoxy)phenyl]methyl (S)-4-Chloro-alpha-(1-methylethyl)benzeneacetate (4-Aminoesfenvalerate), Fenvalerate Haptens, Benzyl 4-[3-[Cyano[(S)-2-(4-chlorophenyl)-3-methyl-1-oxobutanoxy]methyl]]phenoxy]benzenepropanoate, Fenvalerate Haptens, Benzyl 3-[Cyano[(S)-2-(4-chlorophenyl)-3-methyl-1-oxobutanoxy]methyl]]phenoxyacetate, Fenvalerate Haptens, 3-[Cyano[(S)-2-(4-chlorophenyl)-3-methyl-1-oxobutanoxy]methyl]]phenoxyacetic Acid, Fenvalerate Haptens, Benzyl 6-[3-[Cyano[(S)-2-(4-chlorophenyl)-3-methyl-1-oxobutanoxy]methyl]]phenoxy] hexanoate, Fenvalerate Haptens, 6-[3-[Cyano[(S)-2-(4-chlorophenyl)-3-methyl-1-oxobutanoxy]methyl]]phenoxy] hexanoic Acid Fenvalerate Haptens, 4-[3-[Cyano[(S)-2-(4-chlorophenyl)-3-methyl-1-oxobutanoxy]methyl]]phenoxy] benzenepropanoic Acid, (S)-fenvalerate Acid, (Structurally related s-triazines), atrazine mercapturate Modification R1=—SCH2CH(NHCOCH3)COOH R2=—NHCH2CH3 R3=—NHCH(CH3)2, Fenthion Hapten, -Methyl O-[3-methyl-4-(methylthio)phenyl] N-(3-carboxypropyl)phosphoramidothioate Modification referred as Hapten B, Fenthion Derivative, Oxidized Fenthion, Fenthion Derivative, Oxidized oxidized Fenthion, pirimiphos-ethyl, 4-(Methylthio)-m-cresol, Chlorpyrifos Derivative, Chlorpyrifos-oxon, Fenchlorphos, O,O-dimethyl O-2,4,5-trichlorophenyl phosphorothioate, Trichloronate, O-Ethyl O-2,4,5-trichlorophenyl ethyl-phosphonothioate, Dichlofenthion, O-2,4-dichlorophenyl O,O-diethyl phosphorothioate, Parathion, O,O-diethyl O-4-nitrophenyl phosphorothioate; Thiophos, Chlorpyrifos Derivative Modification Synthesis of AR1 is described, Chlorpyrifos Derivative, O-Ethyl O-(3,5,6-Trichloro-2-pyridyl)O-(3-Carboxypropyl)Phosphorothioate; (PO), Chlorpyrifos Derivative-O-Ethyl O-(3,5,6-Trichloro-2-pyridyl)N-(5-Carboxyethyl) Phosphoramidothioate; (PN1) (Modification Amide linkage of thiophosphate reagents), Chlorpyrifos Derivative, O-Ethyl O-(3,5,6-Trichloro-2-pyridyl)N-(2-Carboxyethyl) Phosphoramidothioate; (PN1) (Modification Amide linkage of suitable thiophosphate reagents), Triadimefon, (RS)-1-(4-chlorophenoxy)-3,3-dimethyl-1-(1H-1,2,4-triazol-1-yl)butan-2-one, GR151004, (4-[[5-[3-[2-(dimethylamino)ethyl]]-5-benzofuranyl]-3-pyridinyl]acetyl]morpholine dihydrochloride, Diflubenzuron, 1-(4-chlorophenyl)-3-(2,6-difluorobenzoyl)urea, (Structurally related s-triazines)-SprAAT (Modification R1=SCH2CH2COOH R2=NH2 R3=NH2), (Structurally related s-triazines), SBeAAT (Modification R1=S(C6H4)COOH R2=NH2 R3=NH2), (Structurally related s-triazines), SAAT (Modification R1=SH R2=NH2 R3=NH2), (Structurally related s-triazines), CDAT (Modification R1=Cl R2=NH[C(O)CH3] R3=NH2), (Structurally related s-triazines)-CDET (Modification R1=Cl R2=NH[C(O)CH3] R3=NH(CH2CH3), (Structurally related s-triazines)-CDIT (Modification R1=Cl R2=NH[C(O)CH3] R3=NH(CH(CH3)2)), (Structurally related s-triazines), CDDT (Modification R1=Cl R2=NH[C(O)CH3] R3=NH[C(O)CH3]), (Structurally related s-triazines)-ammeline, OAAT (Modification R1=OH R2=NH2 R3=NH2), (Structurally related s-triazines)-ammelide, OOAT (Modification R1=OH R2=OH R3=NH2), (Structurally related s-triazines)-cyanuric acid, OOOT (Modification R1=OH R2=OH R3=OH), (Structurally related s-triazines), melamine, AAAT (Modification R1=NH2 R2=NH2 R3=NH2), Structurally related s-triazines-N-isoropylammeline, OIAT (Modification R1=OH R2=NH[CH(CH3)2] R3=NH2, Structurally related s-triazines-N-ethylammeline, OEAT (Modification R1=OH R2=NHCH2CH3 R3=NH2), Structurally related s-triazines, N-ethylammelide, OOET (Modification R1=OH R2=OH R3=NHCH2CH3), Structurally related s-triazines)-cyromazine, CyPAAT (Modification R1=NH(C3H5) R2=NH2 R3=NH2), Structurally related s-triazines-diamino-s-triazine, HAAT (Modification R1=H R2=NH2 R3=NH2), PCB congeners, 2,5,3',4'-tetrachlorobiphenyl (Modification IUPAC no.: 70), PCB congeners 2,4,5,3',4'-pentachlorobiphenyl (Modification IUPAC no.: 118), PCB congeners-2,2',5,5'-tetrachlorobiphenyl (Modification IUPAC no.: 52), PCB congeners, 6-[3,3',4'-Trichlorobiphenyl-4-yl)oxy]hexanoic Acid, Metolazone, Brand Names: Mykrox; Zaroxolyn, Furfuryl benzoate, DDT Metabolites, DDA, Paraquat, 1,1'-dimethyl-4,4'-bipyridinium ion, Diethylcarbamazine, THP, 2,4,6-triphenyl-N-(4-hydroxyphenyl)-pyridinium, o-DNCP, -dinitrocarboxyphenol, PCB congeners, 3-chlorobiphenylol (Modification IUPAC No. 2), PCB congeners, 3,4'-dichlorobiphenyl (Modification IUPAC No. 13), PCB congeners, 3,5-dichlorobiphenyl (Modification IUPAC No. 14), PCB congeners, 3,4,5,3',4'-pentachlorobiphenyl (Modification IUPAC No. 126), 2,3,3',4'-tetrachlorobiphenyl (Modification IUPAC No. 56), 2',3,4,5-tetrachlorobiphenyl (Modification IUPAC No. 76), 3,3',5,5'-tetrachlorobiphenyl (Modification IUPAC No. 80), 2,4,5,2',5'-pentachlorobiphenyl (Modification IUPAC No. 101), 2,3,3',4,4'-pentachlorobiphenyl (Modification IUPAC No. 105), 2,3,6,3',4'-pentachlorobiphenyl (Modification IUPAC No. 110), 3,3',4,5,5'-pentachlorobiphenyl (Modification IUPAC No. 127), 3,4,5,3',4',5'-hexachlorobiphenyl (Modification IUPAC No. 169), 2,3,3',4,4',5-hexachlorobiphenyl (Modification IUPAC No. 156), 3,4,3',4'-tetrabromobiphenyl, 3,4,5,3,4,5'-hexabromobiphenyl, 2,4,5,2,4,5'-hexabromobiphenyl, Dibenzofurans and Dioxins, 2,3,7,8-tetrachlorobenzofuran, 2,3,7,8-tetrachlorodibenzo-p-dioxin, 3,4',5-trichloro-4-biphenylol, 3,3',5,5'-tetrachloro-4,4'-biphenyldiol, 3,4,3',4'-tetrachlorodiphenyl ether, 1-2-dichlorobenzene, 1,4-dichlorobenzene, 1,2,4-trichlorobenzene, 3,4-dichloroaniline, DDT Metabolites, 4,4'-DDT, 4,4'-DDD Retronecine, 3,4-dichlorobiphenyl Modification IUPAC No. 12, 3,4,3'-trichlorobiphenyl (Modification IUPAC No. 35), PCB Congeners, 3,4,4'-trichlorobiphenyl (Modification IUPAC No. 37), 3,4,3',5-tetrachlorobiphenyl (Modification IUPAC No. 78), 3,4,3',5'-tetrachlorobiphenyl (Modification IUPAC No. 79), 3,4,4',5-tetrachlorobiphenyl (Modification IUPAC No. 81), DDT Metabolites, p,p'-DDT (Modification p,p'-dichlorodiphenyltrichloroethane), o,p'-DDT Modification o,p'-dichlorodiphenyltrichloroethane, p,p'-DDE Modification p,p'-DDE, o,p'-DDE Modification o,p'-DDE, p,p'-DDD Modification p,p'-DDD, o,p'-DDD Modification o,p'-DDD, Dicofol, 4,4-dichloro-a-(trichloromethyl)benzhydrol, Cyprazine, 6-chloro-N-cyclopropyl-N'-(1-methylethyl)-1,3,5-triazine-2,4-diamine, Structurally related s-triazines, Dipropetryn, 6-(ethylthio)-N,N'-bis(1-methylethyl)-1,3,5-triazine-2,4-diamine, Trietazine, 6-chloro-N,N,N'-triethyl-1,3,5-triazine-2,4-diamine, 6-Hydroxyatrazine, hexazinone, 3-cyclohexyl-6-dimethylamino-1-methyl-1,3,5-triazine-2,4 (1H,3H)-dione, TNT, 2,4,6-Trinitrotoluene, Tetraconazole (M14360), 1-[2-(2,4-dichlorophenyl)-3-(1,1,2,2-tetrafluoroethoxy)propyl]-1H-1,2,4-triazole, DTP, 2-(2,4-dichlorophenyl)-3-(1H-1,2,4-triazol-1-yl)propanol, Imazalyl, fenarimol, (RS)-2,4'-dichloro-α-(pyrimidin-5-yl)benzhydryl alcohol, Lupanine metabolites, (+)-lupanine (Modification R=H), Lupanine metabolites, (+)-13-hydroxylupanine (Modification R=OH), Lupanine metabolites, hemisuccinate ester of (+)-13-hydroxylupanine (Modification R=OCO—(CH2) 2.COOH), Lupanine metabolites, cis-hexahydrophthalate ester of (+)-13-hydroxylupanine (Modification R=OCO.C6H10.COOH), Lupanine metabolites, alpha-isolupanine, Lupanine metabolites, -hydroxylupanine, Sparteine, Cysteine, multiflorine, epilupinine, (Structurally related s-triazines), CYANAZINE ACID Modification R1=Cl R2=NHCH2CH3 R3=NHCCOOH(CH3)2, Structurally related s-triazines Modification R1=Cl R2=NHCH2CH3 R3=NH(CH2)3COOH, Structurally related s-triazines (Modification R1=Cl R2=NHCH2CH3 R3=NHCH2COOH), (Structurally related s-triazines) (Modification R1=Cl R2=NHCH2CH3 R3=NH(CH2) 4COOH), norflurazon, 4-chloro-5-(methylamino)-2-[3-(trifluoromethyl)phenyl]-3(2H)-pyridazinone, norflurazon derivative, desmethyl-norflurazon, metflurazon, -chloro-5-(dimethylamino)-2-[(3-trifluoromethyl)phenyl]-3(2H)-pyridazinone, Pyrazon, Chloridazon, 5-amino-4-chloro-2-phenyl-3(2H)-pyridazinone (active ingradient), dichlorophenyl-pyridazone, (Structurally related s-triazines) azidoatrazine (Modification R1=N3 R2=NHCH(CH3)2 R3=NHCH2CH3), ALACHLOR 2-chloro-2',6'-diethyl-N-methoxymethylacetanilide, trichothecolone (Modification R1=H R2=OH R3=H R4=O R5=H), DON derivative, acetyl-T-2, DON derivative, T-2 tetrol tetraacetate, Chlorpyrifos derivatives, mono-dechloro-CP, Bromophos derivative, Bromophos-methyl, Bromophos derivative, Bromophos-ethyl dicapthon, -2-chloro-4-nitrophenyl O,O-dimethyl phosphorothioate, tetrachlorvinphos, (Z)-2-chloro-1-(2,4,5-trichlorophenyl)vinyl dimethyl phosphate, triclopyr, 3,5,6-trichloro-2-pyridyloxyacetic acid, picloram, 4-amino-3,5,6-trichloropyridine-2-carboxylic acid, Formononetin, Biochanin A, 5, 7-dihydroxy-4'-methoxyisoflavone (Modification It is the 4'-methyl ether of genistein), equol, (7-hydroxy-3-(4'-hydroxyphenyl)-chroman, 2'methoxyformononetin, Daidzein, 7-hydroxy-3-(4-hydroxyphenyl)-4H-1-benzopyran-4-one, geninstein, quercetin, 3,3',4',5,7-Pentahydroxyflavone; 3,5,7,3',4'-Pentahydroxyflavone; matheucinol, coumestrol (Structurally related s-triazines), Hydroxysimazine (Modification R1=OHR2=NHCH2CH3R3=NHCH2CH3, angustifoline, Alodan, 1-Methyl-4-phenyl-4-carboethoxypiperidine hydrochloride, Zearalenone, RAL, F-2 Toxin, Fenpropimorph, (RS)-cis-4-[3-(4-tert-butylphenyl)-2-methylpropyl]-2,6-dimethylmorpholine, Tridemorph, 2,6-dimethyl-4-tridecylmorpholine, 2,6-dimethylmorpholine, Amorolfine, Fenpropidine, (RS)-1-[3-(4-tert-butylphenyl)-2-methylpropyl]piperidine, (Structurally related s-triazines) (Modification R1=Cl R2=Cl R3=NHCH2CH3, (Structurally related s-triazines) Modification R1=Cl R2=Cl R3=NHCH(CH3)2, (Structurally related s-triazines) Modification R1=Cl R2=NHCH2CH3 R3=NH(CH2)5COOH, (Structurally related s-triazines) Modification R1=Cl R2=NHCH(CH3)2 R3=NHCH2COOH, (Structurally related s-triazines) (Modification R1=Cl R2=NHCH(CH3)2 R3=NH(CH2)5COOH), Structurally related s-triazines, cyanazine amide (Modification R1=Cl R2=NHCH2CH3 R3=NHCCONH2(CH3)2), hydroxycyanazine acid (Modification R1=OH R2=NHCH2CH3 R3=NHCCOOH(CH3)2), deethylsimazine (Modification R1=Cl R2=NH2 R3=NHCH2CH3), Albendazole sulfoxide, [5-(propylthionyl)-1H-benzimidazol-2-yl]-, methylester, Albendazole sulfone, 5(6)-alkylbenzimidazoles, 2-amino-5-(propylthio)benzimidazole, 5(6)-alkylbenzimidazoles, 2-amino-5-(propylsulfonyl) benzimidazole, oxibendazole, 5-propoxy-benzimidazole-2-methyl carbamate, 5(6)-arylbenzimidazoles, fenbendazole sulfone (Modification sulfone metabolite of fenbendazole), 5(6)-arylbenzimidazoles, 4'-hydroxyfenbendazole, 5(6)-arylbenzimidazoles, oxfendazole (Modification Oxfendazole is the sulfoxide metabolite of fenbendazole), 5(6)-arylbenzimidazoles, flubendazole, benzimidazole Metabolites, 2-aminobenzimidazole, benzimidazole Metabolites, 5-aminobenzimidazole, benzimidazole Metabolites, 2-acetylbenzimidazole, Benzophenone, Diphenylmethanone; phenyl ketone; Diphenyl ketone; Benzoylbenzene, Benzaldehyde, benzoic aldehyde, 4-Bromo-2,5-dichlorophenol, Acephate, O,S-dimethyl acetylphosphoramidothioate, methamidophos, O,S-dimethyl phosphoramidothioate, Dichlorvos, 2,2-dichlorovinyl dimethyl phosphate, Phenthoate, S-α-ethoxycarbonylbenzyl O,O-dimethyl phosphorodithioate, EPN, Ethyl p-nitrophenyl thionobenzenephosphonate, Bioresmethrin, -benzyl-3-furylmethyl (1R,3R)-2,2-dimethyl-3-(2-methylprop-1-enyl) cyclopropanecarboxylate (Modification The unresolved isomeric mixture of this substance has the ISO common name resmethrin), flufenoxuron, 1-[4-(2-chloro-α,α-trifluoro-p-tolyloxy)-2-fluorophenyl]-3-(2,6-difluorobenzoyl) urea, Amitrole, 1H-1,2,4-triazol-3-ylamine, molinate, S-ethyl azepane-1-carbothioate, molinate derivative (Modification S-2-carboxyethyl hexahydroazepine-1-carbothioate), molinate derivative (Modification S-5-carboxypentyl hexahydroazepine-1-carbothioate) molinate derivative (Modification molinate sulfone), molinate derivative (Modification S-(p-aminobenzyl) hexahydroazepine-1-carbothioate), molinate derivative (Modification S-2-(p-aminophenyl) ethyl hexahydroazepine-1-carbothioate), hexamethylenimine, thiobencarb (Bolero), butylate (Sutan), EPTC (Eptam), cycloate (Roneet), pebulate (Tillam), vernolate (Vernam), Aflatoxin M1, AFM1 (Modification AFM1), Aflatoxin B1, AFB1 (Modification AFB1), Aflatoxin G1, AFG1 (Modification AFG1), Aflatoxin M2, AFM2 (Modification AFM2), Aflatoxin B2, AFB2 (Modification AFB2), Aflatoxin G2, AFG2 (Modification AFG2), Aflatoxin B2alpha, AFB2alpha (Modification AFB2alpha), Aflatoxin G2alpha, AFG2alpha (Modification AFG2alpha), KB-6806, 6-amino-5-chloro-1-isopropyl-2-(4-methyl-1-piperazinyl) (Modification R1=NH2 R2=CH(CH3)2 R3=CH3), KB-6806 (Benzimidazole) Derivatives Modification R1=NH2 R2=CH2CH(CH3)2 R3=CH3, Hapten Name KB-6806 (Benzimidazole) Derivatives (Modification R1=NH2 R2=CH(CH2CH3)2 R3=CH3), KB-6806 (Benzimidazole) Derivatives (Modification R1=NHCOCH3 R2=CH(CH3)2 R3=CH3), KB-6806 (Benzimidazole) Derivatives (Modification R1=H R2=CH(CH3)2 R3=CH3), KB-6806 (Benzimidazole) Derivatives (Modification R1=NH2 R2=CH(CH3)2 R3=CH3), KB-6806 (Benzimidazole) Derivatives Modification R1=NH2 R2=CH(CH3)2 R3=N(—>O) CH3 (N-OXIDE), KB-6806 (Benzimidazole) Derivatives Modification R1=NH2 R2=CH(CH3)2 R3=H, KB-6806 (Benzimidazole) Derivatives Modification R1=NH2 R2=CH2CH3 R3=CH3, Aminoparaoxon, phosphoric acid, O,O-diethyl O-(4-aminophenyl) ester, Methylparathion, phosphorothioic acid, O,O-dimethyl O-(4-nitrophenyl) ester, Diethyl phenylphosphate, phenylphosphonic acid, O,O-diethyl ester, Diethyl phosphate, ethylphosphonic acid, O,O-diethyl ester, p-Nitrophenyl phosphate, phosphonic acid, O-(4-nitrophenyl)ester, Phorate, phosphorodithioic acid, O,O-diethyl S-[(ethylthio) methyl] ester, Ethion, bis(phosphorodithioic acid), S,S'-methylene O,O,O',O'-tetraethyl ester, Carbophenthion, phosphorodithioic acid, O,O-diethyl S-[[(4-chlorophenyl)thio]methyl] ester, Disulfoton, phosphorodithioic acid, O,O-diethyl S-[(2-ethylthio)ethyl] ester, TS, N-[4-(Carboxymethyl)-2-thiazolyl)sulfanilamide, NS, N-(4-Nitrophenyl)sulfanilamide, Sulfamoxole, Sulfacetamide, DNP-SL, Spin labelled dinitrophenyl (Modification The synthesis of DNP-SL has been described by Balakrishnan et al (1982) formula can be found in Anglister et al. (1984)), beta ecdysone, Benzimidazole Derivative, 5(6)-[Carboxypentyl)thio]-2-(methoxycarbonyl)amino]-benzimidazole, 2-hydroxybiphenyl HBP, Atrazine Caproic acid, Lysophosphatidic acid (LPA), 1-acyl-2-hydroxy-sn-glycero-3-phosphate), berberine, Palmatine, 9-Acetylberberine, Corydaline, Coptisine, Berberrubine, 8-Oxoberberine, Papaverine, Berberine Derivative, 9-O-carboxymethyl berberine, phencyclidine, 1-(1-phenylcyclohexyl)piperidine, Methoxychlor, Endosulfan Derivative, 4-Oxobutanoic Acid,4-(4,5,6,7,8,8-Hexachloro-3a,4,7,7a-tetrahydro-4,7-methano-1H-indenyl-1-oxy), Endosulfan Derivative, 4-oxybutanoic Acid,4-(1,3,4,5,6,7,8-Octachloro-3a,4,7,7a-tetrahydro-4,7-methanoindanyl-2-oxy, Endosulfan Derivative (Modification Hemisuccinate of Endosulfan diol), Triazole Derivatives, 5-(3-Hydroxypropyl)-3-amino-2H-1,2,4-triazole, Triazole Derivatives, 5-(3-Hydroxypropyl)-3-(2-nitrophenylsulfenyl)amino-2H-1,2,4-triazole, Triazole Derivatives, 3-Amino-5-[(3-succinyloxy)propyl]-2H-1,2,4-triazole, Triazole Derivatives, 3-amino-1,2,4-triazole-5-thiol, Triazole Derivatives, 3-[(2-nitrophenylsulfenyl)amino-2H-1,2,4-triazole-5-thiol, Triazole Derivatives, 2H-1,2,4-triazole-5-thiol, Triazole Derivatives, 4-methyl-1,2,4-triazole-3-thiol, Triazole Derivatives, (1,2,4-triazol-2-yl)acetic acid, 1,2,4-triazole, 4-nitrophenyl 4'-carboxymethylphenyl phosphate, Triazole Derivative, 4-amino-1,2,4-triazole, Triazole Derivative, 3-acetamido-1H-1,2,4-triazole, Triazole Derivative, 3-amino-1,2,4-triazole-5-carboxylic acid hemihydrate, Triazole Derivative, 2-(4-chlorophenyl)-2-(1,2,4-triazol-1-yl)-methylhexanoic acid, succinic acid, Imidazole, L-histidine, L-glutamic acid, Permethrin derivative, 3-phenoxybenzyl 2,2-dimethylcyclopropane-1,3-dicarboxylate, 3-phenoxybenzaldehyde, flucythrinate, Chrysanthemic acid, 2,4-Dinitrophenyl, DNP, Thiram Haptens, Disodium 4-[Carbodithioato(methyl)-amino]butanoate, Thiram Haptens 5,11-Dimethyl-6,10-dithioxo-7,9-dithia-5,11-diazadodecanoic Acid, Thiram Haptens, 2-{[(Dimethylamino)carbothioyl]sulfanyl}ethanoic Acid, Thiram Haptens, 4-{[(Dimethylamino)carbothioyl]sulfanyl}butanoic Acid, Thiram Haptens, 6-{[(Dimethylamino)carbothioyl]sulfanyl}hexanoic Acid, Thiram Haptens, 11-{[(Dimethylamino)carbothioyl]sulfanyl}undecanoic Acid, Thiram Haptens, 2-{[(Dimethylamino)carbothioyl] sulfanyl}ethanoic Acid, Thiram, Tetramethylthiurammonosulfide, Tetraethylthiuram disulfide, Dimethyldithiocarbamic acid sodium salt, Dimethyldithiocarbamic acid zinc salt, Diethyldithiocarbamic acid sodium salt, N,N,N',N'-tetramethylthiourea, Nabam, Zineb, Maneb, Ethylenethiourea, Chlorpyrifos hapten, O,O Diethyl O-[3,5-Dichloro-6-[(2-carboxyethyl)thio]-2-pyridyl] Phosphorothioate, 2-Succinamidobenzimidazole, Methyl 2-Benzimidazolecarbamate, MBC, Benzimidazole, 2-benzimidazolylurea, succinamide, Ethyl carbamate, Urea, N-methylurea, N,N'-dimethylurea, Brevetoxin PbTx-3, Organophosphorous Haptens, O,O-Diethyl O-(5-carboxy-2-fluorophenyl) phosphorothioate, Chlorpyrifos-ethyl, Anandamide hapten, N-Arachidonyl-7-amino-6-hydroxy-heptanoic acid, Anandamide, Arachidonic acid, Docosatetraenoyl ethanolamide, Dihomo-gamma-linolenyl ethanolamide, 2-Arachidonyl glycerol, 2-Arachidonyl glycerol ether, Stearoyl ethanolamide, Heptadecanoyl ethanolamide, Prostaglandin E1, 3-hydroxy-2-(3-hydroxy-1-octenyl)-5-oxocyclopentaneheptanoic acid; alprostadil; PGE1, Prostaglandin D2, PGD2, Prostaglandin A2, PGA2, Prostaglandin B2, PGB2, Prostaglandin F2 alpha, 7-[3,5-dihydroxy-2-(3-hydroxy-1-octenyl)cyclopentyl]-5-heptenoic acid; dinoprost; PGF2alpha, Prostaglandin F1 alpha, PGF1alpha, 6-keto-Prostaglandin F1 alpha, 6-keto-PGF1alpha, 13,14-Dihydro-15-keto-Prostaglandin E2, 13,14-Dihydro-15-keto-PGE2, 13,14-Dihydro-15-keto-Prostaglandin F2alpha, 14-Dihydro-15-keto-PGF2alpha, 5alpha,7alpha-Dihydroxy-11-ketotetranorpostane-1,16-dioic acid, 15-keto-PGF2alpha, TXB2, Prostaglandin E2,7-[3-hydroxy-2-(3-hydroxy-1-octenyl)-5-oxocyclopentyl]-5-heptenoic acid; dinoprostone; PGE2, hCG-alpha-(59-92)-peptide (34 residues), Paraquat Derivative, Paraquat hexanoate (PQ-h), Monoquat, Diquat, 9,10-dihydro-8a, 10a-diazoniaphenanthrene, MPTP, 1-methyl-4-phenyl-1,2,5,6-tetrahydropyridine, 1,2-Naphthoquinone, N-Acetyl-S-(1,2-dihydroxy-4-naphthyl)cysteine, N-Acetyl-S-(1,4-dihydroxy-2-naphthyl)cysteine, N-Acetyl-S-(1,2-dihydroxy-1-hydroxy-1-naphthyl)cysteine, 2-Chloro-2'.6'-diethylacetanilide (CDA) Hapten, 2-[2-Chloro-(2'-6'-diethyl)acetanilido]ethanoic Acid, 2-Chloro-2'.6'-diethylacetanilide (CDA) Hapten, 2-[2-Chloro-(2'-6'-diethyl)acetanilido]butanoic Acid, 2-Chloro-2'.6'-diethylacetanilide (CDA) Hapten, 5-(4-Chloroacetamido-3,5-diethyl)phenoxypentanoic Acid, CDA, 2-Chloro-2'.6'-diethylacetanilide, HDA, 2-Hydroxy-2'.6'-diethylacetanilide, 2,6-diethyl-aniline, Hydroxyalachlor, Alachlor ESA, Alachlor ethanesulfonic acid, Isoproturon Hapten, 3-(4-Isopropylphenyl)-1-carboxypropyl-1-methyl urea, chlorotoluron, 3-(3-chloro-p-tolyl)-1,1-dimethylurea, Metoxuron, 3-(3-chloro-4-methoxyphenyl)-1,1-dimethylurea, metamitron, 4-amino-4,5-dihydro-3-methyl-6-phenyl-1,2,4-triazin-5-one, mecoprop, (RS)-2-(4-chloro-o-tolyloxy) propionic acid, propyzamide, 3,5-dichloro-N-(1,1-dimethylpropynyl)benzamide, Paraquat dichloride, MCPB, 4-(4-chloro-o-tolyloxy)butyric acid, Chlortoluron Hapten, N-(3-Chloro-4-methylphenyl)-N-methyl-N-carboxypropyl Urea, Metsulfuron, Methyl 2-[3-(4-methoxy-6-methyl-1,3,5-triazin-2-yl)ureidosulphonyl]benzoate, Captopril Haptens, Captopril-4-(Maleimidomethyl)-cyclohexane Carboxylic Acid (MCC), Captopril Haptens, Captopril Disulfide Modification, Mercaptoethanol-MCC, Mercaptoethanol-4-(Maleimidomethyl)-cyclohexane Carboxylic Acid Modification, Captopril Haptens, Captopril without MCC, Aculeatiside A, Aculeatiside B, Solamargine, Solasonine, solanine-S; purapurine, Solasodine, Khasianine, Tomatine, lycopersicin, Tomatidine, 3-O-beta-D-Glucopyranosyl-solasodine, O-alpha-L-Rhamnosyl-1(1→2)-3-O-beta-D-glucopyranosyl-solasodine, 3-O-beta-D-Galacopyranosyl-solasidine, O-beta-D-Glucopyranosyl-1(1→3)-3-O-beta-D-galacopyranosyl-solasodine, 12-Hydroxysolamargine, 12-Hydroxysolasonine, Isoanguivine, Solaverine I, Solaverine II, Xylosyl-beta-solamargine, alpha-Solanine, alpha-Chaconine, Dioscine, Indole Derivatives, beta-Indole Acetic Acid, 2-Bromo-4,6-dinitroaniline, 2-Chloro-4,6-dinitroaniline, Tetryl, 2,4,6-trinitrophenyl-n-methylnitramine, nitramine, tetralite, tetril, 2-Amino-4,6-dinitrotoluene, 2,4-Dinitroaniline, 3,5-Dinitroaniline, 2-Amino-4,6-dinitrobenzoic acid, Disperse Blue 79, N-[5-[bis[2-(acetyloxy)ethyl]amino]-2-[(2-bromo-4,6-dinitrophenyl)azo]-4-ethoxyphenyl]acetamide, 1,3-Dinitrobenzene, 2,6-Dinitrotoluene, 4-Amino-2,6-dinitrotoluene, 1,3,5-Trinitrobenzene, Nicergoline, Ethylmorphine, 8-Didehydro-4,5-epoxy-3-ethoxy-17-methylmorphinan-6-ol, Dihydromorphine, Dihydrocodeine, dihydromorphinone, Hydromorphone, Dihydrocodeinone, Hydrocodone, Naltrexone, N-cyclopropylmethyl-14-hydroxydihydromorphinone, Dextromethorphan, (±)-3-Methoxy-17-methylmorphinan, Homatropine, Endorphins Modification Derivative Type: b-Endorphin, Met-enkephalin, DALEA, D-Ala(2)-D-Leu(5)-enkephalinamide, Vincristine, 22-Oxovincaleukoblastine, leurocristine; VCR; LCR, OCT, 22-Oxacalcitriol, OCT-3-HG, 22-oxacalcitriol-3-Hemiglutarate, 24(OH)OCT, 24(OH)-22-oxacalcitriol, 1,20(OH)2-hexanor-D3, Synephrine, Epinephrine, 4-[(1R)-1-Hydroxy-2-(methylamino)ethyl]-1,2-benzenediol, Phenylephrine, Dopamine Derivative, 6-hydroxy dopamine, Tyramine derivative, 3-methoxy tyramine, Phenethylamine, Benzeneethanamine; PEA, m-tyramine, o-tyramine, dimethoxyphenethylamine, Thymidine glycol monophosphate, 5,6-Dihydroxythymidine monophosphate, Thymidine monophosphate, Thymidine glycol, Thymine glycol, 5,6-Dihydrothymidine, Thymidine, Thymine, 5-methyluracil; 2,4-dihydroxy-5-methylpyrimidine, AMP, Adenosine mono phosphate, CMP, Cytidine mono phosphate, Carbamazepine, 5-carbamoyl-5H-dibenz[b,f]azepine, Neopterin isomers, D-erythro-Neopterin, Neopterin isomers, L-erythro-Neopterin, Neopterin isomers, D-threo-Neopterin, Biopterin isomers, L-erythro-Biopterin, Biopterin isomers, D-erythro-Biopterin, Biopterin isomers, L-threo-Biopterin, Biopterin isomers, D-threo-Biopterin, Pterin-6-Carboxylic Acid, C7H5NiO3, Pterin, Thromboxane B2, (5Z,9alpha,13E,15S)-9,11,15-trihydroxythromboxa-5,13-dien-1-oic acid, 15 Ketoprostaglandin F2alpha, Fumonisin B1, macrofusine; FBI, Thyroliberin, TRH; thyrotropin-releasing factor; thyrotropin releasing hormone; TRF; protirelin; lopremone, Thyroliberin-OH, TRH-OH, Diketopiperazine, cyclo (H-P), TRH analogues, Methylated TRH, TRH analogues, TRH elongated peptides, TRH-Gly, TRH elongated peptides, TRH-Gly-Lys-Arg, TRH elongated peptides, TRH-Gly-Lys-Arg-Ala, TRH elongated peptides, P7 (Modification Q-H-P-G-L-R-F), TRH elongated peptides, P10 (Modification S-L-R-Q-H-P-G-L-R-F), TRH elongated peptides, Ps5 Modification pro-TRH[178-199], TRH elongated peptides, TRH-Ps5 (Modification pro-TRH[172-199]), Hypothalmic peptide, LHRH, Cyanoginosin-LA, Cyanoginosin-LB, Cyanoginosin-LR, Cyanoginosin-LY, Cyanoginosin-AY, Cyanoginosin-FR, Cyanoginosin-YR, Ne-acetyllysine-containing peptide, Gly-Lys (Ac)-e-aminocaproic acid (Aca)-Cys, Benzoic Acid, Benzenecarboxylic acid; phenylformic acid; dracylic acid, m-hydroxybenzoic acid, 3-hydroxybenzoic acid, o-methoxybenzoic acid, 2-methoxybenzoic acid, o-toluic acid, 2-Methylbenzoic acid, o-chlorobenzoic acid, 2-chlorobenzoic acid, o-aminobenzoic acid, 2-aminobenzoic acid, thiosalicylic acid, 2-Mercaptobenzoic acid; o-sulfhydrylbenzoic acid, Salicylamide, 2-Hydroxybenzamide, Saligenin, saligenol; o-hydroxybenzyl alcohol; Salicyl alcohol, 2-cyanophenol, 2-hydroxyphenyl acetic acid, p-hydroxybenzoic acid, p-aminobenzoic acid, 4-Aminobenzoic acid; vitamin Bx; bacterial vitamin H1, p-toluic acid, p-methylamino benzoic acid, p-chlorosalicylic acid, 4-chloro-2-hydroxybenzoic acid, 2,4-dihydroxybenzoic acid, beta-Resorcylic Acid; 2,4-dihydroxybenzenecarboxylic acid; BRA, 4-aminosalicylic acid, 4-Amino-2-hydroxybenzoic acid; p-aminosalicylic acid, Gentisic Acid, 2,5-dihydroxybenzoic acid; 5-hydroxysalicylic acid, Picolinic acid, o-Pyridinecarboxylic acid; 2-Pyridinecarboxylic acid, picolinic acid N-oxide, 3-hydroxypicolinic acid, 2-hydroxynicotinic acid, 7-methylguanine, N2-Carboxymethyl-N7-methylguanine, 2-(7-methyl-6-oxo-6,7-dihydro-1H-purin-2-ylamino)acetic acid, 7-methylxanthine, 7-methyluric acid, 7-methyladenine, Guanine, 2-Amino-1,7-dihydro-6H-purin-6-one; 2-aminohypoxanthine, Adenine, 6-aminopurine; 6-amino-1H-purine; 6-amino-3H-purine; 6-amino-9H-purine, 7-(2-Carboxyethyl)guanine, 7-CEGua, 7-Ethylguanine, 2-amino-7-ethyl-1H-purin-6(7H)-one, 7-(2,3-Dihydroxypropyl) guanine, 2-amino-7-(2,3-dihydroxypropyl)-1H-purin-6 (7H)-one, 7-(2-Hydroxyethyl)guanine, 2-amino-7-(2-hydroxyethyl)-1H-purin-6(7H)-one, 7-(2-[(2-Hydroxyethyl)amino]ethyl)-guanine, 2-amino-7-(2-(2-hydroxyethylamino)ethyl)-1H-purin-6(7H)-one, 7-Carboxymethylguanine, or 2-(2-amino-6-oxo-1,6-dihydropurin-7-yl)acetic acid. In some alternatives, the CAR or T cell receptor comprises a fragment specific for the hapten, wherein the CAR or TCR comprises 14G8, Anti 3-methylindole antibodies, 3F12, Anti 3-methylindole antibodies, 4A1G, Anti 3-methylindole antibodies, 8F2, Anti 3-methylindole antibodies, 8H1, Anti 3-methylindole antibodies, Anit-Fumonisin B1 antibodies, Anti-1,2-Naphthoquinone-antibodies, Anti-15-Acetyldeoxynivalenol antibodies, Anti-(2-(2,4-dichlorophenyl)-3(1H-1,2,4-triazol-1-yl)propanol) Antibodies (Anti-DTP antibodies), Anti-22-oxacalcitriol antibodies (As-1, 2 and 3), Anti-(24,25(OH)2D3) Antibodies (Ab11), Anti-(24,25(OH)2D3) Antibodies (Ab3), Anti-(24, 25(OH)2D3) Antibodies (Ab3-4), Anti-2,4,5-Trichlorophenoxyacetic acid antibodies, Anti (2,4,5-Trichlorphenoxyacetic acid) Antibodies, Anti-(2,4,6-Trichlorophenol) Antibodies, Anti-(2,4,6-Trichlorophenol) Antibodies, Anti 2,4,6-Trinitrotoluene (TNT) Antibodies, Anti-2,4-Dichlorophenoxyacetic acid(MAb's B5/C3, E2/B5, E2/G2, F6/C10, and F6/E5), Anti (2,4-Dichlorphenoxyacetic acid) Antibodies, Anti-2-hydroxybiphenyl-antibodies, Anti-(3,5,6-trichloro-2-pyridinol) Antibodies (LIB-MC2, LIB-MC3), Anti (3,5,6-trichloro-2-pyridinol) antibodies (LIB-MC2 MAb), Anti-3-Acetyldeoxynivalenol (3-AcDON) Antibodies, Anti-3-phenoxybenzoic acid (3-PBAc)-Antibodies, Anti-4-Nitrophenol antibodies, anti-4-nitrophenyl 4'-carboxymethylphenyl phosphate antibodies, Anti-7-(Carboxyethyl)guanine (7-CEGua) antibodies (group specific for 7-meGua), Anti-7-methylguanine (7-MEGua) antibodies, Anti-ABA antibodies, Anti Acephate antibodies (Antiserum 8377), Anti-acetyllysine antibodies (mAbs AL3D5, AL11, AKL3H6, AKL5C1), Anti Aculaetiside-A antibody, Anti Aflatoxin M1(AFM1)antibodies (mAbs A1, N12, R16, FF32), Anti-agatharesinol Antibody, Anti-agatharesinol Antibody, Anti Amidochlorantibodies, Anti-Amitrole antibodies (anti 1a-BSA antibodies), Anti ampicillin Antibodies (AMPI I 1D1 and AMPI II 3B5), Anti-anandamide antibodies (9C11.C9C, 30G8.E6C, 7D2.E2b, 13C2 MAbs), Anti atrazine antibodies, Anti-atrazine antibodies, Anti-Atrazine antibodies, Anti Atrazine Antibodies, Anti-Atrazine Antibodies, Anti-Atrazine Antibodies, Anti-Atrazine Antibodies (4063-21-1 MAb cell line mAb and scAbs), Anti-Atrazine Antibodies (4D8 and 6C8 scAb), Anti Atrazine Antibodies (C193), Anti Atrazine Antibodies (In Rabbit/Sheep), Anti Atrazine Antibodies (K4E7), Anti Atrazine Antibodies (MAb: AM7B2.1), Anti Atrazine Antibodies (ScAb), Anti Atrazine Mercapturic acid antibodies, Anti (Azinphos methyl) Antibodies (MAB's LIB-MFH14, LIB-MFH110), Anti benalaxyl antibody, Anti benzimidazolecarboxylic acid, Anti benzimidazoles antibody (Ab 587), Anti-Benzo [a]pyrene antibodies, Anti Benzo(a)pyrene antibodies (10C10 and 4D5 MAbs), Anti-(Benzoylphenylurea)-Antibodies (mainly against Diflubenzuron), Anti-berberine Antibodies, Anti-beta Indole Acetic Acid Antibodies, Anti-Biopterin (L-erythro form) Antibodies, Anti-Brevetoxin PbTx-3-Antibodies, Anti Bromacil Antibodies, Anti-Bromophos Antibodies, Anti-Bromophos ethyl Antibodies, Anti Butachlor antibodies, Anti-Captopril-MCC Antibodies, Anti-Carbamazepine (CBZ)-Antibodies, Anti Carbaryl Antibodies, Anti Carbaryl Antibodies (LIB-CNH32, LIB-CNH33, LIB-CNH36, LIB-CNH37, LIB-CNH45, LIB-CNA38), Anti-Carbaryl Antibodies (LIB/CNH-3.6 MAb), Anti Carbofuran Antibodies (LIB-BFNB-52, LIB-BFNB-62, LIB-BFNB-67), Anti Carbofuran Antibodies (LIB-BFNP21), Anti-CDA-antibodies, Anti-CDA-antibodies (anti-2-[2-Chloro-(2'-6'-diethyl)acetanilido]butanoic Acid), Anti-CDA-antibodies (anti-2-[2-Chloro-(2'-6'-diethyl)acetanilido]ethanoic Acid), Anti-CDA-antibodies (anti-5-(4-Chloroacetamido-3,5-diethyl)phenoxypentanoic Acid), anti-ceftazidime antibody, Anti-(chlorodiamino-s-triazine) Antibodies (Anti-CAAT) (PAb1-8), Anti Chlorothalonil Antibodies, Anti-Chlorpyrifos antibodies, Anti-Chlorpyrifos Antibodies, Anti-Chlorpyrifos Antibodies (LIB-AR1.1, LIB-AR1.4 Mabs), Anti-Chlorpyrifos Antibodies (LIB-C4), Anti (chlorpyrifos) antibodies (LIB-C4 MAb), Anti-Chlorpyrifos Antibodies (LIB-PN1 Mabs), Anti-Chlorpyrifos Antibodies (LIB-PN2 Mabs), Anti-Chlorpyrifos Antibodies (LIB-PO Mabs), Anti-chlorsulfuron antibodies, Anti-Chlorsulfuron antibodies, Anti Chlortoluron Antibodies (Antiserum), Anti-Cyanoginosin-LA antibodies (mAbs 2B2-2, 2B2-7, 2B2-8, 2B2-9, 2B2-10, 2B5-5, 2B5-8, 2B5-14, 2B5-15, 2B5-23), Anti (D-3-methoxy-4-hydroxyphenylglycol) antibodies, Anti-DDA antibodies, Anti DDT antibodies (PAbs and MAbs), Anti-DDT Mabs (LIB1-11, LIB5-21, LIB5-25, LIB5-28, LIB5-212, LIB5-51, LIB5-52, LIB5-53), Anti-DEC Antibodies (Anti diethylcarbamazine Antibodies), Anti DEHA antibodies, Anti-(Delor 103) antibodies, Anti-Deltamethrin Antibodies, Anti Deltamethrin Antibodies (Del 01 to Del 12 MAbs and PAbs), Anti-deoxynivalenol (DON) Antibodies, Anti-Deoxynivalenol (DON) Antibodies, Anti Dexamethasone Antibody, Anti Dexamethasone Antibody, Anti-Dinitrophenyl (DNP)-antibodies, Anti dinitrophenyl spin labeled antibodies (AN01-AN12), Anti Diuron Antoboides (MAb's: 21, 60, 195, 202, 275, 481, 488, 520), Anti-D-MHPG Antibodies, Anti DNC antibodies, Anti-EB1089 antibodies, Anti-ecdysone antibodies, Anti-endosulfan antibodies, Anti-Endosulfan antibodies, Anti Esfenvalerate antibodies (Ab7588), Anti estradiol antibodies, Anti-Fenitrothion antibodies (pAbs and mAbs), Anti-Fenpropimorph antibodies, Anti Fenthion Antibodies, Anti-Fenthion Antibodies, Anti FITC antibodies (B13-DEI), Anti-Flucofuron antibodies (F2A8/1/A4B3), Anti-flufenoxuron antibodies, and Anti-(Benzoylphenylurea)-Antibodies, Anti-Formononetin Antibodies, Anti-Furosemide antibodies (Furo-26, Furo37, furo-72, Furo 73 Mabs), Anti-GR151004 Antibodies, Anti-hCG-alpha-peptide Antibodies (FA36, Anti hydroxyatrazine antibodies (HYB-283-2), Anti-Hydroxysimazine Antibodies, Anti Imazalil Antibodies MoAb's (9C1-1-1, 9C5-1-1, 9C6-1-1, 9C8-1-1, 9C9-1-1, 9C12-1-1, 9C14-1-1, 9C16-1-1, 9C18-1-1, 9C19-1-1, 9E1-1, 9G2-1), Anti Irgarol Antibodies, Anti Isopentenyl adenosine antibodies, Anti Isoproturon Antibodies, Anti-KB-6806 antiserum, Anti-(+)lupanine antibodies, Anti Lysophosphatidic (LPA) acid, Anti M3G Ab1 and Ab2, Anti M3G Ab1 and Ab2, Anti-MBC antibodies (Anti-2-succinamidobenzimidazole antiserum), Anti Metanephrine antibodies, anti (+)methamphetamine antibodies, Anti-Methiocarb Antibodies (LIB-MXNB31, LIB-MXNB-33, LIB-MXNH14 and LIB-MXNH-15 MAbs), Anti Metolachlor antibodies, Anti-Metolachlor Antibodies, Anti-Metolachlor Antibodies (MAb 4082-25-4), Anti Molinate Antibodies, Anti monuron antibodies, Anti-morphine-3-glucuronide (E3 scFv antibody), Anti morphine antibodies, Anti-Morphine Antibodies, Anti-Morphine Antibodies (mAbs 8.2.1, 33.2.9, 35.4.12, 39.3.9, 44.4.1, 76.7F.16, 83.3.10, 115.1.3, 124.2.2, 131.5.13, 158.1.3, 180.2.4), Anti-Neopterin (D-erythro form) Antibodies, Anti-Nicarbazin Antibodies (Nic 6, Nic 7, Nic 8, and Nic 9), Anti Nicergoline Antibodies (Nic-1, Nic-2, Nic-3 & BNA-1, BNA-3), Anti-norflurazon antibodies, Anti NorMetanephrine antibodies, Anti (o-DNCP) Antibodies, Anti-P10 antibodies (TRH elongated peptide), Anti-Paraoxon Antibodies (BD1 and CE3), Anti Paraquat antibodies, Anti-Paraquat antibodies, anti Parathion-methyl antibodies, Anti PCB Antibodies (against 3,3',4,4'-tetrachlorobiphenyl) MAb S2B1, Anti pentachlorophenol antibodies, Anti Pentachlorophenol antibodies, Anti-Pentachlorophenol antibodies, Anti permethrin antibodies (Mabs Py-1, Py-3 and Py-4), Anti-Phencyclidine Antibodies (Mab 6B5 Fab), Anti-phenobarbital antibodies, Anti-phenobarbital antibodies, Anti-(p.p'-DDT)-Antibodies (LIB-DDT-35 and LIB-DDT5-52), Anti permethrin antibodies (Ab549), Anti Propoxur antibodies (LIB-PRNP15, LIB-PRNP21, LIB-PRNB21, LIB-PRNB33), Anti-Prostaglandin E2-antibodies, Anti-p-tyramine antibodies, Anti pyrene antibodies, Anti retronecine antibodies, Anti-Retronecine Antibodies, Anti salicylate antibodies, Anti Sennoside A antibodies (MAb 6(38), Anti Sennoside B antibodies (MAb's: 7H12, 5G6, 5C7), Anti Simizine antibodies, Anti Sulfonamides antibodies (Anti-TS), Anti-Sulocfuron antibodies (S2B5/1/C3), Anti sulphamethazine antibodies (21C7), Anti-synephrine antibodies, Anti-Thiabendazole antibodies (Antibody 300), Anti-Thiabendazole antibodies (Antibody 430 and 448), Anti-Thiram-Antibodies, Anti-THP antibodies (7S and 19S), Anti-Thromboxane B2 Antibodies, Anti-thymidine glycol monophosphate antibodies (mAb 2.6F.6B.6C), Anti-Thyroliberin (TRH) antibodies, Anti TNT antibodies (AB1 and AB2 antiserum), Anti Triadimefon Antibodies, Anti-triazine antibodies (AM1B5.1), Anti-triazine antibodies (AM5C5.3), Anti-triazine antibodies (AM5D1.2), Anti-triazine antibodies (AM7B2.1), Anti-triazine antibodies (SA5A1.1), Anti-Triazine serum (anti-ametryne), Anti-Triazine serum (anti-atrazine), Anti-Triazine serum (anti-simazine), Anti-Triazine serum (anti-simetryne), Anti Trifluralin Antibodies, Anti Trifluralin Antibodies, Anti Vincristine Antibodies, Anti-Zearalenone Antibodies, Anti Zeatin riboside antibodies, E2 G2 and E4 C2, Fab Fragment K411B derived from MAb K4E7 (isotype IgG2b with k light chain), LIB-BFNP23 Mab, MAb's H-7 and H-9 (against O,O-diethyl OP pesticides), MoAb 33A7-1-1, MoAb 33B8-1-1, MoAb 33C3-1-1, MoAb 3C10-1-1 and MoAb 3E17-1-1, MoAb 45D6-5-1, MoAb 45E6-1-1, MoAb 45-1-1, Mutant (GlnL89Glu) in Fab Fragment K411B derived from MAb K4E7 (isotype IgG2b with k light chain), Mutant (GlnL89Glu/ValH37Ile/GluL3Val) in Fab Fragment K411B derived from MAb K4E7 (isotype IgG2b with k light chain), Mutant (GlnL89Glu/ValH37Ile/GluL3Val) in Fab Fragment K411B derived from MAb K4E7 (isotype IgG2b with k light chain), Mutant (GlnL89Glu/ValH37Ile) in Fab Fragment K411B derived from MAb K4E7 (isotype IgG2b with k light chain), Mutant (GlnL89Glu/ValH37Ile) in Fab Fragment K411B derived from MAb K4E7 (isotype IgG2b with k light chain), Mutant (GluH50Gln) in Fab Fragment K411B derived from MAb K4E7 (isotype IgG2b with k light chain), Mutant (GluH50X) in Fab Fragment K411B derived from MAb K4E7 (isotype IgG2b with k light chain), Mutant (GlyH100aAla) in Fab Fragment K411B derived from MAb K4E7 (isotype IgG2b with k light chain), Mutant (GlyH100aSer) in Fab Fragment K411B derived from MAb K4E7 (isotype IgG2b with k light chain), Mutant (HisH95Phe) in Fab Fragment K411B derived from MAb K4E7 (isotype IgG2b with k light chain), Mutant (HisH95Tyr) in Fab Fragment K411B derived from MAb K4E7 (isotype IgG2b with k light chain), Mutant (PheL32Leu) in Fab Fragment K411B derived from MAb K4E7 (isotype IgG2b with k light chain), Mutant (TrpH33Phe,Tyr,Leu) in Fab Fragment K411B derived from MAb K4E7 (isotype IgG2b with k light chain), Mutant (Tryl96Phe) in Fab Fragment K411B derived from MAb K4E7 (isotype IgG2b with k light chain), Mutant (TryL96Phe) in Fab Fragment K411B derived from MAb K4E7 (isotype IgG2b with k light chain), Mutant (ValH37Ile) in Fab Fragment K411B derived from MAb K4E7 (isotype IgG2b with k light chain), Mutant (ValH37Ile) in Fab Fragment K411B derived from MAb K4E7 (isotype IgG2b with k light chain), P6A7 MAb, PNAS2 6/3 56(1)-1-5-1, PNAS2 6/3 56(1)-1-5-2, PNAS2 6/3 56(1)-1-10-4, PNAS2 6/3 56(1)-1-10-5 and PNAS2 6/3 56(1)-3-1-5, Alexa Fluor 405/Cascade Blue dye antibody, Alexa Fluor 488 dye antibody, BODIPY FL dye antibody, Dansyl antibody, Fluorescein/Oregon Green dye antibody, Lucifer yellow dye antibody, Tetramethylrhodamine and Rhodamine Red dye antibody, Texas Red and Texas Red-X dye antibody, Biotin antibody, Dinitrophenyl antibody and/or Nitrotyrosine antibody or any portion thereof of the aforementioned haptens.

In a third aspect, a method of treating, ameliorating, or inhibiting a cancer in a subject is provided, the method comprising: a) introducing, providing, or administering to a subject a composition that comprises a lipid, which comprises a target moiety that is bound to a masking moiety and, optionally, by attachment through a spacer, b) introducing, providing, or administering to said subject a cell comprising a chimeric antigen receptor (CAR) or T cell receptor (TCR), which is specific for the target moiety once the masking moiety is removed from the target moiety, c) removing the masking moiety from the target moiety thereby allowing the target moiety to bind to the CAR present on the cell, and, d) optionally, measuring or evaluating the binding of the cell comprising the CAR to the lipid, after steps a-c and/or e) optionally, measuring or evaluating the treatment, amelioration, or inhibition of said cancer after steps a-d, and/or f) optionally, identifying a subject in need of a therapy for cancer prior to steps a-c. In some alternatives, the lipid comprises a polar head group and a hydrophobic group. In some alternatives, the hydrophobic group is fatty acid such as a carbon chain or an aliphatic chain. In some alternatives, the carbon chain or fatty acid is saturated or unsaturated. In some alternatives, the hydrophobic group comprises an alkyl, alkenyl or alkynyl group. In some alternatives, the hydrophobic group comprises a terpenoid lipid such as a steroid or cholesterol or an aromatic ring. In some alternatives, the hydrophobic group comprises an ether linkage, wherein the ether linkage is between the polar head group and the aliphatic chain. In some alternatives, the lipid is a phospholipid ether. In some alternatives, the polar head comprises a choline, a phosphatidylcholine, sphingomyelin, phosphoethanolamine group, an oligosaccharide residue, a sugar residue, phosphatidyl serine or phosphatidyl inositol. In some alternatives, the sugar is a glycerol. In some alternatives, the target moiety is a hapten, poly(his) tag, Strep-tag, FLAG-tag, V5-tag, Myc-tag, HA-tag, NE-tag, biotin, digoxigenin, dinitrophenol or fluorescein. In some alternatives, the hydrophobic group comprises a carbon alkyl chain. In some alternatives, the carbon alkyl chain comprises at least 8, 9, 10, 11, 12, 13, 14, 15, 16, 17, 18, 19, 20, 21 or 22 carbons or any number that is within a range defined by any two aforementioned values. In some alternatives, the carbon alkyl chain comprises 8-22 carbons, such as 8-12, 12-14, 14-16, or 16-22 carbons. In some alternatives, the polar-head group comprises phosphocholine, a piperidine moiety or a trimethylarseno-ethyl-phosphate moiety. In some alternatives, the spacer comprises a PEG spacer, a Hapten (2×), (3×), (4×), or (5×) spacer, or an alkane chain. In some alternatives, the PEG spacer comprises 1, 2, 3, 4, 5, 6, 7, 8, 9, 10, 11, 12, 13, 14, 15, 16, 17, 18, 19, 20 or 21 PEG molecules, or any amount of PEG molecules that is within a range defined by any two aforementioned values. In some alternatives, the masking moiety comprises a phenolic hydroxyl group or PEG. In some alternatives, the phenolic hydroxyl group is bound to a hydroxyl on a xanthene moiety of fluorescein. In some alternatives, the masking moiety is bound to the target moiety by a cleavable moiety, which is optionally configured to be specifically cleavable in a tumor microenvironment. In some alternatives, the cleavable moiety, which is configured to be cleavable in a tumor microenvironment, is cleaved by a reactive oxygen species reaction, an acidic pH, hypoxia, or nitrosylation. In some alternatives, the cell is provided to the subject 1, 2, 3, 4, 5, 6, 7, 8, 9, 10, 11, 12, 15, 20, 24, 36, 48, 60 or 72 hours after administration of the composition, or any time within a range defined by any two aforementioned values. In some alternatives, the cell is provided to the subject 1, 2, 3, 4, 5, 6, 7, 8, 9, 10, 11, 12, 15, 20, 24, 36 or 48 hours before administration of the composition, or any time within a range defined by any two aforementioned values. In some alternatives, the cell is provided to the subject within seconds or minutes, such as less than an hour, of providing the composition to the subject. In some alternatives, a boost of the cell and/or the composition is provided to the subject. In some alternatives, an additional cancer therapy is provided, such as a small molecule, e.g., a chemical compound, an antibody therapy, e.g., a humanized monoclonal antibody with or without conjugation to a radionuclide, toxin, or drug, surgery, and/or radiation. In some alternatives, the cancer is breast, ovarian, lung, pancreatic, prostate, melanoma, renal, pancreatic, glioblastoma, neuroblastoma, medulloblastoma, sarcoma or liver cancer. In some alternatives, the cell comprising the CAR or TCR is a T cell. In some alternatives, the CAR or TCR is on the surface of the cell or the T cell. In some alternatives, the cell is a precursor T cell. In some alternatives, the precursor T cell is a hematopoietic stem cell. In some alternatives, the cell is a CD8+ T cytotoxic lymphocyte cell selected from the group consisting of naïve CD8+ T cells, central memory CD8+ T cells, effector memory CD8+ T cells and bulk CD8+ T cells. In some alternatives, the cell is a CD4+ T helper lymphocyte cell that is selected from the group consisting of naïve CD4+ T cells, central memory CD4+ T cells, effector memory CD4+ T cells, and bulk CD4+ T cells. In some alternatives, the lipid intercalates in a lipid bilayer of a target cell, such as a cancer cell. In some alternatives, the target cell is a tumor cell. In some alternatives, the target cell is an immune cell. In some alternatives, the masking moiety is removed when the composition is within an acidic environment. In some alternatives, the acidic environment comprises a pH of 4, 5, 6 or 6.5 or any pH in between a range defined by any two aforementioned values. In some alternatives, the masking moiety is removed by nitrosylation. In some alternatives, the hapten, which is a target moiety, comprises Alexa Fluor 405, Cascade Blue, Alexa Fluor 488, BODIPY, Dansyl chloride, Oregon Green, Lucifer yellow, Rhodamine, Tetramethylrhodamine, Nitrotyrosine, digoxigenin, 2,4-Dichlorophenoxyacetic acid, Atrazine (2-Chloro-4-(ethylamino)-6-(isopropylamino)-s-triazine), Nicotine (3-(1-Methyl-2-pyrrolidyl)pyridine, Black Leaf), Morphine (morph, Morphine Sulfate), 2,4-

DINITROCHLOROBENZENE (1-Chloro-2,4-dinitrobenzene; DNCB; Dinitrochlorobenzene), 4-chloro-6-(ethylamino)-1,3,5-triazine-2-(6-aminohexanecarboxylic acid), Structurally related s-triazines (Modifications: H/Cl/C6 R1=NH2- R2=—Cl R3=—NH—(CH2)5-COOH; iPr/Cl/nBu R1=(CH3)2-CH—NH— R2=—Cl R3=—NH—(CH2)3-(CH3)), Ametryn (2-Ethylamino-4-isopropylamino-6-methylthio-1,3,5-triazine), Deethylatrazine (DEA) (Structurally related s-triazines), Deisopropylatrazine (DIA) (Structurally related s-triazines), Deethyldeisopropylatrazine (DEDIA) (Structurally related s-triazines), Deethyldeisopropylatrazine (DEDIA) (Structurally related s-triazines), HydroxyAtrazine (HA) (Structurally related s-triazines), DeisopropylHydroxyAtrazine (DIHA) (Structurally related s-triazines), DeethylDeisopropylHydroxyAtrazine (DEDIHA) (Structurally related s-triazines), Simazine (Structurally related s-triazines), Desmetryne (Structurally related s-triazines), Prometryne (Structurally related s-triazines), 2-hydroxyatrazine (atrazine derivative), 2-hydroxypropazine (structurally related s-triazine), 2-hydroxysimazine, N-(4-Amine-6-hydroxy-[1,3,5]triazin-2-yl)-4-aminobutanoic Acid (Modification: R1=NH2 R2=NH(CH2)3COOH R3=OH), SulcoFuron, 5-chloro-2-{4-chloro-2-[3-(3,4-dichlorophenyl)ureido]phenoxy}benzenesulfonic acid, Fluco-Furon (1,3-bis(4-chloro-α,α,α-trifluoro-m-tolyl)urea), Agatharesinol, Sequirin C, Sugiresinol, Hydroxysugiresinol, Hinokiresinol, Coniferyl alcohol, Cinnamyl alcohol, p-Coumaric acid, Cinnamic acid, p-Coumaric acid, Cinnamic acid, Hinokinin, Guaiacylglycerol-beta-guaiacyl ether, Morphine-3-glucuronide (M3G), Codeine, Nor-Codeine, 6-Monoacetylmorphine, (+) Methamphetamine, Ceftazidime, Phenobarbital, p-hydroxyPhenobarbital, p-aminophenobarbital, Cyclobarbital, 3'-Ketocyclobarbital, 3'-Hydroxycyclobarbital, Secobarbital, Barbital, Metharbital, Barbituric acid, Thiopental, Thiobarbituric acid, Primidone, Glutethimide, Pentobarbital, Heroin, Diacetylmorphine, Levallorphan, L-11-Allyl-1,2,3,9,10,10a-hexahydro-4H-10,4a-iminoethanophenanthren-6-ol, Pethidine (Demerol; Dolantin; Meperidine; Ethyl 1-methyl-4-phenylpiperidine-4-carboxylate; Isonipecaine), Methamphetamine, d-Desoxyephedrine; Methedrine; Tolpropamine; Pratalgin; Pragman. Benzoylecgonine, 3-Carboxymethylmorphine, Cocaine, 5-benzimidazolecarboxylic acid, ABA (4-acetyl benzoic acid), Dexamethasone, Flumethasone, 6alpha, 9 alpha-difluoro-11 beta, 17,21-trihydroxy-16 alpha-methylpregna-1,4-diene-3,20-dione, 9 alpha-fluoro-11 beta,17,21-trihydroxy-16 beta-methylpregna-1,4-diene-3,20-dione, 9-alpha-fluroprednisolone, Desoxymethasone, Triamcinolone, 9 alpha-fluoro-11 beta,16 alpha, 17,21-tetrahydroxypregna-1,4-diene-3,20-dione, Fluocortolone, 6 alpha-fluoro-11 beta,21-dihydroxy-pregna-1,4-diene-3,20-dione, Cortisol, 11 beta, 17,21-trihydroxypregna-4-ene-3,20-dione, Prednisone, 17,21-dihydroxypregn-4-ene-3,11,20-trione, Methylprednisolone, 11 beta, 17,21-trihydroxy-6 alpha-methylpregna-1,4-diene-3,20-dione, Triamcinolone hexacetonide, 21-(3,3-dimethyl-1-oxobutoxy)-9 alpha-fluoro-11-hydroxy-16,17-[(1-methylethylidene) bis(oxy)]pregna-1,4-diene-3,20-dione, Carbofuran, 2,3-dihydro-2,2-dimethyl-7-benzofuranyl methylcarbamate, BFNP (3-[[(2,3-dihydro-2,2-dimethyl-7-benzofuranyloxy)carbonyl]amino]propanoic acid), Carbofuran derivative, 2,3-dihydro-2,2-dimethyl-7-benzofuranol, Bendiocarb, Carbaryl, Methiocarb, Propoxur, Aldicarb, Methomyl, Benalaxyl, methyl N-(phenylacetyl)-N-(2,6-xylyl)-DL-alaninate, Bn-Ba (4-[2-(N-phenylacetyl-N-2,6-xylylamino)propionamido] butyric acid), Bn-COOH (4-[2-(N-phenylacetyl-N-2,6-xylyl-DL-alanine), Benalaxyl derivative, Furalaxyl, Metalaxyl, Acetochlor, Dimetachlor, Metolachlor, 2-chloro-6'-ethyl-N-(2-methoxy-1-methylethyl)acet-o-toluidine, Diethathyl-ethyl, Benzoylprop-ethyl, Benzoylprop-ethyl, 2,4,5-Trichlorophenoxyacetic acid, 2-chloro-6'-ethyl-N-(2-methoxy-1-methylethyl)acet-o-toluidine, Diethathyl-ethyl, Benzoylprop-ethyl, Propachlor, Propachlor, 2,4,5-Trichlorophenoxyacetic acid, 2,4,5,T; Weedone, 2,4-Dichlorophenoxybutyric acid (2,4-DB), 2,4-DB; Butanoic acid, 4-(2,4-dichlorophenoxy)-; Butoxone; Embutone, MCPA, 2-Methyl-4-chlorophenoxyacetic acid; Metaxon, Dichlorprop (2,4-DP), 1-[(2-chloro)phenylsulfonyl]monoamidosuccinic acid, Chlorsulfuron, chlorbromuron, amidosulfuron, chlortoluron, isoproturon, diuron, Linuron O-Methyl-O-(4-nitrophenyl)-N-(4-carboxybutyl)-phosphoramidothioate Parathion-methyl, O,O-dimethyl O-4-nitrophenyl phosphorothioate; Methaphos; Wolfatox; Dimethylparathion; Metacide, Parathion-ethyl, DIETHYL P-NITROPHENYL THIOPHOSPHATE; O,O-DIETHYL O—(P-NITROPHENYL) PHOSPHOROTHIOATE; Fenitrothion, O,O-dimetyl O-4-nitro-m-tolyl phosphorothioate, Fenthion, O,O-dimethyl O-4-methylthio-m-tolyl phosphorothioate, Bromophos, O-4-bromo-2,5-dichlorophenyl O,O-dimethyl phosphorothioate, chlorpyrifos-methyl, O,O-dimethyl O-3,5,6-trichloro-2-pyridyl phosphorothioate, Oxidized parathion-methyl, Paraoxon, phosphoric acid, O,O-diethyl O-(4-nitrophenyl) ester, Diazinon, O,O-diethyl O-2-isopropyl-6-methylpyrimidin-4-yl phosphorothioate, Azinphos-methyl, pirimiphos-methyl, O-2-diethylamino-6-methylpyrimidin-4-yl O,O-dimethyl phosphorothioate, Methidathion, S-2,3-dihydro-5-methoxy-2-oxo-1,3,4-thiadiazol-3-ylmethyl O,O-dimethyl phosphorodithioate, Dimethylchlorothiophosphate, 4-NITROPHENOL, p-nitrophenol, Phenolic derivative (Modification On benzene ring; R1=OH R2=NO2 R3=H R4-CH2COOH R5=H R6=H); 2-Nitrophenol, o-Nitrophenol, 3-Nitrophenol, m-nitrophenol, 2,4-Dinitrophenol, 3,4-Dinitrophenol, 2,5-Dinitrophenol, 2,4-Dinitro-6-methylphenol, 2,3,6-trinitrophenol, 2-Chlorophenol, 4-Chloro-3-methylphenol, Fenitroxon, 3-Methyl-4-nitrophenol, Nonylphenol, HOM(3-[2-hydroxy-5nitro benzylthio] propionic acid, Phenol, Delor 103, Polychlorinated Biphenyls, Delor 104, Polychlorinated Biphenyls, Delor 105, Polychlorinated Biphenyls, Delor 106, 4,4'-Dichlorobiphenyl, PCB congeners, 2,4,4'-Trichlorobiphenyl, PCB congeners, 2,4'-Bichlorobiphenyl, PCB congeners, 2,2'-Dichlorobiphenyl, PCB congeners, 2,4,5-Trichlorobiphenyl, PCB congeners, 3,3',4,4'-Tetrachlorobiphenyl, PCB congeners, PCB congeners, 2,2',4,4',5,5'-Hexachlorobiphenyl, 2-(5-Carboxypentanoylamino)-4,4'-dichlorobiphenyl, Biphenyl derivative, 4-chlorophenoxyacetic acid, 2-Chlorophenoxyacetic acid, DDT,1,1,1-trichloro-2, 2-bis-(p-chlorophenyl)ethane, DDE, 1,1-dichloro-2, 2-bis(p-chlorophenyl)ethylene, p-Chlorophenol, 4-Chlorophenol, m-Chlorophenol 3,4-Dichlorophenol, 3,5-Dichlorophenol, 2,3,4-Trichlorophenol, 2,3,5-Trichlorophenol, 3-methylindole, 3-methylindole Derivatives, 4-(3-methylindol-5-yloxy)butanoic acid, 4-(3-methylindol-5-yloxy)butanoic acid, 3-methylindole Derivatives, 6-[n-3-methylindol-5-yloxy carbonyl)amino]hexanoic acid, 6-[n-3-methylindol-5-yloxy carbonyl)amino]hexanoic acid, 3-methylindole Derivatives, 2-[4-(3-methylindol-6-yl)but-1-ylthio]acetic acid, 2-[4-(3-methylindol-6-yl)but-1-ylthio]acetic acid, 3-methylindole Derivatives, 4-(3-methylindol-6-yl-4-oxo) butanoic acid, 4-(3-methylindol-6-yl-4-oxo)butanoic acid, 3-methylindole Derivatives, 6-(3-methylindol-7-yloxy) hexanoic acid, 6-(3-methylindol-7-yloxy)hexanoic acid, Indole, Indole-3-Carboxylic acid, Indole Derivative-Indole-3-Acetic acid, Indole-3-Acetic acid, Indole Derivative-Indole-3-Propionic acid, Indole-3-Propionic acid, Indole Derivative-Indole-3-Carbinol, Indole-3-Carbinol, Tryptophan, Tryptamine, 5-Methoxyindole-3-carboxaldehyde, 5-Methoxytryptamine, 5-Methoxyindole, 6-Methoxyindole, 7-Methoxyindole,EB1089(Seocalcitol),EB1089(Seocalcitol) Derivative, (22E,24E)-Des-A,B-24-homo-26,27-dimethyl-8-[(E)-N-(2-carboxyethyl)-carbamoylmethylidene]-cholesta-22,24-dien-25-ol, 1 alpha-25-dihydroxyvitamin D3, 25(OH)D3,25-hydroxyvitamin D3,24R,25(OH)2D3, 24R,25-dihydroxyvitamin D3, Vitamin D2, ergocalciferol, Vitamin D3, cholecalciferol,EB1446,EB1436,EB1445, EB1470, DeethylHydroxyAtrazine (DEHA) (Structurally related s-triazines), Irgarol 1051, Flourescein Isothiocyanate, FITC, Metanephrine, NorMetanephrine, Propazine, Terbutylazine, Terbuthylazine, 6-chloro-N-(1,1-dimethylethyl)-N'-ethyl-1,3,5-triazine-2,4-diamine, (Structurally related s-triazines), Ametryn (2-Ethylamino-4-isopropylamino-6-methylthio-1,3,5-triazine (Modification iPr/SCH3/Et R1=(CH3)2-CH—NH— R2=—SCH3 R3=—NH—CH2-CH3, Irgarol, Cyanazine (Modification R1=Cl R2=NHCH2CH3 R3=NHCCN(CH3)2), OH-Terbutylazine, Terbutylazine-2OH, Hydroxytriazine (EQ-0027), Deisopropylatrazine (Structurally related S-triazine), Desethylterbutylazine (Structurally related S-triazine), Desethyl-deisopropylatrazine (Structurally related S-triazine), Atraton, Terbutryn (Structurally related s-triazines), Atrazine derivative (Modification R1=—NHCH(CH3)2 R2=—S(CH2)2COOH R3=—NHC2H5), Cyanuric chloride, Trifluralin, (Structurally related s-triazines) tBu/C4/SCH3 (Modification R1=—NH—C—(CH3)3 R2=—NH(CH2)3COOH R3=—SCH3), Sulphamethazine, (Structurally related s-triazines) 6-[[[4-Chloro-6-(methylamino)]-1,3,5-triazin-2-yl]amino]hexanoic Acid (Modification Me/Cl/C6 R1=—NHCH3 R2=—Cl R3=—NH(CH2)5COOH), (Structurally related s-triazines) Procyazine (Modification R1=—Cl R2=—NHcyclopropyl R3=—NHCCN(CH3)2), (Structurally related s-triazines), Prometon (Modification R1=—OCH3 R2=—NHCH(CH3)2 R3=—NHCH(CH3)2); (Structurally related s-triazines) Atrazine Mercapturic Acid (AM) (Modification R1=—SCH2CH(NHAc)COOH R2=—NHCH2CH3 R3=—NHCH(CH3)2), (Structurally related s-triazines), desethyl atrazine mercapturic acid (desethyl AM) (Modification R1=—NAcCys R2=—NH2 R3=—NHCH(CH3)2), (Structurally related s-triazines), deisopropyl atrazine mercapturic acid (deisopropyl AM) (Modification R1=—NAcCys R2=—NHCH2CH3 R3=—NH2), (Structurally related s-triazines), didealkylated atrazine mercapturic acid (didealkylated AM) (Modification R1=—NAcCys R2=—NH2 R3=—NH2), (Structurally related s-triazines), simazine mercapturate (Modification R1=—NAcCys R2=—NHCH2CH3 R3=—NHCH2CH3), (Structurally related s-triazines) (Modification R1=—S(CH2)2COOH R2=—NHCH2CH3 R3=—NHCH2CH3), (Structurally related s-triazines) (Modification R1=—Cl R2=—NHCH(CH3)2 R3=—NH(CH2)2COOH), (Structurally related s-triazines) (Modification R1=—Cl R2=—NHCH2CH3 R3=—NH(CH2)2COOH), (Structurally related s-triazines), atrazine mercapturic acid methyl ester (AM methyl ester) (Modification R1=—NAcCysME R2=—NHCH2CH3 R3=—NHCH(CH3)2), N-acetylcysteine, S-benzyl mercapturate, (Structurally related s-triazines), simetryn (Modification R1=—SCH3 R2=—NHCH2CH3 R3=—NHCH2CH3), Metribuzin, 4-amino-6-tert-butyl-4,5-dihydro-3-methylthio-1,2,4-triazin-5-one, Sulpha Drugs, N4-acetyl-sulphamethazine (Modification N4-acetyl-sulphamethazine), Sulpha Drugs, Sulphathiazole, Sulphathiazole, Sulphamerazine, Sulphamerazine, Sulphaquinoxaline, Sulphaquinoxaline Sulphachlorpyridazine, Sulphachlorpyridazine, Sulphapyridine, Sulphadimethoxine, Sulphadimethoxine, Sulphamethoxazole, Sulphamethoxazole, Sulphisoxazole, Sulphisoxazole, Sulphamethizole, Sulphamethizole, Sulphanilamide, Sulphanilamide, Sulphaguanidine, Sulphaguanidine, Sulphadiazine, Sulphadiazine, Sulphamethoxypyridazine, Sulphamethoxypyridazine, Pentachlorophenoxypropionic acid, Pentachlorophenol, PCP, 2,3,5,6-Tetrachlorophenol, 1,2,4,5 Tetrachlorobenzene, 2,4,6 Trichlorophenol, 2-Methoxy-3,5,6-trichloropyridine, 1,3,5 Trichlorobenzene, 1,3 Dichlorobenzene, 2,4,5-Trichlorophenol, 2,6-Dichlorophenol, 3,5,6-Trichloro-2-pyridinoxyacetic acid, 3,5,6-Trichloro-2-Pyridinol, TCP, 2,4-Dichlorophenol, 2,5-Dichlorophenol, DNC, 4,4'-dinitrocarbanilide, (Structurally related s-triazines), Dichloroatrazine, (Structurally related s-triazines), Dichlorosimazine, 1-((6-chloropyridin-3-yl)methyl)imidazolidin-2-imin, Pyridine Derivative, 6-chloropyridine-3-carboxylic acid, Nicotinic acid, Pyridine Derivative, N-((6-chloropyridin-3-yl)methyl)-N-methylacetamide, (6-chloropyridin-3-yl)-N-methylmethanamine, (6-chloropyridin-3-yl)methanol, Imidacloprid, 1-(6-chloro-3-pyridylmethyl)-N-nitroimidazolidin-2-ylideneamine, Acetamiprid, (E)-N1-[(6-chloro-3-pyridyl)methyl]-N2-cyano-N1-methylacetamidine, Nitenpyram, Deltamethrin, 1(R)-cis-alpha (S)-3-(2,2-dibromoethenyl)-2,2-dimethylcyclopropane carboxylic acid cyano(3-phenoxyphenyl)methyl ester, DON, deoxynivalenol, DON derivative, 15-AcDON (15-acetyldeoxynivalenol), DON derivative, 3-AcDON (3-acetyldeoxynivalenol), DON derivative, 3,15-DiacDON (3,15-diacetyldeoxynivalenol), DON derivative, 3,7,15-TriacDON (3,7,15-Triacetyldeoxynivalenol), NIV (nivalenol), nivalenol, NIV Derivative, 4-AcNIV (fusarenon X), Flutolanil, alpha,alpha,alpha-trifluoro-3'-isopropoxy-o-toluanilide, Mepronil, Mebenil, Benodanil, 24,25(OH)2D3, (24R)-24,25-dihydroxyvitamin D3, 24S,25(OH)2D3, 24S,25-dihydroxyvitamin D3, 25R,26(OH)2D3, 25R,26-dihydroxyvitamin D3, 25S,26(OH)2D3, 25S,26-dihydroxyvitamin D3, 1,24,25(OH)3D3, 1,24,25-trihydroxyvitamin D3, 1,25-lactone, (23S,25R)-1,25(OH)2 D3 26,23-lactone, 24,25(OH)2-7-DHC, 24,25(OH)2-7-dehydrocholesterol, 25(OH)D3 3S, 25(OH)D3 3-sulfate, 24,25(OH)2D3-Hemiglutarate Derivative, 11 alpha-hemiglutaryloxy-(24R)-24,25-dihydroxyvitamin D3, 24,25(OH)2D3-Hemiglutarate Derivative, (24R)-24,25-dihydroxyvitaminD3-3-hemiglutarate, 24R,25(OH) 2D2, 24S,25(OH)2D2, 25(OH)D2, 1,24(OH)2D3, 2,3,6-Trichlorophenol, Tetrachlorohydroquinone, Pentachloroaniline, Pentachlorobenzene, 2,3-Dinitrotoluene, 4-Dinitrotoluene, 2,4,5-Trichloronitrobenzene, 3-(3-Hydroxy-2,4,6-trichlorophenyl)-propanoic acid, 2,3,4,6-Tetrachlorophenol, 2,4,6-Trichloroanisol, 2,4,6-TCA, Pentabromophenol, PBP, 2,4,6-Tribromophenol, 2,4,6-TBP, 2-Bromo-4-Chlorophenol, 2-B-4-CP 2,4-Dibromophenol, 2,4-DBP, 2,6-Dibromophenol, 2,6-DBP, 4-Bromophenol, 4-BP, Furosemide, Ampicillin, Amoxicillin, 6-amino-penicillanic acid (6-APA), Azlocillin, Bacampicillin, Carbenicillin, Epicillin, Cloxacillin, Dicloxacillin, Metampicillin, Methicillin, Moxalactam, Oxacillin, Penicillin G, benzyl penicillin, Penicillin V, phenoxy methyl penicillin, Pheneticillin, Piperacillin, Ticarcillin, Ampicillin hydrolyzed, Penicillin G hydrolyzed, 3-phenoxybenzoic acid (3-PBAc) Chlorpyrifos, Chlorpyrifos derivatives, HClo1, Synthesized directly from chlorpyrifos technical grade by substitution of the chlorine in position 6 by a 3-mercaptopropanoic acid spacer arm, Chlorpyrifos derivatives, HTCP (Modification HTCP of TCP metabolite was prepared from HClo1 by hydrolysis of the thiophosphate ester), Zeatin Riboside (trans isomer), Zeatin (trans isomer), N6-(2-isopentenyl)- adenosine, IPA, N6-(2-isopentenyl)-adenine, 2-iP, Benzyladenine, Kinetin, monuron, monolinuron, fenuron, neburon, propanil, propham, chloropropham, 4-chloroaniline, Methyl Urea Derivative, 1-(3-Carboxypropyl)-3-(4-chlorophenyl)-1-methylurea, Methyl Urea Derivative, 1-(5-Carboxypentyl)-3-(4-chlorophenyl)-1-methylurea, metobromuron, Sennoside B, SB, Sennoside B possessed a erythro configuration between C-10 and C-10', Sennoside A (Modification Sennoside A possessed a threo configuration between C-10 and C-10'), Rhein, Emodin, Aloe-emodin, Barbaloin, 1,4 Dihydroxyanthraquinone, Rhaponticin, Galic acid, Vanillic acid, Caffeic acid, Homogentisic acid, Esculin, Cinnamtannin B1, Baicalin, Naringin hydrate, Wogonin, Wogonin 7-o-beta-glucuronide, Curcumin, delta1-Tetrahydrocannabinolic acid, delta1-Tetrahydrocannabinol, (+−)-cis-4-Aminopermethrin, 3-(4-Aminophenoxy)benzyl(+−)-cis-3-(2,2-dichloroethenyl)-2,2-dimethylcyclopropanecarboxylate, Permethrin, trans-Permethrin, cis-Permethrin, Cypermethrin, Phenothrin, Resmethrin, Cyfluthrin, trans-Permethrin acid Esfenvalerate, Fluvalinate, Fenpropathrin, cis-permethrin acid, 4-Phenoxybenzoyl alcohol, Diuron Derivative, 1-(3-Carboxypropyl)-3-(3,4-dichlorophenyl)-1-methylurea, Siduron, Terbuthiuron, Barban, acid trifluralin, 2,6-dinitro-N-propyl-N-(2-carboxyethyl)-4-(trifluoromethyl)benzenamine, TR-13, 2-ethyl-7-nitro-1-propyl-5-(trifluoromethyl)-1H-benzimidazole, benefin, 2,6-dinitro-N-butyl-N-ethyl-4-(trifluoromethyl)benzenamine, TR-2, 2,6-dinitro-N-propyl-4-(trifluoromethyl)benzenamine, ethalfluaralin, 2,6-dinitro-N-ethyl-N-(2-methyl-2-propenyl)-4-(trifluoromethyl) benzenamine, TR-40, N-(2,6-dinitro-4-(trifluoromethyl) phenyl)-N-propylpropanamide, TR-15, 2-ethyl-4-nitro-6-(trifluoromethyl)-1H-benzimidazole, TR-3, 2,6-dinitro-4-(trifluoromethyl)benzenamine, TR-6, 3-nitro-5-(trifluoromethyl)-1,2-benzenediamine, TR-9, 5-(trifluoromethyl)-1,2,3-benzenetriamine, TR-21, 4-(dipropylamino)-3,5-dinitrobenzoic acid, TR-36M, 3-methoxy-2,6-dinitro-N,N-dipropyl-4-(trifluoromethyl)benzenamine, oryzalin, 3,5-dinitro-4-(dipropylamino)benzenesulfonamide, pendimethalin, 2,6-dinitro-N-(1-ethylpropyl)-3,4-dimethylbenzenamine, penta galloyl glucose, Pyrene Pyrene-1-carboxaldehyde, Phenanthrene, Benzo(a)pyrene, 3,4-Benzopyrene, Anthracene, 3,4-Benzopyrene, Acenaphthene, Fluorene, Chrysene, 1,2-Benzphenanthrene, Benzo[g,h,i]perylene, Benzo[e]pyrene, Acenaphthylene, Fluoranthene, Benzo(j,k)fluorene, Indeno-1,2,3-cd-pyrene, 1,10-(1,2-Phenylene)pyrene, Benzo[a]anthracene, 1,2-Benzanthracene, Benzo(k)fluoranthene, Naphthalene, Benzo[a]fluoranthene, Dibenzo[ah]anthracene, 1,2:5,6-Dibenzanthracene, 2,3-Diaminonaphthalene, 2,6-Dinitroaniline, 17-beta-estradiol (ED), estra-1,3,5(10)-triene-3,17-beta-diol, Trifluralin derivative, 2,6-dinitro-4-tri-fluoromethylaniline, Trifluralin derivative, N-(2,6-dinitro-4-trifluoromethylphenyl)-6-aminohexanoic acid, Trifluralin derivative, N-(2,6-dinitro-4-trifluoromethylphenyl)-N-methyl-6-aminohexanoic acid, Trifluralin derivative, N-(2,6-dinitro-4-trifluoromethylphenyl)-N-propyl-6-aminohexanoic acid, Trifluralin derivative, N-(2,6-dinitro-4-trifluoromethylphenyl)-6-aminohexanoic acid methyl ester, Trifluralin derivative, N-(2,6-dinitro-4-trifluoromethylphenyl)-6-aminohexanoic acid tert-butyl ester, Benfluralin, Ethalfluralin, Trifluralin derivative, 2,6-Dinitro-4-trifluoromethylphenol, Isopropalin, Aniline, 2-Hydroxybenzotrifluoride, N-propyl-6-aminohexanoic acid, N-methyl-6-aminohexanoic acid, MHPG Derivatives, D-MHPG (D-3-methoxy-4-hydroxyphenylglycol), MHPG Derivatives, L-MHPG (L-3-methoxy-4-hydroxyphenylglycol), MHPG Derivatives, DL-MHPG (DL-3-methoxy-4-hydroxyphenylglycol), Isomeric mixture of D-MHPG and L-MHPG forms, MHPG Derivatives, DL-MHPG-SO4 (DL-3-methoxy-4-hydroxyphenylglycol-sulfate) Modification can include Isomeric mixture of D-MHPG-SO4 and L-MHPG-SO4 forms, Serotonin, 5-HT, 5-hydroxydopamine (5-4HDA), 3,4-dihydroxyphenylglycol (DOPEG), Dopamine, 4-(2-aminoethyl)pyrocatechol; 3-hydroxytyramine; 3,4-dihydroxyphenethylamine; L-3,4-dihydroxyphenylalanine, L-DOPA, Vanillomandelic acid, DL-VMA, Homovanillic acid, Norepinephrine, DL-NE, D-Epinephrine, D-E, 3-methoxytyramine, MTA, 3-methoxytyrosine, MTyr, 3,4-dihydroxymandelic acid, DL-DOMA, 3,4-dihydroxyphenyl acetic acid, DOPAC, L-Phenylalanine, Tyramine, p-tyramine; 4-(2-Aminoethyl)phenol, D-Mandelic acid, Homocatechol, Octopamine, DL-Octopamine, Azinphos-Ethyl, S-(3,4-dihydro-4-oxobenzo[d]-[1,2,3]-triazin-3-ylmethyl) O,O-diethyl phosphorodithioate, Phosmet, O,O-dimethyl S-phthalimidomethyl phosphorodithioate, Folpet, N-[(Trichloromethyl)thio]phthalimide, Tetramethrin, (1-Cyclohexene-1,2-dicarboximido)methyl-2,2-dimethyl-3-(2-methylpropenyl)-cyclopropanecarboxylate, N-(bromomethyl)phthalimide, N-(Chloromethyl)benzazimide, 6-(N-phthalimidoylmethylthio)hexanoic acid (MFH), Bromacil, 5-bromo-3-sec-butyl-6-methyluracil, Bromacil Derivative, 5-bromo-6-(hydroxymethyl)-3-(1-methylpropyl)-2,4(1H,3H)-pyrimidineone, Bromacil Derivative, 5-bromo-3-(2-methylpropyl-6-methyl-2,4(1H,3H)-pyrimidinedione, Metabolite of Bromacil, Bromacil Derivative, 3-hydroxy-1-methylpropyl-6-methyl-2,4(1H,3H)-pyrimidinedione (Modification Bromacil Metabolite), Bromacil Derivative, 6-methyl-3-(1-methylpropyl)-2,4(1H,3H)-pyrimidinedione (Modification Bromacil Metabolite), Terbacil Derivative, [5-chloro-3-(1,1-dimethylethyl)-6-(hydroxymethyl)-2,4 (1H,3H)-pyrimidinedione, Terbacil, 3-tert-butyl-5-chloro-6-methyluracil, Bromacil Derivative, Ethyl-5-(5-Bromo-6-methyl-3-(1-methylpropyl)-2,4(1H,3H)-pyrimidinedione-1-yl)hexanoate, Bromacil Derivative alkylated at N-1, Bromacil Derivative 5-(5-Bromo-6-methyl-3-(1-methylpropyl)-2,4(1H,3H)-pyrimidinedione-1-yl)hexanoic Acid (Modification Bromacil Derivative alkylated at N-1), Bromacil Derivative, -Bromo-6-(Bromomethyl-3-(1-methylpropyl)-2,4(1H,3H)-pyrimidinedione (Modification Bromacil Derivative substituted at the 6-methyl position), Bromacil Derivative-[5-Bromo-3-(1-methylpropyl)-2,4(1H, 3H)-pyrimidinedione-6-yl]-2-carboxylpropanoic Acid (Modification Bromacil Derivative substituted at the 6-methyl position), 3-[5-Bromo-3-(1-methylpropyl)-2,4 (1H,3H)-pyrimidinedione-6-yl]propanoic Acid (Modification Bromacil Derivative substituted at the 6-methyl position), Bromacil Derivative 5-Bromo-1,6-dimethyl-3-(1-methylpropyl)-2,4(1H,3H)-pyrimidinedione, Bromacil Derivative 5-Bromo-1-butyl-6-methyl-3-(1-methylpropyl)-2,4(1H,3H)-pyrimidinedione, Butachlor, N-butoxymethyl-2-chloro-2',6'-diethylacetanilide, Amidochlor, N-[(acetylamino)methyl]-2-chloro-N-(2,6-diethylpenyl)acetamide, Nicarbazin, N,N'-bis(4-nitrophenyl)-compound with 4,6-dimethyl-2(1H)-pyrimidinone (Modification (DNC+HDP)), 2-hydroxy-4,6-dimethylpyrimidine, HDP, Imazalil, [1-(beta-allyloxy-2,4-dichlorophenethyl)imidazole], Imazalil Derivative, EIT-0073 (Modification Have a —O(CH2)5-COOH group instead of original —OCH2CH—CH2 group of imazalil), Penconazole, (RS)-1-(2,4-dichloro-β-propylphenethyl)-1H-1,2,4-triazole, Hexaconazole, (RS)-2-(2,4-dichlorophenyl)-1-(1H-1,2,4-triazol-1-yl)hexan-2-ol, Propiconazole, cis-trans-1-[2-(2,4-dichlorophenyl)-4-propyl-1,3-dioxolan-2-ylmethyl]-1H-1,2,4-triazole, Diclobutrazol, 2RS,3RS)-1-(2,4-dichlorophenyl)-4,4-dimethyl-2-(1H-1,2, 4-triazol-1-yl)pentan-3-ol, Triflumizole, (E)-4-chloro-α,α,α-trifluoro-N-(1-imidazol-1-yl-2-propoxyethylidene)-o-toluidine, Imazalil Derivative, EIT-0183, Imazalil Derivative, EIT-0180, Imazalil Derivative, EIT-0111, Imazalil Derivative, EIT-0158, Imazalil Derivative, K-240, Chlorothalonil, tetrachloroisophthalonitrile Modification On benzene Ring R1=CN R2=Cl R3=CN R4=Cl R5=Cl R6=Cl), Chlorothalonil Derivative-2,4,5,6-tetrachloro-3-cyanobenzamide (Modification On benzene Ring R1=CONH2 R2=Cl R3=CN R4=Cl R5=Cl R6=Cl), Chlorothalonil Derivative-2,5,6-trichloro-4-hydroxyisophthalonitrile (Modification On benzene Ring R1=CN R2=Cl R3=CN R4=OH R5=Cl R6=Cl), 3-carbamyl-2,4,5-trichlorobenzoic acid (Modification On benzene Ring R1=CONH2 R2=Cl R3=COOH R4=H R5=Cl R6=Cl), Pentachloronitrobenzene (Modification On benzene Ring R1=NO2 R2=Cl R3=Cl R4=Cl R5=Cl R6=Cl), Benzene hexachloride, Hexachlorobenzene, BHC, Lindane (Modification On benzene Ring R1=Cl R2=Cl R3=Cl R4=Cl R5=Cl R6=Cl), 2,4,5,6-tetrachlorophenol (Modification On benzene Ring R1=OH R2=Cl R3=H R4=Cl R5=Cl R6=Cl), Carbaryl Derivative, Ethylcarbamate (Modification R1=OCONHCH2CH3 R3=H), 1-Naphthol, 1-naphthaleneacetamide, -(1-naphthyl) acetamide, Carbaryl Derivative, 1-Methylcarbonate (Modification R1=OCOOCH3 R2=H, Carbaryl Derivative, 1-Ethylcarbonate (Modification R1=OCOOCH2CH3 R2=H), Carbaryl Derivative 2-Ethylcarbonate (Modification R1=H R2=OCOOCH2CH3, Carbaryl Derivative, 1-Ethylthiocarbonate (Modification R1=OCOSCH2CH3 R2=H), Carbaryl Derivative, 2-Ethylthiocarbonate (Modification R1=H R2=OCOSCH2CH3), Naptalam, N-1-naphthylphthalamic acid, Carbaryl Derivative, 3-hydroxycarbaryl (Modification R1=OCONHCH3 R2=H R3=OH R4=H R5=H), Carbaryl Derivative 4-hydroxycarbaryl (Modification R1=OCONHCH3 R2=H R3=H R4=OH R5=H), Carbaryl Derivative 5-hydroxycarbaryl (Modification R1=OCONHCH3 R2=H R3=H R4=H R5=OH), Carbaryl Derivative, 1-(5-Carboxypentyl)-3-(1-naphthyl)urea (Modification R1=NHCONH(CH2)5COOH R2=H), (Structurally related s-triazines)-Aziprotryn, 4-azido-N-isopropyl-6-methylthio-1,3,5-triazin-2-ylamine (Modification R1=—SCH3 R2=—N3 R3=—CH(CH3)2), (Structurally related s-triazines), 2-(ethylamino)-4-(methylthio)-6-aminotriazine (Modification R1=—SCH3 R2=—NH—C2H5 R3=—NH2), (Structurally related s-triazines)-2-amino-4-(methylthio)-6-(isopropylamino)triazine (Modification R1=—SCH3 R2=—NH2 R3=—NH—CH(CH3)2), (Structurally related s-triazines)-2-amino-4-methoxy-6-(isopropylamino) triazine (Modification R1=—OCH3 R2=—NH2 R3=—NH—CH(CH3)2), TCP Derivative (3,5,6-trichloro-2-pyridinol Derivative), 3-(3,5-dichloro-6-hydroxy-2-pyridyl)thiopropanoic Acid, p-nitrosuccinanilic acid (PNA-S), PNA-S, PNA-C, p-nitro-cis-1,2-cyclohexanedicarboxanilic acid, Nitroaniline Derivative, 2-nitroaniline, o-Nitroaniline, Nitroaniline Derivative-3-nitroaniline, m-Nitroaniline, Nitroaniline Derivative-4-nitroaniline, p-Nitroaniline, Aeromatic Alcohols, 4-nitrobenzyl alcohol, Aeromatic Alcohols-4-nitrophenethyl alcohol, Aeromatic Alcohols 2-nitrobenzyl alcohol, Aeromatic Alcohols, 3-nitrobenzyl alcohol, Urea Derivative-1-benzyl-3-(4-nitrophenyl)urea, Urea Derivative-1-(3-chlorophenyl)-3-(2-methoxy-5-nitrophenyl)urea, Urea Derivative-1-(3-chlorophenyl)-3-(4-methoxy-3-nitrophenyl)urea, Urea Derivative-1-(4-chlorophenyl)-3-(4-nitrophenyl)urea, Urea Derivative-(2-fluorophenyl)-3-(2-mehtoxy-4-nitrophenyl) urea, 1-(3-mehtoxyphenyl)-3-(3-nitrophenyl)urea, Carbofuran Derivative m Carbofuran-phenol, Carbofuran-hydroxy, Carbofuran-keto, Carbosulfan, 3-dihydro-2,2-dimethylbenzofuran-7-yl (dibutylaminothio) methylcarbamate, Benfuracarb, N-[2,3-dihydro-2,2-dimethylbenzofuran-7-yloxycarbonyl(methyl)aminothio]-N-isopropyl-β-alaninate, Furathiocarb, 2,3-dihydro-2,2-dimethyl-7-benzofuranyl 2,4-dimethyl-5-oxo-6-oxa-3-thia-2,4-diazadecanoate, Carbofuran Derivative, 4-[[(2,3-Dihydro-2,2-dimethyl-7-benzofuranyloxy)carbonyl]-amino]butanoic Acid (BFNB) (Modification n=3X=CH2), Endrin, nendrin, (1R,4S,4aS,5S,6S,7R,8R,8aR)-1,2,3,4,10,10-hexachloro-1,4,4a,5,6,7,8,8a-octahydro-6,7-epoxy-1,4:5,8-dimethanonaphthalene, Heptachlor, 1,4,5,6,7,8,8-heptachloro-3a,4,7,7a-tetrahydro-4,7-, Chlordane, 1,2,4,5,6,7,8,8-octachloro-2,3,3a,4,7,7a-hexahydro-4,7-methanoindene, Endosulfan (Modification isomer mix of alpha and beta forms), Endosulfan (Modification alpha isomeric form), Endosulfan (Modification beta isomeric form), Endosulfan Derivative, Endosulfan sulfate (Modification sulfate form), Endosulfan Derivative, Endosulfan diol, Diol metabolite of endosulfan, Endosulfan Derivative, Endosulfan ether (Modification ether metabolite of endosulfan), Endosulfan Derivative, hydroxy ether, hydroxy ether metabolite of endosulfan, Endosulfan Derivative, Endosulfan lactone (Modification lactone metabolite of endosulfan), Aldrin, Dieldrin, Fenvalerate isomers Modification 1S,2R isomer R: Ph), Fenvalerate isomers (Modification 1R,2S isomer R: Ph), Fenvalerate isomers (Modification 1R,2R isomer R: Ph), Fenvalerate isomers (Modification 1S,2R/S isomer R: Ph), Fenvalerate isomers (Modification 1R,2R/S isomer R: Ph), Fenvalerate isomers, fenvalerate (Modification 1R/S, 2R/S isomer R: Ph), Thiabendazole, 2-(thiazol-4-yl)benzimidazole, Thiabendazole Derivative, 5-hydroxythiabendazole (Modification 5-OH-TBZ), Thiabendazole Derivative, 5-NH2-TBZ, Thiabendazole Derivative, methyl benzimidazole carbamate, Albendazole, Mebendazole, Fenbendazole, Thiabendazole Derivative, 2-succinamidothiabendazole, Thiabendazole Derivative, 2-succinamidothiabendazole, Cambendazole, Fenvalerate Haptens, Cyano[3-(4-aminophenoxy)phenyl]methyl (S)-4-Chloro-alpha-(1-methylethyl)benzeneacetate (4-Aminoesfenvalerate), Fenvalerate Haptens, Benzyl 4-[3-[Cyano[(S)-2-(4-chlorophenyl)-3-methyl-1-oxobutanoxy]methyl]]phenoxy]benzenepropanoate, Fenvalerate Haptens, Benzyl 3-[Cyano[(S)-2-(4-chlorophenyl)-3-methyl-1-oxobutanoxy]methyl]]phenoxyacetate, Fenvalerate Haptens, 3-[Cyano[(S)-2-(4-chlorophenyl)-3-methyl-1-oxobutanoxy]methyl]]phenoxyacetic Acid, Fenvalerate Haptens, Benzyl 6-[3-[Cyano[(S)-2-(4-chlorophenyl)-3-methyl-1-oxobutanoxy]methyl]]phenoxy] hexanoate, Fenvalerate Haptens, 6-[3-[Cyano[(S)-2-(4-chlorophenyl)-3-methyl-1-oxobutanoxy]methyl]]phenoxy] hexanoic Acid Fenvalerate Haptens, 4-[3-[Cyano[(S)-2-(4-chlorophenyl)-3-methyl-1-oxobutanoxy]methyl]]phenoxy] benzenepropanoic Acid, (S)-fenvalerate Acid, (Structurally related s-triazines), atrazine mercapturate Modification R1=—SCH2CH(NHCOCH3)COOH R2=—NHCH2CH3 R3=—NHCH(CH3)2, Fenthion Hapten, -Methyl O-[3-methyl-4-(methylthio)phenyl] N-(3-carboxypropyl)phosphoramidothioate Modification referred as Hapten B, Fenthion Derivative, Oxidized Fenthion, Fenthion Derivative, Oxidized oxidized Fenthion, pirimiphos-ethyl, 4-(Methylthio)-m-cresol, Chlorpyrifos Derivative, Chlorpyrifos-oxon, Fenchlorphos, O,O-dimethyl O-2,4,5-trichlorophenyl phosphorothioate, Trichloronate, O-Ethyl O-2,4,5-trichlorophenyl ethyl-phosphonothioate, Dichlofenthion, O-2,4-dichlorophenyl O,O-diethyl phosphorothioate, Parathion, O,O-diethyl O-4-nitrophenyl phosphorothioate; Thiophos, Chlorpyrifos Derivative Modification Synthesis of AR1 is described, Chlorpyrifos Derivative, O-Ethyl O-(3,5,6-Trichloro-2-pyridyl)O-(3-Carboxypropyl)Phosphorothioate; (PO), Chlorpyrifos Derivative-O-Ethyl O-(3,5,6-Trichloro-2-pyridyl)N-(5-Carboxyethyl) Phosphoramidothioate; (PN1) (Modification Amide linkage of thiophosphate reagents), Chlorpyrifos Derivative, O-Ethyl O-(3,5,6-Trichloro-2-pyridyl)N-(2-Carboxyethyl) Phosphoramidothioate; (PN1) (Modification Amide linkage of suitable thiophosphate reagents), Triadimefon, (RS)-1-(4-chlorophenoxy)-3,3-dimethyl-1-(1H-1,2,4-triazol-1-yl)butan-2-one, GR151004, (4-[[5-[3-[2-(dimethylamino)ethyl]]-5-benzofuranyl]-3-pyridinyl]acetyl]morpholine dihydrochloride, Diflubenzuron, 1-(4-chlorophenyl)-3-(2,6-difluorobenzoyl)urea, (Structurally related s-triazines)-SprAAT (Modification R1=SCH2CH2COOH R2=NH2 R3=NH2), (Structurally related s-triazines), SBeAAT (Modification R1=S(C6H4)COOH R2=NH2 R3=NH2), (Structurally related s-triazines), SAAT (Modification R1=SH R2=NH2 R3=NH2), (Structurally related s-triazines), CDAT (Modification R1=Cl R2=NH[C(O)CH3] R3=NH2), (Structurally related s-triazines)-CDET (Modification R1=Cl R2=NH[C(O)CH3] R3=NH(CH2CH3)), (Structurally related s-triazines)-CDIT (Modification R1=Cl R2=NH[C(O)CH3] R3=NH(CH(CH3)2)), (Structurally related s-triazines), CDDT (Modification R1=Cl R2=NH[C(O)CH3] R3=NH[C(O)CH3]), (Structurally related s-triazines)-ammeline, OAAT (Modification R1=OH R2=NH2 R3=NH2), (Structurally related s-triazines)-ammelide, OOAT (Modification R1=OH R2=OH R3=NH2), (Structurally related s-triazines)-cyanuric acid, OOOT (Modification R1=OH R2=OH R3=OH), (Structurally related s-triazines), melamine, AAAT (Modification R1=NH2 R2=NH2 R3=NH2), Structurally related s-triazines-N-isoropylammeline, OIAT (Modification R1=OH R2=NH[CH(CH3)2] R3=NH2, Structurally related s-triazines-N-ethylammeline, OEAT (Modification R1=OH R2=NHCH2CH3 R3=NH2), Structurally related s-triazines, N-ethylammelide, OOET (Modification R1=OH R2=OH R3=NHCH2CH3), Structurally related s-triazines)-cyromazine, CyPAAT (Modification R1=NH(C3H5) R2=NH2 R3=NH2), Structurally related s-triazines-diamino-s-triazine, HAAT (Modification R1=H R2=NH2 R3=NH2), PCB congeners, 2,5,3',4'-tetrachlorobiphenyl (Modification IUPAC no.: 70), PCB congeners 2,4,5,3',4'-pentachlorobiphenyl (Modification IUPAC no.: 118), PCB congeners-2,2',5,5'-tetrachlorobiphenyl (Modification IUPAC no.: 52), PCB congeners, 6-[3,3',4'-Trichlorobiphenyl-4-yl)oxy]hexanoic Acid, Metolazone, Brand Names: Mykrox; Zaroxolyn, Furfuryl benzoate, DDT Metabolites, DDA, Paraquat, 1,1'-dimethyl-4,4'-bipyridinium ion, Diethylcarbamazine, THP, 2,4,6-triphenyl-N-(4-hydroxyphenyl)-pyridinium, o-DNCP, -dinitrocarboxyphenol, PCB congeners, 3-chlorobiphenylol (Modification IUPAC No. 2), PCB congeners, 3,4'-dichlorobiphenyl (Modification IUPAC No. 13), PCB congeners, 3,5-dichlorobiphenyl (Modification IUPAC No. 14), PCB congeners, 3,4,5,3',4'-pentachlorobiphenyl (Modification IUPAC No. 126), 2,3,3',4'-tetrachlorobiphenyl (Modification IUPAC No. 56), 2',3,4,5-tetrachlorobiphenyl (Modification IUPAC No. 76), 3,3',5,5'-tetrachlorobiphenyl (Modification IUPAC No. 80), 2,4,5,2',5'-pentachlorobiphenyl (Modification IUPAC No. 101), 2,3,3',4,4'-pentachlorobiphenyl (Modification IUPAC No. 105), 2,3,6,3',4'-pentachlorobiphenyl (Modification IUPAC No. 110), 3,3',4,5,5'-pentachlorobiphenyl (Modification IUPAC No. 127), 3,4,5,3',4',5'-hexachlorobiphenyl (Modification IUPAC No. 169), 2,3,3',4,4',5-hexachlorobiphenyl (Modification IUPAC No. 156), 3,4,3',4'-tetrabromobiphenyl, 3,4,5,3',4',5'-hexabromobiphenyl, 2,4,5,2',4',5'-hexabromobiphenyl, Dibenzofurans and Dioxins, 2,3,7,8-tetrachlorobenzofuran, 2,3,7,8-tetrachlorodibenzo-p-dioxin, 3,4',5-trichloro-4-biphenylol, 3,3',5,5'-tetrachloro-4,4'-biphenyldiol, 3,4,3',4'-tetrachlorodiphenyl ether, 1-2-dichlorobenzene, 1,4-dichlorobenzene, 1,2,4-trichlorobenzene, 3,4-dichloroaniline, DDT Metabolites, 4,4'-DDT, 4,4'-DDD Retronecine, 3,4-dichlorobiphenyl Modification IUPAC No. 12, 3,4,3'-trichlorobiphenyl (Modification IUPAC No. 35), PCB Congeners, 3,4,4'-trichlorobiphenyl (Modification IUPAC No. 37), 3,4,3',5-tetrachlorobiphenyl (Modification IUPAC No. 78), 3,4,3',5'-tetrachlorobiphenyl (Modification IUPAC No. 79), 3,4,4',5-tetrachlorobiphenyl (Modification IUPAC No. 81), DDT Metabolites, p,p'-DDT (Modification p,p'-dichlorodiphenyltrichloroethane), o,p'-DDT Modification o,p'-dichlorodiphenyltrichloroethane, p,p'-DDE Modification p,p'-DDE, o,p'-DDE Modification o,p'-DDE, p,p'-DDD Modification p,p'-DDD, o,p'-DDD Modification o,p'-DDD, Dicofol, 4,4-dichloro-a-(trichloromethyl)benzhydrol, Cyprazine, 6-chloro-N-cyclopropyl-N'-(1-methylethyl)-1,3,5-triazine-2,4-diamine, Structurally related s-triazines, Dipropetryn, 6-(ethylthio)-N,N'-bis(1-methylethyl)-1,3,5-triazine-2,4-diamine, Trietazine, 6-chloro-N,N,N'-triethyl-1,3,5-triazine-2,4-diamine, 6-Hydroxyatrazine, hexazinone, 3-cyclohexyl-6-dimethylamino-1-methyl-1,3,5-triazine-2,4 (1H,3H)-dione, TNT, 2,4,6-Trinitrotoluene, Tetraconazole (M14360), 1-[2-(2,4-dichlorophenyl)-3-(1,1,2,2-tetrafluoroethoxy)propyl]-1H-1,2,4-triazole, DTP, 2-(2,4-dichlorophenyl)-3-(1H-1,2,4-triazol-1-yl)propanol, Imazalyl, fenarimol, (RS)-2,4'-dichloro-α-(pyrimidin-5-yl)benzhydryl alcohol, Lupanine metabolites, (+)-lupanine (Modification R=H), Lupanine metabolites, (+)-13-hydroxylupanine (Modification R=OH), Lupanine metabolites, hemisuccinate ester of (+)-13-hydroxylupanine (Modification R=OCO—(CH2)2.COOH), Lupanine metabolites, cis-hexahydrophthalate ester of (+)-13-hydroxylupanine (Modification R=OCO.C6H10.COOH), Lupanine metabolites, alpha-isolupanine, Lupanine metabolites, -hydroxylupanine, Sparteine, Cysteine, multiflorine, epilupinine, (Structurally related s-triazines), CYANAZINE ACID Modification R1=Cl R2=NHCH2CH3 R3=NHCCOOH(CH3)2, Structurally related s-triazines Modification R1=Cl R2=NHCH2CH3 R3=NH(CH2)3COOH, Structurally related s-triazines (Modification R1=Cl R2=NHCH2CH3 R3=NHCH2COOH), (Structurally related s-triazines) (Modification R1=Cl R2=NHCH2CH3 R3=NH(CH2)4COOH), norflurazon, 4-chloro-5-(methylamino)-2-[3-(trifluoromethyl)phenyl]-3(2H)-pyridazinone, norflurazon derivative, desmethyl-norflurazon, metflurazon, -chloro-5-(dimethylamino)-2-[(3-trifluoromethyl)phenyl]-3(2H)-pyridazinone, Pyrazon, Chloridazon, 5-amino-4-chloro-2-phenyl-3(2H)-pyridazinone (active ingradient), dichlorophenyl-pyridazone, (Structurally related s-triazines) azidoatrazine (Modification R1=N3 R2=NHCH(CH3)2 R3=NHCH2CH3), ALACHLOR 2-chloro-2',6'-diethyl-N-methoxymethylacetanilide, trichothecolone (Modification R1=H R2=OH R3=H R4=O R5=H), DON derivative, acetyl-T-2, DON derivative, T-2 tetrol tetraacetate, Chlorpyrifos derivatives, mono-dechloro-CP, Bromophos derivative, Bromophos-methyl, Bromophos derivative, Bromophos-ethyl dicapthon, -2-chloro-4-nitrophenyl O,O-dimethyl phosphorothioate, tetrachlorvinphos, (Z)-2-chloro-1-(2,4,5-trichlorophenyl)vinyl dimethyl phosphate, triclopyr, 3,5,6-trichloro-2-pyridyloxyacetic acid, picloram, 4-amino-3,5,6-trichloropyridine-2-carboxylic acid, Formononetin, Biochanin A, 5, 7-dihydroxy-4'-methoxyisoflavone (Modification It is the 4'-methyl ether of genistein), equol, (7-hydroxy-3-(4'-hydroxyphenyl)-chroman, 2'methoxyformononetin, Daidzein, 7-hydroxy-3-(4-hydroxyphenyl)-4H-1-benzopyran-4-one, geninstein, quercetin, 3,3',4',5,7-Pentahydroxyflavone; 3,5,7,3',4'-Pentahydroxyflavone; matheucinol, coumestrol (Structurally related s-triazines), Hydroxysimazine (Modification R1=OHR2=NHCH2CH3R3=NHCH2CH3, angustifoline, Alodan, 1-Methyl-4-phenyl-4-carboethoxypiperidine hydrochloride, Zearalenone, RAL, F-2 Toxin, Fenpropimorph, (RS)-cis-4-[3-(4-tert-butylphenyl)-2-methylpropyl]-2,6-dimethylmorpholine, Tridemorph, 2,6-dimethyl-4-tridecylmorpholine, 2,6-dimethylmorpholine, Amorolfine, Fenpropidine, (RS)-1-[3-(4-tert-butylphenyl)-2-methylpropyl]piperidine, (Structurally related s-triazines) (Modification R1=Cl R2=Cl R3=NHCH2CH3, (Structurally related s-triazines) Modification R1=Cl R2=Cl R3=NHCH(CH3)2, (Structurally related s-triazines) Modification R1=Cl R2=NHCH2CH3 R3=NH(CH2)5COOH, (Structurally related s-triazines) Modification R1=Cl R2=NHCH(CH3)2 R3=NHCH2COOH, (Structurally related s-triazines) (Modification R1=Cl R2=NHCH(CH3)2 R3=NH(CH2)5COOH), Structurally related s-triazines, cyanazine amide (Modification R1=Cl R2=NHCH2CH3 R3=NHCCONH2(CH3)2), hydroxycyanazine acid (Modification R1=OH R2=NHCH2CH3 R3=NHCCOOH(CH3)2), deethylsimazine (Modification R1=Cl R2=NH2 R3=NHCH2CH3), Albendazole sulfoxide, [5-(propylthionyl)-1H-benzimidazol-2-yl]-, methylester, Albendazole sulfone, 5(6)-alkylbenzimidazoles, 2-amino-5-(propylthio)benzimidazole, 5(6)-alkylbenzimidazoles, 2-amino-5-(propylsulfonyl)benzimidazole, oxibendazole, 5-propoxy-benzimidazole-2-methyl carbamate, 5(6)-arylbenzimidazoles, fenbendazole sulfone (Modification sulfone metabolite of fenbendazole), 5(6)-arylbenzimidazoles, 4'-hydroxyfenbendazole, 5(6)-arylbenzimidazoles, oxfendazole (Modification Oxfendazole is the sulfoxide metabolite of fenbendazole), 5(6)-arylbenzimidazoles, flubendazole, benzimidazole Metabolites, 2-aminobenzimidazole, benzimidazole Metabolites, 5-aminobenzimidazole, benzimidazole Metabolites, 2-acetylbenzimidazole, Benzophenone, Diphenylmethanone; phenyl ketone; Diphenyl ketone; Benzoylbenzene, Benzaldehyde, benzoic aldehyde, 4-Bromo-2,5-dichlorophenol, Acephate, O,S-dimethyl acetylphosphoramidothioate, methamidophos, O,S-dimethyl phosphoramidothioate, Dichlorvos, 2,2-dichlorovinyl dimethyl phosphate, Phenthoate, S-α-ethoxycarbonylbenzyl O,O-dimethyl phosphorodithioate, EPN, Ethyl p-nitrophenyl thionobenzenephosphonate, Bioresmethrin, -benzyl-3-furylmethyl (1R,3R)-2,2-dimethyl-3-(2-methylprop-1-enyl)cyclopropanecarboxylate (Modification The unresolved isomeric mixture of this substance has the ISO common name resmethrin), flufenoxuron, 1-[4-(2-chloro-α,α,α-trifluoro-p-tolyloxy)-2-fluorophenyl]-3-(2,6-difluorobenzoyl)urea, Amitrole, 1H-1,2,4-triazol-3-ylamine, molinate, S-ethyl azepane-1-carbothioate, molinate derivative (Modification S-2-carboxyethyl hexahydroazepine-1-carbothioate), molinate derivative (Modification S-5-carboxypentyl hexahydroazepine-1-carbothioate) molinate derivative (Modification molinate sulfone), molinate derivative (Modification S-(p-aminobenzyl) hexahydroazepine-1-carbothioate), molinate derivative (Modification S-2-(p-aminophenyl)ethyl hexahydroazepine-1-carbothioate), hexamethylenimine, thiobencarb (Bolero), butylate (Sutan), EPTC (Eptam), cycloate (Roneet), pebulate (Tillam), vernolate (Vernam), Aflatoxin M, AFM1 (Modification AFM1), Aflatoxin B1, AFB1 (Modification AFB1), Aflatoxin G1, AFG1 (Modification AFG1), Aflatoxin M2, AFM2 (Modification AFM2), Aflatoxin B2, AFB2 (Modification AFB2), Aflatoxin G2, AFG2 (Modification AFG2), Aflatoxin B2alpha, AFB2alpha (Modification AFB2alpha), Aflatoxin G2alpha, AFG2alpha (Modification AFG2alpha), KB-6806, 6-amino-5-chloro-1-isopropyl-2-(4-methyl-1-piperazinyl) (Modification R1=NH2 R2=CH(CH3)2 R3=CH3), KB-6806 (Benzimidazole) Derivatives Modification R1=NH2 R2=CH2CH(CH3)2 R3=CH3, Hapten Name KB-6806 (Benzimidazole) Derivatives (Modification R1=NH2 R2=CH(CH2CH3)2 R3=CH3), KB-6806 (Benzimidazole) Derivatives (Modification R1=NHCOCH3 R2=CH(CH3)2 R3=CH3), KB-6806 (Benzimidazole) Derivatives (Modification R1=H R2=CH(CH3)2 R3=CH3), KB-6806 (Benzimidazole) Derivatives (Modification R1=NH2 R2=CH(CH3)2 R3=CH3), KB-6806 (Benzimidazole) Derivatives Modification R1=NH2 R2=CH(CH3)2 R3=N(—>O) CH3 (N-OXIDE), KB-6806 (Benzimidazole) Derivatives Modification R1=NH2 R2=CH(CH3)2 R3=H, KB-6806 (Benzimidazole) Derivatives Modification R1=NH2 R2=CH2CH3 R3=CH3, Aminoparaoxon, phosphoric acid, O,O-diethyl O-(4-aminophenyl) ester, Methylparathion, phosphorothioic acid, O,O-dimethyl O-(4-nitrophenyl) ester, Diethyl phenylphosphate, phenylphosphonic acid, O,O-diethyl ester, Diethyl phosphate, ethylphosphonic acid, O,O-diethyl ester, p-Nitrophenyl phosphate, phosphonic acid, O-(4-nitrophenyl)ester, Phorate, phosphorodithioic acid, O,O-diethyl S-[(ethylthio)methyl] ester, Ethion, bis(phosphorodithioic acid), S,S'-methylene O,O,O',O'-tetraethyl ester, Carbophenthion, phosphorodithioic acid, O,O-diethyl S-[[(4-chlorophenyl)thio]methyl] ester, Disulfoton, phosphorodithioic acid, O,O-diethyl S-[(2-ethylthio)ethyl] ester, TS, N-[4-(Carboxymethyl)-2-thiazolyl]sulfanilamide, NS, N-(4-Nitrophenyl)sulfanilamide, Sulfamoxole, Sulfacetamide, DNP-SL, Spin labelled dinitrophenyl (Modification The synthesis of DNP-SL has been described by Balakrishnan et al (1982) formula can be found in Anglister et al. (1984)), beta ecdysone, Benzimidazole Derivative, 5(6)-[Carboxypentyl)thio]-2-(methoxycarbonyl)amino]-benzimidazole, 2-hydroxybiphenyl HBP, Atrazine Caproic acid, Lysophosphatidic acid (LPA), 1-acyl-2-hydroxy-sn-glycero-3-phosphate), berberine, Palmatine, 9-Acetylberberine, Corydaline, Coptisine, Berberrubine, 8-Oxoberberine, Papaverine, Berberine Derivative, 9-O-carboxymethyl berberine, phencyclidine, 1-(1-phenylcyclohexyl)piperidine, Methoxychlor, Endosulfan Derivative, 4-Oxobutanoic Acid,4-(4,5,6,7,8,8-Hexachloro-3a,4,7,7a-tetrahydro-4,7-methano-1H-indenyl-1-oxy), Endosulfan Derivative, 4-oxybutanoic Acid,4-(1,3,4,5,6,7,8-Octachloro-3a,4,7,7a-tetrahydro-4,7-methanoindanyl-2-oxy, Endosulfan Derivative (Modification Hemisuccinate of Endosulfan diol), Triazole Derivatives, 5-(3-Hydroxypropyl)-3-amino-2H-1,2,4-triazole, Triazole Derivatives, 5-(3-Hydroxypropyl)-3-(2-nitrophenylsulfenyl)amino-2H-1,2,4-triazole, Triazole Derivatives, 3-Amino-5-[(3-succinyloxy)propyl]-2H-1,2,4-triazole, Triazole Derivatives, 3-amino-1,2,4-triazole-5-thiol, Triazole Derivatives, 3-[(2-nitrophenylsulfenyl)amino-2H-1,2,4-triazole-5-thiol, Triazole Derivatives, 2H-1,2,4-triazole-5-thiol, Triazole Derivatives, 4-methyl-1,2,4-triazole-3-thiol, Triazole Derivatives, (1,2,4-triazol-2-yl)acetic acid, 1,2,4-triazole, 4-nitrophenyl 4'-carboxymethylphenyl phosphate, Triazole Derivative, 4-amino-1,2,4-triazole, Triazole Derivative, 3-acetamido-1H-1,2,4-triazole, Triazole Derivative, 3-amino-1,2,4-triazole-5-carboxylic acid hemihydrate, Triazole Derivative, 2-(4-chlorophenyl)-2-(1,2,4-triazol-1-yl)-methylhexanoic acid, succinic acid, Imidazole, L-histidine, L-glutamic acid, Permethrin derivative, 3-phenoxybenzyl 2,2-dimethylcyclopropane-1,3-dicarboxylate, 3-phenoxybenzaldehyde, flucythrinate, Chrysanthemic acid, 2,4-Dinitrophenyl, DNP, Thiram Haptens, Disodium 4-[Carbodithioato(methyl)-amino]butanoate, Thiram Haptens 5,11-Dimethyl-6,10-dithioxo-7,9-dithia-5,11-diazadodecanoic Acid, Thiram Haptens, 2-{[(Dimethylamino)carbothioyl]sulfanyl}ethanoic Acid, Thiram Haptens, 4-{[(Dimethylamino)carbothioyl]sulfanyl}butanoic Acid, Thiram Haptens, 6-{[(Dimethylamino)carbothioyl]sulfanyl}hexanoic Acid, Thiram Haptens, 11-{[(Dimethylamino)carbothioyl]sulfanyl}undecanoic Acid, Thiram Haptens, 2-{[(Dimethylamino)carbothioyl] sulfanyl}ethanoic Acid, Thiram, Tetramethylthiurammonosulfide, Tetraethylthiuram disulfide, Dimethyldithiocarbamic acid sodium salt, Dimethyldithiocarbamic acid zinc salt, Diethyldithiocarbamic acid sodium salt, N,N,N',N'-tetramethylthiourea, Nabam, Zineb, Maneb, Ethylenethiourea, Chlorpyrifos hapten, O,O Diethyl O-[3,5-Dichloro-6-[(2-carboxyethyl)thio]-2-pyridyl] Phosphorothioate, 2-Succinamidobenzimidazole, Methyl 2-Benzimidazolecarbamate, MBC, Benzimidazole, 2-benzimidazolylurea, succinamide, Ethyl carbamate, Urea, N-methylurea, N,N'-dimethylurea, Brevetoxin PbTx-3, Organophosphorous Haptens, O,O-Diethyl O-(5-carboxy-2-fluorophenyl) phosphorothioate, Chlorpyrifos-ethyl, Anandamide hapten, N-Arachidonyl-7-amino-6-hydroxy-heptanoic acid, Anandamide, Arachidonic acid, Docosatetraenoyl ethanolamide, Dihomo-gamma-linolenyl ethanolamide, 2-Arachidonyl glycerol, 2-Arachidonyl glycerol ether, Stearoyl ethanolamide, Heptadecanoyl ethanolamide, Prostaglandin E1, 3-hydroxy-2-(3-hydroxy-1-octenyl)-5-oxocyclopentaneheptanoic acid; alprostadil; PGE1, Prostaglandin D2, PGD2, Prostaglandin A2, PGA2, Prostaglandin B2, PGB2, Prostaglandin F2 alpha, 7-[3,5-dihydroxy-2-(3-hydroxy-1-octenyl)cyclopentyl]-5-heptenoic acid; dinoprost; PGF2alpha, Prostaglandin F1 alpha, PGFlalpha, 6-keto-Prostaglandin F1 alpha, 6-keto-PGFlalpha, 13,14-Dihydro-15-keto-Prostaglandin E2, 13,14-Dihydro-15-keto-PGE2, 13,14-Dihydro-15-keto-Prostaglandin F2alpha, 14-Dihydro-15-keto-PGF2alpha, 5alpha,7alpha-Dihydroxy-11-ketotetranorpostane-1,16-dioic acid, 15-keto-PGF2alpha, TXB2, Prostaglandin E2,7-[3-hydroxy-2-(3-hydroxy-1-octenyl)-5-oxocyclopentyl]-5-heptenoic acid; dinoprostone; PGE2, hCG-alpha-(59-92)-peptide (34 residues), Paraquat Derivative, Paraquat hexanoate (PQ-h), Monoquat, Diquat, 9,10-dihydro-8a,10a-diazoniaphenanthrene, MPTP, 1-methyl-4-phenyl-1,2,5,6-tetrahydropyridine, 1,2-Naphthoquinone, N-Acetyl-S-(1,2-dihydroxy-4-naphthyl)cysteine, N-Acetyl-S-(1,4-dihydroxy-2-naphthyl)cysteine, N-Acetyl-S-(1,2-dihydroxy-1-hydroxy-1-naphthyl)cysteine, 2-Chloro-2'.6'-diethylacetanilide (CDA) Hapten, 2-[2-Chloro-(2'-6'-diethyl)acetanilido]ethanoic Acid, 2-Chloro-2'.6'-diethylacetanilide (CDA) Hapten, 2-[2-Chloro-(2'-6'-diethyl)acetanilido]butanoic Acid, 2-Chloro-2'.6'-diethylacetanilide (CDA) Hapten, 5-(4-Chloroacetamido-3,5-diethyl)phenoxypentanoic Acid, CDA, 2-Chloro-2'.6'-diethylacetanilide, HDA, 2-Hydroxy-2'.6'-diethylacetanilide, 2,6-diethyl-aniline, Hydroxyalachlor, Alachlor ESA, Alachlor ethanesulfonic acid, Isoproturon Hapten, 3-(4-Isopropylphenyl)-1-carboxypropyl-1-methyl urea, chlorotoluron, 3-(3-chloro-p-tolyl)-1,1-dimethylurea, Metoxuron, 3-(3-chloro-4-methoxyphenyl)-1,1-dimethylurea, metamitron, 4-amino-4,5-dihydro-3-methyl-6-phenyl-1,2,4-triazin-5-one, mecoprop, (RS)-2-(4-chloro-o-tolyloxy) propionic acid, propyzamide, 3,5-dichloro-N-(1,1-dimethylpropynyl)benzamide, Paraquat dichloride, MCPB, 4-(4-chloro-o-tolyloxy)butyric acid, Chlortoluron Hapten, N-(3-Chloro-4-methylphenyl)-N-methyl-N-carboxypropyl Urea, Metsulfuron, Methyl 2-[3-(4-methoxy-6-methyl-1,3,5-triazin-2-yl)ureidosulphonyl]benzoate, Captopril Haptens, Captopril-4-(Maleimidomethyl)-cyclohexane Carboxylic Acid (MCC), Captopril Haptens, Captopril Disulfide Modification, Mercaptoethanol-MCC, Mercaptoethanol-4-(Maleimidomethyl)-cyclohexane Carboxylic Acid Modification, Captopril Haptens, Captopril without MCC, Aculeatiside A, Aculeatiside B, Solamargine, Solasonine, solanine-S; purapurine, Solasodine, Khasianine, Tomatine, lycopersicin, Tomatidine, 3-O-beta-D-Glucopyranosyl-solasodine, O-alpha-L-Rhamnosyl-1(1→2)-3-O-beta-D-glucopyranosyl-solasodine, 3-O-beta-D-Galacopyranosyl-solasidine, O-beta-D-Glucopyranosyl-1(1→3)-3-O-beta-D-galacopyranosyl-solasodine, 12-Hydroxysolamargine, 12-Hydroxysolasonine, Isoanguivine, Solaverine I, Solaverine II, Xylosyl-beta-solamargine, alpha-Solanine, alpha-Chaconine, Dioscine, Indole Derivatives, beta-Indole Acetic Acid, 2-Bromo-4,6-dinitroaniline, 2-Chloro-4,6-dinitroaniline, Tetryl, 2,4,6-trinitrophenyl-n-methylnitramine, nitramine, tetralite, tetril, 2-Amino-4,6-dinitrotoluene, 2,4-Dinitroaniline, 3,5-Dinitroaniline, 2-Amino-4,6-dinitrobenzoic acid, Disperse Blue 79, N-[5-[bis[2-(acetyloxy)ethyl]amino]-2-[(2-bromo-4,6-dinitrophenyl)azo]-4-ethoxyphenyl]acetamide, 1,3-Dinitrobenzene, 2,6-Dinitrotoluene, 4-Amino-2,6-dinitrotoluene, 1,3,5-Trinitrobenzene, Nicergoline, Ethylmorphine, 8-Didehydro-4,5-epoxy-3-ethoxy-17-methylmorphinan-6-ol, Dihydromorphine, Dihydrocodeine, dihydromorphinone, Hydromorphone, Dihydrocodeinone, Hydrocodone, Naltrexone, N-cyclopropylmethyl-14-hydroxydihydromorphinone, Dextromethorphan, (±)-3-Methoxy-17-methylmorphinan, Homatropine, Endorphins Modification Derivative Type: b-Endorphin, Met-enkephalin, DALEA, D-Ala(2)-D-Leu(5)-enkephalinamide, Vincristine, 22-Oxovincaleukoblastine, leurocristine; VCR; LCR, OCT, 22-Oxacalcitriol, OCT-3-HG, 22-oxacalcitriol-3-Hemiglutarate, 24(OH)OCT, 24(OH)-22-oxacalcitriol, 1,20(OH)2-hexanor-D3, Synephrine, Epinephrine, 4-[(1R)-1-Hydroxy-2-(methylamino)ethyl]-1,2-benzenediol, Phenylephrine, Dopamine Derivative, 6-hydroxy dopamine, Tyramine derivative, 3-methoxy tyramine, Phenethylamine, Benzeneethanamine; PEA, m-tyramine, o-tyramine, dimethoxyphenethylamine, Thymidine glycol monophosphate, 5,6-Dihydroxythymidine monophosphate, Thymidine monophosphate, Thymidine glycol, Thymine glycol, 5,6-Dihydrothymidine, Thymidine, Thymine, 5-methyluracil; 2,4-dihydroxy-5-methylpyrimidine, AMP, Adenosine mono phosphate, CMP, Cytidine mono phosphate, Carbamazepine, 5-carbamoyl-5H-dibenz[b,f]azepine, Neopterin isomers, D-erythro-Neopterin, Neopterin isomers, L-erythro-Neopterin, Neopterin isomers, D-threo-Neopterin, Biopterin isomers, L-erythro-Biopterin, Biopterin isomers, D-erythro-Biopterin, Biopterin isomers, L-threo-Biopterin, Biopterin isomers, D-threo-Biopterin, Pterin-6-Carboxylic Acid, C7H5NiO3, Pterin, Thromboxane B2, (5Z,9alpha,13E,15S)-9,11,15-trihydroxythromboxa-5,13-dien-1-oic acid, 15 Ketoprostaglandin F2alpha, Fumonisin B1, macrofusine; FBI, Thyroliberin, TRH; thyrotropin-releasing factor; thyrotropin releasing hormone; TRF; protirelin; lopremone, Thyroliberin-OH, TRH-OH, Diketopiperazine, cyclo (H-P), TRH analogues, Methylated TRH, TRH analogues, TRH elongated peptides, TRH-Gly, TRH elongated peptides, TRH-Gly-Lys-Arg, TRH elongated peptides, TRH-Gly-Lys-Arg-Ala, TRH elongated peptides, P7 (Modification Q-H-P-G-L-R-F), TRH elongated peptides, P10 (Modification S-L-R-Q-H-P-G-L-R-F), TRH elongated peptides, Ps5 Modification pro-TRH[178-199], TRH elongated peptides, TRH-Ps5 (Modification pro-TRH[172-199]), Hypothalmic peptide, LHRH, Cyanoginosin-LA, Cyanoginosin-LB, Cyanoginosin-LR, Cyanoginosin-LY, Cyanoginosin-AY, Cyanoginosin-FR, Cyanoginosin-YR, Ne-acetyllysine-containing peptide, Gly-Lys (Ac)-e-aminocaproic acid (Aca)-Cys, Benzoic Acid, Benzenecarboxylic acid; phenylformic acid; dracylic acid, m-hydroxybenzoic acid, 3-hydroxybenzoic acid, o-methoxybenzoic acid, 2-methoxybenzoic acid, o-toluic acid, 2-Methylbenzoic acid, o-chlorobenzoic acid, 2-chlorobenzoic acid, o-aminobenzoic acid, 2-aminobenzoic acid, thiosalicylic acid, 2-Mercaptobenzoic acid; o-sulfhydrylbenzoic acid, Salicylamide, 2-Hydroxybenzamide, Saligenin, saligenol; o-hydroxybenzyl alcohol; Salicyl alcohol, 2-cyanophenol, 2-hydroxyphenyl acetic acid, p-hydroxybenzoic acid, p-aminobenzoic acid, 4-Aminobenzoic acid; vitamin Bx; bacterial vitamin H1, p-toluic acid, p-methylamino benzoic acid, p-chlorosalicylic acid, 4-chloro-2-hydroxybenzoic acid, 2,4-dihydroxybenzoic acid, beta-Resorcylic Acid; 2,4-dihydroxybenzenecarboxylic acid; BRA, 4-aminosalicylic acid, 4-Amino-2-hydroxybenzoic acid; p-aminosalicylic acid, Gentisic Acid, 2,5-dihydroxybenzoic acid; 5-hydroxysalicylic acid, Picolinic acid, o-Pyridinecarboxylic acid; 2-Pyridinecarboxylic acid, picolinic acid N-oxide, 3-hydroxypicolinic acid, 2-hydroxynicotinic acid, 7-methylguanine, N2-Carboxymethyl-N7-methylguanine, 2-(7-methyl-6-oxo-6,7-dihydro-1H-purin-2-ylamino)acetic acid, 7-methylxanthine, 7-methyluric acid, 7-methyladenine, Guanine, 2-Amino-1,7-dihydro-6H-purin-6-one; 2-aminohypoxanthine, Adenine, 6-aminopurine; 6-amino-1H-purine; 6-amino-3H-purine; 6-amino-9H-purine, 7-(2-Carboxyethyl)guanine, 7-CEGua, 7-Ethylguanine, 2-amino-7-ethyl-1H-purin-6(7H)-one, 7-(2,3-Dihydroxypropyl) guanine, 2-amino-7-(2,3-dihydroxypropyl)-1H-purin-6 (7H)-one, 7-(2-Hydroxyethyl)guanine, 2-amino-7-(2-hydroxyethyl)-1H-purin-6(7H)-one, 7-(2-[(2-Hydroxyethyl) amino]ethyl)-guanine, 2-amino-7-(2-(2-hydroxyethylamino)ethyl)-1H-purin-6(7H)-one, 7-Carboxymethylguanine, or 2-(2-amino-6-oxo-1,6-dihydropurin-7-yl)acetic acid. In some alternatives, the CAR or T cell receptor comprises a fragment specific for the hapten, wherein the CAR or TCR comprises 14G8, Anti 3-methylindole antibodies, 3F12, Anti 3-methylindole antibodies, 4A1G, Anti 3-methylindole antibodies, 8F2, Anti 3-methylindole antibodies, 8H1, Anti 3-methylindole antibodies, Anit-Fumonisin B1 antibodies, Anti-1,2-Naphthoquinone-antibodies, Anti-15-Acetyldeoxynivalenol antibodies, Anti-(2-(2,4-dichlorophenyl)-3(1H-1,2,4-triazol-1-yl)propanol) Antibodies (Anti-DTP antibodies), Anti-22-oxacalcitriol antibodies (As-1, 2 and 3), Anti-(24,25(OH)2D3) Antibodies (Ab11), Anti-(24,25(OH)2D3) Antibodies (Ab3), Anti-(24, 25(OH)2D3) Antibodies (Ab3-4), Anti-2,4,5-Trichlorophenoxyacetic acid antibodies, Anti (2,4,5-Trichlorphenoxyacetic acid) Antibodies, Anti-(2,4,6-Trichlorophenol) Antibodies, Anti-(2,4,6-Trichlorophenol) Antibodies, Anti 2,4,6-Trinitrotoluene (TNT) Antibodies, Anti-2,4-Dichlorophenoxyacetic acid(MAb's B5/C3, E2/B5, E2/G2, F6/C10, and F6/E5), Anti (2,4-Dichlorphenoxyacetic acid) Antibodies, Anti-2-hydroxybiphenyl-antibodies, Anti-(3,5,6-trichloro-2-pyridinol) Antibodies (LIB-MC2, LIB-MC3), Anti (3,5,6-trichloro-2-pyridinol) antibodies (LIB-MC2 MAb), Anti-3-Acetyldeoxynivalenol (3-AcDON) Antibodies, Anti-3-phenoxybenzoic acid (3-PBAc)-Antibodies, Anti-4-Nitrophenol antibodies, anti-4-nitrophenyl 4'-carboxymethylphenyl phosphate antibodies, Anti-7-(Carboxyethyl)guanine (7-CEGua) antibodies (group specific for 7-meGua), Anti-7-methylguanine (7-MEGua) antibodies, Anti-ABA antibodies, Anti Acephate antibodies (Antiserum 8377), Anti-acetyllysine antibodies (mAbs AL3D5, AL11, AKL3H6, AKL5C1), Anti Aculaetiside-A antibody, Anti Aflatoxin M1(AFM1)antibodies (mAbs A1, N12, R16, FF32), Anti-agatharesinol Antibody, Anti-agatharesinol Antibody, Anti Amidochlorantibodies, Anti-Amitrole antibodies (anti 1a-BSA antibodies), Anti ampicillin Antibodies (AMPI I 1D1 and AMPI II 3B5), Anti-anandamide antibodies (9C11.C9C, 30G8.E6C, 7D2.E2b, 13C2 MAbs), Anti atrazine antibodies, Anti-atrazine antibodies, Anti-Atrazine antibodies, Anti Atrazine Antibodies, Anti-Atrazine Antibodies, Anti-Atrazine Antibodies, Anti-Atrazine Antibodies (4063-21-1 MAb cell line mAb and scAbs), Anti-Atrazine Antibodies (4D8 and 6C8 scAb), Anti Atrazine Antibodies (C193), Anti Atrazine Antibodies (In Rabbit/Sheep), Anti Atrazine Antibodies (K4E7), Anti Atrazine Antibodies (MAb: AM7B2.1), Anti Atrazine Antibodies (ScAb), Anti Atrazine Mercapturic acid antibodies, Anti (Azinphos methyl) Antibodies (MAB's LIB-MFH14, LIB-MFH110), Anti benalaxyl antibody, Anti benzimidazolecarboxylic acid, Anti benzimidazoles antibody (Ab 587), Anti-Benzo [a]pyrene antibodies, Anti Benzo(a)pyrene antibodies (10C10 and 4D5 MAbs), Anti-(Benzoylphenylurea)-Antibodies (mainly against Diflubenzuron), Anti-berberine Antibodies, Anti-beta Indole Acetic Acid Antibodies, Anti-Biopterin (L-erythro form) Antibodies, Anti-Brevetoxin PbTx-3-Antibodies, Anti Bromacil Antibodies, Anti-Bromophos Antibodies, Anti-Bromophos ethyl Antibodies, Anti Butachlor antibodies, Anti-Captopril-MCC Antibodies, Anti-Carbamazepine (CBZ)-Antibodies, Anti Carbaryl Antibodies, Anti Carbaryl Antibodies (LIB-CNH32, LIB-CNH33, LIB-CNH36, LIB-CNH37, LIB-CNH45, LIB-CNA38), Anti-Carbaryl Antibodies (LIB/CNH-3.6 MAb), Anti Carbofuran Antibodies (LIB-BFNB-52, LIB-BFNB-62, LIB-BFNB-67), Anti Carbofuran Antibodies (LIB-BFNP21), Anti-CDA-antibodies, Anti-CDA-antibodies (anti-2-[2-Chloro-(2'-6'-diethyl)acetanilido]butanoic Acid), Anti-CDA-antibodies (anti-2-[2-Chloro-(2'-6'-diethyl)acetanilido]ethanoic Acid), Anti-CDA-antibodies (anti-5-(4-Chloroacetamido-3,5-diethyl)phenoxypentanoic Acid), anti-ceftazidime antibody, Anti-(chlorodiamino-s-triazine) Antibodies (Anti-CAAT) (PAb1-8), Anti Chlorothalonil Antibodies, Anti-Chlorpyrifos antibodies, Anti-Chlorpyrifos Antibodies, Anti-Chlorpyrifos Antibodies (LIB-AR1.1, LIB-AR1.4 Mabs), Anti-Chlorpyrifos Antibodies (LIB-C4), Anti (chlorpyrifos) antibodies (LIB-C4 MAb), Anti-Chlorpyrifos Antibodies (LIB-PN1 Mabs), Anti-Chlorpyrifos Antibodies (LIB-PN2 Mabs), Anti-Chlorpyrifos Antibodies (LIB-PO Mabs), Anti-chlorsulfuron antibodies, Anti-Chlorsulfuron antibodies, Anti Chlortoluron Antibodies (Antiserum), Anti-Cyanoginosin-LA antibodies (mAbs 2B2-2, 2B2-7, 2B2-8, 2B2-9, 2B2-10, 2B5-5, 2B5-8, 2B5-14, 2B5-15, 2B5-23), Anti (D-3-methoxy-4-hydroxyphenylglycol) antibodies, Anti-DDA antibodies, Anti DDT antibodies (PAbs and MAbs), Anti-DDT Mabs (LIB1-11, LIB5-21, LIB5-25, LIB5-28, LIB5-212, LIB5-51, LIB5-52, LIB5-53), Anti-DEC Antibodies (Anti diethylcarbamazine Antibodies), Anti DEHA antibodies, Anti-(Delor 103) antibodies, Anti-Deltamethrin Antibodies, Anti Deltamethrin Antibodies (Del 01 to Del 12 MAbs and PAbs), Anti-deoxynivalenol (DON) Antibodies, Anti-Deoxynivalenol (DON) Antibodies, Anti Dexamethasone Antibody, Anti Dexamethasone Antibody, Anti-Dinitrophenyl (DNP)-antibodies, Anti dinitrophenyl spin labeled antibodies (AN01-AN12), Anti Diuron Antoboides (MAb's: 21, 60, 195, 202, 275, 481, 488, 520), Anti-D-MHPG Antibodies, Anti DNC antibodies, Anti-EB1089 antibodies, Anti-ecdysone antibodies, Anti-endosulfan antibodies, Anti-Endosulfan antibodies, Anti Esfenvalerate antibodies (Ab7588), Anti estradiol antibodies, Anti-Fenitrothion antibodies (pAbs and mAbs), Anti-Fenpropimorph antibodies, Anti Fenthion Antibodies, Anti-Fenthion Antibodies, Anti FITC antibodies (B13-DEI), Anti-Flucofuron antibodies (F2A8/1/A4B3), Anti-flufenoxuron antibodies, and Anti-(Benzoylphenylurea)-Antibodies, Anti-Formononetin Antibodies, Anti-Furosemide antibodies (Furo-26, Furo37, furo-72, Furo 73 Mabs), Anti-GR151004 Antibodies, Anti-hCG-alpha-peptide Antibodies (FA36, Anti hydroxyatrazine antibodies (HYB-283-2), Anti-Hydroxysimazine Antibodies, Anti Imazalil Antibodies MoAb's (9C1-1-1, 9C5-1-1, 9C6-1-1, 9C8-1-1, 9C9-1-1, 9C12-1-1, 9C14-1-1, 9C16-1-1, 9C18-1-1, 9C19-1-1, 9E1-1, 9G2-1), Anti Irgarol Antibodies, Anti Isopentenyl adenosine antibodies, Anti Isoproturon Antibodies, Anti-KB-6806 antiserum, Anti-(+)lupanine antibodies, Anti Lysophosphatidic (LPA) acid, Anti M3G Ab1 and Ab2, Anti M3G Ab1 and Ab2, Anti-MBC antibodies (Anti-2-succinamidobenzimidazole antiserum), Anti Metanephrine antibodies, anti (+)methamphetamine antibodies, Anti-Methiocarb Antibodies (LIB-MXNB31, LIB-MXNB-33, LIB-MXNH14 and LIB-MXNH-15 MAbs), Anti Metolachlor antibodies, Anti-Metolachlor Antibodies, Anti-Metolachlor Antibodies (MAb 4082-25-4), Anti Molinate Antibodies, Anti monuron antibodies, Anti-morphine-3-glucuronide (E3 scFv antibody), Anti morphine antibodies, Anti-Morphine antibodies, Anti-Morphine Antibodies (mAbs 8.2.1, 33.2.9, 35.4.12, 39.3.9, 44.4.1, 76.7F.16, 83.3.10, 115.1.3, 124.2.2, 131.5.13, 158.1.3, 180.2.4), Anti-Neopterin (D-erythro form) Antibodies, Anti-Nicarbazin Antibodies (Nic 6, Nic 7, Nic 8, and Nic 9), Anti Nicergoline Antibodies (Nic-1, Nic-2, Nic-3 & BNA-1, BNA-3), Anti-norflurazon antibodies, Anti NorMetanephrine antibodies, Anti (o-DNCP) Antibodies, Anti-P10 antibodies (TRH elongated peptide), Anti-Paraoxon Antibodies (BD1 and CE3), Anti Paraquat antibodies, Anti-Paraquat antibodies, anti Parathion-methyl antibodies, Anti PCB Antibodies (against 3,3',4,4'-tetrachlorobiphenyl) MAb S2B1, Anti pentachlorophenol antibodies, Anti Pentachlorophenol antibodies, Anti-Pentachlorophenol antibodies, Anti permethrin antibodies (Mabs Py-1, Py-3 and Py-4), Anti-Phencyclidine Antibodies (Mab 6B5 Fab), Anti-phenobarbital antibodies, Anti-phenobarbital antibodies, Anti-(p.p'-DDT)-Antibodies (LIB-DDT-35 and LIB-DDT5-52), Anti permethrin antibodies (Ab549), Anti Propoxur antibodies (LIB-PRNP15, LIB-PRNP21, LIB-PRNB21, LIB-PRNB33), Anti-Prostaglandin E2-antibodies, Anti-p-tyramine antibodies, Anti pyrene antibodies, Anti retronecine antibodies, Anti-Retronecine Antibodies, Anti salicylate antibodies, Anti Sennoside A antibodies (MAb 6G8), Anti Sennoside B antibodies (MAb's: 7H12, 5G6, 5C7), Anti Simizine antibodies, Anti Sulfonamides antibodies (Anti-TS), Anti-Sulocfuron antibodies (S2B5/1/C3), Anti sulphamethazine antibodies (21C7), Anti-synephrine antibodies, Anti-Thiabendazole antibodies (Antibody 300), Anti-Thiabendazole antibodies (Antibody 430 and 448), Anti-Thiram-Antibodies, Anti-THP antibodies (7S and 19S), Anti-Thromboxane B2 Antibodies, Anti-thymidine glycol monophosphate antibodies (mAb 2.6F.6B.6C), Anti-Thyroliberin (TRH) antibodies, Anti TNT antibodies (AB1 and AB2 antiserum), Anti Triadimefon Antibodies, Anti-triazine antibodies (AM1B5.1), Anti-triazine antibodies (AM5C5.3), Anti-triazine antibodies (AM5D1.2), Anti-triazine antibodies (AM7B2.1), Anti-triazine antibodies (SA5A1.1), Anti-Triazine serum (anti-ametryne), Anti-Triazine serum (anti-atrazine), Anti-Triazine serum (anti-simazine), Anti-Triazine serum (anti-simetryne), Anti Trifluralin Antibodies, Anti Trifluralin Antibodies, Anti Vincristine Antibodies, Anti-Zearalenone Antibodies, Anti Zeatin riboside antibodies, E2 G2 and E4 C2, Fab Fragment K411B derived from MAb K4E7 (isotype IgG2b with k light chain), LIB-BFNP23 Mab, MAb's H-7 and H-9 (against O,O-diethyl OP pesticides), MoAb 33A7-1-1, MoAb 33B8-1-1, MoAb 33C3-1-1, MoAb 3C10-1-1 and MoAb 3E17-1-1, MoAb 45D6-5-1, MoAb 45E6-1-1, MoAb 45-1-1, Mutant (GlnL89Glu) in Fab Fragment K411B derived from MAb K4E7 (isotype IgG2b with k light chain), Mutant (GlnL89Glu/ValH37Ile/GluL3Val) in Fab Fragment K411B derived from MAb K4E7 (isotype IgG2b with k light chain), Mutant (GlnL89Glu/ValH37Ile/GluL3Val) in Fab Fragment K411B derived from MAb K4E7 (isotype IgG2b with k light chain), Mutant (GlnL89Glu/ValH37Ile) in Fab Fragment K411B derived from MAb K4E7 (isotype IgG2b with k light chain), Mutant (GlnL89Glu/ValH37Ile) in Fab Fragment K411B derived from MAb K4E7 (isotype IgG2b with k light chain), Mutant (GluH50Gln) in Fab Fragment K411B derived from MAb K4E7 (isotype IgG2b with k light chain), Mutant (GluH50X) in Fab Fragment K411B derived from MAb K4E7 (isotype IgG2b with k light chain), Mutant (GlyH100aAla) in Fab Fragment K411B derived from MAb K4E7 (isotype IgG2b with k light chain), Mutant (GlyH100aSer) in Fab Fragment K411B derived from MAb K4E7 (isotype IgG2b with k light chain), Mutant (HisH95Phe) in Fab Fragment K411B derived from MAb K4E7 (isotype IgG2b with k light chain), Mutant (HisH95Tyr) in Fab Fragment K411B derived from MAb K4E7 (isotype IgG2b with k light chain), Mutant (PheL32Leu) in Fab Fragment K411B derived from MAb K4E7 (isotype IgG2b with k light chain), Mutant (TrpH33Phe,Tyr,Leu) in Fab Fragment K411B derived from MAb K4E7 (isotype IgG2b with k light chain), Mutant (Tryl96Phe) in Fab Fragment K411B derived from MAb K4E7 (isotype IgG2b with k light chain), Mutant (TryL96Phe) in Fab Fragment K411B derived from MAb K4E7 (isotype IgG2b with k light chain), Mutant (ValH37Ile) in Fab Fragment K411B derived from MAb K4E7 (isotype IgG2b with k light chain), Mutant (ValH37Ile) in Fab Fragment K411B derived from MAb K4E7 (isotype IgG2b with k light chain), P6A7 MAb, PNAS2 6/3 56(1)-1-5-1, PNAS2 6/3 56(1)-1-5-2, PNAS2 6/3 56(1)-1-10-4, PNAS2 6/3 56(1)-1-10-5 and PNAS2 6/3 56(1)-3-1-5, Alexa Fluor 405/Cascade Blue dye antibody, Alexa Fluor 488 dye antibody, BODIPY FL dye antibody, Dansyl antibody, Fluorescein/Oregon Green dye antibody, Lucifer yellow dye antibody, Tetramethylrhodamine and Rhodamine Red dye antibody, Texas Red and Texas Red-X dye antibody, Biotin antibody, Dinitrophenyl antibody and/or Nitrotyrosine antibody or any portion thereof of the aforementioned haptens.

In a fourth aspect, a composition is provided, wherein the composition comprises a lipid, and wherein the lipid comprises a target moiety that is bound to a masking moiety. In some alternatives, the target is bound to the masking moiety through a spacer. In some alternatives, the masking moiety is removed when the composition is in a tumor microenvironment. In some alternatives, the masking moiety is removed when the composition is in a ROS rich tumor environment. In some alternatives, the masking moiety is removed when the composition is within an acidic environment. In some alternatives, the acidic environment comprises a pH of 4, 5, 6 or 6.5 or any pH in between a range defined by any two aforementioned values. In some alternatives, the masking moiety is removed by nitrosylation.

In a fifth aspect, a method of treating, ameliorating, or inhibiting a cancer in a subject is provided, wherein the method comprises: a) introducing, providing, or administering to a subject the composition of any one of the alternatives herein, wherein the composition comprises a lipid, which comprises a target moiety that is bound to a masking moiety and, optionally, by attachment through a spacer, b) introducing, providing, or administering to said subject a cell comprising a chimeric antigen receptor (CAR) or T cell receptor (TCR), which is specific for the target moiety once the masking moiety is removed from the target moiety, c) removing the masking moiety from the target moiety thereby allowing the target moiety to bind to the CAR present on the cell, and, d) optionally, measuring or evaluating the binding of the cell comprising the CAR to the lipid, after steps a-c and/or e) optionally, measuring or evaluating the treatment, amelioration, or inhibition of said cancer after steps a-d, and/or f) optionally, identifying a subject in need of a therapy for cancer prior to steps a-c. In some alternatives, the composition comprises a lipid, wherein the lipid comprises a target moiety that is bound to a masking moiety. In some alternatives, the target is bound to the masking moiety through a spacer. In some alternatives, the masking moiety is removed when the composition is in a tumor microenvironment. In some alternatives, the masking moiety is removed when the composition is in a ROS rich tumor environment. In some alternatives, the lipid comprises a polar head group and a hydrophobic group. In some alternatives, the hydrophobic group is fatty acid such as an aliphatic chain. In some alternatives, the fatty acid is saturated or unsaturated. In some alternatives, the hydrophobic group comprises an alkyl, alkenyl or alkynyl group. In some alternatives, the hydrophobic group comprises a terpenoid lipid such as a steroid or cholesterol. In some alternatives, the hydrophobic group comprises an ether linkage, wherein the ether linkage is between the polar head group and the aliphatic chain. In some alternatives, the lipid is a phospholipid ether (PLE). In some alternatives, the polar head comprises a choline, a phosphatidylcholine, sphingomyelin, phosphoethanolamine group, an oligosaccharide residue, a sugar residue, phosphatidyl serine or phosphatidyl inositol. In some alternatives, the sugar is a glycerol. In some alternatives, the target moiety is a hapten, poly(his) tag, Strep-tag, FLAG-tag, V5-tag, Myc-tag, HA-tag, NE-tag, biotin, digoxigenin, dinitrophenol or fluorescein. In some alternatives, the hydrophobic group comprises a carbon alkyl chain. In some alternatives, the carbon alkyl chain comprises 8, 9, 10, 11, 12, 13, 14, 15, 16, 17, 18, 19, 20, 21 or 22 carbons or any number that is within a range defined by any two aforementioned values. In some alternatives, the carbon alkyl chain comprises 18 carbons. In some alternatives, the polar-head group comprises phosphocholine, a piperidine moiety or a trimethylarseno-ethyl-phosphate moiety. In some alternatives, the spacer comprises a PEG spacer, a Hapten (2×) spacer, a Hapten (3×) spacer, a Hapten (4×) spacer, a Hapten (5×) spacer, or an alkane chain. In some alternatives, the PEG spacer comprises 1, 2, 3, 4, 5, 6, 7, 8, 9, 10, 11, 12, 13, 14, 15, 16, 17, 18, 19, 20 or 21 PEG molecules, or any amount of PEG molecules that is within a range defined by any two aforementioned values. In some alternatives, the masking moiety comprises a phenolic hydroxyl group or PEG. In some alternatives, the phenolic hydroxyl group is bound to a hydroxyl on a xanthene moiety of fluorescein. In some alternatives, the masking moiety is bound to the target moiety by a cleavable moiety, which is optionally configured to be specifically cleavable in a tumor microenvironment. In some alternatives, the cleavable moiety, which is configured to be cleavable in a tumor microenvironment, is cleaved by a reactive oxygen species reaction, an acidic pH, hypoxia, or nitrosylation. In some alternatives, the cell is provided to the subject 1, 2, 3, 4, 5, 6, 7, 8, 9, 10, 11, 12, 15, 20, 24, 36, 48, 60 or 72 hours after administration of the composition, or any time within a range defined by any two aforementioned values. In some alternatives, the cell is provided to the subject 1, 2, 3, 4, 5, 6, 7, 8, 9, 10, 11, 12, 15, 20, 24, 36 or 48 hours before administration of the composition, or any time within a range defined by any two aforementioned values. In some alternatives, the cell is provided to the subject within seconds or minutes, such as less than an hour, of providing the composition to the subject. In some alternatives, a boost of the cell and/or the composition is provided to the subject. In some alternatives, an additional cancer therapy is provided, such as a small molecule, e.g., a chemical compound, an antibody therapy, e.g., a humanized monoclonal antibody with or without conjugation to a radionuclide, toxin, or drug, surgery, and/or radiation. In some alternatives, the cancer is breast, ovarian, lung, pancreatic, prostate, melanoma, renal, pancreatic, glioblastoma, neuroblastoma, medulloblastoma, sarcoma or liver cancer. In some alternatives, the cell comprising the CAR or TCR is a T cell. In some alternatives, the CAR or TCR is on the surface of the cell or the T cell. In some alternatives, the cell is a precursor T cell. In some alternatives, the precursor T cell is a hematopoietic stem cell. In some alternatives, the cell is a CD8+ T cytotoxic lymphocyte cell selected from the group consisting of naïve CD8+ T cells, central memory CD8+ T cells, effector memory CD8+ T cells and bulk CD8+ T cells. In some alternatives, the cell is a CD4+ T helper lymphocyte cell that is selected from the group consisting of naïve CD4+ T cells, central memory CD4+ T cells, effector memory CD4+ T cells, and bulk CD4+ T cells. In some alternatives, the lipid intercalates in a lipid bilayer of a target cell. In some alternatives, the target cell is a tumor cell. In some alternatives, the target cell is an immune cell. In some alternatives, the immune cell is a T cell or a B cell. In some alternatives, the target cell is in a tumor microenvironment. In some alternatives, the masking moiety is removed when the composition is within an acidic environment. In some alternatives, the acidic environment comprises a pH of 4, 5, 6 or 6.5 or any pH in between a range defined by any two aforementioned values. In some alternatives, the masking moiety is removed by nitrosylation. In some alternatives, the hapten used comprises Alexa Fluor 405, Cascade Blue, Alexa Fluor 488, BODIPY, Dansyl chloride, Oregon Green, Lucifer yellow, Rhodamine, Tetramethylrhodamine, Nitrotyrosine, digoxigenin, 2,4-Dichlorophenoxyacetic acid, Atrazine (2-Chloro-4-(ethylamino)-6-(isopropylamino)-s-triazine), Nicotine (3-(1-Methyl-2-pyrrolidyl)pyridine, Black Leaf), Morphine (morph, Morphine Sulfate), 2,4-DINITROCHLOROBENZENE (1-Chloro-2,4-dinitrobenzene; DNCB; Dinitrochlorobenzene), 4-chloro-6-(ethylamino)-1,3,5-triazine-2-(6-aminohexanecarboxylic acid), Structurally related s-triazines (Modifications: H/Cl/C6 R1=NH2- R2=—Cl R3=—NH—(CH2)5-COOH; iPr/Cl/nBu R1=(CH3)2-CH—NH— R2=—Cl R3=—NH—(CH2)3-(CH3)), Ametryn (2-Ethylamino-4-isopropylamino-6-methylthio-1,3,5-triazine), Deethylatrazine (DEA) (Structurally related s-triazines), Deisopropylatrazine (DIA) (Structurally related s-triazines), Deethyldeisopropylatrazine (DEDIA) (Structurally related s-triazines), Deethyldeisopropylatrazine (DEDIA) (Structurally related s-triazines), HydroxyAtrazine (HA) (Structurally related s-triazines), DeisopropylHydroxyAtrazine (DIHA) (Structurally related s-triazines), DeethylDeisopropylHydroxyAtrazine (DEDIHA) (Structurally related s-triazines), Simazine (Structurally related s-triazines), Desmetryne (Structurally related s-triazines), Prometryne (Structurally related s-triazines), 2-hydroxyatrazine (atrazine derivative), 2-hydroxypropazine (structurally related s-triazine), 2-hydroxysimazine, N-(4-Amine-6-hydroxy-[1,3,5]triazin-2-yl)-4-aminobutanoic Acid (Modification: R1=NH2 R2=NH(CH2)3COOH R3=OH), SulcoFuron, 5-chloro-2-{4-chloro-2-[3-(3,4-dichlorophenyl)ureido] phenoxy}benzenesulfonic acid, FlucoFuron (1,3-bis(4-chloro-α,α,α-trifluoro-m-tolyl)urea), Agatharesinol, Sequirin C, Sugiresinol, Hydroxysugiresinol, Hinokiresinol, Coniferyl alcohol, Cinnamyl alcohol, p-Coumaric acid, Cinnamic acid, p-Coumaric acid, Cinnamic acid, Hinokinin, Guaiacylglycerol-beta-guaiacyl ether, Morphine-3-glucuronide (M3G), Codeine, Nor-Codeine, 6-Monoacetylmorphine, (+) Methamphetamine, Ceftazidime, Phenobarbital, p-hydroxyPhenobarbital, p-aminophenobarbital, Cyclobarbital, 3'-Ketocyclobarbital, 3'-Hydroxycyclobarbital, Secobarbital, Barbital, Metharbital, Barbituric acid, Thiopental, Thiobarbituric acid, Primidone, Glutethimide, Pentobarbital, Heroin, Diacetylmorphine, Levallorphan, L-11-Allyl-1,2,3,9,10,10a-hexahydro-4H-10,4a-iminoethano-phenanthren-6-ol, Pethidine (Demerol; Dolantin; Meperidine; Ethyl 1-methyl-4-phenylpiperidine-4-carboxylate; Isonipecaine), Methamphetamine, d-Desoxyephedrine; Methedrine; Tolpropamine; Pratalgin; Pragman. Benzoylecgonine, 3-Carboxymethylmorphine, Cocaine, 5-benzimidazolecarboxylic acid, ABA (4-acetyl benzoic acid), Dexamethasone, Flumethasone, 6alpha, 9 alpha-difluoro-11 beta, 17,21-trihydroxy-16 alpha-methylpregna-1,4-diene-3, 20-dione, 9 alpha-fluoro-11 beta,17,21-trihydroxy-16 beta-methylpregna-1,4-diene-3,20-dione, 9-alpha-fluroprednisolone, Desoxymethasone, Triamcinolone, 9 alpha-fluoro-11 beta,16 alpha, 17,21-tetrahydroxypregna-1,4-diene-3,20-dione, Fluocortolone, 6 alpha-fluoro-11 beta,21-dihydroxypregna-1,4-diene-3,20-dione, Cortisol, 11 beta, 17,21-trihydroxypregna-4-ene-3,20-dione, Prednisone, 17,21-dihydroxypregn-4-ene-3,11,20-trione, Methylprednisolone, 11 beta, 17,21-trihydroxy-6 alpha-methylpregna-1,4-diene-3,20-dione, Triamcinolone hexacetonide, 21-(3,3-dimethyl-1-oxobutoxy)-9 alpha-fluoro-11-hydroxy-16,17-[(1-methylethylidene) bis(oxy)]pregna-1,4-diene-3,20-dione, Carbofuran, 2,3-dihydro-2,2-dimethyl-7-benzofuranyl methylcarbamate, BFNP (3-[[(2,3-dihydro-2,2-dimethyl-7-benzofuranyloxy)carbonyl]amino]propanoic acid), Carbofuran derivative, 2,3-dihydro-2,2-dimethyl-7-benzofuranol, Bendiocarb, Carbaryl, Methiocarb, Propoxur, Aldicarb, Methomyl, Benalaxyl, methyl N-(phenylacetyl)-N-(2,6-xylyl)-DL-alaninate, Bn-Ba (4-[2-(N-phenylacetyl-N-2,6-xylylamino)propionamido] butyric acid), Bn-COOH (4-[2-(N-phenylacetyl-N-2,6-xylyl-DL-alanine), Benalaxyl derivative, Furalaxyl, Metalaxyl, Acetochlor, Dimetachlor, Metolachlor, 2-chloro-6'-ethyl-N-(2-methoxy-1-methylethyl)acet-o-toluidine, Diethathyl-ethyl, Benzoylprop-ethyl, Benzoylprop-ethyl, 2,4,5-Trichlorophenoxyacetic acid, 2-chloro-6'-ethyl-N-(2-methoxy-1-methylethyl)acet-o-toluidine, Diethathyl-ethyl, Benzoylprop-ethyl, Propachlor, Propachlor, 2,4,5-Trichlorophenoxyacetic acid, 2,4,5;T; Weedone, 2,4-Dichlorophenoxybutyric acid (2,4-DB), 2,4-DB; Butanoic acid, 4-(2,4-dichlorophenoxy)-; Butoxone; Embutone, MCPA, 2-Methyl-4-chlorophenoxyacetic acid; Metaxon, Dichlorprop (2,4-DP), 1-[(2-chloro)phenylsulfonyl]monoamidosuccinic acid, Chlorsulfuron, chlorbromuron, amidosulfuron, chlortoluron, isoproturon, diuron, Linuron O-Methyl-O-(4-nitrophenyl)-N-(4-carboxybutyl)-phosphoramidothioate Parathion-methyl, O,O-dimethyl O-4-nitrophenyl phosphorothioate; Methaphos; Wolfatox; Dimethylparathion; Metacide, Parathion-ethyl, DIETHYL P-NITROPHENYL THIOPHOSPHATE; O,O-DIETHYL O—(P-NITROPHENYL) PHOSPHOROTHIOATE; Fenitrothion, O,O-dimetyl O-4-nitro-m-tolyl phosphorothioate, Fenthion, O,O-dimethyl O-4-methylthio-m-tolyl phosphorothioate, Bromophos, O-4-bromo-2,5-dichlorophenyl O,O-dimethyl phosphorothioate, chlorpyrifos-methyl, O,O-dimethyl O-3,5,6-trichloro-2-pyridyl phosphorothioate, Oxidized parathion-methyl, Paraoxon, phosphoric acid, O,O-diethyl O-(4-nitrophenyl) ester, Diazinon, O,O-diethyl O-2-isopropyl-6-methylpyrimidin-4-yl phosphorothioate, Azinphos-methyl, pirimiphos-methyl, O-2-diethylamino-6-methylpyrimidin-4-yl O,O-dimethyl phosphorothioate, Methidathion, S-2,3-dihydro-5-methoxy-2-oxo-1,3,4-thiadiazol-3-ylmethyl O,O-dimethyl phosphorodithioate, Dimethylchlorothiophosphate, 4-NITROPHENOL, p-nitrophenol, Phenolic derivative (Modification On benzene ring; R1=OH R2=NO2 R3=H R4-CH2COOH R5=H R6=H); 2-Nitrophenol, o-Nitrophenol, 3-Nitrophenol, m-nitrophenol, 2,4-Dinitrophenol, 3,4-Dinitrophenol, 2,5-Dinitrophenol, 2,4-Dinitro-6-methylphenol, 2,3,6-trinitrophenol, 2-Chlorophenol, 4-Chloro-3-methylphenol, Fenitroxon, 3-Methyl-4-nitrophenol, Nonylphenol, HOM(3-[2-hydroxy-5nitro benzylthio] propionic acid, Phenol, Delor 103, Polychlorinated Biphenyls, Delor 104, Polychlorinated Biphenyls, Delor 105, Polychlorinated Biphenyls, Delor 106, 4,4'-Dichlorobiphenyl, PCB congeners, 2,4,4'-Trichlorobiphenyl, PCB congeners, 2,4'-Bichlorobiphenyl, PCB congeners, 2,2'-Dichlorobiphenyl, PCB congeners, 2,4,5-Trichlorobiphenyl, PCB congeners, 3,3',4,4'-Tetrachlorobiphenyl, PCB congeners, PCB congeners, 2,2',4,4',5,5'-Hexachlorobiphenyl, 2-(5-Carboxypentanoylamino)-4,4'-dichlorobiphenyl, Biphenyl derivative, 4-chlorophenoxyacetic acid, 2-Chlorophenoxyacetic acid, DDT,1,1,1-trichloro-2, 2-bis-(p-chlorophenyl)ethane, DDE, 1,1-dichloro-2, 2-bis(p-chlorophenyl)ethylene, p-Chlorophenol, 4-Chlorophenol, m-Chlorophenol 3,4-Dichlorophenol, 3,5-Dichlorophenol, 2,3,4-Trichlorophenol, 2,3,5-Trichlorophenol, 3-methylindole, 3-methylindole Derivatives, 4-(3-methylindol-5-yloxy)butanoic acid, 4-(3-methylindol-5-yloxy)butanoic acid, 3-methylindole Derivatives, 6-[n-3-methylindol-5-yloxy carbonyl)amino]hexanoic acid, 6-[n-3-methylindol-5-yloxy carbonyl)amino]hexanoic acid, 3-methylindole Derivatives, 2-[4-(3-methylindol-6-yl)but-1-ylthio]acetic acid, 2-[4-(3-methylindol-6-yl)but-1-ylthio]acetic acid, 3-methylindole Derivatives, 4-(3-methylindol-6-yl-4-oxo) butanoic acid, 4-(3-methylindol-6-yl-4-oxo)butanoic acid, 3-methylindole Derivatives, 6-(3-methylindol-7-yloxy) hexanoic acid, 6-(3-methylindol-7-yloxy)hexanoic acid, Indole, Indole-3-Carboxylic acid, Indole Derivative-Indole-3-Acetic acid, Indole-3-Acetic acid, Indole Derivative-Indole-3-Propionic acid, Indole-3-Propionic acid, Indole Derivative-Indole-3-Carbinol, Indole-3-Carbinol, Tryptophan, Tryptamine, 5-Methoxyindole-3-carboxaldehyde, 5-Methoxytryptamine, 5-Methoxyindole, 6-Methoxyindole, 7-Methoxyindole,EB1089(Seocalcitol),EB1089(Seocalcitol) Derivative, (22E,24E)-Des-A,B-24-homo-26,27-dimethyl-8-[(E)-N-(2-carboxyethyl)-carbamoylmethylidene]-cholesta-22,24-dien-25-ol, 1 alpha-25-dihydroxyvitamin D3, 25(OH)D3,25-hydroxyvitamin D3,24R,25(OH)2D3, 24R,25-dihydroxyvitamin D3, Vitamin D2, ergocalciferol, Vitamin D3, cholecalciferol,EB1446,EB1436,EB1445, EB1470, DeethylHydroxyAtrazine (DEHA) (Structurally related s-triazines), Irgarol 1051, Flourescein Isothiocyanate, FITC, Metanephrine, NorMetanephrine, Propazine, Terbutylazine, Terbutylazine, 6-chloro-N-(1,1-dimethylethyl)-N'-ethyl-1,3,5-triazine-2,4-diamine, (Structurally related s-triazines), Ametryn (2-Ethylamino-4-isopropylamino-6-methylthio-1,3,5-triazine (Modification iPr/SCH3/Et R1=(CH3)2-CH—NH— R2=—SCH3 R3=—NH—CH2-CH3, Irgarol, Cyanazine (Modification R1=Cl R2=NHCH2CH3 R3=NHCCN(CH3)2), OH-Terbutylazine, Terbutylazine-2OH, Hydroxytriazine (EQ-0027), Deisopropylatrazine (Structurally related S-triazine), Desethylterbutylazine (Structurally related S-triazine), Desethyl-deisopropylatrazine (Structurally related S-triazine), Atraton, Terbutryn (Structurally related s-triazines), Atrazine derivative (Modification R1=—NHCH(CH3)2 R2=—S(CH2)2COOH R3=—NHC2H5), Cyanuric chloride, Trifluralin, (Structurally related s-triazines) tBu/C4/SCH3 (Modification R1=—NH—C—(CH3)3 R2=—NH(CH2)3COOH R3=—SCH3), Sulphamethazine, (Structurally related s-triazines) 6-[[[4-Chloro-6-(methylamino)]-1,3,5-triazin-2-yl]amino]hexanoic Acid (Modification Me/Cl/C6 R1=—NHCH3 R2=—Cl R3=—NH(CH2)5COOH), (Structurally related s-triazines) Procyazine (Modification R1=—Cl R2=—NHcyclopropyl R3=—NHCCN(CH3)2), (Structurally related s-triazines), Prometon (Modification R1=—OCH3 R2=—NHCH(CH3)2 R3=—NHCH(CH3)2); (Structurally related s-triazines) Atrazine Mercapturic Acid (AM) (Modification R1=—SCH2CH(NHAc)COOH R2=—NHCH2CH3 R3=—NHCH(CH3)2), (Structurally related s-triazines), desethyl atrazine mercapturic acid (desethyl AM) (Modification R1=—NAcCys R2=—NH2 R3=—NHCH(CH3)2), (Structurally related s-triazines), deisopropyl atrazine mercapturic acid (deisopropyl AM) (Modification R1=—NAcCys R2=—NHCH2CH3 R3=—NH2), (Structurally related s-triazines), didealkylated atrazine mercapturic acid (didealkylated AM) (Modification R1=—NAcCys R2=—NH2 R3=—NH2), (Structurally related s-triazines), simazine mercapturate (Modification R1=—NAcCys R2=—NHCH2CH3 R3=—NHCH2CH3), (Structurally related s-triazines) (Modification R1=—S(CH2)2COOH R2=—NHCH2CH3 R3=—NHCH2CH3), (Structurally related s-triazines) (Modification R1=—Cl R2=—NHCH(CH3)2 R3=—NH(CH2)2COOH), (Structurally related s-triazines) (Modification R1=—Cl R2=—NHCH2CH3 R3=—NH(CH2)2COOH), (Structurally related s-triazines), atrazine mercapturic acid methyl ester (AM methyl ester) (Modification R1=—NAcCysME R2=—NHCH2CH3 R3=—NHCH(CH3)2), N-acetylcysteine, S-benzyl mercapturate, (Structurally related s-triazines), simetryn (Modification R1=—SCH3 R2=—NHCH2CH3 R3=—NHCH2CH3), Metribuzin, 4-amino-6-tert-butyl-4,5-dihydro-3-methylthio-1,2,4-triazin-5-one, Sulpha Drugs, N4-acetyl-sulphamethazine (Modification N4-acetyl-sulphamethazine), Sulpha Drugs, Sulphathiazole, Sulphathiazole, Sulphamerazine, Sulphamerazine, Sulphaquinoxaline, Sulphaquinoxaline Sulphachlorpyridazine, Sulphachlorpyridazine, Sulphapyridine, Sulphadimethoxine, Sulphadimethoxine, Sulphamethoxazole, Sulphamethoxazole, Sulphisoxazole, Sulphisoxazole, Sulphamethizole, Sulphamethizole, Sulphanilamide, Sulphanilamide, Sulphaguanidine, Sulphaguanidine, Sulphadiazine, Sulphadiazine, Sulphamethoxypyridazine, Sulphamethoxypyridazine, Pentachlorophenoxypropionic acid, Pentachlorophenol, PCP, 2,3,5,6-Tetrachlorophenol, 1,2,4,5 Tetrachlorobenzene, 2,4,6 Trichlorophenol, 2-Methoxy-3,5,6-trichloropyridine, 1,3,5 Trichlorobenzene, 1,3 Dichlorobenzene, 2,4,5-Trichlorophenol, 2,6-Dichlorophenol, 3,5,6-Trichloro-2-pyridinoxyacetic acid, 3,5,6-Trichloro-2-Pyridinol, TCP, 2,4-Dichlorophenol, 2,5-Dichlorophenol, DNC, 4,4'-dinitrocarbanilide, (Structurally related s-triazines), Dichloroatrazine, (Structurally related s-triazines), Dichlorosimazine, 1-((6-chloropyridin-3-yl)methyl)imidazolidin-2-imin, Pyridine Derivative, 6-chloropyridine-3-carboxylic acid, Nicotinic acid, Pyridine Derivative, N-((6-chloropyridin-3-yl)methyl)-N-methylacetamide, (6-chloropyridin-3-yl)-N-methylmethanamine, (6-chloropyridin-3-yl)methanol, Imidacloprid, 1-(6-chloro-3-pyridylmethyl)-N-nitroimidazolidin-2-ylideneamine, Acetamiprid, (E)-N1-[(6-chloro-3-pyridyl)methyl]-N2-cyano-N1-methylacetamidine, Nitenpyram, Deltamethrin, 1(R)-cis-alpha (S)-3-(2,2-dibromoethenyl)-2,2-dimethylcyclopropane carboxylic acid cyano(3-phenoxyphenyl)methyl ester, DON, deoxynivalenol, DON derivative, 15-AcDON (15-acetyldeoxynivalenol), DON derivative, 3-AcDON (3-acetyldeoxynivalenol), DON derivative, 3,15-DiacDON (3,15-diacetyldeoxynivalenol), DON derivative, 3,7,15-TriacDON (3,7,15-Triacetyldeoxynivalenol), NIV (nivalenol), nivalenol, NIV Derivative, 4-AcNIV (fusarenon X), Flutolanil, alpha,alpha,alpha-trifluoro-3'-isopropoxy-o-toluanilide, Mepronil, Mebenil, Benodanil, 24,25(OH)2D3, (24R)-24,25-dihydroxyvitamin D3, 24S,25(OH)2D3, 24S,25-dihydroxyvitamin D3, 25R,26(OH)2D3, 25R,26-dihydroxyvitamin D3, 25S,26(OH)2D3, 25S,26-dihydroxyvitamin D3, 1,24,25 (OH)3D3, 1,24,25-trihydroxyvitamin D3, 1,25-lactone, (23S,25R)-1,25(OH)2 D3 26,23-lactone, 24,25(OH)2-7-DHC, 24,25(OH)2-7-dehydrocholesterol, 25(OH)D3 3S, 25(OH)D3 3-sulfate, 24,25(OH)2D3-Hemiglutarate Derivative, 11 alpha-hemiglutaryloxy-(24R)-24,25-dihydroxyvitamin D3, 24,25(OH)2D3-Hemiglutarate Derivative, (24R)-24,25-dihydroxyvitaminD3-3-hemiglutarate, 24R,25(OH)2D2, 24S,25(OH)2D2, 25(OH)D2, 1,24(OH)2D3, 2,3,6-Trichlorophenol, Tetrachlorohydroquinone, Pentachloroaniline, Pentachlorobenzene, 2,3-Dinitrotoluene, 4-Dinitrotoluene, 2,4,5-Trichloronitrobenzene, 3-(3-Hydroxy-2,4,6-trichlorophenyl)-propanoic acid, 2,3,4,6-Tetrachlorophenol, 2,4,6-Trichloroanisol, 2,4,6-TCA, Pentabromophenol, PBP, 2,4,6-Tribromophenol, 2,4,6-TBP, 2-Bromo-4-Chlorophenol, 2-B-4-CP 2,4-Dibromophenol, 2,4-DBP, 2,6-Dibromophenol, 2,6-DBP, 4-Bromophenol, 4-BP, Furosemide, Ampicillin, Amoxicillin, 6-amino-penicillanic acid (6-APA), Azlocillin, Bacampicillin, Carbenicillin, Epicillin, Cloxacillin, Dicloxacillin, Metampicillin, Methicillin, Moxalactam, Oxacillin, Penicillin G, benzyl penicillin, Penicillin V, phenoxy methyl penicillin, Pheneticillin, Piperacillin, Ticarcillin, Ampicillin hydrolyzed, Penicillin G hydrolyzed, 3-phenoxybenzoic acid (3-PBAc) Chlorpyrifos, Chlorpyrifos derivatives, HClo1, Synthesized directly from chlorpyrifos technical grade by substitution of the chlorine in position 6 by a 3-mercaptopropanoic acid spacer arm, Chlorpyrifos derivatives, HTCP (Modification HTCP of TCP metabolite was prepared from HClo1 by hydrolysis of the thiophosphate ester), Zeatin Riboside (trans isomer), Zeatin (trans isomer), N6-(2-isopentenyl)-adenosine, IPA, N6-(2-isopentenyl)-adenine, 2-iP, Benzyladenine, Kinetin, monuron, monolinuron, fenuron, neburon, propanil, propham, chloropropham, 4-chloroaniline, Methyl Urea Derivative, 1-(3-Carboxypropyl)-3-(4-chlorophenyl)-1-methylurea, Methyl Urea Derivative, 1-(5-Carboxypentyl)-3-(4-chlorophenyl)-1-methylurea, metobromuron, Sennoside B, SB, Sennoside B possessed a erythro configuration between C-10 and C-10', Sennoside A (Modification Sennoside A possessed a threo configuration between C-10 and C-10'), Rhein, Emodin, Aloe-emodin, Barbaloin, 1,4 Dihydroxyanthraquinone, Rhaponticin, Galic acid, Vanillic acid, Caffeic acid, Homogentisic acid, Esculin, Cinnamtannin B1, Baicalin, Naringin hydrate, Wogonin, Wogonin 7-o-beta-glucuronide, Curcumin, delta1-Tetrahydrocannabinolic acid, delta1-Tetrahydrocannabinol, (+−)-cis-4-Aminopermethrin, 3-(4-Aminophenoxy)benzyl(+−)-cis-3-(2,2-dichloroethenyl)-2,2-dimethylcyclopropanecarboxylate, Permethrin, trans-Permethrin, cis-Permethrin, Cypermethrin, Phenothrin, Resmethrin, Cyfluthrin, trans-Permethrin acid Esfenvalerate, Fluvalinate, Fenpropathrin, cis-permethrin acid, 4-Phenoxybenzoyl alcohol, Diuron Derivative, 1-(3-Carboxypropyl)-3-(3,4-dichlorophenyl)-1-methylurea, Siduron, Terbuthiuron, Barban, acid trifluralin, 2,6-dinitro-N-propyl-N-(2-carboxyethyl)-4-(trifluoromethyl)benzenamine, TR-13, 2-ethyl-7-nitro-1-propyl-5-(trifluoromethyl)-1H-benzimidazole, benefin, 2,6-dinitro-N-butyl-N-ethyl-4-(trifluoromethyl)benzenamine, TR-2, 2,6-dinitro-N-propyl-4-(trifluoromethyl)benzenamine, ethalfluaralin, 2,6-dinitro-N-ethyl-N-(2-methyl-2-propenyl)-4-(trifluoromethyl)benzenamine, TR-40, N-(2,6-dinitro-4-(trifluoromethyl)phenyl)-N-propylpropanamide, TR-15, 2-ethyl-4-nitro-6-(trifluoromethyl)-1H-benzimidazole, TR-3, 2,6-dinitro-4-(trifluoromethyl)benzenamine, TR-6, 3-nitro-5-(trifluoromethyl)-1,2-benzenediamine, TR-9, 5-(trifluoromethyl)-1,2,3-benzenetriamine, TR-21, 4-(dipropylamino)-3,5-dinitrobenzoic acid, TR-36M, 3-methoxy-2,6-dinitro-N,N-dipropyl-4-(trifluoromethyl)benzenamine, oryzalin, 3,5-dinitro-4-(dipropylamino)benzenesulfonamide, pendimethalin, 2,6-dinitro-N-(1-ethylpropyl)-3,4-dimethylbenzenamine, penta galloyl glucose, Pyrene Pyrene-1-carboxaldehyde, Phenanthrene, Benzo(a)pyrene, 3,4-Benzopyrene, Anthracene, 3,4-Benzopyrene, Acenaphthene, Fluorene, Chrysene, 1,2-Benzphenanthrene, Benzo[g,h,i]perylene, Benzo[e]pyrene, Acenaphthylene, Fluoranthene, Benzo(j,k)fluorene, Indeno-1,2,3-cd-pyrene, 1,10-(1,2-Phenylene)pyrene, Benzo[a]anthracene, 1,2-Benzanthracene, Benzo(k)fluoranthene, Naphthalene, Benzo[a]fluoranthene, Dibenzo[ah]anthracene, 1,2:5,6-Dibenzanthracene, 2,3-Diaminonaphthalene, 2,6-Dinitroaniline, 17-beta-estradiol (ED), estra-1,3,5(10)-triene-3,17-beta-diol, Trifluralin derivative, 2,6-dinitro-4-tri-fluoromethylaniline, Trifluralin derivative, N-(2,6-dinitro-4-trifluoromethylphenyl)-6-aminohexanoic acid, Trifluralin derivative, N-(2,6-dinitro-4-trifluoromethylphenyl)-N-methyl-6-aminohexanoic acid, Trifluralin derivative, N-(2,6-dinitro-4-trifluoromethylphenyl)-N-propyl-6-aminohexanoic acid, Trifluralin derivative, N-(2,6-dinitro-4-trifluoromethylphenyl)-6-aminohexanoic acid methyl ester, Trifluralin derivative, N-(2,6-dinitro-4-trifluoromethylphenyl)-6-aminohexanoic acid tert-butyl ester, Benfluralin, Ethalfluralin, Trifluralin derivative, 2,6-Dinitro-4-trifluoromethylphenol, Isopropalin, Aniline, 2-Hydroxybenzotrifluoride, N-propyl-6-aminohexanoic acid, N-methyl-6-aminohexanoic acid, MHPG Derivatives, D-MHPG (D-3-methoxy-4-hydroxyphenylglycol), MHPG Derivatives, L-MHPG (L-3-methoxy-4-hydroxyphenylglycol), MHPG Derivatives, DL-MHPG (DL-3-methoxy-4-hydroxyphenylglycol), Isomeric mixture of D-MHPG and L-MHPG forms, MHPG Derivatives, DL-MHPG-SO4 (DL-3-methoxy-4-hydroxyphenylglycol-sulfate) Modification can include Isomeric mixture of D-MHPG-SO4 and L-MHPG-SO4 forms, Serotonin, 5-HT, 5-hydroxydopamine (5-4HDA), 3,4-dihydroxyphenylglycol (DOPEG), Dopamine, 4-(2-aminoethyl)pyrocatechol; 3-hydroxytyramine; 3,4-dihydroxyphenethylamine; L-3,4-dihydroxyphenylalanine, L-DOPA, Vanillomandelic acid, DL-VMA, Homovanillic acid, Norepinephrine, DL-NE, D-Epinephrine, D-E, 3-methoxytyramine, MTA, 3-methoxytyrosine, MTyr, 3,4-dihydroxymandelic acid, DL-DOMA, 3,4-dihydroxyphenyl acetic acid, DOPAC, L-Phenylalanine, Tyramine, p-tyramine; 4-(2-Aminoethyl)phenol, D-Mandelic acid, Homocatechol, Octopamine, DL-Octopamine, Azinphos-Ethyl, S-(3,4-dihydro-4-oxobenzo[d]-[1,2,3]-triazin-3-ylmethyl) O,O-diethyl phosphorodithioate, Phosmet, O,O-dimethyl S-phthalimidomethyl phosphorodithioate, Folpet, N-[(Trichloromethyl)thio]phthalimide, Tetramethrin, (1-Cyclohexene-1,2-dicarboximido)methyl-2,2-dimethyl-3-(2-methylpropenyl)-cyclopropanecarboxylate, N-(bromomethyl)phthalimide, N-(Chloromethyl)benzazimide, 6-(N-phthalimidoylmethylthio)hexanoic acid (MFH), Bromacil, 5-bromo-3-sec-butyl-6-methyluracil, Bromacil Derivative, 5-bromo-6-(hydroxymethyl)-3-(1-methylpropyl)-2,4(1H,3H)-pyrimidineone, Bromacil Derivative, 5-bromo-3-(2-methylpropyl-6-methyl-2,4(1H,3H)-pyrimidinedione, Metabolite of Bromacil, Bromacil Derivative, 3-hydroxy-1-methylpropyl-6-methyl-2,4(1H,3H)-pyrimidinedione (Modification Bromacil Metabolite), Bromacil Derivative, 6-methyl-3-(1-methylpropyl)-2,4(1H,3H)-pyrimidinedione (Modification Bromacil Metabolite), Terbacil Derivative, [5-chloro-3-(1,1-dimethylethyl)-6-(hydroxymethyl)-2,4 (1H,3H)-pyrimidinedione, Terbacil, 3-tert-butyl-5-chloro-6-methyluracil, Bromacil Derivative, Ethyl-5-(5-Bromo-6-methyl-3-(1-methylpropyl)-2,4(1H,3H)-pyrimidinedione-1-yl)hexanoate, Bromacil Derivative alkylated at N-1, Bromacil Derivative 5-(5-Bromo-6-methyl-3-(1-methylpropyl)-2,4(1H,3H)-pyrimidinedione-1-yl)hexanoic Acid (Modification Bromacil Derivative alkylated at N-1), Bromacil Derivative, -Bromo-6-(Bromomethyl-3-(1-methylpropyl)-2,4(1H,3H)-pyrimidinedione (Modification Bromacil Derivative substituted at the 6-methyl position), Bromacil Derivative-[5-Bromo-3-(1-methylpropyl)-2,4(1H,3H)-pyrimidinedione-6-yl]-2-carboxylpropanoic Acid (Modification Bromacil Derivative substituted at the 6-methyl position), 3-[5-Bromo-3-(1-methylpropyl)-2,4 (1H,3H)-pyrimidinedione-6-yl]propanoic Acid (Modification Bromacil Derivative substituted at the 6-methyl position), Bromacil Derivative 5-Bromo-1,6-dimethyl-3-(1-methylpropyl)-2,4(1H,3H)-pyrimidinedione, Bromacil Derivative 5-Bromo-1-butyl-6-methyl-3-(1-methylpropyl)-2,4(1H,3H)-pyrimidinedione, Butachlor, N-butoxymethyl-2-chloro-2',6-diethylacetanilide, Amidochlor, N-[(acetylamino)methyl]-2-chloro-N-(2,6-diethylpenyl)acetamide, Nicarbazin, N,N'-bis(4-nitrophenyl)-compound with 4,6-dimethyl-2(1H)-pyrimidinone (Modification (DNC+HDP)), 2-hydroxy-4,6-dimethylpyrimidine, HDP, Imazalil, [1-(beta-allyloxy-2,4-dichlorophenethyl)imidazole], Imazalil Derivative, EIT-0073 (Modification Have a —O(CH2)5-COOH group instead of original —OCH2CH—CH2 group of imazalil), Penconazole, (RS)-1-(2,4-dichloro-β-propylphenethyl)-1H-1,2,4-triazole, Hexaconazole, (RS)-2-(2,4-dichlorophenyl)-1-(1H-1,2,4-triazol-1-yl)hexan-2-ol, Propiconazole, cis-trans-1-[2-(2,4-dichlorophenyl)-4-propyl-1,3-dioxolan-2-ylmethyl]-1H-1,2,4-triazole, Diclobutrazol, 2RS,3RS)-1-(2,4-dichlorophenyl)-4,4-dimethyl-2-(1H-1,2,4-triazol-1-yl)pentan-3-ol, Triflumizole, (E)-4-chloro-α,α,α-trifluoro-N-(1-imidazol-1-yl-2-propoxyethylidene)-o-toluidine, Imazalil Derivative, EIT-0183, Imazalil Derivative, EIT-0180, Imazalil Derivative, EIT-0111, Imazalil Derivative, EIT-0158, Imazalil Derivative, K-240, Chlorothalonil, tetrachloroisophthalonitrile Modification On benzene Ring R1=CN R2=Cl R3=CN R4=Cl R5=Cl R6=Cl), Chlorothalonil Derivative-2,4,5,6-tetrachloro-3-cyanobenzamide (Modification On benzene Ring R1=CONH2 R2=Cl R3=CN R4=Cl R5=Cl R6=Cl), Chlorothalonil Derivative-2,5,6-trichloro-4-hydroxyisophthalonitrile (Modification On benzene Ring R1=CN R2=Cl R3=CN R4=OH R5=Cl R6=Cl), 3-carbamyl-2,4,5-trichlorobenzoic acid (Modification On benzene Ring R1=CONH2

R2=Cl R3=COOH R4=H R5=Cl R6=Cl), Pentachloronitrobenzene (Modification On benzene Ring R1=NO2 R2=Cl R3=Cl R4=Cl R5=Cl R6=Cl), Benzene hexachloride, Hexachlorobenzene, BHC, Lindane (Modification On benzene Ring R1=Cl R2=Cl R3=Cl R4=Cl R5=Cl R6=Cl), 2,4,5,6-tetrachlorophenol (Modification On benzene Ring R1=OH R2=Cl R3=H R4=Cl R5=Cl R6=Cl), Carbaryl Derivative, Ethylcarbamate (Modification R1=OCONHCH2CH3 R3=H), 1-Naphthol, 1-naphthaleneacetamide, -(1-naphthyl)acetamide, Carbaryl Derivative, 1-Methylcarbonate (Modification R1=OCOOCH3 R2=H, Carbaryl Derivative, 1-Ethylcarbonate (Modification R1=OCOOCH2CH3 R2=H), Carbaryl Derivative 2-Ethylcarbonate (Modification R1=H R2=OCOOCH2CH3, Carbaryl Derivative, 1-Ethylthiocarbonate (Modification R1=OCOSCH2CH3 R2=H), Carbaryl Derivative, 2-Ethylthiocarbonate (Modification R1=H R2=OCOSCH2CH3), Naptalam, N-1-naphthylphthalamic acid, Carbaryl Derivative, 3-hydroxycarbaryl (Modification R1=OCONHCH3 R2=H R3=OH R4=H R5=H), Carbaryl Derivative 4-hydroxycarbaryl (Modification R1=OCONHCH3 R2=H R3=H R4=OH R5=H), Carbaryl Derivative 5-hydroxycarbaryl (Modification R1=OCONHCH3 R2=H R3=H R4=H R5=OH), Carbaryl Derivative, 1-(5-Carboxypentyl)-3-(1-naphthyl)urea (Modification R1=NHCONH(CH2)5COOH R2=H), (Structurally related s-triazines)-Aziprotryn, 4-azido-N-isopropyl-6-methylthio-1,3,5-triazin-2-ylamine (Modification R1=—SCH3 R2=—N3 R3=—CH(CH3)2), (Structurally related s-triazines), 2-(ethylamino)-4-(methylthio)-6-aminotriazine (Modification R1=—SCH3 R2=—NH—C2H5 R3=—NH2), (Structurally related s-triazines)-2-amino-4-(methylthio)-6-(isopropylamino)triazine (Modification R1=—SCH3 R2=—NH2 R3=—NH—CH(CH3)2), (Structurally related s-triazines)-2-amino-4-methoxy-6-(isopropylamino)triazine (Modification R1=—OCH3 R2=—NH2 R3=—NH—CH(CH3)2), TCP Derivative (3,5,6-trichloro-2-pyridinol Derivative), 3-(3,5-dichloro-6-hydroxy-2-pyridyl)thiopropanoic Acid, p-nitrosuccinanilic acid (PNA-S), PNA-S, PNA-C, p-nitro-cis-1,2-cyclohexanedicarboxanilic acid, Nitroaniline Derivative, 2-nitroaniline, o-Nitroaniline, Nitroaniline Derivative-3-nitroaniline, m-Nitroaniline, Nitroaniline Derivative-4-nitroaniline, p-Nitroaniline, Aeromatic Alcohols, 4-nitrobenzyl alcohol, Aeromatic Alcohols-4-nitrophenethyl alcohol, Aeromatic Alcohols 2-nitrobenzyl alcohol, Aeromatic Alcohols, 3-nitrobenzyl alcohol, Urea Derivative-1-benzyl-3-(4-nitrophenyl)urea, Urea Derivative-1-(3-chlorophenyl)-3-(2-methoxy-5-nitrophenyl)urea, Urea Derivative-1-(3-chlorophenyl)-3-(4-methoxy-3-nitrophenyl)urea, Urea Derivative-1-(4-chlorophenyl)-3-(4-nitrophenyl)urea, Urea Derivative-(2-fluorophenyl)-3-(2-mehtoxy-4-nitrophenyl)urea, 1-(3-mehtoxyphenyl)-3-(3-nitrophenyl)urea, Carbofuran Derivative m Carbofuran-phenol, Carbofuran-hydroxy, Carbofuran-keto, Carbosulfan, 3-dihydro-2,2-dimethylbenzofuran-7-yl (dibutylaminothio) methylcarbamate, Benfuracarb, N-[2,3-dihydro-2,2-dimethylbenzofuran-7-yloxycarbonyl(methyl)aminothio]-N-isopropyl-β-alaninate, Furathiocarb, 2,3-dihydro-2,2-dimethyl-7-benzofuranyl 2,4-dimethyl-5-oxo-6-oxa-3-thia-2,4-diazadecanoate, Carbofuran Derivative, 4-[[(2,3-Dihydro-2,2-dimethyl-7-benzofuranyloxy)carbonyl]-amino]butanoic Acid (BFNB) (Modification n=3 X=CH2), Endrin, nendrin, (1R,4S,4aS,5S,6S,7R,8R,8aR)-1,2,3,4,10,1-hexachloro-1,4,4a,5,6,7,8,8a-octahydro-6,7-epoxy-1,4:5,8-dimethanonaphthalene, Heptachlor, 1,4,5,6,7,8,8-heptachloro-3a,4,7,7a-tetrahydro-4,7-, Chlordane, 1,2,4,5,6,7,8,8-octachloro-2,3,3a,4,7,7a-hexahydro-4,7-methanoindene, Endosulfan (Modification isomer mix of alpha and beta forms), Endosulfan (Modification alpha isomeric form), Endosulfan (Modification beta isomeric form), Endosulfan Derivative, Endosulfan sulfate (Modification sulfate form), Endosulfan Derivative, Endosulfan diol, Diol metabolite of endosulfan, Endosulfan Derivative, Endosulfan ether (Modification ether metabolite of endosulfan), Endosulfan Derivative, hydroxy ether, hydroxy ether metabolite of endosulfan, Endosulfan Derivative, Endosulfan lactone (Modification lactone metabolite of endosulfan), Aldrin, Dieldrin, Fenvalerate isomers Modification 1S,2R isomer R: Ph), Fenvalerate isomers (Modification 1R,2S isomer R: Ph), Fenvalerate isomers (Modification 1R,2R isomer R: Ph), Fenvalerate isomers (Modification 1S,2R/S isomer R: Ph), Fenvalerate isomers (Modification 1R,2R/S isomer R: Ph), Fenvalerate isomers, fenvalerate (Modification 1R/S, 2R/S isomer R: Ph), Thiabendazole, 2-(thiazol-4-yl)benzimidazole, Thiabendazole Derivative, 5-hydroxythiabendazole (Modification 5-OH-TBZ), Thiabendazole Derivative, 5-NH2-TBZ, Thiabendazole Derivative, methyl benzimidazole carbamate, Albendazole, Mebendazole, Fenbendazole, Thiabendazole Derivative, 2-succinamidothiabendazole, Thiabendazole Derivative, 2-succinamidothiabendazole, Cambendazole, Fenvalerate Haptens, Cyano[3-(4-aminophenoxy)phenyl]methyl (S)-4-Chloro-alpha-(1-methylethyl)benzeneacetate (4-Aminoesfenvalerate), Fenvalerate Haptens, Benzyl 4-[3-[Cyano[(S)-2-(4-chlorophenyl)-3-methyl-1-oxobutanoxy]methyl]phenoxy]benzenepropanoate, Fenvalerate Haptens, Benzyl 3-[Cyano[(S)-2-(4-chlorophenyl)-3-methyl-1-oxobutanoxy]methyl]phenoxyacetate, Fenvalerate Haptens, 3-[Cyano[(S)-2-(4-chlorophenyl)-3-methyl-1-oxobutanoxy]methyl]phenoxyacetic Acid, Fenvalerate Haptens, Benzyl 6-[3-[Cyano[(S)-2-(4-chlorophenyl)-3-methyl-1-oxobutanoxy]methyl]phenoxy]hexanoate, Fenvalerate Haptens, 6-[3-[Cyano[(S)-2-(4-chlorophenyl)-3-methyl-1-oxobutanoxy]methyl]phenoxy]hexanoic Acid Fenvalerate Haptens, 4-[3-[Cyano[(S)-2-(4-chlorophenyl)-3-methyl-1-oxobutanoxy]methyl]phenoxy]benzenepropanoic Acid, (S)-fenvalerate Acid, (Structurally related s-triazines), atrazine mercapturate Modification R1=—SCH2CH(NHCOCH3)COOH R2=—NHCH2CH3 R3=—NHCH(CH3)2, Fenthion Hapten, -Methyl O-[3-methyl-4-(methylthio)phenyl] N-(3-carboxypropyl)phosphoramidothioate Modification referred as Hapten B, Fenthion Derivative, Oxidized Fenthion, Fenthion Derivative, Oxidized oxidized Fenthion, pirimiphos-ethyl, 4-(Methylthio)-m-cresol, Chlorpyrifos Derivative, Chlorpyrifos-oxon, Fenchlorphos, O,O-dimethyl O-2,4,5-trichlorophenyl phosphorothioate, Trichloronate, O-Ethyl O-2,4,5-trichlorophenyl ethyl-phosphonothioate, Dichlofenthion, O-2,4-dichlorophenyl O,O-diethyl phosphorothioate, Parathion, O,O-diethyl O-4-nitrophenyl phosphorothioate; Thiophos, Chlorpyrifos Derivative Modification Synthesis of AR1 is described, Chlorpyrifos Derivative, O-Ethyl O-(3,5,6-Trichloro-2-pyridyl)O-(3-Carboxypropyl)Phosphorothioate; (PO), Chlorpyrifos Derivative-O-Ethyl O-(3,5,6-Trichloro-2-pyridyl)N-(5-Carboxyethyl) Phosphoramidothioate; (PN1) (Modification Amide linkage of thiophosphate reagents), Chlorpyrifos Derivative, O-Ethyl O-(3,5,6-Trichloro-2-pyridyl)N-(2-Carboxyethyl) Phosphoramidothioate; (PN1) (Modification Amide linkage of suitable thiophosphate reagents), Triadimefon, (RS)-1-(4-chlorophenoxy)-3,3-dimethyl-1-(1H-1,2,4-triazol-1-yl)butan-2-one, GR151004, (4-[[5-[3-[2-(dimethylamino)ethyl]]-5-benzofuranyl]-3-pyridinyl]acetyl]morpholine dihydrochloride, Diflubenzuron, 1-(4-chlorophenyl)-3-(2,6-difluorobenzoyl)urea, (Structurally related s-triazines)-SprAAT (Modification R1=SCH2CH2COOH R2=NH2

R3=NH2), (Structurally related s-triazines), SBeAAT (Modification R1=S(C6H4)COOH R2=NH2 R3=NH2), (Structurally related s-triazines), SAAT (Modification R1=SH R2=NH2 R3=NH2), (Structurally related s-triazines), CDAT (Modification R1=Cl R2=NH[C(O)CH3] R3=NH2), (Structurally related s-triazines)-CDET (Modification R1=Cl R2=NH[C(O)CH3] R3=NH(CH2CH3)), (Structurally related s-triazines)-CDIT (Modification R1=Cl R2=NH[C(O)CH3] R3=NH(CH(CH3)2)), (Structurally related s-triazines), CDDT (Modification R1=Cl R2=NH[C(O)CH3] R3=NH[C(O)CH3]), (Structurally related s-triazines)-ammeline, OAAT (Modification R1=OH R2=NH2 R3=NH2), (Structurally related s-triazines)-ammelide, OOAT (Modification R1=OH R2=OH R3=NH2), (Structurally related s-triazines)-cyanuric acid, OOOT (Modification R1=OH R2=OH R3=OH), (Structurally related s-triazines), melamine, AAAT (Modification R1=NH2 R2=NH2 R3=NH2), Structurally related s-triazines-N-isoropylammeline, OIAT (Modification R1=OH R2=NH[CH(CH3)2] R3=NH2, Structurally related s-triazines-N-ethylammeline, OEAT (Modification R1=OH R2=NHCH2CH3 R3=NH2), Structurally related s-triazines, N-ethylammelide, OOET (Modification R1=OH R2=OH R3=NHCH2CH3), Structurally related s-triazines)-cyromazine, CyPAAT (Modification R1=NH(C3H5) R2=NH2 R3=NH2), Structurally related s-triazines-diamino-s-triazine, HAAT (Modification R1=H R2=NH2 R3=NH2), PCB congeners, 2,5,3',4'-tetrachlorobiphenyl (Modification IUPAC no.: 70), PCB congeners 2,4,5,3',4'-pentachlorobiphenyl (Modification IUPAC no.: 118), PCB congeners-2,2',5,5'-tetrachlorobiphenyl (Modification IUPAC no.: 52), PCB congeners, 6-[3,3',4'-Trichlorobiphenyl-4-yl)oxy]hexanoic Acid, Metolazone, Brand Names: Mykrox; Zaroxolyn, Furfuryl benzoate, DDT Metabolites, DDA, Paraquat, 1,1'-dimethyl-4,4'-bipyridinium ion, Diethylcarbamazine, THP, 2,4,6-triphenyl-N-(4-hydroxyphenyl)-pyridinium, o-DNCP, -dinitrocarboxyphenol, PCB congeners, 3-chlorobiphenylol (Modification IUPAC No. 2), PCB congeners, 3,4'-dichlorobiphenyl (Modification IUPAC No. 13), PCB congeners, 3,5-dichlorobiphenyl (Modification IUPAC No. 14), PCB congeners, 3,4,5,3',4'-pentachlorobiphenyl (Modification IUPAC No. 126), 2,3,3',4'-tetrachlorobiphenyl (Modification IUPAC No. 56), 2',3,4,5-tetrachlorobiphenyl (Modification IUPAC No. 76), 3,3',5,5'-tetrachlorobiphenyl (Modification IUPAC No. 80), 2,4,5,2',5'-pentachlorobiphenyl (Modification IUPAC No. 101), 2,3,3',4,4'-pentachlorobiphenyl (Modification IUPAC No. 105), 2,3,6,3',4'-pentachlorobiphenyl (Modification IUPAC No. 110), 3,3',4,5,5'-pentachlorobiphenyl (Modification IUPAC No. 127), 3,4,5,3',4',5'-hexachlorobiphenyl (Modification IUPAC No. 169), 2,3,3',4,4',5-hexachlorobiphenyl (Modification IUPAC No. 156), 3,4,3',4'-tetrabromobiphenyl, 3,4,5,3',4',5'-hexabromobiphenyl, 2,4,5,2',4',5'-hexabromobiphenyl, Dibenzofurans and Dioxins, 2,3,7,8-tetrachlorobenzofuran, 2,3,7,8-tetrachlorodibenzo-p-dioxin, 3,4',5-trichloro-4-biphenylol, 3,3',5,5'-tetrachloro-4,4'-biphenyldiol, 3,4,3',4'-tetrachlorodiphenyl ether, 1-2-dichlorobenzene, 1,4-dichlorobenzene, 1,2,4-trichlorobenzene, 3,4-dichloroaniline, DDT Metabolites, 4,4'-DDT, 4,4'-DDD Retronecine, 3,4-dichlorobiphenyl Modification IUPAC No. 12, 3,4,3'-trichlorobiphenyl (Modification IUPAC No. 35), PCB Congeners, 3,4,4'-trichlorobiphenyl (Modification IUPAC No. 37), 3,4,3',5-tetrachlorobiphenyl (Modification IUPAC No. 78), 3,4,3',5'-tetrachlorobiphenyl (Modification IUPAC No. 79), 3,4,4',5-tetrachlorobiphenyl (Modification IUPAC No. 81), DDT Metabolites, p,p'-DDT (Modification p,p'-dichlorodiphenyltrichloroethane), o,p'-DDT Modification o,p'-dichlorodiphenyltrichloroethane, p,p'-DDE Modification p,p'-DDE, o,p'-DDE Modification o,p'-DDE, p,p'-DDD Modification p,p'-DDD, o,p'-DDD Modification o,p'-DDD, Dicofol 4,4-dichloro-a-(trichloromethyl)benzhydrol, Cyprazine, 6-chloro-N-cyclopropyl-N'-(1-methylethyl)-1,3,5-triazine-2,4-diamine, Structurally related s-triazines, Dipropetryn, 6-(ethylthio)-N,N'-bis(1-methylethyl)-1,3,5-triazine-2,4-diamine, Trietazine, 6-chloro-N,N,N'-triethyl-1,3,5-triazine-2,4-diamine, 6-Hydroxyatrazine, hexazinone, 3-cyclohexyl-6-dimethylamino-1-methyl-1,3,5-triazine-2,4 (1H,3H)-dione, TNT, 2,4,6-Trinitrotoluene, Tetraconazole (M14360), 1-[2-(2,4-dichlorophenyl)-3-(1,1,2,2-tetrafluoroethoxy)propyl]-1H-1,2,4-triazole, DTP, 2-(2,4-dichlorophenyl)-3-(1H-1,2,4-triazol-1-yl)propanol, Imazalyl, fenarimol, (RS)-2,4'-dichloro-α-(pyrimidin-5-yl)benzhydryl alcohol, Lupanine metabolites, (+)-lupanine (Modification R=H), Lupanine metabolites, (+)-13-hydroxylupanine (Modification R=OH), Lupanine metabolites, hemisuccinate ester of (+)-13-hydroxylupanine (Modification R=OCO—(CH2) 2.COOH), Lupanine metabolites, cis-hexahydrophthalate ester of (+)-13-hydroxylupanine (Modification R=OCO.C6H10.COOH), Lupanine metabolites, alpha-isolupanine, Lupanine metabolites, -hydroxylupanine, Sparteine, Cysteine, multiflorine, epilupinine, (Structurally related s-triazines), CYANAZINE ACID Modification R1=Cl R2=NHCH2CH3 R3=NHCCOOH(CH3)2, Structurally related s-triazines Modification R1=Cl R2=NHCH2CH3 R3=NH(CH2)3COOH, Structurally related s-triazines (Modification R1=Cl R2=NHCH2CH3 R3=NHCH2COOH), (Structurally related s-triazines) (Modification R1=Cl R2=NHCH2CH3 R3=NH(CH2) 4COOH), norflurazon, 4-chloro-5-(methylamino)-2-[3-(trifluoromethyl)phenyl]-3(2H)-pyridazinone, norflurazon derivative, desmethyl-norflurazon, metflurazon, -chloro-5-(dimethylamino)-2-[(3-trifluoromethyl)phenyl]-3(2H)-pyridazinone, Pyrazon, Chloridazon, 5-amino-4-chloro-2-phenyl-3(2H)-pyridazinone (active ingradient), dichlorophenyl-pyridazone, (Structurally related s-triazines) azidoatrazine (Modification R1=N3 R2=NHCH(CH3)2 R3=NHCH2CH3), ALACHLOR 2-chloro-2',6'-diethyl-N-methoxymethylacetanilide, trichothecolone (Modification R1=H R2=OH R3=H R4=O R5=H), DON derivative, acetyl-T-2, DON derivative, T-2 tetrol tetraacetate, Chlorpyrifos derivatives, mono-dechloro-CP, Bromophos derivative, Bromophos-methyl, Bromophos derivative, Bromophos-ethyl dicapthon, -2-chloro-4-nitrophenyl O,O-dimethyl phosphorothioate, tetrachlorvinphos, (Z)-2-chloro-1-(2,4,5-trichlorophenyl)vinyl dimethyl phosphate, triclopyr, 3,5,6-trichloro-2-pyridyloxyacetic acid, picloram, 4-amino-3,5,6-trichloropyridine-2-carboxylic acid, Formononetin, Biochanin A, 5, 7-dihydroxy-4'-methoxyisoflavone (Modification It is the 4'-methyl ether of genistein), equol, (7-hydroxy-3-(4'-hydroxyphenyl)-chroman, 2'methoxyformononetin, Daidzein, 7-hydroxy-3-(4-hydroxyphenyl)-4H-1-benzopyran-4-one, geninstein, quercetin, 3,3',4',5,7-Pentahydroxyflavone; 3,5,7,3',4'-Pentahydroxyflavone; matheucinol, coumestrol (Structurally related s-triazines), Hydroxysimazine (Modification R1=OHR2=NHCH2CH3R3=NHCH2CH3, angustifoline, Alodan, 1-Methyl-4-phenyl-4-carboethoxypiperidine hydrochloride, Zearalenone, RAL, F-2 Toxin, Fenpropimorph, (RS)-cis-4-[3-(4-tert-butylphenyl)-2-methylpropyl]-2,6-dimethylmorpholine, Tridemorph, 2,6-dimethyl-4-tridecylmorpholine, 2,6-dimethylmorpholine, Amorolfine, Fenpropidine, (RS)-1-[3-(4-tert-butylphenyl)-2-methylpropyl]piperidine, (Structurally related s-triazines) (Modification R1=Cl R2=Cl R3=NHCH2CH3, (Structurally related s-triazines) Modification R1=Cl R2=Cl R3=NHCH(CH3)2, (Structurally related s-triazines) Modification R1=Cl R2=NHCH2CH3 R3=NH(CH2)5COOH, (Structurally related s-triazines) Modification R1=Cl R2=NHCH(CH3)2 R3=NHCH2COOH, (Structurally related s-triazines) (Modification R1=Cl R2=NHCH(CH3)2 R3=NH(CH2)5COOH), Structurally related s-triazines, cyanazine amide (Modification R1=Cl R2=NHCH2CH3 R3=NHCCONH2(CH3)2), hydroxycyanazine acid (Modification R1=OH R2=NHCH2CH3 R3=NHCCOOH(CH3)2), deethylsimazine (Modification R1=Cl R2=NH2 R3=NHCH2CH3), Albendazole sulfoxide, [5-(propylthionyl)-1H-benzimidazol-2-yl]-, methylester, Albendazole sulfone, 5(6)-alkylbenzimidazoles, 2-amino-5-(propylthio)benzimidazole, 5(6)-alkylbenzimidazoles, 2-amino-5-(propylsulfonyl) benzimidazole, oxibendazole, 5-propoxy-benzimidazole-2-methyl carbamate, 5(6)-arylbenzimidazoles, fenbendazole sulfone (Modification sulfone metabolite of fenbendazole), 5(6)-arylbenzimidazoles, 4'-hydroxyfenbendazole, 5(6)-arylbenzimidazoles, oxfendazole (Modification Oxfendazole is the sulfoxide metabolite of fenbendazole), 5(6)-arylbenzimidazoles, flubendazole, benzimidazole Metabolites, 2-aminobenzimidazole, benzimidazole Metabolites, 5-aminobenzimidazole, benzimidazole Metabolites, 2-acetylbenzimidazole, Benzophenone, Diphenylmethanone; phenyl ketone; Diphenyl ketone; Benzoyl-benzene, Benzaldehyde, benzoic aldehyde, 4-Bromo-2,5-dichlorophenol, Acephate, O,S-dimethyl acetylphosphoramidothioate, methamidophos, O,S-dimethyl phosphoramidothioate, Dichlorvos, 2,2-dichlorovinyl dimethyl phosphate, Phenthoate, S-α-ethoxycarbonylbenzyl O,O-dimethyl phosphorodithioate, EPN, Ethyl p-nitrophenyl thionobenzenephosphonate, Bioresmethrin, -benzyl-3-furylmethyl (1R,3R)-2,2-dimethyl-3-(2-methylprop-1-enyl) cyclopropanecarboxylate (Modification The unresolved isomeric mixture of this substance has the ISO common name resmethrin), flufenoxuron, 1-[4-(2-chloro-α,α,α-trifluoro-p-tolyloxy)-2-fluorophenyl]-3-(2,6-difluorobenzoyl) urea, Amitrole, 1H-1,2,4-triazol-3-ylamine, molinate, S-ethyl azepane-1-carbothioate, molinate derivative (Modification S-2-carboxyethyl hexahydroazepine-1-carbothioate), molinate derivative (Modification S-5-carboxypentyl hexahydroazepine-1-carbothioate) molinate derivative (Modification molinate sulfone), molinate derivative (Modification S-(p-aminobenzyl) hexahydroazepine-1-carbothioate), molinate derivative (Modification S-2-(p-aminophenyl) ethyl hexahydroazepine-1-carbothioate), hexamethylenimine, thiobencarb (Bolero), butylate (Sutan), EPTC (Eptam), cycloate (Roneet), pebulate (Tillam), vernolate (Vernam), Aflatoxin M1, AFM1 (Modification AFM1), Aflatoxin B1, AFB1 (Modification AFB1), Aflatoxin G1, AFG1 (Modification AFG1), Aflatoxin M2, AFM2 (Modification AFM2), Aflatoxin B2, AFB2 (Modification AFB2), Aflatoxin G2, AFG2 (Modification AFG2), Aflatoxin B2alpha, AFB2alpha (Modification AFB2alpha), Aflatoxin G2alpha, AFG2alpha (Modification AFG2alpha), KB-6806, 6-amino-5-chloro-1-isopropyl-2-(4-methyl-1-piperazinyl) (Modification R1=NH2 R2=CH(CH3)2 R3=CH3), KB-6806 (Benzimidazole) Derivatives Modification R1=NH2 R2=CH2CH(CH3)2 R3=CH3, Hapten Name KB-6806 (Benzimidazole) Derivatives (Modification R1=NH2 R2=CH(CH2CH3)2 R3=CH3), KB-6806 (Benzimidazole) Derivatives (Modification R1=NHCOCH3 R2=CH(CH3)2 R3=CH3), KB-6806 (Benzimidazole) Derivatives (Modification R1=H R2=CH(CH3)2 R3=CH3), KB-6806 (Benzimidazole) Derivatives (Modification R1=NH2 R2=CH(CH3)2 R3=CH3), KB-6806 (Benzimidazole) Derivatives Modification R1=NH2 R2=CH(CH3)2 R3=N(—>O) CH3 (N-OXIDE), KB-6806 (Benzimidazole) Derivatives Modification R1=NH2 R2=CH(CH3)2 R3=H, KB-6806 (Benzimidazole) Derivatives Modification R1=NH2 R2=CH2CH3 R3=CH3, Aminoparaoxon, phosphoric acid, O,O-diethyl O-(4-aminophenyl) ester, Methylparathion, phosphorothioic acid, O,O-dimethyl O-(4-nitrophenyl) ester, Diethyl phenylphosphate, phenylphosphonic acid, O,O-diethyl ester, Diethyl phosphate, ethylphosphonic acid, O,O-diethyl ester, p-Nitorphenyl phosphate, phosphonic acid, O-(4-nitrophenyl)ester, Phorate, phosphorodithioic acid, O,O-diethyl S-[(ethylthio) methyl] ester, Ethion, bis(phosphorodithioic acid), S,S'-methylene O,O,O',O'-tetraethyl ester, Carbophenthion, phosphorodithioic acid, O,O-diethyl S-[[(4-chlorophenyl) thio]methyl] ester, Disulfoton, phosphorodithioic acid, O,O-diethyl S-[(2-ethylthio)ethyl] ester, TS, N-[4-(Carboxymethyl)-2-thiazolyl]sulfanilamide, NS, N-(4-Nitrophenyl) sulfanilamide, Sulfamoxole, Sulfacetamide, DNP-SL, Spin labelled dinitrophenyl (Modification The synthesis of DNP-SL has been described by Balakrishnan et al (1982) formula can be found in Anglister et al. (1984)), beta ecdysone, Benzimidazole Derivative, 5(6)-[Carboxypentyl)thio]-2-(methoxycarbonyl)amino]-benzimidazole, 2-hydroxybiphenyl HBP, Atrazine Caproic acid, Lysophosphatidic acid (LPA), 1-acyl-2-hydroxy-sn-glycero-3-phosphate), berberine, Palmatine, 9-Acetylberberine, Corydaline, Coptisine, Berberrubine, 8-Oxoberberine, Papaverine, Berberine Derivative, 9-O-carboxymethyl berberine, phencyclidine, 1-(1-phenylcyclohexyl)piperidine, Methoxychlor, Endosulfan Derivative, 4-Oxobutanoic Acid,4-(4,5,6,7,8,8-Hexachloro-3a,4,7,7a-tetrahydro-4,7-methano-1H-indenyl-1-oxy), Endosulfan Derivative, 4-oxybutanoic Acid,4-(1,3,4, 5,6,7,8-Octachloro-3a,4,7,7a-tetrahydro-4,7-methanoindanyl-2-oxy, Endosulfan Derivative (Modification Hemisuccinate of Endosulfan diol), Triazole Derivatives, 5-(3-Hydroxypropyl)-3-amino-2H-1,2,4-triazole, Triazole Derivatives, 5-(3-Hydroxypropyl)-3-(2-nitrophenylsulfenyl)amino-2H-1,2,4-triazole, Triazole Derivatives, 3-Amino-5-[(3-succinyloxy)propyl]-2H-1,2,4-triazole, Triazole Derivatives, 3-amino-1,2,4-triazole-5-thiol, Triazole Derivatives, 3-[(2-nitrophenylsulfenyl) amino-2H-1,2,4-triazole-5-thiol, Triazole Derivatives, 2H-1,2,4-triazole-5-thiol, Triazole Derivatives, 4-methyl-1, 2,4-triazole-3-thiol, Triazole Derivatives, (1,2,4-triazol-2-yl)acetic acid, 1,2,4-triazole, 4-nitrophenyl 4'-carboxymethylphenyl phosphate, Triazole Derivative, 4-amino-1,2,4-triazole, Triazole Derivative, 3-acetamido-1H-1,2,4-triazole, Triazole Derivative, 3-amino-1,2,4-triazole-5-carboxylic acid hemihydrate, Triazole Derivative, 2-(4-chlorophenyl)-2-(1,2,4-triazol-1-yl)-methylhexanoic acid, succinic acid, Imidazole, L-histidine, L-glutamic acid, Permethrin derivative, 3-phenoxybenzyl 2,2-dimethylcyclopropane-1,3-dicarboxylate, 3-phenoxybenzaldehyde, flucythrinate, Chrysanthemic acid, 2,4-Dinitrophenyl, DNP, Thiram Haptens, Disodium 4-[Carbodithioato(methyl)-amino]butanoate, Thiram Haptens 5,11-Dimethyl-6,10-dithioxo-7,9-dithia-5,11-diazadodecanoic Acid, Thiram Haptens, 2-{[(Dimethylamino)carbothioyl]sulfanyl}ethanoic Acid, Thiram Haptens, 4-{[(Dimethylamino)carbothioyl] sulfanyl}butanoic Acid, Thiram Haptens, 6-{[(Dimethylamino)carbothioyl]sulfanyl}hexanoic Acid, Thiram Haptens, 11-{[(Dimethylamino)carbothioyl] sulfanyl}undecanoic Acid, Thiram Haptens, 2-{[(Dimethylamino)carbothioyl] sulfanyl}ethanoic Acid, Thiram, Tetramethylthiurammonosulfide, Tetraethylthiuram disulfide, Dimethyldithiocarbamic acid sodium salt, Dimethyldithiocarbamic acid zinc salt, Diethyldithiocarbamic acid sodium salt, N,N,N',N'-tetramethylthiourea, Nabam, Zineb, Maneb, Ethylenethiourea, Chlorpyrifos hapten, O,O Diethyl O-[3,5-Dichloro-6-[(2-carboxyethyl)thio]-2-pyridyl] Phosphorothioate, 2-Succinamidobenzimidazole, Methyl 2-Benzimidazolecarbamate, MBC, Benzimidazole, 2-benzimidazolylurea, succinamide, Ethyl carbamate, Urea, N-methylurea, N,N'-dimethylurea, Brevetoxin PbTx-3, Organophosphorous Haptens, O,O-Diethyl O-(5-carboxy-2-fluorophenyl) phosphorothioate, Chlorpyrifos-ethyl, Anandamide hapten, N-Arachidonyl-7-amino-6-hydroxy-heptanoic acid, Anandamide, Arachidonic acid, Docosatetraenoyl ethanolamide, Dihomo-gamma-linolenyl ethanolamide, 2-Arachidonyl glycerol, 2-Arachidonyl glycerol ether, Stearoyl ethanolamide, Heptadecanoyl ethanolamide, Prostaglandin E1, 3-hydroxy-2-(3-hydroxy-1-octenyl)-5-oxocyclopentaneheptanoic acid; alprostadil; PGE1, Prostaglandin D2, PGD2, Prostaglandin A2, PGA2, Prostaglandin B2, PGB2, Prostaglandin F2 alpha, 7-[3,5-dihydroxy-2-(3-hydroxy-1-octenyl)cyclopentyl]-5-heptenoic acid; dinoprost; PGF2alpha, Prostaglandin F1 alpha, PGF1alpha, 6-keto-Prostaglandin F1 alpha, 6-keto-PGF1alpha, 13,14-Dihydro-15-keto-Prostaglandin E2, 13,14-Dihydro-15-keto-PGE2, 13,14-Dihydro-15-keto-Prostaglandin F2alpha, 14-Dihydro-15-keto-PGF2alpha, 5alpha,7alpha-Dihydroxy-11-ketotetranorpostane-1,16-dioic acid, 15-keto-PGF2alpha, TXB2, Prostaglandin E2,7-[3-hydroxy-2-(3-hydroxy-1-octenyl)-5-oxocyclopentyl]-5-heptenoic acid; dinoprostone; PGE2, hCG-alpha-(59-92)-peptide (34 residues), Paraquat Derivative, Paraquat hexanoate (PQ-h), Monoquat, Diquat, 9,10-dihydro-8a,10a-diazoniaphenanthrene, MPTP, 1-methyl-4-phenyl-1,2,5,6-tetrahydropyridine, 1,2-Naphthoquinone, N-Acetyl-S-(1,2-dihydroxy-4-naphthyl)cysteine, N-Acetyl-S-(1,4-dihydroxy-2-naphthyl)cysteine, N-Acetyl-S-(1,2-dihydroxy-1-hydroxy-1-naphthyl)cysteine, 2-Chloro-2'.6'-diethylacetanilide (CDA) Hapten, 2-[2-Chloro-(2'-6'-diethyl)acetanilido]ethanoic Acid, 2-Chloro-2'.6'-diethylacetanilide (CDA) Hapten, 2-[2-Chloro-(2'-6'-diethyl)acetanilido]butanoic Acid, 2-Chloro-2'.6'-diethylacetanilide (CDA) Hapten, 5-(4-Chloroacetamido-3,5-diethyl)phenoxypentanoic Acid, CDA, 2-Chloro-2'.6'-diethylacetanilide, HDA, 2-Hydroxy-2'.6'-diethylacetanilide, 2,6-diethyl-aniline, Hydroxyalachlor, Alachlor ESA, Alachlor ethanesulfonic acid, Isoproturon Hapten, 3-(4-Isopropylphenyl)-1-carboxypropyl-1-methyl urea, chlorotoluron, 3-(3-chloro-p-tolyl)-1,1-dimethylurea, Metoxuron, 3-(3-chloro-4-methoxyphenyl)-1,1-dimethylurea, metamitron, 4-amino-4,5-dihydro-3-methyl-6-phenyl-1,2,4-triazin-5-one, mecoprop, (RS)-2-(4-chloro-o-tolyloxy) propionic acid, propyzamide, 3,5-dichloro-N-(1,1-dimethylpropynyl)benzamide, Paraquat dichloride, MCPB, 4-(4-chloro-o-tolyloxy)butyric acid, Chlortoluron Hapten, N-(3-Chloro-4-methylphenyl)-N-methyl-N-carboxypropyl Urea, Metsulfuron, Methyl 2-[3-(4-methoxy-6-methyl-1,3,5-triazin-2-yl)ureidosulphonyl]benzoate, Captopril Haptens, Captopril-4-(Maleimidomethyl)-cyclohexane Carboxylic Acid (MCC), Captopril Haptens, Captopril Disulfide Modification, Mercaptoethanol-MCC, Mercaptoethanol-4-(Maleimidomethyl)-cyclohexane Carboxylic Acid Modification, Captopril Haptens, Captopril without MCC, Aculeatiside A, Aculeatiside B, Solamargine, Solasonine, solanine-S; purapurine, Solasodine, Khasianine, Tomatine, lycopersicin, Tomatidine, 3-O-beta-D-Glucopyranosyl-solasodine, O-alpha-L-Rhamnosyl-1(1→2)-3-O-beta-D-glucopyranosyl-solasodine, 3-O-beta-D-Galacopyranosyl-solasidine, O-beta-D-Glucopyranosyl-1(1→3)-3-O-beta-D-galacopyranosyl-solasodine, 12-Hydroxysolamargine, 12-Hydroxysolasonine, Isoanguivine, Solaverine I, Solaverine II, Xylosyl-beta-solamargine, alpha-Solanine, alpha-Chaconine, Dioscine, Indole Derivatives, beta-Indole Acetic Acid, 2-Bromo-4,6-dinitroaniline, 2-Chloro-4,6-dinitroaniline, Tetryl, 2,4,6-trinitrophenyl-n-methylnitramine, nitramine, tetralite, tetril, 2-Amino-4,6-dinitrotoluene, 2,4-Dinitroaniline, 3,5-Dinitroaniline, 2-Amino-4,6-dinitrobenzoic acid, Disperse Blue 79, N-[5-[bis[2-(acetyloxy)ethyl]amino]-2-[(2-bromo-4,6-dinitrophenyl) azo]-4-ethoxyphenyl]acetamide, 1,3-Dinitrobenzene, 2,6-Dinitrotoluene, 4-Amino-2,6-dinitrotoluene, 1,3,5-Trinitrobenzene, Nicergoline, Ethylmorphine, 8-Didehydro-4,5-epoxy-3-ethoxy-17-methylmorphinan-6-ol, Dihydromorphine, Dihydrocodeine, dihydromorphinone, Hydromorphone, Dihydrocodeinone, Hydrocodone, Naltrexone, N-cyclopropylmethyl-14-hydroxydihydromorphinone, Dextromethorphan, (±)-3-Methoxy-17-methylmorphinan, Homatropine, Endorphins Modification Derivative Type: b-Endorphin, Met-enkephalin, DALEA, D-Ala(2)-D-Leu(5)-enkephalinamide, Vincristine, 22-Oxovincaleukoblastine, leurocristine; VCR; LCR, OCT, 22-Oxacalcitriol, OCT-3-HG, 22-oxacalcitriol-3-Hemiglutarate, 24(OH)OCT, 24(OH)-22-oxacalcitriol, 1,20(OH)2-hexanor-D3, Synephrine, Epinephrine, 4-[(1R)-1-Hydroxy-2-(methylamino)ethyl]-1,2-benzenediol, Phenylephrine, Dopamine Derivative, 6-hydroxy dopamine, Tyramine derivative, 3-methoxy tyramine, Phenethylamine, Benzeneethanamine; PEA, m-tyramine, o-tyramine, dimethoxyphenethylamine, Thymidine glycol monophosphate, 5,6-Dihydroxythymidine monophosphate, Thymidine monophosphate, Thymidine glycol, Thymine glycol, 5,6-Dihydrothymidine, Thymidine, Thymine, 5-methyluracil; 2,4-dihydroxy-5-methylpyrimidine, AMP, Adenosine mono phosphate, CMP, Cytidine mono phosphate, Carbamazepine, 5-carbamoyl-5H-dibenz[b,f]azepine, Neopterin isomers, D-erythro-Neopterin, Neopterin isomers, L-erythro-Neopterin, Neopterin isomers, D-threo-Neopterin, Biopterin isomers, L-erythro-Biopterin, Biopterin isomers, D-erythro-Biopterin, Biopterin isomers, L-threo-Biopterin, Biopterin isomers, D-threo-Biopterin, Pterin-6-Carboxylic Acid, C7H5NiO3, Pterin, Thromboxane B2, (5Z,9alpha,13E,15S)-9,11,15-trihydroxythromboxa-5,13-dien-1-oic acid, 15 Ketoprostaglandin F2alpha, Fumonisin B1, macrofusine; FBI, Thyroliberin, TRH; thyrotropin-releasing factor; thyrotropin releasing hormone; TRF; protirelin; lopremone, Thyroliberin-OH, TRH-OH, Diketopiperazine, cyclo (H-P), TRH analogues, Methylated TRH, TRH analogues, TRH elongated peptides, TRH-Gly, TRH elongated peptides, TRH-Gly-Lys-Arg, TRH elongated peptides, TRH-Gly-Lys-Arg-Ala, TRH elongated peptides, P7 (Modification Q-H-P-G-L-R-F), TRH elongated peptides, P10 (Modification S-L-R-Q-H-P-G-L-R-F), TRH elongated peptides, Ps5 Modification pro-TRH[178-199], TRH elongated peptides, TRH-Ps5 (Modification pro-TRH[172-199]), Hypothalmic peptide, LHRH, Cyanoginosin-LA, Cyanoginosin-LB, Cyanoginosin-LR, Cyanoginosin-LY, Cyanoginosin-AY, Cyanoginosin-FR, Cyanoginosin-YR, Ne-acetyllysine-containing peptide, Gly-Lys (Ac)-e-aminocaproic acid (Aca)-Cys, Benzoic Acid, Benzenecarboxylic acid; phenylformic acid; dracylic acid, m-hydroxybenzoic acid, 3-hydroxybenzoic acid, o-methoxybenzoic acid, 2-methoxybenzoic acid, o-toluic acid, 2-Methylbenzoic acid, o-chlorobenzoic acid, 2-chlorobenzoic acid, o-aminobenzoic acid, 2-aminobenzoic acid, thiosalicylic acid, 2-Mercaptobenzoic acid; o-sulfhydrylbenzoic acid, Salicylamide, 2-Hydroxybenzamide, Saligenin, saligenol; o-hydroxybenzyl alcohol; Salicyl alcohol, 2-cyanophenol, 2-hydroxyphenyl acetic acid, p-hydroxybenzoic acid, p-aminobenzoic acid, 4-Aminobenzoic acid; vitamin Bx; bacterial vitamin H1, p-toluic acid, p-methylamino benzoic acid, p-chlorosalicylic acid, 4-chloro-2-hydroxybenzoic acid, 2,4-dihydroxybenzoic acid, beta-Resorcylic Acid; 2,4-dihydroxybenzenecarboxylic acid; BRA, 4-aminosalicylic acid, 4-Amino-2-hydroxybenzoic acid; p-aminosalicylic acid, Gentisic Acid, 2,5-dihydroxybenzoic acid; 5-hydroxysalicylic acid, Picolinic acid, o-Pyridinecarboxylic acid; 2-Pyridinecarboxylic acid, picolinic acid N-oxide, 3-hydroxypicolinic acid, 2-hydroxynicotinic acid, 7-methylguanine, N2-Carboxymethyl-N7-methylguanine, 2-(7-methyl-6-oxo-6,7-dihydro-1H-purin-2-ylamino)acetic acid, 7-methylxanthine, 7-methyluric acid, 7-methyladenine, Guanine, 2-Amino-1,7-dihydro-6H-purin-6-one; 2-aminohypoxanthine, Adenine, 6-aminopurine; 6-amino-1H-purine; 6-amino-3H-purine; 6-amino-9H-purine, 7-(2-Carboxyethyl)guanine, 7-CEGua, 7-Ethylguanine, 2-amino-7-ethyl-1H-purin-6(7H)-one, 7-(2,3-Dihydroxypropyl) guanine, 2-amino-7-(2,3-dihydroxypropyl)-1H-purin-6 (7H)-one, 7-(2-Hydroxyethyl)guanine, 2-amino-7-(2-hydroxyethyl)-1H-purin-6(7H)-one, 7-(2-[(2-Hydroxyethyl) amino]ethyl)-guanine, 2-amino-7-(2-(2-hydroxyethylamino)ethyl)-1H-purin-6(7H)-one, 7-Carboxymethylguanine, or 2-(2-amino-6-oxo-1,6-dihydropurin-7-yl)acetic acid. In some alternatives, the CAR or T cell receptor comprises a fragment specific for the hapten, wherein the CAR or TCR comprises 14G8, Anti 3-methylindole antibodies, 3F12, Anti 3-methylindole antibodies, 4A1G, Anti 3-methylindole antibodies, 8F2, Anti 3-methylindole antibodies, 8H1, Anti 3-methylindole antibodies, Anit-Fumonisin B1 antibodies, Anti-1,2-Naphthoquinone-antibodies, Anti-15-Acetyldeoxynivalenol antibodies, Anti-(2-(2,4-dichlorophenyl)-3(1H-1,2,4-triazol-1-yl)propanol) Antibodies (Anti-DTP antibodies), Anti-22-oxacalcitriol antibodies (As-1, 2 and 3), Anti-(24,25(OH)2D3) Antibodies (Ab11), Anti-(24,25(OH)2D3) Antibodies (Ab3), Anti-(24, 25(OH)2D3) Antibodies (Ab3-4), Anti-2,4,5-Trichlorophenoxyacetic acid antibodies, Anti (2,4,5-Trichlorphenoxyacetic acid) Antibodies, Anti-(2,4,6-Trichlorophenol) Antibodies, Anti-(2,4,6-Trichlorophenol) Antibodies, Anti 2,4,6-Trinitrotoluene (TNT) Antibodies, Anti-2,4-Dichlorophenoxyacetic acid (MAb's B5/C3, E2/B5, E2/G2, F6/C10, and F6/E5), Anti (2,4-Dichlorphenoxyacetic acid) Antibodies, Anti-2-hydroxybiphenyl-antibodies, Anti-(3,5,6-trichloro-2-pyridinol) Antibodies (LIB-MC2, LIB-MC3), Anti (3,5,6-trichloro-2-pyridinol) antibodies (LIB-MC2 MAb), Anti-3-Acetyldeoxynivalenol (3-AcDON) Antibodies, Anti-3-phenoxybenzoic acid (3-PBAc)-Antibodies, Anti-4-Nitrophenol antibodies, anti-4-nitrophenyl 4'-carboxymethylphenyl phosphate antibodies, Anti-7-(Carboxyethyl)guanine (7-CEGua) antibodies (group specific for 7-meGua), Anti-7-methylguanine (7-MEGua) antibodies, Anti-ABA antibodies, Anti Acephate antibodies (Antiserum 8377), Anti-acetyllysine antibodies (mAbs AL3D5, AL11, AKL3H6, AKL5C1), Anti Aculaetiside-A antibody, Anti Aflatoxin M1(AFM1)antibodies (mAbs A1, N12, R16, FF32), Anti-agatharesinol Antibody, Anti-agatharesinol Antibody, Anti Amidochlorantibodies, Anti-Amitrole antibodies (anti 1a-BSA antibodies), Anti ampicillin Antibodies (AMPI I 1D1 and AMPI II 3B5), Anti-anandamide antibodies (9C11.C9C, 30G8.E6C, 7D2.E2b, 13C2 MAbs), Anti atrazine antibodies, Anti-atrazine antibodies, Anti-Atrazine antibodies, Anti Atrazine Antibodies, Anti Atrazine Antibodies, Anti-Atrazine Antibodies, Anti-Atrazine Antibodies (4063-21-1 MAb cell line mAb and scAbs), Anti-Atrazine Antibodies (4D8 and 6C8 scAb), Anti Atrazine Antibodies (C193), Anti Atrazine Antibodies (In Rabbit/Sheep), Anti Atrazine Antibodies (K4E7), Anti Atrazine Antibodies (MAb: AM7B2.1), Anti Atrazine Antibodies (ScAb), Anti Atrazine Mercapturic acid antibodies, Anti (Azinphos methyl) Antibodies (MAB's LIB-MFH14, LIB-MFH110), Anti benalaxyl antibody, Anti benzimidazolecarboxylic acid, Anti benzimidazoles antibody (Ab 587), Anti-Benzo[a]pyrene antibodies, Anti Benzo(a)pyrene antibodies (10C10 and 4D5 MAbs), Anti-(Benzoylphenylurea)-Antibodies (mainly against Diflubenzuron), Anti-berberine Antibodies, Anti-beta Indole Acetic Acid Antibodies, Anti-Biopterin (L-erythro form) Antibodies, Anti-Brevetoxin PbTx-3-Antibodies, Anti Bromacil Antibodies, Anti-Bromophos Antibodies, Anti-Bromophos ethyl Antibodies, Anti Butachlor antibodies, Anti-Captopril-MCC Antibodies, Anti-Carbamazepine (CBZ)-Antibodies, Anti Carbaryl Antibodies, Anti Carbaryl Antibodies (LIB-CNH32, LIB-CNH33, LIB-CNH36, LIB-CNH37, LIB-CNH45, LIB-CNA38), Anti-Carbaryl Antibodies (LIB/CNH-3.6 MAb), Anti Carbofuran Antibodies (LIB-BFNB-52, LIB-BFNB-62, LIB-BFNB-67), Anti Carbofuran Antibodies (LIB-BFNP21), Anti-CDA-antibodies, Anti-CDA-antibodies (anti-2-[2-Chloro-(2'-6'-diethyl)acetanilido]butanoic Acid), Anti-CDA-antibodies (anti-2-[2-Chloro-(2'-6'-diethyl)acetanilido]ethanoic Acid), Anti-CDA-antibodies (anti-5-(4-Chloroacetamido-3,5-diethyl)phenoxypentanoic Acid), anti-ceftazidime antibody, Anti-(chlorodiamino-s-triazine) Antibodies (Anti-CAAT) (PAb1-8), Anti Chlorothalonil Antibodies, Anti-Chlorpyrifos antibodies, Anti-Chlorpyrifos Antibodies, Anti-Chlorpyrifos Antibodies (LIB-AR1.1, LIB-AR1.4 Mabs), Anti-Chlorpyrifos Antibodies (LIB-C4), Anti (chlorpyrifos) antibodies (LIB-C4 MAb), Anti-Chlorpyrifos Antibodies (LIB-PN1 Mabs), Anti-Chlorpyrifos Antibodies (LIB-PN2 Mabs), Anti-Chlorpyrifos Antibodies (LIB-PO Mabs), Anti-chlorsulfuron antibodies, Anti-Chlorsulfuron antibodies, Anti Chlortoluron Antibodies (Antiserum), Anti-Cyanoginosin-LA antibodies (mAbs 2B2-2, 2B2-7, 2B2-8, 2B2-9, 2B2-10, 2B5-5, 2B5-8, 2B5-14, 2B5-15, 2B5-23), Anti (D-3-methoxy-4-hydroxyphenylglycol) antibodies, Anti-DDA antibodies, Anti DDT antibodies (PAbs and MAbs), Anti-DDT Mabs (LIB1-11, LIB5-21, LIB5-25, LIB5-28, LIB5-212, LIB5-51, LIB5-52, LIB5-53), Anti-DEC Antibodies (Anti diethylcarbamazine Antibodies), Anti DEHA antibodies, Anti-(Delor 103) antibodies, Anti-Deltamethrin Antibodies, Anti Deltamethrin Antibodies (Del 01 to Del 12 MAbs and PAbs), Anti-deoxynivalenol (DON) Antibodies, Anti-Deoxynivalenol (DON) Antibodies, Anti Dexamethasone Antibody, Anti Dexamethasone Antibody, Anti-Dinitrophenyl (DNP)-antibodies, Anti dinitrophenyl spin labeled antibodies (AN01-AN12), Anti Diuron Antoboides (MAb's: 21, 60, 195, 202, 275, 481, 488, 520), Anti-D-MHPG Antibodies, Anti DNC antibodies, Anti-EB1089 antibodies, Anti-ecdysone antibodies, Anti-endosulfan antibodies, Anti-Endosulfan Antibodies, Anti Esfenvalerate antibodies (Ab7588), Anti estradiol antibodies, Anti-Fenitrothion antibodies (pAbs and mAbs), Anti-Fenpropimorph antibodies, Anti Fenthion Antibodies, Anti-Fenthion Antibodies, Anti FITC antibodies (B13-DEI), Anti-Flucofuron antibodies (F2A8/1/A4B3), Anti-flufenoxuron antibodies, and Anti-(Benzoylphenylurea)-Antibodies, Anti-Formononetin Antibodies, Anti-Furosemide antibodies (Furo-26, Furo37, furo-72, Furo 73 Mabs), Anti-GR151004 Antibodies, Anti-hCG-alpha-peptide Antibodies (FA36, Anti hydroxyatrazine antibodies (HYB-283-2), Anti-Hydroxysimazine Antibodies, Anti Imazalil Antibodies MoAb's (9C1-1-1, 9C5-1-1, 9C6-1-1, 9C8-1-1, 9C9-1-1, 9C12-1-1, 9C14-1-1, 9C16-1-1, 9C18-1-1, 9C19-1-1, 9E1-1, 9G2-1), Anti Irgarol Antibodies, Anti Isopentenyl adenosine antibodies, Anti Isoproturon Antibodies, Anti-KB-6806 antiserum, Anti-(+)lupanine antibodies, Anti Lysophosphatidic (LPA) acid, Anti M3G Ab1 and Ab2, Anti M3G Ab1 and ab2, Anti-MBC antibodies (Anti-2-succinamidobenzimidazole antiserum), Anti Metanephrine antibodies, anti (+)methamphetamine antibodies, Anti-Methiocarb Antibodies (LIB-MXNB31, LIB-MXNB-33, LIB-MXNH14 and LIB-MXNH-15 MAbs), Anti Metolachlor antibodies, Anti-Metolachlor Antibodies, Anti-Metolachlor Antibodies (MAb 4082-25-4), Anti Molinate Antibodies, Anti monuron antibodies, Anti-morphine-3-glucuronide (E3 scFv antibody), Anti morphine antibodies, Anti-Morphine antibodies, Anti-Morphine Antibodies (mAbs 8.2.1, 33.2.9, 35.4.12, 39.3.9, 44.4.1, 76.7F.16, 83.3.10, 115.1.3, 124.2.2, 131.5.13, 158.1.3, 180.2.4), Anti-Neopterin (D-erythro form) Antibodies, Anti-Nicarbazin Antibodies (Nic 6, Nic 7, Nic 8, and Nic 9), Anti Nicergoline Antibodies (Nic-1, Nic-2, Nic-3 & BNA-1, BNA-3), Anti-norflurazon antibodies, Anti NorMetanephrine antibodies, Anti (o-DNCP) Antibodies, Anti-P10 antibodies (TRH elongated peptide), Anti-Paraoxon Antibodies (BD1 and CE3), Anti Paraquat antibodies, Anti-Paraquat antibodies, anti Parathion-methyl antibodies, Anti PCB Antibodies (against 3,3',4,4'-tetrachlorobiphenyl) MAb S2B1, Anti pentachlorophenol antibodies, Anti Pentachlorophenol antibodies, Anti-Pentachlorophenol antibodies, Anti permethrin antibodies (Mabs Py-1, Py-3 and Py-4), Anti-Phencyclidine Antibodies (Mab 6B5 Fab), Anti-phenobarbital antibodies, Anti-phenobarbital antibodies, Anti-(p.p'-DDT)-Antibodies (LIB-DDT-35 and LIB-DDT5-52), Anti permethrin antibodies (Ab549), Anti Propoxur antibodies (LIB-PRNP15, LIB-PRNP21, LIB-PRNB21, LIB-PRNB33), Anti-Prostaglandin E2-antibodies, Anti-p-tyramine antibodies, Anti pyrene antibodies, Anti retronecine antibodies, Anti-Retronecine Antibodies, Anti salicylate antibodies, Anti Sennoside A antibodies (MAb 6G8), Anti Sennoside B antibodies (MAb's: 7H12, 5G6, 5C7), Anti Simizine antibodies, Anti Sulfonamides antibodies (Anti-TS), Anti-Sulocfuron antibodies (S2B5/1/C3), Anti sulphamethazine antibodies (21C7), Anti-synephrine antibodies, Anti-Thiabendazole antibodies (Antibody 300), Anti-Thiabendazole antibodies (Antibody 430 and 448), Anti-Thiram-Antibodies, Anti-THP antibodies (7S and 19S), Anti-Thromboxane B2 Antibodies, Anti-thymidine glycol monophosphate antibodies (mAb 2.6F.6B.6C), Anti-Thyroliberin (TRH) antibodies, Anti TNT antibodies (AB1 and AB2 antiserum), Anti Triadimefon Antibodies, Anti-triazine antibodies (AM1B5.1), Anti-triazine antibodies (AM5C5.3), Anti-triazine antibodies (AM5D1.2), Anti-triazine antibodies (AM7B2.1), Anti-triazine antibodies (SA5A0.1), Anti-Triazine serum (anti-ametryne), Anti-Triazine serum (anti-atrazine), Anti-Triazine serum (anti-simazine), Anti-Triazine serum (anti-simetryne), Anti Trifluralin Antibodies, Anti Trifluralin Antibodies, Anti Vincristine Antibodies, Anti-Zearalenone Antibodies, Anti Zeatin riboside antibodies, E2 G2 and E4 C2, Fab Fragment K411B derived from MAb K4E7 (isotype IgG2b with k light chain), LIB-BFNP23 Mab, MAb's H-7 and H-9 (against O,O-diethyl OP pesticides), MoAb 33A7-1-1, MoAb 33B8-1-1, MoAb 33C3-1-1, MoAb 3C10-1-1 and MoAb 3E17-1-1, MoAb 45D6-5-1, MoAb 45E6-1-1, MoAb 45-1-1, Mutant (GlnL89Glu) in Fab Fragment K411B derived from MAb K4E7 (isotype IgG2b with k light chain), Mutant (GlnL89Glu/ValH37Ile/GluL3Val) in Fab Fragment K411B derived from MAb K4E7 (isotype IgG2b with k light chain), Mutant (GlnL89Glu/ValH37Ile/GluL3Val) in Fab Fragment K411B derived from MAb K4E7 (isotype IgG2b with k light chain), Mutant (GlnL89Glu/ValH37Ile) in Fab Fragment K411B derived from MAb K4E7 (isotype IgG2b with k light chain), Mutant (GlnL89Glu/ValH37Ile) in Fab Fragment K411B derived from MAb K4E7 (isotype IgG2b with k light chain), Mutant (GluH50Gln) in Fab Fragment K411B derived from MAb K4E7 (isotype IgG2b with k light chain), Mutant (GluH50X) in Fab Fragment K411B derived from MAb K4E7 (isotype IgG2b with k light chain), Mutant (GlyH100aAla) in Fab Fragment K411B derived from MAb K4E7 (isotype IgG2b with k light chain), Mutant (GlyH100aSer) in Fab Fragment K411B derived from MAb K4E7 (isotype IgG2b with k light chain), Mutant (HisH95Phe) in Fab Fragment K411B derived from MAb K4E7 (isotype IgG2b with k light chain), Mutant (HisH95Tyr) in Fab Fragment K411B derived from MAb K4E7 (isotype IgG2b with k light chain), Mutant (PheL32Leu) in Fab Fragment K411B derived from MAb K4E7 (isotype IgG2b with k light chain), Mutant (TrpH33Phe,Tyr,Leu) in Fab Fragment K411B derived from MAb K4E7 (isotype IgG2b with k light chain), Mutant (TryI96Phe) in Fab Fragment K411B derived from MAb K4E7 (isotype IgG2b with k light chain), Mutant (TryL96Phe) in Fab Fragment K411B derived from MAb K4E7 (isotype IgG2b with k light chain), Mutant (ValH37Ile) in Fab Fragment K411B derived from MAb K4E7 (isotype IgG2b with k light chain), Mutant (ValH37Ile) in Fab Fragment K411B derived from MAb K4E7 (isotype IgG2b with k light chain), P6A7 MAb, PNAS2 6/3 56(1)-1-5-1, PNAS2 6/3 56(1)-1-5-2, PNAS2 6/3 56(1)-1-10-4, PNAS2 6/3 56(1)-1-10-5 and PNAS2 6/3 56(1)-3-1-5, Alexa Fluor 405/Cascade Blue dye antibody, Alexa Fluor 488 dye antibody, BODIPY FL dye antibody, Dansyl antibody, Fluorescein/Oregon Green dye antibody, Lucifer yellow dye antibody, Tetramethylrhodamine and Rhodamine Red dye antibody, Texas Red and Texas Red-X dye antibody, Biotin antibody, Dinitrophenyl antibody and/or Nitrotyrosine antibody or any portion thereof of the aforementioned haptens.

In a sixth aspect, a complex is provided, wherein the complex comprises a chimeric antigen receptor (CAR) or a T cell receptor (TCR), wherein the CAR or TCR is joined to a peptide (which, optionally, may comprise one or more haptens joined thereto, e.g., by way of covalent or disulfide bonds), an antibody or binding fragment thereof through a CAR or TCR-mediated interaction with said target moiety and, wherein said antibody or binding fragment thereof is specific for an antigen present on a cancer cell, virus, or bacterial cell. In some alternatives, said target moiety is a hapten, poly(his) tag, Strep-tag, FLAG-tag, V5-tag, Myc-tag, HA-tag, NE-tag, biotin, digoxigenin, dinitrophenol, green fluorescent protein (GFP), yellow fluorescent protein, orange fluorescent protein, red fluorescent protein, far red fluorescent protein, or fluorescein (e.g., Fluorescein isothiocyanate (FITC)). In some alternatives, the CAR or TCR is expressed by a cell or a T cell. In some alternatives, the CAR or TCR is on the surface of a cell or a T cell. In some alternatives, the cell is a precursor T cell. In some alternatives, the precursor T cell is a hematopoietic stem cell. In some alternatives, the cell is a CD8+ T cytotoxic lymphocyte cell selected from the group consisting of naïve CD8+ T cells, central memory CD8+ T cells, effector memory CD8+ T cells and bulk CD8+ T cells. In some alternatives, the cell is a CD4+ T helper lymphocyte cell that is selected from the group consisting of naïve CD4+ T cells, central memory CD4+ T cells, effector memory CD4+ T cells, and bulk CD4+ T cells. In some alternatives, the peptide, which comprises a target moiety, such as fluorescin, is an albumin, a mutant albumin, or a fragment thereof, a cyclic peptide PEGA, or CREKA. In some alternatives, the antibody or binding fragment thereof, which comprises a target moiety, such as fluorescin, is abagovomab, abituzumab, adecatumumab, afutuzumab, alacizumab pegol, alemtuzumab, altumomab pentetate, amatuximab, anatumomab mefanetox, anetumab ravtansine, apolizumab, arcitumomab, ascrinvacumab, aselizumab, atezolizumab, atlizumab, avelumab, bapineuzumab, bavituximab, bectumomab, belimumab, besilesomab, bevacizumab, bivatuzumab mertansine, blinatumomab, blontuvetmab, brentuximab, brontictuzumab, cantuzumab mertansine, cantuzumab ravansine, capromab pendetide, carlumab, carotuximab, catumaxomab, cBR96-doxorubicin immunoconjugate, cedelizumab, certolizumab pegol, cetuximab, cidfusituzumab, cidtuzumab, citatuzumab bogatox, cixutumumab, clivatuzumab tetraxetan, codrituzumab, coltuximab ravtansine, conatumumab, dacetuzumab, daclizumab, dalotuzumab, daratumumab, demcizumab, denintuzumab mafodotin, denosumab, depatuxizumab mafodotin, derlotuximab biotin, detumomab, dinutuximab, drozitumab, duligotumab, durvalumab, dusigitumab, duvortuxizumab, ecromeximab, eculizumab, edrecolomab, efalizumab, elgemtumab, elotuzumab, emactuzumab, emibetuzumab, enavatuzumab, enfortumab vedotin, enoblituzumab, enoticumab, ensituximab, epratuzumab, erlizumab, ertumaxomab, etaracizumab, farletuzumab, FBTA05, femzumab, ficlatuzumab, figitumumab, flanvotumab, fontolizumab, futuximab, galiximab, ganitumab, gemtuzumab ozogamicin, girentuximab, glembatumumab vedotin, ibritumomab, icrucumab, igovomab, IMAB362, imalumab, imgatuzumab, indatuximab ravtansine, indusatumab vedotin, intetumumab, inotuzumab ozogamicin, intetumumab, ipilimumab, iratumumab, isatuximab, labetuzumab, lambrolizumab, lexatumumab, lifastuzumab vedotin, lilotomab satetraxetan, lintuzumab, lorvotuzumab mertansine, lucatumumab, lumiliximab, lumretuzumab, mapatumumab, margetuximab, matuzumab, mepolizumab, milatuzumab, minretumomab, mirvetuximab soravtansine, mitumomab, mogamulizumab, moxetumomab pasudotox, nacolomab tafenatox, naptumomab estafenatox, narnatumab, natalizumab, necitumumab, nesvacumab, nimotuzumab, nivolumab, nofetumomab merpentan, obinutuzumab, ocaratuzumab, ocrelizumab, ofatumumab, olaratumab, omalizumab, onartuzumab, ontuxizumab, oportuzumab monatox, oregovomab, otlertuzumab, panitumumab, pankomab, parsatuzumab, pascolizumab, pasotuxizumab, patritumab, pecfusituzumab, pectuzumab, pembrolizumab, pemtumomab, pertuzumab, pexelizumab, pidilizumab, pinatuzumab vedotin, pintumomab, polatuzumab vedotin, pritumumab, racotumomab, radretumab, ramucirumab, ranibizumab, reslizumab, rilotumumab, rituximab, robatumumab, rovelizumab, ruplizumab, sacituzumab govitecan, samalizumab, satumomab pendetide, seribantumab, sibrotuzumab, SGN-CD19A, SGN-CD33A, simtuzumab, siplizumab, siltuximab, sofituzumab vedotin, solitomab, sontuzumab, tabalumab, tacatuzumab tetraxetan, tadocizumab, talizumab, tamtuvetmab, taplitumomab paptox, tarextumab, tenatumomab, teprotumumab, TGN1412, ticilimumab (tremelimumab), tigatuzumab, TNX-650, tocilizumab, toralizumab, tositumomab, tovetumab, trastuzumab, TRB S07, tremelimumab, tucotuzumab celmoleukin, tucusituzumab, ublituximab, ulocuplumab, urelumab, urtoxazumab, ustekinumab, vandortuzumab vedotin, vanticturmab, vanucizumab, veltuzumab, vesencumab, visilizumab, volociximab, vorsetuzumab mafodotin, votumumab, zalutumamab, zanolimumab, zatuximab, cosfroviximab, diridavumab, exbiviximab, felvizumab, foravirumab, larcaviximab, libiviramab, motavizumab, motovizumab, nolovizumab, numavizumab, palivizumab, porgaviximab, PRO 140, rafivirumab, ralivizumab, regavirumab, reslivizumab, resyvizumab, sevirumab, suvizumab, tuvirumab, umavizumab, edobacomab, nebacumab, pagibaximab, panobacumab, raxibacumab, or tefibazumab or a binding fragment thereof. In some alternatives, the hapten used comprises Alexa Fluor 405, Cascade Blue, Alexa Fluor 488, BODIPY, Dansyl chloride, Oregon Green, Lucifer yellow, Rhodamine, Tetramethylrhodamine, Nitrotyrosine, digoxigenin, 2,4-Dichlorophenoxyacetic acid, Atrazine (2-Chloro-4-(ethylamino)-6-(isopropylamino)-s-triazine), Nicotine (3-(1-Methyl-2-pyrrolidyl) pyridine, Black Leaf), Morphine (morph, Morphine Sulfate), 2,4-DINITROCHLOROBENZENE (1-Chloro-2, 4-dinitrobenzene; DNCB; Dinitrochlorobenzene), 4-chloro-6-(ethylamino)-1,3,5-triazine-2-(6-aminohexanecarboxylic acid), Structurally related s-triazines (Modifications: H/Cl/C6 R1=NH2- R2=—Cl R3=—NH—(CH2)5-COOH; iPr/Cl/nBu R1=(CH3)2-CH—NH— R2=—Cl R3=—NH—(CH2) 3-(CH3)), Ametryn (2-Ethylamino-4-isopropylamino-6-methylthio-1,3,5-triazine), Deethylatrazine (DEA) (Structurally related s-triazines), Deisopropylatrazine (DIA) (Structurally related s-triazines), Deethyldeisopropylatrazine (DEDIA) (Structurally related s-triazines), Deethyldeisopropylatrazine (DEDIA) (Structurally related s-triazines), HydroxyAtrazine (HA) (Structurally related s-triazines), DeisopropylHydroxyAtrazine (DIHA) (Structurally related s-triazines), DeethylDeisopropylHydroxyAtrazine (DEDIHA) (Structurally related s-triazines), Simazine (Structurally related s-triazines), Desmetryne (Structurally related s-triazines), Prometryne (Structurally related s-triazines), 2-hydroxyatrazine (atrazine derivative), 2-hydroxypropazine (structurally related s-triazine), 2-hydroxysimazine, N-(4-Amine-6-hydroxy-[1,3,5]triazin-2-yl)-4-aminobutanoic Acid (Modification: R1=NH2 R2=NH(CH2)3COOH R3=OH), SulcoFuron, 5-chloro-2-{4-chloro-2-[3-(3,4-dichlorophenyl)ureido]phenoxy}benzenesulfonic acid, FlucoFuron (1,3-bis(4-chloro-α,α,α-trifluoro-m-tolyl)urea), Agatharesinol, Sequirin C, Sugiresinol, Hydroxysugiresinol, Hinokiresinol, Coniferyl alcohol, Cinnamyl alcohol, p-Coumaric acid, Cinnamic acid, p-Coumaric acid, Cinnamic acid, Hinokinin, Guaiacylglycerol-beta-guaiacyl ether, Morphine-3-glucuronide (M3G), Codeine, Nor-Codeine, 6-Monoacetylmorphine, (+) Methamphetamine, Ceftazidime, Phenobarbital, p-hydroxyPhenobarbital, p-aminophenobarbital, Cyclobarbital, 3-Ketocyclobarbital, 3'-Hydroxycyclobarbital, Secobarbital, Barbital, Metharbital, Barbituric acid, Thiopental, Thiobarbituric acid, Primidone, Glutethimide, Pentobarbital, Heroin, Diacetylmorphine, Levallorphan, L-11-Allyl-1,2,3,9,10,10a-hexahydro-4H-10,4a-iminoethanophenanthren-6-ol, Pethidine (Demerol; Dolantin; Meperidine; Ethyl 1-methyl-4-phenylpiperidine-4-carboxylate; Isonipecaine), Methamphetamine, d-Desoxyephedrine; Methedrine; Tolpropamine; Pratalgin; Pragman. Benzoylecgonine, 3-Carboxymethylmorphine, Cocaine, 5-benzimidazolecarboxylic acid, ABA (4-acetyl benzoic acid), Dexamethasone, Flumethasone, 6alpha, 9 alpha-difluoro-11 beta, 17,21-trihydroxy-16 alpha-methylpregna-1,4-diene-3, 20-dione, 9 alpha-fluoro-11 beta,17,21-trihydroxy-16 beta-methylpregna-1,4-diene-3,20-dione, 9-alpha-fluroprednisolone, Desoxymethasone, Triamcinolone, 9 alpha-fluoro-11 beta,16 alpha, 17,21-tetrahydroxypregna-1,4-diene-3,20-dione, Fluocortolone, 6 alpha-fluoro-11 beta,21-dihydroxypregna-1,4-diene-3,20-dione, Cortisol, 11 beta, 17,21-trihydroxypregna-4-ene-3,20-dione, Prednisone, 17,21-dihydroxypregn-4-ene-3,11,20-trione, Methylprednisolone, 11 beta, 17,21-trihydroxy-6 alpha-methylpregna-1,4-diene- 3,20-dione, Triamcinolone hexacetonide, 21-(3,3-dimethyl-1-oxobutoxy)-9 alpha-fluoro-11-hydroxy-16,17-[(1-methylethylidene) bis(oxy)]pregna-1,4-diene-3,20-dione, Carbofuran, 2,3-dihydro-2,2-dimethyl-7-benzofuranyl methylcarbamate, BFNP (3-[[(2,3-dihydro-2,2-dimethyl-7-benzofuranyloxy)carbonyl]amino]propanoic acid), Carbofuran derivative, 2,3-dihydro-2,2-dimethyl-7-benzofuranol, Bendiocarb, Carbaryl, Methiocarb, Propoxur, Aldicarb, Methomyl, Benalaxyl, methyl N-(phenylacetyl)-N-(2,6-xylyl)-DL-alaninate, Bn-Ba (4-[2-(N-phenylacetyl-N-2,6-xylylamino)propionamido] butyric acid), Bn-COOH (4-[2-(N-phenylacetyl-N-2,6-xylyl-DL-alanine), Benalaxyl derivative, Furalaxyl, Metalaxyl, Acetochlor, Dimetachlor, Metolachlor, 2-chloro-6'-ethyl-N-(2-methoxy-1-methylethyl)acet-o-toluidine, Diethathyl-ethyl, Benzoylprop-ethyl, Benzoylprop-ethyl, 2,4,5-Trichlorophenoxyacetic acid, 2-chloro-6'-ethyl-N-(2-methoxy-1-methylethyl)acet-o-toluidine, Diethathyl-ethyl, Benzoylprop-ethyl, Propachlor, Propachlor, 2,4,5-Trichlorophenoxyacetic acid, 2,4,5,T; Weedone, 2,4-Dichlorophenoxybutyric acid (2,4-DB), 2,4-DB; Butanoic acid, 4-(2,4-dichlorophenoxy)-; Butoxone; Embutone, MCPA, 2-Methyl-4-chlorophenoxyacetic acid; Metaxon, Dichlorprop (2,4-DP), 1-[(2-chloro)phenylsulfonyl]monoamidosuccinic acid, Chlorsulfuron, chlorbromuron, amidosulfuron, chlortoluron, isoproturon, diuron, Linuron O-Methyl-O-(4-nitrophenyl)-N-(4-carboxybutyl)-phosphoramidothioate Parathion-methyl, O,O-dimethyl O-4-nitrophenyl phosphorothioate; Methaphos; Wolfatox; Dimethylparathion; Metacide, Parathion-ethyl, DIETHYL P-NITROPHENYL THIOPHOSPHATE; O,O-DIETHYL O—(P-NITROPHENYL) PHOSPHOROTHIOATE; Fenitrothion, O,O-dimetyl O-4-nitro-m-tolyl phosphorothioate, Fenthion, O,O-dimethyl O-4-methylthio-m-tolyl phosphorothioate, Bromophos, O-4-bromo-2,5-dichlorophenyl O,O-dimethyl phosphorothioate, chlorpyrifos-methyl, O,O-dimethyl O-3,5,6-trichloro-2-pyridyl phosphorothioate, Oxidized parathion-methyl, Paraoxon, phosphoric acid, O,O-diethyl O-(4-nitrophenyl) ester, Diazinon, O,O-diethyl O-2-isopropyl-6-methylpyrimidin-4-yl phosphorothioate, Azinphos-methyl, pirimiphos-methyl, O-2-diethylamino-6-methylpyrimidin-4-yl O,O-dimethyl phosphorothioate, Methidathion, S-2,3-dihydro-5-methoxy-2-oxo-1,3,4-thiadiazol-3-ylmethyl O,O-dimethyl phosphorodithioate, Dimethylchlorothiophosphate, 4-NITROPHENOL, p-nitrophenol, Phenolic derivative (Modification On benzene ring; R1=OH R2=NO2 R3=H R4-CH2COOH R5=H R6=H); 2-Nitrophenol, o-Nitrophenol, 3-Nitrophenol, m-nitrophenol, 2,4-Dinitrophenol, 3,4-Dinitrophenol, 2,5-Dinitrophenol, 2,4-Dinitro-6-methylphenol, 2,3,6-trinitrophenol, 2-Chlorophenol, 4-Chloro-3-methylphenol, Fenitroxon, 3-Methyl-4-nitrophenol, Nonylphenol, HOM(3-[2-hydroxy-5nitro benzylthio] propionic acid, Phenol, Delor 103, Polychlorinated Biphenyls, Delor 104, Polychlorinated Biphenyls, Delor 105, Polychlorinated Biphenyls, Delor 106, 4,4'-Dichlorobiphenyl, PCB congeners, 2,4,4'-Trichlorobiphenyl, PCB congeners, 2,4'-Bichlorobiphenyl, PCB congeners, 2,2'-Dichlorobiphenyl, PCB congeners, 2,4,5-Trichlorobiphenyl, PCB congeners, 3,3',4,4'-Tetrachlorobiphenyl, PCB congeners, PCB congeners, 2,2',4,4',5,5'-Hexachlorobiphenyl, 2-(5-Carboxypentanoylamino)-4,4'-dichlorobiphenyl, Biphenyl derivative, 4-chlorophenoxyacetic acid, 2-Chlorophenoxyacetic acid, DDT,1,1,1-trichloro-2, 2-bis-(p-chlorophenyl)ethane, DDE, 1,1-dichloro-2, 2-bis(p-chlorophenyl)ethylene, p-Chlorophenol, 4-Chlorophenol, m-Chlorophenol 3,4-Dichlorophenol, 3,5-Dichlorophenol, 2,3,4-Trichlorophenol, 2,3,5-Trichlorophenol, 3-methylindole, 3-methylindole Derivatives, 4-(3-methylindol-5-yloxy)butanoic acid, 4-(3-methylindol-5-yloxy)butanoic acid, 3-methylindole Derivatives, 6-[n-3-methylindol-5-yloxy carbonyl)amino]hexanoic acid, 6-[n-3-methylindol-5-yloxy carbonyl)amino]hexanoic acid, 3-methylindole Derivatives, 2-[4-(3-methylindol-6-yl)but-1-ylthio]acetic acid, 2-[4-(3-methylindol-6-yl)but-1-ylthio]acetic acid, 3-methylindole Derivatives, 4-(3-methylindol-6-yl-4-oxo) butanoic acid, 4-(3-methylindol-6-yl-4-oxo)butanoic acid, 3-methylindole Derivatives, 6-(3-methylindol-7-yloxy) hexanoic acid, 6-(3-methylindol-7-yloxy)hexanoic acid, Indole, Indole-3-Carboxylic acid, Indole Derivative-Indole-3-Acetic acid, Indole-3-Acetic acid, Indole Derivative-Indole-3-Propionic acid, Indole-3-Propionic acid, Indole Derivative-Indole-3-Carbinol, Indole-3-Carbinol, Tryptophan, Tryptamine, 5-Methoxyindole-3-carboxaldehyde, 5-Methoxytryptamine, 5-Methoxyindole, 6-Methoxyindole, 7-Methoxyindole,EB1089(Seocalcitol),EB1089(Seocalcitol) Derivative, (22E,24E)-Des-A,B-24-homo-26,27-dimethyl-8-[(E)-N-(2-carboxyethyl)-carbamoylmethylidene]-cholesta-22,24-dien-25-ol, 1 alpha-25-dihydroxyvitamin D3, 25(OH)D3,25-hydroxyvitamin D3,24R,25(OH)2D3, 24R,25-dihydroxyvitamin D3, Vitamin D2, ergocalciferol, Vitamin D3, cholecalciferol,EB1446,EB1436,EB1445, EB1470, DeethylHydroxyAtrazine (DEHA) (Structurally related s-triazines), Irgarol 1051, Flourescein Isothiocyanate, FITC, Metanephrine, NorMetanephrine, Propazine, Terbutylazine, Terbuthylazine, 6-chloro-N-(1,1-dimethylethyl)-N'-ethyl-1,3,5-triazine-2,4-diamine, (Structurally related s-triazines), Ametryn (2-Ethylamino-4-isopropylamino-6-methylthio-1,3,5-triazine (Modification iPr/SCH3/Et R1=(CH3)2-CH—NH— R2=—SCH3 R3=—NH—CH2-CH3, Irgarol, Cyanazine (Modification R1=Cl R2=NHCH2CH3 R3=NHCCN(CH3)2), OH-Terbutylazine, Terbutylazine-2OH, Hydroxytriazine (EQ-0027), Deisopropylatrazine (Structurally related S-triazine), Desethylterbutylazine (Structurally related S-triazine), Desethyl-deisopropylatrazine (Structurally related S-triazine), Atraton, Terbutryn (Structurally related s-triazines), Atrazine derivative (Modification R1=—NHCH(CH3)2 R2=—S(CH2)2COOH R3=—NHC2H5), Cyanuric chloride, Trifluralin, (Structurally related s-triazines) tBu/C4/SCH3 (Modification R1=—NH—C—(CH3)3 R2=—NH(CH2) 3COOH R3=—SCH3), Sulphamethazine, (Structurally related s-triazines) 6-[[[4-Chloro-6-(methylamino)]-1,3,5-triazin-2-yl]amino]hexanoic Acid (Modification Me/Cl/C6 R1=—NHCH3 R2=—Cl R3=—NH(CH2)5COOH), (Structurally related s-triazines) Procyazine (Modification R1=—Cl R2=—NHcyclopropyl R3=—NHCCN(CH3)2), (Structurally related s-triazines), Prometon (Modification R1=—OCH3 R2=—NHCH(CH3)2 R3=—NHCH(CH3)2); (Structurally related s-triazines) Atrazine Mercapturic Acid (AM) (Modification R1=—SCH2CH(NHAc)COOH R2=—NHCH2CH3 R3=—NHCH(CH3)2), (Structurally related s-triazines), desethyl atrazine mercapturic acid (desethyl AM) (Modification R1=—NAcCys R2=—NH2 R3=—NHCH(CH3)2), (Structurally related s-triazines), deisopropyl atrazine mercapturic acid (deisopropyl AM) (Modification R1=—NAcCys R2=—NHCH2CH3 R3=—NH2), (Structurally related s-triazines), didealkylated atrazine mercapturic acid (didealkylated AM) (Modification R1=—NAcCys R2=—NH2 R3=—NH2), (Structurally related s-triazines), simazine mercapturate (Modification R1=—NAcCys R2=—NHCH2CH3 R3=—NHCH2CH3), (Structurally related s-triazines) (Modification R1=—S(CH2)2COOH R2=—NHCH2CH3 R3=—NHCH2CH3), (Structurally related s-triazines) (Modification R1=—Cl R2=—NHCH(CH3)2 R3=—NH (CH2)2COOH), (Structurally related s-triazines) (Modification R1═—Cl R2═—NHCH2CH3 R3═—NH(CH2) 2COOH), (Structurally related s-triazines), atrazine mercapturic acid methyl ester (AM methyl ester) (Modification R1═—NAcCysME R2═—NHCH2CH3 R3═—NHCH(CH3)2), N-acetylcysteine, S-benzyl mercapturate, (Structurally related s-triazines), simetryn (Modification R1═—SCH3 R2═—NHCH2CH3 R3═— NHCH2CH3), Metribuzin, 4-amino-6-tert-butyl-4,5-dihydro-3-methylthio-1,2,4-triazin-5-one, Sulpha Drugs, N4-acetyl-sulphamethazine (Modification N4-acetyl-sulphamethazine), Sulpha Drugs, Sulphathiazole, Sulphathiazole, Sulphamerazine, Sulphamerazine, Sulphaquinoxaline, Sulphaquinoxaline Sulphachlorpyridazine, Sulphachlorpyridazine, Sulphapyridine, Sulphadimethoxine, Sulphadimethoxine, Sulphamethoxazole, Sulphamethoxazole, Sulphisoxazole, Sulphisoxazole, Sulphamethizole, Sulphamethizole, Sulphanilamide, Sulphanilamide, Sulphaguanidine, Sulphaguanidine, Sulphadiazine, Sulphadiazine, Sulphamethoxypyridazine, Sulphamethoxypyridazine, Pentachlorophenoxypropionic acid, Pentachlorophenol, PCP, 2,3,5,6-Tetrachlorophenol, 1,2,4,5 Tetrachlorobenzene, 2,4,6 Trichlorophenol, 2-Methoxy-3,5,6-trichloropyridine, 1,3,5 Trichlorobenzene, 1,3 Dichlorobenzene, 2,4,5-Trichlorophenol, 2,6-Dichlorophenol, 3,5,6-Trichloro-2-pyridinoxyacetic acid, 3,5,6-Trichloro-2-Pyridinol, TCP, 2,4-Dichlorophenol, 2,5-Dichlorophenol, DNC, 4,4'-dinitrocarbanilide, (Structurally related s-triazines), Dichloroatrazine, (Structurally related s-triazines), Dichlorosimazine, 1-((6-chloropyridin-3-yl)methyl)imidazolidin-2-imin, Pyridine Derivative, 6-chloropyridine-3-carboxylic acid, Nicotinic acid, Pyridine Derivative, N-((6-chloropyridin-3-yl) methyl)-N-methylacetamide, (6-chloropyridin-3-yl)-N-methylmethanamine, (6-chloropyridin-3-yl)methanol, Imidacloprid, 1-(6-chloro-3-pyridylmethyl)-N-nitroimidazolidin-2-ylideneamine, Acetamiprid, (E)-N1-[(6-chloro-3-pyridyl)methyl]-N2-cyano-N1-methylacetamidine, Nitenpyram, Deltamethrin, 1(R)-cis-alpha (S)-3-(2,2-dibromoethenyl)-2,2-dimethylcyclopropane carboxylic acid cyano(3-phenoxyphenyl)methyl ester, DON, deoxynivalenol, DON derivative, 15-AcDON (15-acetyldeoxynivalenol), DON derivative, 3-AcDON (3-acetyldeoxynivalenol), DON derivative, 3,15-DiacDON (3,15-diacetyldeoxynivalenol), DON derivative, 3,7,15-TriacDON (3,7,15-Triacetyldeoxynivalenol), NIV (nivalenol), nivalenol, NIV Derivative, 4-AcNIV (fusarenon X), Flutolanil, alpha,alpha, alpha-trifluoro-3'-isopropoxy-o-toluanilide, Mepronil, Mebenil, Benodanil, 24,25(OH)2D3, (24R)-24,25-dihydroxyvitamin D3, 24S,25(OH)2D3, 24S,25-dihydroxyvitamin D3, 25R,26(OH)2D3, 25R,26-dihydroxyvitamin D3, 25S,26(OH)2D3, 25S,26-dihydroxyvitamin D3, 1,24,25 (OH)3D3, 1,24,25-trihydroxyvitamin D3, 1,25-lactone, (23S,25R)-1,25(OH)2 D3 26,23-lactone, 24,25(OH)2-7-DHC, 24,25(OH)2-7-dehydrocholesterol, 25(OH)D3 3S, 25(OH)D3 3-sulfate, 24,25(OH)2D3-Hemiglutarate Derivative, 11 alpha-hemiglutaryloxy-(24R)-24,25-dihydroxyvitamin D3, 24,25(OH)2D3-Hemiglutarate Derivative, (24R)-24,25-dihydroxyvitaminD3-3-hemiglutarate, 24R,25(OH) 2D2, 24S,25(OH)2D2, 25(OH)D2, 1,24(OH)2D3, 2,3,6-Trichlorophenol, Tetrachlorohydroquinone, Pentachloroaniline, Pentachlorobenzene, 2,3-Dinitrotoluene, 4-Dinitrotoluene, 2,4,5-Trichloronitrobenzene, 3-(3-Hydroxy-2,4,6-trichlorophenyl)-propanoic acid, 2,3,4,6-Tetrachlorophenol, 2,4,6-Trichloroanisol, 2,4,6-TCA, Pentabromophenol, PBP, 2,4,6-Tribromophenol, 2,4,6-TBP, 2-Bromo-4-Chlorophenol, 2-B-4-CP 2,4-Dibromophenol, 2,4-DBP, 2,6-Dibromophenol, 2,6-DBP, 4-Bromophenol, 4-BP, Furosemide, Ampicillin, Amoxicillin, 6-amino-penicillanic acid (6-APA), Azlocillin, Bacampicillin, Carbenicillin, Epicillin, Cloxacillin, Dicloxacillin, Metampicillin, Methicillin, Moxalactam, Oxacillin, Penicillin G, benzyl penicillin, Penicillin V, phenoxy methyl penicillin, Pheneticillin, Piperacillin, Ticarcillin, Ampicillin hydrolyzed, Penicillin G hydrolyzed, 3-phenoxybenzoic acid (3-PBAc) Chlorpyrifos, Chlorpyrifos derivatives, HClo1, Synthesized directly from chlorpyrifos technical grade by substitution of the chlorine in position 6 by a 3-mercaptopropanoic acid spacer arm, Chlorpyrifos derivatives, HTCP (Modification HTCP of TCP metabolite was prepared from HClo1 by hydrolysis of the thiophosphate ester), Zeatin Riboside (trans isomer), Zeatin (trans isomer), N6-(2-isopentenyl)-adenosine, IPA, N6-(2-isopentenyl)-adenine, 2-iP, Benzyladenine, Kinetin, monuron, monolinuron, fenuron, neburon, propanil, propham, chloropropham, 4-chloroaniline, Methyl Urea Derivative, 1-(3-Carboxypropyl)-3-(4-chlorophenyl)-1-methylurea, Methyl Urea Derivative, 1-(5-Carboxypentyl)-3-(4-chlorophenyl)-1-methylurea, metobromuron, Sennoside B, SB, Sennoside B possessed a erythro configuration between C-10 and C-10', Sennoside A (Modification Sennoside A possessed a threo configuration between C-10 and C-10'), Rhein, Emodin, Aloe-emodin, Barbaloin, 1,4 Dihydroxyanthraquinone, Rhaponticin, Galic acid, Vanillic acid, Caffeic acid, Homogentisic acid, Esculin, Cinnamtannin B1, Baicalin, Naringin hydrate, Wogonin, Wogonin 7-o-beta-glucuronide, Curcumin, delta1-Tetrahydrocannabinolic acid, delta1-Tetrahydrocannabinol, (+−)-cis-4-Aminopermethrin, 3-(4-Aminophenoxy)benzyl(+−)-cis-3-(2,2-dichloroethenyl)-2,2-dimethylcyclopropanecarboxylate, Permethrin, trans-Permethrin, cis-Permethrin, Cypermethrin, Phenothrin, Resmethrin, Cyfluthrin, trans-Permethrin acid Esfenvalerate, Fluvalinate, Fenpropathrin, cis-permethrin acid, 4-Phenoxybenzoyl alcohol, Diuron Derivative, 1-(3-Carboxypropyl)-3-(3,4-dichlorophenyl)-1-methylurea, Siduron, Terbuthiuron, Barban, acid trifluralin, 2,6-dinitro-N-propyl-N-(2-carboxyethyl)-4-(trifluoromethyl)benzenamine, TR-13, 2-ethyl-7-nitro-1-propyl-5-(trifluoromethyl)-1H-benzimidazole, benefin, 2,6-dinitro-N-butyl-N-ethyl-4-(trifluoromethyl)benzenamine, TR-2, 2,6-dinitro-N-propyl-4-(trifluoromethyl)benzenamine, ethalfluaralin, 2,6-dinitro-N-ethyl-N-(2-methyl-2-propenyl)-4-(trifluoromethyl) benzenamine, TR-40, N-(2,6-dinitro-4-(trifluoromethyl) phenyl)-N-propylpropanamide, TR-15, 2-ethyl-4-nitro-6-(trifluoromethyl)-1H-benzimidazole, TR-3, 2,6-dinitro-4-(trifluoromethyl)benzenamine, TR-6, 3-nitro-5-(trifluoromethyl)-1,2-benzenediamine, TR-9, 5-(trifluoromethyl)-1,2,3-benzenetriamine, TR-21, 4-(dipropylamino)-3,5-dinitrobenzoic acid, TR-36M, 3-methoxy-2, 6-dinitro-N,N-dipropyl-4-(trifluoromethyl)benzenamine, oryzalin, 3,5-dinitro-4-(dipropylamino)benzenesulfonamide, pendimethalin, 2,6-dinitro-N-(1-ethylpropyl)-3,4-dimethylbenzenamine, penta galloyl glucose, Pyrene Pyrene-1-carboxaldehyde, Phenanthrene, Benzo(a)pyrene, 3,4-Benzopyrene, Anthracene, 3,4-Benzopyrene, Acenaphthene, Fluorene, Chrysene, 1,2-Benzphenanthrene, Benzo[g,h,i]perylene, Benzo[e]pyrene, Acenaphthylene, Fluoranthene, Benzo(j,k)fluorene, Indeno-1,2,3-cd-pyrene, 1,10-(1,2-Phenylene)pyrene, Benzo[a]anthracene, 1,2-Benzanthracene, Benzo(k)fluoranthene, Naphthalene, Benzo[a]fluoranthene, Dibenzo[ah]anthracene, 1,2:5,6-Dibenzanthracene, 2,3-Diaminonaphthalene, 2,6-Dinitroaniline, 17-beta-estradiol (ED), estra-1,3,5(10)-triene-3,17-beta-diol, Trifluralin derivative, 2,6-dinitro-4-tri-fluoromethylaniline, Trifluralin derivative, N-(2,6-dinitro-4-trifluoromethylphenyl)-6-aminohexanoic acid, Trifluralin derivative, N-(2,6-dinitro-4-trifluoromethylphenyl)-N-methyl-6-aminohexanoic acid, Trifluralin derivative, N-(2,6-dinitro-4-trifluoromethylphenyl)-N-propyl-6-aminohexanoic acid, Trifluralin derivative, N-(2,6-dinitro-4-trifluoromethylphenyl)-6-aminohexanoic acid methyl ester, Trifluralin derivative, N-(2,6-dinitro-4-trifluoromethylphenyl)-6-aminohexanoic acid tert-butyl ester, Benfluralin, Ethalfluralin, Trifluralin derivative, 2,6-Dinitro-4-trifluoromethylphenol, Isopropalin, Aniline, 2-Hydroxybenzotrifluoride, N-propyl-6-aminohexanoic acid, N-methyl-6-aminohexanoic acid, MHPG Derivatives, D-MHPG (D-3-methoxy-4-hydroxyphenylglycol), MHPG Derivatives, L-MHPG (L-3-methoxy-4-hydroxyphenylglycol), MHPG Derivatives, DL-MHPG (DL-3-methoxy-4-hydroxyphenylglycol), Isomeric mixture of D-MHPG and L-MHPG forms, MHPG Derivatives, DL-MHPG-SO4 (DL-3-methoxy-4-hydroxyphenylglycol-sulfate) Modification can include Isomeric mixture of D-MHPG-SO4 and L-MHPG-SO4 forms, Serotonin, 5-HT, 5-hydroxydopamine (5-4HDA), 3,4-dihydroxyphenylglycol (DOPEG), Dopamine, 4-(2-aminoethyl)pyrocatechol; 3-hydroxytyramine; 3,4-dihydroxyphenethylamine; L-3,4-dihydroxyphenylalanine, L-DOPA, Vanillomandelic acid, DL-VMA, Homovanillic acid, Norepinephrine, DL-NE, D-Epinephrine, D-E, 3-methoxytyramine, MTA, 3-methoxytyramine, MTyr, 3,4-dihydroxymandelic acid, DL-DOMA, 3,4-dihydroxyphenyl acetic acid, DOPAC, L-Phenylalanine, Tyramine, p-tyramine; 4-(2-Aminoethyl)phenol, D-Mandelic acid, Homocatechol, Octopamine, DL-Octopamine, Azinphos-Ethyl, S-(3,4-dihydro-4-oxobenzo[d]-[1,2,3]-triazin-3-ylmethyl) O,O-diethyl phosphorodithioate, Phosmet, O,O-dimethyl S-phthalimidomethyl phosphorodithioate, Folpet, N-[(Trichloromethyl)thio]phthalimide, Tetramethrin, (1-Cyclohexene-1,2-dicarboximido)methyl-2,2-dimethyl-3-(2-methylpropenyl)-cyclopropanecarboxylate, N-(bromomethyl)phthalimide, N-(Chloromethyl)benzazimide, 6-(N-phthalimidoylmethylthio)hexanoic acid (MFH), Bromacil, 5-bromo-3-sec-butyl-6-methyluracil, Bromacil Derivative, 5-bromo-6-(hydroxymethyl)-3-(1-methylpropyl)-2,4(1H,3H)-pyrimidineone, Bromacil Derivative, 5-bromo-3-(2-methylpropyl-6-methyl-2,4(1H,3H)-pyrimidinedione, Metabolite of Bromacil, Bromacil Derivative, 3-hydroxy-1-methylpropyl-6-methyl-2,4(1H,3H)-pyrimidinedione (Modification Bromacil Metabolite), Bromacil Derivative, 6-methyl-3-(1-methylpropyl)-2,4(1H,3H)-pyrimidinedione (Modification Bromacil Metabolite), Terbacil Derivative, [5-chloro-3-(1,1-dimethylethyl)-6-(hydroxymethyl)-2,4 (1H,3H)-pyrimidinedione, Terbacil, 3-tert-butyl-5-chloro-6-methyluracil, Bromacil Derivative, Ethyl-5-(5-Bromo-6-methyl-3-(1-methylpropyl)-2,4(1H,3H)-pyrimidinedione-1-yl)hexanoate, Bromacil Derivative alkylated at N-1, Bromacil Derivative 5-(5-Bromo-6-methyl-3-(1-methylpropyl)-2,4(1H,3H)-pyrimidinedione-1-yl)hexanoic Acid (Modification Bromacil Derivative alkylated at N-1), Bromacil Derivative, -Bromo-6-(Bromomethyl-3-(1-methylpropyl)-2,4(1H,3H)-pyrimidinedione (Modification Bromacil Derivative substituted at the 6-methyl position), Bromacil Derivative-[5-Bromo-3-(1-methylpropyl)-2,4(1H,3H)-pyrimidinedione-6-yl]-2-carboxylpropanoic Acid (Modification Bromacil Derivative substituted at the 6-methyl position), 3-[5-Bromo-3-(1-methylpropyl)-2,4 (1H,3H)-pyrimidinedione-6-yl]propanoic Acid (Modification Bromacil Derivative substituted at the 6-methyl position), Bromacil Derivative 5-Bromo-1,6-dimethyl-3-(1-methylpropyl)-2,4(1H,3H)-pyrimidinedione, Bromacil Derivative 5-Bromo-1-butyl-6-methyl-3-(1-methylpropyl)-2,4(1H,3H)-pyrimidinedione, Butachlor, N-butoxymethyl-2-chloro-2',6'-diethylacetanilide, Amidochlor, N-[(acetylamino)methyl]-2-chloro-N-(2,6-diethylpenyl)acetamide, Nicarbazin, N,N'-bis(4-nitrophenyl)-compound with 4,6-dimethyl-2(1H)-pyrimidinone (Modification (DNC+HDP)), 2-hydroxy-4,6-dimethylpyrimidine, HDP, Imazalil, [1-(beta-allyloxy-2,4-dichlorophenethyl)imidazole], Imazalil Derivative, EIT-0073 (Modification Have a —O(CH2)5-COOH group instead of original —OCH2CH—CH2 group of imazalil), Penconazole, (RS)-1-(2,4-dichloro-β-propylphenethyl)-1H-1,2,4-triazole, Hexaconazole, (RS)-2-(2,4-dichlorophenyl)-1-(1H-1,2,4-triazol-1-yl)hexan-2-ol, Propiconazole, cis-trans-1-[2-(2,4-dichlorophenyl)-4-propyl-1,3-dioxolan-2-ylmethyl]-1H-1,2,4-triazole, Diclobutrazol, 2RS,3RS)-1-(2,4-dichlorophenyl)-4,4-dimethyl-2-(1H-1,2,4-triazol-1-yl)pentan-3-ol, Triflumizole, (E)-4-chloro-α,α,α-trifluoro-N-(1-imidazol-1-yl-2-propoxyethylidene)-o-toluidine, Imazalil Derivative, EIT-0183, Imazalil Derivative, EIT-0180, Imazalil Derivative, EIT-0111, Imazalil Derivative, EIT-0158, Imazalil Derivative, K-240, Chlorothalonil, tetrachloroisophthalonitrile Modification On benzene Ring R1=CN R2=Cl R3=CN R4=Cl R5=Cl R6=Cl), Chlorothalonil Derivative-2,4,5,6-tetrachloro-3-cyanobenzamide (Modification On benzene Ring R1=CONH2 R2=Cl R3=CN R4=Cl R5=Cl R6=Cl), Chlorothalonil Derivative-2,5,6-trichloro-4-hydroxyisophthalonitrile (Modification On benzene Ring R1=CN R2=Cl R3=CN R4=OH R5=Cl R6=Cl), 3-carbamyl-2,4,5-trichlorobenzoic acid (Modification On benzene Ring R1=CONH2 R2=Cl R3=COOH R4=H R5=Cl R6=Cl), Pentachloronitrobenzene (Modification On benzene Ring R1=NO2 R2=Cl R3=Cl R4=Cl R5=Cl R6=Cl), Benzene hexachloride, Hexachlorobenzene, BHC, Lindane (Modification On benzene Ring R1=Cl R2=Cl R3=Cl R4=Cl R5=Cl R6=Cl), 2,4,5,6-tetrachlorophenol (Modification On benzene Ring R1=OH R2=Cl R3=H R4=Cl R5=Cl R6=Cl), Carbaryl Derivative, Ethylcarbamate (Modification R1=OCONHCH2CH3 R3=H), 1-Naphthol, 1-naphthaleneacetamide, -(1-naphthyl) acetamide, Carbaryl Derivative, 1-Methylcarbonate (Modification R1=OCOOCH3 R2=H, Carbaryl Derivative, 1-Ethylcarbonate (Modification R1=OCOOCH2CH3 R2=H), Carbaryl Derivative 2-Ethylcarbonate (Modification R1=H R2=OCOOCH2CH3, Carbaryl Derivative, 1-Ethylthiocarbonate (Modification R1=OCOSCH2CH3 R2=H), Carbaryl Derivative, 2-Ethylthiocarbonate (Modification R1=H R2=OCOSCH2CH3), Naptalam, N-1-naphthylphthalamic acid, Carbaryl Derivative, 3-hydroxycarbaryl (Modification R1=OCONHCH3 R2=H R3=OH R4=H R5=H), Carbaryl Derivative 4-hydroxycarbaryl (Modification R1=OCONHCH3 R2=H R3=H R4=OH R5=H), Carbaryl Derivative 5-hydroxycarbaryl (Modification R1=OCONHCH3 R2=H R3=H R4=H R5=OH), Carbaryl Derivative, 1-(5-Carboxypentyl)-3-(1-naphthyl)urea (Modification R1=NHCONH(CH2)5COOH R2=H), (Structurally related s-triazines)-Aziprotryn, 4-azido-N-isopropyl-6-methylthio-1,3,5-triazin-2-ylamine (Modification R1=—SCH3 R2=—N3 R3=—CH(CH3)2), (Structurally related s-triazines), 2-(ethylamino)-4-(methylthio)-6-aminotriazine (Modification R1=—SCH3 R2=—NH—C2H5 R3=—NH2), (Structurally related s-triazines)-2-amino-4-(methylthio)-6-(isopropylamino)triazine (Modification R1=—SCH3 R2=—NH2 R3=—NH—CH(CH3)2), (Structurally related s-triazines)-2-amino-4-methoxy-6-(isopropylamino)triazine (Modification R1=—OCH3 R2=—NH2 R3=—NH—CH(CH3)2), TCP Derivative (3,5,6-trichloro-2-pyridinol Derivative), 3-(3,5-dichloro-6-hydroxy-2-pyridyl)thiopropanoic Acid, p-nitrosuccinanilic acid (PNA-S), PNA-S, PNA-C, p-nitro-cis-1,2- cyclohexanedicarboxanilic acid, Nitroaniline Derivative, 2-nitroaniline, o-Nitroaniline, Nitroaniline Derivative-3-nitroaniline, m-Nitroaniline, Nitroaniline Derivative-4-nitroaniline, p-Nitroaniline, Aeromatic Alcohols, 4-nitrobenzyl alcohol, Aeromatic Alcohols-4-nitrophenethyl alcohol, Aeromatic Alcohols 2-nitrobenzyl alcohol, Aeromatic Alcohols, 3-nitrobenzyl alcohol, Urea Derivative-1-benzyl-3-(4-nitrophenyl)urea, Urea Derivative-1-(3-chlorophenyl)-3-(2-methoxy-5-nitrophenyl)urea, Urea Derivative-1-(3-chlorophenyl)-3-(4-methoxy-3-nitrophenyl)urea, Urea Derivative-1-(4-chlorophenyl)-3-(4-nitrophenyl)urea, Urea Derivative-(2-fluorophenyl)-3-(2-mehtoxy-4-nitrophenyl) urea, 1-(3-mehtoxyphenyl)-3-(3-nitrophenyl)urea, Carbofuran Derivative m Carbofuran-phenol, Carbofuran-hydroxy, Carbofuran-keto, Carbosulfan, 3-dihydro-2,2-dimethylbenzofuran-7-yl (dibutylaminothio) methylcarbamate, Benfuracarb, N-[2,3-dihydro-2,2-dimethylbenzofuran-7-yloxycarbonyl(methyl)aminothio]-N-isopropyl-β-alaninate, Furathiocarb, 2,3-dihydro-2,2-dimethyl-7-benzofuranyl 2,4-dimethyl-5-oxo-6-oxa-3-thia-2,4-diazadecanoate, Carbofuran Derivative, 4-[[(2,3-Dihydro-2,2-dimethyl-7-benzofuranyloxy)carbonyl]-amino]butanoic Acid (BFNB) (Modification n=3 X=CH2), Endrin, nendrin, (1R,4S,4aS,5S,6S,7R,8R,8aR)-1,2,3,4,10,10-hexachloro-1,4,4a,5,6,7,8,8a-octahydro-6,7-epoxy-1,4: 5,8-dimethanonaphthalene, Heptachlor, 1,4,5,6,7,8,8-heptachloro-3a,4,7,7a-tetrahydro-4,7-, Chlordane, 1,2,4,5,6,7,8, 8-octachloro-2,3,3a,4,7,7a-hexahydro-4,7-methanoindene, Endosulfan (Modification isomer mix of alpha and beta forms), Endosulfan (Modification alpha isomeric form), Endosulfan (Modification beta isomeric form), Endosulfan Derivative, Endosulfan sulfate (Modification sulfate form), Endosulfan Derivative, Endosulfan diol, Diol metabolite of endosulfan, Endosulfan Derivative, Endosulfan ether (Modification ether metabolite of endosulfan), Endosulfan Derivative, hydroxy ether, hydroxy ether metabolite of endosulfan, Endosulfan Derivative, Endosulfan lactone (Modification lactone metabolite of endosulfan), Aldrin, Dieldrin, Fenvalerate isomers Modification 1S,2R isomer R: Ph), Fenvalerate isomers (Modification 1R,2S isomer R: Ph), Fenvalerate isomers (Modification 1R,2R isomer R: Ph), Fenvalerate isomers (Modification 1S,2R/S isomer R: Ph), Fenvalerate isomers (Modification 1R,2R/S isomer R: Ph), Fenvalerate isomers, fenvalerate (Modification 1R/S, 2R/S isomer R: Ph), Thiabendazole, 2-(thiazol-4-yl)benzimidazole, Thiabendazole Derivative, 5-hydroxythiabendazole (Modification 5-OH-TBZ), Thiabendazole Derivative, 5-NH2-TBZ, Thiabendazole Derivative, methyl benzimidazole carbamate, Albendazole, Mebendazole, Fenbendazole, Thiabendazole Derivative, 2-succinamidothiabendazole, Thiabendazole Derivative, 2-succinamidothiabendazole, Cambendazole, Fenvalerate Haptens, Cyano[3-(4-aminophenoxy)phenyl]methyl (S)-4-Chloro-alpha-(1-methylethyl)benzeneacetate (4-Aminoesfenvalerate), Fenvalerate Haptens, Benzyl 4-[3-[Cyano[(S)-2-(4-chlorophenyl)-3-methyl-1-oxobutanoxy]methyl]]phenoxy]benzenepropanoate, Fenvalerate Haptens, Benzyl 3-[Cyano[(S)-2-(4-chlorophenyl)-3-methyl-1-oxobutanoxy]methyl]]phenoxyacetate, Fenvalerate Haptens, 3-[Cyano[(S)-2-(4-chlorophenyl)-3-methyl-1-oxobutanoxy]methyl]]phenoxyacetic Acid, Fenvalerate Haptens, Benzyl 6-[3-[Cyano[(S)-2-(4-chlorophenyl)-3-methyl-1-oxobutanoxy]methyl]]phenoxy] hexanoate, Fenvalerate Haptens, 6-[3-[Cyano[(S)-2-(4-chlorophenyl)-3-methyl-1-oxobutanoxy]methyl]]phenoxy] hexanoic Acid Fenvalerate Haptens, 4-[3-[Cyano[(S)-2-(4-chlorophenyl)-3-methyl-1-oxobutanoxy]methyl]]phenoxy] benzenepropanoic Acid, (S)-fenvalerate Acid, (Structurally related s-triazines), atrazine mercapturate Modification R1=—SCH2CH(NHCOCH3)COOH R2=—NHCH2CH3 R3=—NHCH(CH3)2, Fenthion Hapten, -Methyl O-[3-methyl-4-(methylthio)phenyl] N-(3-carboxypropyl)phosphoramidothioate Modification referred as Hapten B, Fenthion Derivative, Oxidized Fenthion, Fenthion Derivative, Oxidized oxidized Fenthion, pirimiphos-ethyl, 4-(Methylthio)-m-cresol, Chlorpyrifos Derivative, Chlorpyrifos-oxon, Fenchlorphos, O,O-dimethyl O-2,4,5-trichlorophenyl phosphorothioate, Trichloronate, O-Ethyl O-2,4,5-trichlorophenyl ethyl-phosphonothioate, Dichlofenthion, O-2,4-dichlorophenyl O,O-diethyl phosphorothioate, Parathion, O,O-diethyl O-4-nitrophenyl phosphorothioate; Thiophos, Chlorpyrifos Derivative Modification Synthesis of AR1 is described, Chlorpyrifos Derivative, O-Ethyl O-(3,5,6-Trichloro-2-pyridyl)O-(3-Carboxypropyl)Phosphorothioate; (PO), Chlorpyrifos Derivative-O-Ethyl O-(3,5,6-Trichloro-2-pyridyl)N-(5-Carboxyethyl) Phosphoramidothioate; (PN1) (Modification Amide linkage of thiophosphate reagents), Chlorpyrifos Derivative, O-Ethyl O-(3,5,6-Trichloro-2-pyridyl)N-(2-Carboxyethyl) Phosphoramidothioate; (PN1) (Modification Amide linkage of suitable thiophosphate reagents), Triadimefon, (RS)-1-(4-chlorophenoxy)-3,3-dimethyl-1-(1H-1,2,4-triazol-1-yl)butan-2-one, GR151004, (4-[[5-[3-[2-(dimethylamino)ethyl]]-5-benzofuranyl]-3-pyridinyl]acetyl]morpholine dihydrochloride, Diflubenzuron, 1-(4-chlorophenyl)-3-(2,6-difluorobenzoyl)urea, (Structurally related s-triazines)-SprAAT (Modification R1=SCH2CH2COOH R2=NH2 R3=NH2), (Structurally related s-triazines), SBeAAT (Modification R1=S(C6H4)COOH R2=NH2 R3=NH2), (Structurally related s-triazines), SAAT (Modification R1=SH R2=NH2 R3=NH2), (Structurally related s-triazines), CDAT (Modification R1=Cl R2=NH[C(O)CH3] R3=NH2), (Structurally related s-triazines)-CDET (Modification R1=Cl R2=NH[C(O)CH3] R3=NH(CH2CH3), (Structurally related s-triazines)-CDIT (Modification R1=Cl R2=NH[C(O)CH3] R3=NH(CH(CH3)2)), (Structurally related s-triazines), CDDT (Modification R1=Cl R2=NH[C(O)CH3] R3=NH[C(O)CH3]), (Structurally related s-triazines)-ammeline, OAAT (Modification R1=OH R2=NH2 R3=NH2), (Structurally related s-triazines)-ammelide, OOAT (Modification R1=OH R2=OH R3=NH2), (Structurally related s-triazines)-cyanuric acid, OOOT (Modification R1=OH R2=OH R3=OH), (Structurally related s-triazines), melamine, AAAT (Modification R1=NH2 R2=NH2 R3=NH2), Structurally related s-triazines-N-isoropylammeline, OIAT (Modification R1=OH R2=NH[CH(CH3)2] R3=NH2, Structurally related s-triazines-N-ethylammeline, OEAT (Modification R1=OH R2=NHCH2CH3 R3=NH2), Structurally related s-triazines, N-ethylammelide, OOET (Modification R1=OH R2=OH R3=NHCH2CH3), Structurally related s-triazines)-cyromazine, CyPAAT (Modification R1=NH(C3H5) R2=NH2 R3=NH2), Structurally related s-triazines-diamino-s-triazine, HAAT (Modification R1=H R2=NH2 R3=NH2), PCB congeners, 2,5,3',4'-tetrachlorobiphenyl (Modification IUPAC no.: 70), PCB congeners 2,4, 5,3',4'-pentachlorobiphenyl (Modification IUPAC no.: 118), PCB congeners-2,2',5,5'-tetrachlorobiphenyl (Modification IUPAC no.: 52), PCB congeners, 6-[3,3',4'-Trichlorobiphenyl-4-yl)oxy]hexanoic Acid, Metolazone, Brand Names: Mykrox; Zaroxolyn, Furfuryl benzoate, DDT Metabolites, DDA, Paraquat, 1,1'-dimethyl-4,4'-bipyridinium ion, Diethylcarbamazine, THP, 2,4,6-triphenyl-N-(4-hydroxyphenyl)-pyridinium, o-DNCP, -dinitrocarboxyphenol, PCB congeners, 3-chlorobiphenylol (Modification IUPAC No. 2), PCB congeners, 3,4'-dichlorobiphenyl (Modification IUPAC No.

13), PCB congeners, 3,5-dichlorobiphenyl (Modification IUPAC No. 14), PCB congeners, 3,4,5,3',4'-pentachlorobiphenyl (Modification IUPAC No. 126), 2,3,3',4'-tetrachlorobiphenyl (Modification IUPAC No. 56), 2',3,4,5-tetrachlorobiphenyl (Modification IUPAC No. 76), 3,3',5,5'-tetrachlorobiphenyl (Modification IUPAC No. 80), 2,4,5,2',5'-pentachlorobiphenyl (Modification IUPAC No. 101), 2,3,3',4,4'-pentachlorobiphenyl (Modification IUPAC No. 105), 2,3,6,3',4'-pentachlorobiphenyl (Modification IUPAC No. 110), 3,3',4,5,5'-pentachlorobiphenyl (Modification IUPAC No. 127), 3,4,5,3',4',5'-hexachlorobiphenyl (Modification IUPAC No. 169), 2,3,3',4,4',5-hexachlorobiphenyl (Modification IUPAC No. 156), 3,4,3',4'-tetrabromobiphenyl, 3,4,5,3',4',5'-hexabromobiphenyl, 2,4,5,2',4',5'-hexabromobiphenyl, Dibenzofurans and Dioxins, 2,3,7,8-tetrachlorobenzofuran, 2,3,7,8-tetrachlorodibenzo-p-dioxin, 3,4',5-trichloro-4-biphenylol, 3,3',5,5'-tetrachloro-4,4'-biphenyldiol, 3,4,3',4'-tetrachlorodiphenyl ether, 1-2-dichlorobenzene, 1,4-dichlorobenzene, 1,2,4-trichlorobenzene, 3,4-dichloroaniline, DDT Metabolites, 4,4'-DDT, 4,4'-DDD Retronecine, 3,4-dichlorobiphenyl Modification IUPAC No. 12, 3,4,3'-trichlorobiphenyl (Modification IUPAC No. 35), PCB Congeners, 3,4,4'-trichlorobiphenyl (Modification IUPAC No. 37), 3,4,3',5-tetrachlorobiphenyl (Modification IUPAC No. 78), 3,4,3',5'-tetrachlorobiphenyl (Modification IUPAC No. 79), 3,4,4',5-tetrachlorobiphenyl (Modification IUPAC No. 81), DDT Metabolites, p,p'-DDT (Modification p,p'-dichlorodiphenyltrichloroethane), o,p'-DDT Modification o,p'-dichlorodiphenyltrichloroethane, p,p'-DDE Modification p,p'-DDE, o,p'-DDE Modification o,p'-DDE, p,p'-DDD Modification p,p'-DDD, o,p'-DDD Modification o,p'-DDD, Dicofol, 4,4-dichloro-a-(trichloromethyl)benzhydrol, Cyprazine, 6-chloro-N-cyclopropyl-N'-(1-methylethyl)-1,3,5-triazine-2,4-diamine, Structurally related s-triazines, Dipropetryn, 6-(ethylthio)-N,N'-bis(1-methylethyl)-1,3,5-triazine-2,4-diamine, Trietazine, 6-chloro-N,N,N'-triethyl-1,3,5-triazine-2,4-diamine, 6-Hydroxyatrazine, hexazinone, 3-cyclohexyl-6-dimethylamino-1-methyl-1,3,5-triazine-2,4 (1H,3H)-dione, TNT, 2,4,6-Trinitrotoluene, Tetraconazole (M14360), 1-[2-(2,4-dichlorophenyl)-3-(1,1,2,2-tetrafluoroethoxy)propyl]-1H-1,2,4-triazole, DTP, 2-(2,4-dichlorophenyl)-3-(1H-1,2,4-triazol-1-yl)propanol, Imazalyl, fenarimol, (RS)-2,4'-dichloro-α-(pyrimidin-5-yl)benzhydryl alcohol, Lupanine metabolites, (+)-lupanine (Modification R=H), Lupanine metabolites, (+)-13-hydroxylupanine (Modification R=OH), Lupanine metabolites, hemisuccinate ester of (+)-13-hydroxylupanine (Modification R=OCO—(CH2)2.COOH), Lupanine metabolites, cis-hexahydrophthalate ester of (+)-13-hydroxylupanine (Modification R=OCO.C6H10.COOH), Lupanine metabolites, alpha-isolupanine, Lupanine metabolites, -hydroxylupanine, Sparteine, Cysteine, multiflorine, epilupinine, (Structurally related s-triazines), CYANAZINE ACID Modification R1=Cl R2=NHCH2CH3 R3=NHCCOOH(CH3)2, Structurally related s-triazines Modification R1=Cl R2=NHCH2CH3 R3=NH(CH2)3COOH, Structurally related s-triazines (Modification R1=Cl R2=NHCH2CH3 R3=NHCH2COOH), (Structurally related s-triazines) (Modification R1=Cl R2=NHCH2CH3 R3=NH(CH2)4COOH), norflurazon, 4-chloro-5-(methylamino)-2-[3-(trifluoromethyl)phenyl]-3(2H)-pyridazinone, norflurazon derivative, desmethyl-norflurazon, metflurazon, -chloro-5-(dimethylamino)-2-[(3-trifluoromethyl)phenyl]-3(2H)-pyridazinone, Pyrazon, Chloridazon, 5-amino-4-chloro-2-phenyl-3(2H)-pyridazinone (active ingradient), dichlorophenyl-pyridazone, (Structurally related s-triazines) azidoatrazine (Modification R1=N3 R2=NHCH(CH3)2 R3=NHCH2CH3), ALACHLOR 2-chloro-2',6'-diethyl-N-methoxymethylacetanilide, trichothecolone (Modification R1=H R2=OH R3=H R4=O R5=H), DON derivative, acetyl-T-2, DON derivative, T-2 tetrol tetraacetate, Chlorpyrifos derivatives, mono-dechloro-CP, Bromophos derivative, Bromophos-methyl, Bromophos derivative, Bromophos-ethyl dicapthon, -2-chloro-4-nitrophenyl O,O-dimethyl phosphorothioate, tetrachlorvinphos, (Z)-2-chloro-1-(2,4,5-trichlorophenyl)vinyl dimethyl phosphate, triclopyr, 3,5,6-trichloro-2-pyridyloxyacetic acid, picloram, 4-amino-3,5,6-trichloropyridine-2-carboxylic acid, Formononetin, Biochanin A, 5, 7-dihydroxy-4'-methoxyisoflavone (Modification It is the 4'-methyl ether of genistein), equol, (7-hydroxy-3-(4'-hydroxyphenyl)-chroman, 2'methoxyformononetin, Daidzein, 7-hydroxy-3-(4-hydroxyphenyl)-4H-1-benzopyran-4-one, geninstein, quercetin, 3,3',4',5,7-Pentahydroxyflavone; 3,5,7,3',4'-Pentahydroxyflavone; matheucinol, coumestrol (Structurally related s-triazines), Hydroxysimazine (Modification R1=OHR2=NHCH2CH3R3=NHCH2CH3, angustifoline, Alodan, 1-Methyl-4-phenyl-4-carboethoxypiperidine hydrochloride, Zearalenone, RAL, F-2 Toxin, Fenpropimorph, (RS)-cis-4-[3-(4-tert-butylphenyl)-2-methylpropyl]-2,6-dimethylmorpholine, Tridemorph, 2,6-dimethyl-4-tridecylmorpholine, 2,6-dimethylmorpholine, Amorolfine, Fenpropidine, (RS)-1-[3-(4-tert-butylphenyl)-2-methylpropyl]piperidine, (Structurally related s-triazines) (Modification R1=Cl R2=Cl R3=NHCH2CH3, (Structurally related s-triazines) Modification R1=Cl R2=Cl R3=NHCH(CH3)2, (Structurally related s-triazines) Modification R1=Cl R2=NHCH2CH3 R3=NH(CH2)5COOH, (Structurally related s-triazines) Modification R1=Cl R2=NHCH(CH3)2 R3=NHCH2COOH, (Structurally related s-triazines) (Modification R1=Cl R2=NHCH(CH3)2 R3=NH(CH2)5COOH), Structurally related s-triazines, cyanazine amide (Modification R1=Cl R2=NHCH2CH3 R3=NHCCONH2(CH3)2), hydroxycyanazine acid (Modification R1=OH R2=NHCH2CH3 R3=NHCCOOH(CH3)2), deethylsimazine (Modification R1=Cl R2=NH2 R3=NHCH2CH3), Albendazole sulfoxide, [5-(propylthionyl)-1H-benzimidazol-2-yl]-, methylester, Albendazole sulfone, 5(6)-alkylbenzimidazoles, 2-amino-5-(propylthio)benzimidazole, 5(6)-alkylbenzimidazoles, 2-amino-5-(propylsulfonyl) benzimidazole, oxibendazole, 5-propoxy-benzimidazole-2-methyl carbamate, 5(6)-arylbenzimidazoles, fenbendazole sulfone (Modification sulfone metabolite of fenbendazole), 5(6)-arylbenzimidazoles, 4'-hydroxyfenbendazole, 5(6)-arylbenzimidazoles, oxfendazole (Modification Oxfendazole is the sulfoxide metabolite of fenbendazole), 5(6)-arylbenzimidazoles, flubendazole, benzimidazole Metabolites, 2-aminobenzimidazole, benzimidazole Metabolites, 5-aminobenzimidazole, benzimidazole Metabolites, 2-acetylbenzimidazole, Benzophenone, Diphenylmethanone; phenyl ketone; Diphenyl ketone; Benzoylbenzene, Benzaldehyde, benzoic aldehyde, 4-Bromo-2,5-dichlorophenol, Acephate, O,S-dimethyl acetylphosphoramidothioate, methamidophos, O,S-dimethyl phosphoramidothioate, Dichlorvos, 2,2-dichlorovinyl dimethyl phosphate, Phenthoate, S-α-ethoxycarbonylbenzyl O,O-dimethyl phosphorodithioate, EPN, Ethyl p-nitrophenyl thionobenzenephosphonate, Bioresmethrin, -benzyl-3-furylmethyl (1R,3R)-2,2-dimethyl-3-(2-methylprop-1-enyl) cyclopropanecarboxylate (Modification The unresolved isomeric mixture of this substance has the ISO common name resmethrin), flufenoxuron, 1-[4-(2-chloro-α,α,α-trifluoro-p-tolyloxy)-2-fluorophenyl]-3-(2,6-difluorobenzoyl) urea, Amitrole, 1H-1,2,4-triazol-3-ylamine, molinate, S-ethyl azepane-1-carbothioate, molinate derivative (Modification S-2-carboxyethyl hexahydroazepine-1-carbothioate), molinate derivative (Modification S-5-carboxypentyl hexahydroazepine-1-carbothioate) molinate derivative (Modification molinate sulfone), molinate derivative (Modification S-(p-aminobenzyl) hexahydroazepine-1-carbothioate), molinate derivative (Modification S-2-(p-aminophenyl) ethyl hexahydroazepine-1-carbothioate), hexamethylenimine, thiobencarb (Bolero), butylate (Sutan), EPTC (Eptam), cycloate (Roneet), pebulate (Tillam), vernolate (Vernam), Aflatoxin M1, AFM1 (Modification AFM1), Aflatoxin B1, AFB1 (Modification AFB1), Aflatoxin G1, AFG1 (Modification AFG1), Aflatoxin M2, AFM2 (Modification AFM2), Aflatoxin B2, AFB2 (Modification AFB2), Aflatoxin G2, AFG2 (Modification AFG2), Aflatoxin B2alpha, AFB2alpha (Modification AFB2alpha), Aflatoxin G2alpha, AFG2alpha (Modification AFG2alpha), KB-6806, 6-amino-5-chloro-1-isopropyl-2-(4-methyl-1-piperazinyl) (Modification R1=NH2 R2=CH(CH3)2 R3=CH3), KB-6806 (Benzimidazole) Derivatives Modification R1=NH2 R2=CH2CH(CH3)2 R3=CH3, Hapten Name KB-6806 (Benzimidazole) Derivatives (Modification R1=NH2 R2=CH(CH2CH3)2 R3=CH3), KB-6806 (Benzimidazole) Derivatives (Modification R1=NHCOCH3 R2=CH(CH3)2 R3=CH3), KB-6806 (Benzimidazole) Derivatives (Modification R1=H R2=CH(CH3)2 R3=CH3), KB-6806 (Benzimidazole) Derivatives (Modification R1=NH2 R2=CH(CH3)2 R3=CH3), KB-6806 (Benzimidazole) Derivatives Modification R1=NH2 R2=CH(CH3)2 R3==N(—>O) CH3 (N-OXIDE), KB-6806 (Benzimidazole) Derivatives Modification R1=NH2 R2=CH(CH3)2 R3=H, KB-6806 (Benzimidazole) Derivatives Modification R1=NH2 R2=CH2CH3 R3=CH3, Aminoparaoxon, phosphoric acid, O,O-diethyl O-(4-aminophenyl) ester, Methylparathion, phosphorothioic acid, O,O-dimethyl O-(4-nitrophenyl) ester, Diethyl phenylphosphate, phenylphosphonic acid, O,O-diethyl ester, Diethyl phosphate, ethylphosphonic acid, O,O-diethyl ester, p-Nitrophenyl phosphate, phosphonic acid, O-(4-nitrophenyl)ester, Phorate, phosphorodithioic acid, O,O-diethyl S-[(ethylthio)methyl] ester, Ethion, bis(phosphorodithioic acid), S,S'-methylene O,O,O',O'-tetraethyl ester, Carbophenthion, phosphorodithioic acid, O,O-diethyl S-[[(4-chlorophenyl)thio]methyl] ester, Disulfoton, phosphorodithioic acid, O,O-diethyl S-[(2-ethylthio)ethyl] ester, TS, N-[4-(Carboxymethyl)-2-thiazolyl)sulfanilamide, NS, N-(4-Nitrophenyl)sulfanilamide, Sulfamoxole, Sulfacetamide, DNP-SL, Spin labelled dinitrophenyl (Modification The synthesis of DNP-SL has been described by Balakrishnan et al (1982) formula can be found in Anglister et al. (1984)), beta ecdysone, Benzimidazole Derivative, 5(6)-[Carboxypentyl)thio]-2-(methoxycarbonyl)amino]-benzimidazole, 2-hydroxybiphenyl HBP, Atrazine Caproic acid, Lysophosphatidic acid (LPA), 1-acyl-2-hydroxy-sn-glycero-3-phosphate), berberine, Palmatine, 9-Acetylberberine, Corydaline, Coptisine, Berberrubine, 8-Oxoberberine, Papaverine, Berberine Derivative, 9-O-carboxymethyl berberine, phencyclidine, 1-(1-phenylcyclohexyl)piperidine, Methoxychlor, Endosulfan Derivative, 4-Oxobutanoic Acid,4-(4,5,6,7,8,8-Hexachloro-3a,4,7,7a-tetrahydro-4,7-methano-1H-indenyl-1-oxy), Endosulfan Derivative, 4-oxybutanoic Acid,4-(1,3,4,5,6,7,8-Octachloro-3a,4,7,7a-tetrahydro-4,7-methanoindanyl-2-oxy), Endosulfan Derivative (Modification Hemisuccinate of Endosulfan diol), Triazole Derivatives, 5-(3-Hydroxypropyl)-3-amino-2H-1,2,4-triazole, Triazole Derivatives, 5-(3-Hydroxypropyl)-3-(2-nitrophenylsulfenyl)amino-2H-1,2,4-triazole, Triazole Derivatives, 3-Amino-5-[(3-succinyloxy)propyl]-2H-1,2,4-triazole, Triazole Derivatives, 3-amino-1,2,4-triazole-5-thiol, Triazole Derivatives, 3-[(2-nitrophenylsulfenyl)amino-2H-1,2,4-triazole-5-thiol, Triazole Derivatives, 2H-1,2,4-triazole-5-thiol, Triazole Derivatives, 4-methyl-1,2,4-triazole-3-thiol, Triazole Derivatives, (1,2,4-triazol-2-yl)acetic acid, 1,2,4-triazole, 4-nitrophenyl 4'-carboxymethylphenyl phosphate, Triazole Derivative, 4-amino-1,2,4-triazole, Triazole Derivative, 3-acetamido-1H-1,2,4-triazole, Triazole Derivative, 3-amino-1,2,4-triazole-5-carboxylic acid hemihydrate, Triazole Derivative, 2-(4-chlorophenyl)-2-(1,2,4-triazol-1-yl)-methylhexanoic acid, succinic acid, Imidazole, L-histidine, L-glutamic acid, Permethrin derivative, 3-phenoxybenzyl 2,2-dimethylcyclopropane-1,3-dicarboxylate, 3-phenoxybenzaldehyde, flucythrinate, Chrysanthemic acid, 2,4-Dinitrophenyl, DNP, Thiram Haptens, Disodium 4-[Carbodithioato(methyl)-amino]butanoate, Thiram Haptens 5,11-Dimethyl-6,10-dithioxo-7,9-dithia-5,11-diazadodecanoic Acid, Thiram Haptens, 2-{[(Dimethylamino)carbothioyl]sulfanyl}ethanoic Acid, Thiram Haptens, 4-{[(Dimethylamino)carbothioyl]sulfanyl}butanoic Acid, Thiram Haptens, 6-{[(Dimethylamino)carbothioyl]sulfanyl}hexanoic Acid, Thiram Haptens, 11-{[(Dimethylamino)carbothioyl]sulfanyl}undecanoic Acid, Thiram Haptens, 2-{[(Dimethylamino)carbothioyl] sulfanyl}ethanoic Acid, Thiram, Tetramethylthiurammonosulfide, Tetraethylthiuram disulfide, Dimethyldithiocarbamic acid sodium salt, Dimethyldithiocarbamic acid zinc salt, Diethyldithiocarbamic acid sodium salt, N,N,N',N'-tetramethylthiourea, Nabam, Zineb, Maneb, Ethylenethiourea, Chlorpyrifos hapten, O,O Diethyl O-[3,5-Dichloro-6-[(2-carboxyethyl)thio]-2-pyridyl] Phosphorothioate, 2-Succinamidobenzimidazole, Methyl 2-Benzimidazolecarbamate, MBC, Benzimidazole, 2-benzimidazolylurea, succinamide, Ethyl carbamate, Urea, N-methylurea, N,N'-dimethylurea, Brevetoxin PbTx-3, Organophosphorous Haptens, O,O-Diethyl O-(5-carboxy-2-fluorophenyl) phosphorothioate, Chlorpyrifos-ethyl, Anandamide hapten, N-Arachidonyl-7-amino-6-hydroxy-heptanoic acid, Anandamide, Arachidonic acid, Docosatetraenoyl ethanolamide, Dihomo-gamma-linolenyl ethanolamide, 2-Arachidonyl glycerol, 2-Arachidonyl glycerol ether, Stearoyl ethanolamide, Heptadecanoyl ethanolamide, Prostaglandin E1, 3-hydroxy-2-(3-hydroxy-1-octenyl)-5-oxocyclopentaneheptanoic acid; alprostadil; PGE1, Prostaglandin D2, PGD2, Prostaglandin A2, PGA2, Prostaglandin B2, PGB2, Prostaglandin F2 alpha, 7-[3,5-dihydroxy-2-(3-hydroxy-1-octenyl)cyclopentyl]-5-heptenoic acid; dinoprost; PGF2alpha, Prostaglandin F1 alpha, PGF1alpha, 6-keto-Prostaglandin F1 alpha, 6-keto-PGFlalpha, 13,14-Dihydro-15-keto-Prostaglandin E2, 13,14-Dihydro-15-keto-PGE2, 13,14-Dihydro-15-keto-Prostaglandin F2alpha, 14-Dihydro-15-keto-PGF2alpha, 5alpha,7alpha-Dihydroxy-11-ketotetranorpostane-1,16-dioic acid, 15-keto-PGF2alpha, TXB2, Prostaglandin E2,7-[3-hydroxy-2-(3-hydroxy-1-octenyl)-5-oxocyclopentyl]-5-heptenoic acid; dinoprostone; PGE2, hCG-alpha-(59-92)-peptide (34 residues), Paraquat Derivative, Paraquat hexanoate (PQ-h), Monoquat, Diquat, 9,10-dihydro-8a, 10a-diazoniaphenanthrene, MPTP, 1-methyl-4-phenyl-1,2,5,6-tetrahydropyridine, 1,2-Naphthoquinone, N-Acetyl-S-(1,2-dihydroxy-4-naphthyl)cysteine, N-Acetyl-S-(1,4-dihydroxy-2-naphthyl)cysteine, N-Acetyl-S-(1,2-dihydroxy-1-hydroxy-1-naphthyl)cysteine, 2-Chloro-2'.6'-diethylacetanilide (CDA) Hapten, 2-[2-Chloro-(2'-6'-diethyl)acetanilido]ethanoic Acid, 2-Chloro-2'.6'-diethylacetanilide (CDA) Hapten, 2-[2-Chloro-(2'-6'-diethyl)acetanilido]butanoic Acid, 2-Chloro-2'.6'-diethylacetanilide (CDA) Hapten, 5-(4-Chloroacetamido-3,5-diethyl)phenoxypentanoic Acid, CDA, 2-Chloro-2'.6'-diethylacetanilide, HDA, 2-Hydroxy-2'.6'-diethylacetanilide, 2,6-diethyl-aniline, Hydroxyalachlor, Alachlor ESA, Alachlor ethanesulfonic acid, Isoproturon Hapten, 3-(4-Isopropylphenyl)-1-carboxypropyl-1-methyl urea, chlorotoluron, 3-(3-chloro-p-tolyl)-1,1-dimethylurea, Metoxuron, 3-(3-chloro-4-methoxyphenyl)-1,1-dimethylurea, metamitron, 4-amino-4,5-dihydro-3-methyl-6-phenyl-1,2,4-triazin-5-one, mecoprop, (RS)-2-(4-chloro-o-tolyloxy) propionic acid, propyzamide, 3,5-dichloro-N-(1,1-dimethylpropynyl)benzamide, Paraquat dichloride, MCPB, 4-(4-chloro-o-tolyloxy)butyric acid, Chlortoluron Hapten, N-(3-Chloro-4-methylphenyl)-N-methyl-N-carboxypropyl Urea, Metsulfuron, Methyl 2-[3-(4-methoxy-6-methyl-1,3, 5-triazin-2-yl)ureidosulphonyl]benzoate, Captopril Haptens, Captopril-4-(Maleimidomethyl)-cyclohexane Carboxylic Acid (MCC), Captopril Haptens, Captopril Disulfide Modification, Mercaptoethanol-MCC, Mercaptoethanol-4-(Maleimidomethyl)-cyclohexane Carboxylic Acid Modification, Captopril Haptens, Captopril without MCC, Aculeatiside A, Aculeatiside B, Solamargine, Solasonine, solanine-S; purapurine, Solasodine, Khasianine, Tomatine, lycopersicin, Tomatidine, 3-O-beta-D-Glucopyranosyl-solasodine, O-alpha-L-Rhamnosyl-1(1→2)-3-O-beta-D-glucopyranosyl-solasodine, 3-O-beta-D-Galacopyranosyl-solasidine, O-beta-D-Glucopyranosyl-1(1→3)-3-O-beta-D-galacopyranosyl-solasodine, 12-Hydroxysolamargine, 12-Hydroxysolasonine, Isoanguivine, Solaverine I, Solaverine II, Xylosyl-beta-solamargine, alpha-Solanine, alpha-Chaconine, Dioscine, Indole Derivatives, beta-Indole Acetic Acid, 2-Bromo-4,6-dinitroaniline, 2-Chloro-4,6-dinitroaniline, Tetryl, 2,4,6-trinitrophenyl-n-methylnitramine, nitramine, tetralite, tetril, 2-Amino-4,6-dinitrotoluene, 2,4-Dinitroaniline, 3,5-Dinitroaniline, 2-Amino-4,6-dinitrobenzoic acid, Disperse Blue 79, N-[5-[bis[2-(acetyloxy)ethyl]amino]-2-[(2-bromo-4,6-dinitrophenyl) azo]-4-ethoxyphenyl]acetamide, 1,3-Dinitrobenzene, 2,6-Dinitrotoluene, 4-Amino-2,6-dinitrotoluene, 1,3,5-Trinitrobenzene, Nicergoline, Ethylmorphine, 8-Didehydro-4,5-epoxy-3-ethoxy-17-methylmorphinan-6-ol, Dihydromorphine, Dihydrocodeine, dihydromorphinone, Hydromorphone, Dihydrocodeinone, Hydrocodone, Naltrexone, N-cyclopropylmethyl-14-hydroxydihydromorphinone, Dextromethorphan, (±)-3-Methoxy-17-methyl-morphinan, Homatropine, Endorphins Modification Derivative Type: b-Endorphin, Met-enkephalin, DALEA, D-Ala(2)-D-Leu(5)-enkephalinamide, Vincristine, 22-Oxovincaleukoblastine, leurocristine; VCR; LCR, OCT, 22-Oxacalcitriol, OCT-3-HG, 22-oxacalcitriol-3-Hemiglutarate, 24(OH)OCT, 24(OH)-22-oxacalcitriol, 1,20(OH)2-hexanor-D3, Synephrine, Epinephrine, 4-[(1R)-1-Hydroxy-2-(methylamino)ethyl]-1,2-benzenediol, Phenylephrine, Dopamine Derivative, 6-hydroxy dopamine, Tyramine derivative, 3-methoxy tyramine, Phenethylamine, Benzeneethanamine; PEA, m-tyramine, o-tyramine, dimethoxyphenethylamine, Thymidine glycol monophosphate, 5,6-Dihydroxythymidine monophosphate, Thymidine monophosphate, Thymidine glycol, Thymine glycol, 5,6-Dihydrothymidine, Thymidine, Thymine, 5-methyluracil; 2,4-dihydroxy-5-methylpyrimidine, AMP, Adenosine mono phosphate, CMP, Cytidine mono phosphate, Carbamazepine, 5-carbamoyl-5H-dibenz[b,f]azepine, Neopterin isomers, D-erythro-Neopterin, Neopterin isomers, L-erythro-Neopterin, Neopterin isomers, D-threo-Neopterin, Biopterin isomers, L-erythro-Biopterin, Biopterin isomers, D-erythro-Biopterin, Biopterin isomers, L-threo-Biopterin, Biopterin isomers, D-threo-Biopterin, Pterin-6-Carboxylic Acid, C7H5NiO3, Pterin, Thromboxane B2, (5Z,9alpha,13E,15S)-9,11,15-trihydroxythromboxa-5,13-dien-1-oic acid, 15 Ketoprostaglandin F2alpha, Fumonisin B1, macrofusine; FBI, Thyroliberin, TRH; thyrotropin-releasing factor; thyrotropin releasing hormone; TRF; protirelin; lopremone, Thyroliberin-OH, TRH-OH, Diketopiperazine, cyclo (H-P), TRH analogues, Methylated TRH, TRH analogues, TRH elongated peptides, TRH-Gly, TRH elongated peptides, TRH-Gly-Lys-Arg, TRH elongated peptides, TRH-Gly-Lys-Arg-Ala, TRH elongated peptides, P7 (Modification Q-H-P-G-L-R-F), TRH elongated peptides, P10 (Modification S-L-R-Q-H-P-G-L-R-F), TRH elongated peptides, Ps5 Modification pro-TRH[178-199], TRH elongated peptides, TRH-Ps5 (Modification pro-TRH[172-199]), Hypothalmic peptide, LHRH, Cyanoginosin-LA, Cyanoginosin-LB, Cyanoginosin-LR, Cyanoginosin-LY, Cyanoginosin-AY, Cyanoginosin-FR, Cyanoginosin-YR, Ne-acetyllysine-containing peptide, Gly-Lys (Ac)-e-aminocaproic acid (Aca)-Cys, Benzoic Acid, Benzenecarboxylic acid; phenylformic acid; dracylic acid, m-hydroxybenzoic acid, 3-hydroxybenzoic acid, o-methoxybenzoic acid, 2-methoxybenzoic acid, o-toluic acid, 2-Methylbenzoic acid, o-chlorobenzoic acid, 2-chlorobenzoic acid, o-aminobenzoic acid, 2-aminobenzoic acid, thiosalicylic acid, 2-Mercaptobenzoic acid; o-sulfhydrylbenzoic acid, Salicylamide, 2-Hydroxybenzamide, Saligenin, saligenol; o-hydroxybenzyl alcohol; Salicyl alcohol, 2-cyanophenol, 2-hydroxyphenyl acetic acid, p-hydroxybenzoic acid, p-aminobenzoic acid, 4-Aminobenzoic acid; vitamin Bx; bacterial vitamin H1, p-toluic acid, p-methylamino benzoic acid, p-chlorosalicylic acid, 4-chloro-2-hydroxybenzoic acid, 2,4-dihydroxybenzoic acid, beta-Resorcylic Acid; 2,4-dihydroxybenzenecarboxylic acid; BRA, 4-aminosalicylic acid, 4-Amino-2-hydroxybenzoic acid; p-aminosalicylic acid, Gentisic Acid, 2,5-dihydroxybenzoic acid; 5-hydroxysalicylic acid, Picolinic acid, o-Pyridinecarboxylic acid; 2-Pyridinecarboxylic acid, picolinic acid N-oxide, 3-hydroxypicolinic acid, 2-hydroxynicotinic acid, 7-methylguanine, N2-Carboxymethyl-N7-methylguanine, 2-(7-methyl-6-oxo-6,7-dihydro-1H-purin-2-ylamino)acetic acid, 7-methylxanthine, 7-methyluric acid, 7-methyladenine, Guanine, 2-Amino-1,7-dihydro-6H-purin-6-one; 2-aminohypoxanthine, Adenine, 6-aminopurine; 6-amino-1H-purine; 6-amino-3H-purine; 6-amino-9H-purine, 7-(2-Carboxyethyl)guanine, 7-CEGua, 7-Ethylguanine, 2-amino-7-ethyl-1H-purin-6(7H)-one, 7-(2,3-Dihydroxypropyl) guanine, 2-amino-7-(2,3-dihydroxypropyl)-1H-purin-6 (7H)-one, 7-(2-Hydroxyethyl)guanine, 2-amino-7-(2-hydroxyethyl)-1H-purin-6(7H)-one, 7-(2-[(2-Hydroxyethyl) amino]ethyl)-guanine, 2-amino-7-(2-(2-hydroxyethylamino)ethyl)-1H-purin-6(7H)-one, 7-Carboxymethylguanine, or 2-(2-amino-6-oxo-1,6-dihydropurin-7-yl)acetic acid. In some alternatives, the CAR or T cell receptor comprises a fragment specific for the hapten, wherein the CAR or TCR comprises 14G8, Anti 3-methylindole antibodies, 3F12, Anti 3-methylindole antibodies, 4A1G, Anti 3-methylindole antibodies, 8F2, Anti 3-methylindole antibodies, 8H1, Anti 3-methylindole antibodies, Anit-Fumonisin B1 antibodies, Anti-1,2-Naphthoquinone-antibodies, Anti-15-Acetyldeoxynivalenol antibodies, Anti-(2-(2,4-dichlorophenyl)-3(1H-1,2,4-triazol-1-yl)propanol) Antibodies (Anti-DTP antibodies), Anti-22-oxacalcitriol antibodies (As-1, 2 and 3), Anti-(24,25(OH)2D3) Antibodies (Ab11), Anti-(24,25(OH)2D3) Antibodies (Ab3), Anti-(24, 25(OH)2D3) Antibodies (Ab3-4), Anti-2,4,5-Trichlorophenoxyacetic acid antibodies, Anti (2,4,5-Trichlorphenoxyacetic acid) Antibodies, Anti-(2,4,6-Trichlorophenol) Antibodies, Anti-(2,4,6-Trichlorophenol) Antibodies, Anti 2,4,6-Trinitrotoluene (TNT) Antibodies, Anti-2,4-Dichlorphenoxyacetic acid (MAb's B5/C3, E2/B5, E2/G2, F6/C10, and F6/E5), Anti (2,4-Dichlorphenoxyacetic acid) Antibodies, Anti-2-hydroxybiphenyl-antibodies, Anti-(3,5,6-trichloro-2-pyridinol) Antibodies (LIB-MC2, LIB-MC3), Anti (3,5,6-trichloro-2-pyridinol) antibodies (LIB-MC2 MAb), Anti-3-Acetyldeoxynivalenol (3-AcDON) Antibodies, Anti-3-phenoxybenzoic acid (3-PBAc)-Antibodies, Anti-4-Nitrophenol antibodies, anti-4-nitrophenyl 4'-carboxymethylphenyl phosphate antibodies, Anti-7-(Carboxyethyl)guanine (7-CEGua) antibodies (group specific for 7-meGua), Anti-7-methylguanine (7-MEGua) antibodies, Anti-ABA antibodies, Anti Acephate antibodies (Antiserum 8377), Anti-acetyllysine antibodies (mAbs AL3D5, AL11, AKL3H6, AKL5C1), Anti Aculaetiside-A antibody, Anti Aflatoxin M1(AFM1)antibodies (mAbs A1, N12, R16, FF32), Anti-agatharesinol Antibody, Anti-agatharesinol Antibody, Anti Amidochlorantibodies, Anti-Amitrole antibodies (anti 1a-BSA antibodies), Anti ampicillin Antibodies (AMPI I 1D1 and AMPI II 3B5), Anti-anandamide antibodies (9C11.C9C, 30G8.E6C, 7D2.E2b, 13C2 MAbs), Anti atrazine antibodies, Anti-atrazine antibodies, Anti-Atrazine antibodies, Anti Atrazine Antibodies, Anti-Atrazine Antibodies, Anti-Atrazine Antibodies, Anti-Atrazine Antibodies (4063-21-1 MAb cell line mAb and scAbs), Anti-Atrazine Antibodies (4D8 and 6C8 scAb), Anti Atrazine Antibodies (C193), Anti Atrazine Antibodies (In Rabbit/Sheep), Anti Atrazine Antibodies (K4E7), Anti Atrazine Antibodies (MAb: AM7B2.1), Anti Atrazine Antibodies (ScAb), Anti Atrazine Mercapturic acid antibodies, Anti (Azinphos methyl) Antibodies (MAB's LIB-MFH14, LIB-MFH110), Anti benalaxyl antibody, Anti benzimidazolecarboxylic acid, Anti benzimidazoles antibody (Ab 587), Anti-Benzo[a]pyrene antibodies, Anti Benzo(a)pyrene antibodies (10C10 and 4D5 MAbs), Anti-(Benzoylphenylurea)-Antibodies (mainly against Diflubenzuron), Anti-berberine Antibodies, Anti-beta Indole Acetic Acid Antibodies, Anti-Biopterin (L-erythro form) Antibodies, Anti-Brevetoxin PbTx-3-Antibodies, Anti Bromacil Antibodies, Anti-Bromophos Antibodies, Anti-Bromophos ethyl Antibodies, Anti Butachlor antibodies, Anti-Captopril-MCC Antibodies, Anti-Carbamazepine (CBZ)-Antibodies, Anti Carbaryl Antibodies, Anti Carbaryl Antibodies (LIB-CNH32, LIB-CNH33, LIB-CNH36, LIB-CNH37, LIB-CNH45, LIB-CNA38), Anti-Carbaryl Antibodies (LIB/CNH-3.6 MAb), Anti Carbofuran Antibodies (LIB-BFNB-52, LIB-BFNB-62, LIB-BFNB-67), Anti Carbofuran Antibodies (LIB-BFNP21), Anti-CDA-antibodies, Anti-CDA-antibodies (anti-2-[2-Chloro-(2'-6'-diethyl)acetanilido]butanoic Acid), Anti-CDA-antibodies (anti-2-[2-Chloro-(2'-6'-diethyl)acetanilido]ethanoic Acid), Anti-CDA-antibodies (anti-5-(4-Chloroacetamido-3,5-diethyl)phenoxypentanoic Acid), anti-ceftazidime antibody, Anti-(chlorodiamino-s-triazine) Antibodies (Anti-CAAT) (PAb1-8), Anti Chlorothalonil Antibodies, Anti-Chlorpyrifos antibodies, Anti-Chlorpyrifos Antibodies, Anti-Chlorpyrifos Antibodies (LIB-AR1.1, LIB-AR1.4 Mabs), Anti-Chlorpyrifos Antibodies (LIB-C4), Anti (chlorpyrifos) antibodies (LIB-C4 MAb), Anti-Chlorpyrifos Antibodies (LIB-PN1 Mabs), Anti-Chlorpyrifos Antibodies (LIB-PN2 Mabs), Anti-Chlorpyrifos Antibodies (LIB-PO Mabs), Anti-chlorsulfuron antibodies, Anti-Chlorsulfuron antibodies, Anti Chlortoluron Antibodies (Antiserum), Anti-Cyanoginosin-LA antibodies (mAbs 2B2-2, 2B2-7, 2B2-8, 2B2-9, 2B2-10, 2B5-5, 2B5-8, 2B5-14, 2B5-15, 2B5-23), Anti (D-3-methoxy-4-hydroxyphenylglycol) antibodies, Anti-DDA antibodies, Anti DDT antibodies (PAbs and MAbs), Anti-DDT Mabs (LIB1-11, LIB5-21, LIB5-25, LIB5-28, LIB5-212, LIB5-51, LIB5-52, LIB5-53), Anti-DEC Antibodies (Anti diethylcarbamazine Antibodies), Anti DEHA antibodies, Anti-(Delor 103) antibodies, Anti-Deltamethrin Antibodies, Anti Deltamethrin Antibodies (Del 01 to Del 12 MAbs and PAbs), Anti-deoxynivalenol (DON) Antibodies, Anti-Deoxynivalenol (DON) Antibodies, Anti Dexamethasone Antibody, Anti Dexamethasone Antibody, Anti-Dinitrophenyl (DNP)-antibodies, Anti dinitrophenyl spin labeled antibodies (AN01-AN12), Anti Diuron Antoboides (MAb's: 21, 60, 195, 202, 275, 481, 488, 520), Anti-D-MHPG Antibodies, Anti DNC antibodies, Anti-EB1089 antibodies, Anti-ecdysone antibodies, Anti-endosulfan antibodies, Anti-Endosulfan antibodies, Anti Esfenvalerate antibodies (Ab7588), Anti estradiol antibodies, Anti-Fenitrothion antibodies (pAbs and mAbs), Anti-Fenpropimorph antibodies, Anti Fenthion Antibodies, Anti-Fenthion Antibodies, Anti FITC antibodies (B13-DEI), Anti-Flucofuron antibodies (F2A8/1/A4B3), Anti-flufenoxuron antibodies, and Anti-(Benzoylphenylurea)-Antibodies, Anti-Formononetin Antibodies, Anti-Furosemide antibodies (Furo-26, Furo37, furo-72, Furo 73 Mabs), Anti-GR151004 Antibodies, Anti-hCG-alpha-peptide Antibodies (FA36, Anti hydroxyatrazine antibodies (HYB-283-2), Anti-Hydroxysimazine Antibodies, Anti Imazalil Antibodies MoAb's (9C1-1-1, 9C5-1-1, 9C6-1-1, 9C8-1-1, 9C9-1-1, 9C12-1-1, 9C14-1-1, 9C16-1-1, 9C18-1-1, 9C19-1-1, 9E1-1, 9G2-1), Anti Irgarol Antibodies, Anti Isopentenyl adenosine antibodies, Anti Isoproturon Antibodies, Anti-KB-6806 antiserum, Anti-(+)lupanine antibodies, Anti Lysophosphatidic (LPA) acid, Anti M3G Ab1 and Ab2, Anti M3G Ab1 and Ab2, Anti-MBC antibodies (Anti-2-succinamidobenzimidazole antiserum), Anti Metanephrine antibodies, anti (+)methamphetamine antibodies, Anti-Methiocarb Antibodies (LIB-MXNB31, LIB-MXNB-33, LIB-MXNH14 and LIB-MXNH-15 MAbs), Anti Metolachlor antibodies, Anti-Metolachlor Antibodies, Anti-Metolachlor Antibodies (MAb 4082-25-4), Anti Molinate Antibodies, Anti monuron antibodies, Anti-morphine-3-glucuronide (E3 scFv antibody), Anti morphine antibodies, Anti-Morphine antibodies, Anti-Morphine Antibodies (mAbs 8.2.1, 33.2.9, 35.4.12, 39.3.9, 44.4.1, 76.7F.16, 83.3.10, 115.1.3, 124.2.2, 131.5.13, 158.1.3, 180.2.4), Anti-Neopterin (D-erythro form) Antibodies, Anti-Nicarbazin Antibodies (Nic 6, Nic 7, Nic 8, and Nic 9), Anti Nicergoline Antibodies (Nic-1, Nic-2, Nic-3 & BNA-1, BNA-3), Anti-norflurazon antibodies, Anti NorMetanephrine antibodies, Anti (o-DNCP) Antibodies, Anti-P10 antibodies (TRH elongated peptide), Anti-Paraoxon Antibodies (BD1 and CE3), Anti Paraquat antibodies, Anti-Paraquat antibodies, anti Parathion-methyl antibodies, Anti PCB Antibodies (against 3,3',4,4'-tetrachlorobiphenyl) MAb S2B1, Anti pentachlorophenol antibodies, Anti Pentachlorophenol antibodies, Anti-Pentachlorophenol antibodies, Anti permethrin antibodies (Mabs Py-1, Py-3 and Py-4), Anti-Phencyclidine Antibodies (Mab 6B5 Fab), Anti-phenobarbital antibodies, Anti-phenobarbital antibodies, Anti-(p.p'-DDT)-Antibodies (LIB-DDT-35 and LIB-DDT5-52), Anti permethrin antibodies (Ab549), Anti Propoxur antibodies (LIB-PRNP15, LIB-PRNP21, LIB-PRNB21, LIB-PRNB33), Anti-Prostaglandin E2-antibodies, Anti-p-tyramine antibodies, Anti pyrene antibodies, Anti retronecine antibodies, Anti-Retronecine Antibodies, Anti salicylate antibodies, Anti Sennoside A antibodies (MAb 6G8), Anti Sennoside B antibodies (MAb's: 7H12, 5G6, 5C7), Anti Simizine antibodies, Anti Sulfonamides antibodies (Anti-TS), Anti-Sulocfuron antibodies (S2B5/1/C3), Anti sulphamethazine antibodies (21C7), Anti-synephrine antibodies, Anti-Thiabendazole antibodies (Antibody 300), Anti-Thiabendazole antibodies (Antibody 430 and 448), Anti-Thiram-Antibodies, Anti-THP antibodies (7S and 19S), Anti-Thromboxane B2 Antibodies, Anti-thymidine glycol monophosphate antibodies (mAb 2.6F.6B.6C), Anti-Thyroliberin (TRH) antibodies, Anti TNT antibodies (AB1 and AB2 antiserum), Anti Triadimefon Antibodies, Anti-triazine antibodies (AM1B5.1), Anti-triazine antibodies (AM5C5.3), Anti-triazine antibodies (AM5D1.2), Anti-triazine antibodies (AM7B2.1), Anti-triazine antibodies (SA5A0.1), Anti-Triazine serum (anti-ametryne), Anti-Triazine serum (anti-atrazine), Anti-Triazine serum (anti-simazine), Anti-Triazine serum (anti-simetryne), Anti Trifluralin Antibodies, Anti Trifluralin Antibodies, Anti Vincristine Antibodies, Anti-Zearalenone Antibodies, Anti Zeatin riboside antibodies, E2 G2 and E4 C2, Fab Fragment K411B derived from MAb K4E7 (isotype IgG2b with k light chain), LIB-BFNP23 Mab, MAb's H-7 and H-9 (against O,O-diethyl OP pesticides), MoAb 33A7-1-1, MoAb 33B8-1-1, MoAb 33C3-1-1, MoAb 3C10-1-1 and MoAb 3E17-1-1, MoAb 45D6-5-1, MoAb 45E6-1-1, MoAb 45-1-1, Mutant (GlnL89Glu) in Fab Fragment K411B derived from MAb K4E7 (isotype IgG2b with k light chain), Mutant (GlnL89Glu/ValH37Ile/GluL3Val) in Fab Fragment K411B derived from MAb K4E7 (isotype IgG2b with k light chain), Mutant (GlnL89Glu/ValH37Ile/GluL3Val) in Fab Fragment K411B derived from MAb K4E7 (isotype IgG2b with k light chain), Mutant (GlnL89Glu/ValH37Ile) in Fab Fragment K411B derived from MAb K4E7 (isotype IgG2b with k light chain), Mutant (GlnL89Glu/ValH37Ile) in Fab Fragment K411B derived from MAb K4E7 (isotype IgG2b with k light chain), Mutant (GluH50Gln) in Fab Fragment K411B derived from MAb K4E7 (isotype IgG2b with k light chain), Mutant (GluH50X) in Fab Fragment K411B derived from MAb K4E7 (isotype IgG2b with k light chain), Mutant (GlyH100aAla) in Fab Fragment K411B derived from MAb K4E7 (isotype IgG2b with k light chain), Mutant (GlyH100aSer) in Fab Fragment K411B derived from MAb K4E7 (isotype IgG2b with k light chain), Mutant (HisH95Phe) in Fab Fragment K411B derived from MAb K4E7 (isotype IgG2b with k light chain), Mutant (HisH95Tyr) in Fab Fragment K411B derived from MAb K4E7 (isotype IgG2b with k light chain), Mutant (PheL32Leu) in Fab Fragment K411B derived from MAb K4E7 (isotype IgG2b with k light chain), Mutant (TrpH33Phe,Tyr,Leu) in Fab Fragment K411B derived from MAb K4E7 (isotype IgG2b with k light chain), Mutant (Tryl96Phe) in Fab Fragment K411B derived from MAb K4E7 (isotype IgG2b with k light chain), Mutant (TryL96Phe) in Fab Fragment K411B derived from MAb K4E7 (isotype IgG2b with k light chain), Mutant (ValH37Ile) in Fab Fragment K411B derived from MAb K4E7 (isotype IgG2b with k light chain), Mutant (ValH37Ile) in Fab Fragment K411B derived from MAb K4E7 (isotype IgG2b with k light chain), P6A7 MAb, PNAS2 6/3 56(1)-1-5-1, PNAS2 6/3 56(1)-1-5-2, PNAS2 6/3 56(1)-1-10-4, PNAS2 6/3 56(1)-1-10-5 and PNAS2 6/3 56(1)-3-1-5, Alexa Fluor 405/Cascade Blue dye antibody, Alexa Fluor 488 dye antibody, BODIPY FL dye antibody, Dansyl antibody, Fluorescein/Oregon Green dye antibody, Lucifer yellow dye antibody, Tetramethylrhodamine and Rhodamine Red dye antibody, Texas Red and Texas Red-X dye antibody, Biotin antibody, Dinitrophenyl antibody and/or Nitrotyrosine antibody or any portion thereof of the aforementioned haptens.

In a seventh aspect, a cell comprising a chimeric antigen receptor (CAR) or T cell receptor (TCR) is provided, wherein the CAR or TCR is configured to bind with an antibody or binding fragment thereof comprising a target moiety through a CAR or TCR-mediated interaction with said target moiety and, wherein said antibody or binding fragment thereof is specific for an antigen present on a cancer cell, virus, or bacterial cell. In some alternatives, said target moiety is a hapten, poly(his) tag, Strep-tag, FLAG-tag, V5-tag, Myc-tag, HA-tag, NE-tag, biotin, digoxigenin, dinitrophenol or fluorescein (e.g., Fluorescein isothiocyanate (FITC)). In some alternatives, the cell is a precursor T cell. In some alternatives, the precursor T cell is a hematopoietic stem cell. In some alternatives, the cell is a CD8+ T cytotoxic lymphocyte cell selected from the group consisting of naïve CD8+ T cells, central memory CD8+ T cells, effector memory CD8+ T cells and bulk CD8+ T cells. In some alternatives, the cell is a CD4+ T helper lymphocyte cell that is selected from the group consisting of naïve CD4+ T cells, central memory CD4+ T cells, effector memory CD4+ T cells, and bulk CD4+ T cells. In some alternatives, the hapten used comprises Alexa Fluor 405, Cascade Blue, Alexa Fluor 488, BODIPY, Dansyl chloride, Oregon Green, Lucifer yellow, Rhodamine, Tetramethylrhodamine, Nitrotyrosine, digoxigenin, 2,4-Dichlorophenoxyacetic acid, Atrazine (2-Chloro-4-(ethylamino)-6-(isopropylamino)-s-triazine), Nicotine (3-(1-Methyl-2-pyrrolidyl)pyridine, Black Leaf), Morphine (morph, Morphine Sulfate), 2,4-DINITROCHLOROBENZENE (1-Chloro-2,4-dinitrobenzene; DNCB; Dinitrochlorobenzene), 4-chloro-6-(ethylamino)-1,3,5-triazine-2-(6-aminohexanecarboxylic acid), Structurally related s-triazines (Modifications: H/Cl/C6 R1=NH2- R2=—Cl R3=—NH—(CH2)5-COOH; iPr/Cl/nBu R1=(CH3)2-CH—NH— R2=—Cl R3=—NH—(CH2) 3-(CH3)), Ametryn (2-Ethylamino-4-isopropylamino-6-methylthio-1,3,5-triazine), Deethylatrazine (DEA) (Structurally related s-triazines), Deisopropylatrazine (DIA) (Structurally related s-triazines), Deethyldeisopropylatrazine (DEDIA) (Structurally related s-triazines), Deethyldeisopropylatrazine (DEDIA) (Structurally related s-triazines), HydroxyAtrazine (HA) (Structurally related s-triazines), DeisopropylHydroxyAtrazine (DIHA) (Structurally related s-triazines), DeethylDeisopropylHydroxyAtrazine (DE-DIHA) (Structurally related s-triazines), Simazine (Structurally related s-triazines), Desmetryne (Structurally related s-triazines), Prometryne (Structurally related s-triazines), 2-hydroxyatrazine (atrazine derivative), 2-hydroxypropazine (structurally related s-triazine), 2-hydroxysimazine, N-(4-Amine-6-hydroxy-[1,3,5]triazin-2-yl)-4-aminobutanoic Acid (Modification: R1=NH2 R2=NH(CH2)3COOH R3=OH), SulcoFuron, 5-chloro-2-{4-chloro-2-[3-(3,4-dichlorophenyl)ureido]phenoxy}benzenesulfonic acid, FlucoFuron (1,3-bis(4-chloro-α,α,α-trifluoro-m-tolyl)urea), Agatharesinol, Sequirin C, Sugiresinol, Hydroxysugiresinol, Hinokiresinol, Coniferyl alcohol, Cinnamyl alcohol, p-Coumaric acid, Cinnamic acid, p-Coumaric acid, Cinnamic acid, Hinokinin, Guaiacylglycerol-beta-guaiacyl ether, Morphine-3-glucuronide (M3G), Codeine, Nor-Codeine, 6-Mono-acetylmorphine, (+) Methamphetamine, Ceftazidime, Phenobarbital, p-hydroxyPhenobarbital, p-aminophenobarbital, Cyclobarbital, 3'-Ketocyclobarbital, 3'-Hydroxycyclobarbital, Secobarbital, Barbital, Metharbital, Barbituric acid, Thiopental, Thiobarbituric acid, Primidone, Glutethimide, Pentobarbital, Heroin, Diacetylmorphine, Levallorphan, L-11-Allyl-1,2,3,9,10,10a-hexahydro-4H-10,4a-iminoethanophenanthren-6-ol, Pethidine (Demerol; Dolantin; Meperidine; Ethyl 1-methyl-4-phenylpiperidine-4-carboxylate;

Isonipecaine), Methamphetamine, d-Desoxyephedrine; Methedrine; Tolpropamine; Pratalgin; Pragman. Benzoylecgonine, 3-Carboxymethylmorphine, Cocaine, 5-benzimidazolecarboxylic acid, ABA (4-acetyl benzoic acid), Dexamethasone, Flumethasone, 6alpha, 9 alpha-difluoro-11 beta, 17,21-trihydroxy-16 alpha-methylpregna-1,4-diene-3,20-dione, 9 alpha-fluoro-11 beta,17,21-trihydroxy-16 beta-methylpregna-1,4-diene-3,20-dione, 9-alpha-fluoroprednisolone, Desoxymethasone, Triamcinolone, 9 alpha-fluoro-11 beta,16 alpha, 17,21-tetrahydroxypregna-1,4-diene-3,20-dione, Fluocortolone, 6 alpha-fluoro-11 beta,21-dihydroxypregna-1,4-diene-3,20-dione, Cortisol, 11 beta, 17,21-trihydroxypregna-4-ene-3,20-dione, Prednisone, 17,21-dihydroxypregn-4-ene-3,11,20-trione, Methylprednisolone, 11 beta,17,21-trihydroxy-6 alpha-methylpregna-1,4-diene-3,20-dione, Triamcinolone hexacetonide, 21-(3,3-dimethyl-1-oxobutoxy)-9 alpha-fluoro-11-hydroxy-16,17-[(1-methylethylidene) bis(oxy)]pregna-1,4-diene-3,20-dione, Carbofuran, 2,3-dihydro-2,2-dimethyl-7-benzofuranyl methylcarbamate, BFNP (3-[[(2,3-dihydro-2,2-dimethyl-7-benzofuranyloxy)carbonyl]amino]propanoic acid), Carbofuran derivative, 2,3-dihydro-2,2-dimethyl-7-benzofuranol, Bendiocarb, Carbaryl, Methiocarb, Propoxur, Aldicarb, Methomyl, Benalaxyl, methyl N-(phenylacetyl)-N-(2,6-xylyl)-DL-alaninate, Bn-Ba (4-[2-(N-phenylacetyl-N-2,6-xylylamino)propionamido] butyric acid), Bn-COOH (4-[2-(N-phenylacetyl-N-2,6-xylyl-DL-alanine), Benalaxyl derivative, Furalaxyl, Metalaxyl, Acetochlor, Dimetachlor, Metolachlor, 2-chloro-6'-ethyl-N-(2-methoxy-1-methylethyl)acet-o-toluidine, Diethathyl-ethyl, Benzoylprop-ethyl, Benzoylprop-ethyl, 2,4,5-Trichlorophenoxyacetic acid, 2-chloro-6'-ethyl-N-(2-methoxy-1-methylethyl)acet-o-toluidine, Diethathyl-ethyl, Benzoylprop-ethyl, Propachlor, Propachlor, 2,4,5-Trichlorophenoxyacetic acid, 2,4,5,T; Weedone, 2,4-Dichlorophenoxybutyric acid (2,4-DB), 2,4-DB; Butanoic acid, 4-(2,4-dichlorophenoxy)-; Butoxone; Embutone, MCPA, 2-Methyl-4-chlorophenoxyacetic acid; Metaxon, Dichlorprop (2,4-DP), 1-[(2-chloro)phenylsulfonyl]monoamidosuccinic acid, Chlorsulfuron, chlorbromuron, amidosulfuron, chlortoluron, isoproturon, diuron, Linuron O-Methyl-O-(4-nitrophenyl)-N-(4-carboxybutyl)-phosphoramidothioate Parathion-methyl, O,O-dimethyl O-4-nitrophenyl phosphorothioate; Methaphos; Wolfatox; Dimethylparathion; Metacide, Parathion-ethyl, DIETHYL P-NITROPHENYL THIOPHOSPHATE; O,O-DIETHYL O—(P-NITROPHENYL) PHOSPHOROTHIOATE; Fenitrothion, O,O-dimetyl O-4-nitro-m-tolyl phosphorothioate, Fenthion, O,O-dimethyl O-4-methylthio-m-tolyl phosphorothioate, Bromophos, O-4-bromo-2,5-dichlorophenyl O,O-dimethyl phosphorothioate, chlorpyrifos-methyl, O,O-dimethyl O-3,5,6-trichloro-2-pyridyl phosphorothioate, Oxidized parathion-methyl, Paraoxon, phosphoric acid, O,O-diethyl O-(4-nitrophenyl) ester, Diazinon, O,O-diethyl O-2-isopropyl-6-methylpyrimidin-4-yl phosphorothioate, Azinphos-methyl, pirimiphos-methyl, O-2-diethylamino-6-methylpyrimidin-4-yl O,O-dimethyl phosphorothioate, Methidathion, S-2,3-dihydro-5-methoxy-2-oxo-1,3,4-thiadiazol-3-ylmethyl O,O-dimethyl phosphorodithioate, Dimethylchlorothiophosphate, 4-NITROPHENOL, p-nitrophenol, Phenolic derivative (Modification On benzene ring; R1=OH R2=NO2 R3=H R4-CH2COOH R5=H R6=H); 2-Nitrophenol, o-Nitrophenol, 3-Nitrophenol, m-nitrophenol, 2,4-Dinitrophenol, 3,4-Dinitrophenol, 2,5-Dinitrophenol, 2,4-Dinitro-6-methylphenol, 2,3,6-trinitrophenol, 2-Chlorophenol, 4-Chloro-3-methylphenol, Fenitroxon, 3-Methyl-4-nitrophenol, Nonylphenol, HOM(3-[2-hydroxy-5nitro benzylthio] propionic acid, Phenol, Delor 103, Polychlorinated Biphenyls, Delor 104, Polychlorinated Biphenyls, Delor 105, Polychlorinated Biphenyls, Delor 106, 4,4'-Dichlorobiphenyl, PCB congeners, 2,4,4'-Trichlorobiphenyl, PCB congeners, 2,4'-Bichlorobiphenyl, PCB congeners, 2,2'-Dichlorobiphenyl, PCB congeners, 2,4,5-Trichlorobiphenyl, PCB congeners, 3,3',4,4'-Tetrachlorobiphenyl, PCB congeners, PCB congeners, 2,2',4,4',5,5'-Hexachlorobiphenyl, 2-(5-Carboxypentanoylamino)-4,4'-dichlorobiphenyl, Biphenyl derivative, 4-chlorophenoxyacetic acid, 2-Chlorophenoxyacetic acid, DDT,1,1,1-trichloro-2, 2-bis-(p-chlorophenyl)ethane, DDE, 1,1-dichloro-2, 2-bis(p-chlorophenyl)ethylene, p-Chlorophenol, 4-Chlorophenol, m-Chlorophenol 3,4-Dichlorophenol, 3,5-Dichlorophenol, 2,3,4-Trichlorophenol, 2,3,5-Trichlorophenol, 3-methylindole, 3-methylindole Derivatives, 4-(3-methylindol-5-yloxy)butanoic acid, 4-(3-methylindol-5-yloxy)butanoic acid, 3-methylindole Derivatives, 6-[n-3-methylindol-5-yloxy carbonyl)amino]hexanoic acid, 6-[n-3-methylindol-5-yloxy carbonyl)amino]hexanoic acid, 3-methylindole Derivatives, 2-[4-(3-methylindol-6-yl)but-1-ylthio]acetic acid, 2-[4-(3-methylindol-6-yl)but-1-ylthio]acetic acid, 3-methylindole Derivatives, 4-(3-methylindol-6-yl-4-oxo) butanoic acid, 4-(3-methylindol-6-yl-4-oxo)butanoic acid, 3-methylindole Derivatives, 6-(3-methylindol-7-yloxy) hexanoic acid, 6-(3-methylindol-7-yloxy)hexanoic acid, Indole, Indole-3-Carboxylic acid, Indole Derivative-Indole-3-Acetic acid, Indole-3-Acetic acid, Indole Derivative-Indole-3-Propionic acid, Indole-3-Propionic acid, Indole Derivative-Indole-3-Carbinol, Indole-3-Carbinol, Tryptophan, Tryptamine, 5-Methoxyindole-3-carboxaldehyde, 5-Methoxytryptamine, 5-Methoxyindole, 6-Methoxyindole, 7-Methoxyindole,EB1089(Seocalcitol),EB1089(Seocalcitol) Derivative, (22E,24E)-Des-A,B-24-homo-26,27-dimethyl-8-[(E)-N-(2-carboxyethyl)-carbamoylmethylidene]-cholesta-22,24-dien-25-ol, 1 alpha-25-dihydroxyvitamin D3, 25(OH)D3,25-hydroxyvitamin D3,24R,25(OH)2D3, 24R,25-dihydroxyvitamin D3, Vitamin D2, ergocalciferol, Vitamin D3, cholecalciferol,EB1446,EB1436,EB1445, EB1470, DeethylHydroxyAtrazine (DEHA) (Structurally related s-triazines), Irgarol 1051, Flourescein Isothiocyanate, FITC, Metanephrine, NorMetanephrine, Propazine, Terbutylazine, Terbuthylazine, 6-chloro-N-(1,1-dimethylethyl)-N'-ethyl-1,3,5-triazine-2,4-diamine, (Structurally related s-triazines), Ametryn (2-Ethylamino-4-isopropylamino-6-methylthio-1,3,5-triazine (Modification iPr/SCH3/Et R1=(CH3)2-CH—NH— R2=—SCH3 R3=—NH—CH2-CH3, Irgarol, Cyanazine (Modification R1=Cl R2=NHCH2CH3 R3=NHCCN(CH3)2), OH-Terbutylazine, Terbutylazine-2OH, Hydroxytriazine (EQ-0027), Deisopropylatrazine (Structurally related S-triazine), Desethylterbutylazine (Structurally related S-triazine), Desethyl-deisopropylatrazine (Structurally related S-triazine), Atraton, Terbutryn (Structurally related s-triazines), Atrazine derivative (Modification R1=—NHCH(CH3)2 R2=—S(CH2)2COOH R3=—NHC2H5), Cyanuric chloride, Trifluralin, (Structurally related s-triazines) tBu/C4/SCH3 (Modification R1=—NH—C—(CH3)3 R2=—NH (CH2)3COOH R3=—SCH3), Sulphamethazine, (Structurally related s-triazines) 6-[[[4-Chloro-6-(methylamino)]-1,3,5-triazin-2-yl]amino]hexanoic Acid (Modification Me/Cl/C6 R1=—NHCH3 R2=—Cl R3=—NH(CH2) 5COOH), (Structurally related s-triazines) Procyazine (Modification R1=—Cl R2=—NHcyclopropyl R3=—NHCCN(CH3)2), (Structurally related s-triazines), Prometon (Modification R1=—OCH3 R2=—NHCH(CH3)2 R3=—NHCH(CH3)2); (Structurally related s-triazines) Atrazine Mercapturic Acid (AM) (Modification R1=—SCH2CH(NHAc)COOH R2=—NHCH2CH3 R3=—NHCH(CH3)2), (Structurally related s-triazines), desethyl atrazine mercapturic acid (desethyl AM) (Modification R1=—NAcCys R2=—NH2 R3=—NHCH(CH3)2), (Structurally related s-triazines), deisopropyl atrazine mercapturic acid (deisopropyl AM) (Modification R1=—NAcCys R2=—NHCH2CH3 R3=—NH2), (Structurally related s-triazines), didealkylated atrazine mercapturic acid (didealkylated AM) (Modification R1=—NAcCys R2=—NH2 R3=—NH2), (Structurally related s-triazines), simazine mercapturate (Modification R1=—NAcCys R2=—NHCH2CH3 R3=—NHCH2CH3), (Structurally related s-triazines) (Modification R1=—S(CH2)2COOH R2=—NHCH2CH3 R3=—NHCH2CH3), (Structurally related s-triazines) (Modification R1=—Cl R2=—NHCH(CH3)2 R3=—NH(CH2)2COOH), (Structurally related s-triazines) (Modification R1=—Cl R2=—NHCH2CH3 R3=—NH(CH2)2COOH), (Structurally related s-triazines), atrazine mercapturic acid methyl ester (AM methyl ester) (Modification R1=—NAcCysME R2=—NHCH2CH3 R3=—NHCH(CH3)2), N-acetylcysteine, S-benzyl mercapturate, (Structurally related s-triazines), simetryn (Modification R1=—SCH3 R2=—NHCH2CH3 R3=—NHCH2CH3), Metribuzin, 4-amino-6-tert-butyl-4,5-dihydro-3-methylthio-1,2,4-triazin-5-one, Sulpha Drugs, N4-acetyl-sulphamethazine (Modification N4-acetyl-sulphamethazine), Sulpha Drugs, Sulphathiazole, Sulphathiazole, Sulphamerazine, Sulphamerazine, Sulphaquinoxaline, Sulphaquinoxaline Sulphachlorpyridazine, Sulphachlorpyridazine, Sulphapyridine, Sulphadimethoxine, Sulphadimethoxine, Sulphamethoxazole, Sulphamethoxazole, Sulphisoxazole, Sulphisoxazole, Sulphamethizole, Sulphamethizole, Sulphanilamide, Sulphanilamide, Sulphaguanidine, Sulphaguanidine, Sulphadiazine, Sulphadiazine, Sulphamethoxypyridazine, Sulphamethoxypyridazine, Pentachlorophenoxypropionic acid, Pentachlorophenol, PCP, 2,3,5,6-Tetrachlorophenol, 1,2,4,5 Tetrachlorobenzene, 2,4,6 Trichlorophenol, 2-Methoxy-3,5,6-trichloropyridine, 1,3,5 Trichlorobenzene, 1,3 Dichlorobenzene, 2,4,5-Trichlorophenol, 2,6-Dichlorophenol, 3,5,6-Trichloro-2-pyridinoxyacetic acid, 3,5,6-Trichloro-2-Pyridinol, TCP, 2,4-Dichlorophenol, 2,5-Dichlorophenol, DNC, 4,4'-dinitrocarbanilide, (Structurally related s-triazines), Dichloroatrazine, (Structurally related s-triazines), Dichlorosimazine, 1-((6-chloropyridin-3-yl)methyl)imidazolidin-2-imin, Pyridine Derivative, 6-chloropyridine-3-carboxylic acid, Nicotinic acid, Pyridine Derivative, N-((6-chloropyridin-3-yl)methyl)-N-methylacetamide, (6-chloropyridin-3-yl)-N-methylmethanamine, (6-chloropyridin-3-yl)methanol, Imidacloprid, 1-(6-chloro-3-pyridylmethyl)-N-nitroimidazolidin-2-ylideneamine, Acetamiprid, (E)-N1-[(6-chloro-3-pyridyl)methyl]-N2-cyano-N1-methylacetamidine, Nitenpyram, Deltamethrin, 1(R)-cis-alpha (S)-3-(2,2-dibromoethenyl)-2,2-dimethylcyclopropane carboxylic acid cyano(3-phenoxyphenyl)methyl ester, DON, deoxynivalenol, DON derivative, 15-AcDON (15-acetyldeoxynivalenol), DON derivative, 3-AcDON (3-acetyldeoxynivalenol), DON derivative, 3,15-DiacDON (3,15-diacetyldeoxynivalenol), DON derivative, 3,7,15-TriacDON (3,7,15-Triacetyldeoxynivalenol), NIV (nivalenol), nivalenol, NIV Derivative, 4-AcNIV (fusarenon X), Flutolanil, alpha,alpha,alpha-trifluoro-3'-isopropoxy-o-toluanilide, Mepronil, Mebenil, Benodanil, 24,25(OH)2D3, (24R)-24,25-dihydroxyvitamin D3, 24S,25(OH)2D3, 24S,25-dihydroxyvitamin D3, 25R,26(OH)2D3, 25R,26-dihydroxyvitamin D3, 25S,26(OH)2D3, 25S,26-dihydroxyvitamin D3, 1,24,25(OH)3D3, 1,24,25-trihydroxyvitamin D3, 1,25-lactone, (23S,25R)-1,25(OH)2 D3 26,23-lactone, 24,25(OH)2-7-DHC, 24,25(OH)2-7-dehydrocholesterol, 25(OH)D3 3S, 25(OH)D3 3-sulfate, 24,25(OH)2D3-Hemiglutarate Derivative, 11 alpha-hemiglutaryloxy-(24R)-24,25-dihydroxyvitamin D3, 24,25(OH)2D3-Hemiglutarate Derivative, (24R)-24,25-dihydroxyvitaminD3-3-hemiglutarate, 24R,25(OH)2D2, 24S,25(OH)2D2, 25(OH)D2, 1,24(OH)2D3, 2,3,6-Trichlorophenol, Tetrachlorohydroquinone, Pentachloroaniline, Pentachlorobenzene, 2,3-Dinitrotoluene, 4-Dinitrotoluene, 2,4,5-Trichloronitrobenzene, 3-(3-Hydroxy-2,4,6-trichlorophenyl)-propanoic acid, 2,3,4,6-Tetrachlorophenol, 2,4,6-Trichloroanisol, 2,4,6-TCA, Pentabromophenol, PBP, 2,4,6-Tribromophenol, 2,4,6-TBP, 2-Bromo-4-Chlorophenol, 2-B-4-CP 2,4-Dibromophenol, 2,4-DBP, 2,6-Dibromophenol, 2,6-DBP, 4-Bromophenol, 4-BP, Furosemide, Ampicillin, Amoxicillin, 6-amino-penicillanic acid (6-APA), Azlocillin, Bacampicillin, Carbenicillin, Epicillin, Cloxacillin, Dicloxacillin, Metampicillin, Methicillin, Moxalactam, Oxacillin, Penicillin G, benzyl penicillin, Penicillin V, phenoxy methyl penicillin, Pheneticillin, Piperacillin, Ticarcillin, Ampicillin hydrolyzed, Penicillin G hydrolyzed, 3-phenoxybenzoic acid (3-PBAc) Chlorpyrifos, Chlorpyrifos derivatives, HClo1, Synthesized directly from chlorpyrifos technical grade by substitution of the chlorine in position 6 by a 3-mercaptopropanoic acid spacer arm, Chlorpyrifos derivatives, HTCP (Modification HTCP of TCP metabolite was prepared from HClo1 by hydrolysis of the thiophosphate ester), Zeatin Riboside (trans isomer), Zeatin (trans isomer), N6-(2-isopentenyl)-adenosine, IPA, N6-(2-isopentenyl)-adenine, 2-iP, Benzyladenine, Kinetin, monuron, monolinuron, fenuron, neburon, propanil, propham, chloropropham, 4-chloroaniline, Methyl Urea Derivative, 1-(3-Carboxypropyl)-3-(4-chlorophenyl)-1-methylurea, Methyl Urea Derivative, 1-(5-Carboxypentyl)-3-(4-chlorophenyl)-1-methylurea, metobromuron, Sennoside B, SB, Sennoside B possessed a erythro configuration between C-10 and C-10', Sennoside A (Modification Sennoside A possessed a threo configuration between C-10 and C-10'), Rhein, Emodin, Aloe-emodin, Barbaloin, 1,4 Dihydroxyanthraquinone, Rhaponticin, Galic acid, Vanillic acid, Caffeic acid, Homogentisic acid, Esculin, Cinnamtannin B1, Baicalin, Naringin hydrate, Wogonin, Wogonin 7-o-beta-glucuronide, Curcumin, delta1-Tetrahydrocannabinolic acid, delta1-Tetrahydrocannabinol, (+−)-cis-4-Aminopermethrin, 3-(4-Aminophenoxy)benzyl(+−)-cis-3-(2,2-dichloroethenyl)-2,2-dimethylcyclopropanecarboxylate, Permethrin, trans-Permethrin, cis-Permethrin, Cypermethrin, Phenothrin, Resmethrin, Cyfluthrin, trans-Permethrin acid Esfenvalerate, Fluvalinate, Fenpropathrin, cis-permethrin acid, 4-Phenoxybenzoyl alcohol, Diuron Derivative, 1-(3-Carboxypropyl)-3-(3,4-dichlorophenyl)-1-methylurea, Siduron, Terbuthiuron, Barban, acid trifluralin, 2,6-dinitro-N-propyl-N-(2-carboxyethyl)-4-(trifluoromethyl)benzenamine, TR-13, 2-ethyl-7-nitro-1-propyl-5-(trifluoromethyl)-1H-benzimidazole, benefin, 2,6-dinitro-N-butyl-N-ethyl-4-(trifluoromethyl)benzenamine, TR-2, 2,6-dinitro-N-propyl-4-(trifluoromethyl)benzenamine, ethalfluaralin, 2,6-dinitro-N-ethyl-N-(2-methyl-2-propenyl)-4-(trifluoromethyl) benzenamine, TR-40, N-(2,6-dinitro-4-(trifluoromethyl) phenyl)-N-propylpropanamide, TR-15, 2-ethyl-4-nitro-6-(trifluoromethyl)-1H-benzimidazole, TR-3, 2,6-dinitro-4-(trifluoromethyl)benzenamine, TR-6, 3-nitro-5-(trifluoromethyl)-1,2-benzenediamine, TR-9, 5-(trifluoromethyl)-1,2,3-benzenetriamine, TR-21, 4-(dipropylamino)-3,5-dinitrobenzoic acid, TR-36M, 3-methoxy-2,6-dinitro-N,N-dipropyl-4-(trifluoromethyl)benzenamine, oryzalin, 3,5-dinitro-4-(dipropylamino)benzenesulfonamide, pendimethalin, 2,6-dinitro-N-(1-ethylpropyl)-3,4-dimethylbenzenamine, penta galloyl glucose, Pyrene Pyrene-1-carboxaldehyde, Phenanthrene, Benzo(a)pyrene, 3,4-Benzopyrene, Anthracene, 3,4-Benzopyrene, Acenaphthene, Fluorene, Chrysene, 1,2-Benzphenanthrene, Benzo[g,h,i]perylene, Benzo[e]pyrene, Acenaphthylene, Fluoranthene, Benzo(j,k)fluorene, Indeno-1,2,3-cd-pyrene, 1,10-(1,2-Phenylene)pyrene, Benzo[a]anthracene, 1,2-Benzanthracene, Benzo(k)fluoranthene, Naphthalene, Benzo[a]fluoranthene, Dibenzo[ah]anthracene, 1,2:5,6-Dibenzanthracene, 2,3-Diaminonaphthalene, 2,6-Dinitroaniline, 17-beta-estradiol (ED), estra-1,3,5(10)-triene-3,17-beta-diol, Trifluralin derivative, 2,6-dinitro-4-tri-fluoromethylaniline, Trifluralin derivative, N-(2,6-dinitro-4-trifluoromethylphenyl)-6-aminohexanoic acid, Trifluralin derivative, N-(2,6-dinitro-4-trifluoromethylphenyl)-N-methyl-6-aminohexanoic acid, Trifluralin derivative, N-(2,6-dinitro-4-trifluoromethylphenyl)-N-propyl-6-aminohexanoic acid, Trifluralin derivative, N-(2,6-dinitro-4-trifluoromethylphenyl)-6-aminohexanoic acid methyl ester, Trifluralin derivative, N-(2,6-dinitro-4-trifluoromethylphenyl)-6-aminohexanoic acid tert-butyl ester, Benfluralin, Ethalfluralin, Trifluralin derivative, 2,6-Dinitro-4-trifluoromethylphenol, Isopropalin, Aniline, 2-Hydroxybenzotrifluoride, N-propyl-6-aminohexanoic acid, N-methyl-6-aminohexanoic acid, MHPG Derivatives, D-MHPG (D-3-methoxy-4-hydroxyphenylglycol), MHPG Derivatives, L-MHPG (L-3-methoxy-4-hydroxyphenylglycol), MHPG Derivatives, DL-MHPG (DL-3-methoxy-4-hydroxyphenylglycol), Isomeric mixture of D-MHPG and L-MHPG forms, MHPG Derivatives, DL-MHPG-SO4 (DL-3-methoxy-4-hydroxyphenylglycol-sulfate) Modification can include Isomeric mixture of D-MHPG-SO4 and L-MHPG-SO4 forms, Serotonin, 5-HT, 5-hydroxydopamine (5-4HDA), 3,4-dihydroxyphenylglycol (DOPEG), Dopamine, 4-(2-aminoethyl)pyrocatechol; 3-hydroxytyramine; 3,4-dihydroxyphenethylamine; L-3,4-dihydroxyphenylalanine, L-DOPA, Vanillomandelic acid, DL-VMA, Homovanillic acid, Norepinephrine, DL-NE, D-Epinephrine, D-E, 3-methoxytyramine, MTA, 3-methoxytyrosine, MTyr, 3,4-dihydroxymandelic acid, DL-DOMA, 3,4-dihydroxyphenyl acetic acid, DOPAC, L-Phenylalanine, Tyramine, p-tyramine; 4-(2-Aminoethyl)phenol, D-Mandelic acid, Homocatechol, Octopamine, DL-Octopamine, Azinphos-Ethyl, S-(3,4-dihydro-4-oxobenzo[d]-[1,2,3]-triazin-3-ylmethyl) O,O-diethyl phosphorodithioate, Phosmet, O,O-dimethyl S-phthalimidomethyl phosphorodithioate, Folpet, N-[(Trichloromethyl)thio]phthalimide, Tetramethrin, (1-Cyclohexene-1,2-dicarboximido)methyl-2,2-dimethyl-3-(2-methylpropenyl)-cyclopropanecarboxylate, N-(bromomethyl)phthalimide, N-(Chloromethyl)benzazimide, 6-(N-phthalimidoylmethylthio)hexanoic acid (MFH), Bromacil, 5-bromo-3-sec-butyl-6-methyluracil, Bromacil Derivative, 5-bromo-6-(hydroxymethyl)-3-(1-methylpropyl)-2,4(1H,3H)-pyrimidineone, Bromacil Derivative, 5-bromo-3-(2-methylpropyl-6-methyl-2,4(1H,3H)-pyrimidinedione, Metabolite of Bromacil, Bromacil Derivative, 3-hydroxy-1-methylpropyl-6-methyl-2,4(1H,3H)-pyrimidinedione (Modification Bromacil Metabolite), Bromacil Derivative, 6-methyl-3-(1-methylpropyl)-2,4(1H,3H)-pyrimidinedione (Modification Bromacil Metabolite), Terbacil Derivative, [5-chloro-3-(1,1-dimethylethyl)-6-(hydroxymethyl)-2,4 (1H,3H)-pyrimidinedione, Terbacil, 3-tert-butyl-5-chloro-6-methyluracil, Bromacil Derivative, Ethyl-5-(5-Bromo-6-methyl-3-(1-methylpropyl)-2,4(1H,3H)-pyrimidinedione-1-yl)hexanoate, Bromacil Derivative alkylated at N-1, Bromacil Derivative 5-(5-Bromo-6-methyl-3-(1-methylpropyl)-2,4(1H,3H)-pyrimidinedione-1-yl)hexanoic Acid (Modification Bromacil Derivative alkylated at N-1), Bromacil Derivative, -Bromo-6-(Bromomethyl-3-(1-methylpropyl)-2,4(1H,3H)-pyrimidinedione (Modification Bromacil Derivative substituted at the 6-methyl position), Bromacil Derivative-[5-Bromo-3-(1-methylpropyl)-2,4(1H,3H)-pyrimidinedione-6-yl]-2-carboxylpropanoic Acid (Modification Bromacil Derivative substituted at the 6-methyl position), 3-[5-Bromo-3-(1-methylpropyl)-2,4 (1H,3H)-pyrimidinedione-6-yl]propanoic Acid (Modification Bromacil Derivative substituted at the 6-methyl position), Bromacil Derivative 5-Bromo-1,6-dimethyl-3-(1-methylpropyl)-2,4(1H,3H)-pyrimidinedione, Bromacil Derivative 5-Bromo-1-butyl-6-methyl-3-(1-methylpropyl)-2,4(1H,3H)-pyrimidinedione, Butachlor, N-butoxymethyl-2-chloro-2',6'-diethylacetanilide, Amidochlor, N-[(acetylamino)methyl]-2-chloro-N-(2,6-diethylpenyl)acetamide, Nicarbazin, N,N'-bis(4-nitrophenyl)-compound with 4,6-dimethyl-2(1H)-pyrimidinone (Modification (DNC+HDP)), 2-hydroxy-4,6-dimethylpyrimidine, HDP, Imazalil, [1-(beta-allyloxy-2,4-dichlorophenethyl)imidazole], Imazalil Derivative, EIT-0073 (Modification Have a —O(CH2)5-COOH group instead of original —OCH2CH—CH2 group of imazalil), Penconazole, (RS)-1-(2,4-dichloro-β-propylphenethyl)-1H-1,2,4-triazole, Hexaconazole, (RS)-2-(2,4-dichlorophenyl)-1-(1H-1,2,4-triazol-1-yl)hexan-2-ol, Propiconazole, cis-trans-1-[2-(2,4-dichlorophenyl)-4-propyl-1,3-dioxolan-2-ylmethyl]-1H-1,2,4-triazole, Diclobutrazol, 2RS,3RS)-1-(2,4-dichlorophenyl)-4,4-dimethyl-2-(1H-1,2, 4-triazol-1-yl)pentan-3-ol, Triflumizole, (E)-4-chloro-α,α, α-trifluoro-N-(1-imidazol-1-yl-2-propoxyethylidene)-o-toluidine, Imazalil Derivative, EIT-0183, Imazalil Derivative, EIT-0180, Imazalil Derivative, EIT-0111, Imazalil Derivative, EIT-0158, Imazalil Derivative, K-240, Chlorothalonil, tetrachloroisophthalonitrile Modification On benzene Ring R1=CN R2=Cl R3=CN R4=Cl R5=Cl R6=Cl), Chlorothalonil Derivative-2,4,5,6-tetrachloro-3-cyanobenzamide (Modification On benzene Ring R1=CONH2 R2=Cl R3=CN R4=Cl R5=Cl R6=Cl), Chlorothalonil Derivative-2,5,6-trichloro-4-hydroxyisophthalonitrile (Modification On benzene Ring R1=CN R2=Cl R3=CN R4=OH R5=Cl R6=Cl), 3-carbamyl-2,4,5-trichlorobenzoic acid (Modification On benzene Ring R1=CONH2 R2=Cl R3=COOH R4=H R5=Cl R6=Cl), Pentachloronitrobenzene (Modification On benzene Ring R1=NO2 R2=Cl R3=Cl R4=Cl R5=Cl R6=Cl), Benzene hexachloride, Hexachlorobenzene, BHC, Lindane (Modification On benzene Ring R1=Cl R2=Cl R3=Cl R4=Cl R5=Cl R6=Cl), 2,4,5,6-tetrachlorophenol (Modification On benzene Ring R1=OH R2=Cl R3=H R4=Cl R5=Cl R6=Cl), Carbaryl Derivative, Ethylcarbamate (Modification R1=OCONHCH2CH3 R3=H), 1-Naphthol, 1-naphthaleneacetamide, -(1-naphthyl) acetamide, Carbaryl Derivative, 1-Methylcarbonate (Modification R1=OCOOCH3 R2=H, Carbaryl Derivative, 1-Ethylcarbonate (Modification R1=OCOOCH2CH3 R2=H), Carbaryl Derivative 2-Ethylcarbonate (Modification R1=H R2=OCOOCH2CH3, Carbaryl Derivative, 1-Ethylthiocarbonate (Modification R1=OCOSCH2CH3 R2=H), Carbaryl Derivative, 2-Ethylthiocarbonate (Modification R1=H R2=OCOSCH2CH3), Naptalam, N-1-naphthylphthalamic acid, Carbaryl Derivative, 3-hydroxycarbaryl (Modification R1=OCONHCH3 R2=H R3=OH R4=H R5=H), Carbaryl Derivative 4-hydroxycarbaryl (Modification R1=OCONHCH3 R2=H R3=H R4=OH R5=H), Carbaryl Derivative 5-hydroxycarbaryl (Modification R1=OCONHCH3 R2=H R3=H R4=H R5=OH), Carbaryl Derivative, 1-(5-Carboxypentyl)-3-(1-naphthyl)urea (Modification R1=NHCONH(CH2)5COOH R2=H), (Structurally related s-triazines)-Aziprotryn, 4-azido-N-isopropyl-6-methylthio-1,3,5-triazin-2-ylamine (Modification R1=—SCH3 R2=—N3 R3=—CH(CH3)2), (Structurally related s-triazines), 2-(ethylamino)-4-(methylthio)-6-amino-triazine (Modification R1=—SCH3 R2=—NH—C2H5 R3=—NH2), (Structurally related s-triazines)-2-amino-4-(methylthio)-6-(isopropylamino)triazine (Modification R1=—SCH3 R2=—NH2 R3=—NH—CH(CH3)2), (Structurally related s-triazines)-2-amino-4-methoxy-6-(isopropylamino)triazine (Modification R1=—OCH3 R2=—NH2 R3=—NH—CH(CH3)2), TCP Derivative (3,5,6-trichloro-2-pyridinol Derivative), 3-(3,5-dichloro-6-hydroxy-2-pyridyl)thiopropanoic Acid, p-nitrosuccinanilic acid (PNA-S), PNA-S, PNA-C, p-nitro-cis-1,2-cyclohexanedicarboxanilic acid, Nitroaniline Derivative, 2-nitroaniline, o-Nitroaniline, Nitroaniline Derivative-3-nitroaniline, m-Nitroaniline, Nitroaniline Derivative-4-nitroaniline, p-Nitroaniline, Aeromatic Alcohols, 4-nitrobenzyl alcohol, Aeromatic Alcohols-4-nitrophenethyl alcohol, Aeromatic Alcohols 2-nitrobenzyl alcohol, Aeromatic Alcohols, 3-nitrobenzyl alcohol, Urea Derivative-1-benzyl-3-(4-nitrophenyl)urea, Urea Derivative-1-(3-chlorophenyl)-3-(2-methoxy-5-nitrophenyl)urea, Urea Derivative-1-(3-chlorophenyl)-3-(4-methoxy-3-nitrophenyl)urea, Urea Derivative-1-(4-chlorophenyl)-3-(4-nitrophenyl)urea, Urea Derivative-(2-fluorophenyl)-3-(2-mehtoxy-4-nitrophenyl) urea, 1-(3-mehtoxyphenyl)-3-(3-nitrophenyl)urea, Carbofuran Derivative m Carbofuran-phenol, Carbofuran-hydroxy, Carbofuran-keto, Carbosulfan, 3-dihydro-2,2-dimethylbenzofuran-7-yl (dibutylaminothio) methylcarbamate, Benfuracarb, N-[2,3-dihydro-2,2-dimethylbenzofuran-7-yloxycarbonyl(methyl)aminothio]-N-isopropyl-β-alaninate, Furathiocarb, 2,3-dihydro-2,2-dimethyl-7-benzofuranyl 2,4-dimethyl-5-oxo-6-oxa-3-thia-2,4-diazadecanoate, Carbofuran Derivative, 4-[[(2,3-Dihydro-2,2-dimethyl-7-benzofuranyloxy)carbonyl]-amino]butanoic Acid (BFNB) (Modification n=3 X=CH2), Endrin, nendrin, (1R,4S,4aS,5S,6S,7R,8R,8aR)-1,2,3,4,10,10-hexachloro-1,4,4a,5,6,7,8,8a-octahydro-6,7-epoxy-1,4:5,8-dimethanonaphthalene, Heptachlor, 1,4,5,6,7,8,8-heptachloro-3a,4,7,7a-tetrahydro-4,7-, Chlordane, 1,2,4,5,6,7,8,8-octachloro-2,3,3a,4,7,7a-hexahydro-4,7-methanoindene, Endosulfan (Modification isomer mix of alpha and beta forms), Endosulfan (Modification alpha isomeric form), Endosulfan (Modification beta isomeric form), Endosulfan Derivative, Endosulfan sulfate (Modification sulfate form), Endosulfan Derivative, Endosulfan diol, Diol metabolite of endosulfan, Endosulfan Derivative, Endosulfan ether (Modification ether metabolite of endosulfan), Endosulfan Derivative, hydroxy ether, hydroxy ether metabolite of endosulfan, Endosulfan Derivative, Endosulfan lactone (Modification lactone metabolite of endosulfan), Aldrin, Dieldrin, Fenvalerate isomers Modification 1S,2R isomer R: Ph), Fenvalerate isomers (Modification 1R,2S isomer R: Ph), Fenvalerate isomers (Modification 1S,2R isomer R: Ph), Fenvalerate isomers (Modification 1S,2R/S isomer R: Ph), Fenvalerate isomers (Modification 1R,2R/S isomer R: Ph), Fenvalerate isomers, fenvalerate (Modification 1R/S, 2R/S isomer R: Ph), Thiabendazole, 2-(thiazol-4-yl)benzimidazole, Thiabendazole Derivative, 5-hydroxythiabendazole (Modification 5-OH-TBZ), Thiabendazole Derivative, 5-NH2-TBZ, Thiabendazole Derivative, methyl benzimidazole carbamate, Albendazole, Mebendazole, Fenbendazole, Thiabendazole Derivative, 2-succinamidothiabendazole, Thiabendazole Derivative, 2-succinamidothiabendazole, Cambendazole, Fenvalerate Haptens, Cyano[3-(4-aminophenoxy)phenyl]methyl (S)-4-Chloro-alpha-(1-methylethyl)benzeneacetate (4-Aminoesfenvalerate), Fenvalerate Haptens, Benzyl 4-[3-[Cyano[(S)-2-(4-chlorophenyl)-3-methyl-1-oxobutanoxy]methyl]]phenoxy]benzenepropanoate, Fenvalerate Haptens, Benzyl 3-[Cyano[(S)-2-(4-chlorophenyl)-3-methyl-1-oxobutanoxy]methyl]]phenoxyacetate, Fenvalerate Haptens, 3-[Cyano[(S)-2-(4-chlorophenyl)-3-methyl-1-oxobutanoxy]methyl]]phenoxyacetic Acid, Fenvalerate Haptens, Benzyl 6-[3-[Cyano[(S)-2-(4-chlorophenyl)-3-methyl-1-oxobutanoxy] methyl]]phenoxy] hexanoate, Fenvalerate Haptens, 6-[3-[Cyano[(S)-2-(4-chlorophenyl)-3-methyl-1-oxobutanoxy]methyl]]phenoxy] hexanoic Acid Fenvalerate Haptens, 4-[3-[Cyano[(S)-2-(4-chlorophenyl)-3-methyl-1-oxobutanoxy]methyl]]phenoxy] benzenepropanoic Acid, (S)-fenvalerate Acid, (Structurally related s-triazines), atrazine mercapturate Modification R1=—SCH2CH(NHCOCH3)COOH R2=—NHCH2CH3 R3=—NHCH(CH3)2, Fenthion Hapten, -Methyl O-[3-methyl-4-(methylthio)phenyl] N-(3-carboxypropyl)phosphoramidothioate Modification referred as Hapten B, Fenthion Derivative, Oxidized Fenthion, Fenthion Derivative, Oxidized oxidized Fenthion, pirimiphos-ethyl, 4-(Methylthio)-m-cresol, Chlorpyrifos Derivative, Chlorpyrifos-oxon, Fenchlorphos, O,O-dimethyl O-2,4,5-trichlorophenyl phosphorothioate, Trichloronate, O-Ethyl O-2,4,5-trichlorophenyl ethyl-phosphonothioate, Dichlofenthion, O-2,4-dichlorophenyl O,O-diethyl phosphorothioate, Parathion, O,O-diethyl O-4-nitrophenyl phosphorothioate; Thiophos, Chlorpyrifos Derivative Modification Synthesis of AR1 is described, Chlorpyrifos Derivative, O-Ethyl O-(3,5,6-Trichloro-2-pyridyl)O-(3-Carboxypropyl)Phosphorothioate; (PO), Chlorpyrifos Derivative-O-Ethyl O-(3,5,6-Trichloro-2-pyridyl)N-(5-Carboxyethyl) Phosphoramidothioate; (PN1) (Modification Amide linkage of thiophosphate reagents), Chlorpyrifos Derivative, O-Ethyl O-(3,5,6-Trichloro-2-pyridyl)N-(2-Carboxyethyl) Phosphoramidothioate; (PN1) (Modification Amide linkage of suitable thiophosphate reagents), Triadimefon, (RS)-1-(4-chlorophenoxy)-3,3-dimethyl-1-(1H-1,2,4-triazol-1-yl)butan-2-one, GR151004, (4-[[5-[3-[2-(dimethylamino)ethyl]]-5-benzofuranyl]-3-pyridinyl]acetyl]morpholine dihydrochloride, Diflubenzuron, 1-(4-chlorophenyl)-3-(2,6-difluorobenzoyl)urea, (Structurally related s-triazines)-SprAAT (Modification R1=SCH2CH2COOH R2=NH2 R3=NH2), (Structurally related s-triazines), SBeAAT (Modification R1=S(C6H4)COOH R2=NH2 R3=NH2), (Structurally related s-triazines), SAAT (Modification R1=SH R2=NH2 R3=NH2), (Structurally related s-triazines), CDAT (Modification R1=Cl R2=NH[C(O)CH3] R3=NH2), (Structurally related s-triazines)-CDET (Modification R1=Cl R2=NH[C(O)CH3] R3=NH(CH2CH3), (Structurally related s-triazines)-CDIT (Modification R1=Cl R2=NH[C(O)CH3] R3=NH(CH(CH3)2)), (Structurally related s-triazines), CDDT (Modification R1=Cl R2=NH[C(O)CH3] R3=NH[C(O)CH3]), (Structurally related s-triazines)-ammeline, OAAT (Modification R1=OH R2=NH2 R3=NH2), (Structurally related s-triazines)-ammelide, OOAT (Modification R1=OH R2=OH R3=NH2), (Structurally related s-triazines)-cyanuric acid, OOOT (Modification R1=OH R2=OH R3=OH), (Structurally related s-triazines), melamine, AAAT (Modification R1=NH2 R2=NH2 R3=NH2), Structurally related s-triazines-N-isoropylammeline, OIAT (Modification R1=OH R2=NH[CH(CH3)2] R3=NH2, Structurally related s-triazines-N-ethylammeline, OEAT (Modification R1=OH R2=NHCH2CH3 R3=NH2), Structurally related s-triazines, N-ethylammelide, OOET (Modification R1=OH R2=OH R3=NHCH2CH3), Structurally related s-triazines)-cyromazine, CyPAAT (Modification R1=NH(C3H5) R2=NH2 R3=NH2), Structurally related s-triazines-diamino-s-triazine, HAAT (Modification R1=H R2=NH2 R3=NH2), PCB congeners, 2,5,3',4'-tetrachlorobiphenyl (Modification IUPAC no.: 70), PCB congeners 2,4,5,3',4'-pentachlorobiphenyl (Modification IUPAC no.: 118), PCB congeners-2,2',5,5'-tetrachlorobiphenyl (Modification IUPAC no.: 52), PCB congeners, 6-[3,3',4'-Trichlorobiphenyl-4-yl)oxy]hexanoic Acid, Metolazone, Brand Names: Mykrox; Zaroxolyn, Furfuryl benzoate, DDT Metabolites, DDA, Paraquat, 1,1'-dimethyl-4,4'-bipyridinium ion, Diethylcarbamazine, THP, 2,4,6-triphenyl-N-(4-hydroxyphenyl)-pyridinium, o-DNCP, -dinitrocarboxyphenol, PCB congeners, 3-chlorobiphenylol (Modification IUPAC No. 2), PCB congeners, 3,4'-dichlorobiphenyl (Modification IUPAC No. 13), PCB congeners, 3,5-dichlorobiphenyl (Modification IUPAC No. 14), PCB congeners, 3,4,5,3',4'-pentachlorobiphenyl (Modification IUPAC No. 126), 2,3,3',4'-tetrachlorobiphenyl (Modification IUPAC No. 56), 2',3,4,5-tetrachlorobiphenyl (Modification IUPAC No. 76), 3,3',5,5'-tetrachlorobiphenyl (Modification IUPAC No. 80), 2,4,5,2',5'-pentachlorobiphenyl (Modification IUPAC No. 101), 2,3,3',4,4'-pentachlorobiphenyl (Modification IUPAC No. 105), 2,3,6,3',4'-pentachlorobiphenyl (Modification IUPAC No. 110), 3,3',4,5,5'-pentachlorobiphenyl (Modification IUPAC No. 127), 3,4,5,3',4',5'-hexachlorobiphenyl (Modification IUPAC No. 169), 2,3,3',4,4',5-hexachlorobiphenyl (Modification IUPAC No. 156), 3,4,3',4'-tetrabromobiphenyl, 3,4,5,3',4',5'-hexabromobiphenyl, 2,4,5,2',4',5'-hexabromobiphenyl, Dibenzofurans and Dioxins, 2,3,7,8-tetrachlorobenzofuran, 2,3,7,8-tetrachlorodibenzo-p-dioxin, 3,4',5-trichloro-4-biphenylol, 3,3',5,5'-tetrachloro-4,4'-biphenyldiol, 3,4,3',4'-tetrachlorodiphenyl ether, 1-2-dichlorobenzene, 1,4-dichlorobenzene, 1,2,4-trichlorobenzene, 3,4-dichloroaniline, DDT Metabolites, 4,4'-DDT, 4,4'-DDD Retronecine, 3,4-dichlorobiphenyl Modification IUPAC No. 12, 3,4,3'-trichlorobiphenyl (Modification IUPAC No. 35), PCB Congeners, 3,4,4'-trichlorobiphenyl (Modification IUPAC No. 37), 3,4,3',5-tetrachlorobiphenyl (Modification IUPAC No. 78), 3,4,3',5'-tetrachlorobiphenyl (Modification IUPAC No. 79), 3,4,4',5-tetrachlorobiphenyl (Modification IUPAC No. 81), DDT Metabolites, p,p'-DDT (Modification p,p'-dichlorodiphenyltrichloroethane), o,p'-DDT Modification o,p'-dichlorodiphenyltrichloroethane, p,p'-DDE Modification p,p'-DDE, o,p'-DDE Modification o,p'-DDE, p,p'-DDD Modification p,p'-DDD, o,p'-DDD Modification o,p'-DDD, Dicofol, 4,4-dichloro-a-(trichloromethyl)benzhydrol, Cyprazine, 6-chloro-N-cyclopropyl-N'-(1-methylethyl)-1,3,5-triazine-2,4-diamine, Structurally related s-triazines, Dipropetryn, 6-(ethylthio)-N,N'-bis(1-methylethyl)-1,3,5-triazine-2,4-diamine, Trietazine, 6-chloro-N,N,N'-triethyl-1,3,5-triazine-2,4-diamine, 6-Hydroxyatrazine, hexazinone, 3-cyclohexyl-6-dimethylamino-1-methyl-1,3,5-triazine-2,4 (1H,3H)-dione, TNT, 2,4,6-Trinitrotoluene, Tetraconazole (M14360), 1-[2-(2,4-dichlorophenyl)-3-(1,1,2,2-tetrafluoroethoxy)propyl]-1H-1,2,4-triazole, DTP, 2-(2,4-dichlorophenyl)-3-(1H-1,2,4-triazol-1-yl)propanol, Imazalyl, fenarimol, (RS)-2,4'-dichloro-α-(pyrimidin-5-yl)benzhydryl alcohol, Lupanine metabolites, (+)-lupanine (Modification R=H), Lupanine metabolites, (+)-13-hydroxylupanine (Modification R=OH), Lupanine metabolites, hemisuccinate ester of (+)-13-hydroxylupanine (Modification R=OCO—(CH2)2.COOH), Lupanine metabolites, cis-hexahydrophthalate ester of (+)-13-hydroxylupanine (Modification R=OCO.C6H10.COOH), Lupanine metabolites, alpha-iso-lupanine, Lupanine metabolites, -hydroxylupanine, Sparteine, Cysteine, multiflorine, epilupinine, (Structurally related s-triazines), CYANAZINE ACID Modification R1=Cl R2=NHCH2CH3 R3=NHCCOOH(CH3)2, Structurally related s-triazines Modification R1=Cl R2=NHCH2CH3 R3=NH(CH2)3COOH, Structurally related s-triazines (Modification R1=Cl R2=NHCH2CH3 R3=NHCH2COOH), (Structurally related s-triazines) (Modification R1=Cl R2=NHCH2CH3 R3=NH(CH2)4COOH), norflurazon, 4-chloro-5-(methylamino)-2-[3-(trifluoromethyl)phenyl]-3(2H)-pyridazinone, norflurazon derivative, desmethyl-norflurazon, metflurazon, -chloro-5-(dimethylamino)-2-[(3-trifluoromethyl)phenyl]-3(2H)-pyridazinone, Pyrazon, Chloridazon, 5-amino-4-chloro-2-phenyl-3(2H)-pyridazinone (active ingradient), dichlorophenyl-pyridazone, (Structurally related s-triazines) azidoatrazine (Modification R1=N3 R2=NHCH(CH3)2 R3=NHCH2CH3), ALACHLOR 2-chloro-2',6'-diethyl-N-methoxymethylacetanilide, trichothecolone (Modification R1=H R2=OH R3=H R4=O R5=H), DON derivative, acetyl-T-2, DON derivative, T-2 tetrol tetraacetate, Chlorpyrifos derivatives, mono-dechloro-CP, Bromophos derivative, Bromophos-methyl, Bromophos derivative, Bromophos-ethyl dicapthon, -2-chloro-4-nitrophenyl O,O-dimethyl phosphorothioate, tetrachlorvinphos, (Z)-2-chloro-1-(2,4,5-trichlorophenyl)vinyl dimethyl phosphate, triclopyr, 3,5,6-trichloro-2-pyridyloxyacetic acid, picloram, 4-amino-3,5,6-trichloropyridine-2-carboxylic acid, Formononetin, Biochanin A, 5, 7-dihydroxy-4'-methoxyisoflavone (Modification It is the 4'-methyl ether of genistein), equol, (7-hydroxy-3-(4'-hydroxyphenyl)-chroman, 2'methoxyformononetin, Daidzein, 7-hydroxy-3-(4-hydroxyphenyl)-4H-1-benzopyran-4-one, geninstein, quercetin, 3,3',4',5,7-Pentahydroxyflavone; 3,5,7,3',4'-Pentahydroxyflavone; matheucinol, coumestrol (Structurally related s-triazines), Hydroxysimazine (Modification R1=OH R2=NHCH2CH3 R3=NHCH2CH3, angustifoline, Alodan, 1-Methyl-4-phenyl-4-carboethoxypiperidine hydrochloride, Zearalenone, RAL, F-2 Toxin, Fenpropimorph, (RS)-cis-4-[3-(4-tert-butylphenyl)-2-methylpropyl]-2,6-dimethylmorpholine, Tridemorph, 2,6-dimethyl-4-tridecylmorpholine, 2,6-dimethylmorpholine, Amorolfine, Fenpropidine, (RS)-1-[3-(4-tert-butylphenyl)-2-methylpropyl]piperidine, (Structurally related s-triazines) (Modification R1=Cl R2=Cl R3=NHCH2CH3, (Structurally related s-triazines) Modification R1=Cl R2=Cl R3=NHCH(CH3)2, (Structurally related s-triazines) Modification R1=Cl R2=NHCH2CH3 R3=NH(CH2)5COOH, (Structurally related s-triazines) Modification R1=Cl R2=NHCH(CH3)2 R3=NHCH2COOH, (Structurally related s-triazines) (Modification R1=Cl R2=NHCH(CH3)2 R3=NH(CH2)5COOH), Structurally related s-triazines, cyanazine amide (Modification R1=Cl R2=NHCH2CH3 R3=NHCCONH2(CH3)2), hydroxycyanazine acid (Modification R1=OH R2=NHCH2CH3 R3=NHCCOOH(CH3)2), deethylsimazine (Modification R1=Cl R2=NH2 R3=NHCH2CH3), Albendazole sulfoxide, [5-(propylthionyl)-1H-benzimidazol-2-yl]-, methylester, Albendazole sulfone, 5(6)-alkylbenzimidazoles, 2-amino-5-(propylthio)benzimidazole, 5(6)-alkylbenzimidazoles, 2-amino-5-(propylsulfonyl) benzimidazole, oxibendazole, 5-propoxy-benzimidazole-2-methyl carbamate, 5(6)-arylbenzimidazoles, fenbendazole sulfone (Modification sulfone metabolite of fenbendazole), 5(6)-arylbenzimidazoles, 4'-hydroxyfenbendazole, 5(6)-arylbenzimidazoles, oxfendazole (Modification Oxfendazole is the sulfoxide metabolite of fenbendazole), 5(6)-arylbenzimidazoles, flubendazole, benzimidazole Metabolites, 2-aminobenzimidazole, benzimidazole Metabolites, 5-aminobenzimidazole, benzimidazole Metabolites, 2-acetylbenzimidazole, Benzophenone, Diphenylmethanone; phenyl ketone; Diphenyl ketone; Benzoylbenzene, Benzaldehyde, benzoic aldehyde, 4-Bromo-2,5-dichlorophenol, Acephate, O,S-dimethyl acetylphosphoramidothioate, methamidophos, O,S-dimethyl phosphoramidothioate, Dichlorvos, 2,2-dichlorovinyl dimethyl phosphate, Phenthoate, S-α-ethoxycarbonylbenzyl O,O-dimethyl phosphorodithioate, EPN, Ethyl p-nitrophenyl thionobenzenephosphonate, Bioresmethrin, -benzyl-3-furylmethyl (1R,3R)-2,2-dimethyl-3-(2-methylprop-1-enyl) cyclopropanecarboxylate (Modification The unresolved isomeric mixture of this substance has the ISO common name resmethrin), flufenoxuron, 1-[4-(2-chloro-α,α,α-trifluoro-p-tolyloxy)-2-fluorophenyl]-3-(2,6-difluorobenzoyl) urea, Amitrole, 1H-1,2,4-triazol-3-ylamine, molinate, S-ethyl azepane-1-carbothioate, molinate derivative (Modification S-2-carboxyethyl hexahydroazepine-1-carbothioate), molinate derivative (Modification S-5-carboxypentyl hexahydroazepine-1-carbothioate) molinate derivative (Modification molinate sulfone), molinate derivative (Modification S-(p-aminobenzyl) hexahydroazepine-1-carbothioate), molinate derivative (Modification S-2-(p-aminophenyl) ethyl hexahydroazepine-1-carbothioate), hexamethylenimine, thiobencarb (Bolero), butylate (Sutan), EPTC (Eptam), cycloate (Roneet), pebulate (Tillam), vernolate (Vernam), Aflatoxin M1, AFM1 (Modification AFM1), Aflatoxin B1, AFB1 (Modification AFB1), Aflatoxin G1, AFG1 (Modification AFG1), Aflatoxin M2, AFM2 (Modification AFM2), Aflatoxin B2, AFB2 (Modification AFB2), Aflatoxin G2, AFG2 (Modification AFG2), Aflatoxin B2alpha, AFB2alpha (Modification AFB2alpha), Aflatoxin G2alpha, AFG2alpha (Modification AFG2alpha), KB-6806, 6-amino-5-chloro-1-isopropyl-2-(4-methyl-1-piperazinyl) (Modification R1=NH2 R2=CH(CH3)2 R3=CH3), KB-6806 (Benzimidazole) Derivatives Modification R1=NH2 R2=CH2CH(CH3)2 R3=CH3, Hapten Name KB-6806 (Benzimidazole) Derivatives (Modification R1=NH2 R2=CH(CH2CH3)2 R3=CH3), KB-6806 (Benzimidazole) Derivatives (Modification R1=NHCOCH3 R2=CH(CH3)2 R3=CH3), KB-6806 (Benzimidazole) Derivatives (Modification R1=H R2=CH(CH3)2 R3=CH3), KB-6806 (Benzimidazole) Derivatives (Modification R1=NH2 R2=CH(CH3)2 R3=CH3), KB-6806 (Benzimidazole) Derivatives Modification R1=NH2 R2=CH(CH3)2 R3==N(—>O) CH3 (N-OXIDE), KB-6806 (Benzimidazole) Derivatives Modification R1=NH2 R2=CH(CH3)2 R3=H, KB-6806 (Benzimidazole) Derivatives Modification R1=NH2 R2=CH2CH3 R3=CH3, Aminoparaoxon, phosphoric acid, O,O-diethyl O-(4-aminophenyl) ester, Methylparathion, phosphorothioic acid, O,O-dimethyl O-(4-nitrophenyl) ester, Diethyl phenylphosphate, phenylphosphonic acid, O,O-diethyl ester, Diethyl phosphate, ethylphosphonic acid, O,O-diethyl ester, p-Nitrophenyl phosphate, phosphonic acid, O-(4-nitrophenyl)ester, Phorate, phosphorodithioic acid, O,O-diethyl S-[(ethylthio) methyl] ester, Ethion, bis(phosphorodithioic acid), S,S'-methylene O,O,O',O'-tetraethyl ester, Carbophenthion, phosphorodithioic acid, O,O-diethyl S-[[(4-chlorophenyl) thio]methyl] ester, Disulfoton, phosphorodithioic acid, O,O-diethyl S-[(2-ethylthio)ethyl] ester, TS, N-[4-(Carboxymethyl)-2-thiazolyl)sulfanilamide, NS, N-(4-Nitrophenyl) sulfanilamide, Sulfamoxole, Sulfacetamide, DNP-SL, Spin labelled dinitrophenyl (Modification The synthesis of DNP-SL has been described by Balakrishnan et al (1982) formula can be found in Anglister et al. (1984)), beta ecdysone, Benzimidazole Derivative, 5(6)-[Carboxypentyl)thio]-2-(methoxycarbonyl)amino]-benzimidazole, 2-hydroxybiphenyl HBP, Atrazine Caproic acid, Lysophosphatidic acid (LPA), 1-acyl-2-hydroxy-sn-glycero-3-phosphate), berberine, Palmatine, 9-Acetylberberine, Corydaline, Coptisine, Berberrubine, 8-Oxoberberine, Papaverine, Berberine Derivative, 9-O-carboxymethyl berberine, phencyclidine, 1-(1-phenylcyclohexyl)piperidine, Methoxychlor, Endosulfan Derivative, 4-Oxobutanoic Acid,4-(4,5,6,7,8,8-Hexachloro-3a,4,7,7a-tetrahydro-4,7-methano-1H-indenyl-1-oxy), Endosulfan Derivative, 4-oxybutanoic Acid,4-(1,3,4, 5,6,7,8-Octachloro-3a,4,7,7a-tetrahydro-4,7-methanoindanyl-2-oxy, Endosulfan Derivative (Modification Hemisuccinate of Endosulfan diol), Triazole Derivatives, 5-(3-Hydroxypropyl)-3-amino-2H-1,2,4-triazole, Triazole Derivatives, 5-(3-Hydroxypropyl)-3-(2-nitrophenylsulfenyl)amino-2H-1,2,4-triazole, Triazole Derivatives, 3-Amino-5-[(3-succinyloxy)propyl]-2H-1,2,4-triazole, Triazole Derivatives, 3-amino-1,2,4-triazole-5-thiol, Triazole Derivatives, 3-[(2-nitrophenylsulfenyl) amino-2H-1,2,4-triazole-5-thiol, Triazole Derivatives, 2H-1,2,4-triazole-5-thiol, Triazole Derivatives, 4-methyl-1, 2,4-triazole-3-thiol, Triazole Derivatives, (1,2,4-triazol-2-yl)acetic acid, 1,2,4-triazole, 4-nitrophenyl 4'-carboxymethylphenyl phosphate, Triazole Derivative, 4-amino-1,2,4-triazole, Triazole Derivative, 3-acetamido-1H-1,2,4-triazole, Triazole Derivative, 3-amino-1,2,4-triazole-5-carboxylic acid hemihydrate, Triazole Derivative, 2-(4-chlorophenyl)-2-(1,2,4-triazol-1-yl)-methylhexanoic acid, succinic acid, Imidazole, L-histidine, L-glutamic acid, Permethrin derivative, 3-phenoxybenzyl 2,2-dimethylcyclopropane-1,3-dicarboxylate, 3-phenoxybenzaldehyde, flucythrinate, Chrysanthemic acid, 2,4-Dinitrophenyl, DNP, Thiram Haptens, Disodium 4-[Carbodithioato(methyl)-amino]butanoate, Thiram Haptens 5,11-Dimethyl-6,10-dithioxo-7,9-dithia-5,11-diazadodecanoic Acid, Thiram Haptens, 2-{[(Dimethylamino)carbothioyl]sulfanyl}ethanoic Acid, Thiram Haptens, 4-{[(Dimethylamino)carbothioyl] sulfanyl}butanoic Acid, Thiram Haptens, 6-{[(Dimethylamino)carbothioyl]sulfanyl}hexanoic Acid, Thiram Haptens, 11-{[(Dimethylamino)carbothioyl] sulfanyl}undecanoic Acid, Thiram Haptens, 2-{[(Dimethylamino)carbothioyl] sulfanyl}ethanoic Acid, Thiram, Tetramethylthiurammonosulfide, Tetraethylthiuram disulfide, Dimethyldithiocarbamic acid sodium salt, Dimethyldithiocarbamic acid zinc salt, Diethyldithiocarbamic acid sodium salt, N,N,N',N'-tetramethylthiourea, Nabam, Zineb, Maneb, Ethylenethiourea, Chlorpyrifos hapten, O,O Diethyl O-[3,5-Dichloro-6-[(2-carboxyethyl)thio]-2-pyridyl] Phosphorothioate, 2-Succinamidobenzimidazole, Methyl 2-Benzimidazolecarbamate, MBC, Benzimidazole, 2-benzimidazolylurea, succinamide, Ethyl carbamate, Urea, N-methylurea, N,N'-dimethylurea, Brevetoxin PbTx-3, Organophosphorous Haptens, O,O-Diethyl O-(5-carboxy-2-fluorophenyl) phosphorothioate, Chlorpyrifos-ethyl, Anandamide hapten, N-Arachidonyl-7-amino-6-hydroxy-heptanoic acid, Anandamide, Arachidonic acid, Docosatetraenoyl ethanolamide, Dihomo-gamma-linolenyl ethanolamide, 2-Arachidonyl glycerol, 2-Arachidonyl glycerol ether, Stearoyl ethanolamide, Heptadecanoyl ethanolamide, Prostaglandin E1, 3-hydroxy-2-(3-hydroxy-1-octenyl)-5-oxocyclopentaneheptanoic acid; alprostadil; PGE1, Prostaglandin D2, PGD2, Prostaglandin A2, PGA2, Prostaglandin B2, PGB2, Prostaglandin F2 alpha, 7-[3,5-dihydroxy-2-(3-hydroxy-1-octenyl)cyclopentyl]-5-heptenoic acid; dinoprost; PGF2alpha, Prostaglandin F1 alpha, PGF1alpha, 6-keto-Prostaglandin F1 alpha, 6-keto-PGF1alpha, 13,14-Dihydro-15-keto-Prostaglandin E2, 13,14-Dihydro-15-keto-PGE2, 13,14-Dihydro-15-keto-Prostaglandin F2alpha, 14-Dihydro-15-keto-PGF2alpha, 5alpha,7alpha-Dihydroxy-11-ketotetranorpostane-1,16-dioic acid, 15-keto-PGF2alpha, TXB2, Prostaglandin E2,7-[3-hydroxy-2-(3-hydroxy-1-octenyl)-5-oxocyclopentyl]-5-heptenoic acid; dinoprostone; PGE2, hCG-alpha-(59-92)-peptide (34 residues), Paraquat Derivative, Paraquat hexanoate (PQ-h), Monoquat, Diquat, 9,10-dihydro-8a, 10a-diazoniaphenanthrene, MPTP, 1-methyl-4-phenyl-1,2,5,6-tetrahydropyridine, 1,2-Naphthoquinone, N-Acetyl-S-(1,2-dihydroxy-4-naphthyl)cysteine, N-Acetyl-S-(1,4-dihydroxy-2-naphthyl)cysteine, N-Acetyl-S-(1,2-dihydroxy-1-hydroxy-1-naphthyl)cysteine, 2-Chloro-2'.6'-diethylacetanilide (CDA) Hapten, 2-[2-Chloro-(2'-6'-diethyl)acetanilido]ethanoic Acid, 2-Chloro-2'.6'-diethylacetanilide (CDA) Hapten, 2-[2-Chloro-(2'-6'-diethyl)acetanilido]butanoic Acid, 2-Chloro-2'.6'-diethylacetanilide (CDA) Hapten, 5-(4-Chloroacetamido-3,5-diethyl)phenoxypentanoic Acid, CDA, 2-Chloro-2'.6'-diethylacetanilide, HDA, 2-Hydroxy-2'.6'-diethylacetanilide, 2,6-diethyl-aniline, Hydroxyalachlor, Alachlor ESA, Alachlor ethanesulfonic acid, Isoproturon Hapten, 3-(4-Isopropylphenyl)-1-carboxypropyl-1-methyl urea, chlorotoluron, 3-(3-chloro-p-tolyl)-1,1-dimethylurea, Metoxuron, 3-(3-chloro-4-methoxyphenyl)-1,1-dimethylurea, metamitron, 4-amino-4,5-dihydro-3-methyl-6-phenyl-1,2,4-triazin-5-one, mecoprop, (RS)-2-(4-chloro-o-tolyloxy) propionic acid, propyzamide, 3,5-dichloro-N-(1,1-dimethylpropynyl)benzamide, Paraquat dichloride, MCPB, 4-(4-chloro-o-tolyloxy)butyric acid, Chlortoluron Hapten, N-(3-Chloro-4-methylphenyl)-N-methyl-N-carboxypropyl Urea, Metsulfuron, Methyl 2-[3-(4-methoxy-6-methyl-1,3,5-triazin-2-yl)ureidosulphonyl]benzoate, Captopril Haptens, Captopril-4-(Maleimidomethyl)-cyclohexane Carboxylic Acid (MCC), Captopril Haptens, Captopril Disulfide Modification, Mercaptoethanol-MCC, Mercaptoethanol-4-(Maleimidomethyl)-cyclohexane Carboxylic Acid Modification, Captopril Haptens, Captopril without MCC, Aculeatiside A, Aculeatiside B, Solamargine, Solasonine, solanine-S; purapurine, Solasodine, Khasianine, Tomatine, lycopersicin, Tomatidine, 3-O-beta-D-Glucopyranosyl-solasodine, O-alpha-L-Rhamnosyl-1(1→2)-3-O-beta-D-glucopyranosyl-solasodine, 3-O-beta-D-Galacopyranosyl-solasidine, O-beta-D-Glucopyranosyl-1(1→3)-3-O-beta-D-galacopyranosyl-solasodine, 12-Hydroxysolamargine, 12-Hydroxysolasonine, Isoanguivine, Solaverine I, Solaverine II, Xylosyl-beta-solamargine, alpha-Solanine, alpha-Chaconine, Dioscine, Indole Derivatives, beta-Indole Acetic Acid, 2-Bromo-4,6-dinitroaniline, 2-Chloro-4,6-dinitroaniline, Tetryl, 2,4,6-trinitrophenyl-n-methylnitramine, nitramine, tetralite, tetril, 2-Amino-4,6-dinitrotoluene, 2,4-Dinitroaniline, 3,5-Dinitroaniline, 2-Amino-4,6-dinitrobenzoic acid, Disperse Blue 79, N-[5-[bis[2-(acetyloxy)ethyl]amino]-2-[(2-bromo-4,6-dinitrophenyl) azo]-4-ethoxyphenyl]acetamide, 1,3-Dinitrobenzene, 2,6-Dinitrotoluene, 4-Amino-2,6-dinitrotoluene, 1,3,5-Trinitrobenzene, Nicergoline, Ethylmorphine, 8-Didehydro-4,5-epoxy-3-ethoxy-17-methylmorphinan-6-ol, Dihydromorphine, Dihydrocodeine, dihydromorphinone, Hydromorphone, Dihydrocodeinone, Hydrocodone, Naltrexone, N-cyclopropylmethyl-14-hydroxydihydromorphinone, Dextromethorphan, (±)-3-Methoxy-17-methylmorphinan, Homatropine, Endorphins Modification Derivative Type: b-Endorphin, Met-enkephalin, DALEA, D-Ala(2)-D-Leu(5)-enkephalinamide, Vincristine, 22-Oxovincaleukoblastine, leurocristine; VCR; LCR, OCT, 22-Oxacalcitriol, OCT-3-HG, 22-oxacalcitriol-3-Hemiglutarate, 24(OH)OCT, 24(OH)-22-oxacalcitriol, 1,20(OH)2-hexanor-D3, Synephrine, Epinephrine, 4-[(1R)-1-Hydroxy-2-(methylamino)ethyl]-1,2-benzenediol, Phenylephrine, Dopamine Derivative, 6-hydroxy dopamine, Tyramine derivative, 3-methoxy tyramine, Phenethylamine, Benzeneethanamine; PEA, m-tyramine, o-tyramine, dimethoxyphenethylamine, Thymidine glycol monophosphate, 5,6-Dihydroxythymidine monophosphate, Thymidine monophosphate, Thymidine glycol, Thymine glycol, 5,6-Dihydrothymidine, Thymidine, Thymine, 5-methyluracil; 2,4-dihydroxy-5-methylpyrimidine, AMP, Adenosine mono phosphate, CMP, Cytidine mono phosphate, Carbamazepine, 5-carbamoyl-5H-dibenz[b,f]azepine, Neopterin isomers, D-erythro-Neopterin, Neopterin isomers, L-erythro-Neopterin, Neopterin isomers, D-threo-Neopterin, Biopterin isomers, L-erythro-Biopterin, Biopterin isomers, D-erythro-Biopterin, Biopterin isomers, L-threo-Biopterin, Biopterin isomers, D-threo-Biopterin, Pterin-6-Carboxylic Acid, C7H5NiO3, Pterin, Thromboxane B2, (5Z,9alpha,13E,15S)-9,11,15-trihydroxythromboxa-5,13-dien-1-oic acid, 15 Ketoprostaglandin F2alpha, Fumonisin B1, macrofusine; FBI, Thyroliberin, TRH; thyrotropin-releasing factor; thyrotropin releasing hormone; TRF; protirelin; lopremone, Thyroliberin-OH, TRH-OH, Diketopiperazine, cyclo (H-P), TRH analogues, Methylated TRH, TRH analogues, TRH elongated peptides, TRH-Gly, TRH elongated peptides, TRH-Gly-Lys-Arg, TRH elongated peptides, TRH-Gly-Lys-Arg-Ala, TRH elongated peptides, P7 (Modification Q-H-P-G-L-R-F), TRH elongated peptides, P10 (Modification S-L-R-Q-H-P-G-L-R-F), TRH elongated peptides, Ps5 Modification pro-TRH[178-199], TRH elongated peptides, TRH-Ps5 (Modification pro-TRH[172-199]), Hypothalmic peptide, LHRH, Cyanoginosin-LA, Cyanoginosin-LB, Cyanoginosin-LR, Cyanoginosin-LY, Cyanoginosin-AY, Cyanoginosin-FR, Cyanoginosin-YR, Ne-acetyllysine-containing peptide, Gly-Lys (Ac)-e-aminocaproic acid (Aca)-Cys, Benzoic Acid, Benzenecarboxylic acid; phenylformic acid; dracylic acid, m-hydroxybenzoic acid, 3-hydroxybenzoic acid, o-methoxybenzoic acid, 2-methoxybenzoic acid, o-toluic acid, 2-Methylbenzoic acid, o-chlorobenzoic acid, 2-chlorobenzoic acid, o-aminobenzoic acid, 2-aminobenzoic acid, thiosalicylic acid, 2-Mercaptobenzoic acid; o-sulfhydrylbenzoic acid, Salicylamide, 2-Hydroxybenzamide, Saligenin, saligenol; o-hydroxybenzyl alcohol; Salicyl alcohol, 2-cyanophenol, 2-hydroxyphenyl acetic acid, p-hydroxybenzoic acid, p-aminobenzoic acid, 4-Aminobenzoic acid; vitamin Bx; bacterial vitamin H1, p-toluic acid, p-methylamino benzoic acid, p-chlorosalicylic acid, 4-chloro-2-hydroxybenzoic acid, 2,4-dihydroxybenzoic acid, beta-Resorcylic Acid; 2,4-dihydroxybenzenecarboxylic acid; BRA, 4-aminosalicylic acid, 4-Amino-2-hydroxybenzoic acid; p-aminosalicylic acid, Gentisic Acid, 2,5-dihydroxybenzoic acid; 5-hydroxysalicylic acid, Picolinic acid, o-Pyridinecarboxylic acid; 2-Pyridinecarboxylic acid, picolinic acid N-oxide, 3-hydroxypicolinic acid, 2-hydroxynicotinic acid, 7-methylguanine, N2-Carboxymethyl-N7-methylguanine, 2-(7-methyl-6-oxo-6,7-dihydro-1H-purin-2-ylamino)acetic acid, 7-methylxanthine, 7-methyluric acid, 7-methyladenine, Guanine, 2-Amino-1,7-dihydro-6H-purin-6-one; 2-aminohypoxanthine, Adenine, 6-aminopurine; 6-amino-1H-purine; 6-amino-3H-purine; 6-amino-9H-purine, 7-(2-Carboxyethyl)guanine, 7-CEGua, 7-Ethylguanine, 2-amino-7-ethyl-1H-purin-6(7H)-one, 7-(2,3-Dihydroxypropyl) guanine, 2-amino-7-(2,3-dihydroxypropyl)-1H-purin-6 (7H)-one, 7-(2-Hydroxyethyl)guanine, 2-amino-7-(2-hydroxyethyl)-1H-purin-6(7H)-one, 7-(2-[(2-Hydroxyethyl) amino]ethyl)-guanine, 2-amino-7-(2-(2-hydroxyethylamino)ethyl)-1H-purin-6(7H)-one, 7-Carboxymethylguanine, or 2-(2-amino-6-oxo-1,6-dihydropurin-7-yl)acetic acid. In some alternatives, the CAR or T cell receptor comprises a fragment specific for the hapten, wherein the CAR or TCR comprises 14G8, Anti 3-methylindole antibodies, 3F12, Anti 3-methylindole antibodies, 4A1G, Anti 3-methylindole antibodies, 8F2, Anti 3-methylindole antibodies, 8H1, Anti 3-methylindole antibodies, Anit-Fumonisin B1 antibodies, Anti-1,2-Naphthoquinone-antibodies, Anti-15-Acetyldeoxynivalenol antibodies, Anti-(2-(2,4-dichlorophenyl)-3(1H-1,2,4-triazol-1-yl)propanol) Antibodies (Anti-DTP antibodies), Anti-22-oxacalcitriol antibodies (As-1, 2 and 3), Anti-(24,25(OH)2D3) Antibodies (Ab11), Anti-(24,25(OH)2D3) Antibodies (Ab3), Anti-(24,25(OH)2D3) Antibodies (Ab3-4), Anti-2,4,5-Trichlorophenoxyacetic acid antibodies, Anti (2,4,5-Trichlorphenoxyacetic acid) Antibodies, Anti-(2,4,6-Trichlorophenol) Antibodies, Anti-(2,4,6-Trichlorophenol) Antibodies, Anti 2,4,6-Trinitrotoluene (TNT) Antibodies, Anti-2,4-Dichlorophenoxyacetic acid (MAb's B5/C3, E2/B5, E2/G2, F6/C10, and F6/E5), Anti (2,4-Dichlorphenoxyacetic acid) Antibodies, Anti-2-hydroxybiphenyl-antibodies, Anti-(3,5,6-trichloro-2-pyridinol) Antibodies (LIB-MC2, LIB-MC3), Anti (3,5,6-trichloro-2-pyridinol) antibodies (LIB-MC2 MAb), Anti-3-Acetyldeoxynivalenol (3-AcDON) Antibodies, Anti-3-phenoxybenzoic acid (3-PBAc)-Antibodies, Anti-4-Nitrophenol antibodies, anti-4-nitrophenyl 4'-carboxymethylphenyl phosphate antibodies, Anti-7-(Carboxyethyl)guanine (7-CEGua) antibodies (group specific for 7-meGua), Anti-7-methylguanine (7-MEGua) antibodies, Anti-ABA antibodies, Anti Acephate antibodies (Antiserum 8377), Anti-acetyllysine antibodies (mAbs AL3D5, AL11, AKL3H6, AKL5C1), Anti Aculaetiside-A antibody, Anti Aflatoxin M1(AFM1)antibodies (mAbs A1, N12, R16, FF32), Anti-agatharesinol Antibody, Anti-agatharesinol Antibody, Anti Amidochlorantibodies, Anti-Amitrole antibodies (anti 1a-BSA antibodies), Anti ampicillin Antibodies (AMPI I 1D1 and AMPI II 3B5), Anti-anandamide antibodies (9C11.C9C, 30G8.E6C, 7D2.E2b, 13C2 MAbs), Anti atrazine antibodies, Anti-atrazine antibodies, Anti-Atrazine antibodies, Anti Atrazine Antibodies, Anti-Atrazine Antibodies, Anti-Atrazine Antibodies, Anti-Atrazine Antibodies (4063-21-1 MAb cell line mAb and scAbs), Anti-Atrazine Antibodies (4D8 and 6C8 scAb), Anti Atrazine Antibodies (C193), Anti Atrazine Antibodies (In Rabbit/Sheep), Anti Atrazine Antibodies (K4E7), Anti Atrazine Antibodies (MAb: AM7B2.1), Anti Atrazine Antibodies (ScAb), Anti Atrazine Mercapturic acid antibodies, Anti (Azinphos methyl) Antibodies (MAB's LIB-MFH14, LIB-MFH110), Anti benalaxyl antibody, Anti benzimidazolecarboxylic acid, Anti benzimidazoles antibody (Ab 587), Anti-Benzo[a]pyrene antibodies, Anti Benzo(a)pyrene antibodies (10C10 and 4D5 MAbs), Anti-(Benzoylphenylurea)-Antibodies (mainly against Diflubenzuron), Anti-berberine Antibodies, Anti-beta Indole Acetic Acid Antibodies, Anti-Biopterin (L-erythro form) Antibodies, Anti-Brevetoxin PbTx-3-Antibodies, Anti Bromacil Antibodies, Anti-Bromophos Antibodies, Anti-Bromophos ethyl Antibodies, Anti Butachlor antibodies, Anti-Captopril-MCC Antibodies, Anti-Carbamazepine (CBZ)-Antibodies, Anti Carbaryl Antibodies, Anti Carbaryl Antibodies (LIB-CNH32, LIB-CNH33, LIB-CNH36, LIB-CNH37, LIB-CNH45, LIB-CNA38), Anti-Carbaryl Antibodies (LIB/CNH-3.6 MAb), Anti Carbofuran Antibodies (LIB-BFNB-52, LIB-BFNB-62, LIB-BFNB-67), Anti Carbofuran Antibodies (LIB-BFNP21), Anti-CDA-antibodies, Anti-CDA-antibodies (anti-2-[2-Chloro-(2'-6'-diethyl)acetanilido]butanoic Acid), Anti-CDA-antibodies (anti-2-[2-Chloro-(2'-6'-diethyl)acetanilido]ethanoic Acid), Anti-CDA-antibodies (anti-5-(4-Chloroacetamido-3,5-diethyl)phenoxypentanoic Acid), anti-ceftazidime antibody, Anti-(chlorodiamino-s-triazine) Antibodies (Anti-CAAT) (PAb1-8), Anti Chlorothalonil Antibodies, Anti-Chlorpyrifos antibodies, Anti-Chlorpyrifos Antibodies, Anti-Chlorpyrifos Antibodies (LIB-AR1.1, LIB-AR1.4 Mabs), Anti-Chlorpyrifos Antibodies (LIB-C4), Anti (chlorpyrifos) antibodies (LIB-C4 MAb), Anti-Chlorpyrifos Antibodies (LIB-PN1 Mabs), Anti-Chlorpyrifos Antibodies (LIB-PN2 Mabs), Anti-Chlorpyrifos Antibodies (LIB-PO Mabs), Anti-chlorsulfuron antibodies, Anti-Chlorsulfuron antibodies, Anti Chlortoluron Antibodies (Antiserum), Anti-Cyanoginosin-LA antibodies (mAbs 2B2-2, 2B2-7, 2B2-8, 2B2-9, 2B2-10, 2B5-5, 2B5-8, 2B5-14, 2B5-15, 2B5-23), Anti (D-3-methoxy-4-hydroxyphenylglycol) antibodies, Anti-DDA antibodies, Anti DDT antibodies (PAbs and MAbs), Anti-DDT Mabs (LIB1-11, LIB5-21, LIB5-25, LIB5-28, LIB5-212, LIB5-51, LIB5-52, LIB5-53), Anti-DEC Antibodies (Anti diethylcarbamazine Antibodies), Anti DEHA antibodies, Anti-(Delor 103) antibodies, Anti-Deltamethrin Antibodies, Anti Deltamethrin Antibodies (Del 01 to Del 12 MAbs and PAbs), Anti-deoxynivalenol (DON) Antibodies, Anti-Deoxynivalenol (DON) Antibodies, Anti Dexamethasone Antibody, Anti Dexamethasone Antibody, Anti-Dinitrophenyl (DNP)-antibodies, Anti dinitrophenyl spin labeled antibodies (AN01-AN12), Anti Diuron Antoboides (MAb's: 21, 60, 195, 202, 275, 481, 488, 520), Anti-D-MHPG Antibodies, Anti DNC antibodies, Anti-EB1089 antibodies, Anti-ecdysone antibodies, Anti-endosulfan antibodies, Anti-Endosulfan Antibodies, Anti Esfenvalerate antibodies (Ab7588), Anti estradiol antibodies, Anti-Fenitrothion antibodies (pAbs and mAbs), Anti-Fenpropimorph antibodies, Anti Fenthion Antibodies, Anti-Fenthion Antibodies, Anti FITC antibodies (B13-DEI), Anti-Flucofuron antibodies (F2A8/1/A4B3), Anti-flufenoxuron antibodies, and Anti-(Benzoylphenylurea)-Antibodies, Anti-Formononetin Antibodies, Anti-Furosemide antibodies (Furo-26, Furo37, furo-72, Furo 73 Mabs), Anti-GR151004 Antibodies, Anti-hCG-alpha-peptide Antibodies (FA36, Anti hydroxyatrazine antibodies (HYB-283-2), Anti-Hydroxysimazine Antibodies, Anti Imazalil Antibodies MoAb's (9C1-1-1, 9C5-1-1, 9C6-1-1, 9C8-1-1, 9C9-1-1, 9C12-1-1, 9C14-1-1, 9C16-1-1, 9C18-1-1, 9C19-1-1, 9E1-1, 9G2-1), Anti Irgarol Antibodies, Anti Isopentenyl adenosine antibodies, Anti Isoproturon Antibodies, Anti-KB-6806 antiserum, Anti-(+)lupanine antibodies, Anti Lysophosphatidic (LPA) acid, Anti M3G Ab1 and Ab2, Anti M3G Ab1 and Ab2, Anti-MBC antibodies (Anti-2-succinamidobenzimidazole antiserum), Anti Metanephrine antibodies, anti (+)methamphetamine antibodies, Anti-Methiocarb Antibodies (LIB-MXNB31, LIB-MXNB-33, LIB-MXNH14 and LIB-MXNH-15 MAbs), Anti Metolachlor antibodies, Anti-Metolachlor Antibodies, Anti-Metolachlor Antibodies (MAb 4082-25-4), Anti Molinate Antibodies, Anti monuron antibodies, Anti-morphine-3-glucuronide (E3 scFv antibody), Anti morphine antibodies, Anti-Morphine antibodies, Anti-Morphine antibodies (mAbs 8.2.1, 33.2.9, 35.4.12, 39.3.9, 44.4.1, 76.7F.16, 83.3.10, 115.1.3, 124.2.2, 131.5.13, 158.1.3, 180.2.4), Anti-Neopterin (D-erythro form) Antibodies, Anti-Nicarbazin Antibodies (Nic 6, Nic 7, Nic 8, and Nic 9), Anti Nicergoline Antibodies (Nic-1, Nic-2, Nic-3 & BNA-1, BNA-3), Anti-norflurazon antibodies, Anti NorMetanephrine antibodies, Anti (o-DNCP) Antibodies, Anti-P10 antibodies (TRH elongated peptide), Anti-Paraoxon Antibodies (BD1 and CE3), Anti Paraquat antibodies, Anti-Paraquat antibodies, anti Parathion-methyl antibodies, Anti PCB Antibodies (against 3,3',4,4'-tetrachlorobiphenyl) MAb S2B1, Anti pentachlorophenol antibodies, Anti Pentachlorophenol antibodies, Anti-Pentachlorophenol antibodies, Anti permethrin antibodies (Mabs Py-1, Py-3 and Py-4), Anti-Phencyclidine Antibodies (Mab 6B5 Fab), Anti-phenobarbital antibodies, Anti-phenobarbital antibodies, Anti-(p.p'-DDT)-Antibodies (LIB-DDT-35 and LIB-DDT5-52), Anti permethrin antibodies (Ab549), Anti Propoxur antibodies (LIB-PRNP15, LIB-PRNP21, LIB-PRNB21, LIB-PRNB33), Anti-Prostaglandin E2-antibodies, Anti-p-tyramine antibodies, Anti pyrene antibodies, Anti retronecine antibodies, Anti-Retronecine Antibodies, Anti salicylate antibodies, Anti Sennoside A antibodies (MAb 6G8), Anti Sennoside B antibodies (MAb's: 7H12, 5G6, 5C7), Anti Simizine antibodies, Anti Sulfonamides antibodies (Anti-TS), Anti-Sulocfuron antibodies (S2B5/1/C3), Anti sulphamethazine antibodies (21C7), Anti-synephrine antibodies, Anti-Thiabendazole antibodies (Antibody 300), Anti-Thiabendazole antibodies (Antibody 430 and 448), Anti-Thiram-Antibodies, Anti-THP antibodies (7S and 19S), Anti-Thromboxane B2 Antibodies, Anti-thymidine glycol monophosphate antibodies (mAb 2.6F.6B.6C), Anti-Thyroliberin (TRH) antibodies, Anti TNT antibodies (AB1 and AB2 antiserum), Anti Triadimefon Antibodies, Anti-triazine antibodies (AM1B5.1), Anti-triazine antibodies (AM5C5.3), Anti-triazine antibodies (AM5D1.2), Anti-triazine antibodies (AM7B2.1), Anti-triazine antibodies (SA5A0.1), Anti-Triazine serum (anti-ametryne), Anti-Triazine serum (anti-atrazine), Anti-Triazine serum (anti-simazine), Anti-Triazine serum (anti-simetryne), Anti Trifluralin Antibodies, Anti Trifluralin Antibodies, Anti Vincristine Antibodies, Anti-Zearalenone Antibodies, Anti Zeatin riboside antibodies, E2 G2 and E4 C2, Fab Fragment K411B derived from MAb K4E7 (isotype IgG2b with k light chain), LIB-BFNP23 Mab, MAb's H-7 and H-9 (against O,O-diethyl OP pesticides), MoAb 33A7-1-1, MoAb 33B8-1-1, MoAb 33C3-1-1, MoAb 3C10-1-1 and MoAb 3E17-1-1, MoAb 45D6-5-1, MoAb 45E6-1-1, MoAb 45-1-1, Mutant (GlnL89Glu) in Fab Fragment K411B derived from MAb K4E7 (isotype IgG2b with k light chain), Mutant (GlnL89Glu/ValH37Ile/GluL3Val) in Fab Fragment K411B derived from MAb K4E7 (isotype IgG2b with k light chain), Mutant (GlnL89Glu/ValH37Ile/GluL3Val) in Fab Fragment K411B derived from MAb K4E7 (isotype IgG2b with k light chain), Mutant (GlnL89Glu/ValH37Ile) in Fab Fragment K411B derived from MAb K4E7 (isotype IgG2b with k light chain), Mutant (GlnL89Glu/ValH37Ile) in Fab Fragment K411B derived from MAb K4E7 (isotype IgG2b with k light chain), Mutant (GluH50Gln) in Fab Fragment K411B derived from MAb K4E7 (isotype IgG2b with k light chain), Mutant (GluH50X) in Fab Fragment K411B derived from MAb K4E7 (isotype IgG2b with k light chain), Mutant (GlyH100aAla) in Fab Fragment K411B derived from MAb K4E7 (isotype IgG2b with k light chain), Mutant (GlyH100aSer) in Fab Fragment K411B derived from MAb K4E7 (isotype IgG2b with k light chain), Mutant (HisH95Phe) in Fab Fragment K411B derived from MAb K4E7 (isotype IgG2b with k light chain), Mutant (HisH95Tyr) in Fab Fragment K411B derived from MAb K4E7 (isotype IgG2b with k light chain), Mutant (PheL32Leu) in Fab Fragment K411B derived from MAb K4E7 (isotype IgG2b with k light chain), Mutant (TrpH33Phe,Tyr,Leu) in Fab Fragment K411B derived from MAb K4E7 (isotype IgG2b with k light chain), Mutant (TryL96Phe) in Fab Fragment K411B derived from MAb K4E7 (isotype IgG2b with k light chain), Mutant (TryL96Phe) in Fab Fragment K411B derived from MAb K4E7 (isotype IgG2b with k light chain), Mutant (ValH37Ile) in Fab Fragment K411B derived from MAb K4E7 (isotype IgG2b with k light chain), Mutant (ValH37Ile) in Fab Fragment K411B derived from MAb K4E7 (isotype IgG2b with k light chain), P6A7 MAb, PNAS2 6/3 56(1)-1-5-1, PNAS2 6/3 56(1)-1-5-2, PNAS2 6/3 56(1)-1-10-4, PNAS2 6/3 56(1)-1-10-5 and PNAS2 6/3 56(1)-3-1-5, Alexa Fluor 405/Cascade Blue dye antibody, Alexa Fluor 488 dye antibody, BODIPY FL dye antibody, Dansyl antibody, Fluorescein/Oregon Green dye antibody, Lucifer yellow dye antibody, Tetramethylrhodamine and Rhodamine Red dye antibody, Texas Red and Texas Red-X dye antibody, Biotin antibody, Dinitrophenyl antibody and/or Nitrotyrosine antibody or any portion thereof of the aforementioned haptens.

In an eighth aspect, a method of treating, ameliorating, or inhibiting a cancer in a subject is provided, wherein the method comprises a) introducing, providing, or administering to a subject a composition that comprises an antibody or binding fragment thereof, which comprises a target moiety such as, a hapten, poly(his) tag, Strep-tag, FLAG-tag, V5-tag, Myc-tag, HA-tag, NE-tag, biotin, digoxigenin, dinotrophenol or fluorescein (e.g., Fluorescein isothiocyanate (FITC)); and b) introducing, providing, or administering to said subject a cell that comprises a chimeric antigen receptor (CAR) or T cell receptor (TCR), wherein the CAR or TCR is specific for the target moiety. In some alternatives, the cell is a precursor T cell. In some alternatives, the precursor T cell is a hematopoietic stem cell. In some alternatives, the cell is a CD8+ T cytotoxic lymphocyte cell selected from the group consisting of naïve CD8+ T cells, central memory CD8+ T cells, effector memory CD8+ T cells and bulk CD8+ T cells. In some alternatives, the cell is a CD4+ T helper lymphocyte cell that is selected from the group consisting of naïve CD4+ T cells, central memory CD4+ T cells, effector memory CD4+ T cells, and bulk CD4+ T cells. In some alternatives, the antibody or binding fragment thereof, which comprises the target moiety, is specific for a target or selected cell, such as a cancer cell. In some alternatives, the target cell is a tumor cell. In some alternatives, the target cell is an immune cell. In some alternatives, the target immune cell is a T cell or a B cell. In some alternatives, the target cell exists in a tumor microenvironment. In some alternatives, the antibody or binding fragment thereof, which comprises the target moiety, is specific for a viral or bacterial antigen. In some alternatives, the cell comprises a chimeric antigen receptor (CAR) or T cell receptor (TCR), wherein the CAR or TCR is configured to bind with an antibody or binding fragment thereof comprising a target moiety through a CAR or TCR-mediated interaction with said target moiety and, wherein said antibody or binding fragment thereof is specific for an antigen present on a cancer cell, virus, or bacterial cell. In some alternatives, said target moiety is a hapten, poly(his) tag, Strep-tag, FLAG-tag, V5-tag, Myc-tag, HA-tag, NE-tag, biotin, digoxigenin, dinitrophenol or fluorescein (e.g., Fluorescein isothiocyanate (FITC)). In some alternatives, the cell is a precursor T cell. In some alternatives, the precursor T cell is a hematopoietic stem cell. In some alternatives, the cell is a CD8+ T cytotoxic lymphocyte cell selected from the group consisting of naïve CD8+ T cells, central memory CD8+ T cells, effector memory CD8+ T cells and bulk CD8+ T cells. In some alternatives, the cell is a CD4+ T helper lymphocyte cell that is selected from the group consisting of naïve CD4+ T cells, central memory CD4+ T cells, effector memory CD4+ T cells, and bulk CD4+ T cells. In some alternatives of the method, the cell is provided to the subject within seconds or minutes, such as less than an hour, of providing the composition to the subject. In some alternatives of the method, a boost of the cell and/or the composition is provided to the subject. In some alternatives of the method, an additional therapy is provided, such as a small molecule, e.g., a chemical compound, an antibody therapy, e.g., a humanized monoclonal antibody with or without conjugation to a radionuclide, toxin, or drug, surgery, and/or radiation. In some alternatives, the antibody or binding fragment thereof, which is conjugated to the target moiety, is abagovomab, abituzumab, adecatumumab, afutuzumab, alacizumab pegol, alemtuzumab, altumomab pentetate, amatuximab, anatumomab mefanetox, anetumab ravtansine, apolizumab, arcitumomab, ascrinvacumab, aselizumab, atezolizumab, atlizumab, avelumab, bapineuzumab, bavituximab, bectumomab, belimumab, besilesomab, bevacizumab, bivatuzumab mertansine, blinatumomab, blontuvetmab, brentuximab, brontictuzumab, cantuzumab mertansine, cantuzumab ravansine, capromab pendetide, carlumab, carotuximab, catumaxomab, cBR96-doxorubicin immunoconjugate, cedelizumab, certolizumab pegol, cetuximab, cidfusituzumab, cidtuzumab, citatuzumab bogatox, cixutumumab, clivatuzumab tetraxetan, codrituzumab, coltuximab ravtansine, conatumumab, dacetuzumab, daclizumab, dalotuzumab, daratumumab, demcizumab, denintuzumab mafodotin, denosumab, depatuxizumab mafodotin, derlotuximab biotin, detumomab, dinutuximab, drozitumab, duligotumab, durvalumab, dusigitumab, duvortuxizumab, ecromeximab, eculizumab, edrecolomab, efalizumab, elgemtumab, elotuzumab, emactuzumab, emibetuzumab, enavatuzumab, enfortumab vedotin, enoblituzumab, enoticumab, ensituximab, epratuzumab, erlizumab, ertumaxomab, etaracizumab, farletuzumab, FBTA05, femzumab, ficlatuzumab, figitumumab, flanvotumab, fontolizumab, futuximab, galiximab, ganitumab, gemtuzumab ozogamicin, girentuximab, glembatumumab vedotin, ibritumomab, icrucumab, igovomab, IMAB362, imalumab, imgatuzumab, indatuximab ravtansine, indusatumab vedotin, intetumumab, inotuzumab ozogamicin, intetumumab, ipilimumab, iratumumab, isatuzimab, labetuzumab, lambrolizumab, lexatumumab, lifastuzumab vedotin, lilotomab satetraxetan, lintuzumab, lorvotuzumab mertansine, lucatumumab, lumiliximab, lumretuzumab, mapatumumab, margetuximab, matuzumab, mepolizumab, milatuzumab, minretumomab, mirvetuximab soravtansine, mitumomab, mogamulizumab, moxetumomab pasudotox, nacolomab tafenatox, naptumomab estafenatox, narnatumab, natalizumab, necitumumab, nesvacumab, nimotuzumab, nivolumab, nofetumomab merpentan, obinutuzumab, ocaratuzumab, ocrelizumab, ofatumumab, olaratumab, omalizumab, onartuzumab, ontuxizumab, oportuzumab monatox, oregovomab, otlertuzumab, panitumumab, pankomab, parsatuzumab, pascolizumab, pasotuxizumab, patritumab, pecfusituzumab, pectuzumab, pembrolizumab, pemtumomab, pertuzumab, pexelizumab, pidilizumab, pinatuzumab vedotin, pintumomab, polatuzumab vedotin, pritumumab, racotumomab, radretumab, ramucirumab, ranibizumab, reslizumab, rilotumumab, rituximab, robatumumab, rovelizumab, ruplizumab, sacituzumab govitecan, samalizumab, satumomab pendetide, seribantumab, sibrotuzumab, SGN-CD19A, SGN-CD33A, simtuzumab, siplizumab, siltuximab, sofituzumab vedotin, solitomab, sontuzumab, tabalumab, tacatuzumab tetraxetan, tadocizumab, talizumab, tamtuvetmab, taplitumomab paptox, tarextumab, tenatumomab, teprotumumab, TGN1412, ticilimumab (tremelimumab), tigatuzumab, TNX-650, tocilizumab, toralizumab, tositumomab, tovetumab, trastuzumab, TRB S07, tremelimumab, tucotuzumab celmoleukin, tucusituzumab, ublituximab, ulocuplumab, urelumab, urtoxazumab, ustekinumab, vandortuzumab vedotin, vantictumab, vanucizumab, veltuzumab, vesencumab, visilizumab, volociximab, vorsetuzumab mafodotin, votumumab, zalutumamab, zanolimumab, zatuximab, cosfroviximab, diridavumab, exbivirumab, felvizumab, foravirumab, larcaviximab, libivirumab, motavizumab, motovizumab, nolovizumab, numavizumab, palivizumab, porgaviximab, PRO 140, rafivirumab, ralivizumab, regavirumab, reslivizumab, resyvizumab, sevirumab, suvizumab, tuvirumab, umavizumab, edobacomab, nebacumab, pagibaximab, panobacumab, raxibacumab, or tefibazumab or a binding fragment thereof. In some alternatives, the hapten used comprises Alexa Fluor 405, Cascade Blue, Alexa Fluor 488, BODIPY, Dansyl chloride, Oregon Green, Lucifer yellow, Rhodamine, Tetramethylrhodamine, Nitrotyrosine, digoxigenin, 2,4-Dichlorophenoxyacetic acid, Atrazine (2-Chloro-4-(ethylamino)-6-(isopropylamino)-s-triazine), Nicotine (3-(1-Methyl-2-pyrrolidyl)pyridine, Black Leaf), Morphine (morph, Morphine Sulfate), 2,4-DINITROCHLOROBENZENE (1-Chloro-2,4-dinitrobenzene; DNCB; Dinitrochlorobenzene), 4-chloro-6-(ethylamino)-1,3,5-triazine-2-(6-aminohexanecarboxylic acid), Structurally related s-triazines (Modifications: H/Cl/C6 R1=NH2- R2=—Cl R3=—NH—(CH2)5-COOH; iPr/Cl/nBu R1=(CH3)2-CH— NH— R2=—Cl R3=—NH—(CH2)3-(CH3)), Ametryn (2-Ethylamino-4-isopropylamino-6-methylthio-1,3,5-triazine), Deethylatrazine (DEA) (Structurally related s-triazines), Deisopropylatrazine (DIA) (Structurally related s-triazines), Deethyldeisopropylatrazine (DEDIA) (Structurally related s-triazines), Deethyldeisopropylatrazine (DEDIA) (Structurally related s-triazines), HydroxyAtrazine (HA) (Structurally related s-triazines), DeisopropylHydroxyAtrazine (DIHA) (Structurally related s-triazines), DeethylDeisopropylHydroxyAtrazine (DEDIHA) (Structurally related s-triazines), Simazine (Structurally related s-triazines), Desmetryne (Structurally related s-triazines), Prometryne (Structurally related s-triazines), 2-hydroxyatrazine (atrazine derivative), 2-hydroxypropazine (structurally related s-triazine), 2-hydroxysimazine, N-(4-Amine-6-hydroxy-[1, 3,5]triazin-2-yl)-4-aminobutanoic Acid (Modification: R1=NH2 R2=NH(CH2)3COOH R3=OH), SulcoFuron, 5-chloro-2-{4-chloro-2-[3-(3,4-dichlorophenyl)ureido] phenoxy}benzenesulfonic acid, FlucoFuron (1,3-bis(4-chloro-α,α,α-trifluoro-m-tolyl)urea), Agatharesinol, Sequirin C, Sugiresinol, Hydroxysugiresinol, Hinokiresinol, Coniferyl alcohol, Cinnamyl alcohol, p-Coumaric acid, Cinnamic acid, p-Coumaric acid, Cinnamic acid, Hinokinin, Guaiacylglycerol-beta-guaiacyl ether, Morphine-3-glucuronide (M3G), Codeine, Nor-Codeine, 6-Monoacetylmorphine, (+) Methamphetamine, Ceftazidime, Phenobarbital, p-hydroxyPhenobarbital, p-aminophenobarbital, Cyclobarbital, 3'-Ketocyclobarbital, 3'-Hydroxycyclobarbital, Secobarbital, Barbital, Metharbital, Barbituric acid, Thiopental, Thiobarbituric acid, Primidone, Glutethimide, Pentobarbital, Heroin, Diacetylmorphine, Levallorphan, L-11-Allyl-1, 2,3,9,10,10a-hexahydro-4H-10,4a-iminoethano-phenanthren-6-ol, Pethidine (Demerol; Dolantin; Meperidine; Ethyl 1-methyl-4-phenylpiperidine-4-carboxylate; Isonipecaine), Methamphetamine, d-Desoxyephedrine; Methedrine; Tolpropamine; Pratalgin; Pragman. Benzoylecgonine, 3-Carboxymethylmorphine, Cocaine, 5-benzimidazolecarboxylic acid, ABA (4-acetyl benzoic acid), Dexamethasone, Flumethasone, 6alpha, 9 alpha-difluoro-11 beta, 17,21-trihydroxy-16 alpha-methylpregna-1,4-diene-3, 20-dione, 9 alpha-fluoro-11 beta,17,21-trihydroxy-16 beta-methylpregna-1,4-diene-3,20-dione, 9-alpha-fluroprednisolone, Desoxymethasone, Triamcinolone, 9 alpha-fluoro-11 beta,16 alpha, 17,21-tetrahydroxypregna-1,4-diene-3,20-dione, Fluocortolone, 6 alpha-fluoro-11 beta,21-dihydroxypregna-1,4-diene-3,20-dione, Cortisol, 11 beta, 17,21-trihydroxypregna-4-ene-3,20-dione, Prednisone, 17,21-dihydroxypregn-4-ene-3,11,20-trione, Methylprednisolone, 11 beta, 17,21-trihydroxy-6 alpha-methylpregna-1,4-diene-3,20-dione, Triamcinolone hexacetonide, 21-(3,3-dimethyl-1-oxobutoxy)-9 alpha-fluoro-11-hydroxy-16,17-[(1-methylethylidene) bis(oxy)]pregna-1,4-diene-3,20-dione, Carbofuran, 2,3-dihydro-2,2-dimethyl-7-benzofuranyl methylcarbamate, BFNP (3-[[(2,3-dihydro-2,2-dimethyl-7-benzofuranyloxy)carbonyl]amino]propanoic acid), Carbofuran derivative, 2,3-dihydro-2,2-dimethyl-7-benzofuranol, Bendiocarb, Carbaryl, Methiocarb, Propoxur, Aldicarb, Methomyl, Benalaxyl, methyl N-(phenylacetyl)-N-(2,6-xylyl)-DL-alaninate, Bn-Ba (4-[2-(N-phenylacetyl-N-2,6-xylylamino)propionamido] butyric acid), Bn-COOH (4-[2-(N-phenylacetyl-N-2,6-xylyl-DL-alanine), Benalaxyl derivative, Furalaxyl, Metalaxyl, Acetochlor, Dimetachlor, Metolachlor, 2-chloro-6'-ethyl-N-(2-methoxy-1-methylethyl)acet-o-toluidine, Diethathyl-ethyl, Benzoylprop-ethyl, Benzoylprop-ethyl, 2,4,5-Trichlorophenoxyacetic acid, 2-chloro-6'-ethyl-N-(2-methoxy-1-methylethyl)acet-o-toluidine, Diethathyl-ethyl, Benzoylprop-ethyl, Propachlor, Propachlor, 2,4,5-Trichlorophenoxyacetic acid, 2,4,5,T; Weedone, 2,4-Dichlorophenoxybutyric acid (2,4-DB), 2,4-DB; Butanoic acid, 4-(2,4-dichlorophenoxy)-; Butoxone; Embutone, MCPA, 2-Methyl-4-chlorophenoxyacetic acid; Metaxon, Dichlorprop (2,4-DP), 1-[(2-chloro)phenylsulfonyl]monoamidosuccinic acid, Chlorsulfuron, chlorbromuron, amidosulfuron, chlortoluron, isoproturon, diuron, Linuron O-Methyl-O-(4-nitrophenyl)-N-(4-carboxybutyl)-phosphoramidothioate Parathion-methyl, O,O-dimethyl O-4-nitrophenyl phosphorothioate; Methaphos; Wolfatox; Dimethylparathion; Metacide, Parathion-ethyl, DIETHYL P-NITROPHENYL THIOPHOSPHATE; O,O-DIETHYL O—(P-NITROPHENYL) PHOSPHOROTHIOATE; Fenitrothion, O,O-dimetyl O-4-nitro-m-tolyl phosphorothioate, Fenthion, O,O-dimethyl O-4-methylthio-m-tolyl phosphorothioate, Bromophos, O-4-bromo-2,5-dichlorophenyl O,O-dimethyl phosphorothioate, chlorpyrifos-methyl, O,O-dimethyl O-3,5,6-trichloro-2-pyridyl phosphorothioate, Oxidized parathion-methyl, Paraoxon, phosphoric acid, O,O-diethyl O-(4-nitrophenyl) ester, Diazinon, O,O-diethyl O-2-isopropyl-6-methylpyrimidin-4-yl phosphorothioate, Azinphos-methyl, pirimiphos-methyl, O-2-diethylamino-6-methylpyrimidin-4-yl O,O-dimethyl phosphorothioate, Methidathion, S-2,3-dihydro-5-methoxy-2-oxo-1,3,4-thiadiazol-3-ylmethyl O,O-dimethyl phosphorodithioate, Dimethylchlorothiophosphate, 4-NITROPHENOL, p-nitrophenol, Phenolic derivative (Modification On benzene ring; R1=OH R2=NO2 R3=H R4-CH2COOH R5=H R6=H); 2-Nitrophenol, o-Nitrophenol, 3-Nitrophenol, m-nitrophenol, 2,4-Dinitrophenol, 3,4-Dinitrophenol, 2,5-Dinitrophenol, 2,4-Dinitro-6-methylphenol, 2,3,6-trinitrophenol, 2-Chlorophenol, 4-Chloro-3-methylphenol, Fenitroxon, 3-Methyl-4-nitrophenol, Nonylphenol, HOM(3-[2-hydroxy-5nitro benzylthio] propionic acid, Phenol, Delor 103, Polychlorinated Biphenyls, Delor 104, Polychlorinated Biphenyls, Delor 105, Polychlorinated Biphenyls, Delor 106, 4,4'-Dichlorobiphenyl, PCB congeners, 2,4,4'-Trichlorobiphenyl, PCB congeners, 2,4'-Bichlorobiphenyl, PCB congeners, 2,2'-Dichlorobiphenyl, PCB congeners, 2,4,5-Trichlorobiphenyl, PCB congeners, 3,3',4,4'-Tetrachlorobiphenyl, PCB congeners, PCB congeners, 2,2',4,4',5,5'-Hexachlorobiphenyl, 2-(5-Carboxypentanoylamino)-4,4'-dichlorobiphenyl, Biphenyl derivative, 4-chlorophenoxyacetic acid, 2-Chlorophenoxyacetic acid, DDT,1,1,1-trichloro-2, 2-bis-(p-chlorophenyl)ethane, DDE, 1,1-dichloro-2, 2-bis(p-chlorophenyl)ethylene, p-Chlorophenol, 4-Chlorophenol, m-Chlorophenol 3,4-Dichlorophenol, 3,5-Dichlorophenol, 2,3,4-Trichlorophenol, 2,3,5-Trichlorophenol, 3-methylindole, 3-methylindole Derivatives, 4-(3-methylindol-5-yloxy)butanoic acid, 4-(3-methylindol-5-yloxy)butanoic acid, 3-methylindole Derivatives, 6-[n-3-methylindol-5-yloxy carbonyl)amino]hexanoic acid, 6-[n-3-methylindol-5-yloxy carbonyl)amino]hexanoic acid, 3-methylindole Derivatives, 2-[4-(3-methylindol-6-yl)but-1-ylthio]acetic acid, 2-[4-(3-methylindol-6-yl)but-1-ylthio]acetic acid, 3-methylindole Derivatives, 4-(3-methylindol-6-yl-4-oxo) butanoic acid, 4-(3-methylindol-6-yl-4-oxo)butanoic acid, 3-methylindole Derivatives, 6-(3-methylindol-7-yloxy) hexanoic acid, 6-(3-methylindol-7-yloxy)hexanoic acid, Indole, Indole-3-Carboxylic acid, Indole Derivative-Indole-3-Acetic acid, Indole-3-Acetic acid, Indole Derivative-Indole-3-Propionic acid, Indole-3-Propionic acid, Indole Derivative-Indole-3-Carbinol, Indole-3-Carbinol, Tryptophan, Tryptamine, 5-Methoxyindole-3-carboxaldehyde, 5-Methoxytryptamine, 5-Methoxyindole, 6-Methoxyindole, 7-Methoxyindole,EB1089(Seocalcitol),EB1089(Seocalcitol) Derivative, (22E,24E)-Des-A,B-24-homo-26,27-dimethyl-8-[(E)-N-(2-carboxyethyl)-carbamoylmethylidene]-cholesta-22,24-dien-25-ol, 1 alpha-25-dihydroxyvitamin D3, 25(OH)D3,25-hydroxyvitamin D3,24R,25(OH)2D3, 24R,25-dihydroxyvitamin D3, Vitamin D2, ergocalciferol, Vitamin D3, cholecalciferol,EB1446,EB1436,EB1445, EB1470, DeethylHydroxyAtrazine (DEHA) (Structurally related s-triazines), Irgarol 1051, Flourescein Isothiocyanate, FITC, Metanephrine, NorMetanephrine, Propazine, Terbutylazine, Terbuthylazine, 6-chloro-N-(1,1-dimethylethyl)-N'-ethyl-1,3,5-triazine-2,4-diamine, (Structurally related s-triazines), Ametryn (2-Ethylamino-4-isopropylamino-6-methylthio-1,3,5-triazine (Modification iPr/SCH3/Et R1=(CH3)2-CH—NH— R2=—SCH3 R3=—NH—CH2-CH3, Irgarol, Cyanazine (Modification R1=Cl R2=NHCH2CH3 R3=NHCCN(CH3)2), OH-Terbutylazine, Terbutylazine-2OH, Hydroxytriazine (EQ-0027), Deisopropylatrazine (Structurally related S-triazine), Desethylterbutylazine (Structurally related S-triazine), Desethyl-deisopropylatrazine (Structurally related S-triazine), Atraton, Terbutryn (Structurally related s-triazines), Atrazine derivative (Modification R1=—NHCH(CH3)2 R2=—S(CH2)2COOH R3=—NHC2H5), Cyanuric chloride, Trifluralin, (Structurally related s-triazines) tBu/C4/SCH3 (Modification R1=—NH—C—(CH3)3 R2=—NH (CH2)3COOH R3=—SCH3), Sulphamethazine, (Structurally related s-triazines) 6-[[[4-Chloro-6-(methylamino)]-1,3,5-triazin-2-yl]amino]hexanoic Acid (Modification Me/Cl/C6 R1=—NHCH3 R2=—Cl R3=—NH(CH2) 5COOH), (Structurally related s-triazines) Procyazine (Modification R1=—Cl R2=—NHcyclopropyl R3=—NHCCN(CH3)2), (Structurally related s-triazines), Prometon (Modification R1=—OCH3 R2=—NHCH(CH3)2 R3=—NHCH(CH3)2); (Structurally related s-triazines) Atrazine Mercapturic Acid (AM) (Modification R1=—SCH2CH(NHAc)COOH R2=—NHCH2CH3 R3=—NHCH(CH3)2), (Structurally related s-triazines), desethyl atrazine mercapturic acid (desethyl AM) (Modification R1=—NAcCys R2=—NH2 R3=—NHCH(CH3)2), (Structurally related s-triazines), deisopropyl atrazine mercapturic acid (deisopropyl AM) (Modification R1= —NAcCys R2=—NHCH2CH3 R3=—NH2), (Structurally related s-triazines), didealkylated atrazine mercapturic acid (didealkylated AM) (Modification R1=—NAcCys R2=—NH2 R3=—NH2), (Structurally related s-triazines), simazine mercapturate (Modification R1=—NAcCys R2=—NHCH2CH3 R3=—NHCH2CH3), (Structurally related s-triazines) (Modification R1=—S(CH2)2COOH R2=—NHCH2CH3 R3=—NHCH2CH3), (Structurally related s-triazines) (Modification R1=—Cl R2=—NHCH(CH3)2 R3=—NH(CH2)2COOH), (Structurally related s-triazines) (Modification R1=—Cl R2=—NHCH2CH3 R3=—NH(CH2)2COOH), (Structurally related s-triazines), atrazine mercapturic acid methyl ester (AM methyl ester) (Modification R1=—NAcCysME R2=—NHCH2CH3 R3=—NHCH(CH3)2), N-acetylcysteine, S-benzyl mercapturate, (Structurally related s-triazines), simetryn (Modification R1=—SCH3 R2=—NHCH2CH3 R3=—NHCH2CH3), Metribuzin, 4-amino-6-tert-butyl-4,5-dihydro-3-methylthio-1,2,4-triazin-5-one, Sulpha Drugs, N4-acetyl-sulphamethazine (Modification N4-acetyl-sulphamethazine), Sulpha Drugs, Sulphathiazole, Sulphathiazole, Sulphamerazine, Sulphamerazine, Sulphaquinoxaline, Sulphaquinoxaline Sulphachlorpyridazine, Sulphachlorpyridazine, Sulphapyridine, Sulphadimethoxine, Sulphadimethoxine, Sulphamethoxazole, Sulphamethoxazole, Sulphisoxazole, Sulphisoxazole, Sulphamethizole, Sulphamethizole, Sulphanilamide, Sulphanilamide, Sulphaguanidine, Sulphaguanidine, Sulphadiazine, Sulphadiazine, Sulphamethoxypyridazine, Sulphamethoxypyridazine, Pentachlorophenoxypropionic acid, Pentachlorophenol, PCP, 2,3,5,6-Tetrachlorophenol, 1,2,4,5 Tetrachlorobenzene, 2,4,6 Trichlorophenol, 2-Methoxy-3,5,6-trichloropyridine, 1,3,5 Trichlorobenzene, 1,3 Dichlorobenzene, 2,4,5-Trichlorophenol, 2,6-Dichlorophenol, 3,5,6-Trichloro-2-pyridinoxyacetic acid, 3,5,6-Trichloro-2-Pyridinol, TCP, 2,4-Dichlorophenol, 2,5-Dichlorophenol, DNC, 4,4'-dinitrocarbanilide, (Structurally related s-triazines), Dichloroatrazine, (Structurally related s-triazines), Dichlorosimazine, 1-((6-chloropyridin-3-yl)methyl)imidazolidin-2-imin, Pyridine Derivative, 6-chloropyridine-3-carboxylic acid, Nicotinic acid, Pyridine Derivative, N-((6-chloropyridin-3-yl)methyl)-N-methylacetamide, (6-chloropyridin-3-yl)-N-methylmethanamine, (6-chloropyridin-3-yl)methanol, Imidacloprid, 1-(6-chloro-3-pyridylmethyl)-N-nitroimidazolidin-2-ylideneamine, Acetamiprid, (E)-N1-[(6-chloro-3-pyridyl)methyl]-N2-cyano-N1-methylacetamidine, Nitenpyram, Deltamethrin 1(R)-cis-alpha (S)-3-(2,2-dibromoethenyl)-2,2-dimethylcyclopropane carboxylic acid cyano(3-phenoxyphenyl)methyl ester, DON, deoxynivalenol, DON derivative, 15-AcDON (15-acetyldeoxynivalenol), DON derivative, 3-AcDON (3-acetyldeoxynivalenol), DON derivative, 3,15-DiacDON (3,15-diacetyldeoxynivalenol), DON derivative, 3,7,15-TriacDON (3,7,15-Triacetyldeoxynivalenol), NIV (nivalenol), nivalenol, NIV Derivative, 4-AcNIV (fusarenon X), Flutolanil, alpha,alpha,alpha-trifluoro-3'-isopropoxy-o-toluanilide, Mepronil, Mebenil, Benodanil, 24,25(OH)2D3, (24R)-24,25-dihydroxyvitamin D3, 24S,25(OH)2D3, 24S,25-dihydroxyvitamin D3, 25R,26(OH)2D3, 25R,26-dihydroxyvitamin D3, 25S,26(OH)2D3, 25S,26-dihydroxyvitamin D3, 1,24,25(OH)3D3, 1,24,25-trihydroxyvitamin D3, 1,25-lactone, (23S,25R)-1,25(OH)2 D3 26,23-lactone, 24,25(OH)2-7-DHC, 24,25(OH)2-7-dehydrocholesterol, 25(OH)D3 3S, 25(OH)D3 3-sulfate, 24,25(OH)2D3-Hemiglutarate Derivative, 11 alpha-hemiglutaryloxy-(24R)-24,25-dihydroxyvitamin D3, 24,25(OH)2D3-Hemiglutarate Derivative, (24R)-24,25-dihydroxyvitaminD3-3-hemiglutarate, 24R,25(OH) 2D2, 24S,25(OH)2D2, 25(OH)D2, 1,24(OH)2D3, 2,3,6-Trichlorophenol, Tetrachlorohydroquinone, Pentachloroaniline, Pentachlorobenzene, 2,3-Dinitrotoluene, 4-Dinitrotoluene, 2,4,5-Trichloronitrobenzene, 3-(3-Hydroxy-2,4,6-trichlorophenyl)-propanoic acid, 2,3,4,6-Tetrachlorophenol, 2,4,6-Trichloroanisol, 2,4,6-TCA, Pentabromophenol, PBP, 2,4,6-Tribromophenol, 2,4,6-TBP, 2-Bromo-4-Chlorophenol, 2-B-4-CP 2,4-Dibromophenol, 2,4-DBP, 2,6-Dibromophenol, 2,6-DBP, 4-Bromophenol, 4-BP, Furosemide, Ampicillin, Amoxicillin, 6-amino-penicillanic acid (6-APA), Azlocillin, Bacampicillin, Carbenicillin, Epicillin, Cloxacillin, Dicloxacillin, Metampicillin, Methicillin, Moxalactam, Oxacillin, Penicillin G, benzyl penicillin, Penicillin V, phenoxy methyl penicillin, Pheneticillin, Piperacillin, Ticarcillin, Ampicillin hydrolyzed, Penicillin G hydrolyzed, 3-phenoxybenzoic acid (3-PBAc) Chlorpyrifos, Chlorpyrifos derivatives, HClo1, Synthesized directly from chlorpyrifos technical grade by substitution of the chlorine in position 6 by a 3-mercaptopropanoic acid spacer arm, Chlorpyrifos derivatives, HTCP (Modification HTCP of TCP metabolite was prepared from HClo1 by hydrolysis of the thiophosphate ester), Zeatin Riboside (trans isomer), Zeatin (trans isomer), N6-(2-isopentenyl)-adenosine, IPA, N6-(2-isopentenyl)-adenine, 2-iP, Benzyladenine, Kinetin, monuron, monolinuron, fenuron, neburon, propanil, propham, chloropropham, 4-chloroaniline, Methyl Urea Derivative, 1-(3-Carboxypropyl)-3-(4-chlorophenyl)-1-methylurea, Methyl Urea Derivative, 1-(5-Carboxypentyl)-3-(4-chlorophenyl)-1-methylurea, metobromuron, Sennoside B, SB, Sennoside B possessed a erythro configuration between C-10 and C-10', Sennoside A (Modification Sennoside A possessed a threo configuration between C-10 and C-10'), Rhein, Emodin, Aloe-emodin, Barbaloin, 1,4 Dihydroxyanthraquinone, Rhaponticin, Galic acid, Vanillic acid, Caffeic acid, Homogentisic acid, Esculin, Cinnamtannin B1, Baicalin, Naringin hydrate, Wogonin, Wogonin 7-o-beta-glucuronide, Curcumin, delta1-Tetrahydrocannabinolic acid, delta1-Tetrahydrocannabinol, (+−)-cis-4-Aminopermethrin, 3-(4-Aminophenoxy)benzyl(+−)-cis-3-(2,2-dichloroethenyl)-2,2-dimethylcyclopropanecarboxylate, Permethrin, trans-Permethrin, cis-Permethrin, Cypermethrin, Phenothrin, Resmethrin, Cyfluthrin, trans-Permethrin acid Esfenvalerate, Fluvalinate, Fenpropathrin, cis-permethrin acid, 4-Phenoxybenzoyl alcohol, Diuron Derivative, 1-(3-Carboxypropyl)-3-(3,4-dichlorophenyl)-1-methylurea, Siduron, Terbuthiuron, Barban, acid trifluralin, 2,6-dinitro-N-propyl-N-(2-carboxyethyl)-4-(trifluoromethyl)benzenamine, TR-13, 2-ethyl-7-nitro-1-propyl-5-(trifluoromethyl)-1H-benzimidazole, benefin, 2,6-dinitro-N-butyl-N-ethyl-4-(trifluoromethyl)benzenamine, TR-2, 2,6-dinitro-N-propyl-4-(trifluoromethyl)benzenamine, ethalfluaralin, 2,6-dinitro-N-ethyl-N-(2-methyl-2-propenyl)-4-(trifluoromethyl) benzenamine, TR-40, N-(2,6-dinitro-4-(trifluoromethyl)phenyl)-N-propylpropanamide, TR-15, 2-ethyl-4-nitro-6-(trifluoromethyl)-1H-benzimidazole, TR-3, 2,6-dinitro-4-(trifluoromethyl)benzenamine, TR-6, 3-nitro-5-(trifluoromethyl)-1,2-benzenediamine, TR-9, 5-(trifluoromethyl)-1,2,3-benzenetriamine, TR-21, 4-(dipropylamino)-3,5-dinitrobenzoic acid, TR-36M, 3-methoxy-2,6-dinitro-N,N-dipropyl-4-(trifluoromethyl)benzenamine, oryzalin, 3,5-dinitro-4-(dipropylamino)benzenesulfonamide, pendimethalin, 2,6-dinitro-N-(1-ethylpropyl)-3,4-dimethylbenzenamine, penta galloyl glucose, Pyrene Pyrene-1-carboxaldehyde, Phenanthrene, Benzo(a)pyrene, 3,4-Benzopyrene, Anthracene, 3,4-Benzopyrene, Acenaphthene, Fluorene, Chrysene, 1,2-Benzphenanthrene, Benzo[g,h,i]perylene, Benzo[e]pyrene, Acenaphthylene, Fluoranthene, Benzo(j,k)fluorene, Indeno-1,2,3-cd-pyrene, 1,10-(1,2-Phenylene)pyrene, Benzo[a]anthracene, 1,2-Benzanthracene, Benzo(k)fluoranthene, Naphthalene, Benzo[a]fluoranthene, Dibenzo[ah]anthracene, 1,2:5,6-Dibenzanthracene, 2,3-Diaminonaphthalene, 2,6-Dinitroaniline, 17-beta-estradiol (ED), estra-1,3,5(10)-triene-3,17-beta-diol, Trifluralin derivative, 2,6-dinitro-4-tri-fluoromethylaniline, Trifluralin derivative, N-(2,6-dinitro-4-trifluoromethylphenyl)-6-aminohexanoic acid, Trifluralin derivative, N-(2,6-dinitro-4-trifluoromethylphenyl)-N-methyl-6-aminohexanoic acid, Trifluralin derivative, N-(2,6-dinitro-4-trifluoromethylphenyl)-N-propyl-6-aminohexanoic acid, Trifluralin derivative, N-(2,6-dinitro-4-trifluoromethylphenyl)-6-aminohexanoic acid methyl ester, Trifluralin derivative, N-(2,6-dinitro-4-trifluoromethylphenyl)-6-aminohexanoic acid tert-butyl ester, Benfluralin, Ethalfluralin, Trifluralin derivative, 2,6-Dinitro-4-trifluoromethylphenol, Isopropalin, Aniline, 2-Hydroxybenzotrifluoride, N-propyl-6-aminohexanoic acid, N-methyl-6-aminohexanoic acid, MHPG Derivatives, D-MHPG (D-3-methoxy-4-hydroxyphenylglycol), MHPG Derivatives, L-MHPG (L-3-methoxy-4-hydroxyphenylglycol), MHPG Derivatives, DL-MHPG (DL-3-methoxy-4-hydroxyphenylglycol), Isomeric mixture of D-MHPG and L-MHPG forms, MHPG Derivatives, DL-MHPG-SO4 (DL-3-methoxy-4-hydroxyphenylglycol-sulfate) Modification can include Isomeric mixture of D-MHPG-SO4 and L-MHPG-SO4 forms, Serotonin, 5-HT, 5-hydroxydopamine (5-4HDA), 3,4-dihydroxyphenylglycol (DOPEG), Dopamine, 4-(2-aminoethyl)pyrocatechol; 3-hydroxytyramine; 3,4-dihydroxyphenethylamine; L-3,4-dihydroxyphenylalanine, L-DOPA, Vanillomandelic acid, DL-VMA, Homovanillic acid, Norepinephrine, DL-NE, D-Epinephrine, D-E, 3-methoxytyramine, MTA, 3-methoxytyrosine, MTyr, 3,4-dihydroxymandelic acid, DL-DOMA, 3,4-dihydroxyphenyl acetic acid, DOPAC, L-Phenylalanine, Tyramine, p-tyramine; 4-(2-Aminoethyl)phenol, D-Mandelic acid, Homocatechol, Octopamine, DL-Octopamine, Azinphos-Ethyl, S-(3,4-dihydro-4-oxobenzo[d]-[1,2,3]-triazin-3-ylmethyl) O,O-diethyl phosphorodithioate, Phosmet, O,O-dimethyl S-phthalimidomethyl phosphorodithioate, Folpet, N-[(Trichloromethyl)thio]phthalimide, Tetramethrin, (1-Cyclohexene-1,2-dicarboximido)methyl-2,2-dimethyl-3-(2-methylpropenyl)-cyclopropanecarboxylate, N-(bromomethyl)phthalimide, N-(Chloromethyl)benzazimide, 6-(N-phthalimidoylmethylthio)hexanoic acid (MFH), Bromacil, 5-bromo-3-sec-butyl-6-methyluracil, Bromacil Derivative, 5-bromo-6-(hydroxymethyl)-3-(1-methylpropyl)-2,4(1H, 3H)-pyrimidineone, Bromacil Derivative, 5-bromo-3-(2-methylpropyl-6-methyl-2,4(1H,3H)-pyrimidinedione, Metabolite of Bromacil, Bromacil Derivative, 3-hydroxy-1-methylpropyl-6-methyl-2,4(1H,3H)-pyrimidinedione (Modification Bromacil Metabolite), Bromacil Derivative, 6-methyl-3-(1-methylpropyl)-2,4(1H,3H)-pyrimidinedione (Modification Bromacil Metabolite), Terbacil Derivative, [5-chloro-3-(1,1-dimethylethyl)-6-(hydroxymethyl)-2,4 (1H,3H)-pyrimidinedione, Terbacil, 3-tert-butyl-5-chloro-6-methyluracil, Bromacil Derivative, Ethyl-5-(5-Bromo-6-methyl-3-(1-methylpropyl)-2,4(1H,3H)-pyrimidinedione-1-yl)hexanoate, Bromacil Derivative alkylated at N-1, Bromacil Derivative 5-(5-Bromo-6-methyl-3-(1-methylpropyl)-2,4(1H,3H)-pyrimidinedione-1-yl)hexanoic Acid (Modification Bromacil Derivative alkylated at N-1), Bromacil Derivative, -Bromo-6-(Bromomethyl-3-(1-methylpropyl)-2,4(1H,3H)-pyrimidinedione (Modification Bromacil Derivative substituted at the 6-methyl position), Bromacil Derivative-[5-Bromo-3-(1-methylpropyl)-2,4(1H, 3H)-pyrimidinedione-6-yl]-2-carboxylpropanoic Acid (Modification Bromacil Derivative substituted at the 6-methyl position), 3-[5-Bromo-3-(1-methylpropyl)-2,4 (1H,3H)-pyrimidinedione-6-yl]propanoic Acid (Modification Bromacil Derivative substituted at the 6-methyl position), Bromacil Derivative 5-Bromo-1,6-dimethyl-3-(1-methylpropyl)-2,4(1H,3H)-pyrimidinedione, Bromacil Derivative 5-Bromo-1-butyl-6-methyl-3-(1-methylpropyl)-2,4(1H,3H)-pyrimidinedione, Butachlor, N-butoxymethyl-2-chloro-2',6'-diethylacetanilide, Amidochlor, N-[(acetylamino)methyl]-2-chloro-N-(2,6-diethylpenyl)acetamide, Nicarbazin, N,N'-bis(4-nitrophenyl)-compound with 4,6-dimethyl-2(1H)-pyrimidinone (Modification (DNC+HDP)), 2-hydroxy-4,6-dimethylpyrimidine, HDP, Imazalil, [1-(beta-allyloxy-2,4-dichlorophenethyl)imidazole], Imazalil Derivative, EIT-0073 (Modification Have a —O(CH2)5-COOH group instead of original —OCH2CH—CH2 group of imazalil), Penconazole, (RS)-1-(2,4-dichloro-β-propylphenethyl)-1H-1,2,4-triazole, Hexaconazole, (RS)-2-(2,4-dichlorophenyl)-1-(1H-1,2,4-triazol-1-yl)hexan-2-ol, Propiconazole, cis-trans-1-[2-(2,4-dichlorophenyl)-4-propyl-1,3-dioxolan-2-ylmethyl]-1H-1,2,4-triazole, Diclobutrazol, 2RS,3RS)-1-(2,4-dichlorophenyl)-4,4-dimethyl-2-(1H-1,2, 4-triazol-1-yl)pentan-3-ol, Triflumizole, (E)-4-chloro-α,α, α-trifluoro-N-(1-imidazol-1-yl-2-propoxyethylidene)-o-toluidine, Imazalil Derivative, EIT-0183, Imazalil Derivative, EIT-0180, Imazalil Derivative, EIT-0111, Imazalil Derivative, EIT-0158, Imazalil Derivative, K-240, Chlorothalonil, tetrachloroisophthalonitrile Modification On benzene Ring R1=CN R2=Cl R3=CN R4=Cl R5=Cl R6=Cl), Chlorothalonil Derivative-2,4,5,6-tetrachloro-3-cyanobenzamide (Modification On benzene Ring R1=CONH2 R2=Cl R3=CN R4=Cl R5=Cl R6=Cl), Chlorothalonil Derivative-2,5,6-trichloro-4-hydroxyisophthalonitrile (Modification On benzene Ring R1=CN R2=Cl R3=CN R4=OH R5=Cl R6=Cl), 3-carbamyl-2,4,5-trichlorobenzoic acid (Modification On benzene Ring R1=CONH2 R2=Cl R3=COOH R4=H R5=Cl R6=Cl), Pentachloronitrobenzene (Modification On benzene Ring R1=NO2 R2=Cl R3=Cl R4=Cl R5=Cl R6=Cl), Benzene hexachloride, Hexachlorobenzene, BHC, Lindane (Modification On benzene Ring R1=Cl R2=Cl R3=Cl R4=Cl R5=Cl R6=Cl), 2,4,5,6-tetrachlorophenol (Modification On benzene Ring R1=OH R2=Cl R3=H R4=Cl R5=Cl R6=Cl), Carbaryl Derivative, Ethylcarbamate (Modification R1=OCONHCH2CH3 R3=H), 1-Naphthol, 1-naphthaleneacetamide, -(1-naphthyl) acetamide, Carbaryl Derivative, 1-Methylcarbonate (Modification R1=OCOOCH3 R2=H, Carbaryl Derivative, 1-Ethylcarbonate (Modification R1=OCOOCH2CH3 R2=H), Carbaryl Derivative 2-Ethylcarbonate (Modification R1=H R2=OCOOCH2CH3, Carbaryl Derivative, 1-Ethylthiocarbonate (Modification R1=OCOSCH2CH3 R2=H), Carbaryl Derivative, 2-Ethylthiocarbonate (Modification R1=H R2=OCOSCH2CH3), Naptalam, N-1-naphthylphthalamic acid, Carbaryl Derivative, 3-hydroxycarbaryl (Modification R1=OCONHCH3 R2=H R3=OH R4=H R5=H), Carbaryl Derivative 4-hydroxycarbaryl (Modification R1=OCONHCH3 R2=H R3=H R4=OH R5=H), Carbaryl Derivative 5-hydroxycarbaryl (Modification R1=OCONHCH3 R2=H R3=H R4=H R5=OH), Carbaryl Derivative, 1-(5-Carboxypentyl)-3-(1-naphthyl)urea (Modification R1=NHCONH(CH2)5COOH R2=H), (Structurally related s-triazines)-Aziprotryn, 4-azido-N-isopropyl-6-methylthio-1,3,5-triazin-2-ylamine (Modification R1=—SCH3 R2=—N3 R3=—CH(CH3)2), (Structurally related s-triazines), 2-(ethylamino)-4-(methylthio)-6-amino-triazine (Modification R1=—SCH3 R2=—NH—C2H5 R3=—NH2), (Structurally related s-triazines)-2-amino-4-(methylthio)-6-(isopropylamino)triazine (Modification R1=—SCH3 R2=—NH2 R3=—NH—CH(CH3)2), (Structurally related s-triazines)-2-amino-4-methoxy-6-(isopropylamino)triazine (Modification R1=—OCH3 R2=—NH2 R3=—NH—CH(CH3)2), TCP Derivative (3,5,6-trichloro-2-pyridinol Derivative), 3-(3,5-dichloro-6-hydroxy-2-pyridyl)thiopropanoic Acid, p-nitrosuccinanilic acid (PNA-S), PNA-S, PNA-C, p-nitro-cis-1,2-cyclohexanedicarboxanilic acid, Nitroaniline Derivative, 2-nitroaniline, o-Nitroaniline, Nitroaniline Derivative-3-nitroaniline, m-Nitroaniline, Nitroaniline Derivative-4-nitroaniline, p-Nitroaniline, Aeromatic Alcohols, 4-nitrobenzyl alcohol, Aeromatic Alcohols-4-nitrophenethyl alcohol, Aeromatic Alcohols 2-nitrobenzyl alcohol, Aeromatic Alcohols, 3-nitrobenzyl alcohol, Urea Derivative-1-benzyl-3-(4-nitrophenyl)urea, Urea Derivative-1-(3-chlorophenyl)-3-(2-methoxy-5-nitrophenyl)urea, Urea Derivative-1-(3-chlorophenyl)-3-(4-methoxy-3-nitrophenyl)urea, Urea Derivative-1-(4-chlorophenyl)-3-(4-nitrophenyl)urea, Urea Derivative-(2-fluorophenyl)-3-(2-mehtoxy-4-nitrophenyl)urea, 1-(3-mehtoxyphenyl)-3-(3-nitrophenyl)urea, Carbofuran Derivative m Carbofuran-phenol, Carbofuran-hydroxy, Carbofuran-keto, Carbosulfan, 3-dihydro-2,2-dimethylbenzofuran-7-yl (dibutylaminothio) methylcarbamate, Benfuracarb, N-[2,3-dihydro-2,2-dimethylbenzofuran-7-yloxycarbonyl(methyl)aminothio]-N-isopropyl-β-alaninate, Furathiocarb, 2,3-dihydro-2,2-dimethyl-7-benzofuranyl 2,4-dimethyl-5-oxo-6-oxa-3-thia-2,4-diazadecanoate, Carbofuran Derivative, 4-[[(2,3-Dihydro-2,2-dimethyl-7-benzofuranyloxy)carbonyl]-amino]butanoic Acid (BFNB) (Modification n=3 X=CH2), Endrin, nendrin, (1R,4S,4aS,5S,6S,7R,8R,8aR)-1,2,3,4,10, 10-hexachloro-1,4,4a,5,6,7,8,8a-octahydro-6,7-epoxy-1,4: 5,8-dimethanonaphthalene, Heptachlor, 1,4,5,6,7,8,8-heptachloro-3a,4,7,7a-tetrahydro-4,7-, Chlordane, 1,2,4,5,6,7,8, 8-octachloro-2,3,3a,4,7,7a-hexahydro-4,7-methanoindene, Endosulfan (Modification isomer mix of alpha and beta forms), Endosulfan (Modification alpha isomeric form), Endosulfan (Modification beta isomeric form), Endosulfan Derivative, Endosulfan sulfate (Modification sulfate form), Endosulfan Derivative, Endosulfan diol, Diol metabolite of endosulfan, Endosulfan Derivative, Endosulfan ether (Modification ether metabolite of endosulfan), Endosulfan Derivative, hydroxy ether, hydroxy ether metabolite of endosulfan, Endosulfan Derivative, Endosulfan lactone (Modification lactone metabolite of endosulfan), Aldrin, Dieldrin, Fenvalerate isomers Modification 1S,2R isomer R: Ph), Fenvalerate isomers (Modification 1R,2S isomer R: Ph), Fenvalerate isomers (Modification 1R,2R isomer R: Ph), Fenvalerate isomers (Modification 1S,2R/S isomer R: Ph), Fenvalerate isomers (Modification 1R,2R/S isomer R: Ph), Fenvalerate isomers, fenvalerate (Modification 1R/S, 2R/S isomer R: Ph), Thiabendazole, 2-(thiazol-4-yl)benzimidazole, Thiabendazole Derivative, 5-hydroxythiabendazole (Modification 5-OH-TBZ), Thiabendazole Derivative, 5-NH2-TBZ, Thiabendazole Derivative, methyl benzimidazole carbamate, Albendazole, Mebendazole, Fenbendazole, Thiabendazole Derivative, 2-succinamidothiabendazole, Thiabendazole Derivative, 2-succinamidothiabendazole, Cambendazole, Fenvalerate Haptens, Cyano[3-(4-aminophenoxy)phenyl]methyl (S)-4-Chloro-alpha-(1-methylethyl)benzeneacetate (4-Aminoesfenvalerate), Fenvalerate Haptens, Benzyl 4-[3-[Cyano[(S)-2-(4-chlorophenyl)-3-methyl-1-oxobutanoxy]methyl]phenoxy]benzenepropanoate, Fenvalerate Haptens, Benzyl 3-[Cyano[(S)-2-(4-chlorophenyl)-3-methyl-1-oxobutanoxy]methyl]phenoxyacetate, Fenvalerate Haptens, 3-[Cyano[(S)-2-(4-chlorophenyl)-3-methyl-1-oxobutanoxy]methyl]phenoxyacetic Acid, Fenvalerate Haptens, Benzyl 6-[3-[Cyano[(S)-2-(4-chlorophenyl)-3-methyl-1-oxobutanoxy]methyl]phenoxy] hexanoate, Fenvalerate Haptens, 6-[3-[Cyano[(S)-2-(4-chlorophenyl)-3-methyl-1-oxobutanoxy]methyl]phenoxy] hexanoic Acid Fenvalerate Haptens, 4-[3-[Cyano[(S)-2-(4-chlorophenyl)-3-methyl-1-oxobutanoxy]methyl]phenoxy] benzenepropanoic Acid, (S)-fenvalerate Acid, (Structurally related s-triazines), atrazine mercapturate Modification R1=—SCH2CH(NHCOCH3)COOH R2=—NHCH2CH3 R3=—NHCH(CH3)2, Fenthion Hapten, -Methyl O-[3-methyl-4-(methylthio)phenyl] N-(3-carboxypropyl)phosphoramidothioate Modification referred as Hapten B, Fenthion Derivative, Oxidized Fenthion, Fenthion Derivative, Oxidized oxidized Fenthion, pirimiphos-ethyl, 4-(Methylthio)-m-cresol, Chlorpyrifos Derivative, Chlorpyrifos-oxon, Fenchlorphos, O,O-dimethyl O-2,4,5-trichlorophenyl phosphorothioate, Trichloronate, O-Ethyl O-2,4,5-trichlorophenyl ethyl-phosphonothioate, Dichlofenthion, O-2,4-dichlorophenyl O,O-diethyl phosphorothioate, Parathion, O,O-diethyl O-4-nitrophenyl phosphorothioate; Thiophos, Chlorpyrifos Derivative Modification Synthesis of AR1 is described, Chlorpyrifos Derivative, O-Ethyl O-(3,5,6-Trichloro-2-pyridyl)O-(3-Carboxypropyl)Phosphorothioate; (PO), Chlorpyrifos Derivative-O-Ethyl O-(3,5,6-Trichloro-2-pyridyl)N-(5-Carboxyethyl) Phosphoramidothioate; (PN1) (Modification Amide linkage of thiophosphate reagents), Chlorpyrifos Derivative, O-Ethyl O-(3,5,6-Trichloro-2-pyridyl)N-(2-Carboxyethyl) Phosphoramidothioate; (PN1) (Modification Amide linkage of suitable thiophosphate reagents), Triadimefon, (RS)-1-(4-chlorophenoxy)-3,3-dimethyl-1-(1H-1,2,4-triazol-1-yl)butan-2-one, GR151004, (4-[[5-[3-[2-(dimethylamino)ethyl]]-5-benzofuranyl]-3-pyridinyl]acetyl]morpholine dihydrochloride, Diflubenzuron, 1-(4-chlorophenyl)-3-(2,6-difluorobenzoyl)urea, (Structurally related s-triazines)-SprAAT (Modification R1=SCH2CH2COOH R2=NH2 R3=NH2), (Structurally related s-triazines), SBeAAT (Modification R1=S(C6H4)COOH R2=NH2 R3=NH2), (Structurally related s-triazines), SAAT (Modification R1=SH R2=NH2 R3=NH2), (Structurally related s-triazines), CDAT (Modification R1=Cl R2=NH[C(O)CH3] R3=NH2), (Structurally related s-triazines)-CDET (Modification R1=Cl R2=NH[C(O)CH3] R3=NH(CH2CH3), (Structurally related s-triazines)-CDIT (Modification R1=Cl R2=NH[C(O)CH3] R3=NH(CH(CH3)2)), (Structurally related s-triazines), CDDT (Modification R1=Cl R2=NH[C(O)CH3] R3=NH[C(O)CH3]), (Structurally related s-triazines)-ammeline, OAAT (Modification R1=OH R2=NH2 R3=NH2), (Structurally related s-triazines)-ammelide, OOAT (Modification R1=OH R2=OH R3=NH2), (Structurally related s-triazines)-cyanuric acid, OOOT (Modification R1=OH R2=OH R3=OH), (Structurally related s-triazines), melamine, AAAT (Modification R1=NH2 R2=NH2 R3=NH2), Structurally related s-triazines-N-isopropylammeline, OIAT (Modification R1=OH R2=NH[CH(CH3)2] R3=NH2, Structurally related s-triazines-N-ethylammeline, OEAT (Modification R1=OH R2=NHCH2CH3 R3=NH2), Structurally related s-triazines, N-ethylammelide, OOET (Modification R1=OH R2=OH R3=NHCH2CH3), Structurally related s-triazines-cyromazine, CyPAAT (Modification R1=NH(C3H5) R2=NH2 R3=NH2), Structurally related s-triazines-diamino-s-triazine, HAAT (Modification R1=H R2=NH2 R3=NH2), PCB congeners, 2,5,3',4'-tetrachlorobiphenyl (Modification IUPAC no.: 70), PCB congeners 2,4, 5,3',4'-pentachlorobiphenyl (Modification IUPAC no.: 118), PCB congeners-2,2',5,5'-tetrachlorobiphenyl (Modification IUPAC no.: 52), PCB congeners, 6-[3,3',4'-Trichlorobiphenyl-4-yl)oxy]hexanoic Acid, Metolazone, Brand Names: Mykrox; Zaroxolyn, Furfuryl benzoate, DDT Metabolites, DDA, Paraquat, 1,1'-dimethyl-4,4'-bipyridinium ion, Diethylcarbamazine, THP, 2,4,6-triphenyl-N-(4-hydroxyphenyl)-pyridinium, o-DNCP, -dinitrocarboxyphenol, PCB congeners, 3-chlorobiphenylol (Modification IUPAC No. 2), PCB congeners, 3,4'-dichlorobiphenyl (Modification IUPAC No. 13), PCB congeners, 3,5-dichlorobiphenyl (Modification IUPAC No. 14), PCB congeners, 3,4,5,3',4'-pentachlorobiphenyl (Modification IUPAC No. 126), 2,3,3',4'-tetrachlorobiphenyl (Modification IUPAC No. 56), 2',3,4,5-tetrachlorobiphenyl (Modification IUPAC No. 76), 3,3',5,5'-tetrachlorobiphenyl (Modification IUPAC No. 80), 2,4,5,2',5'-pentachlorobiphenyl (Modification IUPAC No. 101), 2,3,3',4,4'-pentachlorobiphenyl (Modification IUPAC No. 105), 2,3,6,3',4'-pentachlorobiphenyl (Modification IUPAC No. 110), 3,3',4,5,5'-pentachlorobiphenyl (Modification IUPAC No. 127), 3,4,5,3',4',5'-hexachlorobiphenyl (Modification IUPAC No. 169), 2,3,3',4,4',5-hexachlorobiphenyl (Modification IUPAC No. 156), 3,4,3',4'-tetrabromobiphenyl, 3,4,5,3',4',5'-hexabromobiphenyl, 2,4,5,2',4',5'-hexabromobiphenyl, Dibenzofurans and Dioxins, 2,3,7,8-tetrachlorobenzofuran, 2,3,7,8-tetrachlorodibenzo-p-dioxin, 3,4',5-trichloro-4-biphenylol, 3,3',5,5'-tetrachloro-4,4'-biphenyldiol, 3,4,3',4'-tetrachlorodiphenyl ether, 1-2-dichlorobenzene, 1,4-dichlorobenzene, 1,2,4-trichlorobenzene, 3,4-dichloroaniline, DDT Metabolites, 4,4'-DDT, 4,4'-DDD Retronecine, 3,4-dichlorobiphenyl Modification IUPAC No. 12, 3,4,3'-trichlorobiphenyl (Modification IUPAC No. 35), PCB Congeners, 3,4,4'-trichlorobiphenyl (Modification IUPAC No. 37), 3,4,3',5-tetrachlorobiphenyl (Modification IUPAC No. 78), 3,4,3',5'-tetrachlorobiphenyl (Modification IUPAC No. 79), 3,4,4',5-tetrachlorobiphenyl (Modification IUPAC No. 81), DDT Metabolites, p,p'-DDT (Modification p,p'-dichlorodiphenyltrichloroethane), o,p'-DDT Modification o,p'-dichlorodiphenyltrichloroethane, p,p'-DDE Modification p,p'-DDE, o,p'-DDE Modification o,p'-DDE, p,p'-DDD Modification p,p'-DDD, o,p'-DDD Modification o,p'-DDD, Dicofol, 4,4-dichloro-a-(trichloromethyl)benzhydrol, Cyprazine, 6-chloro-N-cyclopropyl-N'-(1-methylethyl)-1,3,5-triazine-2,4-diamine, Structurally related s-triazines, Dipropetryn, 6-(ethylthio)-N,N'-bis(1-methylethyl)-1,3,5-triazine-2,4-diamine, Trietazine, 6-chloro-N,N,N'-triethyl-1,3,5-triazine-2,4-diamine, 6-Hydroxyatrazine, hexazinone, 3-cyclohexyl-6-dimethylamino-1-methyl-1,3,5-triazine-2,4 (1H,3H)-dione, TNT, 2,4,6-Trinitrotoluene, Tetraconazole (M14360), 1-[2-(2,4-dichlorophenyl)-3-(1,1,2,2-tetrafluoro-ethoxy)propyl]-1H-1,2,4-triazole, DTP, 2-(2,4-dichlorophenyl)-3-(1H-1,2,4-triazol-1-yl)propanol, Imazalyl, fenarimol, (RS)-2,4'-dichloro-α-(pyrimidin-5-yl)benzhydryl alcohol, Lupanine metabolites, (+)-lupanine (Modification R=H), Lupanine metabolites, (+)-13-hydroxylupanine (Modification R=OH), Lupanine metabolites, hemisuccinate ester of (+)-13-hydroxylupanine (Modification R=OCO—(CH2)2.COOH), Lupanine metabolites, cis-hexahydrophthalate ester of (+)-13-hydroxylupanine (Modification R=OCO.C6H10.COOH), Lupanine metabolites, alpha-isolupanine, Lupanine metabolites, -hydroxylupanine, Sparteine, Cysteine, multiflorine, epilupinine, (Structurally related s-triazines), CYANAZINE ACID Modification R1=Cl R2=NHCH2CH3 R3=NHCCOOH(CH3)2, Structurally related s-triazines Modification R1=Cl R2=NHCH2CH3 R3=NH(CH2)3COOH, Structurally related s-triazines (Modification R1=Cl R2=NHCH2CH3 R3=NHCH2COOH), (Structurally related s-triazines) (Modification R1=Cl R2=NHCH2CH3 R3=NH(CH2)4COOH), norflurazon, 4-chloro-5-(methylamino)-2-[3-(trifluoromethyl)phenyl]-3(2H)-pyridazinone, norflurazon derivative, desmethyl-norflurazon, metflurazon, -chloro-5-(dimethylamino)-2-[(3-trifluoromethyl)phenyl]-3(2H)-pyridazinone, Pyrazon, Chloridazon, 5-amino-4-chloro-2-phenyl-3(2H)-pyridazinone (active ingradient), dichlorophenyl-pyridazone, (Structurally related s-triazines) azidoatrazine (Modification R1=N3 R2=NHCH(CH3)2 R3=NHCH2CH3), ALACHLOR 2-chloro-2',6'-diethyl-N-methoxymethylacetanilide, trichothecolone (Modification R1=H R2=OH R3=H R4=O R5=H), DON derivative, acetyl-T-2, DON derivative, T-2 tetrol tetraacetate, Chlorpyrifos derivatives, mono-dechloro-CP, Bromophos derivative, Bromophos-methyl, Bromophos derivative, Bromophos-ethyl dicapthon, -2-chloro-4-nitrophenyl O,O-dimethyl phosphorothioate, tetrachlorvinphos, (Z)-2-chloro-1-(2,4,5-trichlorophenyl)vinyl dimethyl phosphate, triclopyr, 3,5,6-trichloro-2-pyridyloxyacetic acid, picloram, 4-amino-3,5,6-trichloropyridine-2-carboxylic acid, Formononetin, Biochanin A, 5, 7-dihydroxy-4'-methoxyisoflavone (Modification It is the 4'-methyl ether of genistein), equol, (7-hydroxy-3-(4'-hydroxyphenyl)-chroman, 2'methoxyformononetin, Daidzein, 7-hydroxy-3-(4-hydroxyphenyl)-4H-1-benzopyran-4-one, geninstein, quercetin, 3,3',4',5,7-Pentahydroxyflavone; 3,5,7,3',4'-Pentahydroxyflavone; matheucinol, coumestrol (Structurally related s-triazines), Hydroxysimazine (Modification R1=OHR2=NHCH2CH3R3=NHCH2CH3, angustifoline, Alodan, 1-Methyl-4-phenyl-4-carboethoxypiperidine hydrochloride, Zearalenone, RAL, F-2 Toxin, Fenpropimorph, (RS)-cis-4-[3-(4-tert-butylphenyl)-2-methylpropyl]-2,6-dimethylmorpholine, Tridemorph, 2,6-dimethyl-4-tridecylmorpholine, 2,6-dimethylmorpholine, Amorolfine, Fenpropidine, (RS)-1-[3-(4-tert-butylphenyl)-2-methylpropyl]piperidine, (Structurally related s-triazines) (Modification R1=Cl R2=Cl R3=NHCH2CH3, (Structurally related s-triazines) Modification R1=Cl R2=Cl R3=NHCH(CH3)2, (Structurally related s-triazines) Modification R1=Cl R2=NHCH2CH3 R3=NH(CH2)5COOH, (Structurally related s-triazines) Modification R1=Cl R2=NHCH(CH3)2 R3=NHCH2COOH, (Structurally related s-triazines) (Modification R1=Cl R2=NHCH(CH3)2 R3=NH(CH2)5COOH), Structurally related s-triazines, cyanazine amide (Modification R1=Cl R2=NHCH2CH3 R3=NHCCONH2(CH3)2), hydroxycyanazine acid (Modification R1=OH R2=NHCH2CH3 R3=NHCCOOH(CH3)2), deethylsimazine (Modification R1=Cl R2=NH2 R3=NHCH2CH3), Albendazole sulfoxide, [5-(propylthionyl)-1H-benzimidazol-2-yl]-, methylester, Albendazole sulfone, 5(6)-alkylbenzimidazoles, 2-amino-5-(propylthio)benzimidazole, 5(6)-alkylbenzimidazoles, 2-amino-5-(propylsulfonyl)benzimidazole, oxibendazole, 5-propoxy-benzimidazole-2-methyl carbamate, 5(6)-arylbenzimidazoles, fenbendazole sulfone (Modification sulfone metabolite of fenbendazole), 5(6)-arylbenzimidazoles, 4'-hydroxyfenbendazole, 5(6)-arylbenzimidazoles, oxfendazole (Modification Oxfendazole is the sulfoxide metabolite of fenbendazole), 5(6)-arylbenzimidazoles, flubendazole, benzimidazole Metabolites, 2-aminobenzimidazole, benzimidazole Metabolites, 5-aminobenzimidazole, benzimidazole Metabolites, 2-acetylbenzimidazole, Benzophenone, Diphenylmethanone; phenyl ketone; Diphenyl ketone; Benzoylbenzene, Benzaldehyde, benzoic aldehyde, 4-Bromo-2,5-dichlorophenol, Acephate, O,S-dimethyl acetylphosphoramidothioate, methamidophos, O,S-dimethyl phosphoramidothioate, Dichlorvos, 2,2-dichlorovinyl dimethyl phosphate, Phenthoate, S-α-ethoxycarbonylbenzyl O,O-dimethyl phosphorodithioate, EPN, Ethyl p-nitrophenyl thionobenzenephosphonate, Bioresmethrin, -benzyl-3-furylmethyl (1R,3R)-2,2-dimethyl-3-(2-methylprop-1-enyl)cyclopropanecarboxylate (Modification The unresolved isomeric mixture of this substance has the ISO common name resmethrin), flufenoxuron, 1-[4-(2-chloro-α,α,α-trifluoro-p-tolyloxy)-2-fluorophenyl]-3-(2,6-difluorobenzoyl) urea, Amitrole, 1H-1,2,4-triazol-3-ylamine, molinate, S-ethyl azepane-1-carbothioate, molinate derivative (Modification S-2-carboxyethyl hexahydroazepine-1-carbothioate), molinate derivative (Modification S-5-carboxypentyl hexahydroazepine-1-carbothioate) molinate derivative (Modification molinate sulfone), molinate derivative (Modification S-(p-aminobenzyl) hexahydroazepine-1-carbothioate), molinate derivative (Modification S-2-(p-aminophenyl) ethyl hexahydroazepine-1-carbothioate), hexamethylenimine, thiobencarb (Bolero), butylate (Sutan), EPTC (Eptam), cycloate (Roneet), pebulate (Tillam), vernolate (Vernam), Aflatoxin M1, AFM1 (Modification AFM1), Aflatoxin B1, AFB1 (Modification AFB1), Aflatoxin G1, AFG1 (Modification AFG1), Aflatoxin M2, AFM2 (Modification AFM2), Aflatoxin B2, AFB2 (Modification AFB2), Aflatoxin G2, AFG2 (Modification AFG2), Aflatoxin B2alpha, AFB2alpha (Modification AFB2alpha), Aflatoxin G2alpha, AFG2alpha (Modification AFG2alpha), KB-6806, 6-amino-5-chloro-1-isopropyl-2-(4-methyl-1-piperazinyl) (Modification R1=NH2 R2=CH(CH3)2 R3=CH3), KB-6806 (Benzimidazole) Derivatives Modification R1=NH2 R2=CH2CH(CH3)2 R3=CH3, Hapten Name KB-6806 (Benzimidazole) Derivatives (Modification R1=NH2 R2=CH(CH2CH3)2 R3=CH3), KB-6806 (Benzimidazole) Derivatives (Modification R1=NHCOCH3 R2=CH(CH3)2 R3=CH3), KB-6806 (Benzimidazole) Derivatives (Modification R1=H R2=CH(CH3)2 R3=CH3), KB-6806 (Benzimidazole) Derivatives (Modification R1=NH2 R2=CH(CH3)2 R3=CH3), KB-6806 (Benzimidazole) Derivatives Modification R1=NH2 R2=CH(CH3)2 R3=N(—>O) CH3 (N-OXIDE), KB-6806 (Benzimidazole) Derivatives Modification R1=NH2 R2=CH(CH3)2 R3=H, KB-6806 (Benzimidazole) Derivatives Modification R1=NH2 R2=CH2CH3 R3=CH3, Aminoparaoxon, phosphoric acid, O,O-diethyl O-(4-aminophenyl) ester, Methylparathion, phosphorothioic acid, O,O-dimethyl O-(4-nitrophenyl) ester, Diethyl phenylphosphate, phenylphosphonic acid, O,O-diethyl ester, Diethyl phosphate, ethylphosphonic acid, O,O-diethyl ester, p-Nitorphenyl phosphate, phosphonic acid, O-(4-nitrophenyl)ester, Phorate, phosphorodithioic acid, O,O-diethyl S-[(ethylthio)methyl] ester, Ethion, bis(phosphorodithioic acid), S,S'-methylene O,O,O',O'-tetraethyl ester, Carbophenthion, phosphorodithioic acid, O,O-diethyl S-[[(4-chlorophenyl)thio]methyl] ester, Disulfoton, phosphorodithioic acid, O,O-diethyl S-[(2-ethylthio)ethyl] ester, TS, N-[4-(Carboxymethyl)-2-thiazolyl)sulfanilamide, NS, N-(4-Nitrophenyl)sulfanilamide, Sulfamoxole, Sulfacetamide, DNP-SL, Spin labelled dinitrophenyl (Modification The synthesis of DNP-SL has been described by Balakrishnan et al (1982) formula can be found in Anglister et al. (1984)), beta ecdysone, Benzimidazole Derivative, 5(6)-[Carboxypentyl)thio]-2-(methoxycarbonyl)amino]-benzimidazole, 2-hydroxybiphenyl HBP, Atrazine Caproic acid, Lysophosphatidic acid (LPA), 1-acyl-2-hydroxy-sn-glycero-3-phosphate), berberine, Palmatine, 9-Acetylberberine, Corydaline, Coptisine, Berberrubine, 8-Oxoberberine, Papaverine, Berberine Derivative, 9-O-carboxymethyl berberine, phencyclidine, 1-(1-phenylcyclohexyl)piperidine, Methoxychlor, Endosulfan Derivative, 4-Oxobutanoic Acid,4-(4,5,6,7,8,8-Hexachloro-3a,4,7,7a-tetrahydro-4,7-methano-1H-indenyl-1-oxy), Endosulfan Derivative, 4-oxybutanoic Acid,4-(1,3,4,5,6,7,8-Octachloro-3a,4,7,7a-tetrahydro-4,7-methanoindanyl-2-oxy, Endosulfan Derivative (Modification Hemisuccinate of Endosulfan diol), Triazole Derivatives, 5-(3-Hydroxypropyl)-3-amino-2H-1,2,4-triazole, Triazole Derivatives, 5-(3-Hydroxypropyl)-3-(2-nitrophenylsulfenyl)amino-2H-1,2,4-triazole, Triazole Derivatives, 3-Amino-5-[(3-succinyloxy)propyl]-2H-1,2,4-triazole, Triazole Derivatives, 3-amino-1,2,4-triazole-5-thiol, Triazole Derivatives, 3-[(2-nitrophenylsulfenyl)amino-2H-1,2,4-triazole-5-thiol, Triazole Derivatives, 2H-1,2,4-triazole-5-thiol, Triazole Derivatives, 4-methyl-1,2,4-triazole-3-thiol, Triazole Derivatives, (1,2,4-triazol-2-yl)acetic acid, 1,2,4-triazole, 4-nitrophenyl 4'-carboxymethylphenyl phosphate, Triazole Derivative, 4-amino-1,2,4-triazole, Triazole Derivative, 3-acetamido-1H-1,2,4-triazole, Triazole Derivative, 3-amino-1,2,4-triazole-5-carboxylic acid hemihydrate, Triazole Derivative, 2-(4-chlorophenyl)-2-(1,2,4-triazol-1-yl)-methylhexanoic acid, succinic acid, Imidazole, L-histidine, L-glutamic acid, Permethrin derivative, 3-phenoxybenzyl 2,2-dimethylcyclopropane-1,3-dicarboxylate, 3-phenoxybenzaldehyde, flucythrinate, Chrysanthemic acid, 2,4-Dinitrophenyl, DNP, Thiram Haptens, Disodium 4-[Carbodithioato(methyl)-amino]butanoate, Thiram Haptens 5,11-Dimethyl-6,10-dithioxo-7,9-dithia-5,11-diazadodecanoic Acid, Thiram Haptens, 2-{[(Dimethylamino)carbothioyl]sulfanyl}ethanoic Acid, Thiram Haptens, 4-{[(Dimethylamino)carbothioyl]sulfanyl}butanoic Acid, Thiram Haptens, 6-{[(Dimethylamino)carbothioyl]sulfanyl}hexanoic Acid, Thiram Haptens, 11-{[(Dimethylamino)carbothioyl]sulfanyl}undecanoic Acid, Thiram Haptens, 2-{[(Dimethylamino)carbothioyl] sulfanyl}ethanoic Acid, Thiram, Tetramethylthiurammonosulfide, Tetraethylthiuram disulfide, Dimethyldithiocarbamic acid sodium salt, Dimethyldithiocarbamic acid zinc salt, Diethyldithiocarbamic acid sodium salt, N,N,N',N'-tetramethylthiourea, Nabam, Zineb, Maneb, Ethylenethiourea, Chlorpyrifos hapten, O,O Diethyl O-[3,5-Dichloro-6-[(2-carboxyethyl)thio]-2-pyridyl] Phosphorothioate, 2-Succinamidobenzimidazole, Methyl 2-Benzimidazolecarbamate, MBC, Benzimidazole, 2-benzimidazolylurea, succinamide, Ethyl carbamate, Urea, N-methylurea, N,N'-dimethylurea, Brevetoxin PbTx-3, Organophosphorous Haptens, O,O-Diethyl O-(5-carboxy-2-fluorophenyl) phosphorothioate, Chlorpyrifos-ethyl, Anandamide hapten, N-Arachidonyl-7-amino-6-hydroxy-heptanoic acid, Anandamide, Arachidonic acid, Docosatetraenoyl ethanolamide, Dihomo-gamma-linolenyl ethanolamide, 2-Arachidonyl glycerol, 2-Arachidonyl glycerol ether, Stearoyl ethanolamide, Heptadecanoyl ethanolamide, Prostaglandin E1, 3-hydroxy-2-(3-hydroxy-1-octenyl)-5-oxocyclopentaneheptanoic acid; alprostadil; PGE1, Prostaglandin D2, PGD2, Prostaglandin A2, PGA2, Prostaglandin B2, PGB2, Prostaglandin F2 alpha, 7-[3,5-dihydroxy-2-(3-hydroxy-1-octenyl)cyclopentyl]-5-heptenoic acid; dinoprost; PGF2alpha, Prostaglandin F1 alpha, PGF1alpha, 6-keto-Prostaglandin F1 alpha, 6-keto-PGF1alpha, 13,14-Dihydro-15-keto-Prostaglandin E2, 13,14-Dihydro-15-keto-PGE2, 13,14-Dihydro-15-keto-Prostaglandin F2alpha, 14-Dihydro-15-keto-PGF2alpha, 5alpha,7alpha-Dihydroxy-11-ketotetranorpostane-1,16-dioic acid, 15-keto-PGF2alpha, TXB2, Prostaglandin E2,7-[3-hydroxy-2-(3-hydroxy-1-octenyl)-5-oxocyclopentyl]-5-heptenoic acid; dinoprostone; PGE2, hCG-alpha-(59-92)-peptide (34 residues), Paraquat Derivative, Paraquat hexanoate (PQ-h), Monoquat, Diquat, 9,10-dihydro-8a, 10a-diazoniaphenanthrene, MPTP, 1-methyl-4-phenyl-1,2,5,6-tetrahydropyridine, 1,2-Naphthoquinone, N-Acetyl-S-(1,2-dihydroxy-4-naphthyl)cysteine, N-Acetyl-S-(1,4-dihydroxy-2-naphthyl)cysteine, N-Acetyl-S-(1,2-dihydroxy-1-hydroxy-1-naphthyl)cysteine, 2-Chloro-2'.6'-diethylacetanilide (CDA) Hapten, 2-[2-Chloro-(2'-6'-diethyl)acetanilido]ethanoic Acid, 2-Chloro-2'.6'-diethylacetanilide (CDA) Hapten, 2-[2-Chloro-(2'-6'-diethyl)acetanilido]butanoic Acid, 2-Chloro-2'.6'-diethylacetanilide (CDA) Hapten, 5-(4-Chloroacetamido-3,5-diethyl)phenoxypentanoic Acid, CDA, 2-Chloro-2'.6'-diethylacetanilide, HDA, 2-Hydroxy-2'.6'-diethylacetanilide, 2,6-diethyl-aniline, Hydroxyalachlor, Alachlor ESA, Alachlor ethanesulfonic acid, Isoproturon Hapten, 3-(4-Isopropylphenyl)-1-carboxypropyl-1-methyl urea, chlorotoluron, 3-(3-chloro-p-tolyl)-1,1-dimethylurea, Metoxuron, 3-(3-chloro-4-methoxyphenyl)-1,1-dimethyl-urea, metamitron, 4-amino-4,5-dihydro-3-methyl-6-phenyl-1,2,4-triazin-5-one, mecoprop, (RS)-2-(4-chloro-o-tolyloxy) propionic acid, propyzamide, 3,5-dichloro-N-(1,1-dimethylpropynyl)benzamide, Paraquat dichloride, MCPB, 4-(4-chloro-o-tolyloxy)butyric acid, Chlortoluron Hapten, N-(3-Chloro-4-methylphenyl)-N-methyl-N-carboxypropyl Urea, Metsulfuron, Methyl 2-[3-(4-methoxy-6-methyl-1,3,5-triazin-2-yl)ureidosulphonyl]benzoate, Captopril Haptens, Captopril-4-(Maleimidomethyl)-cyclohexane Carboxylic Acid (MCC), Captopril Haptens, Captopril Disulfide Modification, Mercaptoethanol-MCC, Mercaptoethanol-4-(Maleimidomethyl)-cyclohexane Carboxylic Acid Modification, Captopril Haptens, Captopril without MCC, Aculeatiside A, Aculeatiside B, Solamargine, Solasonine, solanine-S; purapurine, Solasodine, Khasianine, Tomatine, lycopersicin, Tomatidine, 3-O-beta-D-Glucopyranosyl-solasodine, O-alpha-L-Rhamnosyl-1(1→2)-3-O-beta-D-glucopyranosyl-solasodine, 3-O-beta-D-Galacopyranosyl-solasidine, O-beta-D-Glucopyranosyl-1(1→3)-3-O-beta-D-galacopyranosyl-solasodine, 12-Hydroxysolamargine, 12-Hydroxysolasonine, Isoanguivine, Solaverine I, Solaverine II, Xylosyl-beta-solamargine, alpha-Solanine, alpha-Chaconine, Dioscine, Indole Derivatives, beta-Indole Acetic Acid, 2-Bromo-4,6-dinitroaniline, 2-Chloro-4,6-dinitroaniline, Tetryl, 2,4,6-trinitrophenyl-n-methylnitramine, nitramine, tetralite, tetril, 2-Amino-4,6-dinitrotoluene, 2,4-Dinitroaniline, 3,5-Dinitroaniline, 2-Amino-4,6-dinitrobenzoic acid, Disperse Blue 79, N-[5-[bis[2-(acetyloxy)ethyl]amino]-2-[(2-bromo-4,6-dinitrophenyl) azo]-4-ethoxyphenyl]acetamide, 1,3-Dinitrobenzene, 2,6-Dinitrotoluene, 4-Amino-2,6-dinitrotoluene, 1,3,5-Trinitrobenzene, Nicergoline, Ethylmorphine, 8-Didehydro-4,5-epoxy-3-ethoxy-17-methylmorphinan-6-ol, Dihydromorphine, Dihydrocodeine, dihydromorphinone, Hydromorphone, Dihydrocodeinone, Hydrocodone, Naltrexone, N-cyclopropylmethyl-14-hydroxydihydromorphinone, Dextromethorphan, (±)-3-Methoxy-17-methylmorphinan, Homatropine, Endorphins Modification Derivative Type: b-Endorphin, Met-enkephalin, DALEA, D-Ala(2)-D-Leu(5)-enkephalinamide, Vincristine, 22-Oxovincaleukoblastine, leurocristine; VCR; LCR, OCT, 22-Oxacalcitriol, OCT-3-HG, 22-oxacalcitriol-3-Hemiglutarate, 24(OH)OCT, 24(OH)-22-oxacalcitriol, 1,20(OH)2-hexanor-D3, Synephrine, Epinephrine, 4-[(1R)-1-Hydroxy-2-(methylamino)ethyl]-1,2-benzenediol, Phenylephrine, Dopamine Derivative, 6-hydroxy dopamine, Tyramine derivative, 3-methoxy tyramine, Phenethylamine, Benzeneethanamine; PEA, m-tyramine, o-tyramine, dimethoxyphenethylamine, Thymidine glycol monophosphate, 5,6-Dihydroxythymidine monophosphate, Thymidine monophosphate, Thymidine glycol, Thymine glycol, 5,6-Dihydrothymidine, Thymidine, Thymine, 5-methyluracil; 2,4-dihydroxy-5-methylpyrimidine, AMP, Adenosine mono phosphate, CMP, Cytidine mono phosphate, Carbamazepine, 5-carbamoyl-5H-dibenz[b,f]azepine, Neopterin isomers, D-erythro-Neopterin, Neopterin isomers, L-erythro-Neopterin, Neopterin isomers, D-threo-Neopterin, Biopterin isomers, L-erythro-Biopterin, Biopterin isomers, D-erythro-Biopterin, Biopterin isomers, L-threo-Biopterin, Biopterin isomers, D-threo-Biopterin, Pterin-6-Carboxylic Acid, C7H5NiO3, Pterin, Thromboxane B2, (5Z,9alpha,13E,15S)-9,11,15-trihydroxythromboxa-5,13-dien-1-oic acid, 15 Ketoprostaglandin F2alpha, Fumonisin B1, macrofusine; FBI, Thyroliberin, TRH; thyrotropin-releasing factor; thyrotropin releasing hormone; TRF; protirelin; lopremone, Thyroliberin-OH, TRH-OH, Diketopiperazine, cyclo (H-P), TRH analogues, Methylated TRH, TRH analogues, TRH elongated peptides, TRH-Gly, TRH elongated peptides, TRH-Gly-Lys-Arg, TRH elongated peptides, TRH-Gly-Lys-Arg-Ala, TRH elongated peptides, P7 (Modification Q-H-P-G-L-R-F), TRH elongated peptides, P10 (Modification S-L-R-Q-H-P-G-L-R-F), TRH elongated peptides, Ps5 Modification pro-TRH[178-199], TRH elongated peptides, TRH-Ps5 (Modification pro-TRH[172-199]), Hypothalmic peptide, LHRH, Cyanoginosin-LA, Cyanoginosin-LB, Cyanoginosin-LR, Cyanoginosin-LY, Cyanoginosin-AY, Cyanoginosin-FR, Cyanoginosin-YR, Ne-acetyllysine-containing peptide, Gly-Lys (Ac)-e-aminocaproic acid (Aca)-Cys, Benzoic Acid, Benzenecarboxylic acid; phenylformic acid; dracylic acid, m-hydroxybenzoic acid, 3-hydroxybenzoic acid, o-methoxybenzoic acid, 2-methoxybenzoic acid, o-toluic acid, 2-Methylbenzoic acid, o-chlorobenzoic acid, 2-chlorobenzoic acid, o-aminobenzoic acid, 2-aminobenzoic acid, thiosalicylic acid, 2-Mercaptobenzoic acid; o-sulfhydrylbenzoic acid, Salicylamide, 2-Hydroxybenzamide, Saligenin, saligenol; o-hydroxybenzyl alcohol; Salicyl alcohol, 2-cyanophenol, 2-hydroxyphenyl acetic acid, p-hydroxybenzoic acid, p-aminobenzoic acid, 4-Aminobenzoic acid; vitamin Bx; bacterial vitamin H1, p-toluic acid, p-methylamino benzoic acid, p-chlorosalicylic acid, 4-chloro-2-hydroxybenzoic acid, 2,4-dihydroxybenzoic acid, beta-Resorcylic Acid; 2,4-dihydroxybenzenecarboxylic acid; BRA, 4-aminosalicylic acid, 4-Amino-2-hydroxybenzoic acid; p-aminosalicylic acid, Gentisic Acid, 2,5-dihydroxybenzoic acid; 5-hydroxysalicylic acid, Picolinic acid, o-Pyridinecarboxylic acid; 2-Pyridinecarboxylic acid, picolinic acid N-oxide, 3-hydroxypicolinic acid, 2-hydroxynicotinic acid, 7-methylguanine, N2-Carboxymethyl-N7-methylguanine, 2-(7-methyl-6-oxo-6,7-dihydro-1H-purin-2-ylamino)acetic acid, 7-methylxanthine, 7-methyluric acid, 7-methyladenine, Guanine, 2-Amino-1,7-dihydro-6H-purin-6-one; 2-aminohypoxanthine, Adenine, 6-aminopurine; 6-amino-1H-purine; 6-amino-3H-purine; 6-amino-9H-purine, 7-(2-Carboxyethyl)guanine, 7-CEGua, 7-Ethylguanine, 2-amino-7-ethyl-1H-purin-6(7H)-one, 7-(2,3-Dihydroxypropyl) guanine, 2-amino-7-(2,3-dihydroxypropyl)-1H-purin-6 (7H)-one, 7-(2-Hydroxyethyl)guanine, 2-amino-7-(2-hydroxyethyl)-1H-purin-6(7H)-one, 7-(2-[(2-Hydroxyethyl) amino]ethyl)-guanine, 2-amino-7-(2-(2-hydroxyethylamino)ethyl)-1H-purin-6(7H)-one, 7-Carboxymethylguanine, or 2-(2-amino-6-oxo-1,6-dihydropurin-7-yl)acetic acid. In some alternatives, the CAR or T cell receptor comprises a fragment specific for the hapten, wherein the CAR or TCR comprises 14G8, Anti 3-methylindole antibodies, 3F12, Anti 3-methylindole antibodies, 4A1G, Anti 3-methylindole antibodies, 8F2, Anti 3-methylindole antibodies, 8H1, Anti 3-methylindole antibodies, Anit-Fumonisin B1 antibodies, Anti-1,2-Naphthoquinoneantibodies, Anti-15-Acetyldeoxynivalenol antibodies, Anti-(2-(2,4-dichlorophenyl)-3(1H-1,2,4-triazol-1-yl)propanol) Antibodies (Anti-DTP antibodies), Anti-22-oxacalcitriol antibodies (As-1, 2 and 3), Anti-(24,25(OH)2D3) Antibodies (Ab11), Anti-(24,25(OH)2D3) Antibodies (Ab3), Anti-(24, 25(OH)2D3) Antibodies (Ab3-4), Anti-2,4,5-Trichlorophenoxyacetic acid antibodies, Anti (2,4,5-Trichlorphenoxyacetic acid) Antibodies, Anti-(2,4,6-Trichlorophenol) Antibodies, Anti-(2,4,6-Trichlorophenol) Antibodies, Anti 2,4,6-Trinitrotoluene (TNT) Antibodies, Anti-2,4-Dichlorophenoxyacetic acid (MAb's B5/C3, E2/B5, E2/G2, F6/C10, and F6/E5), Anti (2,4-Dichlorphenoxyacetic acid) Antibodies, Anti-2-hydroxybiphenyl-antibodies, Anti-(3,5,6-trichloro-2-pyridinol) Antibodies (LIB-MC2, LIB-MC3), Anti (3,5,6-trichloro-2-pyridinol) antibodies (LIB-MC2 MAb), Anti-3-Acetyldeoxynivalenol (3-AcDON) Antibodies, Anti-3-phenoxybenzoic acid (3-PBAc)-Antibodies, Anti-4-Nitrophenol antibodies, anti-4-nitrophenyl 4'-carboxymethylphenyl phosphate antibodies, Anti-7-(Carboxyethyl)guanine (7-CEGua) antibodies (group specific for 7-meGua), Anti-7-methylguanine (7-MEGua) antibodies, Anti-ABA antibodies, Anti Acephate antibodies (Antiserum 8377), Anti-acetyllysine antibodies (mAbs AL3D5, AL11, AKL3H6, AKL5C1), Anti Aculaetiside-A antibody, Anti Aflatoxin M1(AFM1)antibodies (mAbs A1, N12, R16, FF32), Anti-agatharesinol Antibody, Anti-agatharesinol Antibody, Anti Amidochlorantibodies, Anti-Amitrole antibodies (anti 1a-BSA antibodies), Anti ampicillin Antibodies (AMPI I 1D1 and AMPI II 3B5), Anti-anandamide antibodies (9C11.C9C, 30G8.E6C, 7D2.E2b, 13C2 MAbs), Anti atrazine antibodies, Anti-atrazine antibodies, Anti-Atrazine antibodies, Anti Atrazine Antibodies, Anti-Atrazine Antibodies, Anti-Atrazine Antibodies, Anti-Atrazine Antibodies (4063-21-1 MAb cell line mAb and scAbs), Anti-Atrazine Antibodies (4D8 and 6C8 scAb), Anti Atrazine Antibodies (C193), Anti Atrazine Antibodies (In Rabbit/Sheep), Anti Atrazine Antibodies (K4E7), Anti Atrazine Antibodies (MAb: AM7B2.1), Anti Atrazine Antibodies (ScAb), Anti Atrazine Mercapturic acid antibodies, Anti (Azinphos methyl) Antibodies (MAB's LIB-MFH14, LIB-MFH110), Anti benalaxyl antibody, Anti benzimidazolecarboxylic acid, Anti benzimidazoles antibody (Ab 587), Anti-Benzo[a]pyrene antibodies, Anti Benzo(a)pyrene antibodies (10C10 and 4D5 MAbs), Anti-(Benzoylphenylurea)-Antibodies (mainly against Diflubenzuron), Anti-berberine Antibodies, Anti-beta Indole Acetic Acid Antibodies, Anti-Biopterin (L-erythro form) Antibodies, Anti-Brevetoxin PbTx-3-Antibodies, Anti Bromacil Antibodies, Anti-Bromophos Antibodies, Anti-Bromophos ethyl Antibodies, Anti Butachlor antibodies, Anti-Captopril-MCC Antibodies, Anti-Carbamazepine (CBZ)-Antibodies, Anti Carbaryl Antibodies, Anti Carbaryl Antibodies (LIB-CNH32, LIB-CNH33, LIB-CNH36, LIB-CNH37, LIB-CNH45, LIB-CNA38), Anti-Carbaryl Antibodies (LIB/CNH-3.6 MAb), Anti Carbofuran Antibodies (LIB-BFNB-52, LIB-BFNB-62, LIB-BFNB-67), Anti Carbofuran Antibodies (LIB-BFNP21), Anti-CDA-antibodies, Anti-CDA-antibodies (anti-2-[2-Chloro-(2'-6'-diethyl)acetanilido]butanoic Acid), Anti-CDA-antibodies (anti-2-[2-Chloro-(2'-6'-diethyl)acetanilido]ethanoic Acid), Anti-CDA-antibodies (anti-5-(4-Chloroacetamido-3,5-diethyl)phenoxypentanoic Acid), anti-ceftazidime antibody, Anti-(chlorodiamino-s-triazine) Antibodies (Anti-CAAT) (PAb1-8), Anti Chlorothalonil Antibodies, Anti-Chlorpyrifos antibodies, Anti-Chlorpyrifos Antibodies, Anti-Chlorpyrifos Antibodies (LIB-AR1.1, LIB-AR1.4 Mabs), Anti-Chlorpyrifos Antibodies (LIB-C4), Anti (chlorpyrifos) antibodies (LIB-C4 MAb), Anti-Chlorpyrifos Antibodies (LIB-PN1 Mabs), Anti-Chlorpyrifos Antibodies (LIB-PN2 Mabs), Anti-Chlorpyrifos Antibodies (LIB-PO Mabs), Anti-chlorsulfuron antibodies, Anti-Chlorsulfuron antibodies, Anti Chlortoluron Antibodies (Antiserum), Anti-Cyanoginosin-LA antibodies (mAbs 2B2-2, 2B2-7, 2B2-8, 2B2-9, 2B2-10, 2B5-5, 2B5-8, 2B5-14, 2B5-15, 2B5-23), Anti (D-3-methoxy-4-hydroxyphenylglycol) antibodies, Anti-DDA antibodies, Anti DDT antibodies (PAbs and MAbs), Anti-DDT Mabs (LIB1-11, LIB5-21, LIB5-25, LIB5-28, LIB5-212, LIB5-51, LIB5-52, LIB5-53), Anti-DEC Antibodies (Anti diethylcarbamazine Antibodies), Anti DEHA antibodies, Anti-(Delor 103) antibodies, Anti-Deltamethrin Antibodies, Anti Deltamethrin Antibodies (Del 01 to Del 12 MAbs and PAbs), Anti-deoxynivalenol (DON) Antibodies, Anti-Deoxynivalenol (DON) Antibodies, Anti Dexamethasone Antibody, Anti Dexamethasone Antibody, Anti-Dinitrophenyl (DNP)-antibodies, Anti dinitrophenyl spin labeled antibodies (AN01-AN12), Anti Diuron Antoboides (MAb's: 21, 60, 195, 202, 275, 481, 488, 520), Anti-D-MHPG Antibodies, Anti DNC antibodies, Anti-EB1089 antibodies, Anti-ecdysone antibodies, Anti-endosulfan antibodies, Anti-Endosulfan antibodies, Anti Esfenvalerate antibodies (Ab7588), Anti estradiol antibodies, Anti-Fenitrothion antibodies (pAbs and mAbs), Anti-Fenpropimorph antibodies, Anti Fenthion Antibodies, Anti-Fenthion Antibodies, Anti FITC antibodies (B13-DEI), Anti-Flucofuron antibodies (F2A8/1/A4B3), Anti-flufenoxuron antibodies, and Anti-(Benzoylphenylurea)-Antibodies, Anti-Formononetin Antibodies, Anti-Furosemide antibodies (Furo-26, Furo37, furo-72, Furo 73 Mabs), Anti-GR151004 Antibodies, Anti-hCG-alpha-peptide Antibodies (FA36, Anti hydroxyatrazine antibodies (HYB-283-2), Anti-Hydroxysimazine Antibodies, Anti Imazalil Antibodies MoAb's (9C1-1-1, 9C5-1-1, 9C6-1-1, 9C8-1-1, 9C9-1-1, 9C12-1-1, 9C14-1-1, 9C16-1-1, 9C18-1-1, 9C19-1-1, 9E1-1, 9G2-1), Anti Irgarol Antibodies, Anti Isopentenyl adenosine antibodies, Anti Isoproturon Antibodies, Anti-KB-6806 antiserum, Anti-(+)lupanine antibodies, Anti Lysophosphatidic (LPA) acid, Anti M3G Ab1 and Ab2, Anti M3G Ab1 and Ab2, Anti-MBC antibodies (Anti-2-succinamidobenzimidazole antiserum), Anti Metanephrine antibodies, anti (+)methamphetamine antibodies, Anti-Methiocarb Antibodies (LIB-MXNB31, LIB-MXNB-33, LIB-MXNH14 and LIB-MXNH-15 MAbs), Anti Metolachlor antibodies, Anti-Metolachlor Antibodies, Anti-Metolachlor Antibodies (MAb 4082-25-4), Anti Molinate Antibodies, Anti monuron antibodies, Anti-morphine-3-glucuronide (E3 scFv antibody), Anti morphine antibodies, Anti-Morphine antibodies, Anti-Morphine Antibodies (mAbs 8.2.1, 33.2.9, 35.4.12, 39.3.9, 44.4.1, 76.7F.16, 83.3.10, 115.1.3, 124.2.2, 131.5.13, 158.1.3, 180.2.4), Anti-Neopterin (D-erythro form) Antibodies, Anti-Nicarbazin Antibodies (Nic 6, Nic 7, Nic 8, and Nic 9), Anti Nicergoline Antibodies (Nic-1, Nic-2, Nic-3 & BNA-1, BNA-3), Anti-norflurazon antibodies, Anti NorMetanephrine antibodies, Anti (o-DNCP) Antibodies, Anti-P10 antibodies (TRH elongated peptide), Anti-Paraoxon Antibodies (BD1 and CE3), Anti Paraquat antibodies, Anti-Paraquat antibodies, anti Parathion-methyl antibodies, Anti PCB Antibodies (against 3,3',4,4'-tetrachlorobiphenyl) MAb S2B1, Anti pentachlorophenol antibodies, Anti Pentachlorophenol antibodies, Anti-Pentachlorophenol antibodies, Anti permethrin antibodies (Mabs Py-1, Py-3 and Py-4), Anti-Phencyclidine Antibodies (Mab 6B5 Fab), Anti-phenobarbital antibodies, Anti-phenobarbital antibodies, Anti-(p.p'-DDT)-Antibodies (LIB-DDT-35 and LIB-DDT5-52), Anti permethrin antibodies (Ab549), Anti Propoxur antibodies (LIB-PRNP15, LIB-PRNP21, LIB-PRNB21, LIB- PRNB33), Anti-Prostaglandin E2-antibodies, Anti-p-tyramine antibodies, Anti pyrene antibodies, Anti retronecine antibodies, Anti-Retronecine Antibodies, Anti salicylate antibodies, Anti Sennoside A antibodies (MAb 6G8), Anti Sennoside B antibodies (MAb's: 7H12, 5G6, 5C7), Anti Simizine antibodies, Anti Sulfonamides antibodies (Anti-TS), Anti-Sulocfuron antibodies (S2B5/1/C3), Anti sulphamethazine antibodies (21C7), Anti-synephrine antibodies, Anti-Thiabendazole antibodies (Antibody 300), Anti-Thiabendazole antibodies (Antibody 430 and 448), Anti-Thiram-Antibodies, Anti-THP antibodies (7S and 19S), Anti-Thromboxane B2 Antibodies, Anti-thymidine glycol monophosphate antibodies (mAb 2.6F.6B.6C), Anti-Thyroliberin (TRH) antibodies, Anti TNT antibodies (AB1 and AB2 antiserum), Anti Triadimefon Antibodies, Anti-triazine antibodies (AM1B5.1), Anti-triazine antibodies (AM5C5.3), Anti-triazine antibodies (AM5D1.2), Anti-triazine antibodies (AM7B2.1), Anti-triazine antibodies (SA5A0.1), Anti-Triazine serum (anti-ametryne), Anti-Triazine serum (anti-atrazine), Anti-Triazine serum (anti-simazine), Anti-Triazine serum (anti-simetryne), Anti Trifluralin Antibodies, Anti Trifluralin Antibodies, Anti Vincristine Antibodies, Anti-Zearalenone Antibodies, Anti Zeatin riboside antibodies, E2 G2 and E4 C2, Fab Fragment K411B derived from MAb K4E7 (isotype IgG2b with k light chain), LIB-BFNP23 Mab, MAb's H-7 and H-9 (against O,O-diethyl OP pesticides), MoAb 33A7-1-1, MoAb 33B8-1-1, MoAb 33C3-1-1, MoAb 3C10-1-1 and MoAb 3E17-1-1, MoAb 45D6-5-1, MoAb 45E6-1-1, MoAb 45-1-1, Mutant (GlnL89Glu) in Fab Fragment K411B derived from MAb K4E7 (isotype IgG2b with k light chain), Mutant (GlnL89Glu/ValH37Ile/GluL3Val) in Fab Fragment K411B derived from MAb K4E7 (isotype IgG2b with k light chain), Mutant (GlnL89Glu/ValH37Ile/GluL3Val) in Fab Fragment K411B derived from MAb K4E7 (isotype IgG2b with k light chain), Mutant (GlnL89Glu/ValH37Ile) in Fab Fragment K411B derived from MAb K4E7 (isotype IgG2b with k light chain), Mutant (GlnL89Glu/ValH37Ile) in Fab Fragment K411B derived from MAb K4E7 (isotype IgG2b with k light chain), Mutant (GluH50Gln) in Fab Fragment K411B derived from MAb K4E7 (isotype IgG2b with k light chain), Mutant (GluH50X) in Fab Fragment K411B derived from MAb K4E7 (isotype IgG2b with k light chain), Mutant (GlyH100aAla) in Fab Fragment K411B derived from MAb K4E7 (isotype IgG2b with k light chain), Mutant (GlyH100aSer) in Fab Fragment K411B derived from MAb K4E7 (isotype IgG2b with k light chain), Mutant (HisH95Phe) in Fab Fragment K411B derived from MAb K4E7 (isotype IgG2b with k light chain), Mutant (HisH95Tyr) in Fab Fragment K411B derived from MAb K4E7 (isotype IgG2b with k light chain), Mutant (PheL32Leu) in Fab Fragment K411B derived from MAb K4E7 (isotype IgG2b with k light chain), Mutant (TrpH33Phe,Tyr,Leu) in Fab Fragment K411B derived from MAb K4E7 (isotype IgG2b with k light chain), Mutant (Tryl96Phe) in Fab Fragment K411B derived from MAb K4E7 (isotype IgG2b with k light chain), Mutant (TryL96Phe) in Fab Fragment K411B derived from MAb K4E7 (isotype IgG2b with k light chain), Mutant (ValH37Ile) in Fab Fragment K411B derived from MAb K4E7 (isotype IgG2b with k light chain), Mutant (ValH37Ile) in Fab Fragment K411B derived from MAb K4E7 (isotype IgG2b with k light chain), P6A7 MAb, PNAS2 6/3 56(1)-1-5-1, PNAS2 6/3 56(1)-1-5-2, PNAS2 6/3 56(1)-1-10-4, PNAS2 6/3 56(1)-1-10-5 and PNAS2 6/3 56(1)-3-1-5, Alexa Fluor 405/Cascade Blue dye antibody, Alexa Fluor 488 dye antibody, BODIPY FL dye antibody, Dansyl antibody, Fluorescein/Oregon Green dye antibody, Lucifer yellow dye antibody, Tetramethylrhodamine and Rhodamine Red dye antibody, Texas Red and Texas Red-X dye antibody, Biotin antibody, Dinitrophenyl antibody and/or Nitrotyrosine antibody or any portion thereof of the aforementioned haptens.

In a ninth aspect, a method of screening cells that comprise a CAR or TCR is provided, whereby cells, such as T cells, which comprise a CAR or TCR are evaluated for the ability to bind or interact with a target moiety, such as a hapten, poly(his) tag, Strep-tag, FLAG-tag, V5-tag, Myc-tag, HA-tag, NE-tag, biotin, digoxigenin, dinotrophenol or fluorescein, dinitrophenol, green fluorescent protein (GFP), yellow fluorescent protein, orange fluorescent protein, red fluorescent protein, far red fluorescent protein, or fluorescein (e.g., Fluorescein isothiocyanate (FITC)), which is present on a substrate, such as a membrane, bead, or support (e.g., a well) or a binding agent, such as a lipid (e.g., PLE), hapten, ligand, or antibody, or binding fragment thereof, preferably a binding agent that has specificity for an antigen present on a cancer cell or pathogen such as, a virus or bacteria. By one approach, the substrate or binding agent comprising the desired target moiety is contacted with a plurality of cells comprising a CAR or TCR specific for said target moiety and the level or amount of binding of the cells comprising the CAR or TCR to the target moiety present on the substrate or binding agent is determined. Such an evaluation of binding may include staining for cells bound to target moieties or evaluation of fluorescence or loss of fluorescence. In some approaches, a target cell is also provided such that the method comprises contacting a cell, such as a T cell, which comprises a CAR or TCR that is specific for a target moiety, such as a hapten, poly(his) tag, Strep-tag, FLAG-tag, V5-tag, Myc-tag, HA-tag, NE-tag, biotin, digoxigenin, dinitrophenol, green fluorescent protein (GFP), yellow fluorescent protein, orange fluorescent protein, red fluorescent protein, far red fluorescent protein, or fluorescein (e.g., Fluorescein isothiocyanate (FITC)), with a binding agent such as a hapten, ligand, or antibody or antibody fragment thereof joined to said target moiety in the presence of a target cell, such as a cancer cell or bacterial cell, or a target virus and evaluating the binding of the cell comprising the CAR or TCR to the binding agent and/or evaluating the binding of the cell comprising the CAR or TCR to the target cell or target virus. Accordingly, methods of making a complex and the complex itself comprising a cell, such as a T cell, which comprises a CAR or TCR specific for a target moiety, such as a hapten, poly(his) tag, Strep-tag, FLAG-tag, V5-tag, Myc-tag, HA-tag, NE-tag, biotin, digoxigenin, dinitrophenol, green fluorescent protein (GFP), yellow fluorescent protein, orange fluorescent protein, red fluorescent protein, far red fluorescent protein, or fluorescein (e.g., Fluorescein isothiocyanate (FITC)), joined to a binding agent, such as a hapten, ligand, or antibody or antibody fragment thereof comprising said target moiety, through a CAR or TCR mediated binding to said target moiety, wherein said binding agent is further bound to or interacts with a target cell, such as a cancer cell or bacterial cell, or a target virus are contemplated. In some alternatives, the antibody or binding fragment thereof, which is conjugated to the target moiety, is abagovomab, abituzumab, adecatumumab, afutuzumab, alacizumab pegol, alemtuzumab, altumomab pentetate, amatuximab, anatumomab mefanetox, anetumab ravtansine, apolizumab, arcitumomab, ascrinvacumab, aselizumab, atezolizumab, atlizumab, avelumab, bapineuzumab, bavituximab, bectumomab, belimumab, besilesomab, bevacizumab, bivatuzumab mertansine, blinatumomab, blontuvetmab, brentuximab, brontictuzumab, cantuzumab mertansine, cantuzumab ravansine, capromab pendetide, carlumab, carotuximab, catumaxomab, cBR96-doxorubicin immunoconjugate, cedelizumab, certolizumab pegol, cetuximab, cidfusituzumab, cidtuzumab, citatuzumab bogatox, cixutumumab, clivatuzumab tetraxetan, codrituzumab, coltuximab ravtansine, conatumumab, dacetuzumab, daclizumab, dalotuzumab, daratumumab, demcizumab, denintuzumab mafodotin, denosumab, depatuxizumab mafodotin, derlotuximab biotin, detumomab, dinutuximab, drozitumab, duligotumab, durvalumab, dusigitumab, duvortuxizumab, ecromeximab, eculizumab, edrecolomab, efalizumab, elgemtumab, elotuzumab, emactuzumab, emibetuzumab, enavatuzumab, enfortumab vedotin, enoblituzumab, enoticumab, ensituximab, epratuzumab, erlizumab, ertumaxomab, etaracizumab, farletuzumab, FBTA05, femzumab, ficlatuzumab, figitumumab, flanvotumab, fontolizumab, futuximab, galiximab, ganitumab, gemtuzumab ozogamicin, girentuximab, glembatumumab vedotin, ibritumomab, icrucumab, igovomab, IMAB362, imalumab, imgatuzumab, indatuximab ravtansine, indusatumab vedotin, intetumumab, inotuzumab ozogamicin, intetumumab, ipilimumab, iratumumab, isatuximab, labetuzumab, lambrolizumab, lexatumumab, lifastuzumab vedotin, lilotomab satetraxetan, lintuzumab, lorvotuzumab mertansine, lucatumumab, lumiliximab, lumretuzumab, mapatumumab, margetuximab, matuzumab, mepolizumab, milatuzumab, minretumomab, mirvetuximab soravtansine, mitumomab, mogamulizumab, moxetumomab pasudotox, nacolomab tafenatox, naptumomab estafenatox, narnatumab, natalizumab, necitumumab, nesvacumab, nimotuzumab, nivolumab, nofetumomab merpentan, obinutuzumab, ocaratuzumab, ocrelizumab, ofatumumab, olaratumab, omalizumab, onartuzumab, ontuxizumab, oportuzumab monatox, oregovomab, otlertuzumab, panitumumab, pankomab, parsatuzumab, pascolizumab, pasotuxizumab, patritumab, pecfusituzumab, pectuzumab, pembrolizumab, pemtumomab, pertuzumab, pexelizumab, pidilizumab, pinatuzumab vedotin, pintumomab, polatuzumab vedotin, pritumumab, racotumomab, radretumab, ramucirumab, ranibizumab, reslizumab, rilotumumab, rituximab, robatumumab, rovelizumab, ruplizumab, sacituzumab govitecan, samalizumab, satumomab pendetide, seribantumab, sibrotuzumab, SGN-CD19A, SGN-CD33A, simtuzumab, siplizumab, siltuximab, sofituzumab vedotin, solitomab, sontuzumab, tabalumab, tacatuzumab tetraxetan, tadocizumab, talizumab, tamtuvetmab, taplitumomab paptox, tarextumab, tenatumomab, teprotumumab, TGN1412, ticilimumab (tremelimumab), tigatuzumab, TNX-650, tocilizumab, toralizumab, tositumomab, tovetumab, trastuzumab, TRB S07, tremelimumab, tucotuzumab celmoleukin, tucusituzumab, ublituximab, ulocuplumab, urelumab, urtoxazumab, ustekinumab, vandortuzumab vedotin, vantictumab, vanucizumab, veltuzumab, vesencumab, visilizumab, volociximab, vorsetuzumab mafodotin, votumumab, zalutumamab, zanolimumab, zatuximab, cosfroviximab, diridavumab, exbivirumab, felvizumab, foravirumab, larcaviximab, libivirumab, motavizumab, motovizumab, nolovizumab, numavizumab, palivizumab, porgaviximab, PRO 140, rafivirumab, ralivizumab, regavirumab, reslivizumab, resyvizumab, sevirumab, suvizumab, tuvirumab, umavizumab, edobacomab, nebacumab, pagibaximab, panobacumab, raxibacumab, or tefibazumab or a binding fragment thereof. In some alternatives, the hapten used comprises Alexa Fluor 405, Cascade Blue, Alexa Fluor 488, BODIPY, Dansyl chloride, Oregon Green, Lucifer yellow, Rhodamine, Tetramethylrhodamine, Nitrotyrosine, digoxigenin, 2,4-Dichlorophenoxyacetic acid, Atrazine (2-Chloro-4-(ethylamino)-6-(isopropylamino)-s-triazine), Nicotine (3-(1-Methyl-2-pyrrolidyl) pyridine, Black Leaf), Morphine (morph, Morphine Sulfate), 2,4-DINITROCHLOROBENZENE (1-Chloro-2, 4-dinitrobenzene; DNCB; Dinitrochlorobenzene), 4-chloro-6-(ethylamino)-1,3,5-triazine-2-(6-aminohexanecarboxylic acid), Structurally related s-triazines (Modifications: H/Cl/ C6 R1=NH2- R2=—Cl R3=—NH—(CH2)5-COOH; iPr/Cl/ nBu R1=(CH3)2-CH—NH— R2=—Cl R3=—NH—(CH2) 3-(CH3)), Ametryn (2-Ethylamino-4-isopropylamino-6-methylthio-1,3,5-triazine), Deethylatrazine (DEA) (Structurally related s-triazines), Deisopropylatrazine (DIA) (Structurally related s-triazines), Deethyldeisopropylatrazine (DEDIA) (Structurally related s-triazines), Deethyldeisopropylatrazine (DEDIA) (Structurally related s-triazines), HydroxyAtrazine (HA) (Structurally related s-triazines), DeisopropylHydroxyAtrazine (DIHA) (Structurally related s-triazines), DeethylDeisopropylHydroxyAtrazine (DE-DIHA) (Structurally related s-triazines), Simazine (Structurally related s-triazines), Desmetryne (Structurally related s-triazines), Prometryne (Structurally related s-triazines), 2-hydroxyatrazine (atrazine derivative), 2-hydroxypropazine (structurally related s-triazine), 2-hydroxysimazine, N-(4-Amine-6-hydroxy-[1,3,5]triazin-2-yl)-4-aminobutanoic Acid (Modification: R1=NH2 R2=NH(CH2)3COOH R3=OH), SulcoFuron, 5-chloro-2-{4-chloro-2-[3-(3,4-dichlorophenyl)ureido]phenoxy}benzenesulfonic acid, FlucoFuron (1,3-bis(4-chloro-α,α,α-trifluoro-m-tolyl)urea), Agatharesinol, Sequirin C, Sugiresinol, Hydroxysugiresinol, Hinokiresinol, Coniferyl alcohol, Cinnamyl alcohol, p-Coumaric acid, Cinnamic acid, p-Coumaric acid, Cinnamic acid, Hinokinin, Guaiacylglycerol-beta-guaiacyl ether, Morphine-3-glucuronide (M3G), Codeine, Nor-Codeine, 6-Monoacetylmorphine, (+) Methamphetamine, Ceftazidime, Phenobarbital, p-hydroxyPhenobarbital, p-aminophenobarbital, Cyclobarbital, 3'-Ketocyclobarbital, 3'-Hydroxycyclobarbital, Secobarbital, Barbital, Metharbital, Barbituric acid, Thiopental, Thiobarbituric acid, Primidone, Glutethimide, Pentobarbital, Heroin, Diacetylmorphine, Levallorphan, L-11-Allyl-1,2,3,9,10,10a-hexahydro-4H-10,4a-iminoethanophenanthren-6-ol, Pethidine (Demerol; Dolantin; Meperidine; Ethyl 1-methyl-4-phenylpiperidine-4-carboxylate; Isonipecaine), Methamphetamine, d-Desoxyephedrine; Methedrine; Tolpropamine; Pratalgin; Pragman. Benzoylecgonine, 3-Carboxymethylmorphine, Cocaine, 5-benzimidazolecarboxylic acid, ABA (4-acetyl benzoic acid), Dexamethasone, Flumethasone, 6alpha, 9 alpha-difluoro-11 beta, 17,21-trihydroxy-16 alpha-methylpregna-1,4-diene-3, 20-dione, 9 alpha-fluoro-11 beta,17,21-trihydroxy-16 betamethylpregna-1,4-diene-3,20-dione, 9-alpha-fluoroprednisolone, Desoxymethasone, Triamcinolone, 9 alpha-fluoro-11 beta,16 alpha, 17,21-tetrahydroxypregna-1,4-diene-3,20-dione, Fluocortolone, 6 alpha-fluoro-11 beta,21-dihydroxypregna-1,4-diene-3,20-dione, Cortisol, 11 beta, 17,21-trihydroxypregna-4-ene-3,20-dione, Prednisone, 17,21-dihydroxypregn-4-ene-3,11,20-trione, Methylprednisolone, 11 beta, 17,21-trihydroxy-6 alpha-methylpregna-1,4-diene-3,20-dione, Triamcinolone hexacetonide, 21-(3,3-dimethyl-1-oxobutoxy)-9 alpha-fluoro-11-hydroxy-16,17-[(1-methylethylidene) bis(oxy)]pregna-1,4-diene-3,20-dione, Carbofuran, 2,3-dihydro-2,2-dimethyl-7-benzofuranyl methylcarbamate, BFNP (3-[[(2,3-dihydro-2,2-dimethyl-7-benzofuranyloxy)carbonyl]amino]propanoic acid), Carbofuran derivative, 2,3-dihydro-2,2-dimethyl-7-benzofuranol, Bendiocarb, Carbaryl, Methiocarb, Propoxur, Aldicarb, Methomyl, Benalaxyl, methyl N-(phenylacetyl)-N-(2,6-xylyl)-DL-alaninate, Bn-Ba (4-[2-(N-phenylacetyl-N-2,6-xylylamino)propionamido] butyric acid), Bn-COOH (4-[2-(N-phenylacetyl-N-2,6-xylyl-DL-alanine), Benalaxyl derivative, Furalaxyl, Metalaxyl, Acetochlor, Dimetachlor, Metolachlor, 2-chloro-6'-ethyl-N-(2-methoxy-1-methylethyl)acet-o-toluidine, Diethathyl-ethyl, Benzoylprop-ethyl, Benzoylprop-ethyl, 2,4,5-Trichlorophenoxyacetic acid, 2-chloro-6'-ethyl-N-(2-methoxy-1-methylethyl)acet-o-toluidine, Diethathyl-ethyl, Benzoylprop-ethyl, Propachlor, Propachlor, 2,4,5-Trichlorophenoxyacetic acid, 2,4,5,T; Weedone, 2,4-Dichlorophenoxybutyric acid (2,4-DB), 2,4-DB; Butanoic acid, 4-(2,4-dichlorophenoxy)-; Butoxone; Embutone, MCPA, 2-Methyl-4-chlorophenoxyacetic acid; Metaxon, Dichlorprop (2,4-DP), 1-[(2-chloro)phenylsulfonyl]monoamidosuccinic acid, Chlorsulfuron, chlorbromuron, amidosulfuron, chlortoluron, isoproturon, diuron, Linuron O-Methyl-O-(4-nitrophenyl)-N-(4-carboxybutyl)-phosphoramidothioate Parathion-methyl, O,O-dimethyl O-4-nitrophenyl phosphorothioate; Methaphos; Wolfatox; Dimethylparathion; Metacide, Parathion-ethyl, DIETHYL P-NITROPHENYL THIOPHOSPHATE; O,O-DIETHYL O—(P-NITROPHENYL) PHOSPHOROTHIOATE; Fenitrothion, O,O-dimetyl O-4-nitro-m-tolyl phosphorothioate, Fenthion, O,O-dimethyl O-4-methylthio-m-tolyl phosphorothioate, Bromophos, O-4-bromo-2,5-dichlorophenyl O,O-dimethyl phosphorothioate, chlorpyrifos-methyl, O,O-dimethyl O-3,5,6-trichloro-2-pyridyl phosphorothioate, Oxidized parathion-methyl, Paraoxon, phosphoric acid, O,O-diethyl O-(4-nitrophenyl) ester, Diazinon, O,O-diethyl O-2-isopropyl-6-methylpyrimidin-4-yl phosphorothioate, Azinphos-methyl, pirimiphos-methyl, O-2-diethylamino-6-methylpyrimidin-4-yl O,O-dimethyl phosphorothioate, Methidathion, S-2,3-dihydro-5-methoxy-2-oxo-1,3,4-thiadiazol-3-ylmethyl O,O-dimethyl phosphorodithioate, Dimethylchlorothiophosphate, 4-NITROPHENOL, p-nitrophenol, Phenolic derivative (Modification On benzene ring; R1=OH R2=NO2 R3=H R4-CH2COOH R5=H R6=H); 2-Nitrophenol, o-Nitrophenol, 3-Nitrophenol, m-nitrophenol, 2,4-Dinitrophenol, 3,4-Dinitrophenol, 2,5-Dinitrophenol, 2,4-Dinitro-6-methylphenol, 2,3,6-trinitrophenol, 2-Chlorophenol, 4-Chloro-3-methylphenol, Fenitroxon, 3-Methyl-4-nitrophenol, Nonylphenol, HOM(3-[2-hydroxy-5nitro benzylthio] propionic acid, Phenol, Delor 103, Polychlorinated Biphenyls, Delor 104, Polychlorinated Biphenyls, Delor 105, Polychlorinated Biphenyls, Delor 106, 4,4'-Dichlorobiphenyl, PCB congeners, 2,4,4'-Trichlorobiphenyl, PCB congeners, 2,4'-Bichlorobiphenyl, PCB congeners, 2,2'-Dichlorobiphenyl, PCB congeners, 2,4,5-Trichlorobiphenyl, PCB congeners, 3,3',4,4'-Tetrachlorobiphenyl, PCB congeners, PCB congeners, 2,2',4,4',5,5'-Hexachlorobiphenyl, 2-(5-Carboxypentanoylamino)-4,4'-dichlorobiphenyl, Biphenyl derivative, 4-chlorophenoxyacetic acid, 2-Chlorophenoxyacetic acid, DDT,1,1,1-trichloro-2, 2-bis-(p-chlorophenyl)ethane, DDE, 1,1-dichloro-2, 2-bis(p-chlorophenyl)ethylene, p-Chlorophenol, 4-Chlorophenol, m-Chlorophenol 3,4-Dichlorophenol, 3,5-Dichlorophenol, 2,3,4-Trichlorophenol, 2,3,5-Trichlorophenol, 3-methylindole, 3-methylindole Derivatives, 4-(3-methylindol-5-yloxy)butanoic acid, 4-(3-methylindol-5-yloxy)butanoic acid, 3-methylindole Derivatives, 6-[n-3-methylindol-5-yloxy carbonyl)amino]hexanoic acid, 6-[n-3-methylindol-5-yloxy carbonyl)amino]hexanoic acid, 3-methylindole Derivatives, 2-[4-(3-methylindol-6-yl)but-1-ylthio]acetic acid, 2-[4-(3-methylindol-6-yl)but-1-ylthio]acetic acid, 3-methylindole Derivatives, 4-(3-methylindol-6-yl-4-oxo) butanoic acid, 4-(3-methylindol-6-yl-4-oxo)butanoic acid, 3-methylindole Derivatives, 6-(3-methylindol-7-yloxy) hexanoic acid, 6-(3-methylindol-7-yloxy)hexanoic acid, Indole, Indole-3-Carboxylic acid, Indole Derivative-Indole-3-Acetic acid, Indole-3-Acetic acid, Indole Derivative-Indole-3-Propionic acid, Indole-3-Propionic acid, Indole Derivative-Indole-3-Carbinol, Indole-3-Carbinol, Tryptophan, Tryptamine, 5-Methoxyindole-3-carboxaldehyde, 5-Methoxytryptamine, 5-Methoxyindole, 6-Methoxyindole, 7-Methoxyindole,EB1089(Seocalcitol),EB1089(Seocalcitol) Derivative, (22E,24E)-Des-A,B-24-homo-26,27-dimethyl-8-[(E)-N-(2-carboxyethyl)-carbamoylmethylidene]-cholesta-22,24-dien-25-ol, 1 alpha-25-dihydroxyvitamin D3, 25(OH)D3,25-hydroxyvitamin D3,24R,25(OH)2D3, 24R,25-dihydroxyvitamin D3, Vitamin D2, ergocalciferol, Vitamin D3, cholecalciferol,EB1446,EB1436,EB1445, EB1470, DeethylHydroxyAtrazine (DEHA) (Structurally related s-triazines), Irgarol 1051, Flourescein Isothiocyanate, FITC, Metanephrine, NorMetanephrine, Propazine, Terbutylazine, Terbuthylazine, 6-chloro-N-(1,1-dimethylethyl)-N'-ethyl-1,3,5-triazine-2,4-diamine, (Structurally related s-triazines), Ametryn (2-Ethylamino-4-isopropylamino-6-methylthio-1,3,5-triazine (Modification iPr/SCH3/Et R1=(CH3)2-CH—NH— R2=—SCH3 R3=—NH—CH2-CH3, Irgarol, Cyanazine (Modification R1=Cl R2=NHCH2CH3 R3=NHCCN(CH3)2), OH-Terbutylazine, Terbutylazine-2OH, Hydroxytriazine (EQ-0027), Deisopropylatrazine (Structurally related S-triazine), Desethylterbutylazine (Structurally related S-triazine), Desethyl-deisopropylatrazine (Structurally related S-triazine), Atraton, Terbutryn (Structurally related s-triazines), Atrazine derivative (Modification R1=—NHCH(CH3)2 R2=—S(CH2)2COOH R3=—NHC2H5), Cyanuric chloride, Trifluralin, (Structurally related s-triazines) tBu/C4/SCH3 (Modification R1=—NH—C—(CH3)3 R2=—NH (CH2)3COOH R3=—SCH3), Sulphamethazine, (Structurally related s-triazines) 6-[[[4-Chloro-6-(methylamino)]-1,3,5-triazin-2-yl]amino]hexanoic Acid (Modification Me/Cl/C6 R1=—NHCH3 R2=—Cl R3=—NH(CH2) 5COOH), (Structurally related s-triazines) Procyazine (Modification R1=—Cl R2=—NHcyclopropyl R3=—NHCCN(CH3)2), (Structurally related s-triazines), Prometon (Modification R1=—OCH3 R2=—NHCH(CH3)2 R3=—NHCH(CH3)2); (Structurally related s-triazines) Atrazine Mercapturic Acid (AM) (Modification R1=—SCH2CH(NHAc)COOH R2=—NHCH2CH3 R3=—NHCH(CH3)2), (Structurally related s-triazines), desethyl atrazine mercapturic acid (desethyl AM) (Modification R1=—NAcCys R2=—NH2 R3=—NHCH(CH3)2), (Structurally related s-triazines), deisopropyl atrazine mercapturic acid (deisopropyl AM) (Modification R1=—NAcCys R2=—NHCH2CH3 R3=—NH2), (Structurally related s-triazines), didealkylated atrazine mercapturic acid (didealkylated AM) (Modification R1=—NAcCys R2=—NH2 R3=—NH2), (Structurally related s-triazines), simazine mercapturate (Modification R1=—NAcCys R2=—NHCH2CH3 R3=—NHCH2CH3), (Structurally related s-triazines) (Modification R1=—S(CH2)2COOH R2=—NHCH2CH3 R3=—NHCH2CH3), (Structurally related s-triazines) (Modification R1=—Cl R2=—NHCH (CH3)2 R3=—NH(CH2)2COOH), (Structurally related s-triazines) (Modification R1=—Cl R2=—NHCH2CH3 R3=—NH(CH2)2COOH), (Structurally related s-triazines), atrazine mercapturic acid methyl ester (AM methyl ester) (Modification R1=—NAcCysME R2=—NHCH2CH3 R3=—NHCH(CH3)2), N-acetylcysteine, S-benzyl mercapturate, (Structurally related s-triazines), simetryn (Modification R1=—SCH3 R2=—NHCH2CH3 R3=—NHCH2CH3), Metribuzin, 4-amino-6-tert-butyl-4,5-dihydro-3-methylthio-1,2,4-triazin-5-one, Sulpha Drugs, N4-acetyl-sulphamethazine (Modification N4-acetyl-sulphamethazine), Sulpha Drugs, Sulphathiazole, Sulphathiazole, Sulphamerazine, Sulphamerazine, Sulphaquinoxaline, Sulphaquinoxaline Sulphachlorpyridazine, Sulphachlorpyridazine, Sulphapyridine, Sulphadimethoxine, Sulphadimethoxine, Sulphamethoxazole, Sulphamethoxazole, Sulphisoxazole, Sulphisoxazole, Sulphamethizole, Sulphamethizole, Sulphanilamide, Sulphanilamide, Sulphaguanidine, Sulphaguanidine, Sulphadiazine, Sulphadiazine, Sulphamethoxypyridazine, Sulphamethoxypyridazine, Pentachlorophenoxypropionic acid, Pentachlorophenol, PCP, 2,3,5,6-Tetrachlorophenol, 1,2,4,5 Tetrachlorobenzene, 2,4,6 Trichlorophenol, 2-Methoxy-3,5,6-trichloropyridine, 1,3,5 Trichlorobenzene, 1,3 Dichlorobenzene, 2,4,5-Trichlorophenol, 2,6-Dichlorophenol, 3,5,6-Trichloro-2-pyridinoxyacetic acid, 3,5,6-Trichloro-2-Pyridinol, TCP, 2,4-Dichlorophenol, 2,5-Dichlorophenol, DNC, 4,4'-dinitrocarbanilide, (Structurally related s-triazines), Dichloroatrazine, (Structurally related s-triazines), Dichlorosimazine, 1-((6-chloropyridin-3-yl)methyl)imidazolidin-2-imin, Pyridine Derivative, 6-chloropyridine-3-carboxylic acid, Nicotinic acid, Pyridine Derivative, N-((6-chloropyridin-3-yl)methyl)-N-methylacetamide, (6-chloropyridin-3-yl)-N-methylmethanamine, (6-chloropyridin-3-yl)methanol, Imidacloprid, 1-(6-chloro-3-pyridylmethyl)-N-nitroimidazolidin-2-ylideneamine, Acetamiprid, (E)-N1-[(6-chloro-3-pyridyl)methyl]-N2-cyano-N1-methylacetamidine, Nitenpyram, Deltamethrin, 1(R)-cis-alpha (S)-3-(2,2-dibromoethenyl)-2,2-dimethylcyclopropane carboxylic acid cyano(3-phenoxyphenyl)methyl ester, DON, deoxynivalenol, DON derivative, 15-AcDON (15-acetyldeoxynivalenol), DON derivative, 3-AcDON (3-acetyldeoxynivalenol), DON derivative, 3,15-DiacDON (3,15-diacetyldeoxynivalenol), DON derivative, 3,7,15-TriacDON (3,7,15-Triacetyldeoxynivalenol), NIV (nivalenol), nivalenol, NIV Derivative, 4-AcNIV (fusarenon X), Flutolanil, alpha,alpha,alpha-trifluoro-3'-isopropoxy-o-toluanilide, Mepronil, Mebenil, Benodanil, 24,25(OH)2D3, (24R)-24,25-dihydroxyvitamin D3, 24S,25(OH)2D3, 24S,25-dihydroxyvitamin D3, 25R,26(OH)2D3, 25R,26-dihydroxyvitamin D3, 25S,26(OH)2D3, 25S,26-dihydroxyvitamin D3, 1,24,25(OH)3D3, 1,24,25-trihydroxyvitamin D3, 1,25-lactone, (23S,25R)-1,25(OH)2 D3 26,23-lactone, 24,25(OH)2-7-DHC, 24,25(OH)2-7-dehydrocholesterol, 25(OH)D3 3S, 25(OH)D3 3-sulfate, 24,25(OH)2D3-Hemiglutarate Derivative, 11 alpha-hemiglutaryloxy-(24R)-24,25-dihydroxyvitamin D3, 24,25(OH)2D3-Hemiglutarate Derivative, (24R)-24,25-dihydroxyvitaminD3-3-hemiglutarate, 24R,25(OH)2D2, 24S,25(OH)2D2, 25(OH)D2, 1,24(OH)2D3, 2,3,6-Trichlorophenol, Tetrachlorohydroquinone, Pentachloroaniline, Pentachlorobenzene, 2,3-Dinitrotoluene, 4-Dinitrotoluene, 2,4,5-Trichloronitrobenzene, 3-(3-Hydroxy-2,4,6-trichlorophenyl)-propanoic acid, 2,3,4,6-Tetrachlorophenol, 2,4,6-Trichloroanisol, 2,4,6-TCA, Pentabromophenol, PBP, 2,4,6-Tribromophenol, 2,4,6-TBP, 2-Bromo-4-Chlorophenol, 2-B-4-CP 2,4-Dibromophenol, 2,4-DBP, 2,6-Dibromophenol, 2,6-DBP, 4-Bromophenol, 4-BP, Furosemide, Ampicillin, Amoxicillin, 6-amino-penicillanic acid (6-APA), Azlocillin, Bacampicillin, Carbenicillin, Epicillin, Cloxacillin, Dicloxacillin, Metampicillin, Methicillin, Moxalactam, Oxacillin, Penicillin G, benzyl penicillin, Penicillin V, phenoxy methyl penicillin, Pheneticillin, Piperacillin, Ticarcillin, Ampicillin hydrolyzed, Penicillin G hydrolyzed, 3-phenoxybenzoic acid (3-PBAc) Chlorpyrifos, Chlorpyrifos derivatives, HClo1, Synthesized directly from chlorpyrifos technical grade by substitution of the chlorine in position 6 by a 3-mercaptopropanoic acid spacer arm, Chlorpyrifos derivatives, HTCP (Modification HTCP of TCP metabolite was prepared from HClo1 by hydrolysis of the thiophosphate ester), Zeatin Riboside (trans isomer), Zeatin (trans isomer), N6-(2-isopentenyl)-adenosine, IPA, N6-(2-isopentenyl)-adenine, 2-iP, Benzyladenine, Kinetin, monuron, monolinuron, fenuron, neburon, propanil, propham, chloropropham, 4-chloroaniline, Methyl Urea Derivative, 1-(3-Carboxypropyl)-3-(4-chlorophenyl)-1-methylurea, Methyl Urea Derivative, 1-(5-Carboxypentyl)-3-(4-chlorophenyl)-1-methylurea, metobromuron, Sennoside B, SB, Sennoside B possessed a erythro configuration between C-10 and C-10', Sennoside A (Modification Sennoside A possessed a threo configuration between C-10 and C-10'), Rhein, Emodin, Aloe-emodin, Barbaloin, 1,4 Dihydroxyanthraquinone, Rhaponticin, Galic acid, Vanillic acid, Caffeic acid, Homogentisic acid, Esculin, Cinnamtannin B1, Baicalin, Naringin hydrate, Wogonin, Wogonin 7-o-beta-glucuronide, Curcumin, delta1-Tetrahydrocannabinolic acid, delta1-Tetrahydrocannabinol, (+−)-cis-4-Aminopermethrin, 3-(4-Aminophenoxy)benzyl(+−)-cis-3-(2,2-dichloroethenyl)-2,2-dimethylcyclopropanecarboxylate, Permethrin, trans-Permethrin, cis-Permethrin, Cypermethrin, Phenothrin, Resmethrin, Cyfluthrin, trans-Permethrin acid Esfenvalerate, Fluvalinate, Fenpropathrin, cis-permethrin acid, 4-Phenoxybenzoyl alcohol, Diuron Derivative, 1-(3-Carboxypropyl)-3-(3,4-dichlorophenyl)-1-methylurea, Siduron, Terbuthiuron, Barban, acid trifluralin, 2,6-dinitro-N-propyl-N-(2-carboxyethyl)-4-(trifluoromethyl)benzenamine, TR-13, 2-ethyl-7-nitro-1-propyl-5-(trifluoromethyl)-1H-benzimidazole, benefin, 2,6-dinitro-N-butyl-N-ethyl-4-(trifluoromethyl)benzenamine, TR-2, 2,6-dinitro-N-propyl-4-(trifluoromethyl)benzenamine, ethalfluaralin, 2,6-dinitro-N-ethyl-N-(2-methyl-2-propenyl)-4-(trifluoromethyl)benzenamine, TR-40, N-(2,6-dinitro-4-(trifluoromethyl)phenyl)-N-propylpropanamide, TR-15, 2-ethyl-4-nitro-6-(trifluoromethyl)-1H-benzimidazole, TR-3, 2,6-dinitro-4-(trifluoromethyl)benzenamine, TR-6, 3-nitro-5-(trifluoromethyl)-1,2-benzenediamine, TR-9, 5-(trifluoromethyl)-1,2,3-benzenetriamine, TR-21, 4-(dipropylamino)-3,5-dinitrobenzoic acid, TR-36M, 3-methoxy-2,6-dinitro-N,N-dipropyl-4-(trifluoromethyl)benzenamine, oryzalin, 3,5-dinitro-4-(dipropylamino)benzenesulfonamide, pendimethalin, 2,6-dinitro-N-(1-ethylpropyl)-3,4-dimethylbenzenamine, penta galloyl glucose, Pyrene Pyrene-1-carboxaldehyde, Phenanthrene, Benzo(a)pyrene, 3,4-Benzopyrene, Anthracene, 3,4-Benzopyrene, Acenaphthene, Fluorene, Chrysene, 1,2-Benzphenanthrene, Benzo[g,h,i]perylene, Benzo[e]pyrene, Acenaphthylene, Fluoranthene, Benzo(j,k)fluorene, Indeno-1,2,3-cd-pyrene, 1,10-(1,2-Phenylene)pyrene, Benzo[a]anthracene, 1,2-Benzanthracene, Benzo(k)fluoranthene, Naphthalene, Benzo[a]fluoranthene, Dibenzo[ah]anthracene, 1,2:5,6-Dibenzanthracene, 2,3-Diaminonaphthalene, 2,6-Dinitroaniline, 17-beta-estradiol (ED), estra-1,3,5(10)-triene-3,17-beta-diol, Trifluralin derivative, 2,6-dinitro-4-tri-fluoromethylaniline, Trifluralin derivative, N-(2,6-dinitro-4-trifluoromethylphenyl)-6-aminohexanoic acid, Trifluralin derivative, N-(2,6-dinitro-4-trifluoromethylphenyl)-N-methyl-6-aminohexanoic acid, Trifluralin derivative, N-(2,6-dinitro-4-trifluoromethylphenyl)-N-propyl-6-aminohexanoic acid, Trifluralin derivative, N-(2,6-dinitro-4-trifluoromethylphenyl)-6-aminohexanoic acid methyl ester, Trifluralin derivative, N-(2,6-dinitro-4-trifluoromethylphenyl)-6-aminohexanoic acid tert-butyl ester, Benfluralin, Ethalfluralin, Trifluralin derivative, 2,6-Dinitro-4-trifluoromethylphenol, Isopropalin, Aniline, 2-Hydroxybenzotrifluoride, N-propyl-6-aminohexanoic acid, N-methyl-6-aminohexanoic acid, MHPG Derivatives, D-MHPG (D-3-methoxy-4-hydroxyphenylglycol), MHPG Derivatives, L-MHPG (L-3-methoxy-4-hydroxyphenylglycol), MHPG Derivatives, DL-MHPG (DL-3-methoxy-4-hydroxyphenylglycol), Isomeric mixture of D-MHPG and L-MHPG forms, MHPG Derivatives, DL-MHPG-SO4 (DL-3-methoxy-4-hydroxyphenylglycol-sulfate) Modification can include Isomeric mixture of D-MHPG-SO4 and L-MHPG-SO4 forms, Serotonin, 5-HT, 5-hydroxydopamine (5-4HDA), 3,4-dihydroxyphenylglycol (DOPEG), Dopamine, 4-(2-aminoethyl)pyrocatechol; 3-hydroxytyramine; 3,4-dihydroxyphenethylamine; L-3,4-dihydroxyphenylalanine, L-DOPA, Vanillomandelic acid, DL-VMA, Homovanillic acid, Norepinephrine, DL-NE, D-Epinephrine, D-E, 3-methoxytyramine, MTA, 3-methoxytyrosine, MTyr, 3,4-dihydroxymandelic acid, DL-DOMA, 3,4-dihydroxyphenyl acetic acid, DOPAC, L-Phenylalanine, Tyramine, p-tyramine; 4-(2-Aminoethyl)phenol, D-Mandelic acid, Homocatechol, Octopamine, DL-Octopamine, Azinphos-Ethyl, S-(3,4-dihydro-4-oxobenzo[d]-[1,2,3]-triazin-3-ylmethyl) O,O-diethyl phosphorodithioate, Phosmet, O,O-dimethyl S-phthalimidomethyl phosphorodithioate, Folpet, N-[(Trichloromethyl)thio]phthalimide, Tetramethrin, (1-Cyclohexene-1,2-dicarboximido)methyl-2,2-dimethyl-3-(2-methylpropenyl)-cyclopropanecarboxylate, N-(bromomethyl)phthalimide, N-(Chloromethyl)benzazimide, 6-(N-phthalimidoylmethylthio)hexanoic acid (MFH), Bromacil, 5-bromo-3-sec-butyl-6-methyluracil, Bromacil Derivative, 5-bromo-6-(hydroxymethyl)-3-(1-methylpropyl)-2,4(1H, 3H)-pyrimidineone, Bromacil Derivative, 5-bromo-3-(2-methylpropyl-6-methyl-2,4(1H,3H)-pyrimidinedione, Metabolite of Bromacil, Bromacil Derivative, 3-hydroxy-1-methylpropyl-6-methyl-2,4(1H,3H)-pyrimidinedione (Modification Bromacil Metabolite), Bromacil Derivative, 6-methyl-3-(1-methylpropyl)-2,4(1H,3H)-pyrimidinedione (Modification Bromacil Metabolite), Terbacil Derivative, [5-chloro-3-(1,1-dimethylethyl)-6-(hydroxymethyl)-2,4 (1H,3H)-pyrimidinedione, Terbacil, 3-tert-butyl-5-chloro-6-methyluracil, Bromacil Derivative, Ethyl-5-(5-Bromo-6-methyl-3-(1-methylpropyl)-2,4(1H,3H)-pyrimidinedione-1-yl)hexanoate, Bromacil Derivative alkylated at N-1, Bromacil Derivative 5-(5-Bromo-6-methyl-3-(1-methylpropyl)-2,4(1H,3H)-pyrimidinedione-1-yl)hexanoic Acid (Modification Bromacil Derivative alkylated at N-1), Bromacil Derivative, -Bromo-6-(Bromomethyl-3-(1-methylpropyl)-2,4(1H,3H)-pyrimidinedione (Modification Bromacil Derivative substituted at the 6-methyl position), Bromacil Derivative-[5-Bromo-3-(1-methylpropyl)-2,4(1H, 3H)-pyrimidinedione-6-yl]-2-carboxylpropanoic Acid (Modification Bromacil Derivative substituted at the 6-methyl position), 3-[5-Bromo-3-(1-methylpropyl)-2,4 (1H,3H)-pyrimidinedione-6-yl]propanoic Acid (Modification Bromacil Derivative substituted at the 6-methyl position), Bromacil Derivative 5-Bromo-1,6-dimethyl-3-(1-methylpropyl)-2,4(1H,3H)-pyrimidinedione, Bromacil Derivative 5-Bromo-1-butyl-6-methyl-3-(1-methylpropyl)-2,4(1H,3H)-pyrimidinedione, Butachlor, N-butoxymethyl-2-chloro-2',6'-diethylacetanilide, Amidochlor, N-[(acetylamino)methyl]-2-chloro-N-(2,6-diethylpenyl)acetamide, Nicarbazin, N,N'-bis(4-nitrophenyl)-compound with 4,6-dimethyl-2(1H)-pyrimidinone (Modification (DNC+HDP)), 2-hydroxy-4,6-dimethylpyrimidine, HDP, Imazalil, [1-(beta-allyloxy-2,4-dichlorophenethyl)imidazole], Imazalil Derivative, EIT-0073 (Modification Have a —O(CH2)5-COOH group instead of original —OCH2CH—CH2 group of imazalil), Penconazole, (RS)-1-(2,4-dichloro-β-propylphenethyl)-1H-1,2,4-triazole, Hexaconazole, (RS)-2-(2,4-dichlorophenyl)-1-(1H-1,2,4-triazol-1-yl)hexan-2-ol, Propiconazole, cis-trans-1-[2-(2,4-dichlorophenyl)-4-propyl-1,3-dioxolan-2-ylmethyl]-1H-1,2,4-triazole, Diclobutrazol, 2RS,3RS)-1-(2,4-dichlorophenyl)-4,4-dimethyl-2-(1H-1,2, 4-triazol-1-yl)pentan-3-ol, Triflumizole, (E)-4-chloro-α,α, α-trifluoro-N-(1-imidazol-1-yl-2-propoxyethylidene)-o-toluidine, Imazalil Derivative, EIT-0183, Imazalil Derivative, EIT-0180, Imazalil Derivative, EIT-0111, Imazalil Derivative, EIT-0158, Imazalil Derivative, K-240, Chlorothalonil, tetrachloroisophthalonitrile Modification On benzene Ring R1=CN R2=Cl R3=CN R4=Cl R5=Cl R6=Cl), Chlorothalonil Derivative-2,4,5,6-tetrachloro-3-cyanobenzamide (Modification On benzene Ring R1=CONH2 R2=Cl R3=CN R4=Cl R5=Cl R6=Cl), Chlorothalonil Derivative-2,5,6-trichloro-4-hydroxyisophthalonitrile (Modification On benzene Ring R1=CN R2=Cl R3=CN R4=OH R5=Cl R6=Cl), 3-carbamyl-2,4,5-trichlorobenzoic acid (Modification On benzene Ring R1=CONH2 R2=Cl R3=COOH R4=H R5=Cl R6=Cl), Pentachloronitrobenzene (Modification On benzene Ring R1=NO2 R2=Cl R3=Cl R4=Cl R5=Cl R6=Cl), Benzene hexachloride, Hexachlorobenzene, BHC, Lindane (Modification On benzene Ring R1=Cl R2=Cl R3=Cl R4=Cl R5=Cl R6=Cl), 2,4,5,6-tetrachlorophenol (Modification On benzene Ring R1=OH R2=Cl R3=H R4=Cl R5=Cl R6=Cl), Carbaryl Derivative, Ethylcarbamate (Modification R1=OCONHCH2CH3 R3=H), 1-Naphthol, 1-naphthaleneacetamide, -(1-naphthyl) acetamide, Carbaryl Derivative, 1-Methylcarbonate (Modification R1=OCOOCH3 R2=H, Carbaryl Derivative, 1-Ethylcarbonate (Modification R1=OCOOCH2CH3 R2=H), Carbaryl Derivative 2-Ethylcarbonate (Modification R1=H R2=OCOOCH2CH3, Carbaryl Derivative, 1-Ethylthiocarbonate (Modification R1=OCOSCH2CH3 R2=H), Carbaryl Derivative, 2-Ethylthiocarbonate (Modification R1=H R2=OCOSCH2CH3), Naptalam, N-1-naphthylphthalamic acid, Carbaryl Derivative, 3-hydroxycarbaryl (Modification R1=OCONHCH3 R2=H R3=OH R4=H R5=H), Carbaryl Derivative 4-hydroxycarbaryl (Modification R1=OCONHCH3 R2=H R3=H R4=OH R5=H), Carbaryl Derivative 5-hydroxycarbaryl (Modification R1=OCONHCH3 R2=H R3=H R4=H R5=OH), Carbaryl Derivative, 1-(5-Carboxypentyl)-3-(1-naphthyl)urea (Modification R1=NHCONH(CH2)5COOH R2=H), (Structurally related s-triazines)-Aziprotryn, 4-azido-N-isopropyl-6-methylthio-1,3,5-triazin-2-ylamine (Modification R1=—SCH3 R2=—N3 R3=—CH(CH3)2), (Structurally related s-triazines), 2-(ethylamino)-4-(methylthio)-6-aminotriazine (Modification R1=—SCH3 R2=—NH—C2H5 R3=—NH2), (Structurally related s-triazines)-2-amino-4-(methylthio)-6-(isopropylamino)triazine (Modification R1=—SCH3 R2=—NH2 R3=—NH—CH(CH3)2), (Structurally related s-triazines)-2-amino-4-methoxy-6-(isopropylamino)triazine (Modification R1=—OCH3 R2=—NH2 R3=—NH—CH(CH3)2), TCP Derivative (3,5,6-trichloro-2-pyridinol Derivative), 3-(3,5-dichloro-6-hydroxy-2-pyridyl)thiopropanoic Acid, p-nitrosuccinanilic acid (PNA-S), PNA-S, PNA-C, p-nitro-cis-1,2-cyclohexanedicarboxanilic acid, Nitroaniline Derivative, 2-nitroaniline, o-Nitroaniline, Nitroaniline Derivative-3-nitroaniline, m-Nitroaniline, Nitroaniline Derivative-4-nitroaniline, p-Nitroaniline, Aeromatic Alcohols, 4-nitrobenzyl alcohol, Aeromatic Alcohols-4-nitrophenethyl alcohol, Aeromatic Alcohols 2-nitrobenzyl alcohol, Aeromatic Alcohols, 3-nitrobenzyl alcohol, Urea Derivative-1-benzyl-3-(4-nitrophenyl)urea, Urea Derivative-1-(3-chlorophenyl)-3-(2-methoxy-5-nitrophenyl)urea, Urea Derivative-1-(3-chlorophenyl)-3-(4-methoxy-3-nitrophenyl)urea, Urea Derivative-1-(4-chlorophenyl)-3-(4-nitrophenyl)urea, Urea Derivative-(2-fluorophenyl)-3-(2-mehtoxy-4-nitrophenyl) urea, 1-(3-mehtoxyphenyl)-3-(3-nitrophenyl)urea, Carbofuran Derivative m Carbofuran-phenol, Carbofuran-hydroxy, Carbofuran-keto, Carbosulfan, 3-dihydro-2,2-dimethylbenzofuran-7-yl (dibutylaminothio) methylcarbamate, Benfuracarb, N-[2,3-dihydro-2,2-dimethylbenzofuran-7-yloxycarbonyl(methyl)aminothio]-N-isopropyl-β-alaninate, Furathiocarb, 2,3-dihydro-2,2-dimethyl-7-benzofuranyl 2,4-dimethyl-5-oxo-6-oxa-3-thia-2,4-diazadecanoate, Carbofuran Derivative, 4-[[(2,3-Dihydro-2,2-dimethyl-7-benzofuranyloxy)carbonyl]-amino]butanoic Acid (BFNB) (Modification n=3 X=CH2), Endrin, nendrin, (1R,4S,4aS,5S,6S,7R,8R,8aR)-1,2,3,4,10,10-hexachloro-1,4,4a,5,6,7,8,8a-octahydro-6,7-epoxy-1,4: 5,8-dimethanonaphthalene, Heptachlor, 1,4,5,6,7,8,8-heptachloro-3a,4,7,7a-tetrahydro-4,7-, Chlordane, 1,2,4,5,6,7,8,8-octachloro-2,3,3a,4,7,7a-hexahydro-4,7-methanoindene, Endosulfan (Modification isomer mix of alpha and beta forms), Endosulfan (Modification alpha isomeric form), Endosulfan (Modification beta isomeric form), Endosulfan Derivative, Endosulfan sulfate (Modification sulfate form), Endosulfan Derivative, Endosulfan diol, Diol metabolite of endosulfan, Endosulfan Derivative, Endosulfan ether (Modification ether metabolite of endosulfan), Endosulfan Derivative, hydroxy ether, hydroxy ether metabolite of endosulfan, Endosulfan Derivative, Endosulfan lactone (Modification lactone metabolite of endosulfan), Aldrin, Dieldrin, Fenvalerate isomers Modification 1S,2R isomer R: Ph), Fenvalerate isomers (Modification 1R,2S isomer R: Ph), Fenvalerate isomers (Modification 1R,2R isomer R: Ph), Fenvalerate isomers (Modification 1S,2R/S isomer R: Ph), Fenvalerate isomers (Modification 1R,2R/S isomer R: Ph), Fenvalerate isomers, fenvalerate (Modification 1R/S, 2R/S isomer R: Ph), Thiabendazole, 2-(thiazol-4-yl)benzimidazole, Thiabendazole Derivative, 5-hydroxythiabendazole (Modification 5-OH-TBZ), Thiabendazole Derivative, 5-NH2-TBZ, Thiabendazole Derivative, methyl benzimidazole carbamate, Albendazole, Mebendazole, Fenbendazole, Thiabendazole Derivative, 2-succinamidothiabendazole, Thiabendazole Derivative, 2-succinamidothiabendazole, Cambendazole, Fenvalerate Haptens, Cyano[3-(4-aminophenoxy)phenyl]methyl (S)-4-Chloro-alpha-(1-methylethyl)benzeneacetate (4-Aminoesfenvalerate), Fenvalerate Haptens, Benzyl 4-[3-[Cyano[(S)-2-(4-chlorophenyl)-3-methyl-1-oxobutanoxy]methyl]]phenoxy]benzenepropanoate, Fenvalerate Haptens, Benzyl 3-[Cyano[(S)-2-(4-chlorophenyl)-3-methyl-1-oxobutanoxy]methyl]]phenoxyacetate, Fenvalerate Haptens, 3-[Cyano[(S)-2-(4-chlorophenyl)-3-methyl-1-oxobutanoxy]methyl]]phenoxyacetic Acid, Fenvalerate Haptens, Benzyl 6-[3-[Cyano[(S)-2-(4-chlorophenyl)-3-methyl-1-oxobutanoxy]methyl]]phenoxy] hexanoate, Fenvalerate Haptens, 6-[3-[Cyano[(S)-2-(4-chlorophenyl)-3-methyl-1-oxobutanoxy]methyl]]phenoxy] hexanoic Acid Fenvalerate Haptens, 4-[3-[Cyano[(S)-2-(4-chlorophenyl)-3-methyl-1-oxobutanoxy]methyl]]phenoxy] benzenepropanoic Acid, (S)-fenvalerate Acid, (Structurally related s-triazines), atrazine mercapturate Modification R1=—SCH2CH(NHCOCH3)COOH R2=—NHCH2CH3 R3=—NHCH(CH3)2, Fenthion Hapten, -Methyl O-[3-methyl-4-(methylthio)phenyl] N-(3-carboxypropyl)phosphoramidothioate Modification referred as Hapten B, Fenthion Derivative, Oxidized Fenthion, Fenthion Derivative, Oxidized oxidized Fenthion, pirimiphos-ethyl, 4-(Methylthio)-m-cresol, Chlorpyrifos Derivative, Chlorpyrifos-oxon, Fenchlorphos, O,O-dimethyl O-2,4,5-trichlorphenyl phosphorothioate, Trichloronate, O-Ethyl O-2,4,5-trichlorophenyl ethyl-phosphonothioate, Dichlofenthion, O-2,4-dichlorophenyl O,O-diethyl phosphorothioate, Parathion, O,O-diethyl O-4-nitrophenyl phosphorothioate; Thiophos, Chlorpyrifos Derivative Modification Synthesis of AR1 is described, Chlorpyrifos Derivative, O-Ethyl O-(3,5,6-Trichloro-2-pyridyl)O-(3-Carboxypropyl)Phosphorothioate; (PO), Chlorpyrifos Derivative-O-Ethyl O-(3,5,6-Trichloro-2-pyridyl)N-(5-Carboxyethyl) Phosphoramidothioate; (PN1) (Modification Amide linkage of thiophosphate reagents), Chlorpyrifos Derivative, O-Ethyl O-(3,5,6-Trichloro-2-pyridyl)N-(2-Carboxyethyl) Phosphoramidothioate; (PN1) (Modification Amide linkage of suitable thiophosphate reagents), Triadimefon, (RS)-1-(4-chlorophenoxy)-3,3-dimethyl-1-(1H-1,2,4-triazol-1-yl)butan-2-one, GR151004, (4-[[5-[3-[2-(dimethylamino)ethyl]]-5-benzofuranyl]-3-pyridinyl]acetyl]morpholine dihydrochloride, Diflubenzuron, 1-(4-chlorophenyl)-3-(2,6-difluorobenzoyl)urea, (Structurally related s-triazines)-SprAAT (Modification R1=SCH2CH2COOH R2=NH2 R3=NH2), (Structurally related s-triazines), SBeAAT (Modification R1=S(C6H4)COOH R2=NH2 R3=NH2), (Structurally related s-triazines), SAAT (Modification R1=SH R2=NH2 R3=NH2), (Structurally related s-triazines), CDAT (Modification R1=Cl R2=NH[C(O)CH3) R3=NH2), (Structurally related s-triazines)-CDET (Modification R1=Cl R2=NH[C(O)CH3] R3=NH(CH2CH3), (Structurally related s-triazines)-CDIT (Modification R1=Cl R2=NH[C(O)CH3] R3=NH(CH(CH3)2)), (Structurally related s-triazines), CDDT (Modification R1=Cl R2=NH[C(O)CH3] R3=NH[C(O)CH3)), (Structurally related s-triazines)-ammeline, OAAT (Modification R1=OH R2=NH2 R3=NH2), (Structurally related s-triazines)-ammelide, OOAT (Modification R1=OH R2=OH R3=NH2), (Structurally related s-triazines)-cyanuric acid, OOOT (Modification R1=OH R2=OH R3=OH), (Structurally related s-triazines), melamine, AAAT (Modification R1=NH2 R2=NH2 R3=NH2), Structurally related s-triazines-N-isopylammeline, OIAT (Modification R1=OH R2=NH[CH(CH3)2] R3=NH2, Structurally related s-triazines-N-ethylammeline, OEAT (Modification R1=OH R2=NHCH2CH3 R3=NH2), Structurally related s-triazines, N-ethylammelide, OOET (Modification R1=OH R2=OH R3=NHCH2CH3), Structurally related s-triazines)-cyromazine, CyPAAT (Modification R1=NH(C3H5) R2=NH2 R3=NH2), Structurally related s-triazines-diamino-s-triazine, HAAT (Modification R1=H R2=NH2 R3=NH2), PCB congeners, 2,5,3',4'-tetrachlorobiphenyl (Modification IUPAC no.: 70), PCB congeners 2,4,5,3',4'-pentachlorobiphenyl (Modification IUPAC no.: 118), PCB congeners-2,2',5,5'-tetrachlorobiphenyl (Modification IUPAC no.: 52), PCB congeners, 6-[3,3',4'-Trichlorobiphenyl-4-yl)oxy]hexanoic Acid, Metolazone, Brand Names: Mykrox; Zaroxolyn, Furfuryl benzoate, DDT Metabolites, DDA, Paraquat, 1,1'-dimethyl-4,4'-bipyridinium ion, Diethylcarbamazine, THP, 2,4,6-triphenyl-N-(4-hydroxyphenyl)-pyridinium, o-DNCP, -dinitrocarboxyphenol, PCB congeners, 3-chlorobiphenylol (Modification IUPAC No. 2), PCB congeners, 3,4'-dichlorobiphenyl (Modification IUPAC No. 13), PCB congeners, 3,5-dichlorobiphenyl (Modification IUPAC No. 14), PCB congeners, 3,4,5,3',4'-pentachlorobiphenyl (Modification IUPAC No. 126), 2,3,3',4'-tetrachlorobiphenyl (Modification IUPAC No. 56), 2',3,4,5-tetrachlorobiphenyl (Modification IUPAC No. 76), 3,3',5,5'-tetrachlorobiphenyl (Modification IUPAC No. 80), 2,4,5,2',5'-pentachlorobiphenyl (Modification IUPAC No. 101), 2,3,3',4,4'-pentachlorobiphenyl (Modification IUPAC No. 105), 2,3,6,3',4'-pentachlorobiphenyl (Modification IUPAC No. 110), 3,3',4,5,5'-pentachlorobiphenyl (Modification IUPAC No. 127), 3,4,5,3',4',5'-hexachlorobiphenyl (Modification IUPAC No. 169), 2,3,3',4,4',5-hexachlorobiphenyl (Modification IUPAC No. 156), 3,4,3',4'-tetrabromobiphenyl, 3,4,5,3',4',5'-hexabromobiphenyl, 2,4,5,2',4',5'-hexabromobiphenyl, Dibenzofurans and Dioxins, 2,3,7,8-tetrachlorobenzofuran, 2,3,7,8-tetrachlorodibenzo-p-dioxin, 3,4',5-trichloro-4-biphenylol, 3,3',5,5'-tetrachloro-4,4'-biphenyldiol, 3,4,3',4'-tetrachlorodiphenyl ether, 1-2-dichlorobenzene, 1,4-dichlorobenzene, 1,2,4-trichlorobenzene, 3,4-dichloroaniline, DDT Metabolites, 4,4'-DDT, 4,4'-DDD Retronecine, 3,4-dichlorobiphenyl Modification IUPAC No. 12, 3,4,3'-trichlorobiphenyl (Modification IUPAC No. 35), PCB Congeners, 3,4,4'-trichlorobiphenyl (Modification IUPAC No. 37), 3,4,3',5-tetrachlorobiphenyl (Modification IUPAC No. 78), 3,4,3',5'-tetrachlorobiphenyl (Modification IUPAC No. 79), 3,4,4',5-tetrachlorobiphenyl (Modification IUPAC No. 81), DDT Metabolites, p,p'-DDT (Modification p,p'-dichlorodiphenyltrichloroethane), o,p'-DDT Modification o,p'-dichlorodiphenyltrichloroethane, p,p'-DDE Modification p,p'-DDE, o,p'-DDE Modification o,p'-DDE, p,p'-DDD Modification p,p'-DDD, o,p'-DDD Modification o,p'-DDD, Dicofol, 4,4-dichloro-a-(trichloromethyl)benzhydrol, Cyprazine, 6-chloro-N-cyclopropyl-N'-(1-methylethyl)-1,3,5-triazine-2,4-diamine, Structurally related s-triazines, Dipropetryn, 6-(ethylthio)-N,N'-bis(1-methylethyl)-1,3,5-triazine-2,4-diamine, Trietazine, 6-chloro-N,N,N'-triethyl-1,3,5-triazine-2,4-diamine, 6-Hydroxatrazine, hexazinone, 3-cyclohexyl-6-dimethylamino-1-methyl-1,3,5-triazine-2,4 (1H,3H)-dione, TNT, 2,4,6-Trinitrotoluene, Tetraconazole (M14360), 1-[2-(2,4-dichlorophenyl)-3-(1,1,2,2-tetrafluoroethoxy)propyl]-1H-1,2,4-triazole, DTP, 2-(2,4-dichlorophenyl)-3-(1H-1,2,4-triazol-1-yl)propanol, Imazalyl, fenarimol, (RS)-2,4'-dichloro-α-(pyrimidin-5-yl)benzhydryl alcohol, Lupanine metabolites, (+)-lupanine (Modification R=H), Lupanine metabolites, (+)-13-hydroxylupanine (Modification R=OH), Lupanine metabolites, hemisuccinate ester of (+)-13-hydroxylupanine (Modification R=OCO—(CH2) 2.COOH), Lupanine metabolites, cis-hexahydrophthalate ester of (+)-13-hydroxylupanine (Modification R=OCO.C6H10.COOH), Lupanine metabolites, alpha-isolupanine, Lupanine metabolites, -hydroxylupanine, Sparteine, Cysteine, multiflorine, epilupinine, (Structurally related s-triazines), CYANAZINE ACID Modification R1=Cl R2=NHCH2CH3 R3=NHCCOOH(CH3)2, Structurally related s-triazines Modification R1=Cl R2=NHCH2CH3 R3=NH(CH2)3COOH, Structurally related s-triazines (Modification R1=Cl R2=NHCH2CH3 R3=NHCH2COOH), (Structurally related s-triazines) (Modification R1=Cl R2=NHCH2CH3 R3=NH(CH2)4COOH), norflurazon, 4-chloro-5-(methylamino)-2-[3-(trifluoromethyl)phenyl]-3(2H)-pyridazinone, norflurazon derivative, desmethyl-norflurazon, metflurazon, -chloro-5-(dimethylamino)-2-[(3-trifluoromethyl)phenyl]-3(2H)-pyridazinone, Pyrazon, Chloridazon, 5-amino-4-chloro-2-phenyl-3(2H)-pyridazinone (active ingradient), dichlorophenyl-pyridazone, (Structurally related s-triazines) azidoatrazine (Modification R1=N3 R2=NHCH(CH3)2 R3=NHCH2CH3), ALACHLOR 2-chloro-2',6'-diethyl-N-methoxymethylacetanilide, trichothecolone (Modification R1=H R2=OH R3=H R4=O R5=H), DON derivative, acetyl-T-2, DON derivative, T-2 tetrol tetraacetate, Chlorpyrifos derivatives, mono-dechloro-CP, Bromophos derivative, Bromophos-methyl, Bromophos derivative, Bromophosethyl dicapthon, -2-chloro-4-nitrophenyl O,O-dimethyl phosphorothioate, tetrachlorvinphos, (Z)-2-chloro-1-(2,4,5-trichlorophenyl)vinyl dimethyl phosphate, triclopyr, 3,5,6-trichloro-2-pyridyloxyacetic acid, picloram, 4-amino-3,5,6-trichloropyridine-2-carboxylic acid, Formononetin, Biochanin A, 5, 7-dihydroxy-4'-methoxyisoflavone (Modification It is the 4'-methyl ether of genistein), equol, (7-hydroxy-3-(4'-hydroxyphenyl)-chroman, 2'methoxyformononetin, Daidzein, 7-hydroxy-3-(4-hydroxyphenyl)-4H-1-benzopyran-4-one, geninstein, quercetin, 3,3',4',5,7-Pentahydroxyflavone; 3,5,7,3',4'-Pentahydroxyflavone; matheucinol, coumestrol (Structurally related s-triazines), Hydroxysimazine (Modification R1=OHR2=NHCH2CH3R3=NHCH2CH3, angustifoline, Alodan, 1-Methyl-4-phenyl-4-carboethoxypiperidine hydrochloride, Zearalenone, RAL, F-2 Toxin, Fenpropimorph, (RS)-cis-4-[3-(4-tert-butylphenyl)-2-methylpropyl]-2,6-dimethylmorpholine, Tridemorph, 2,6-dimethyl-4-tridecylmorpholine, 2,6-dimethylmorpholine, Amorolfine, Fenpropidine, (RS)-1-[3-(4-tert-butylphenyl)-2-methylpropyl]piperidine, (Structurally related s-triazines) (Modification R1=Cl R2=Cl R3=NHCH2CH3, (Structurally related s-triazines) Modification R1=Cl R2=Cl R3=NHCH(CH3)2, (Structurally related s-triazines) Modification R1=Cl R2=NHCH2CH3 R3=NH(CH2)5COOH, (Structurally related s-triazines) Modification R1=Cl R2=NHCH(CH3)2 R3=NHCH2COOH, (Structurally related s-triazines) (Modification R1=Cl R2=NHCH(CH3)2 R3=NH(CH2)5COOH), Structurally related s-triazines, cyanazine amide (Modification R1=Cl R2=NHCH2CH3 R3=NHCCONH2(CH3)2), hydroxycyanazine acid (Modification R1=OH R2=NHCH2CH3 R3=NHCCOOH(CH3)2), deethylsimazine (Modification R1=Cl R2=NH2 R3=NHCH2CH3), Albendazole sulfoxide, [5-(propylthionyl)-1H-benzimidazol-2-yl]-, methylester, Albendazole sulfone, 5(6)-alkylbenzimidazoles, 2-amino-5-(propylthio)benzimidazole, 5(6)-alkylbenzimidazoles, 2-amino-5-(propylsulfonyl) benzimidazole, oxibendazole, 5-propoxy-benzimidazole-2-methyl carbamate, 5(6)-arylbenzimidazoles, fenbendazole sulfone (Modification sulfone metabolite of fenbendazole), 5(6)-arylbenzimidazoles, 4'-hydroxyfenbendazole, 5(6)-arylbenzimidazoles, oxfendazole (Modification Oxfendazole is the sulfoxide metabolite of fenbendazole), 5(6)-arylbenzimidazoles, flubendazole, benzimidazole Metabolites, 2-aminobenzimidazole, benzimidazole Metabolites, 5-aminobenzimidazole, benzimidazole Metabolites, 2-acetylbenzimidazole, Benzophenone, Diphenylmethanone; phenyl ketone; Diphenyl ketone; Benzoylbenzene, Benzaldehyde, benzoic aldehyde, 4-Bromo-2,5-dichlorophenol, Acephate, O,S-dimethyl acetylphosphoramidothioate, methamidophos, O,S-dimethyl phosphoramidothioate, Dichlorvos, 2,2-dichlorovinyl dimethyl phosphate, Phenthoate, S-α-ethoxycarbonylbenzyl O,O-dimethyl phosphorodithioate, EPN, Ethyl p-nitrophenyl thionobenzenephosphonate, Bioresmethrin, -benzyl-3-furylmethyl (1R,3R)-2,2-dimethyl-3-(2-methylprop-1-enyl) cyclopropanecarboxylate (Modification The unresolved isomeric mixture of this substance has the ISO common name resmethrin), flufenoxuron, 1-[4-(2-chloro-α,α,α-trifluoro-p-tolyloxy)-2-fluorophenyl]-3-(2,6-difluorobenzoyl) urea, Amitrole, 1H-1,2,4-triazol-3-ylamine, molinate, S-ethyl azepane-1-carbothioate, molinate derivative (Modification S-2-carboxyethyl hexahydroazepine-1-carbothioate), molinate derivative (Modification S-5-carboxypentyl hexahydroazepine-1-carbothioate) molinate derivative (Modification molinate sulfone), molinate derivative (Modification S-(p-aminobenzyl) hexahydroazepine-1-carbothioate), molinate derivative (Modification S-2-(p-aminophenyl) ethyl hexahydroazepine-1-carbothioate), hexamethylenimine, thiobencarb (Bolero), butylate (Sutan), EPTC (Eptam), cycloate (Roneet), pebulate (Tillam), vernolate (Vernam), Aflatoxin M1, AFM1 (Modification AFM1), Aflatoxin B1, AFB1 (Modification AFB1), Aflatoxin G1, AFG1 (Modification AFG1), Aflatoxin M2, AFM2 (Modification AFM2), Aflatoxin B2, AFB2 (Modification AFB2), Aflatoxin G2, AFG2 (Modification AFG2), Aflatoxin B2alpha, AFB2alpha (Modification AFB2alpha), Aflatoxin G2alpha, AFG2alpha (Modification AFG2alpha), KB-6806, 6-amino-5-chloro-1-isopropyl-2-(4-methyl-1-piperazinyl) (Modification R1=NH2 R2=CH(CH3)2 R3=CH3), KB-6806 (Benzimidazole) Derivatives Modification R1=NH2 R2=CH2CH(CH3)2 R3=CH3, Hapten Name KB-6806 (Benzimidazole) Derivatives (Modification R1=NH2 R2=CH(CH2CH3)2 R3=CH3), KB-6806 (Benzimidazole) Derivatives (Modification R1=NHCOCH3 R2=CH(CH3)2 R3=CH3), KB-6806 (Benzimidazole) Derivatives (Modification R1=H R2=CH(CH3)2 R3=CH3), KB-6806 (Benzimidazole) Derivatives (Modification R1=NH2 R2=CH(CH3)2 R3=CH3), KB-6806 (Benzimidazole) Derivatives Modification R1=NH2 R2=CH(CH3)2 R3==N(—>O) CH3 (N-OXIDE), KB-6806 (Benzimidazole) Derivatives Modification R1=NH2 R2=CH(CH3)2 R3=H, KB-6806 (Benzimidazole) Derivatives Modification R1=NH2 R2=CH2CH3 R3=CH3, Aminoparaoxon, phosphoric acid, O,O-diethyl O-(4-aminophenyl) ester, Methylparathion, phosphorothioic acid, O,O-dimethyl O-(4-nitrophenyl) ester, Diethyl phenylphosphate, phenylphosphonic acid, O,O-diethyl ester, Diethyl phosphate, ethylphosphonic acid, O,O-diethyl ester, p-Nitrophenyl phosphate, phosphonic acid, O-(4-nitrophenyl)ester, Phorate, phosphorodithioic acid, O,O-diethyl S-[(ethylthio) methyl] ester, Ethion, bis(phosphorodithioic acid), S,S'-methylene O,O,O',O'-tetraethyl ester, Carbophenthion, phosphorodithioic acid, O,O-diethyl S-[[(4-chlorophenyl) thio]methyl] ester, Disulfoton, phosphorodithioic acid, O,O-diethyl S-[(2-ethylthio)ethyl] ester, TS, N-[4-(Carboxymethyl)-2-thiazolyl)sulfanilamide, NS, N-(4-Nitrophenyl) sulfanilamide, Sulfamoxole, Sulfacetamide, DNP-SL, Spin labelled dinitrophenyl (Modification The synthesis of DNP-SL has been described by Balakrishnan et al (1982) formula can be found in Anglister et al. (1984)), beta ecdysone, Benzimidazole Derivative, 5(6)-[Carboxypentyl)thio]-2-(methoxycarbonyl)amino]-benzimidazole, 2-hydroxybiphenyl HBP, Atrazine Caproic acid, Lysophosphatidic acid (LPA), 1-acyl-2-hydroxy-sn-glycero-3-phosphate), berberine, Palmatine, 9-Acetylberberine, Corydaline, Coptisine, Berberrubine, 8-Oxoberberine, Papaverine, Berberine Derivative, 9-O-carboxymethyl berberine, phencyclidine, 1-(1-phenylcyclohexyl)piperidine, Methoxychlor, Endosulfan Derivative, 4-Oxobutanoic Acid,4-(4,5,6,7,8,8-Hexachloro-3a,4,7,7a-tetrahydro-4,7-methano-1H-indenyl-1-oxy), Endosulfan Derivative, 4-oxybutanoic Acid,4-(1,3,4,5,6,7,8-Octachloro-3a,4,7,7a-tetrahydro-4,7-methanoindanyl-2-oxy, Endosulfan Derivative (Modification Hemisuccinate of Endosulfan diol), Triazole Derivatives, 5-(3-Hydroxypropyl)-3-amino-2H-1,2,4-triazole, Triazole Derivatives, 5-(3-Hydroxypropyl)-3-(2-nitrophenylsulfenyl)amino-2H-1,2,4-triazole, Triazole Derivatives, 3-Amino-5-[(3-succinyloxy)propyl]-2H-1,2,4-triazole, Triazole Derivatives, 3-amino-1,2,4-triazole-5-thiol, Triazole Derivatives, 3-[(2-nitrophenylsulfenyl) amino-2H-1,2,4-triazole-5-thiol, Triazole Derivatives, 2H-1,2,4-triazole-5-thiol, Triazole Derivatives, 4-methyl-1,2,4-triazole-3-thiol, Triazole Derivatives, (1,2,4-triazol-2-yl)acetic acid, 1,2,4-triazole, 4-nitrophenyl 4'-carboxymethylphenyl phosphate, Triazole Derivative, 4-amino-1,2,4-triazole, Triazole Derivative, 3-acetamido-1H-1,2,4-triazole, Triazole Derivative, 3-amino-1,2,4-triazole-5-carboxylic acid hemihydrate, Triazole Derivative, 2-(4-chlorophenyl)-2-(1,2,4-triazol-1-yl)-methylhexanoic acid, succinic acid, Imidazole, L-histidine, L-glutamic acid, Permethrin derivative, 3-phenoxybenzyl 2,2-dimethylcyclopropane-1,3-dicarboxylate, 3-phenoxybenzaldehyde, flucythrinate, Chrysanthemic acid, 2,4-Dinitrophenyl, DNP, Thiram Haptens, Disodium 4-[Carbodithioato(methyl)-amino]butanoate, Thiram Haptens 5,11-Dimethyl-6,10-dithioxo-7,9-dithia-5,11-diazadodecanoic Acid, Thiram Haptens, 2-{[(Dimethylamino)carbothioyl]sulfanyl}ethanoic Acid, Thiram Haptens, 4-{[(Dimethylamino)carbothioyl] sulfanyl}butanoic Acid, Thiram Haptens, 6-{[(Dimethylamino)carbothioyl]sulfanyl}hexanoic Acid, Thiram Haptens, 11-{[(Dimethylamino)carbothioyl] sulfanyl}undecanoic Acid, Thiram Haptens, 2-{[(Dimethylamino)carbothioyl] sulfanyl}ethanoic Acid, Thiram, Tetramethylthiurammonosulfide, Tetraethylthiuram disulfide, Dimethyldithiocarbamic acid sodium salt, Dimethyldithiocarbamic acid zinc salt, Diethyldithiocarbamic acid sodium salt, N,N,N',N'-tetramethylthiourea, Nabam, Zineb, Maneb, Ethylenethiourea, Chlorpyrifos hapten, O,O Diethyl O-[3,5-Dichloro-6-[(2-carboxyethyl)thio]-2-pyridyl] Phosphorothioate, 2-Succinamidobenzimidazole, Methyl 2-Benzimidazolecarbamate, MBC, Benzimidazole, 2-benzimidazolylurea, succinamide, Ethyl carbamate, Urea, N-methylurea, N,N'-dimethylurea, Brevetoxin PbTx-3, Organophosphorous Haptens, O,O-Diethyl O-(5-carboxy-2-fluorophenyl) phosphorothioate, Chlorpyrifos-ethyl, Anandamide hapten, N-Arachidonyl-7-amino-6-hydroxy-heptanoic acid, Anandamide, Arachidonic acid, Docosatetraenoyl ethanolamide, Dihomo-gamma-linolenyl ethanolamide, 2-Arachidonyl glycerol, 2-Arachidonyl glycerol ether, Stearoyl ethanolamide, Heptadecanoyl ethanolamide, Prostaglandin E1, 3-hydroxy-2-(3-hydroxy-1-octenyl)-5-oxocyclopentaneheptanoic acid; alprostadil; PGE1, Prostaglandin D2, PGD2, Prostaglandin A2, PGA2, Prostaglandin B2, PGB2, Prostaglandin F2 alpha, 7-[3,5-dihydroxy-2-(3-hydroxy-1-octenyl)cyclopentyl]-5-heptenoic acid; dinoprost; PGF2alpha, Prostaglandin F1 alpha, PGF1alpha, 6-keto-Prostaglandin F1 alpha, 6-keto-PGF1alpha, 13,14-Dihydro-15-keto-Prostaglandin E2, 13,14-Dihydro-15-keto-PGE2, 13,14-Dihydro-15-keto-Prostaglandin F2alpha, 14-Dihydro-15-keto-PGF2alpha, 5alpha,7alpha-Dihydroxy-11-ketotetranorpostane-1,16-dioic acid, 15-keto-PGF2alpha, TXB2, Prostaglandin E2,7-[3-hydroxy-2-(3-hydroxy-1-octenyl)-5-oxocyclopentyl]-5-heptenoic acid; dinoprostone; PGE2, hCG-alpha-(59-92)-peptide (34 residues), Paraquat Derivative, Paraquat hexanoate (PQ-h), Monoquat, Diquat, 9,10-dihydro-8a, 10a-diazoniaphenanthrene, MPTP, 1-methyl-4-phenyl-1,2,5,6-tetrahydropyridine, 1,2-Naphthoquinone, N-Acetyl-S-(1,2-dihydroxy-4-naphthyl)cysteine, N-Acetyl-S-(1,4-dihydroxy-2-naphthyl)cysteine, N-Acetyl-S-(1,2-dihydroxy-1-hydroxy-1-naphthyl)cysteine, 2-Chloro-2'.6'-diethylacetanilide (CDA) Hapten, 2-[2-Chloro-(2'-6'-diethyl)acetanilido]ethanoic Acid, 2-Chloro-2'.6'-diethylacetanilide (CDA) Hapten, 2-[2-Chloro-(2'-6'-diethyl)acetanilido]butanoic Acid, 2-Chloro-2'.6'-diethylacetanilide (CDA) Hapten, 5-(4-Chloroacetamido-3,5-diethyl)phenoxypentanoic Acid, CDA, 2-Chloro-2'.6'-diethylacetanilide, HDA, 2-Hydroxy-2'.6'-diethylacetanilide, 2,6-diethyl-aniline, Hydroxyalachlor, Alachlor ESA, Alachlor ethanesulfonic acid, Isoproturon Hapten, 3-(4-Isopropylphenyl)-1-carboxypropyl-1-methyl urea, chlorotoluron, 3-(3-chloro-p-tolyl)-1,1-dimethylurea, Metoxuron, 3-(3-chloro-4-methoxyphenyl)-1,1-dimethylurea, metamitron, 4-amino-4,5-dihydro-3-methyl-6-phenyl-1,2,4-triazin-5-one, mecoprop, (RS)-2-(4-chloro-o-tolyloxy)

propionic acid, propyzamide, 3,5-dichloro-N-(1,1-dimethylpropynyl)benzamide, Paraquat dichloride, MCPB, 4-(4-chloro-o-tolyloxy)butyric acid, Chlortoluron Hapten, N-(3-Chloro-4-methylphenyl)-N-methyl-N-carboxypropyl Urea, Metsulfuron, Methyl 2-[3-(4-methoxy-6-methyl-1,3,5-triazin-2-yl)ureidosulphonyl]benzoate, Captopril Haptens, Captopril-4-(Maleimidomethyl)-cyclohexane Carboxylic Acid (MCC), Captopril Haptens, Captopril Disulfide Modification, Mercaptoethanol-MCC, Mercaptoethanol-4-(Maleimidomethyl)-cyclohexane Carboxylic Acid Modification, Captopril Haptens, Captopril without MCC, Aculeatiside A, Aculeatiside B, Solamargine, Solasonine, solanine-S; purapurine, Solasodine, Khasianine, Tomatine, lycopersicin, Tomatidine, 3-O-beta-D-Glucopyranosyl-solasodine, O-alpha-L-Rhamnosyl-1(1→2)-3-O-beta-D-glucopyranosyl-solasodine, 3-O-beta-D-Galacopyranosyl-solasidine, O-beta-D-Glucopyranosyl-1(1→3)-3-O-beta-D-galacopyranosyl-solasodine, 12-Hydroxysolamargine, 12-Hydroxysolasonine, Isoanguivine, Solaverine I, Solaverine II, Xylosyl-beta-solamargine, alpha-Solanine, alpha-Chaconine, Dioscine, Indole Derivatives, beta-Indole Acetic Acid, 2-Bromo-4,6-dinitroaniline, 2-Chloro-4,6-dinitroaniline, Tetryl, 2,4,6-trinitrophenyl-n-methylnitramine, nitramine, tetralite, tetril, 2-Amino-4,6-dinitrotolune, 2,4-Dinitroaniline, 3,5-Dinitroaniline, 2-Amino-4,6-dinitrobenzoic acid, Disperse Blue 79, N-[5-[bis[2-(acetyloxy)ethyl]amino]-2-[(2-bromo-4,6-dinitrophenyl)azo]-4-ethoxyphenyl]acetamide, 1,3-Dinitrobenzene, 2,6-Dinitrotoluene, 4-Amino-2,6-dinitrotoluene, 1,3,5-Trinitrobenzene, Nicergoline, Ethylmorphine, 8-Didehydro-4,5-epoxy-3-ethoxy-17-methylmorphinan-6-ol, Dihydromorphine, Dihydrocodeine, dihydromorphinone, Hydromorphone, Dihydrocodeinone, Hydrocodone, Naltrexone, N-cyclopropylmethyl-14-hydroxydihydromorphinone, Dextromethorphan, (±)-3-Methoxy-17-methylmorphinan, Homatropine, Endorphins Modification Derivative Type: b-Endorphin, Met-enkephalin, DALEA, D-Ala(2)-D-Leu(5)-enkephalinamide, Vincristine, 22-Oxovincaleukoblastine, leurocristine; VCR; LCR, OCT, 22-Oxacalcitriol, OCT-3-HG, 22-oxacalcitriol-3-Hemiglutarate, 24(OH)OCT, 24(OH)-22-oxacalcitriol, 1,20(OH)2-hexanor-D3, Synephrine, Epinephrine, 4-[(1R)-1-Hydroxy-2-(methylamino)ethyl]-1,2-benzenediol, Phenylephrine, Dopamine Derivative, 6-hydroxy dopamine, Tyramine derivative, 3-methoxy tyramine, Phenethylamine, Benzeneethanamine; PEA, m-tyramine, o-tyramine, dimethoxyphenethylamine, Thymidine glycol monophosphate, 5,6-Dihydroxythymidine monophosphate, Thymidine monophosphate, Thymidine glycol, Thymine glycol, 5,6-Dihydrothymidine, Thymidine, Thymine, 5-methyluracil; 2,4-dihydroxy-5-methylpyrimidine, AMP, Adenosine mono phosphate, CMP, Cytidine mono phosphate, Carbamazepine, 5-carbamoyl-5H-dibenz[b,f]azepine, Neopterin isomers, D-erythro-Neopterin, Neopterin isomers, L-erythro-Neopterin, Neopterin isomers, D-threo-Neopterin, Biopterin isomers, L-erythro-Biopterin, Biopterin isomers, D-erythro-Biopterin, Biopterin isomers, L-threo-Biopterin, Biopterin isomers, D-threo-Biopterin, Pterin-6-Carboxylic Acid, C7H5NiO3, Pterin, Thromboxane B2, (5Z,9alpha,13E,15S)-9,11,15-trihydroxythromboxa-5,13-dien-1-oic acid, 15 Ketoprostaglandin F2alpha, Fumonisin B1, macrofusine; FBI, Thyroliberin, TRH; thyrotropin-releasing factor; thyrotropin releasing hormone; TRF; protirelin; lopremone, Thyroliberin-OH, TRH-OH, Diketopiperazine, cyclo (H-P), TRH analogues, Methylated TRH, TRH analogues, TRH elongated peptides, TRH-Gly, TRH elongated peptides, TRH-Gly-Lys-Arg, TRH elongated peptides, TRH-Gly-Lys-Arg-Ala, TRH elongated peptides, P7 (Modification Q-H-P-G-L-R-F), TRH elongated peptides, P10 (Modification S-L-R-Q-H-P-G-L-R-F), TRH elongated peptides, Ps5 Modification pro-TRH[178-199], TRH elongated peptides, TRH-Ps5 (Modification pro-TRH[172-199]), Hypothalmic peptide, LHRH, Cyanoginosin-LA, Cyanoginosin-LB, Cyanoginosin-LR, Cyanoginosin-LY, Cyanoginosin-AY, Cyanoginosin-FR, Cyanoginosin-YR, Ne-acetyllysine-containing peptide, Gly-Lys (Ac)-e-aminocaproic acid (Aca)-Cys, Benzoic Acid, Benzenecarboxylic acid; phenylformic acid; dracylic acid, m-hydroxybenzoic acid, 3-hydroxybenzoic acid, o-methoxybenzoic acid, 2-methoxybenzoic acid, o-toluic acid, 2-Methylbenzoic acid, o-chlorobenzoic acid, 2-chlorobenzoic acid, o-aminobenzoic acid, 2-aminobenzoic acid, thiosalicylic acid, 2-Mercaptobenzoic acid; o-sulfhydrylbenzoic acid, Salicylamide, 2-Hydroxybenzamide, Saligenin, saligenol; o-hydroxybenzyl alcohol; Salicyl alcohol, 2-cyanophenol, 2-hydroxyphenyl acetic acid, p-hydroxybenzoic acid, p-aminobenzoic acid, 4-Aminobenzoic acid; vitamin Bx; bacterial vitamin H1, p-toluic acid, p-methylamino benzoic acid, p-chlorosalicylic acid, 4-chloro-2-hydroxybenzoic acid, 2,4-dihydroxybenzoic acid, beta-Resorcylic Acid; 2,4-dihydroxybenzenecarboxylic acid; BRA, 4-aminosalicylic acid, 4-Amino-2-hydroxybenzoic acid; p-aminosalicylic acid, Gentisic Acid, 2,5-dihydroxybenzoic acid; 5-hydroxysalicylic acid, Picolinic acid, o-Pyridinecarboxylic acid; 2-Pyridinecarboxylic acid, picolinic acid N-oxide, 3-hydroxypicolinic acid, 2-hydroxynicotinic acid, 7-methylguanine, N2-Carboxymethyl-N7-methylguanine, 2-(7-methyl-6-oxo-6,7-dihydro-1H-purin-2-ylamino)acetic acid, 7-methylxanthine, 7-methyluric acid, 7-methyladenine, Guanine, 2-Amino-1,7-dihydro-6H-purin-6-one; 2-aminohypoxanthine, Adenine, 6-aminopurine; 6-amino-1H-purine; 6-amino-3H-purine; 6-amino-9H-purine, 7-(2-Carboxyethyl)guanine, 7-CEGua, 7-Ethylguanine, 2-amino-7-ethyl-1H-purin-6(7H)-one, 7-(2,3-Dihydroxypropyl)guanine, 2-amino-7-(2,3-dihydroxypropyl)-1H-purin-6(7H)-one, 7-(2-Hydroxyethyl)guanine, 2-amino-7-(2-hydroxyethyl)-1H-purin-6(7H)-one, 7-(2-[(2-Hydroxyethyl)amino]ethyl)-guanine, 2-amino-7-(2-(2-hydroxyethylamino)ethyl)-1H-purin-6(7H)-one, 7-Carboxymethylguanine, or 2-(2-amino-6-oxo-1,6-dihydropurin-7-yl)acetic acid. In some alternatives, the CAR or T cell receptor comprises a fragment specific for the hapten, wherein the CAR or TCR comprises 14G8, Anti 3-methylindole antibodies, 3F12, Anti 3-methylindole antibodies, 4A1G, Anti 3-methylindole antibodies, 8F2, Anti 3-methylindole antibodies, 8H1, Anti 3-methylindole antibodies, Anit-Fumonisin B1 antibodies, Anti-1,2-Naphthoquinone-antibodies, Anti-15-Acetyldeoxynivalenol antibodies, Anti-(2-(2,4-dichlorophenyl)-3(1H-1,2,4-triazol-1-yl)propanol) Antibodies (Anti-DTP antibodies), Anti-22-oxacalcitriol antibodies (As-1, 2 and 3), Anti-(24,25(OH)2D3) Antibodies (Ab11), Anti-(24,25(OH)2D3) Antibodies (Ab3), Anti-(24,25(OH)2D3) Antibodies (Ab3-4), Anti-2,4,5-Trichlorophenoxyacetic acid antibodies, Anti (2,4,5-Trichlorphenoxyacetic acid) Antibodies, Anti-(2,4,6-Trichlorophenol) Antibodies, Anti-(2,4,6-Trichlorophenol) Antibodies, Anti 2,4,6-Trinitrotoluene (TNT) Antibodies, Anti-2,4-Dichlorophenoxyacetic acid (MAb's B5/C3, E2/B5, E2/G2, F6/C10, and F6/E5), Anti (2,4-Dichlorphenoxyacetic acid) Antibodies, Anti-2-hydroxybiphenyl-antibodies, Anti-(3,5,6-trichloro-2-pyridinol) Antibodies (LIB-MC2, LIB-MC3), Anti (3,5,6-trichloro-2-pyridinol) antibodies (LIB-MC2 MAb), Anti-3-Acetyldeoxynivalenol (3-AcDON) Antibodies, Anti-3-phenoxybenzoic acid (3-PBAc)-Antibodies, Anti-4-Nitrophenol antibodies, anti-4-nitrophenyl 4'-carboxymethylphenyl phosphate antibodies, Anti-7-(Carboxyethyl)guanine (7-CEGua) antibodies (group specific for 7-meGua), Anti-7-methylguanine (7-MEGua) antibodies, Anti-ABA antibodies, Anti Acephate antibodies (Antiserum 8377), Anti-acetyllysine antibodies (mAbs AL3D5, AL11, AKL3H6, AKL5C1), Anti Aculaetiside-A antibody, Anti Aflatoxin M1(AFM1)antibodies (mAbs A1, N12, R16, FF32), Anti-agatharesinol Antibody, Anti-agatharesinol Antibody, Anti Amidochlorantibodies, Anti-Amitrole antibodies (anti 1a-BSA antibodies), Anti ampicillin Antibodies (AMPI I 1D1 and AMPI II 3B5), Anti-anandamide antibodies (9C11.C9C, 30G8.E6C, 7D2.E2b, 13C2 MAbs), Anti atrazine antibodies, Anti-atrazine antibodies, Anti-Atrazine antibodies, Anti Atrazine Antibodies, Anti-Atrazine Antibodies, Anti-Atrazine Antibodies, Anti-Atrazine Antibodies (4063-21-1 MAb cell line mAb and scAbs), Anti-Atrazine Antibodies (4D8 and 6C8 scAb), Anti Atrazine Antibodies (C193), Anti Atrazine Antibodies (In Rabbit/Sheep), Anti Atrazine Antibodies (K4E7), Anti Atrazine Antibodies (MAb: AM7B2.1), Anti Atrazine Antibodies (ScAb), Anti Atrazine Mercapturic acid antibodies, Anti (Azinphos methyl) Antibodies (MAB's LIB-MFH14, LIB-MFH110), Anti benalaxyl antibody, Anti benzimidazolecarboxylic acid, Anti benzimidazoles antibody (Ab 587), Anti-Benzo[a]pyrene antibodies, Anti Benzo(a)pyrene antibodies (10C10 and 4D5 MAbs), Anti-(Benzoylphenylurea)-Antibodies (mainly against Diflubenzuron), Anti-berberine Antibodies, Anti-beta Indole Acetic Acid Antibodies, Anti-Biopterin (L-erythro form) Antibodies, Anti-Brevetoxin PbTx-3-Antibodies, Anti Bromacil Antibodies, Anti-Bromophos Antibodies, Anti-Bromophos ethyl Antibodies, Anti Butachlor antibodies, Anti-Captopril-MCC Antibodies, Anti-Carbamazepine (CBZ)-Antibodies, Anti Carbaryl Antibodies, Anti Carbaryl Antibodies (LIB-CNH32, LIB-CNH33, LIB-CNH36, LIB-CNH37, LIB-CNH45, LIB-CNA38), Anti-Carbaryl Antibodies (LIB/CNH-3.6 MAb), Anti Carbofuran Antibodies (LIB-BFNB-52, LIB-BFNB-62, LIB-BFNB-67), Anti Carbofuran Antibodies (LIB-BFNP21), Anti-CDA-antibodies, Anti-CDA-antibodies (anti-2-[2-Chloro-(2'-6'-diethyl)acetanilido]butanoic Acid), Anti-CDA-antibodies (anti-2-[2-Chloro-(2'-6'-diethyl)acetanilido]ethanoic Acid), Anti-CDA-antibodies (anti-5-(4-Chloroacetamido-3,5-diethyl)phenoxypentanoic Acid), anti-ceftazidime antibody, Anti-(chlorodiamino-s-triazine) Antibodies (Anti-CAAT) (PAb1-8), Anti Chlorothalonil Antibodies, Anti-Chlorpyrifos antibodies, Anti-Chlorpyrifos Antibodies, Anti-Chlorpyrifos Antibodies (LIB-AR1.1, LIB-AR1.4 Mabs), Anti-Chlorpyrifos Antibodies (LIB-C4), Anti (chlorpyrifos) antibodies (LIB-C4 MAb), Anti-Chlorpyrifos Antibodies (LIB-PN1 Mabs), Anti-Chlorpyrifos Antibodies (LIB-PN2 Mabs), Anti-Chlorpyrifos Antibodies (LIB-PO Mabs), Anti-chlorsulfuron antibodies, Anti-Chlorsulfuron antibodies, Anti Chlortoluron Antibodies (Antiserum), Anti-Cyanoginosin-LA antibodies (mAbs 2B2-2, 2B2-7, 2B2-8, 2B2-9, 2B2-10, 2B5-5, 2B5-8, 2B5-14, 2B5-15, 2B5-23), Anti (D-3-methoxy-4-hydroxyphenylglycol) antibodies, Anti-DDA antibodies, Anti DDT antibodies (PAbs and MAbs), Anti-DDT Mabs (LIB1-11, LIB5-21, LIB5-25, LIB5-28, LIB5-212, LIB5-51, LIB5-52, LIB5-53), Anti-DEC Antibodies (Anti diethylcarbamazine Antibodies), Anti DEHA antibodies, Anti-(Delor 103) antibodies, Anti-Deltamethrin Antibodies, Anti Deltamethrin Antibodies (Del 01 to Del 12 MAbs and PAbs), Anti-deoxynivalenol (DON) Antibodies, Anti-Deoxynivalenol (DON) Antibodies, Anti Dexamethasone Antibody, Anti Dexamethasone Antibody, Anti-Dinitrophenyl (DNP)-antibodies, Anti dinitrophenyl spin labeled antibodies (AN01-AN12), Anti Diuron Antoboides (MAb's: 21, 60, 195, 202, 275, 481, 488, 520), Anti-D-MHPG Antibodies, Anti DNC antibodies, Anti-EB1089 antibodies, Anti-ecdysone antibodies, Anti-endosulfan antibodies, Anti-Endosulfan Antibodies, Anti Esfenvalerate antibodies (Ab7588), Anti estradiol antibodies, Anti-Fenitrothion antibodies (pAbs and mAbs), Anti-Fenpropimorph antibodies, Anti Fenthion Antibodies, Anti-Fenthion Antibodies, Anti FITC antibodies (B13-DEI), Anti-Flucofuron antibodies (F2A8/1/A4B3), Anti-flufenoxuron antibodies, and Anti-(Benzoylphenylurea)-Antibodies, Anti-Formononetin Antibodies, Anti-Furosemide antibodies (Furo-26, Furo37, furo-72, Furo 73 Mabs), Anti-GR151004 Antibodies, Anti-hCG-alpha-peptide Antibodies (FA36, Anti hydroxyatrazine antibodies (HYB-283-2), Anti-Hydroxysimazine Antibodies, Anti Imazalil Antibodies MoAb's (9C1-1-1, 9C5-1-1, 9C6-1-1, 9C8-1-1, 9C9-1-1, 9C12-1-1, 9C14-1-1, 9C16-1-1, 9C18-1-1, 9C19-1-1, 9E1-1, 9G2-1), Anti Irgarol Antibodies, Anti Isopentenyl adenosine antibodies, Anti Isoproturon Antibodies, Anti-KB-6806 antiserum, Anti-(+)lupanine antibodies, Anti Lysophosphatidic (LPA) acid, Anti M3G Ab1 and Ab2, Anti M3G Ab1 and Ab2, Anti-MBC antibodies (Anti-2-succinamidobenzimidazole antiserum), Anti Metanephrine antibodies, anti (+)methamphetamine antibodies, Anti-Methiocarb Antibodies (LIB-MXNB31, LIB-MXNB-33, LIB-MXNH14 and LIB-MXNH-15 MAbs), Anti Metolachlor antibodies, Anti-Metolachlor Antibodies, Anti-Metolachlor Antibodies (MAb 4082-25-4), Anti Molinate Antibodies, Anti monuron antibodies, Anti-morphine-3-glucuronide (E3 scFv antibody), Anti morphine antibodies, Anti-Morphine antibodies, Anti-Morphine Antibodies (mAbs 8.2.1, 33.2.9, 35.4.12, 39.3.9, 44.4.1, 76.7F.16, 83.3.10, 115.1.3, 124.2.2, 131.5.13, 158.1.3, 180.2.4), Anti-Neopterin (D-erythro form) Antibodies, Anti-Nicarbazin Antibodies (Nic 6, Nic 7, Nic 8, and Nic 9), Anti Nicergoline Antibodies (Nic-1, Nic-2, Nic-3 & BNA-1, BNA-3), Anti-norflurazon antibodies, Anti NorMetanephrine antibodies, Anti (o-DNCP) Antibodies, Anti-P10 antibodies (TRH elongated peptide), Anti-Paraoxon Antibodies (BD1 and CE3), Anti Paraquat antibodies, Anti-Paraquat antibodies, anti Parathion-methyl antibodies, Anti PCB Antibodies (against 3,3',4,4'-tetrachlorobiphenyl) MAb S2B1, Anti pentachlorophenol antibodies, Anti Pentachlorophenol antibodies, Anti-Pentachlorophenol antibodies, Anti permethrin antibodies (Mabs Py-1, Py-3 and Py-4), Anti-Phencyclidine Antibodies (Mab 6B5 Fab), Anti-phenobarbital antibodies, Anti-phenobarbital antibodies, Anti-(p.p'-DDT)-Antibodies (LIB-DDT-35 and LIB-DDT5-52), Anti permethrin antibodies (Ab549), Anti Propoxur antibodies (LIB-PRNP15, LIB-PRNP21, LIB-PRNB21, LIB-PRNB33), Anti-Prostaglandin E2-antibodies, Anti-p-tyramine antibodies, Anti pyrene antibodies, Anti retronecine antibodies, Anti-Retronecine Antibodies, Anti salicylate antibodies, Anti Sennoside A antibodies (MAb 6G8), Anti Sennoside B antibodies (MAb's: 7H12, 5G6, 5C7), Anti Simizine antibodies, Anti Sulfonamides antibodies (Anti-TS), Anti-Sulocfuron antibodies (S2B5/1/C3), Anti sulphamethazine antibodies (21C7), Anti-synephrine antibodies, Anti-Thiabendazole antibodies (Antibody 300), Anti-Thiabendazole antibodies (Antibody 430 and 448), Anti-Thiram-Antibodies, Anti-THP antibodies (7S and 19S), Anti-Thromboxane B2 Antibodies, Anti-thymidine glycol monophosphate antibodies (mAb 2.6F.6B.6C), Anti-Thyroliberin (TRH) antibodies, Anti TNT antibodies (AB1 and AB2 antiserum), Anti Triadimefon Antibodies, Anti-triazine antibodies (AM1B5.1), Anti-triazine antibodies (AM5C5.3), Anti-triazine antibodies (AM5D1.2), Anti-triazine antibodies (AM7B2.1), Anti-triazine antibodies (SA5A0.1), Anti-Triazine serum (anti-ametryne), Anti-Triazine serum (anti-atrazine), Anti-Triazine serum (anti-simazine), Anti-Triazine serum (anti-simetryne), Anti Trifluralin Antibodies, Anti Trifluralin Antibodies, Anti Vincristine Antibodies, Anti-Zearalenone Antibodies, Anti Zeatin riboside antibodies, E2 G2 and E4 C2, Fab Fragment K411B derived from MAb K4E7 (isotype IgG2b with k light chain), LIB-BFNP23 Mab, MAb's H-7 and H-9 (against O,O-diethyl OP pesticides), MoAb 33A7-1-1, MoAb 33B8-1-1, MoAb 33C3-1-1, MoAb 3C10-1-1 and MoAb 3E17-1-1, MoAb 45D6-5-1, MoAb 45E6-1-1, MoAb 45-1-1, Mutant (GlnL89Glu) in Fab Fragment K411B derived from MAb K4E7 (isotype IgG2b with k light chain), Mutant (GlnL89Glu/ValH37Ile/GluL3Val) in Fab Fragment K411B derived from MAb K4E7 (isotype IgG2b with k light chain), Mutant (GlnL89Glu/ValH37Ile/GluL3Val) in Fab Fragment K411B derived from MAb K4E7 (isotype IgG2b with k light chain), Mutant (GlnL89Glu/ValH37Ile) in Fab Fragment K411B derived from MAb K4E7 (isotype IgG2b with k light chain), Mutant (GlnL89Glu/ValH37Ile) in Fab Fragment K411B derived from MAb K4E7 (isotype IgG2b with k light chain), Mutant (GluH50Gln) in Fab Fragment K411B derived from MAb K4E7 (isotype IgG2b with k light chain), Mutant (GluH50X) in Fab Fragment K411B derived from MAb K4E7 (isotype IgG2b with k light chain), Mutant (GlyH100aAla) in Fab Fragment K411B derived from MAb K4E7 (isotype IgG2b with k light chain), Mutant (GlyH100aSer) in Fab Fragment K411B derived from MAb K4E7 (isotype IgG2b with k light chain), Mutant (HisH95Phe) in Fab Fragment K411B derived from MAb K4E7 (isotype IgG2b with k light chain), Mutant (HisH95Tyr) in Fab Fragment K411B derived from MAb K4E7 (isotype IgG2b with k light chain), Mutant (PheL32Leu) in Fab Fragment K411B derived from MAb K4E7 (isotype IgG2b with k light chain), Mutant (TrpH33Phe,Tyr,Leu) in Fab Fragment K411B derived from MAb K4E7 (isotype IgG2b with k light chain), Mutant (Tryl96Phe) in Fab Fragment K411B derived from MAb K4E7 (isotype IgG2b with k light chain), Mutant (TryL96Phe) in Fab Fragment K411B derived from MAb K4E7 (isotype IgG2b with k light chain), Mutant (ValH37Ile) in Fab Fragment K411B derived from MAb K4E7 (isotype IgG2b with k light chain), Mutant (ValH37Ile) in Fab Fragment K411B derived from MAb K4E7 (isotype IgG2b with k light chain), P6A7 MAb, PNAS2 6/3 56(1)-1-5-1, PNAS2 6/3 56(1)-1-5-2, PNAS2 6/3 56(1)-1-10-4, PNAS2 6/3 56(1)-1-10-5 and PNAS2 6/3 56(1)-3-1-5, Alexa Fluor 405/Cascade Blue dye antibody, Alexa Fluor 488 dye antibody, BODIPY FL dye antibody, Dansyl antibody, Fluorescein/Oregon Green dye antibody, Lucifer yellow dye antibody, Tetramethylrhodamine and Rhodamine Red dye antibody, Texas Red and Texas Red-X dye antibody, Biotin antibody, Dinitrophenyl antibody and/or Nitrotyrosine antibody or any portion thereof of the aforementioned haptens.

BRIEF DESCRIPTION OF THE DRAWINGS

As shown in FIG. 8, the anti-FL antibody is bound to the FL-PLE.

In FIG. 9C, the CD8+ antiFL CAR cells exhibited better 11-2, TNFα and IFN γ release than the CD8+ mock cells.

TERMS

Figure 1A:
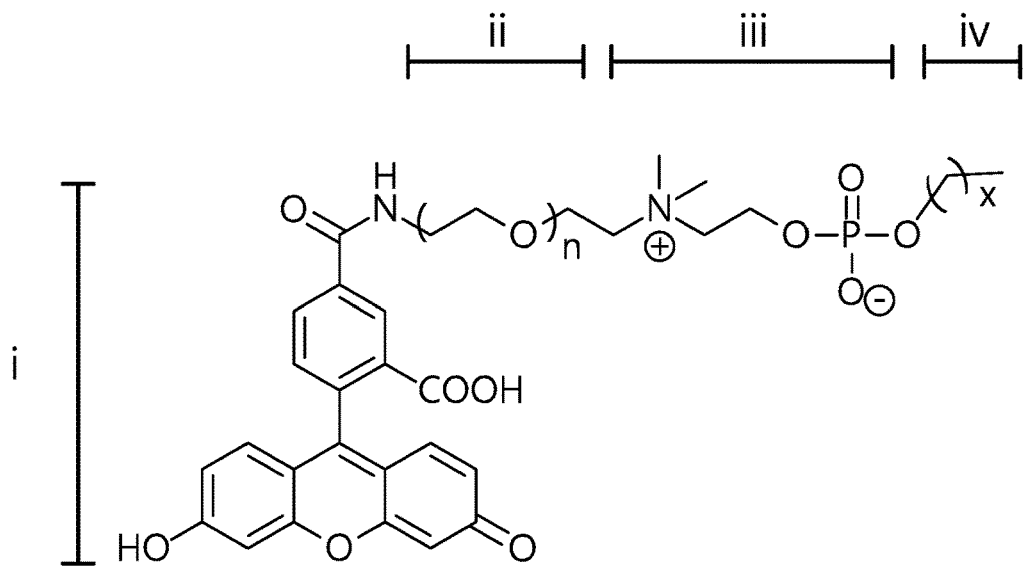
FIGS. 1A and 1B shows the initial phospholipid ether (PLE) CAR T cell tumor targeting or cancer cell targeting (CTCT) agents. As shown in panels A and B are the structure of FL-PLE (1A) and ProFL-PLE (1B). (i) FL (fluorescein), the target for CAR T cells. (ii) Polyetheneglycol (PEG), the spacer used to extend the target an ideal distance from the cell surface. (iii & iv) PLE, iii is the polar head group and iv is the hydrophobic tail for incorporation or tethering into the cell plasma membrane. (v) Masking moiety, to prevent anti-FLCAR T cell recognition. (vi) The cleavage point where ProFL-PLE is unmasked. Unmasking to occur once or just before anti-FLCAR T-cells are in the reactive oxygen species (ROS) rich environment afforded by the tumor. This will in turn create the FL-PLE.

In the description that follows, the terms should be given their plain and ordinary meaning when read in light of the specification. One of skill in the art would understand the terms as used in view of the whole specification.

As used herein, "a" or "an" may mean one or more than one.

As used herein, the term "about" indicates that a value includes the inherent variation of error for the method being employed to determine a value, or the variation that exists among experiments.

"Chimeric antigen receptor" or "CAR" or "Chimeric T cell receptor have their plain and ordinary meaning when read in light of the specification, and may include but is not limited to, for example, a synthetically designed receptor comprising a ligand binding domain of an antibody or other protein sequence that binds to a molecule associated with the disease or disorder and is linked via a spacer domain to one or more intracellular signaling domains of a T cell or other receptors, such as a costimulatory domain. Chimeric receptor can also be referred to as artificial T cell receptors, chimeric T cell receptors, chimeric immunoreceptors, and chimeric antigen receptors (CARs). These CARs are engineered receptors that can graft an arbitrary specificity onto an immune receptor cell. The term chimeric antigen receptors or "CARs" are also considered by some investigators to include the antibody or antibody fragment, the spacer, signaling domain, and transmembrane region. However, due to the surprising effects of modifying the different components or domains of the CAR described herein, such as the epitope binding region (for example, antibody fragment, scFv, or portion thereof), spacer, transmembrane domain, and/or signaling domain), the components of the CAR are frequently distinguished throughout this disclosure in terms of independent elements. In some alternatives, the spacer for the chimeric antigen receptor is selected (e.g., for a particular length of amino acids in the spacer) to achieve desired binding characteristics for the CAR. CARs having varying lengths of spacers, e.g., presented on cells are then screened for the ability to bind or interact with a target moiety to which the CAR is directed. Exemplary target moieties include a hapten, poly(his) tag, Strep-tag, FLAG-tag, V5-tag, Myc-tag, HA-tag, NE-tag, biotin, digoxigenin, dinitrophenol, green fluorescent protein (GFP), yellow fluorescent protein, orange fluorescent protein, red fluorescent protein, far red fluorescent protein, or fluorescein (e.g., Fluorescein isothiocyanate (FITC)). The target moieties to which the CARs bind or interact can be presented on a substrate, such as a membrane, bead, or support (e.g., a well) or a binding agent, such as a lipid (e.g., PLE), hapten, ligand, or antibody, or binding fragment thereof, preferably a binding agent that has specificity for an antigen present on a cancer cell or pathogen such as, a virus or bacteria. By one approach, the substrate or binding agent comprising the desired target moiety is contacted with a plurality of cells comprising a CAR or TCR specific for said target moiety and the level or amount of binding of the cells comprising the CAR or TCR to the target moiety present on the substrate or binding agent is determined. Such an evaluation of binding may include staining for cells bound to target moieties or evaluation of fluorescence or loss of fluorescence. Again, modifications to the CAR structure, such as varying spacer lengths, can be evaluated in this manner. In some approaches, a target cell is also provided such that the method comprises contacting a cell, such as a T cell, which comprises a CAR or TCR that is specific for a target moiety, such as a hapten, poly(his) tag, Strep-tag, FLAG-tag, V5-tag, Myc-tag, HA-tag, NE-tag, biotin, digoxigenin, dinitrophenol, green fluorescent protein (GFP), yellow fluorescent protein, orange fluorescent protein, red fluorescent protein, far red fluorescent protein, or fluorescein (e.g., Fluorescein isothiocyanate (FITC)), with a binding agent such as a hapten, ligand, or antibody or antibody fragment thereof joined to said target moiety in the presence of a target cell, such as a cancer cell or bacterial cell, or a target virus and evaluating the binding of the cell comprising the CAR or TCR to the binding agent and/or evaluating the binding of the cell comprising the CAR or TCR to the target cell or target virus. The variation of the different elements of the CAR can, for example, lead to stronger binding affinity for a specific epitope or antigen. In some alternatives, the antibody or binding fragment thereof, which is conjugated to the target moiety, used in these evaluations comprises abagovomab, abituzumab, adecatumumab, afutuzumab, alacizumab pegol, alemtuzumab, altumomab pentetate, amatuximab, anatumomab mefanetox, anetumab ravtansine, apolizumab, arcitumomab, ascrinvacumab, aselizumab, atezolizumab, atlizumab, avelumab, bapineuzumab, bavituximab, bectumomab, belimumab, besilesomab, bevacizumab, bivatuzumab mertansine, blinatumomab, blontuvetmab, brentuximab, brontictuzumab, cantuzumab mertansine, cantuzumab ravansine, capromab pendetide, carlumab, carotuximab, catumaxomab, cBR96-doxorubicin immunoconjugate, cedelizumab, certolizumab pegol, cetuximab, cidfusituzumab, cidtuzumab, citatuzumab bogatox, cixutumumab, clivatuzumab tetraxetan, codrituzumab, coltuximab ravtansine, conatumumab, dacetuzumab, daclizumab, dalotuzumab, daratumumab, demcizumab, denintuzumab mafodotin, denosumab, depatuxizumab mafodotin, derlotuximab biotin, detumomab, dinutuximab, drozitumab, duligotumab, durvalumab, dusigitumab, duvortuxizumab, ecromeximab, eculizumab, edrecolomab, efalizumab, elgemtumab, elotuzumab, emactuzumab, emibetuzumab, enavatuzumab, enfortumab vedotin, enoblituzumab, enoticumab, ensituximab, epratuzumab, erlizumab, ertumaxomab, etaracizumab, farletuzumab, FBTA05, femzumab, ficlatuzumab, figitumumab, flanvotumab, fontolizumab, futuximab, galiximab, ganitumab, gemtuzumab ozogamicin, girentuximab, glembatumumab vedotin, ibritumomab, icrucumab, igovomab, IMAB362, imalumab, imgatuzumab, indatuximab ravtansine, indusatumab vedotin, intetumumab, inotuzumab ozogamicin, intetumumab, ipilimumab, iratumumab, isatuzimab, labetuzumab, lambrolizumab, lexatumumab, lifastuzumab vedotin, lilotomab satetraxetan, lintuzumab, lorvotuzumab mertansine, lucatumumab, lumiliximab, lumretuzumab, mapatumumab, margetuximab, matuzumab, mepolizumab, milatuzumab, minretumomab, mirvetuximab soravtansine, mitumomab, mogamulizumab, moxetumomab pasudotox, nacolomab tafenatox, naptumomab estafenatox, narnatumab, natalizumab, necitumumab, nesvacumab, nimotuzumab, nivolumab, nofetumomab merpentan, obinutuzumab, ocaratuzumab, ocrelizumab, ofatumumab, olaratumab, omalizumab, onartuzumab, ontuxizumab, oportuzumab monatox, oregovomab, otlertuzumab, panitumumab, pankomab, parsatuzumab, pascolizumab, pasotuxizumab, patritumab, pecfusituzumab, pectuzumab, pembrolizumab, pemtumomab, pertuzumab, pexelizumab, pidilizumab, pinatuzumab vedotin, pintumomab, polatuzumab vedotin, pritumumab, racotumomab, radretumab, ramucirumab, ranibizumab, reslizumab, rilotumumab, rituximab, robatumumab, rovelizumab, ruplizumab, sacituzumab govitecan, samalizumab, satumomab pendetide, seribantumab, sibrotuzumab, SGN-CD19A, SGN-CD33A, simtuzumab, siplizumab, siltuximab, sofituzumab vedotin, solitomab, sontuzumab, tabalumab, tacatuzumab tetraxetan, tadocizumab, talizumab, tamtuvetmab, taplitumomab paptox, tarextumab, tenatumomab, teprotumumab, TGN1412, ticilimumab (tremelimumab), tigatuzumab, TNX-650, tocilizumab, toralizumab, tositumomab, tovetumab, trastuzumab, TRB S07, tremelimumab, tucotuzumab celmoleukin, tucusituzumab, ublituximab, ulocuplumab, urelumab, urtoxazumab, ustekinumab, vandortuzumab vedotin, vantictumab, vanucizumab, veltuzumab, vesencumab, visilizumab, volociximab, vorsetuzumab mafodotin, votumumab, zalutumamab, zanolimumab, zatuximab, cosfroviximab, diridavumab, exbivirumab, felvizumab, foravirumab, larcaviximab, libivirumab, motavizumab, motovizumab, nolovizumab, numavizumab, palivizumab, porgaviximab, PRO 140, rafivirumab, ralivizumab, regavirumab, reslivizumab, resyvizumab, sevirumab, suvizumab, tuvirumab, umavizumab, edobacomab, nebacumab, pagibaximab, panobacumab, raxibacumab, tefibazumab, actoxumab, bezlotoxumab, efungumab, obiltoxaximab, suvratoxumab, or urtoxazumab, or a derivative, analogue, or binding fragment thereof.

"Co-stimulatory domain," has its plain and ordinary meaning when read in light of the specification, and may include but is not limited to, for example, a signaling moiety that provides to T cells a signal which, in addition to the primary signal provided by for instance the CD3 zeta chain of the TCR/CD3 complex, mediates a T cell response, including, but not limited to, activation, proliferation, differentiation, cytokine secretion, and the like. A co-stimulatory domain can include all or a portion of, but is not limited to, CD27, CD28, 4-1BB, OX40, CD30, CD40, ICOS, lymphocyte function-associated antigen-1 (LFA-1), CD2, CD7, LIGHT, NKG2C, B7-H3, or a ligand that specifically binds with CD83. In some alternatives, the co-stimulatory domain is an intracellular signaling domain that interacts with other intracellular mediators to mediate a cell response including activation, proliferation, differentiation and cytokine secretion, and the like. In some alternatives, herein the co-stimulatory domain comprises 41bb and CD3zeta. In some alternatives, a T cell is provided, wherein the T cell comprises a CAR specific for the targeting moiety on the composition. In some alternatives, the T cell further comprise an 806 CAR (anti-EGFR(806)(41BB-CD3zeta CAR).

In some alternatives described herein, the CAR is specific for a lipid or peptide that targets a tumor or cancer cell, wherein the lipid or peptide comprises a target moiety and the CAR can specifically bind to said lipid through an interaction with said target moiety. In some alternatives, the lipid is a phospholipid ether. In some alternatives described herein, the CAR is specific for a phospholipid ether, wherein the phospholipid ether comprises a target moiety and the CAR specifically binds to said phospholipid ether through an interaction with said target moiety. In some alternatives herein, the CAR comprises a co-stimulatory domain. In some alternatives the co-stimulatory domain is CD27, CD28, 4-1BB, OX40, CD30, CD40, ICOS, lymphocyte function-associated antigen-1 (LFA-1), CD2, CD7, LIGHT, NKG2C, B7-H3, or a ligand that specifically binds with CD83, or a portion thereof.

In some alternatives, the CAR is specific for a target moiety affixed to an antibody or binding fragment thereof, wherein the CAR specifically binds to said antibody or binding fragment thereof through an interaction with said target moiety. Exemplary target moieties, which can be conjugated to said antibody or binding fragment thereof include a hapten, poly(his) tag, Strep-tag, FLAG-tag, V5-tag, Myc-tag, HA-tag, NE-tag, biotin, digoxigenin, dinitrophenol, green fluorescent protein (GFP), yellow fluorescent protein, orange fluorescent protein, red fluorescent protein, far red fluorescent protein, or fluorescein (e.g., Fluorescein isothiocyanate (FITC)). In some alternatives, the antibody or binding fragment thereof is specific for an antigen or ligand present on a cancer cell or a pathogen (e.g., viral or bacterial pathogen). In some alternatives, the antibody or binding fragment thereof is specific for an antigen or ligand present on a tumor cell, a virus, preferably a chronic virus (e.g., a hepatitis virus, such as HBV or HCV, or HIV), or a bacterial cell. In some alternatives herein, the CAR comprises a co-stimulatory domain. In some alternatives the co-stimulatory domain is CD27, CD28, 4-1BB, OX40, CD30, CD40, ICOS, lymphocyte function-associated antigen-1 (LFA-1), CD2, CD7, LIGHT, NKG2C, B7-H3, or a ligand that specifically binds with CD83, or a portion thereof. In some alternatives, the antibody or binding fragment thereof, which is joined to said target moiety, comprises abagovomab, abituzumab, adecatumumab, afutuzumab, alacizumab pegol, alemtuzumab, altumomab pentetate, amatuximab, anatumomab mefanetox, anetumab ravtansine, apolizumab, arcitumomab, ascrinvacumab, aselizumab, atezolizumab, atlizumab, avelumab, bapineuzumab, bavituximab, bectumomab, belimumab, besilesomab, bevacizumab, bivatuzumab mertansine, blinatumomab, blontuvetmab, brentuximab, brontictuzumab, cantuzumab mertansine, cantuzumab ravansine, capromab pendetide, carlumab, carotuximab, catumaxomab, cBR96-doxorubicin immunoconjugate, cedelizumab, certolizumab pegol, cetuximab, cidfusituzumab, cidtuzumab, citatuzumab bogatox, cixutumumab, clivatuzumab tetraxetan, codrituzumab, coltuximab ravtansine, conatumumab, dacetuzumab, daclizumab, dalotuzumab, daratumumab, demcizumab, denintuzumab mafodotin, denosumab, depatuxizumab mafodotin, derlotuximab biotin, detumomab, dinutuximab, drozitumab, duligotumab, durvalumab, dusigitumab, duvortuxizumab, ecromeximab, eculizumab, edrecolomab, efalizumab, elgemtumab, elotuzumab, emactuzumab, emibetuzumab, enavatuzumab, enfortumab vedotin, enoblituzumab, enoticumab, ensituximab, epratuzumab, erlizumab, ertumaxomab, etaracizumab, farletuzumab, FBTA05, femzumab, ficlatuzumab, figitumumab, flanvotumab, fontolizumab, futuximab, galiximab, ganitumab, gemtuzumab ozogamicin, girentuximab, glembatumumab vedotin, ibritumomab, icrucumab, igovomab, IMAB362, imalumab, imgatuzumab, indatuximab ravtansine, indusatumab vedotin, intetumumab, inotuzumab ozogamicin, intetumumab, ipilimumab, iratumumab, isatuximab, labetuzumab, lambrolizumab, lexatumumab, lifastuzumab vedotin, lilotomab satetraxetan, lintuzumab, lorvotuzumab mertansine, lucatumumab, lumiliximab, lumretuzumab, mapatumumab, margetuximab, matuzumab, mepolizumab, milatuzumab, minretumomab, mirvetuximab soravtansine, mitumomab, mogamulizumab, moxetumomab pasudotox, nacolomab tafenatox, naptumomab estafenatox, narnatumab, natalizumab, necitumumab, nesvacumab, nimotuzumab, nivolumab, nofetumomab merpentan, obinutuzumab, ocaratuzumab, ocrelizumab, ofatumumab, olaratumab, omalizumab, onartuzumab, ontuxizumab, oportuzumab monatox, oregovomab, otlertuzumab, panitumumab, pankomab, parsatuzumab, pascolizumab, pasotuxizumab, patritumab, pecfusituzumab, pectuzumab, pembrolizumab, pemtumomab, pertuzumab, pexelizumab, pidilizumab, pinatuzumab vedotin, pintumomab, polatuzumab vedotin, pritumumab, racotumomab, radretumab, ramucirumab, ranibizumab, reslizumab, rilotumumab, rituximab, robatumumab, rovelizumab, ruplizumab, sacituzumab govitecan, samalizumab, satumomab pendetide, seribantumab, sibrotuzumab, SGN-CD19A, SGN-CD33A, simtuzumab, siplizumab, siltuximab, sofituzumab vedotin, solitomab, sontuzumab, tabalumab, tacatuzumab tetraxetan, tadocizumab, talizumab, tamtuvetmab, taplitumomab paptox, tarextumab, tenatumomab, teprotumumab, TGN1412, ticilimumab (tremelimumab), tigatuzumab, TNX-650, tocilizumab, toralizumab, tositumomab, tovetumab, trastuzumab, TRB S07, tremelimumab, tucotuzumab celmoleukin, tucusituzumab, ublituximab, ulocuplumab, urelumab, urtoxazumab, ustekinumab, vandortuzumab vedotin, vantictumab, vanucizumab, veltuzumab, vesencumab, visilizumab, volociximab, vorsetuzumab mafodotin, votumumab, zalutumamab, zanolimumab, zatuximab, cosfroviximab, diridavumab, exbivirumab, felvizumab, foravirumab, larcaviximab, libivirumab, motavizumab, motovizumab, nolovizumab, numavizumab, palivizumab, porgaviximab, PRO 140, rafivirumab, ralivizumab, regavirumab, reslivizumab, resyvizumab, sevirumab, suvizumab, tuvirumab, umavizumab, edobacomab, nebacumab, pagibaximab, panobacumab, raxibacumab, tefibazumab, actoxumab, bezlotoxumab, efungumab, obiltoxaximab, suvratoxumab, or urtoxazumab, or a derivative, analogue, or binding fragment thereof.

In some alternatives, the chimeric receptor nucleic acid comprises a polynucleotide coding for a transmembrane domain. The transmembrane domain provides for anchoring of the chimeric receptor in the membrane.

In some alternatives, a complex is provided, wherein the complex comprises a chimeric antigen receptor (CAR) or a T cell receptor (TCR) joined to a lipid wherein the lipid comprises a target moiety and the CAR is joined to said lipid through an interaction with said target moiety.

In some alternatives, a complex is provided, wherein the complex comprises a chimeric antigen receptor (CAR) or a T cell receptor (TCR) joined to an antibody or binding fragment thereof, wherein the antibody or binding fragment thereof comprises a target moiety (e.g., a hapten, poly(his) tag, Strep-tag, FLAG-tag, V5-tag, Myc-tag, HA-tag, NE-tag, biotin, digoxigenin, dinitrophenol, green fluorescent protein (GFP), yellow fluorescent protein, orange fluorescent protein, red fluorescent protein, far red fluorescent protein, or fluorescein (e.g., Fluorescein isothiocyanate (FITC)) and the CAR is joined to said antibody or binding fragment thereof through an interaction with said target moiety. In some alternatives, the antibody or binding fragment thereof is further joined to an antigen or ligand present on a cancer cell or a pathogen (e.g., viral or bacterial pathogen). In some alternatives, the antibody or binding fragment thereof is joined to an antigen or ligand present on a tumor cell, a virus, preferably a chronic virus (e.g., a hepatitis virus, such as HBV or HCV, or HIV), or a bacterial cell. In some alternatives, the CAR comprises a co-stimulatory domain. In some alternatives the co-stimulatory domain is CD27, CD28, 4-1BB, OX40, CD30, CD40, ICOS, lymphocyte function-associated antigen-1 (LFA-1), CD2, CD7, LIGHT, NKG2C, B7-H3, or a ligand that specifically binds with CD83, or a portion thereof. In some alternatives, the target moiety is present on an antibody or binding fragment thereof, which are specific for an antigen on a cancer cell or pathogen (e.g., a virus or bacterial cell), and said target moiety is bound by a chimeric antigen receptor present on the surface of a cell (e.g., a T cell) such that the cell having the chimeric antigen receptor is redirected to the cancer cell or pathogen.

A "T cell receptor" or "TCR" has their plain and ordinary meaning when read in light of the specification, and may include but is not limited to, for example, a molecule that is found on the surface of T lymphocytes or T cells that is responsible for the recognition of fragments of antigen bound to a major histocompatibility complex molecule.

"Target moiety" has its plain and ordinary meaning when read in light of the specification, and may include but is not limited to, for example, a specific group or site on a molecule or chemical that is a binding target for another chemical or protein of interest. In some alternatives described herein, the target moiety is a hapten, poly(his) tag, Strep-tag, FLAG-tag, V5-tag, Myc-tag, HA-tag, NE-tag, biotin, digoxigenin, dinitrophenol, green fluorescent protein (GFP), yellow fluorescent protein, orange fluorescent protein, red fluorescent protein, far red fluorescent protein, or fluorescein (e.g., Fluorescein isothiocyanate (FITC)). In some alternatives, a complex is provided, wherein the complex comprises a chimeric antigen receptor (CAR) or a T cell receptor (TCR) joined to a lipid wherein the lipid comprises a target moiety and the CAR is joined to said lipid through an interaction with said target moiety. In further alternatives, a complex is provided, wherein the complex comprises a chimeric antigen receptor (CAR) or a T cell receptor (TCR) joined to an antibody or binding fragment thereof, wherein the antibody or binding fragment thereof comprises a target moiety (e.g., a hapten, poly(his) tag, Strep-tag, FLAG-tag, V5-tag, Myc-tag, HA-tag, NE-tag, biotin, digoxigenin, dinitrophenol, green fluorescent protein (GFP), yellow fluorescent protein, orange fluorescent protein, red fluorescent protein, far red fluorescent protein, or fluorescein (e.g., Fluorescein isothiocyanate (FITC)) and the CAR is joined to said antibody or binding fragment thereof through an interaction with said target moiety. In some alternatives, the antibody or binding fragment thereof is further joined to an antigen or ligand present on a cancer cell or a pathogen (e.g., viral or bacterial pathogen). In some alternatives, the antibody or binding fragment thereof is joined to an antigen or ligand present on a tumor cell, a virus, preferably a chronic virus (e.g., a hepatitis virus, such as HBV or HCV, or HIV), or a bacterial cell. In some alternatives, the CAR comprises a co-stimulatory domain. In some alternatives the co-stimulatory domain is CD27, CD28, 4-1BB, OX40, CD30, CD40, ICOS, lymphocyte function-associated antigen-1 (LFA-1), CD2, CD7, LIGHT, NKG2C, B7-H3, or a ligand that specifically binds with CD83, or a portion thereof. In some alternatives, the target moiety is present on an antibody or binding fragment thereof, which are specific for an antigen on a cancer cell or pathogen (e.g., a virus or bacterial cell), and said target moiety is bound by a chimeric antigen receptor present on the surface of a cell (e.g., a T cell) such that the cell having the chimeric antigen receptor is redirected to the cancer cell or pathogen.

"Biotin" has its plain and ordinary meaning when read in light of the specification, and may include but is not limited to, for example, a water-soluble B-vitamin. In the alternatives herein, biotin is a target moiety on a lipid that is recognized and bound by a chimeric antigen receptor. In some alternatives, the lipid is a phospholipid ether.

"Digoxigenin" or "DIG" as described herein, has their plain and ordinary meaning when read in light of the specification, and may include but is not limited to, for example, a steroid found exclusively in the flowers and leaves of plants. In the alternatives herein, DIG is a target moiety on a lipid that is recognized and bound by a chimeric antigen receptor. In some alternatives, the lipid is a phospholipid ether.

"2,4-Dinitrophenol," "2,4-DNP," "Dinitrophenol" or "DNP" has their plain and ordinary meaning when read in light of the specification, and may include but is not limited to, for example, an organic compound with the formula $HOC_6H_3(NO_2)_2$. In the alternatives herein, DNP is a target moiety on a lipid that is recognized and bound by a chimeric antigen receptor. In some alternatives, the lipid is a phospholipid ether.

"Fluorescein" and fluorescein derivitives has their plain and ordinary meaning when read in light of the specification, and may include but is not limited to, for example, a synthetic organic compound that is soluble in water and alcohol. It is widely used as a fluorescent tracer for many applications. In some alternatives herein, fluorescein is a target moiety on a lipid that is recognized and bound by a chimeric antigen receptor. In some alternatives, the lipid is a phospholipid ether. In some alternatives, fluorescein is a target moiety on an antibody or binding fragment thereof, which are specific for an antigen on a cancer cell or pathogen (e.g., a virus or bacterial cell), and said target moiety is bound by a chimeric antigen receptor present on the surface of a cell (e.g., a T cell) such that the cell having the chimeric antigen receptor is redirected to the cancer cell or pathogen.

"Lipid" has its plain and ordinary meaning when read in light of the specification, and may include but is not limited to, for example, a class of organic compounds that comprise carbon chains, fatty acids or a fatty acid derivative that is typically insoluble in water but can integrate into or mix with hydrophobic or organic solvents. Without being limiting, lipids can include fats, waxes, fat soluble vitamins, monoglycerides, diglycerides, triglycerides, sphingolipids, cerebrosides, ceramides, and phospholipids. As described herein are amphiphilic lipids that can have a polar head group and a hydrophobic moiety or hydrophobic group.

"Hydrophobic group" or hydrophobic moiety has their plain and ordinary meaning when read in light of the specification, and may include but is not limited to, for example, a molecule or a part of a molecule that is repelled from a mass of water and tends to be non-polar. This can include alkanes, oils and fats. Without being limiting, lipids can be glycerolipids, glycerophospholipids, sphingolipids, sterol lipids, prenol lipids, saccharolipids and polyketides. In the alternatives, herein, a complex is provided, wherein the complex comprises a lipid. In some alternatives, the lipid comprises a polar head group and a hydrophobic moiety. In some alternatives, the hydrophobic moiety is a hydrophobic carbon tail. In some alternatives the hydrophobic carbon tail is saturated or unsaturated. In some alternatives, the hydrophobic carbon tail comprises 10, 11, 12, 13, 14, 15, 16, 17, 18, 19, 20, 21, 22, 23, 24 or 25 carbons or any number of carbons in between a range set forth in any aforementioned value. In some alternatives, the hydrophobic moiety is a steroid or a cholesterol. In some alternatives, the lipid comprises a glycerolipid, glycerophospholipid, sphingolipid, sterol lipid, prenol lipid, saccharolipid or polyketide. In some alternatives, the lipid is a phospholipid ether. In some alternatives, the lipid contains branched alkyl tails.

In some alternatives, the lipid can be a sphingolipid. The sphingolipid can contain a backbone of sphingoid bases, such as a set of aliphatic amino alcohols that includes sphingosine. A sphingolipid with an R group consisting of a hydrogen atom only is a ceramide. Other common R groups include phosphocholine, yielding a sphingomyelin, and various sugar monomers or dimers, yielding cerebrosides and globosides, respectively. Cerebrosides and globosides are collectively known as glycosphingolipids. In some alternatives, the lipid is a glycosphingolipid.

As provided herein, the lipid comprises a polar head group and a hydrophobic group. In some alternatives, the hydrophobic group comprises a fatty acid such as an aliphatic chain. In some alternatives, the fatty acid is saturated or unsaturated. In some alternatives, the hydrophobic group comprises an alkyl, alkenyl or alkynyl group. In some alternatives, the hydrophobic group comprises a terpenoid lipid such as a steroid or cholesterol. In some alternatives, the hydrophobic group comprises an ether linkage, wherein the ether linkage is between the polar head group and the aliphatic chain. In some alternatives, the lipid is a phospholipid ether. In some alternatives, the polar head comprises a choline, a phosphatidylcholine, sphingomyelin, phosphoethanolamine group, an oligosaccharide residue, a sugar residue, phosphatidyl serine or phosphatidyl inositol. In some alternatives, the sugar is a glycerol.

In some alternatives, the lipid is a single chain alkylphospholipid.

In some alternatives, the lipids comprise a structure of synthetic alkylphospholipids such as edelfosine, perifosine or erucylphosphocholine. In some alternatives, the lipid is a lysophosphatidylcholine, edelfosine, erucylphosphocholine, D-21805 or perifosine. Such lipids are described for example, in van der Lui et al ("A new class of anticancer alkylphospholipids uses lipid rafts as membrane gateways to induce apoptosis in lymphoma cells" Mol Cancer Ther 2007; 6(8), 2007; incorporated by reference in its entirety). In some alternatives of the lipids described herein, a choline within the polar head group can be substituted with a piperidine moiety. In some alternatives, the lipid is an anticancer alkylphospholipid. Anticancer phospholipids are described by vander Lui et al. ("A new class of anticancer alkylphospholipids uses lipid rafts as membrane gateways to induce apoptosis in lymphoma cells" Mol Cancer Ther 2007; 6(8), 2007; incorporated by reference in its entirety).

In some alternatives, the lipids provided herein are synthetic and structurally related antitumor agents that interact with a cell membrane. These types of synthetic lipids are alkylphospholipids and are described by e.g., van Blitterswijk et al. ("Anticancer mechanisms and clinical application of alkylphopholipids" Biochimica et Biophysica Acta 1831 (2013)663-674; incorporated by reference in its entirety herein). Without being limiting, the synthetic alkylphospholipids can include edelfosine, miltefosine, perifosine, erucylphosphocholine and Erufosine. In some alternatives, the lipid is edelfosine, miltefosine, perifosine, erucylphosphocholine or Erufosine. In some alternatives, the lipid is a stable analog of lysophosphatidylcholine. In some alternatives, the lipid is a thio-ether variant of edelfosine, or 1-hexadecylthio-2-methoxymethyl-rac-glycero-3-phosphocholine. In some alternatives, the lipid is LysoPC, edelfosine, Ilmofosine, Miltefosine, Perifosine, Erucylphophocholine, or Erufosine.

"Polar-head group" has its plain and ordinary meaning when read in light of the specification, and may include but is not limited to, for example, the hydrophilic group of a lipid, such as a phospholipid. "Phospholipids" has its plain and ordinary meaning when read in light of the specification, and may include but is not limited to, for example, a specific class of lipids that can form lipid bilayers due to their amphiphilic characteristic. The phospholipid molecule comprises at least one hydrophobic fatty acid "tail" and a hydrophilic "head" or "polar-head group." In the alternative herein, the phospholipid or phospholipid ether comprises a polar-head group. In some alternatives, the polar-head group comprises phosphocholine, a piperidine moiety or a trimethylarseno-ethyl-phosphate moiety. In some alternatives, the lipid comprises a target moiety and the CAR is joined to said lipid through an interaction with said target moiety. In some alternatives, the lipid comprises a polar-head group (e.g., comprising an aromatic ring) and a carbon alkyl chain. In some alternatives, the carbon alkyl chain comprises at least 8, 9, 10, 11, 12, 13, 14, 15, 16, 17, 18, 19, 20, 21 or 22 carbons or any number that is within a range defined by any two aforementioned values. In some alternatives, the carbon alkyl chain comprises 8-22 carbons, such as 8-12, 12-14, 14-16, or 16-22 carbons. In some alternatives herein, a complex is provided, wherein the complex comprises a lipid. In some alternatives, the lipid comprises a polar head group. In some alternatives, the lipid is a phospholipid ether. In some alternatives, the phospholipid ether comprises a target moiety and the CAR is joined to said phospholipid ether through an interaction with said target moiety. In some alternatives, the phospholipid ether comprises a polar-head group and a carbon alkyl chain. In some alternatives the polar head group comprises a choline, a phosphatidylcholine, sphingomyelin, phosphoethanolamine group, an oligosaccharide residue, a sugar residue, phosphatidyl serine or phosphatidyl inositol. In some alternatives, the polar head group comprises phosphocholine, a piperidine moiety or a trimethylarseno-ethyl-phosphate moiety. In some alternatives, the lipid is a phospholipid ether. In some alternatives, the sugar is a glycerol. In some alternatives, the polar head group comprises a sugar group. In some alternatives, the lipid comprises a mannose-containing head group. In some alternatives, the polar head group comprises sphingosine. In some alternatives, the polar head group comprises a glucose. In some alternatives, the polar head group comprises a di-, tri- or tetra-saccharide. In some alternatives, the lipid is a glucosylcerebroside. In some alternatives, the lipid is a lactosylceramide. In some alternatives, the lipid is a glycolipid. In some alternatives, the glycolipid comprises sugar units such as n-glucose, n-galactose or N-actyl-n-galactosamine. In some alternatives, the lipid comprises a hydrocarbon ring such as a sterol.

In some alternatives, the polar head group of the lipid comprises glycerol. In some alternatives, the polar head group of the lipid comprises a phosphate group. In some alternatives, the polar head group of the lipid comprises choline. In some alternatives, the lipid is a phosphatidylethanolomine. In some alternatives, the lipid is a phosphatidylinositol. In some alternatives, the lipid comprises a sphingoid base backbone. In some alternatives, the lipid comprises a sterol lipid, such as cholesterol or its derivatives. In some alternatives, the lipid comprises saccharolipids. In some alternatives, the polar head group comprises choline, phosphate and/or glycerol.

In some alternatives, the lipid is a glycolipid. In some alternatives, the lipid comprises a sugar. In some alternatives, the lipid is derived from sphingosine. In some alternatives, the lipid is a glycerol-glycolipid or a sphingoglycolipid.

In some alternatives, the lipid is an ether lipid with branched hydrophobic chains.

"Saturated" has its plain and ordinary meaning when read in light of the specification, and may include but is not limited to, for example, a fatty acid molecule, in which there are no double bonds within the carbon molecules. Unsaturated as described herein indicates that there are one or more double bonds in a fatty acid chain. In some alternatives herein a complex comprising a lipid is provided. In some alternatives, the lipid comprises a fatty acid chain, in which the fatty acid is saturated or unsaturated.

"Alkyl" has its plain and ordinary meaning when read in light of the specification, and may include but is not limited to, for example, an alkyl substituent that has a missing hydrogen.

An "alkenyl" group has its plain and ordinary meaning when read in light of the specification, and may include but is not limited to, for example, an unsaturated hydrocarbon that contains at least one carbon-carbon double bond.

An "alkynyl" group has its plain and ordinary meaning when read in light of the specification, and may include but is not limited to, for example, an unsaturated hydrocarbon containing at least one carbon-carbon triple bond.

"Terpenoid" has its plain and ordinary meaning when read in light of the specification, and may include but is not limited to, for example, a molecule that is derived from five carbon isoprene units. Steroids and sterols can be produced from terpenoid precursors. For example steroids and cholesterol can be biosynthesized by terpenoid precursors.

"Phospholipid ether" has its plain and ordinary meaning when read in light of the specification, and may include but is not limited to, for example, a lipid in which one or more of the carbon atoms on a polar head group are bonded to an alkyl chain via an ether linkage as opposed to the more common ester linkage. In some alternatives, the polar head group is a glycerol.

"Antibody" has its plain and ordinary meaning when read in light of the specification. The term antibody refers to an antibody and in some circumstances refers to a binding fragment of an antibody. A labeled antibody includes an antibody or binding fragment thereof, in some circumstances, joined to a detectable moiety (for example, a target moiety such as, a hapten, poly(his) tag, Strep-tag, FLAG-tag, V5-tag, Myc-tag, HA-tag, NE-tag, biotin, digoxigenin, dinitrophenol, green fluorescent protein (GFP), yellow fluorescent protein, orange fluorescent protein, red fluorescent protein, far red fluorescent protein, or fluorescein (e.g., Fluorescein isothiocyanate (FITC))). The labeled antibody or binding fragment thereof described herein includes an antibody or binding fragment thereof that specifically binds an antigen of a cancer cell or an antigen of a pathogen. In some alternatives, the antibody or binding fragment thereof, which can be joined to a target moiety or provided as an additional therapy in any one or more of the therapies described herein comprises abagovomab, abituzumab, adecatumumab, afutuzumab, alacizumab pegol, alemtuzumab, altumomab pentetate, amatuximab, anatumomab mefanetox, anetumab ravtansine, apolizumab, arcitumomab, ascrinvacumab, aselizumab, atezolizumab, atlizumab, avelumab, bapineuzumab, bavituximab, bectumomab, belimumab, besilesomab, bevacizumab, bivatuzumab mertansine, blinatumomab, blontuvetmab, brentuximab, brontictuzumab, cantuzumab mertansine, cantuzumab ravansine, capromab pendetide, carlumab, carotuximab, catumaxomab, cBR96-doxorubicin immunoconjugate, cedelizumab, certolizumab pegol, cetuximab, cidfusituzumab, cidtuzumab, citatuzumab bogatox, cixutumumab, clivatuzumab tetraxetan, codrituzumab, coltuximab ravtansine, conatumumab, dacetuzumab, daclizumab, dalotuzumab, daratumumab, demcizumab, denintuzumab mafodotin, denosumab, depatuxizumab mafodotin, derlotuximab biotin, detumomab, dinutuximab, drozitumab, duligotumab, durvalumab, dusigitumab, duvortuxizumab, ecromeximab, eculizumab, edrecolomab, efalizumab, elgemtumab, elotuzumab, emactuzumab, emibetuzumab, enavatuzumab, enfortumab vedotin, enoblituzumab, enoticumab, ensituximab, epratuzumab, erlizumab, ertumaxomab, etaracizumab, farletuzumab, FBTA05, femzumab, ficlatuzumab, figitumumab, flanvotumab, fontolizumab, futuximab, galiximab, ganitumab, gemtuzumab ozogamicin, girentuximab, glembatumumab vedotin, ibritumomab, icrucumab, igovomab, IMAB362, imalumab, imgatuzumab, indatuximab ravtansine, indusatumab vedotin, intetumumab, inotuzumab ozogamicin, intetumumab, ipilimumab, iratumumab, isatuzimab, labetuzumab, lambrolizumab, lexatumumab, lifastuzumab vedotin, lilotomab satetraxetan, lintuzumab, lorvotuzumab mertansine, lucatumumab, lumiliximab, lumretuzumab, mapatumumab, margetuximab, matuzumab, mepolizumab, milatuzumab, minretumomab, mirvetuximab soravtansine, mitumomab, mogamulizumab, moxetumomab pasudotox, nacolomab tafenatox, naptumomab estafenatox, narnatumab, natalizumab, necitumumab, nesvacumab, nimotuzumab, nivolumab, nofetumomab merpentan, obinutuzumab, ocaratuzumab, ocrelizumab, ofatumumab, olaratumab, omalizumab, onartuzumab, ontuxizumab, oportuzumab monatox, oregovomab, otlertuzumab, panitumumab, pankomab, parsatuzumab, pascolizumab, pasotuxizumab, patritumab, pecfusituzumab, pectuzumab, pembrolizumab, pemtumomab, pertuzumab, pexelizumab, pidilizumab, pinatuzumab vedotin, pintumomab, polatuzumab vedotin, pritumumab, racotumomab, radretumab, ramucirumab, ranibizumab, reslizumab, rilotumumab, rituximab, robatumumab, rovelizumab, ruplizumab, sacituzumab govitecan, samalizumab, satumomab pendetide, seribantumab, sibrotuzumab, SGN-CD19A, SGN-CD33A, simtuzumab, siplizumab, siltuximab, sofituzumab vedotin, solitomab, sontuzumab, tabalumab, tacatuzumab tetraxetan, tadocizumab, talizumab, tamtuvetmab, taplitumomab paptox, tarextumab, tenatumomab, teprotumumab, TGN1412, ticilimumab (tremelimumab), tigatuzumab, TNX-650, tocilizumab, toralizumab, tositumomab, tovetumab, trastuzumab, TRB S07, tremelimumab, tucotuzumab celmoleukin, tucusituzumab, ublituximab, ulocuplumab, urelumab, urtoxazumab, ustekinumab, vandortuzumab vedotin, vantictumab, vanucizumab, veltuzumab, vesencumab, visilizumab, volociximab, vorsetuzumab mafodotin, votumumab, zalutumamab, zanolimumab, zatuximab, cosfroviximab, diridavumab, exbivirumab, felvizumab, foravirumab, larcaviximab, libivirumab, motavizumab, motovizumab, nolovizumab, numavizumab, palivizumab, porgaviximab, PRO 140, rafivirumab, ralivizumab, regavirumab, reslivizumab, resyvizumab, sevirumab, suvizumab, tuvirumab, umavizumab, edobacomab, nebacumab, pagibaximab, panobacumab, raxibacumab, tefibazumab, actoxumab, bezlotoxumab, efungumab, obiltoxaximab, suvratoxumab, or urtoxazumab, or a derivative, analogue, or binding fragment thereof.

Non-limiting examples of an antibody or binding fragment thereof, which can be conjugated with target moieties, include monoclonal antibodies, bispecific antibodies, Fab, Fab2, Fab3, scFv, Bis-scFv, minibody, triabody, diabody, tetrabody, VhH domain, V-NAR domain, IgNAR, and camel Ig. Additional examples of an antibody are IgG (e.g., IgG1, IgG2, IgG3, or IgG4), IgM, IgE, IgD, and IgA. Non-limiting examples of antibodies include human antibodies, humanized antibodies, or chimeric antibodies. Non-limiting examples of recombinant antibodies include antibodies that specifically bind to NGF.

An antibody or binding fragment thereof that specifically binds an antigen of a cancer cell, which can be conjugated with target moieties, may include, for example, abagovomab, abituzumab, adecatumumab, afutuzumab, alacizumab pegol, alemtuzumab, altumomab pentetate, amatuximab, anatumomab mefanetox, anetumab ravtansine, apolizumab, arcitumomab, ascrinvacumab, aselizumab, atezolizumab, atlizumab, avelumab, bapineuzumab, bavituximab, bectumomab, belimumab, besilesomab, bevacizumab, bivatuzumab mertansine, blinatumomab, blontuvetmab, brentuximab, brontictuzumab, cantuzumab mertansine, cantuzumab ravansine, capromab pendetide, carlumab, carotuximab, catumaxomab, cBR96-doxorubicin immunoconjugate, cedelizumab, certolizumab pegol, cetuximab, cidfusituzumab, cidtuzumab, citatuzumab bogatox, cixutumumab, clivatuzumab tetraxetan, codrituzumab, coltuximab ravtansine, conatumumab, dacetuzumab, daclizumab, dalotuzumab, daratumumab, demcizumab, denintuzumab mafodotin, denosumab, depatuxizumab mafodotin, derlotuximab biotin, detumomab, dinutuximab, drozitumab, duligotumab, durvalumab, dusigitumab, duvortuxizumab, ecromeximab, eculizumab, edrecolomab, efalizumab, elgemtumab, elotuzumab, emactuzumab, emibetuzumab, enavatuzumab, enfortumab vedotin, enoblituzumab, enoticumab, ensituximab, epratuzumab, erlizumab, ertumaxomab, etaracizumab, farletuzumab, FBTA05, femzumab, ficlatuzumab, figitumumab, flanvotumab, fontolizumab, futuximab, galiximab, ganitumab, gemtuzumab ozogamicin, girentuximab, glembatumumab vedotin, ibritumomab, icrucumab, igovomab, IMAB362, imalumab, imgatuzumab, indatuximab ravtansine, indusatumab vedotin, intetumumab, inotuzumab ozogamicin, intetumumab, ipilimumab, iratumumab, isatuzimab, labetuzumab, lambrolizumab, lexatumumab, lifastuzumab vedotin, lilotomab satetraxetan, lintuzumab, lorvotuzumab mertansine, lucatumumab, lumiliximab, lumretuzumab, mapatumumab, margetuximab, matuzumab, mepolizumab, milatuzumab, minretumomab, mirvetuximab soravtansine, mitumomab, mogamulizumab, moxetumomab pasudotox, nacolomab tafenatox, naptumomab estafenatox, narnatumab, natalizumab, necitumumab, nesvacumab, nimotuzumab, nivolumab, nofetumomab merpentan, obinutuzumab, ocaratuzumab, ocrelizumab, ofatumumab, olaratumab, omalizumab, onartuzumab, ontuxizumab, oportuzumab monatox, oregovomab, otlertuzumab, panitumumab, pankomab, parsatuzumab, pascolizumab, pasotuxizumab, patritumab, pecfusituzumab, pectuzumab, pembrolizumab, pemtumomab, pertuzumab, pexelizumab, pidilizumab, pinatuzumab vedotin, pintumomab, polatuzumab vedotin, pritumumab, racotumomab, radretumab, ramucirumab, ranibizumab, reslizumab, rilotumumab, rituximab, robatumumab, rovelizumab, ruplizumab, sacituzumab govitecan, samalizumab, satumomab pendetide, seribantumab, sibrotuzumab, SGN-CD19A, SGN-CD33A, simtuzumab, sipluzimab, siltuximab, sofituzumab vedotin, solitomab, sontuzumab, tabalumab, tacatuzumab tetraxetan, tadocizumab, talizumab, tamtuvetmab, taplitumomab paptox, tarextumab, tenatumomab, teprotumumab, TGN1412, ticilimumab (tremelimumab), tigatuzumab, TNX-650, tocilizumab, toralizumab, tositumomab, tovetumab, trastuzumab, TRB S07, tremelimumab, tucotuzumab celmoleukin, tucusituzumab, ublituximab, ulocuplumab, urelumab, urtoxazumab, ustekinumab, vandortuzumab vedotin, vantictumab, vanucizumab, veltuzumab, vesencumab, visilizumab, volociximab, vorsetuzumab mafodotin, votumumab, zalutumamab, zanolimumab, or zatuximab, or a derivative, analogue, or binding fragment thereof. Such antibodies or binding fragments thereof can be joined to a target moiety (e.g., a hapten, poly(his) tag, Strep-tag, FLAG-tag, V5-tag, Myc-tag, HA-tag, NE-tag, biotin, digoxigenin, dinitrophenol, green fluorescent protein (GFP), yellow fluorescent protein, orange fluorescent protein, red fluorescent protein, far red fluorescent protein, or fluorescein (e.g., Fluorescein isothiocyanate (FITC)) and such conjugated antibodies can be administered to patients in conjunction with (e.g., before, after or simultaneous with) cells (e.g., T cells) having chimeric antigen receptors specific for said target moiety such that the cells having the chimeric antigen receptors are redirected to the cancer cells having the antigen specific for the antibodies or binding fragments thereof.

Any of the cancer specific antibodies described herein may bind an antigen on a cancer cell, for example on a tumor cell. Specific tumor cell antigens to which antibodies can be generated, which can be conjugated with target moieties, may include, for example, angiopoietins, transmembrane receptors, cell adhesion molecules, cluster of differentiation molecules, gangliosides, glycoproteins, growth factors, integrins, interleukins, Notch receptors, syn-notch receptors, syn-notch, transmembrane glycoproteins, tumor necrosis factors, or tyrosine kinases. In some embodiments, a tumor cell antigen may include, for example, 5T4, B7-H3, carbonic anhydrase IX, carcinoembryonic antigen, CA-125, CD-3, CD-19, CD-20, CD-22, CD-30, CD-33, CD-38, CD-40, CD-51, CD-52, CD-56, CD-70, CD-74, CD-79b, CD-138, CD-221, CD-319, CD-326, cell adhesion molecule 5, CTLA-4, cytokeratin polypeptides, death receptor 2, DLL4, EGFL7, EGFR, endosialin, EpCAM, FAP, FR-alpha, fibronectin, frizzled receptors, GD2, GPNMB, HER-1, HER-2, HER-3, IGF-IR, IGLF2, LOXL2, mesothelin, MS4A1, mucin 5AC, MUC1, Nectin-4, neuropilin, N-glycolyl GM3, PSMA, SLAMF7, TAG-72, TRAIL, TYRP1, VEGF, or other cancer expressing antigens. Such antibodies or binding fragments thereof can be joined to a target moiety (e.g., a hapten, poly(his) tag, Strep-tag, FLAG-tag, V5-tag, Myc-tag, HA-tag, NE-tag, biotin, digoxigenin, dinitrophenol, green fluorescent protein (GFP), yellow fluorescent protein, orange fluorescent protein, red fluorescent protein, far red fluorescent protein, or fluorescein (e.g., Fluorescein isothiocyanate (FITC)) and such conjugated antibodies can be administered to patients in conjunction with (e.g., before, after or simultaneous with) cells (e.g., T cells) having chimeric antigen receptors specific for said target moiety such that the cells having the chimeric antigen receptors are redirected to the cancer cells having the antigen specific for the antibodies or binding fragments thereof. Administration may be by intravenous administration.

An antibody or binding fragment thereof that specifically binds a pathogen, which can be conjugated with target moieties, may include an antibody or binding fragment thereof that binds a viral antigen on a virus or that binds a bacterial antigen on a bacterial cell. Antibodies that bind a viral antigen may include, for example, cosfroviximab, diridavumab, exbivirumab, felvizumab, foravirumab, larcaviximab, libivirumab, motavizumab, motovizumab, nolovizumab, numavizumab, palivizumab, porgaviximab, PRO 140, rafivirumab, ralivizumab, regavirumab, reslivizumab, resyvizumab, sevirumab, suvizumab, tuvirumab, or umavizumab or a derivative, analogue, or binding fragment thereof. Such antibodies or binding fragments thereof can be joined to a target moiety (e.g., a hapten, poly(his) tag, Strep-tag, FLAG-tag, V5-tag, Myc-tag, HA-tag, NE-tag, biotin, digoxigenin, dinitrophenol, green fluorescent protein (GFP), yellow fluorescent protein, orange fluorescent protein, red fluorescent protein, far red fluorescent protein, or fluorescein (e.g., Fluorescein isothiocyanate (FITC)) and such conjugated antibodies can be administered to patients in conjunction with (e.g., before, after or simultaneous with) cells (e.g., T cells) having chimeric antigen receptors specific for said target moiety such that the cells having the chimeric antigen receptors are redirected to the virus having the antigen specific for the antibodies or binding fragments thereof. Administration may be by intravenous administration.

Antibodies that bind a bacterial antigen, which can be conjugated with target moieties, may include, for example, edobacomab, nebacumab, pagibaximab, panobacumab, raxibacumab, or tefibazumab or a derivative, analogue, or binding fragment thereof. Such antibodies or binding fragments thereof can be joined to a target moiety (e.g., a hapten, poly(his) tag, Strep-tag, FLAG-tag, V5-tag, Myc-tag, HA-tag, NE-tag, biotin, digoxigenin, dinitrophenol, green fluorescent protein (GFP), yellow fluorescent protein, orange fluorescent protein, red fluorescent protein, far red fluorescent protein, or fluorescein (e.g., Fluorescein isothiocyanate (FITC)) and such conjugated antibodies can be administered to patients in conjunction with (e.g., before, after or simultaneous with) cells (e.g., T cells) having chimeric antigen receptors specific for said target moiety such that the cells having the chimeric antigen receptors are redirected to the bacterial cells having the antigen specific for the antibodies or binding fragments thereof. Administration may be by intravenous administration.

Additional pathogenic antibodies, which can be conjugated with target moieties, may include actoxumab, bezlotoxumab, efungumab, obiltoxaximab, suvratoxumab, or urtoxazumab, or a derivative, analogue, or binding fragment thereof. Such antibodies or binding fragments thereof can be joined to a target moiety (e.g., a hapten, poly(his) tag, Strep-tag, FLAG-tag, V5-tag, Myc-tag, HA-tag, NE-tag, biotin, digoxigenin, dinitrophenol, green fluorescent protein (GFP), yellow fluorescent protein, orange fluorescent protein, red fluorescent protein, far red fluorescent protein, or fluorescein (e.g., Fluorescein isothiocyanate (FITC)) and such conjugated antibodies can be administered to patients in conjunction with (e.g., before, after or simultaneous with) cells (e.g., T cells) having chimeric antigen receptors specific for said target moiety such that the cells having the chimeric antigen receptors are redirected to the pathogen having the antigen specific for the antibodies or binding fragments thereof. Administration may be by intravenous administration.

Any of the pathogenic specific antibodies or binding fragments thereof, which can be conjugated with target moieties, may bind specifically to a viral antigen or a bacterial antigen, including, for example by binding to an antigen of a *Bacillus*, a *Candida*, a *Clostridium*, a cytomegalovirus, an Ebola virus, an *Escherichia*, a Gram-negative bacteria, a Gram-positive bacteria, a hepatitis virus, a herpes virus, an HIV, an influenza virus, a *Pseudomonas*, a *Staphylococcus*, or a syncytial virus. Such antibodies or binding fragments thereof can be joined to a target moiety (e.g., a hapten, poly(his) tag, Strep-tag, FLAG-tag, V5-tag, Myc-tag, HA-tag, NE-tag, biotin, digoxigenin, dinitrophenol, green fluorescent protein (GFP), yellow fluorescent protein, orange fluorescent protein, red fluorescent protein, far red fluorescent protein, or fluorescein (e.g., Fluorescein isothiocyanate (FITC)) and such conjugated antibodies can be administered to patients in conjunction with (e.g., before, after or simultaneous with) cells (e.g., T cells) having chimeric antigen receptors specific for said target moiety such that the cells having the chimeric antigen receptors are redirected to the pathogen having the antigen specific for the antibodies or binding fragments thereof. Administration may be by intravenous administration.

Any of the antibodies or binding fragments herein provided herein may be linked to a target moiety as described herein. The target moiety may include, for example, a hapten, poly(his) tag, Strep-tag, FLAG-tag, V5-tag, Myc-tag, HA-tag, NE-tag, biotin, a digoxigenin, a dinotrophenol or a fluorescein. In some embodiments, the target moiety is fluorescein isothiocyanate (FITC). Accordingly, the CAR described herein may bind to the target moiety on the antibody, thereby binding the cancer cell or pathogenic cell through the labeled antibody or fragment thereof.

Several types of "spacers" are contemplated for use with embodiments described herein. The spacer for a chimeric antigen receptor refers to a polypeptide spacer, wherein the length of the spacer is selected to increase or improve the ability of the chimeric antigen receptor to bind its target. The lipid can also comprise a spacer that separates the target moiety from the lipid and is bound to the polar-head group of the lipid. Selected polypeptide spacers for use with chimeric antigen receptors may be screened so as to identify a specific spacer, which promotes a desired binding characteristic to a target moiety (e.g., a desired receptor interaction or a desired avidity with the receptor). Regarding the spacers that are specific for a lipid, the spacer of the lipid can comprise a poly(carboxybetaine), peptide, Polyglycidols, polyethylene, Polyanhydrides, Polyphosphoesters, Polycaprolactone, Poly(ethylene oxide), PEG spacer, PEG spacer, a Hapten spacer, a small peptide or an alkane chain. In some alternatives, the hapten spacer comprises two haptens and is referred to as a hapten (2×) spacer. In some alternatives, the hapten spacer comprises three haptens and is referred to as a hapten (3×) spacer. In some alternatives, the hapten spacer comprises four haptens and is referred to as a hapten (4×) spacer. In some alternatives, the hapten spacer comprises five haptens and is referred to as a hapten (5×) spacer. In some alternatives, the hapten spacer comprises two, three, four or five different haptens. In some alternatives, the lipid comprises a hydrophobic group, such as an alkane chain. In some alternatives, the alkane chain can comprise 2, 3, 4, 5, 6, 7, 8, 9, 10, 11, 12, 13, 14, 15, 16, 17, or 18 carbons, or any number of carbons in between a range defined by any two aforementioned values. In some alternatives, the PEG spacer comprises 1, 2, 3, 4, 5, 6, 7, 8, 9, 10, 11, 12, 13, 14, 15, 16, 17, 18, 19, 20 or 21 PEG molecules, or any amount of PEG molecules that is within a range defined by any two aforementioned values.

"Hapten" has its plain and ordinary meaning when read in light of the specification, and may include but is not limited to, for example, a small molecule binding moiety, which can be substituted for an scFvT or antibody. The three key advantages are that it is designed to (i) not trigger an immune response or a significantly diminished immune response, (ii) bind targets which may or may not be proteins or peptides or may be difficult to create a antibody/scFv binding moiety; and (iii) that it can be better optimized for binding/affinity. In some alternatives, the hapten used comprises Alexa Fluor 405, Cascade Blue, Alexa Fluor 488, BODIPY, Dansyl chloride, Oregon Green, Lucifer yellow, Rhodamine, Tetramethylrhodamine, Nitrotyrosine, digoxigenin, 2,4-Dichlorophenoxyacetic acid, Atrazine (2-Chloro-4-(ethylamino)-6-(isopropylamino)-s-triazine), Nicotine (3-(1-Methyl-2-pyrrolidyl)pyridine, Black Leaf), Morphine (morph, Morphine Sulfate), 2,4-DINITROCHLOROBENZENE (1-Chloro-2,4-dinitrobenzene; DNCB; Dinitrochlorobenzene), 4-chloro-6-(ethylamino)-1,3,5-triazine-2-(6-aminohexanecarboxylic acid), Structurally related s-triazines (Modifications: H/Cl/C6 R1=NH2- R2=—Cl R3=—NH—(CH2)5-COOH; iPr/Cl/nBu R1=(CH3)2-CH—NH— R2=—Cl R3=—NH—(CH2)3-(CH3)), Ametryn (2-Ethylamino-4-isopropylamino-6-methylthio-1,3,5-triazine), Deethylatrazine (DEA) (Structurally related s-triazines), Deisopropylatrazine (DIA) (Structurally related s-triazines), Deethyldeisopropylatrazine (DEDIA) (Structurally related s-triazines), Deethyldeisopropylatrazine (DEDIA) (Structurally related s-triazines), HydroxyAtrazine (HA) (Structurally related s-triazines), DeisopropylHydroxyAtrazine (DIHA) (Structurally related s-triazines), DeethylDeisopropylHydroxyAtrazine (DEDIHA) (Structurally related s-triazines), Simazine (Structurally related s-triazines), Desmetryne (Structurally related s-triazines), Prometryne (Structurally related s-triazines), 2-hydroxyatrazine (atrazine derivative), 2-hydroxypropazine (structurally related s-triazine), 2-hydroxysimazine, N-(4-Amine-6-hydroxy-[1,3,5]triazin-2-yl)-4-aminobutanoic Acid (Modification: R1=NH2 R2=NH(CH2)3COOH R3=OH), SulcoFuron, 5-chloro-2-{4-chloro-2-[3-(3,4-dichlorophenyl)ureido]phenoxy}benzenesulfonic acid, FlucoFuron (1,3-bis(4-chloro-α,α,α-trifluoro-m-tolyl)urea), Agatharesinol, Sequirin C, Sugiresinol, Hydroxysugiresinol, Hinokiresinol, Coniferyl alcohol, Cinnamyl alcohol, p-Coumaric acid, Cinnamic acid, p-Coumaric acid, Cinnamic acid, Hinokinin, Guaiacylglycerol-beta-guaiacyl ether, Morphine-3-glucuronide (M3G), Codeine, Nor-Codeine, 6-Monoacetylmorphine, (+) Methamphetamine, Ceftazidime, Phenobarbital, p-hydroxyPhenobarbital, p-aminophenobarbital, Cyclobarbital, 3'-Ketocyclobarbital, 3'-Hydroxycyclobarbital, Secobarbital, Barbital, Metharbital, Barbituric acid, Thiopental, Thiobarbituric acid, Primidone, Glutethimide, Pentobarbital, Heroin, Diacetylmorphine, Levallorphan, L-11-Allyl-1,2,3,9,10,10a-hexahydro-4H-10,4a-iminoethano-phenanthren-6-ol, Pethidine (Demerol; Dolantin; Meperidine; Ethyl 1-methyl-4-phenylpiperidine-4-carboxylate; Isonipecaine), Methamphetamine, d-Desoxyephedrine; Methedrine; Tolpropamine; Pratalgin; Pragman. Benzoylecgonine, 3-Carboxymethylmorphine, Cocaine, 5-benzimidazolecarboxylic acid, ABA (4-acetyl benzoic acid), Dexamethasone, Flumethasone, 6alpha, 9 alpha-difluoro-11 beta, 17,21-trihydroxy-16 alpha-methylpregna-1,4-diene-3,20-dione, 9 alpha-fluoro-11 beta,17,21-trihydroxy-16 beta-methylpregna-1,4-diene-3,20-dione, 9-alpha-fluroprednisolone, Desoxymethasone, Triamcinolone, 9 alpha-fluoro-11 beta,16 alpha, 17,21-tetrahydroxypregna-1,4-diene-3,20-di-one, Fluocortolone, 6 alpha-fluoro-11 beta,21-dihydroxypregna-1,4-diene-3,20-dione, Cortisol, 11 beta, 17,21-trihydroxypregna-4-ene-3,20-dione, Prednisone, 17,21-dihydroxypregn-4-ene-3,11,20-trione, Methylprednisolone, 11 beta, 17,21-trihydroxy-6 alpha-methylpregna-1,4-diene-3,20-dione, Triamcinolone hexacetonide, 21-(3,3-dimethyl-1-oxobutoxy)-9 alpha-fluoro-11-hydroxy-16,17-[(1-methylethylidene) bis(oxy)]pregna-1,4-diene-3,20-dione, Carbofuran, 2,3-dihydro-2,2-dimethyl-7-benzofuranyl methylcarbamate, BFNP (3-[[(2,3-dihydro-2,2-dimethyl-7-benzofuranyloxy)carbonyl]amino]propanoic acid), Carbofuran derivative, 2,3-dihydro-2,2-dimethyl-7-benzofuranol, Bendiocarb, Carbaryl, Methiocarb, Propoxur, Aldicarb, Methomyl, Benalaxyl, methyl N-(phenylacetyl)-N-(2,6-xylyl)-DL-alaninate, Bn-Ba (4-[2-(N-phenylacetyl-N-2,6-xylylamino)propionamido] butyric acid), Bn-COOH (4-[2-(N-phenylacetyl-N-2,6-xylyl-DL-alanine), Benalaxyl derivative, Furalaxyl, Metalaxyl, Acetochlor, Dimetachlor, Metolachlor, 2-chloro-6'-ethyl-N-(2-methoxy-1-methylethyl)acet-o-toluidine, Diethathyl-ethyl, Benzoylprop-ethyl, Benzoylprop-ethyl, 2,4,5-Trichlorophenoxyacetic acid, 2-chloro-6'-ethyl-N-(2-methoxy-1-methylethyl)acet-o-toluidine, Diethathyl-ethyl, Benzoylprop-ethyl, Propachlor, Propachlor, 2,4,5-Trichlorophenoxyacetic acid, 2,4,5,T; Weedone, 2,4-Dichlorophenoxybutyric acid (2,4-DB), 2,4-DB; Butanoic acid, 4-(2,4-dichlorophenoxy)-; Butoxone; Embutone, MCPA, 2-Methyl-4-chlorophenoxyacetic acid; Metaxon, Dichlorprop (2,4-DP), 1-[(2-chloro)phenylsulfonyl]monoamidosuccinic acid, Chlorsulfuron, chlorbromuron, amidosulfuron, chlortoluron, isoproturon, diuron, Linuron O-Methyl-O-(4-nitrophenyl)-N-(4-carboxybutyl)-phosphoramidothioate Parathion-methyl, O,O-dimethyl O-4-nitrophenyl phosphorothioate; Methaphos; Wolfatox; Dimethylparathion; Metacide, Parathion-ethyl, DIETHYL P-NITROPHENYL THIOPHOSPHATE; O,O-DIETHYL O—(P-NITROPHENYL) PHOSPHOROTHIOATE; Fenitrothion, O,O-dimetyl O-4-nitro-m-tolyl phosphorothioate, Fenthion, O,O-dimethyl O-4-methylthio-m-tolyl phosphorothioate, Bromophos, O-4-bromo-2,5-dichlorophenyl O,O-dimethyl phosphorothioate, chlorpyrifos-methyl, O,O-dimethyl O-3,5,6-trichloro-2-pyridyl phosphorothioate, Oxidized parathion-methyl, Paraoxon, phosphoric acid, O,O-diethyl O-(4-nitrophenyl) ester, Diazinon, O,O-diethyl O-2-isopropyl-6-methylpyrimidin-4-yl phosphorothioate, Azinphos-methyl, pirimiphos-methyl, O-2-diethylamino-6-methylpyrimidin-4-yl O,O-dimethyl phosphorothioate, Methidathion, S-2,3-dihydro-5-methoxy-2-oxo-1,3,4-thiadiazol-3-ylmethyl O,O-dimethyl phosphorodithioate, Dimethylchlorothiophosphate, 4-NITROPHENOL, p-nitrophenol, Phenolic derivative (Modification On benzene ring; R1=OH R2=NO2 R3=H R4-CH2COOH R5=H R6=H); 2-Nitrophenol, o-Nitrophenol, 3-Nitrophenol, m-nitrophenol, 2,4-Dinitrophenol, 3,4-Dinitrophenol, 2,5-Dinitrophenol, 2,4-Dinitro-6-methylphenol, 2,3,6-trinitrophenol, 2-Chlorophenol, 4-Chloro-3-methylphenol, Fenitroxon, 3-Methyl-4-nitrophenol, Nonylphenol, HOM(3-[2-hydroxy-5nitro benzylthio] propionic acid, Phenol, Delor 103, Polychlorinated Biphenyls, Delor 104, Polychlorinated Biphenyls, Delor 105, Polychlorinated Biphenyls, Delor 106, 4,4'-Dichlorobiphenyl, PCB congeners, 2,4,4'-Trichlorobiphenyl, PCB congeners, 2,4'-Bichlorobiphenyl, PCB congeners, 2,2'-Dichlorobiphenyl, PCB congeners, 2,4,5-Trichlorobiphenyl, PCB congeners, 3,3',4,4'-Tetrachlorobiphenyl, PCB congeners, PCB congeners, 2,2',4,4',5,5'-Hexachlorobiphenyl, 2-(5-Carboxypentanoylamino)-4,4'-dichlorobiphenyl, Biphenyl derivative, 4-chlorophenoxyacetic acid, 2-Chlorophenoxyacetic acid, DDT,1,1,1-trichloro-2, 2-bis-(p-chlorophenyl)ethane, DDE, 1,1-dichloro-2, 2-bis(p-chlorophenyl)ethylene, p-Chlorophenol, 4-Chlorophenol, m-Chlorophenol 3,4-Dichlorophenol, 3,5-Dichlorophenol, 2,3,4-Trichlorophenol, 2,3,5-Trichlorophenol, 3-methylindole, 3-methylindole Derivatives, 4-(3-methylindol-5-yloxy)butanoic acid, 4-(3-methylindol-5-yloxy)butanoic acid, 3-methylindole Derivatives, 6-[n-3-methylindol-5-yloxy carbonyl)amino]hexanoic acid, 6-[n-3-methylindol-5-yloxy carbonyl)amino]hexanoic acid, 3-methylindole Derivatives, 2-[4-(3-methylindol-6-yl)but-1-ylthio]acetic acid, 2-[4-(3-methylindol-6-yl)but-1-ylthio]acetic acid, 3-methylindole Derivatives, 4-(3-methylindol-6-yl-4-oxo) butanoic acid, 4-(3-methylindol-6-yl-4-oxo)butanoic acid, 3-methylindole Derivatives, 6-(3-methylindol-7-yloxy) hexanoic acid, 6-(3-methylindol-7-yloxy)hexanoic acid, Indole, Indole-3-Carboxylic acid, Indole Derivative-Indole-3-Acetic acid, Indole-3-Acetic acid, Indole Derivative-Indole-3-Propionic acid, Indole-3-Propionic acid, Indole Derivative-Indole-3-Carbinol, Indole-3-Carbinol, Tryptophan, Tryptamine, 5-Methoxyindole-3-carboxaldehyde, 5-Methoxytryptamine, 5-Methoxyindole, 6-Methoxyindole, 7-Methoxyindole,EB1089(Seocalcitol),EB1089(Seocalcitol) Derivative, (22E,24E)-Des-A,B-24-homo-26,27-dimethyl-8-[(E)-N-(2-carboxyethyl)-carbamoylmethylidene]-cholesta-22,24-dien-25-ol, 1 alpha-25-dihydroxyvitamin D3, 25(OH)D3,25-hydroxyvitamin D3,24R,25(OH)2D3, 24R,25-dihydroxyvitamin D3, Vitamin D2, ergocalciferol, Vitamin D3, cholecalciferol,EB1446,EB1436,EB1445, EB1470, DeethylHydroxyAtrazine (DEHA) (Structurally related s-triazines), Irgarol 1051, Flourescein Isothiocyanate, FITC, Metanephrine, NorMetanephrine, Propazine, Terbutylazine, Terbuthylazine, 6-chloro-N-(1,1-dimethylethyl)-N'-ethyl-1,3,5-triazine-2,4-diamine, (Structurally related s-triazines), Ametryn (2-Ethylamino-4-isopropylamino-6-methylthio-1,3,5-triazine (Modification iPr/SCH3/Et R1=(CH3)2-CH—NH— R2=—SCH3 R3=—NH—CH2-CH3, Irgarol, Cyanazine (Modification R1=Cl R2=NHCH2CH3 R3=NHCCN(CH3)2), OH-Terbutylazine, Terbutylazine-2OH, Hydroxytriazine (EQ-0027), Deisopropylatrazine (Structurally related S-triazine), Desethylterbutylazine (Structurally related S-triazine), Desethyl-deisopropylatrazine (Structurally related S-triazine), Atraton, Terbutryn (Structurally related s-triazines), Atrazine derivative (Modification R1=—NHCH(CH3)2 R2=—S(CH2)2COOH R3=—NHC2H5), Cyanuric chloride, Trifluralin, (Structurally related s-triazines) tBu/C4/SCH3 (Modification R1=—NH—C—(CH3)3 R2=—NH (CH2)3COOH R3=—SCH3), Sulphamethazine, (Structurally related s-triazines) 6-[[[4-Chloro-6-(methylamino)]-1,3,5-triazin-2-yl]amino]hexanoic Acid (Modification Me/Cl/C6 R1=—NHCH3 R2=—Cl R3=—NH(CH2) 5COOH), (Structurally related s-triazines) Procyazine (Modification R1=—Cl R2=—NHcyclopropyl R3=—NHCCN(CH3)2), (Structurally related s-triazines), Prometon (Modification R1=—OCH3 R2=—NHCH(CH3)2 R3=—NHCH(CH3)2); (Structurally related s-triazines) Atrazine Mercapturic Acid (AM) (Modification R1=—SCH2CH(NHAc)COOH R2=—NHCH2CH3 R3=—NHCH(CH3)2), (Structurally related s-triazines), desethyl atrazine mercapturic acid (desethyl AM) (Modification R1=—NAcCys R2=—NH2 R3=—NHCH(CH3)2), (Structurally related s-triazines), deisopropyl atrazine mercapturic acid (deisopropyl AM) (Modification R1=—NAcCys R2=—NHCH2CH3 R3=—NH2), (Structurally related s-triazines), didealkylated atrazine mercapturic acid (didealkylated AM) (Modification R1=—NAcCys R2=—NH2 R3=—NH2), (Structurally related s-triazines), simazine mercapturate (Modification R1=—NAcCys R2=—NHCH2CH3 R3=—NHCH2CH3), (Structurally related s-triazines) (Modification R1=—S(CH2)2COOH R2=—NHCH2CH3 R3=—NHCH2CH3), (Structurally related s-triazines) (Modification R1=—Cl R2=—NHCH (CH3)2 R3=—NH(CH2)2COOH), (Structurally related s-triazines) (Modification R1=—Cl R2=—NHCH2CH3 R3=—NH(CH2)2COOH), (Structurally related s-triazines), atrazine mercapturic acid methyl ester (AM methyl ester) (Modification R1=—NAcCysME R2=—NHCH2CH3 R3=—NHCH(CH3)2), N-acetylcysteine, S-benzyl mercapturate, (Structurally related s-triazines), simetryn (Modification R1=—SCH3 R2=—NHCH2CH3 R3=—NHCH2CH3), Metribuzin, 4-amino-6-tert-butyl-4,5-dihydro-3-methylthio-1,2,4-triazin-5-one, Sulpha Drugs, N4-acetyl-sulphamethazine (Modification N4-acetyl-sulphamethazine), Sulpha Drugs, Sulphathiazole, Sulphathiazole, Sulphamerazine, Sulphamerazine, Sulphaquinoxaline, Sulphaquinoxaline Sulphachlorpyridazine, Sulphachlorpyridazine, Sulphapyridine, Sulphadimethoxine, Sulphadimethoxine, Sulphamethoxazole, Sulphamethoxazole, Sulphisoxazole, Sulphisoxazole, Sulphamethizole, Sulphamethizole, Sulphanilamide, Sulphanilamide, Sulphaguanidine, Sulphaguanidine, Sulphadiazine, Sulphadiazine, Sulphamethoxypyridazine, Sulphamethoxypyridazine, Pentachlorophenoxypropionic acid, Pentachlorophenol, PCP, 2,3,5,6-Tetrachlorophenol, 1,2,4,5 Tetrachlorobenzene, 2,4,6 Trichlorophenol, 2-Methoxy-3,5,6-trichloropyridine, 1,3,5 Trichlorobenzene, 1,3 Dichlorobenzene, 2,4,5-Trichlorophenol, 2,6-Dichlorophenol, 3,5,6-Trichloro-2-pyridinoxyacetic acid, 3,5,6-Trichloro-2-Pyridinol, TCP, 2,4-Dichlorophenol, 2,5-Dichlorophenol, DNC, 4,4'-dinitrocarbanilide, (Structurally related s-triazines), Dichloroatrazine, (Structurally related s-triazines), Dichlorosimazine, 1-((6-chloropyridin-3-yl)methyl)imidazolidin-2-imin, Pyridine Derivative, 6-chloropyridine-3-carboxylic acid, Nicotinic acid, Pyridine Derivative, N-((6-chloropyridin-3-yl)methyl)-N-methylacetamide, (6-chloropyridin-3-yl)-N-methylmethanamine, (6-chloropyridin-3-yl)methanol, Imidacloprid, 1-(6-chloro-3-pyridylmethyl)-N-nitroimidazolidin-2-ylideneamine, Acetamiprid, (E)-N1-[(6-chloro-3-pyridyl)methyl]-N2-cyano-N1-methylacetamidine, Nitenpyram, Deltamethrin, 1(R)-cis-alpha (S)-3-(2,2-dibromoethenyl)-2,2-dimethylcyclopropane carboxylic acid cyano(3-phenoxyphenyl)methyl ester, DON, deoxynivalenol, DON derivative, 15-AcDON (15-acetyldeoxynivalenol), DON derivative, 3-AcDON (3-acetyldeoxynivalenol), DON derivative, 3,15-DiacDON (3,15-diacetyldeoxynivalenol), DON derivative, 3,7,15-TriacDON (3,7,15-Triacetyldeoxynivalenol), NIV (nivalenol), nivalenol, NIV Derivative, 4-AcNIV (fusarenon X), Flutolanil, alpha,alpha, alpha-trifluoro-3'-isopropoxy-o-toluanilide, Mepronil, Mebenil, Benodanil, 24,25(OH)2D3, (24R)-24,25-dihydroxyvitamin D3, 24S,25(OH)2D3, 24S,25-dihydroxyvitamin D3, 25R,26(OH)2D3, 25R,26-dihydroxyvitamin D3, 25S,26(OH)2D3, 25S,26-dihydroxyvitamin D3, 1,24,25 (OH)3D3, 1,24,25-trihydroxyvitamin D3, 1,25-lactone, (23S,25R)-1,25(OH)2 D3 26,23-lactone, 24,25(OH)2-7-DHC, 24,25(OH)2-7-dehydrocholesterol, 25(OH)D3 3S, 25(OH)D3 3-sulfate, 24,25(OH)2D3-Hemiglutarate Derivative, 11 alpha-hemiglutaryloxy-(24R)-24,25-dihydroxyvitamin D3, 24,25(OH)2D3-Hemiglutarate Derivative, (24R)-24,25-dihydroxyvitaminD3-3-hemiglutarate, 24R,25(OH) 2D2, 24S,25(OH)2D2, 25(OH)D2, 1,24(OH)2D3, 2,3,6-Trichlorophenol, Tetrachlorohydroquinone, Pentachloroaniline, Pentachlorobenzene, 2,3-Dinitrotoluene, 4-Dinitrotoluene, 2,4,5-Trichloronitrobenzene, 3-(3-Hydroxy-2,4,6-trichlorophenyl)-propanoic acid, 2,3,4,6-Tetrachlorophenol, 2,4,6-Trichloroanisol, 2,4,6-TCA, Pentabromophenol, PBP, 2,4,6-Tribromophenol, 2,4,6-TBP, 2-Bromo-4-Chlorophenol, 2-B-4-CP 2,4-Dibromophenol, 2,4-DBP, 2,6-Dibromophenol, 2,6-DBP, 4-Bromophenol, 4-BP, Furosemide, Ampicillin, Amoxicillin, 6-amino-penicillanic acid (6-APA), Azlocillin, Bacampicillin, Carbenicillin, Epicillin, Cloxacillin, Dicloxacillin, Metampicillin, Methicillin, Moxalactam, Oxacillin, Penicillin G, benzyl penicillin, Penicillin V, phenoxy methyl penicillin, Pheneticillin, Piperacillin, Ticarcillin, Ampicillin hydrolyzed, Penicillin G hydrolyzed, 3-phenoxybenzoic acid (3-PBAc) Chlorpyrifos, Chlorpyrifos derivatives, HClo1, Synthesized directly from chlorpyrifos technical grade by substitution of the chlorine in position 6 by a 3-mercaptopropanoic acid spacer arm, Chlorpyrifos derivatives, HTCP (Modification HTCP of TCP metabolite was prepared from HClo1 by hydrolysis of the thiophosphate ester), Zeatin Riboside (trans isomer), Zeatin (trans isomer), N6-(2-isopentenyl)-adenosine, IPA, N6-(2-isopentenyl)-adenine, 2-iP, Benzyladenine, Kinetin, monuron, monolinuron, fenuron, neburon, propanil, propham, chloropropham, 4-chloroaniline, Methyl Urea Derivative, 1-(3-Carboxypropyl)-3-(4-chlorophenyl)-1-methylurea, Methyl Urea Derivative, 1-(5-Carboxypentyl)-3-(4-chlorophenyl)-1-methylurea, metobromuron, Sennoside B, SB, Sennoside B possessed a erythro configuration between C-10 and C-10', Sennoside A (Modification Sennoside A possessed a threo configuration between C-10 and C-10'), Rhein, Emodin, Aloe-emodin, Barbaloin, 1,4 Dihydroxyanthraquinone, Rhaponticin, Galic acid, Vanillic acid, Caffeic acid, Homogentisic acid, Esculin, Cinnamtannin B1, Baicalin, Naringin hydrate, Wogonin, Wogonin 7-o-beta-glucuronide, Curcumin, delta1-Tetrahydrocannabinolic acid, delta1-Tetrahydrocannabinol, (+−)-cis-4-Aminopermethrin, 3-(4-Aminophenoxy)benzyl(+−)-cis-3-(2,2-dichloroethenyl)-2,2-dimethylcyclopropanecarboxylate, Permethrin, trans-Permethrin, cis-Permethrin, Cypermethrin, Phenothrin, Resmethrin, Cyfluthrin, trans-Permethrin acid Esfenvalerate, Fluvalinate, Fenpropathrin, cis-permethrin acid, 4-Phenoxybenzoyl alcohol, Diuron Derivative, 1-(3-Carboxypropyl)-3-(3,4-dichlorophenyl)-1-methylurea, Siduron, Terbuthiuron, Barban, acid trifluralin, 2,6-dinitro-N-propyl-N-(2-carboxyethyl)-4-(trifluoromethyl)benzenamine, TR-13, 2-ethyl-7-nitro-1-propyl-5-(trifluoromethyl)-1H-benzimidazole, benefin, 2,6-dinitro-N-butyl-N-ethyl-4-(trifluoromethyl)benzenamine, TR-2, 2,6-dinitro-N-propyl-4-(trifluoromethyl)benzenamine, ethalfluaralin, 2,6-dinitro-N-ethyl-N-(2-methyl-2-propenyl)-4-(trifluoromethyl) benzenamine, TR-40, N-(2,6-dinitro-4-(trifluoromethyl)phenyl)-N-propylpropanamide, TR-15, 2-ethyl-4-nitro-6-(trifluoromethyl)-1H-benzimidazole, TR-3, 2,6-dinitro-4-(trifluoromethyl)benzenamine, TR-6, 3-nitro-5-(trifluoromethyl)-1,2-benzenediamine, TR-9, 5-(trifluoromethyl)-1,2,3-benzenetriamine, TR-21, 4-(dipropylamino)-3,5-dinitrobenzoic acid, TR-36M, 3-methoxy-2,6-dinitro-N,N-dipropyl-4-(trifluoromethyl)benzenamine, oryzalin, 3,5-dinitro-4-(dipropylamino)benzenesulfonamide, pendimethalin, 2,6-dinitro-N-(1-ethylpropyl)-3,4-dimethylbenzenamine, penta galloyl glucose, Pyrene Pyrene-1-carboxaldehyde, Phenanthrene, Benzo(a)pyrene, 3,4-Benzopyrene, Anthracene, 3,4-Benzopyrene, Acenaphthene, Fluorene, Chrysene, 1,2-Benzphenanthrene, Benzo[g,h,i]perylene, Benzo[e]pyrene, Acenaphthylene, Fluoranthene, Benzo(j,k)fluorene, Indeno-1,2,3-cd-pyrene, 1,10-(1,2-Phenylene)pyrene, Benzo[a]anthracene, 1,2-Benzanthracene, Benzo(k)fluoranthene, Naphthalene, Benzo[a]fluoranthene, Dibenzo[ah]anthracene, 1,2:5,6-Dibenzanthracene, 2,3-Diaminonaphthalene, 2,6-Dinitroaniline, 17-beta-estradiol (ED), estra-1,3,5(10)-triene-3,17-beta-diol, Trifluralin derivative, 2,6-dinitro-4-tri-fluoromethylaniline, Trifluralin derivative, N-(2,6-dinitro-4-trifluoromethylphenyl)-6-aminohexanoic acid, Trifluralin derivative, N-(2,6-dinitro-4-trifluoromethylphenyl)-N-methyl-6-aminohexanoic acid, Trifluralin derivative, N-(2,6-dinitro-4-trifluoromethylphenyl)-N-propyl-6-aminohexanoic acid, Trifluralin derivative, N-(2,6-dinitro-4-trifluoromethylphenyl)-6-aminohexanoic acid methyl ester, Trifluralin derivative, N-(2,6-dinitro-4-trifluoromethylphenyl)-6-aminohexanoic acid tert-butyl ester, Benfluralin, Ethalfluralin, Trifluralin derivative, 2,6-Dinitro-4-trifluoromethylphenol, Isopropalin, Aniline, 2-Hydroxybenzotrifluoride, N-propyl-6-aminohexanoic acid, N-methyl-6-aminohexanoic acid, MHPG Derivatives, D-MHPG (D-3-methoxy-4-hydroxyphenylglycol), MHPG Derivatives, L-MHPG (L-3-methoxy-4-hydroxyphenylglycol), MHPG Derivatives, DL-MHPG (DL-3-methoxy-4-hydroxyphenylglycol), Isomeric mixture of D-MHPG and L-MHPG forms, MHPG Derivatives, DL-MHPG-SO4 (DL-3-methoxy-4-hydroxyphenylglycol-sulfate) Modification can include Isomeric mixture of D-MHPG-SO4 and L-MHPG-SO4 forms, Serotonin, 5-HT, 5-hydroxydopamine (5-4HDA), 3,4-dihydroxyphenylglycol (DOPEG), Dopamine, 4-(2-aminoethyl)pyrocatechol; 3-hydroxytyramine; 3,4-dihydroxyphenethylamine; L-3,4-dihydroxyphenylalanine, L-DOPA, Vanillomandelic acid, DL-VMA, Homovanillic acid, Norepinephrine, DL-NE, D-Epinephrine, D-E, 3-methoxytyramine, MTA, 3-methoxytyrosine, MTyr, 3,4-dihydroxymandelic acid, DL-DOMA, 3,4-dihydroxyphenyl acetic acid, DOPAC, L-Phenylalanine, Tyramine, p-tyramine; 4-(2-Aminoethyl)phenol, D-Mandelic acid, Homocatechol, Octopamine, DL-Octopamine, Azinphos-Ethyl, S-(3,4-dihydro-4-oxobenzo[d]-[1,2,3]-triazin-3-ylmethyl) O,O-diethyl phosphorodithioate, Phosmet, O,O-dimethyl S-phthalimidomethyl phosphorodithioate, Folpet, N-[(Trichloromethyl)thio]phthalimide, Tetramethrin, (1-Cyclohexene-1,2-dicarboximido)methyl-2,2-dimethyl-3-(2-methylpropenyl)-cyclopropanecarboxylate, N-(bromomethyl)phthalimide, N-(Chloromethyl)benzazimide, 6-(N-phthalimidoylmethylthio)hexanoic acid (MFH), Bromacil, 5-bromo-3-sec-butyl-6-methyluracil, Bromacil Derivative, 5-bromo-6-(hydroxymethyl)-3-(1-methylpropyl)-2,4(1H, 3H)-pyrimidineone, Bromacil Derivative, 5-bromo-3-(2-methylpropyl-6-methyl-2,4(1H,3H)-pyrimidinedione, Metabolite of Bromacil, Bromacil Derivative, 3-hydroxy-1-methylpropyl-6-methyl-2,4(1H,3H)-pyrimidinedione (Modification Bromacil Metabolite), Bromacil Derivative, 6-methyl-3-(1-methylpropyl)-2,4(1H,3H)-pyrimidinedione (Modification Bromacil Metabolite), Terbacil Derivative, [5-chloro-3-(1,1-dimethylethyl)-6-(hydroxymethyl)-2,4 (1H,3H)-pyrimidinedione, Terbacil, 3-tert-butyl-5-chloro-6-methyluracil, Bromacil Derivative, Ethyl-5-(5-Bromo-6-methyl-3-(1-methylpropyl)-2,4(1H,3H)-pyrimidinedione-1-yl)hexanoate, Bromacil Derivative alkylated at N-1, Bromacil Derivative 5-(5-Bromo-6-methyl-3-(1-methylpropyl)-2,4(1H,3H)-pyrimidinedione-1-yl)hexanoic Acid (Modification Bromacil Derivative alkylated at N-1), Bromacil Derivative, -Bromo-6-(Bromomethyl-3-(1-methylpropyl)-2,4(1H,3H)-pyrimidinedione (Modification Bromacil Derivative substituted at the 6-methyl position), Bromacil Derivative-[5-Bromo-3-(1-methylpropyl)-2,4(1H, 3H)-pyrimidinedione-6-yl]-2-carboxylpropanoic Acid (Modification Bromacil Derivative substituted at the 6-methyl position), 3-[5-Bromo-3-(1-methylpropyl)-2,4 (1H,3H)-pyrimidinedione-6-yl]propanoic Acid (Modification Bromacil Derivative substituted at the 6-methyl position), Bromacil Derivative 5-Bromo-1,6-dimethyl-3-(1-methylpropyl)-2,4(1H,3H)-pyrimidinedione, Bromacil Derivative 5-Bromo-1-butyl-6-methyl-3-(1-methylpropyl)-2,4(1H,3H)-pyrimidinedione, Butachlor, N-butoxymethyl-2-chloro-2',6'-diethylacetanilide, Amidochlor, N-[(acetylamino)methyl]-2-chloro-N-(2,6-diethylpenyl)acetamide, Nicarbazin, N,N'-bis(4-nitrophenyl)-compound with 4,6-dimethyl-2(1H)-pyrimidinone (Modification (DNC+HDP)), 2-hydroxy-4,6-dimethylpyrimidine, HDP, Imazalil, [1-(beta-allyloxy-2,4-dichlorophenethyl)imidazole], Imazalil Derivative, EIT-0073 (Modification Have a —O(CH2)5-COOH group instead of original —OCH2CH—CH2 group of imazalil), Penconazole, (RS)-1-(2,4-dichloro-β-propylphenethyl)-1H-1,2,4-triazole, Hexaconazole, (RS)-2-(2,4-dichlorophenyl)-1-(1H-1,2,4-triazol-1-yl)hexan-2-ol, Propiconazole, cis-trans-1-[2-(2,4-dichlorophenyl)-4-propyl-1,3- dioxolan-2-ylmethyl]-1H-1,2,4-triazole, Diclobutrazol, 2RS,3RS)-1-(2,4-dichlorophenyl)-4,4-dimethyl-2-(1H-1,2, 4-triazol-1-yl)pentan-3-ol, Triflumizole, (E)-4-chloro-α,α, α-trifluoro-N-(1-imidazol-1-yl-2-propoxyethylidene)-o-toluidine, Imazalil Derivative, EIT-0183, Imazalil Derivative, EIT-0180, Imazalil Derivative, EIT-0111, Imazalil Derivative, EIT-0158, Imazalil Derivative, K-240, Chlorothalonil, tetrachloroisophthalonitrile Modification On benzene Ring R1=CN R2=Cl R3=CN R4=Cl R5=Cl R6=Cl), Chlorothalonil Derivative-2,4,5,6-tetrachloro-3-cyanobenzamide (Modification On benzene Ring R1=CONH2 R2=Cl R3=CN R4=Cl R5=Cl R6=Cl), Chlorothalonil Derivative-2,5,6-trichloro-4-hydroxyisophthalonitrile (Modification On benzene Ring R1=CN R2=Cl R3=CN R4=OH R5=Cl R6=Cl), 3-carbamyl-2,4,5-trichlorobenzoic acid (Modification On benzene Ring R1=CONH2 R2=Cl R3=COOH R4=H R5=Cl R6=Cl), Pentachloronitrobenzene (Modification On benzene Ring R1=NO2 R2=Cl R3=Cl R4=Cl R5=Cl R6=Cl), Benzene hexachloride, Hexachlorobenzene, BHC, Lindane (Modification On benzene Ring R1=Cl R2=Cl R3=Cl R4=Cl R5=Cl R6=Cl), 2,4,5,6-tetrachlorophenol (Modification On benzene Ring R1=OH R2=Cl R3=H R4=Cl R5=Cl R6=Cl), Carbaryl Derivative, Ethylcarbamate (Modification R1=OCONHCH2CH3 R3=H), 1-Naphthol, 1-naphthaleneacetamide, -(1-naphthyl) acetamide, Carbaryl Derivative, 1-Methylcarbonate (Modification R1=OCOOCH3 R2=H, Carbaryl Derivative, 1-Ethylcarbonate (Modification R1=OCOOCH2CH3 R2=H), Carbaryl Derivative 2-Ethylcarbonate (Modification R1=H R2=OCOOCH2CH3, Carbaryl Derivative, 1-Ethylthiocarbonate (Modification R1=OCOSCH2CH3 R2=H), Carbaryl Derivative, 2-Ethylthiocarbonate (Modification R1=H R2=OCOSCH2CH3), Naptalam, N-1-naphthylphthalamic acid, Carbaryl Derivative, 3-hydroxycarbaryl (Modification R1=OCONHCH3 R2=H R3=OH R4=H R5=H), Carbaryl Derivative 4-hydroxycarbaryl (Modification R1=OCONHCH3 R2=H R3=H R4=OH R5=H), Carbaryl Derivative 5-hydroxycarbaryl (Modification R1=OCONHCH3 R2=H R3=H R4=H R5=OH), Carbaryl Derivative, 1-(5-Carboxypentyl)-3-(1-naphthyl)urea (Modification R1=NHCONH(CH2)5COOH R2=H), (Structurally related s-triazines)-Aziprotryn, 4-azido-N-isopropyl-6-methylthio-1,3,5-triazin-2-ylamine (Modification R1=—SCH3 R2=—N3 R3=—CH(CH3)2), (Structurally related s-triazines), 2-(ethylamino)-4-(methylthio)-6-aminotriazine (Modification R1=—SCH3 R2=—NH—C2H5 R3=—NH2), (Structurally related s-triazines)-2-amino-4-(methylthio)-6-(isopropylamino)triazine (Modification R1=—SCH3 R2=—NH2 R3=—NH—CH(CH3)2), (Structurally related s-triazines)-2-amino-4-methoxy-6-(isopropylamino) triazine (Modification R1=—OCH3 R2=—NH2 R3=—NH—CH(CH3)2), TCP Derivative (3,5,6-trichloro-2-pyridinol Derivative), 3-(3,5-dichloro-6-hydroxy-2-pyridyl) thiopropanoic Acid, p-nitrosuccinanilic acid (PNA-S), PNA-S, PNA-C, p-nitro-cis-1,2-cyclohexanedicarboxanilic acid, Nitroaniline Derivative, 2-nitroaniline, o-Nitroaniline, Nitroaniline Derivative-3-nitroaniline, m-Nitroaniline, Nitroaniline Derivative-4-nitroaniline, p-Nitroaniline, Aeromatic Alcohols, 4-nitrobenzyl alcohol, Aeromatic Alcohols-4-nitrophenethyl alcohol, Aeromatic Alcohols 2-nitrobenzyl alcohol, Aeromatic Alcohols, 3-nitrobenzyl alcohol, Urea Derivative-1-benzyl-3-(4-nitrophenyl)urea, Urea Derivative-1-(3-chlorophenyl)-3-(2-methoxy-5-nitrophenyl)urea, Urea Derivative-1-(3-chlorophenyl)-3-(4-methoxy-3-nitrophenyl)urea, Urea Derivative-1-(4-chlorophenyl)-3-(4-nitrophenyl)urea, Urea Derivative-(2-fluorophenyl)-3-(2-mehtoxy-4-nitrophenyl)urea, 1-(3-mehtoxyphenyl)-3-(3-nitrophenyl)urea, Carbofuran Derivative m Carbofuranphenol, Carbofuran-hydroxy, Carbofuran-keto, Carbosulfan, 3-dihydro-2,2-dimethylbenzofuran-7-yl (dibutylaminothio) methylcarbamate, Benfuracarb, N-[2,3-dihydro-2,2-dimethylbenzofuran-7-yloxycarbonyl(methyl)aminothio]-N-isopropyl-β-alaninate, Furathiocarb, 2,3-dihydro-2,2-dimethyl-7-benzofuranyl 2,4-dimethyl-5-oxo-6-oxa-3-thia-2,4-diazadecanoate, Carbofuran Derivative, 4-[[(2,3-Dihydro-2, 2-dimethyl-7-benzofuranyloxy)carbonyl]-amino]butanoic Acid (BFNB) (Modification n=3 X=CH2), Endrin, nendrin, (1R,4S,4aS,5S,6S,7R,8R,8aR)-1,2,3,4,10,10-hexachloro-1, 4,4a,5,6,7,8,8a-octahydro-6,7-epoxy-1,4:5,8-dimethanonaphthalene, Heptachlor, 1,4,5,6,7,8,8-heptachloro-3a,4,7,7a-tetrahydro-4,7-, Chlordane, 1,2,4,5,6,7,8,8-octachloro-2,3, 3a,4,7,7a-hexahydro-4,7-methanoindene, Endosulfan (Modification isomer mix of alpha and beta forms), Endosulfan (Modification alpha isomeric form), Endosulfan (Modification beta isomeric form), Endosulfan Derivative, Endosulfan sulfate (Modification sulfate form), Endosulfan Derivative, Endosulfan diol, Diol metabolite of endosulfan, Endosulfan Derivative, Endosulfan ether (Modification ether metabolite of endosulfan), Endosulfan Derivative, hydroxy ether, hydroxy ether metabolite of endosulfan, Endosulfan Derivative, Endosulfan lactone (Modification lactone metabolite of endosulfan), Aldrin, Dieldrin, Fenvalerate isomers Modification 1S,2R isomer R: Ph), Fenvalerate isomers (Modification 1R,2S isomer R: Ph), Fenvalerate isomers (Modification 1R,2R isomer R: Ph), Fenvalerate isomers (Modification 1S,2R/S isomer R: Ph), Fenvalerate isomers (Modification 1R,2R/S isomer R: Ph), Fenvalerate isomers, fenvalerate (Modification 1R/S,2R/S isomer R: Ph), Thiabendazole, 2-(thiazol-4-yl)benzimidazole, Thiabendazole Derivative, 5-hydroxythiabendazole (Modification 5-OH-TBZ), Thiabendazole Derivative, 5-NH2-TBZ, Thiabendazole Derivative, methyl benzimidazole carbamate, Albendazole, Mebendazole, Fenbendazole, Thiabendazole Derivative, 2-succinamidothiabendazole, Thiabendazole Derivative, 2-succinamidothiabendazole, Cambendazole, Fenvalerate Haptens, Cyano[3-(4-aminophenoxy)phenyl]methyl (S)-4-Chloro-alpha-(1-methylethyl)benzeneacetate (4-Aminoesfenvalerate), Fenvalerate Haptens, Benzyl 4-[3-[Cyano[(S)-2-(4-chlorophenyl)-3-methyl-1-oxobutanoxy]methyl]]phenoxy]benzenepropanoate, Fenvalerate Haptens, Benzyl 3-[Cyano[(S)-2-(4-chlorophenyl)-3-methyl-1-oxobutanoxy]methyl]]phenoxyacetate, Fenvalerate Haptens, 3-[Cyano[(S)-2-(4-chlorophenyl)-3-methyl-1-oxobutanoxy]methyl]]phenoxyacetic Acid, Fenvalerate Haptens, Benzyl 6-[3-[Cyano[(S)-2-(4-chlorophenyl)-3-methyl-1-oxobutanoxy]methyl]]phenoxy] hexanoate, Fenvalerate Haptens, 6-[3-[Cyano[(S)-2-(4-chlorophenyl)-3-methyl-1-oxobutanoxy]methyl]]phenoxy] hexanoic Acid Fenvalerate Haptens, 4-[3-[Cyano[(S)-2-(4-chlorophenyl)-3-methyl-1-oxobutanoxy]methyl]]phenoxy] benzenepropanoic Acid, (S)-fenvalerate Acid, (Structurally related s-triazines), atrazine mercapturate Modification R1=—SCH2CH(NHCOCH3)COOH R2=—NHCH2CH3 R3=—NHCH(CH3)2, Fenthion Hapten, -Methyl O-[3-methyl-4-(methylthio)phenyl] N-(3-carboxypropyl)phosphoramidothioate Modification referred as Hapten B, Fenthion Derivative, Oxidized Fenthion, Fenthion Derivative, Oxidized oxidized Fenthion, pirimiphos-ethyl, 4-(Methylthio)-m-cresol, Chlorpyrifos Derivative, Chlorpyrifos-oxon, Fenchlorphos, O,O-dimethyl O-2,4,5-trichlorophenyl phosphorothioate, Trichloronate, O-Ethyl O-2,4,5-trichlorophenyl ethyl-phosphonothioate, Dichlofenthion, O-2,4-dichlorophenyl O,O-diethyl phosphorothioate, Parathion, O,O-diethyl O-4-nitrophenyl phosphorothioate; Thiophos, Chlorpyrifos Derivative Modification Synthesis of AR1 is described, Chlorpyrifos Derivative, O-Ethyl O-(3,5,6-Trichloro-2-pyridyl)O-(3-Carboxypropyl)Phosphorothioate; (PO), Chlorpyrifos Derivative-O-Ethyl O-(3,5,6-Trichloro-2-pyridyl)N-(5-Carboxyethyl) Phosphoramidothioate; (PN1) (Modification Amide linkage of thiophosphate reagents), Chlorpyrifos Derivative, O-Ethyl O-(3,5,6-Trichloro-2-pyridyl)N-(2-Carboxyethyl) Phosphoramidothioate; (PN1) (Modification Amide linkage of suitable thiophosphate reagents), Triadimefon, (RS)-1-(4-chlorophenoxy)-3,3-dimethyl-1-(1H-1,2,4-triazol-1-yl)butan-2-one, GR151004, (4-[[5-[3-[2-(dimethylamino)ethyl]]-5-benzofuranyl]-3-pyridinyl]acetyl]morpholine dihydrochloride, Diflubenzuron, 1-(4-chlorophenyl)-3-(2,6-difluorobenzoyl)urea, (Structurally related s-triazines)-SprAAT (Modification R1=SCH2CH2COOH R2=NH2 R3=NH2), (Structurally related s-triazines), SBeAAT (Modification R1=S(C6H4)COOH R2=NH2 R3=NH2), (Structurally related s-triazines), SAAT (Modification R1=SH R2=NH2 R3=NH2), (Structurally related s-triazines), CDAT (Modification R1=Cl R2=NH[C(O)CH3) R3=NH2), (Structurally related s-triazines)-CDET (Modification R1=Cl R2=NH[C(O)CH3) R3=NH(CH2CH3), (Structurally related s-triazines)-CDIT (Modification R1=Cl R2=NH[C(O)CH3) R3=NH(CH(CH3)2)), (Structurally related s-triazines), CDDT (Modification R1=Cl R2=NH[C(O)CH3) R3=NH[C(O)CH3)), (Structurally related s-triazines)-ammeline, OAAT (Modification R1=OH R2=NH2 R3=NH2), (Structurally related s-triazines)-ammelide, OOAT (Modification R1=OH R2=OH R3=NH2), (Structurally related s-triazines)-cyanuric acid, OOOT (Modification R1=OH R2=OH R3=OH), (Structurally related s-triazines), melamine, AAAT (Modification R1=NH2 R2=NH2 R3=NH2), Structurally related s-triazines-N-isoropylammeline, OIAT (Modification R1=OH R2=NH[CH(CH3)2] R3=NH2, Structurally related s-triazines-N-ethylammeline, OEAT (Modification R1=OH R2=NHCH2CH3 R3=NH2), Structurally related s-triazines, N-ethylammelide, OOET (Modification R1=OH R2=OH R3=NHCH2CH3), Structurally related s-triazines)-cyromazine, CyPAAT (Modification R1=NH(C3H5) R2=NH2 R3=NH2), Structurally related s-triazines-diamino-s-triazine, HAAT (Modification R1=H R2=NH2 R3=NH2), PCB congeners, 2,5,3',4'-tetrachlorobiphenyl (Modification IUPAC no.: 70), PCB congeners 2,4,5,3',4'-pentachlorobiphenyl (Modification IUPAC no.: 118), PCB congeners-2,2',5,5'-tetrachlorobiphenyl (Modification IUPAC no.: 52), PCB congeners, 6-[3,3',4'-Trichlorobiphenyl-4-yl)oxy]hexanoic Acid, Metolazone, Brand Names: Mykrox; Zaroxolyn, Furfuryl benzoate, DDT Metabolites, DDA, Paraquat, 1,1'-dimethyl-4,4'-bipyridinium ion, Diethylcarbamazine, THP, 2,4,6-triphenyl-N-(4-hydroxyphenyl)-pyridinium, o-DNCP, -dinitrocarboxyphenol, PCB congeners, 3-chlorobiphenylol (Modification IUPAC No. 2), PCB congeners, 3,4'-dichlorobiphenyl (Modification IUPAC No. 13), PCB congeners, 3,5-dichlorobiphenyl (Modification IUPAC No. 14), PCB congeners, 3,4,5,3',4'-pentachlorobiphenyl (Modification IUPAC No. 126), 2,3,3',4'-tetrachlorobiphenyl (Modification IUPAC No. 56), 2',3,4,5-tetrachlorobiphenyl (Modification IUPAC No. 76), 3,3',5,5'-tetrachlorobiphenyl (Modification IUPAC No. 80), 2,4,5,2,5'-pentachlorobiphenyl (Modification IUPAC No. 101), 2,3,3',4,4'-pentachlorobiphenyl (Modification IUPAC No. 105), 2,3,6,3',4'-pentachlorobiphenyl (Modification IUPAC No. 110), 3,3',4,5,5'-pentachlorobiphenyl (Modification IUPAC No. 127), 3,4,5,3',4',5'-hexachlorobiphenyl (Modification IUPAC No. 169), 2,3,3',4,4',5-hexachlorobiphenyl (Modification IUPAC No. 156), 3,4,3',4'-tetrabromobiphenyl, 3,4,5,3',4',5'-hexabromobiphenyl, 2,4,5,2',4',5'-hexabromobiphenyl, Dibenzofurans and Dioxins, 2,3,7,8-tetrachlorobenzofuran, 2,3,7,8-tetrachlorodibenzo-p-dioxin, 3,4',5-trichloro-4-biphenylol, 3,3',5,5'-tetrachloro-4,4'-biphenyldiol, 3,4,3',4'-tetrachlorodiphenyl ether, 1-2-dichlorobenzene, 1,4-dichlorobenzene, 1,2,4-trichlorobenzene, 3,4-dichloroaniline, DDT Metabolites, 4,4'-DDT, 4,4'-DDD Retronecine, 3,4-dichlorobiphenyl Modification IUPAC No. 12, 3,4,3'-trichlorobiphenyl (Modification IUPAC No. 35), PCB Congeners, 3,4,4'-trichlorobiphenyl (Modification IUPAC No. 37), 3,4,3',5-tetrachlorobiphenyl (Modification IUPAC No. 78), 3,4,3',5'-tetrachlorobiphenyl (Modification IUPAC No. 79), 3,4,4',5-tetrachlorobiphenyl (Modification IUPAC No. 81), DDT Metabolites, p,p'-DDT (Modification p,p'-dichlorodiphenyltrichloroethane), o,p'-DDT Modification o,p'-dichlorodiphenyltrichloroethane, p,p'-DDE Modification p,p'-DDE, o,p'-DDE Modification o,p'-DDE, p,p'-DDD Modification p,p'-DDD, o,p'-DDD Modification o,p'-DDD, Dicofol, 4,4-dichloro-a-(trichloromethyl)benzhydrol, Cyprazine, 6-chloro-N-cyclopropyl-N'-(1-methylethyl)-1,3,5-triazine-2,4-diamine, Structurally related s-triazines, Dipropetryn, 6-(ethylthio)-N,N'-bis(1-methylethyl)-1,3,5-triazine-2,4-diamine, Trietazine, 6-chloro-N,N,N'-triethyl-1,3,5-triazine-2,4-diamine, 6-Hydroxyatrazine, hexazinone, 3-cyclohexyl-6-dimethylamino-1-methyl-1,3,5-triazine-2,4(1H,3H)-dione, TNT, 2,4,6-Trinitrotoluene, Tetraconazole (M14360), 1-[2-(2,4-dichlorophenyl)-3-(1,1,2,2-tetrafluoroethoxy)propyl]-1H-1,2,4-triazole, DTP, 2-(2,4-dichlorophenyl)-3-(1H-1,2,4-triazol-1-yl)propanol, Imazalyl, fenarimol, (RS)-2,4'-dichloro-α-(pyrimidin-5-yl)benzhydryl alcohol, Lupanine metabolites, (+)-lupanine (Modification R=H), Lupanine metabolites, (+)-13-hydroxylupanine (Modification R=OH), Lupanine metabolites, hemisuccinate ester of (+)-13-hydroxylupanine (Modification R=OCO—(CH2)2.COOH), Lupanine metabolites, cis-hexahydrophthalate ester of (+)-13-hydroxylupanine (Modification R=OCO.C6H10.COOH), Lupanine metabolites, alpha-isolupanine, Lupanine metabolites, -hydroxylupanine, Sparteine, Cysteine, multiflorine, epilupinine, (Structurally related s-triazines), CYANAZINE ACID Modification R1=Cl R2=NHCH2CH3 R3=NHCCOOH(CH3)2, Structurally related s-triazines Modification R1=Cl R2=NHCH2CH3 R3=NH(CH2)3COOH, Structurally related s-triazines (Modification R1=Cl R2=NHCH2CH3 R3=NHCH2COOH), (Structurally related s-triazines) (Modification R1=Cl R2=NHCH2CH3 R3=NH(CH2)4COOH), norflurazon, 4-chloro-5-(methylamino)-2-[3-(trifluoromethyl)phenyl]-3(2H)-pyridazinone, norflurazon derivative, desmethyl-norflurazon, metflurazon, -chloro-5-(dimethylamino)-2-[(3-trifluoromethyl)phenyl]-3(2H)-pyridazinone, Pyrazon, Chloridazon, 5-amino-4-chloro-2-phenyl-3(2H)-pyridazinone (active ingradient), dichlorophenyl-pyridazone, (Structurally related s-triazines) azidoatrazine (Modification R1=N3 R2=NHCH(CH3)2 R3=NHCH2CH3), ALACHLOR 2-chloro-2',6'-diethyl-N-methoxymethylacetanilide, trichothecolone (Modification R1=H R2=OH R3=H R4=O R5=H), DON derivative, acetyl-T-2, DON derivative, T-2 tetrol tetraacetate, Chlorpyrifos derivatives, mono-dechloro-CP, Bromophos derivative, Bromophos-methyl, Bromophos derivative, Bromophos-ethyl dicapthon, -2-chloro-4-nitrophenyl O,O-dimethyl phosphorothioate, tetrachlorvinphos, (Z)-2-chloro-1-(2,4,5-trichlorophenyl)vinyl dimethyl phosphate, triclopyr, 3,5,6-trichloro-2-pyridyloxyacetic acid, picloram, 4-amino-3,5,6-trichloropyridine-2-carboxylic acid, Formononetin, Biochanin A, 5, 7-dihydroxy-4'-methoxyisoflavone (Modification It is the 4'-methyl ether of genistein), equol, (7-hydroxy-3-(4'-hydroxyphenyl)-chroman, 2'methoxyformononetin, Daidzein, 7-hydroxy-3-(4-hydroxyphenyl)-4H-1-benzopyran-4-one, geninstein, quercetin, 3,3',4',5,7-Pentahydroxyflavone; 3,5,7,3',4'-Pentahydroxyflavone; matheucinol, coumestrol (Structurally related s-triazines), Hydroxysimazine (Modification R1=OHR2=NHCH2CH3R3=NHCH2CH3, angustifoline, Alodan, 1-Methyl-4-phenyl-4-carboethoxypiperidine hydrochloride, Zearalenone, RAL, F-2 Toxin, Fenpropimorph, (RS)-cis-4-[3-(4-tert-butylphenyl)-2-methylpropyl]-2,6-dimethylmorpholine, Tridemorph, 2,6-dimethyl-4-tridecylmorpholine, 2,6-dimethylmorpholine, Amorolfine, Fenpropidine, (RS)-1-[3-(4-tert-butylphenyl)-2-methylpropyl]piperidine, (Structurally related s-triazines) (Modification R1=Cl R2=Cl R3=NHCH2CH3, (Structurally related s-triazines) Modification R1=Cl R2=Cl R3=NHCH(CH3)2, (Structurally related s-triazines) Modification R1=Cl R2=NHCH2CH3 R3=NH(CH2)5COOH, (Structurally related s-triazines) Modification R1=Cl R2=NHCH(CH3)2 R3=NHCH2COOH, (Structurally related s-triazines) (Modification R1=Cl R2=NHCH(CH3)2 R3=NH(CH2)5COOH), Structurally related s-triazines, cyanazine amide (Modification R1=Cl R2=NHCH2CH3 R3=NHCCONH2(CH3)2), hydroxycyanazine acid (Modification R1=OH R2=NHCH2CH3 R3=NHCCOOH(CH3)2), deethylsimazine (Modification R1=Cl R2=NH2 R3=NHCH2CH3), Albendazole sulfoxide, [5-(propylthionyl)-1H-benzimidazol-2-yl]-, methylester, Albendazole sulfone, 5(6)-alkylbenzimidazoles, 2-amino-5-(propylthio)benzimidazole, 5(6)-alkylbenzimidazoles, 2-amino-5-(propylsulfonyl) benzimidazole, oxibendazole, 5-propoxy-benzimidazole-2-methyl carbamate, 5(6)-arylbenzimidazoles, fenbendazole sulfone (Modification sulfone metabolite of fenbendazole), 5(6)-arylbenzimidazoles, 4'-hydroxyfenbendazole, 5(6)-arylbenzimidazoles, oxfendazole (Modification Oxfendazole is the sulfoxide metabolite of fenbendazole), 5(6)-arylbenzimidazoles, flubendazole, benzimidazole Metabolites, 2-aminobenzimidazole, benzimidazole Metabolites, 5-aminobenzimidazole, benzimidazole Metabolites, 2-acetylbenzimidazole, Benzophenone, Diphenylmethanone; phenyl ketone; Diphenyl ketone; Benzoylbenzene, Benzaldehyde, benzoic aldehyde, 4-Bromo-2,5-dichlorophenol, Acephate, O,S-dimethyl acetylphosphoramidothioate, methamidophos, O,S-dimethyl phosphoramidothioate, Dichlorvos, 2,2-dichlorovinyl dimethyl phosphate, Phenthoate, S-α-ethoxycarbonylbenzyl O,O-dimethyl phosphorodithioate, EPN, Ethyl p-nitrophenyl thionobenzenephosphonate, Bioresmethrin, -benzyl-3-furylmethyl (1R,3R)-2,2-dimethyl-3-(2-methylprop-1-enyl)cyclopropanecarboxylate (Modification The unresolved isomeric mixture of this substance has the ISO common name resmethrin), flufenoxuron, 1-[4-(2-chloro-α,α,α-trifluoro-p-tolyloxy)-2-fluorophenyl]-3-(2,6-difluorobenzoyl) urea, Amitrole, 1H-1,2,4-triazol-3-ylamine, molinate, S-ethyl azepane-1-carbothioate, molinate derivative (Modification S-2-carboxyethyl hexahydroazepine-1-carbothioate), molinate derivative (Modification S-5-carboxypentyl hexahydroazepine-1-carbothioate) molinate derivative (Modification molinate sulfone), molinate derivative (Modification S-(p-aminobenzyl) hexahydroazepine-1-carbothioate), molinate derivative (Modification S-2-(p-aminophenyl) ethyl hexahydroazepine-1-carbothioate), hexamethylenimine, thiobencarb (Bolero), butylate (Sutan), EPTC (Eptam), cycloate (Roneet), pebulate (Tillam), vernolate (Vernam), Aflatoxin M1, AFM1 (Modification AFM1), Aflatoxin B1, AFB1 (Modification AFB1), Aflatoxin G1, AFG1 (Modification AFG1), Aflatoxin M2, AFM2 (Modification AFM2), Aflatoxin B2, AFB2 (Modification AFB2), Aflatoxin G2, AFG2 (Modification AFG2), Aflatoxin B2alpha, AFB2alpha (Modification AFB2alpha), Aflatoxin G2alpha, AFG2alpha (Modification AFG2alpha), KB-6806, 6-amino-5-chloro-1-isopropyl-2-(4-methyl-1-piperazinyl) (Modification R1=NH2 R2=CH(CH3)2 R3=CH3), KB-6806 (Benzimidazole) Derivatives Modification R1=NH2 R2=CH2CH(CH3)2 R3=CH3, Hapten Name KB-6806 (Benzimidazole) Derivatives (Modification R1=NH2 R2=CH(CH2CH3)2 R3=CH3), KB-6806 (Benzimidazole) Derivatives (Modification R1=NHCOCH3 R2=CH(CH3)2 R3=CH3), KB-6806 (Benzimidazole) Derivatives (Modification R1=H R2=CH(CH3)2 R3=CH3), KB-6806 (Benzimidazole) Derivatives (Modification R1=NH2 R2=CH(CH3)2 R3=CH3), KB-6806 (Benzimidazole) Derivatives Modification R1=NH2 R2=CH(CH3)2 R3=N(—>O) CH3 (N-OXIDE), KB-6806 (Benzimidazole) Derivatives Modification R1=NH2 R2=CH(CH3)2 R3=H, KB-6806 (Benzimidazole) Derivatives Modification R1=NH2 R2=CH2CH3 R3=CH3, Aminoparaoxon, phosphoric acid, O,O-diethyl O-(4-aminophenyl) ester, Methylparathion, phosphorothioic acid, O,O-dimethyl O-(4-nitrophenyl) ester, Diethyl phenylphosphate, phenylphosphonic acid, O,O-diethyl ester, Diethyl phosphate, ethylphosphonic acid, O,O-diethyl ester, p-Nitorphenyl phosphate, phosphonic acid, O-(4-nitrophenyl)ester, Phorate, phosphorodithioic acid, O,O-diethyl S-[(ethylthio)methyl] ester, Ethion, bis(phosphorodithioic acid), S,S'-methylene O,O,O',O'-tetraethyl ester, Carbophenthion, phosphorodithioic acid, O,O-diethyl S-[[(4-chlorophenyl)thio]methyl] ester, Disulfoton, phosphorodithioic acid, O,O-diethyl S-[(2-ethylthio)ethyl] ester, TS, N-[4-(Carboxymethyl)-2-thiazolyl]sulfanilamide, NS, N-(4-Nitrophenyl) sulfanilamide, Sulfamoxole, Sulfacetamide, DNP-SL, Spin labelled dinitrophenyl (Modification The synthesis of DNP-SL has been described by Balakrishnan et al (1982) formula can be found in Anglister et al. (1984)), beta ecdysone, Benzimidazole Derivative, 5(6)-[Carboxypentyl)thio]-2-(methoxycarbonyl)amino]-benzimidazole, 2-hydroxybiphenyl HBP, Atrazine Caproic acid, Lysophosphatidic acid (LPA), 1-acyl-2-hydroxy-sn-glycero-3-phosphate), berberine, Palmatine, 9-Acetylberberine, Corydaline, Coptisine, Berberrubine, 8-Oxoberberine, Papaverine, Berberine Derivative, 9-O-carboxymethyl berberine, phencyclidine, 1-(1-phenylcyclohexyl)piperidine, Methoxychlor, Endosulfan Derivative, 4-Oxobutanoic Acid,4-(4,5,6,7,8,8-Hexachloro-3a,4,7,7a-tetrahydro-4,7-methano-1H-indenyl-1-oxy), Endosulfan Derivative, 4-oxybutanoic Acid,4-(1,3,4,5,6,7,8-Octachloro-3a,4,7,7a-tetrahydro-4,7-methanoindanyl-2-oxy, Endosulfan Derivative (Modification Hemisuccinate of Endosulfan diol), Triazole Derivatives, 5-(3-Hydroxypropyl)-3-amino-2H-1,2,4-triazole, Triazole Derivatives, 5-(3-Hydroxypropyl)-3-(2-nitrophenylsulfenyl)amino-2H-1,2,4-triazole, Triazole Derivatives, 3-Amino-5-[(3-succinyloxy)propyl]-2H-1,2,4-triazole, Triazole Derivatives, 3-amino-1,2,4-triazole-5-thiol, Triazole Derivatives, 3-[(2-nitrophenylsulfenyl)amino-2H-1,2,4-triazole-5-thiol, Triazole Derivatives, 2H-1,2,4-triazole-5-thiol, Triazole Derivatives, 4-methyl-1,2,4-triazole-3-thiol, Triazole Derivatives, (1,2,4-triazol-2-yl)acetic acid, 1,2,4-triazole, 4-nitrophenyl 4'-carboxymethylphenyl phosphate, Triazole Derivative, 4-amino-1,2,4-triazole, Triazole Derivative, 3-acetamido-1H-1,2,4-triazole, Triazole Derivative, 3-amino-1,2,4-triazole-5-carboxylic acid hemihydrate, Triazole Derivative, 2-(4-chlorophenyl)-2-(1,2,4-triazol-1-yl)-methylhexanoic acid, succinic acid, Imidazole, L-histidine, L-glutamic acid, Permethrin derivative, 3-phenoxybenzyl 2,2-dimethylcyclopropane-1,3-dicarboxylate, 3-phenoxybenzaldehyde, flucythrinate, Chrysanthemic acid, 2,4-Dinitrophenyl, DNP, Thiram Haptens, Disodium 4-[Carbodithioato(methyl)-amino]butanoate, Thiram Haptens 5,11-Dimethyl-6,10-dithioxo-7,9-dithia-5,11-diazadodecanoic Acid, Thiram Haptens, 2-{[(Dimethylamino)carbothioyl]sulfanyl}ethanoic Acid, Thiram Haptens, 4-{[(Dimethylamino)carbothioyl]sulfanyl}butanoic Acid, Thiram Haptens, 6-{[(Dimethylamino)carbothioyl]sulfanyl}hexanoic Acid, Thiram Haptens, 11-{[(Dimethylamino)carbothioyl]sulfanyl}undecanoic Acid, Thiram Haptens, 2-{[(Dimethylamino)carbothioyl] sulfanyl}ethanoic Acid, Thiram, Tetramethylthiurammonosulfide, Tetraethylthiuram disulfide, Dimethyldithiocarbamic acid sodium salt, Dimethyldithiocarbamic acid zinc salt, Diethyldithiocarbamic acid sodium salt, N,N,N',N'-tetramethylthiourea, Nabam, Zineb, Maneb, Ethylenethiourea, Chlorpyrifos hapten, O,O Diethyl O-[3,5-Dichloro-6-[(2-carboxyethyl)thio]-2-pyridyl] Phosphorothioate, 2-Succinamidobenzimidazole, Methyl 2-Benzimidazolecarbamate, MBC, Benzimidazole, 2-benzimidazolylurea, succinamide, Ethyl carbamate, Urea, N-methylurea, N,N'-dimethylurea, Brevetoxin PbTx-3, Organophosphorous Haptens, O,O-Diethyl O-(5-carboxy-2-fluorophenyl) phosphorothioate, Chlorpyrifos-ethyl, Anandamide hapten, N-Arachidonyl-7-amino-6-hydroxy-heptanoic acid, Anandamide, Arachidonic acid, Docosatetraenoyl ethanolamide, Dihomo-gamma-linolenyl ethanolamide, 2-Arachidonyl glycerol, 2-Arachidonyl glycerol ether, Stearoyl ethanolamide, Heptadecanoyl ethanolamide, Prostaglandin E1, 3-hydroxy-2-(3-hydroxy-1-octenyl)-5-oxocyclopentaneheptanoic acid; alprostadil; PGE1, Prostaglandin D2, PGD2, Prostaglandin A2, PGA2, Prostaglandin B2, PGB2, Prostaglandin F2 alpha, 7-[3,5-dihydroxy-2-(3-hydroxy-1-octenyl)cyclopentyl]-5-heptenoic acid; dinoprost; PGF2alpha, Prostaglandin F1 alpha, PGF1alpha, 6-keto-Prostaglandin F1 alpha, 6-keto-PGF1alpha, 13,14-Dihydro-15-keto-Prostaglandin E2, 13,14-Dihydro-15-keto-PGE2, 13,14-Dihydro-15-keto-Prostaglandin F2alpha, 14-Dihydro-15-keto-PGF2alpha, 5alpha,7alpha-Dihydroxy-11-ketotetranorpostane-1,16-dioic acid, 15-keto-PGF2alpha, TXB2, Prostaglandin E2,7-[3-hydroxy-2-(3-hydroxy-1-octenyl)-5-oxocyclopentyl]-5-heptenoic acid; dinoprostone; PGE2, hCG-alpha-(59-92)-peptide (34 residues), Paraquat Derivative, Paraquat hexanoate (PQ-h), Monoquat, Diquat, 9,10-dihydro-8a, 10a-diazoniaphenanthrene, MPTP, 1-methyl-4-phenyl-1,2,5,6-tetrahydropyridine, 1,2-Naphthoquinone, N-Acetyl-S-(1,2-dihydroxy-4-naphthyl)cysteine, N-Acetyl-S-(1,4-dihydroxy-2-naphthyl)cysteine, N-Acetyl-S-(1,2-dihydroxy-1-hydroxy-1-naphthyl)cysteine, 2-Chloro-2'.6'-diethylacetanilide (CDA) Hapten, 2-[2-Chloro-(2'-6'-diethyl)acetanilido]ethanoic Acid, 2-Chloro-2'.6'-diethylacetanilide (CDA) Hapten, 2-[2-Chloro-(2'-6'-diethyl)acetanilido]butanoic Acid, 2-Chloro-2'.6'-diethylacetanilide (CDA) Hapten, 5-(4-Chloroacetamido-3,5-diethyl)phenoxypentanoic Acid, CDA, 2-Chloro-2'.6'-diethylacetanilide, HDA, 2-Hydroxy-2'.6'-diethylacetanilide, 2,6-diethyl-aniline, Hydroxyalachlor, Alachlor ESA, Alachlor ethanesulfonic acid, Isoproturon Hapten, 3-(4-Isopropylphenyl)-1-carboxypropyl-1-methyl urea, chlorotoluron, 3-(3-chloro-p-tolyl)-1,1-dimethylurea, Metoxuron, 3-(3-chloro-4-methoxyphenyl)-1,1-dimethylurea, metamitron, 4-amino-4,5-dihydro-3-methyl-6-phenyl-1,2,4-triazin-5-one, mecoprop, (RS)-2-(4-chloro-o-tolyloxy) propionic acid, propyzamide, 3,5-dichloro-N-(1,1-dimethylpropynyl)benzamide, Paraquat dichloride, MCPB, 4-(4-chloro-o-tolyloxy)butyric acid, Chlortoluron Hapten, N-(3-Chloro-4-methylphenyl)-N-methyl-N-carboxypropyl Urea, Metsulfuron, Methyl 2-[3-(4-methoxy-6-methyl-1,3,5-triazin-2-yl)ureidosulphonyl]benzoate, Captopril Haptens, Captopril-4-(Maleimidomethyl)-cyclohexane Carboxylic Acid (MCC), Captopril Haptens, Captopril Disulfide Modification, Mercaptoethanol-MCC, Mercaptoethanol-4-(Maleimidomethyl)-cyclohexane Carboxylic Acid Modification, Captopril Haptens, Captopril without MCC, Aculeatiside A, Aculeatiside B, Solamargine, Solasonine, solanine-S; purapurine, Solasodine, Khasianine, Tomatine, lycopersicin, Tomatidine, 3-O-beta-D-Glucopyranosyl-solasodine, O-alpha-L-Rhamnosyl-1(1→2)-3-O-beta-D-glucopyranosyl-solasodine, 3-O-beta-D-Galacopyranosyl-solasidine, O-beta-D-Glucopyranosyl-1(1→3)-3-O-beta-D-galacopyranosyl-solasodine, 12-Hydroxysolamargine, 12-Hydroxysolasonine, Isoanguivine, Solaverine I, Solaverine II, Xylosyl-beta-solamargine, alpha-Solanine, alpha-Chaconine, Dioscine, Indole Derivatives, beta-Indole Acetic Acid, 2-Bromo-4,6-dinitroaniline, 2-Chloro-4,6-dinitroaniline, Tetryl, 2,4,6-trinitrophenyl-n-methylnitramine, nitramine, tetralite, tetril, 2-Amino-4,6-dinitrotoluene, 2,4-Dinitroaniline, 3,5-Dinitroaniline, 2-Amino-4,6-dinitrobenzoic acid, Disperse Blue 79, N-[5-[bis[2-(acetyloxy)ethyl]amino]-2-[(2-bromo-4,6-dinitrophenyl) azo]-4-ethoxyphenyl]acetamide, 1,3-Dinitrobenzene, 2,6-Dinitrotoluene, 4-Amino-2,6-dinitrotoluene, 1,3,5-Trinitrobenzene, Nicergoline, Ethylmorphine, 8-Didehydro-4,5-epoxy-3-ethoxy-17-methylmorphinan-6-ol, Dihydromorphine, Dihydrocodeine, dihydromorphinone, Hydromorphone, Dihydrocodeinone, Hydrocodone, Naltrexone, N-cyclopropylmethyl-14-hydroxydihydromorphinone, Dextromethorphan, (±)-3-Methoxy-17-methylmorphinan, Homatropine, Endorphins Modification Derivative Type: b-Endorphin, Met-enkephalin, DALEA, D-Ala(2)-D-Leu(5)-enkephalinamide, Vincristine, 22-Oxovincaleukoblastine, leurocristine; VCR; LCR, OCT, 22-Oxacalcitriol, OCT-3-HG, 22-oxacalcitriol-3-Hemiglutarate, 24(OH)OCT, 24(OH)-22-oxacalcitriol, 1,20(OH)2-hexanor-D3, Synephrine, Epinephrine, 4-[(1R)-1-Hydroxy-2-(methylamino)ethyl]-1,2-benzenediol, Phenylephrine, Dopamine Derivative, 6-hydroxy dopamine, Tyramine derivative, 3-methoxy tyramine, Phenethylamine, Benzeneethanamine; PEA, m-tyramine, o-tyramine, dimethoxyphenethylamine, Thymidine glycol monophosphate, 5,6-Dihydroxythymidine monophosphate, Thymidine monophosphate, Thymidine glycol, Thymine glycol, 5,6-Dihydrothymidine, Thymidine, Thymine, 5-methyluracil; 2,4-dihydroxy-5-methylpyrimidine, AMP, Adenosine mono phosphate, CMP, Cytidine mono phosphate, Carbamazepine, 5-carbamoyl-5H-dibenz[b,f]azepine, Neopterin isomers, D-erythro-Neopterin, Neopterin isomers, L-erythro-Neopterin, Neopterin isomers, D-threo-Neopterin, Biopterin isomers, L-erythro-Biopterin, Biopterin isomers, D-erythro-Biopterin, Biopterin isomers, L-threo-Biopterin, Biopterin isomers, D-threo-Biopterin, Pterin-6-Carboxylic Acid, C7H5NiO3, Pterin, Thromboxane B2, (5Z,9alpha,13E,15S)-9,11,15-trihydroxythromboxa-5,13-dien-1-oic acid, 15 Ketoprostaglandin F2alpha, Fumonisin B1, macrofusine; FBI, Thyroliberin, TRH; thyrotropin-releasing factor; thyrotropin releasing hormone; TRF; protirelin; lopremone, Thyroliberin-OH, TRH-OH, Diketopiperazine, cyclo (H-P), TRH analogues, Methylated TRH, TRH analogues, TRH elongated peptides, TRH-Gly, TRH elongated peptides, TRH-Gly-Lys-Arg, TRH elongated peptides, TRH-Gly-Lys-Arg-Ala, TRH elongated peptides, P7 (Modification Q-H-P-G-L-R-F), TRH elongated peptides, P10 (Modification S-L-R-Q-H-P-G-L-R-F), TRH elongated peptides, Ps5 Modification pro-TRH[178-199], TRH elongated peptides, TRH-Ps5 (Modification pro-TRH[172-199]), Hypothalmic peptide, LHRH, Cyanoginosin-LA, Cyanoginosin-LB, Cyanoginosin-LR, Cyanoginosin-LY, Cyanoginosin-AY, Cyanoginosin-FR, Cyanoginosin-YR, Nε-acetyllysine-containing peptide, Gly-Lys (Ac)-ε-aminocaproic acid (Aca)-Cys, Benzoic Acid, Benzenecarboxylic acid; phenylformic acid; dracylic acid, m-hydroxybenzoic acid, 3-hydroxybenzoic acid, o-methoxybenzoic acid, 2-methoxybenzoic acid, o-toluic acid, 2-Methylbenzoic acid, o-chlorobenzoic acid, 2-chlorobenzoic acid, o-aminobenzoic acid, 2-aminobenzoic acid, thiosalicylic acid, 2-Mercaptobenzoic acid; o-sulfhydrylbenzoic acid, Salicylamide, 2-Hydroxybenzamide, Saligenin, saligenol; o-hydroxybenzyl alcohol; Salicyl alcohol, 2-cyanophenol, 2-hydroxyphenyl acetic acid, p-hydroxybenzoic acid, p-aminobenzoic acid, 4-Aminobenzoic acid; vitamin Bx; bacterial vitamin H1, p-toluic acid, p-methylamino benzoic acid, p-chlorosalicylic acid, 4-chloro-2-hydroxybenzoic acid, 2,4-dihydroxybenzoic acid, beta-Resorcylic Acid; 2,4-dihydroxybenzenecarboxylic acid; BRA, 4-aminosalicylic acid, 4-Amino-2-hydroxybenzoic acid; p-aminosalicylic acid, Gentisic Acid, 2,5-dihydroxybenzoic acid; 5-hydroxysalicylic acid, Picolinic acid, o-Pyridinecarboxylic acid; 2-Pyridinecarboxylic acid, picolinic acid N-oxide, 3-hydroxypicolinic acid, 2-hydroxynicotinic acid, 7-methylguanine, N2-Carboxymethyl-N7-methylguanine, 2-(7-methyl-6-oxo-6,7-dihydro-1H-purin-2-ylamino)acetic acid, 7-methylxanthine, 7-methyluric acid, 7-methyladenine, Guanine, 2-Amino-1,7-dihydro-6H-purin-6-one; 2-aminohypoxanthine, Adenine, 6-aminopurine; 6-amino-1H-purine; 6-amino-3H-purine; 6-amino-9H-purine, 7-(2-Carboxyethyl)guanine, 7-CEGua, 7-Ethylguanine, 2-amino-7-ethyl-1H-purin-6(7H)-one, 7-(2,3-Dihydroxypropyl) guanine, 2-amino-7-(2,3-dihydroxypropyl)-1H-purin-6 (7H)-one, 7-(2-Hydroxyethyl)guanine, 2-amino-7-(2-hydroxyethyl)-1H-purin-6(7H)-one, 7-(2-[(2-Hydroxyethyl)amino]ethyl)-guanine, 2-amino-7-(2-(2-hydroxyethylamino)ethyl)-1H-purin-6(7H)-one, 7-Carboxymethylguanine, or 2-(2-amino-6-oxo-1,6-dihydropurin-7-yl)acetic acid. In some alternatives, the CAR or T cell receptor comprises a fragment specific for the hapten, wherein the CAR or TCR comprises 14G8, Anti 3-methylindole antibodies, 3F12, Anti 3-methylindole antibodies, 4A1G, Anti 3-methylindole antibodies, 8F2, Anti 3-methylindole antibodies, 8H1, Anti 3-methylindole antibodies, Anit-Fumonisin B1 antibodies, Anti-1,2-Naphthoquinone-antibodies, Anti-15-Acetyldeoxynivalenol antibodies, Anti-(2-(2,4-dichlorophenyl)-3(1H-1,2,4-triazol-1-yl)propanol) Antibodies (Anti-DTP antibodies), Anti-22-oxacalcitriol antibodies (As-1, 2 and 3), Anti-(24,25(OH)2D3) Antibodies (Ab11), Anti-(24,25(OH)2D3) Antibodies (Ab3), Anti-(24,25(OH)2D3) Antibodies (Ab3-4), Anti-2,4,5-Trichlorophenoxyacetic acid antibodies, Anti (2,4,5-Trichlorphenoxyacetic acid) Antibodies, Anti-(2,4,6-Trichlorophenol) Antibodies, Anti-(2,4,6-Trichlorophenol) Antibodies, Anti 2,4,6-Trinitrotoluene (TNT) Antibodies, Anti-2,4-Dichlorophenoxyacetic acid (MAb's B5/C3, E2/B5, E2/G2, F6/C10, and F6/E5), Anti (2,4-Dichlorphenoxyacetic acid) Antibodies, Anti-2-hydroxybiphenyl-antibodies, Anti-(3,5,6-trichloro-2-pyridinol) Antibodies (LIB-MC2, LIB-MC3), Anti (3,5,6-trichloro-2-pyridinol) antibodies (LIB-MC2 MAb), Anti-3-Acetyldeoxynivalenol (3-AcDON) Antibodies, Anti-3-phenoxybenzoic acid (3-PBAc)-Antibodies, Anti-4-Nitrophenol antibodies, anti-4-nitrophenyl 4'-carboxymethylphenyl phosphate antibodies, Anti-7-(Carboxyethyl)guanine (7-CEGua) antibodies (group specific for 7-meGua), Anti-7-methylguanine (7-MEGua) antibodies, Anti-ABA antibodies, Anti Acephate antibodies (Antiserum 8377), Anti-acetyllysine antibodies (mAbs AL3D5, AL11, AKL3H6, AKL5C1), Anti Aculaetiside-A antibody, Anti Aflatoxin M1(AFM1)antibodies (mAbs A1, N12, R16, FF32), Anti-agatharesinol Antibody, Anti-agatharesinol Antibody, Anti Amidochlorantibodies, Anti-Amitrole antibodies (anti 1a-BSA antibodies), Anti ampicillin Antibodies (AMPI I 1D1 and AMPI II 3B5), Anti-anandamide antibodies (9C11.C9C, 30G8.E6C, 7D2.E2b, 13C2 MAbs), Anti atrazine antibodies, Anti-atrazine antibodies, Anti-Atrazine antibodies, Anti Atrazine Antibodies, Anti-Atrazine Antibodies, Anti-Atrazine Antibodies, Anti-Atrazine Antibodies (4063-21-1 MAb cell line mAb and scAbs), Anti-Atrazine Antibodies (4D8 and 6C8 scAb), Anti Atrazine Antibodies (C193), Anti Atrazine Antibodies (In Rabbit/Sheep), Anti Atrazine Antibodies (K4E7), Anti Atrazine Antibodies (MAb: AM7B2.1), Anti Atrazine Antibodies (ScAb), Anti Atrazine Mercapturic acid antibodies, Anti (Azinphos methyl) Antibodies (MAB's LIB-MFH14, LIB-MFH110), Anti benalaxyl antibody, Anti benzimidazolecarboxylic acid, Anti benzimidazoles antibody (Ab 587), Anti-Benzo [a]pyrene antibodies, Anti Benzo(a)pyrene antibodies (10C10 and 4D5 MAbs), Anti-(Benzoylphenylurea)-Antibodies (mainly against Diflubenzuron), Anti-berberine Antibodies, Anti-beta Indole Acetic Acid Antibodies, Anti-Biopterin (L-erythro form) Antibodies, Anti-Brevetoxin PbTx-3-Antibodies, Anti Bromacil Antibodies, Anti-Bromophos Antibodies, Anti-Bromophos ethyl Antibodies, Anti Butachlor antibodies, Anti-Captopril-MCC Antibodies, Anti-Carbamazepine (CBZ)-Antibodies, Anti Carbaryl Antibodies, Anti Carbaryl Antibodies (LIB-CNH32, LIB-CNH33, LIB-CNH36, LIB-CNH37, LIB-CNH45, LIB-CNA38), Anti-Carbaryl Antibodies (LIB/CNH-3.6 MAb), Anti Carbofuran Antibodies (LIB-BFNB-52, LIB-BFNB-62, LIB-BFNB-67), Anti Carbofuran Antibodies (LIB-BFNP21), Anti-CDA-antibodies, Anti-CDA-antibodies (anti-2-[2-Chloro-(2'-6'-diethyl)acetanilido]butanoic Acid), Anti-CDA-antibodies (anti-2-[2-Chloro-(2'-6'-diethyl)acetanilido]ethanoic Acid), Anti-CDA-antibodies (anti-5-(4-Chloroacetamido-3,5-diethyl)phenoxypentanoic Acid), anti-ceftazidime antibody, Anti-(chlorodiamino-s-triazine) Antibodies (Anti-CAAT) (PAb1-8), Anti Chlorothalonil Antibodies, Anti-Chlorpyrifos antibodies, Anti-Chlorpyrifos Antibodies, Anti-Chlorpyrifos Antibodies (LIB-AR1.1, LIB-AR1.4 Mabs), Anti-Chlorpyrifos Antibodies (LIB-C4), Anti (chlorpyrifos) antibodies (LIB-C4 MAb), Anti-Chlorpyrifos Antibodies (LIB-PN1 Mabs), Anti-Chlorpyrifos Antibodies (LIB-PN2 Mabs), Anti-Chlorpyrifos Antibodies (LIB-PO Mabs), Anti-chlorsulfuron antibodies, Anti-Chlorsulfuron antibodies, Anti Chlortoluron Antibodies (Antiserum), Anti-Cyanoginosin-LA antibodies (mAbs 2B2-2, 2B2-7, 2B2-8, 2B2-9, 2B2-10, 2B5-5, 2B5-8, 2B5-14, 2B5-15, 2B5-23), Anti (D-3-methoxy-4-hydroxyphenylglycol) antibodies, Anti-DDA antibodies, Anti DDT antibodies (PAbs and MAbs), Anti-DDT Mabs (LIB1-11, LIB5-21, LIB5-25, LIB5-28, LIB5-212, LIB5-51, LIB5-52, LIB5-53), Anti-DEC Antibodies (Anti diethylcarbamazine Antibodies), Anti DEHA antibodies, Anti-(Delor 103) antibodies, Anti-Deltamethrin Antibodies, Anti Deltamethrin Antibodies (Del 01 to Del 12 MAbs and PAbs), Anti-deoxynivalenol (DON) Antibodies, Anti-Deoxynivalenol (DON) Antibodies, Anti Dexamethasone Antibody, Anti Dexamethasone Antibody, Anti-Dinitrophenyl (DNP)-antibodies, Anti dinitrophenyl spin labeled antibodies (AN01-AN12), Anti Diuron Antoboides (MAb's: 21, 60, 195, 202, 275, 481, 488, 520), Anti-D-MHPG Antibodies, Anti DNC antibodies, Anti-EB1089 antibodies, Anti-ecdysone antibodies, Anti-endosulfan antibodies, Anti-Endosulfan antibodies, Anti Esfenvalerate antibodies (Ab7588), Anti estradiol antibodies, Anti-Fenitrothion antibodies (pAbs and mAbs), Anti-Fenpropimorph antibodies, Anti Fenthion Antibodies, Anti-Fenthion Antibodies, Anti FITC antibodies (B13-DEI), Anti-Flucofuron antibodies (F2A8/1/A4B3), Anti-flufenoxuron antibodies, and Anti-(Benzoylphenylurea)-Antibodies, Anti-Formononetin Antibodies, Anti-Furosemide antibodies (Furo-26, Furo37, furo-72, Furo 73 Mabs), Anti-GR151004 Antibodies, Anti-hCG-alpha-peptide Antibodies (FA36, Anti hydroxyatrazine antibodies (HYB-283-2), Anti-Hydroxysimazine Antibodies, Anti Imazalil Antibodies MoAb's (9C1-1-1, 9C5-1-1, 9C6-1-1, 9C8-1-1, 9C9-1-1, 9C12-1-1, 9C14-1-1, 9C16-1-1, 9C18-1-1, 9C19-1-1, 9E1-1, 9G2-1), Anti Irgarol Antibodies, Anti Isopentenyl adenosine antibodies, Anti Isoproturon Antibodies, Anti-KB-6806 antiserum, Anti-(+)lupanine antibodies, Anti Lysophosphatidic (LPA) acid, Anti M3G Ab1 and Ab2, Anti M3G Ab1 and Ab2, Anti-MBC antibodies (Anti-2-succinamidobenzimidazole antiserum), Anti Metanephrine antibodies, anti (+)methamphetamine antibodies, Anti-Methiocarb Antibodies (LIB-MXNB31, LIB-MXNB-33, LIB-MXNH14 and LIB-MXNH-15 MAbs), Anti Metolachlor antibodies, Anti-Metolachlor Antibodies, Anti-Metolachlor Antibodies (MAb 4082-25-4), Anti Molinate Antibodies, Anti monuron antibodies, Anti-morphine-3-glucuronide (E3 scFv antibody), Anti morphine antibodies, Anti-Morphine antibodies, Anti-Morphine Antibodies (mAbs 8.2.1, 33.2.9, 35.4.12, 39.3.9, 44.4.1, 76.7F.16, 83.3.10, 115.1.3, 124.2.2, 131.5.13, 158.1.3, 180.2.4), Anti-Neopterin (D-erythro form) Antibodies, Anti-Nicarbazin Antibodies (Nic 6, Nic 7, Nic 8, and Nic 9), Anti Nicergoline Antibodies (Nic-1, Nic-2, Nic-3 & BNA-1, BNA-3), Anti-norflurazon antibodies, Anti NorMetanephrine antibodies, Anti (o-DNCP) Antibodies, Anti-P10 antibodies (TRH elongated peptide), Anti-Paraoxon Antibodies (BD1 and CE3), Anti Paraquat antibodies, Anti-Paraquat antibodies, anti Parathion-methyl antibodies, Anti PCB Antibodies (against 3,3',4,4'-tetrachlorobiphenyl) MAb S2B1, Anti pentachlorophenol antibodies, Anti Pentachlorophenol antibodies, Anti-Pentachlorophenol antibodies, Anti permethrin antibodies (Mabs Py-1, Py-3 and Py-4), Anti-Phencyclidine Antibodies (Mab 6B5 Fab), Anti-phenobarbital antibodies, Anti-phenobarbital antibodies, Anti-(p.p'-DDT)-Antibodies (LIB-DDT-35 and LIB-DDT5-52), Anti permethrin antibodies (Ab549), Anti Propoxur antibodies (LIB-PRNP15, LIB-PRNP21, LIB-PRNB21, LIB-PRNB33), Anti-Prostaglandin E2-antibodies, Anti-p-tyramine antibodies, Anti pyrene antibodies, Anti retronecine antibodies, Anti-Retronecine Antibodies, Anti salicylate antibodies, Anti Sennoside A antibodies (MAb 6G8), Anti Sennoside B antibodies (MAb's: 7H12, 5G6, 5C7), Anti Simizine antibodies, Anti Sulfonamides antibodies (Anti-TS), Anti-Sulocfuron antibodies (S2B5/1/C3), Anti sulphamethazine antibodies (21C7), Anti-synephrine antibodies, Anti-Thiabendazole antibodies (Antibody 300), Anti-Thiabendazole antibodies (Antibody 430 and 448), Anti-Thiram-Antibodies, Anti-THP antibodies (7S and 19S), Anti-Thromboxane B2 Antibodies, Anti-thymidine glycol monophosphate antibodies (mAb 2.6F.6B.6C), Anti-Thyroliberin (TRH) antibodies, Anti TNT antibodies (AB1 and AB2 antiserum), Anti Triadimefon Antibodies, Anti-triazine antibodies (AM1B5.1), Anti-triazine antibodies (AM5C5.3), Anti-triazine antibodies (AM5D1.2), Anti-triazine antibodies (AM7B2.1), Anti-triazine antibodies (SA5A0.1), Anti-Triazine serum (anti-ametryne), Anti-Triazine serum (anti-atrazine), Anti-Triazine serum (anti-simazine), Anti-Triazine serum (anti-simetryne), Anti Trifluralin Antibodies, Anti Trifluralin Antibodies, Anti Vincristine Antibodies, Anti-Zearalenone Antibodies, Anti Zeatin riboside antibodies, E2 G2 and E4 C2, Fab Fragment K411B derived from MAb K4E7 (isotype IgG2b with k light chain), LIB-BFNP23 Mab, MAb's H-7 and H-9 (against O,O-diethyl OP pesticides), MoAb 33A7-1-1, MoAb 33B8-1-1, MoAb 33C3-1-1, MoAb 3C10-1-1 and MoAb 3E17-1-1, MoAb 45D6-5-1, MoAb 45E6-1-1, MoAb 45-1-1, Mutant (GlnL89Glu) in Fab Fragment K411B derived from MAb K4E7 (isotype IgG2b with k light chain), Mutant (GlnL89Glu/ValH37Ile/GluL3Val) in Fab Fragment K411B derived from MAb K4E7 (isotype IgG2b with k light chain), Mutant (GlnL89Glu/ValH37Ile/GluL3Val) in Fab Fragment K411B derived from MAb K4E7 (isotype IgG2b with k light chain), Mutant (GlnL89Glu/ValH37Ile) in Fab Fragment K411B derived from MAb K4E7 (isotype IgG2b with k light chain), Mutant (GlnL89Glu/ValH37Ile) in Fab Fragment K411B derived from MAb K4E7 (isotype IgG2b with k light chain), Mutant (GluH50Gln) in Fab Fragment K411B derived from MAb K4E7 (isotype IgG2b with k light chain), Mutant (GluH50X) in Fab Fragment K411B derived from MAb K4E7 (isotype IgG2b with k light chain), Mutant (GlyH100aAla) in Fab Fragment K411B derived from MAb K4E7 (isotype IgG2b with k light chain), Mutant (GlyH100aSer) in Fab Fragment K411B derived from MAb K4E7 (isotype IgG2b with k light chain), Mutant (HisH95Phe) in Fab Fragment K411B derived from MAb K4E7 (isotype IgG2b with k light chain), Mutant (HisH95Tyr) in Fab Fragment K411B derived from MAb K4E7 (isotype IgG2b with k light chain), Mutant (PheL32Leu) in Fab Fragment K411B derived from MAb K4E7 (isotype IgG2b with k light chain), Mutant (TrpH33Phe,Tyr,Leu) in Fab Fragment K411B derived from MAb K4E7 (isotype IgG2b with k light chain), Mutant (Tryl96Phe) in Fab Fragment K411B derived from MAb K4E7 (isotype IgG2b with k light chain), Mutant (TryL96Phe) in Fab Fragment K411B derived from MAb K4E7 (isotype IgG2b with k light chain), Mutant (ValH37Ile) in Fab Fragment K411B derived from MAb K4E7 (isotype IgG2b with k light chain), Mutant (ValH37Ile) in Fab Fragment K411B derived from MAb K4E7 (isotype IgG2b with k light chain), P6A7 MAb, PNAS2 6/3 56(1)-1-5-1, PNAS2 6/3 56(1)-1-5-2, PNAS2 6/3 56(1)-1-10-4, PNAS2 6/3 56(1)-1-10-5 and PNAS2 6/3 56(1)-3-1-5, Alexa Fluor 405/Cascade Blue dye antibody, Alexa Fluor 488 dye antibody, BODIPY FL dye antibody, Dansyl antibody, Fluorescein/Oregon Green dye antibody, Lucifer yellow dye antibody, Tetramethylrhodamine and Rhodamine Red dye antibody, Texas Red and Texas Red-X dye antibody, Biotin antibody, Dinitrophenyl antibody and/or Nitrotyrosine antibody or any portion thereof of the aforementioned haptens.

In some alternatives, herein, the cells provided are cytotoxic T lymphocytes. "Cytotoxic T lymphocyte" (CTL) has its plain and ordinary meaning when read in light of the specification, and may include but is not limited to, for example, a T lymphocyte that expresses CD8 on the surface thereof (e.g., a CD8$^+$ T cell). In some alternatives such cells are preferably "memory" T cells ($T_M$ cells) that are antigen-experienced. In some alternatives, the cell is a precursor T cell. In some alternatives, the precursor T cell is a hematopoietic stem cell. In some alternatives, the cell is a CD8+ T cytotoxic lymphocyte cell selected from the group consisting of naïve CD8+ T cells, central memory CD8+ T cells, effector memory CD8+ T cells and bulk CD8+ T cells. In some alternatives, the cell is a CD4+ T helper lymphocyte cell that is selected from the group consisting of naïve CD4+ T cells, central memory CD4+ T cells, effector memory CD4+ T cells, and bulk CD4+ T cells.

"Masking moiety" has its plain and ordinary meaning when read in light of the specification, and may include but is not limited to, for example, a moiety on the lipid ether that is bound to the target moiety. The masking moiety functions as a protective group to prevent recognition of the lipid's target moiety by blocking binding and recognition of a chimeric antigen receptor that is specific for the target moiety. When the lipid is integrated into a cell, wherein the cell exists in a tumor environment or site of reactive oxygen species, the masking moiety can be self-cleaved, thus allowing binding and recognition of the target moiety by the chimeric antigen receptor. In some alternatives, the lipid is a phospholipid ether. In some alternatives, the masking moiety comprises a phenolic hydroxyl group or PEG. In some alternatives, the phenolic hydroxyl group is bound to a hydroxyl on a xanthene moiety of fluorescein. In some alternatives, the masking moiety is bound to the target moiety by a cleavable moiety, which is optionally configured to be specifically cleavable in a tumor microenvironment. In some alternatives, the cleavable moiety, which is configured to be cleavable in a tumor microenvironment, is cleaved by a reactive oxygen species reaction, an acidic pH, hypoxia, or nitrosylation. In some alternatives, the phospholipid ether comprises a target moiety and the CAR is joined to said phospholipid ether through an interaction with said target moiety. In some alternatives, the phospholipid ether comprises a polar-head group and a carbon alkyl chain. In some alternatives, the carbon alkyl chain comprises at least 8, 9, 10, 11, 12, 13, 14, 15, 16, 17, 18, 19, 20, 21 or 22 carbons or any number that is within a range defined by any two aforementioned values. In some alternatives, the carbon alkyl chain comprises 8-22 carbons, such as 8-12, 12-14, 14-16, or 16-22 carbons. In some alternatives, the masking moiety is removed when the composition is within an acidic environment. In some alternatives, the acidic environment comprises a pH of 4, 5, 6 or 6.5 or any pH in between a range defined by any two aforementioned values. In some alternatives, the masking moiety is removed by nitrosylation.

"Cancer," has its plain and ordinary meaning when read in light of the specification, and may include but is not limited to, for example, a group of diseases involving abnormal cell growth with the potential to invade or spread to other parts of the body. Subjects that can be addressed using the methods described herein include subjects identified or selected as having cancer, including but not limited to colon, lung, liver, breast, renal, prostate, ovarian, skin (including melanoma), bone, and brain cancer, etc. Such identification and/or selection can be made by clinical or diagnostic evaluation. In some alternatives, the tumor associated antigens or molecules are known, such as melanoma, breast cancer, brain cancer, squamous cell carcinoma, colon cancer, leukemia, myeloma, and/or prostate cancer. Examples include but are not limited to B cell lymphoma, breast cancer, brain cancer, prostate cancer, and/or leukemia. In some alternatives, one or more oncogenic polypeptides are associated with kidney, uterine, colon, lung, liver, breast, renal, prostate, ovarian, skin (including melanoma), bone, brain cancer, adenocarcinoma, pancreatic cancer, chronic myelogenous leukemia or leukemia. In some alternatives, a method of treating, ameliorating, or inhibiting a cancer in a subject is provided. In some alternatives, the cancer is breast, ovarian, lung, pancreatic, prostate, melanoma, renal, pancreatic, glioblastoma, neuroblastoma, medulloblastoma, sarcoma, liver, colon, skin (including melanoma), bone or brain cancer. In some alternatives, the subject is selected to receive an additional cancer therapy, which can include a cancer therapeutic, radiation, chemotherapy, or a drug for the treatment of cancer. In some alternatives, the drugs comprise Abiraterone, Alemtuzumab, Anastrozole, Aprepitant, Arsenic trioxide, Atezolizumab, Azacitidine, Bevacizumab, Bleomycin, Bortezomib, Cabazitaxel, Capecitabine, Carboplatin, Cetuximab, Chemotherapy drug combinations, Cisplatin, Crizotinib, Cyclophosphamide, Cytarabine, Denosumab, Docetaxel, Doxorubicin, Eribulin, Erlotinib, Etoposide, Everolimus, Exemestane, Filgrastim, Fluorouracil, Fulvestrant, Gemcitabine, Imatinib, Imiquimod, Ipilimumab, Ixabepilone, Lapatinib, Lenalidomide, Letrozole, Leuprolide, Mesna, Methotrexate, Nivolumab, Oxaliplatin, Paclitaxel, Palonosetron, Pembrolizumab, Pemetrexed, Prednisone, Radium-223, Rituximab, Sipuleucel-T, Sorafenib, Sunitinib, Talc Intrapleural, Tamoxifen, Temozolomide, Temsirolimus, Thalidomide, Trastuzumab, Vinorelbine or Zoledronic acid.

"Tumor microenvironment" has its plain and ordinary meaning when read in light of the specification, and may include but is not limited to, for example, a cellular environment, wherein a tumor exists. Without being limiting, the tumor microenvironment can include surrounding blood vessels, immune cells, fibroblasts, bone marrow-derived inflammatory cells, lymphocytes, signaling molecules and/or the extracellular matrix (ECM).

DETAILED DESCRIPTION

Described herein are synthetic molecular structures that are designed to decorate or label cancer cell membranes, such as tumor cell membranes. These synthetic structures contain recognition moieties that interact specifically with CAR T cells that are designed to target these recognition moieties. The molecular domains of phospholipid ether (PLE) CAR T cell tumor targeting (PLE-CTCT's) agents comprise a cell membrane integrating domain composed of a lipid housing a polar-head group. In some alternatives, the lipid is a phospholipid ether. Without being limiting, the polar-head group can comprise of a phosphocholine and the carbon alkyl chain can comprise a preferred length of 8-22 carbons, such as 8-12, 12-14, 14-16, or 16-22 carbons, preferably 18 carbons. The lipid (PLE) when administered may also target tumor and cancer cells. The lipid (PLE) may be administered intravenously. From this PLE backbone, an extracellular extension from the polar-head group is conceived to be composed of a spacer and a molecular structure to which a CAR binds to at affinities that induce a CAR-expressing effector cell, preferably a T cell, activation signaling. Further, the CAR recognition moiety of the PLE-CTCT is chemically modified such that the target moiety is masked from CAR recognition until it is chemically modified or unmasked by the tumor cell, tumor microenvironment (e.g., proteases present in the tumor microenvironment) or the tumor's milieu. In one exemplary alternative, the target moiety is fluorescein and the masking modification comprising a phenolic hydroxy group, is introduced to a hydroxyl on the xanthene moiety of the fluorescein molecule. In this alternative, the masking modification is removed from the fluorescein in a reactive oxygen species (ROS) reaction, which can occur in a tumor microenvironment. In general, masking elements are conceived that become unmasked by hydrolysis that is dependent on ROS, low pH, hypoxia, nitrosylation, protease digestion, and other chemical reactions taking place in the tumor microenvironment. In some alternatives herein, the unmasking is due to hydrolysis that is dependent on ROS, low pH, hypoxia, or nitrosylation within a tumor microenvironment.

As described in the alternatives herein, human tumor therapy is conceived in which patients receive infusions of PLE-CTCT's in combination with infusions of PLE-CTCT specific CAR T cells. The PLE-CTCT, when administered, may also target tumor and cancer cells. Administration may be by intravenous administration. In this exemplary alternative, this system represents a universal target antigen used in combination with a universal CAR and/or universal CAR expressing anti-tumor effector cell. In order to demonstrate proof-of-concept for this PLE-CTCT system, a PLE (18C alkyl chain) having a fluorescein (FL) appended CAR recognition element appended to the polar-head group's choline via PEG spacers was synthesized for use in the alternatives described herein. It was demonstrated that FL-specific scFv CAR T cells exhibit a redirected antitumor function in vitro and in vivo to tumors loaded with FL PLE-CTCT's. Moreover, a FL PLE-CTCT housing a ROS responsive mask, is described in an exemplary alternative herein for further specification of targeting agent to tumor cells with active ROS microenvironments.

Autologous T cells can be genetically modified to express transgenes that are engineered to enhance efficacy after transfer in vivo. Despite successful adoptive transfer of transgene modified T cells in the setting of CD19 B cell lineage malignancies, no universal CAR target antigen that is present on all forms of cancer but not normal cells has been identified. Thus, the field is hampered by the need to identify cell surface targets that are naturally present on tumor cells and minimally expressed by normal cells/tissues of the body. Thus, CAR T cell therapeutic development is hampered by the prospect of potentially needing tens to hundreds of vetted CAR targets and CARs to cover the majority of cancer types afflicting humans.

The conception of PLE-CTCT's is that a synthetic exogenously delivered molecular construct that A) integrates into all cellular membranes of cancer cells (e.g., tumor cells) but is selectively rapidly catabolized by normal cells relative to tumor cells, and B) is equipped with masking elements that selectively "unmask" on tumor cells, provides for a "universal target" for CAR T cell immunotherapy, wherein the CAR is specific to the unmasked target moiety of the PLE-CTCT.

The PLE's as described herein, have the capacity for differential slow tumor membrane clearance compared to normal cell rapid clearance. These PLE's have been conceived to carry imaging and radiotherapeutic payloads by modification to the alkyl chain of the PLE, which is buried within the lipid bilayers. As described in some alternatives herein, the target moieties were chemically built out from the PLE's polar-head group to present the target moieties to CAR effector cells that would necessarily have to occur on the extracellular side of the tumor cell's plasma membrane.

There are a number of different approaches to cancer therapy. This can include surgery, targeted drug delivery, chemotherapy and radiation. However, these approaches have only limited effectiveness. For example, although radiation therapy is a tool often used to treat cancer in an attempt to improve local tumor control, a key challenge is the limitation of dose escalation due to toxicity of neighboring sensitive normal organs. Additionally, one critical problem with many cancer treatments is that despite initial responses, cancers become resistant to conventional therapies, and the cells that persist after treatment drive disease relapse. As such, the methods provided herein can be used with and without these additional anti-cancer therapies so as to specifically target drug resistant residual disease or cancers.

Figure 1B:
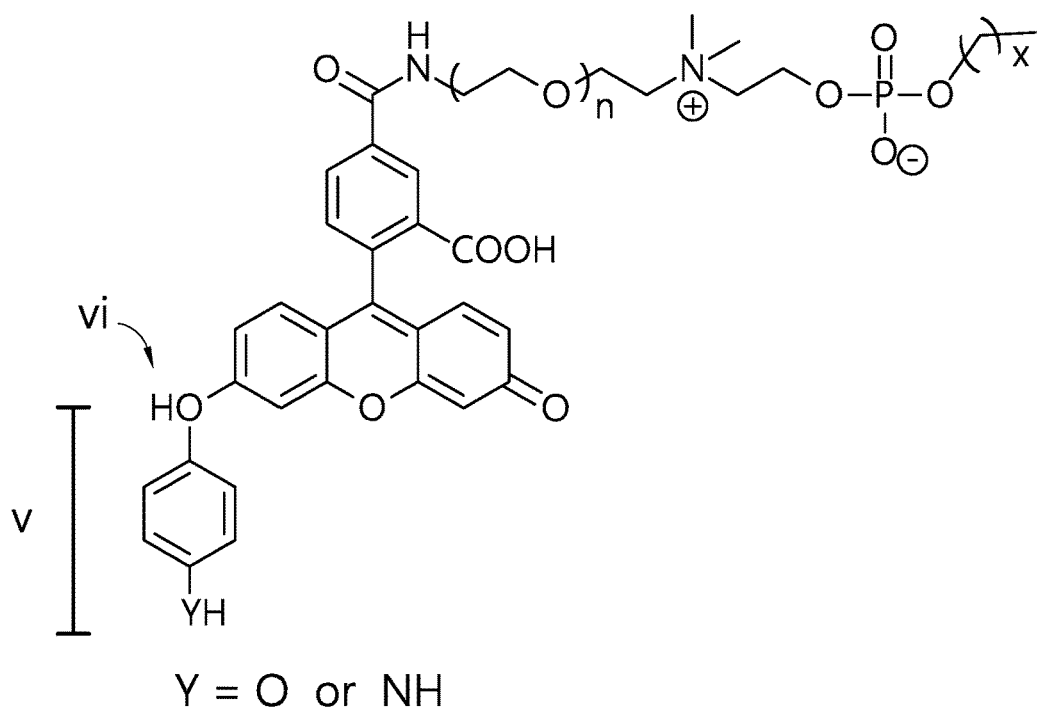

Examples of lipid CAR T cell tumor targeting agents are shown in FIGS. 1A and 1B. As shown are the structure of FL-PLE (1A) and ProFL-PLE (1B). (i) FL (fluorescein), the target for CAR T cells. (ii) Polyetheneglycol (PEG), the spacer used to extend the target an ideal distance from the cell surface. (iii & iv) PLE, iii is the polar head group and iv is the hydrophobic tail for incorporation or tethering into the cell plasma membrane. (v) Masking moiety, to prevent anti-FLCAR T cell recognition. (vi) The cleavage point where ProFL-PLE is unmasked. Unmasking to occur once or just before anti-FLCAR T-cells are in the reactive oxygen species (ROS) rich environment afforded by the tumor. This will in turn create the FL-PLE.

Figure 2:
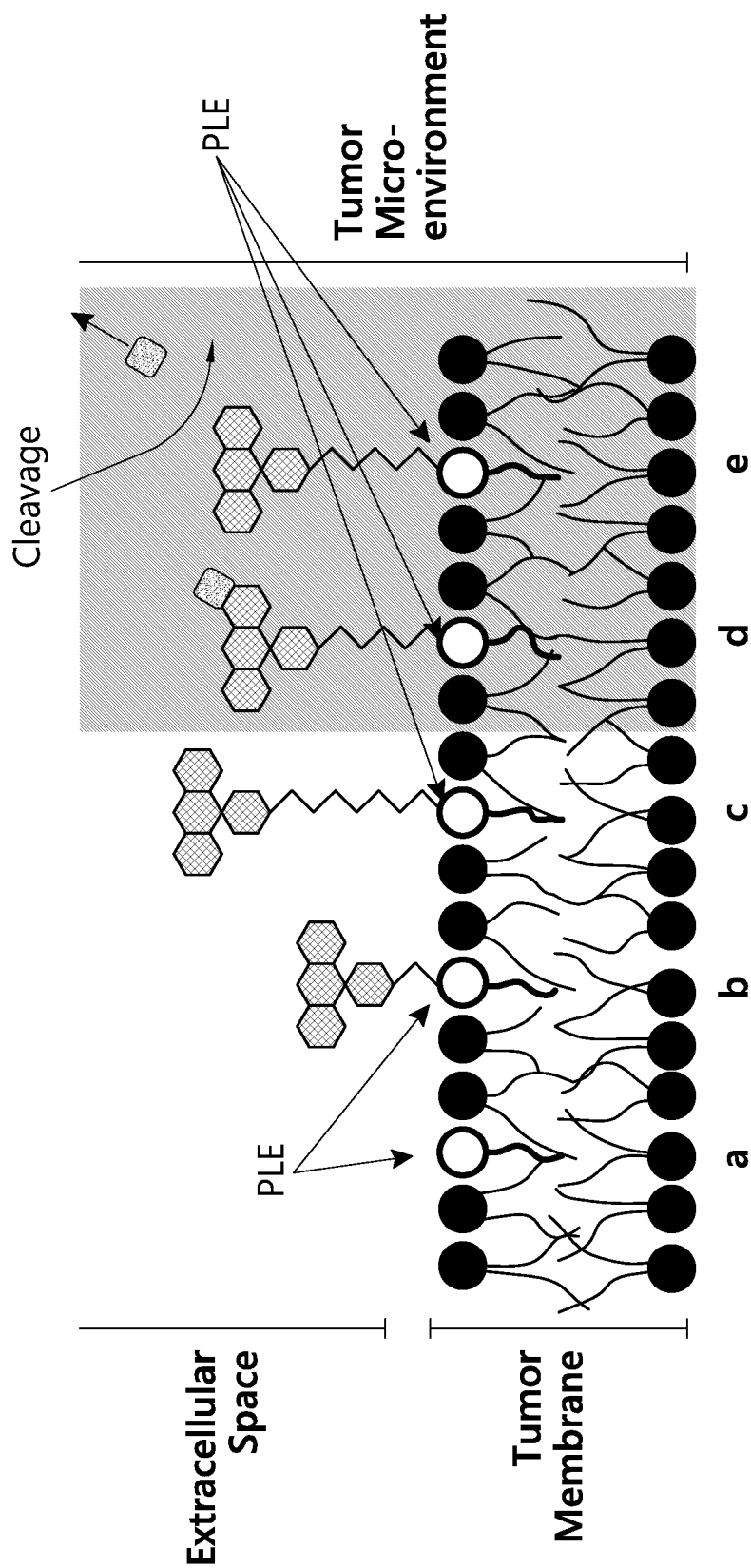
FIG. 2 shows the schematic of FL-PLE and ProFL-PLE. As shown in the letters on the Figure, (a) shows that a PLE is embedded into a lipid raft on the cell membrane of a tumor cell. As shown in (b) is a FL-PLE with a single PEG spacer compared to a four PEG spacer that is shown in (c). The PEG spacer will be varied until the optimal spacer length to antiFL CAR T-cell pair is identified. As shown in (d), is a ProFL-PLE containing a steric hindrance "masking" moiety and an "optimal" PEG spacer. As shown in (e), is the conversion of ProFL-PLE to FL-PLE due to masking moiety cleavage once inside the ROS rich tumor microenvironment. The FL-PLE is now bioavailable to antiFL CAR T-cells.

The lipid CAR T cell tumor targeting (CTCT) agents integrate into the membrane as shown in FIG. 2. The CTCT agent is preferential for a tumor cell, or a tumor cell membrane. The CTCT agent can embed into a lipid raft on the cell membrane of a tumor cell and the masking moiety can be removed inside a ROS rich tumor microenvironment so that recognition and interaction with the specific CAR T cells can take place.

Complexes

Described herein are complexes that comprise a chimeric antigen receptor (CAR) or TCR joined to a lipid, wherein the lipid comprises a target moiety and the CAR is joined to said lipid through an interaction with said target moiety. In some alternatives, the lipid is a phospholipid ether. In the alternatives herein, the lipid may target a tumor or a cancer cell or tumor or cancer cell membrane. The chimeric antigen receptor can comprise an antibody, antibody fragment, ScFv or other binding moiety that is specific for the target moiety. In some alternatives, the chimeric antigen receptor further comprises a spacer region found between the ligand binding domain (the site that recognizes the target moiety on the PLE) and the transmembrane domain of the chimeric receptor. In some alternatives, the spacer region has at least 10 to 229 amino acids, 10 to 200 amino acids, 10 to 175 amino acids, 10 to 150 amino acids, 10 to 125 amino acids, 10 to 100 amino acids, 10 to 75 amino acids, 10 to 50 amino acids, 10 to 40 amino acids, 10 to 30 amino acids, 10 to 20 amino acids, or 10 to 15 amino acids, or a length within a range defined by any two of the aforementioned lengths. In some alternatives, a spacer region has 12 amino acids or less, 119 amino acids or less, or 229 amino acids or less but greater than 1 or 2 amino acids. In some alternatives, the spacer is optimized or selected to increase the flexibility of the chimeric antigen receptor in order to allow binding to the target moiety. In some alternatives, the CAR comprises a co-stimulatory domain. In some alternatives, the lipid comprises a polar head group and a hydrophobic group. In some alternatives, the hydrophobic group is fatty acid such as an aliphatic chain. In some alternatives, the fatty acid is saturated or unsaturated. In some alternatives, the hydrophobic group comprises an alkyl, alkenyl or alkynyl group. In some alternatives, the hydrophobic group comprises a terpenoid lipid such as a steroid or cholesterol. In some alternatives, the hydrophobic group comprises an ether linkage, wherein the ether linkage is between the polar head group and the aliphatic chain. In some alternatives, the lipid is a phospholipid ether. In some alternatives, the polar head comprises a choline, a phosphatidylcholine, sphingomyelin, phosphoethanolamine group, an oligosaccharide residue, a sugar residue, phosphatidyl serine or phosphatidyl inositol. In some alternatives, the sugar is a glycerol. In some alternatives, the target moiety is a hapten, poly(his) tag, Strep-tag, FLAG-tag, V5-tag, Myc-tag, HA-tag, NE-tag, biotin, digoxigenin, dinotrophenol or fluorescein. In some alternatives, the hydrophobic group comprises a carbon alkyl chain, wherein the carbon alkyl chain comprises 8, 9, 10, 11, 12, 13, 14, 15, 16, 17, 18, 19, 20, 21 or 22 carbons or any number that is within a range defined by any two aforementioned values. In some alternatives, the carbon alkyl chain comprises at least 8-22 carbons, such as 8-12, 12-14, 14-16, or 16-22 carbons. In some alternatives, the polar-head group comprises phosphocholine, a piperidine moiety or a trimethylarseno-ethyl-phosphate moiety. In some alternatives, the lipid further comprises a spacer that separates the target moiety from the polar head group. In some alternatives, the spacer comprises a PEG spacer, a hapten (2×), (3×), (4×), or (5×) spacer, or an alkane chain. In some alternatives, the PEG spacer comprises 1, 2, 3, 4, 5, 6, 7, 8, 9, 10, 11, 12, 13, 14, 15, 16, 17, 18, 19, 20 or 21 PEG molecules, or any amount of PEG molecules that is within a range defined by any two aforementioned values. In some alternatives, the CAR or TCR is expressed by a cell or a T cell. In some alternatives, the CAR or TCR is on the surface of a cell or a T cell. In some alternatives, the cell is a precursor T cell. In some alternatives, the precursor T cell is a hematopoietic stem cell. In some alternatives, the cell is a CD8+ T cytotoxic lymphocyte cell selected from the group consisting of naïve CD8+ T cells, central memory CD8+ T cells, effector memory CD8+ T cells and bulk CD8+ T cells. In some alternatives, the cell is a CD4+ T helper lymphocyte cell that is selected from the group consisting of naïve CD4+ T cells, central memory CD4+ T cells, effector memory CD4+ T cells, and bulk CD4+ T cells. In some alternatives, the lipid is intercalated in a lipid bilayer of a target cell, such as a cancer cell. In some alternatives, the target cell is a tumor cell. In some alternatives, the target cell is an immune cell. In some alternatives, the immune cell is a T cell or a B cell. In some alternatives, the target cell exists in a tumor microenvironment.

In some alternatives, the complex comprises a chimeric antigen receptor (CAR) joined to an antibody or fragment thereof, wherein the antibody or fragment thereof comprises a target moiety and the CAR is joined to said antibody or fragment thereof through an interaction with said target moiety.

Complexes

Described herein are complexes that comprise a chimeric antigen receptor (CAR) or TCR joined to a targeting peptide, wherein the targeting peptide targets a tumor cell or a cancer cell, wherein the targeting peptide comprises a target moiety and the CAR is joined to said peptide through an interaction with said target moiety. The chimeric antigen receptor can comprise an antibody, antibody fragment, ScFv or other binding moiety that is specific for the target moiety. In some alternatives, the chimeric antigen receptor further comprises a spacer region found between the ligand binding domain (the site that recognizes the target moiety on the targeting peptide and the transmembrane domain of the chimeric receptor. In some alternatives, the spacer region has at least 10 to 229 amino acids, 10 to 200 amino acids, 10 to 175 amino acids, 10 to 150 amino acids, 10 to 125 amino acids, 10 to 100 amino acids, 10 to 75 amino acids, 10 to 50 amino acids, 10 to 40 amino acids, 10 to 30 amino acids, 10 to 20 amino acids, or 10 to 15 amino acids, or a length within a range defined by any two of the aforementioned lengths. In some alternatives, a spacer region has 12 amino acids or less, 119 amino acids or less, or 229 amino acids or less but greater than 1 or 2 amino acids. In some alternatives, the spacer is optimized or selected to increase the flexibility of the chimeric antigen receptor in order to allow binding to the target moiety. In some alternatives, the CAR comprises a co-stimulatory domain. In some alternatives, the targeting peptide comprises hydrophobic amino acids for integrating into the membrane of the target cell (e.g., a tumor cell or cancer cell). In some alternatives, the target moiety is a hapten, poly(his) tag, Strep-tag, FLAG-tag, V5-tag, Myc-tag, HA-tag, NE-tag, biotin, digoxigenin, dinotrophenol or fluorescein. In some alternatives, the targeting peptide further comprises a spacer that separates the target moiety from the polar head group. In some alternatives, the spacer comprises a poly(carboxybetaine), a peptide spacer, Polyglycidols, polyethylene, Polyanhydrides, Polyphosphoesters, Polycaprolactone, Poly(ethylene oxide), PEG spacer, a Hapten (2×), (3×), (4×), or (5×) spacer, or an alkane chain. In some alternatives, the PEG spacer comprises 1, 2, 3, 4, 5, 6, 7, 8, 9, 10, 11, 12, 13, 14, 15, 16, 17, 18, 19, 20 or 21 PEG molecules, or any amount of PEG molecules that is within a range defined by any two aforementioned values. In some alternatives, the CAR or TCR is expressed by a cell or a T cell. In some alternatives, the CAR or TCR is on the surface of a cell or a T cell. In some alternatives, the cell is a precursor T cell. In some alternatives, the precursor T cell is a hematopoietic stem cell. In some alternatives, the cell is a CD8+ T cytotoxic lymphocyte cell selected from the group consisting of naïve CD8+ T cells, central memory CD8+ T cells, effector memory CD8+ T cells and bulk CD8+ T cells. In some alternatives, the cell is a CD4+ T helper lymphocyte cell that is selected from the group consisting of naïve CD4+ T cells, central memory CD4+ T cells, effector memory CD4+ T cells, and bulk CD4+ T cells. In some alternatives, the targeting peptide is intercalated in a lipid bilayer of a target cell, such as a cancer cell. In some alternatives, the target cell is a tumor cell. In some alternatives, the target cell is an immune cell. In some alternatives, the immune cell is a T cell or a B cell. In some alternatives, the target cell exists in a tumor microenvironment.

In some alternatives, the complex comprises a chimeric antigen receptor (CAR) joined to an antibody or fragment thereof, wherein the antibody or fragment thereof comprises a target moiety and the CAR is joined to said antibody or fragment thereof through an interaction with said target moiety.

Cells

Described herein are cells comprising a chimeric antigen receptor (CAR) or T cell receptor (TCR) bound to a lipid, wherein the lipid comprises a target moiety and the cell comprising the CAR is bound to the target moiety of the lipid. In some alternatives, the lipid is a phospholipid ether. In some alternatives, the chimeric antigen receptor can comprise an antibody, antibody fragment, ScFv or other binding moiety that is specific for the target moiety. In some alternatives, the chimeric antigen receptor further comprises a spacer region found between the ligand binding domain (the site that recognizes the target moiety on the PLE) and the transmembrane domain of the chimeric receptor. In some alternatives, the spacer region has at least 10 to 229 amino acids, 10 to 200 amino acids, 10 to 175 amino acids, 10 to 150 amino acids, 10 to 125 amino acids, 10 to 100 amino acids, 10 to 75 amino acids, 10 to 50 amino acids, 10 to 40 amino acids, 10 to 30 amino acids, 10 to 20 amino acids, or 10 to 15 amino acids, or a length within a range defined by any two of the aforementioned lengths. In some alternatives, a spacer region has 12 amino acids or less, 119 amino acids or less, or 229 amino acids or less but greater than 1 or 2 amino acids. In some alternatives, the spacer is optimized to increase the flexibility of the chimeric antigen receptor in order to allow binding to the target moiety. In some alternatives, the CAR comprises a co-stimulatory domain. In some alternatives, the lipid comprises a polar head group and a hydrophobic group. In some alternatives, the hydrophobic group is fatty acid such as an aliphatic chain. In some alternatives, the fatty acid is saturated or unsaturated. In some alternatives, the hydrophobic group comprises an alkyl, alkenyl or alkynyl group. In some alternatives, the hydrophobic group comprises a terpenoid lipid such as a steroid or cholesterol or an aromatic ring. In some alternatives, the hydrophobic group comprises an ether linkage, wherein the ether linkage is between the polar head group and the aliphatic chain. In some alternatives, the lipid is a phospholipid ether. In some alternatives, the polar head comprises a choline, a phosphatidylcholine, sphingomyelin, phosphoethanolamine group, an oligosaccharide residue, a sugar residue, phosphatidyl serine or phosphatidyl inositol. In some alternatives, the sugar is a glycerol. In some alternatives, the target moiety is a hapten, poly(his) tag, Strep-tag, FLAG-tag, V5-tag, Myc-tag, HA-tag, NE-tag, biotin, digoxigenin, dinotrophenol or fluorescein. In some alternatives, the hydrophobic group comprises a carbon alkyl chain, wherein the carbon alkyl chain comprises 8, 9, 10, 11, 12, 13, 14, 15, 16, 17, 18, 19, 20, 21 or 22 carbons or any number that is within a range defined by any two aforementioned values. In some alternatives, the carbon alkyl chain comprises 8-22 carbons, such as 8-12, 12-14, 14-16, or 16-22 carbons. In some alternatives, the polar-head group comprises phosphocholine, a piperidine moiety or a trimethylarseno-ethyl-phosphate moiety. In some alternatives, the lipid further comprises a spacer group that separates the target moiety from the polar head group. In some alternatives, the spacer comprises a PEG spacer, a hapten (2×) spacer, or an alkane chain. In some alternatives, the PEG spacer comprises 1, 2, 3, 4, 5, 6, 7, 8, 9, 10, 11, 12, 13, 14, 15, 16, 17, 18, 19, 20 or 21 PEG molecules, or any amount of PEG molecules that is within a range defined by any two aforementioned values. In some alternatives, the cell is a precursor T cell. In some alternatives, the precursor T cell is a hematopoietic stem cell. In some alternatives, the cell is a CD8+ T cytotoxic lymphocyte cell selected from the group consisting of naïve CD8+ T cells, central memory CD8+ T cells, effector memory CD8+ T cells and bulk CD8+ T cells. In some alternatives, the cell is a CD4+ T helper lymphocyte cell that is selected from the group consisting of naïve CD4+ T cells, central memory CD4+ T cells, effector memory CD4+ T cells, and bulk CD4+ T cells. In some alternatives, the lipid is intercalated in a lipid bilayer of a target cell, such as a cancer cell. In some alternatives, the target cell is a tumor cell. In some alternatives, the target cell is an immune cell. In some alternatives, the immune cell is a T cell or a B cell. In some alternatives, the target cell exists in a tumor microenvironment.

Also described herein are cells comprising a chimeric antigen receptor (CAR) or T cell receptor (TCR) bound to an antibody or fragment thereof, wherein the antibody or fragment thereof comprises a target moiety and the cell comprising the CAR is bound to the target moiety of the antibody or fragment thereof.

Cells

Described herein are cells comprising a chimeric antigen receptor (CAR) or T cell receptor (TCR) bound to a targeting peptide, wherein the targeting peptide targets a tumor or cancer cell, wherein the targeting peptide comprises a target moiety and the cell comprising the CAR is bound to the target moiety of the lipid. In some alternatives, the chimeric antigen receptor can comprise an antibody, antibody fragment, ScFv or other binding moiety that is specific for the target moiety. In some alternatives, the chimeric antigen receptor further comprises a spacer region found between the ligand binding domain (the site that recognizes the target moiety on the PLE) and the transmembrane domain of the chimeric receptor. In some alternatives, the spacer region has at least 10 to 229 amino acids, 10 to 200 amino acids, 10 to 175 amino acids, 10 to 150 amino acids, 10 to 125 amino acids, 10 to 100 amino acids, 10 to 75 amino acids, 10 to 50 amino acids, 10 to 40 amino acids, 10 to 30 amino acids, 10 to 20 amino acids, or 10 to 15 amino acids, or a length within a range defined by any two of the aforementioned lengths. In some alternatives, a spacer region has 12 amino acids or less, 119 amino acids or less, or 229 amino acids or less but greater than 1 or 2 amino acids. In some alternatives, the spacer is optimized to increase the flexibility of the chimeric antigen receptor in order to allow binding to the target moiety. In some alternatives, the CAR comprises a co-stimulatory domain. In some alternatives, the lipid comprises a polar head group and a hydrophobic group. In some alternatives, targeting peptide comprises hydrophobic amino acids. In some alternatives, the target moiety is a hapten, poly(his) tag, Strep-tag, FLAG-tag, V5-tag, Myc-tag, HA-tag, NE-tag, biotin, digoxigenin, dinitrophenol or fluorescein. In some alternatives, the targeting peptide further comprises a spacer group that separates the target moiety from the polar head group. In some alternatives, the spacer comprises a PEG spacer, a hapten (2×), (3×), (4×), or (5×) spacer, or an alkane chain. In some alternatives, the PEG spacer comprises 1, 2, 3, 4, 5, 6, 7, 8, 9, 10, 11, 12, 13, 14, 15, 16, 17, 18, 19, 20 or 21 PEG molecules, or any amount of PEG molecules that is within a range defined by any two aforementioned values. In some alternatives, the cell is a precursor T cell. In some alternatives, the precursor T cell is a hematopoietic stem cell. In some alternatives, the cell is a CD8+ T cytotoxic lymphocyte cell selected from the group consisting of naïve CD8+ T cells, central memory CD8+ T cells, effector memory CD8+ T cells and bulk CD8+ T cells. In some alternatives, the cell is a CD4+ T helper lymphocyte cell that is selected from the group consisting of naïve CD4+ T cells, central memory CD4+ T cells, effector memory CD4+ T cells, and bulk CD4+ T cells. In some alternatives, the lipid is intercalated in a lipid bilayer of a target cell, such as a cancer cell. In some alternatives, the target cell is a tumor cell. In some alternatives, the target cell is an immune cell. In some alternatives, the immune cell is a T cell or a B cell. In some alternatives, the target cell exists in a tumor microenvironment.

Also described herein are cells comprising a chimeric antigen receptor (CAR) or T cell receptor (TCR) bound to an antibody or fragment thereof, wherein the antibody or fragment thereof comprises a target moiety and the cell comprising the CAR is bound to the target moiety of the antibody or fragment thereof.

Methods

A method of treating, ameliorating, or inhibiting a cancer in a subject is described herein. The method comprises a) introducing, providing, or administering to a subject a composition that comprises a lipid, which comprises a target moiety that is bound to a masking moiety and, optionally, by attachment through a spacer, b) introducing, providing, or administering to said subject a cell comprising a chimeric antigen receptor (CAR) or T cell receptor, which is specific for the target moiety once the masking moiety is removed from the target moiety, c) removing the masking moiety from the target moiety thereby allowing the target moiety to bind to and/or interact with the CAR present on the cell, and, d) optionally, measuring or evaluating the binding of the cell comprising the CAR to the lipid, after steps a-c and/or e) optionally, measuring or evaluating the treatment, amelioration, or inhibition of said cancer after steps a-d, and/or f) optionally, identifying a subject in need of a therapy for cancer prior to steps a-c. In some alternatives, the lipid targets a cell, such as a cancer cell or a tumor cell, or a tumor. In some alternatives, the lipid is a phospholipid ether. In some alternatives, the lipid comprises a polar head group and a hydrophobic group. In some alternatives, the hydrophobic group is fatty acid such as an aliphatic chain. In some alternatives, the fatty acid is saturated or unsaturated. In some alternatives, the hydrophobic group comprises an alkyl, alkenyl or alkynyl group. In some alternatives, the hydrophobic group comprises a terpenoid lipid such as a steroid or cholesterol or an aromatic ring. In some alternatives, the hydrophobic group comprises an ether linkage, wherein the ether linkage is between the polar head group and the aliphatic chain. In some alternatives, the lipid is a phospholipid ether. In some alternatives, the polar head comprises a choline, a phosphatidylcholine, sphingomyelin, phosphoethanolamine group, an oligosaccharide residue, a sugar residue, phosphatidyl serine or phosphatidyl inositol. In some alternatives, the sugar is a glycerol. In some alternatives, the target moiety is a hapten, poly(his) tag, Strep-tag, FLAG-tag, V5-tag, Myc-tag, HA-tag, NE-tag, biotin, digoxigenin, dinotrophenol or fluorescein. Administration of the composition and the CAR T cell may be by intravenous administration. In some alternatives, the hydrophobic group comprises a carbon alkyl chain. In some alternatives, the carbon alkyl chain comprises 8, 9, 10, 11, 12, 13, 14, 15, 16, 17, 18, 19, 20, 21 or 22 carbons or any number that is within a range defined by any two aforementioned values. In some alternatives, the carbon alkyl chain comprises 8-22 carbons, such as 8-12, 12-14, 14-16, or 16-22 carbons. In some alternatives, the polar-head group comprises phosphocholine, a piperidine moiety or a trimethylarseno-ethyl-phosphate moiety. In some alternatives, the spacer comprises a PEG spacer, a hapten (2×) spacer, or an alkane chain. In some alternatives, the PEG spacer comprises 1, 2, 3, 4, 5, 6, 7, 8, 9, 10, 11, 12, 13, 14, 15, 16, 17, 18, 19, 20 or 21 PEG molecules, or any amount of PEG molecules that is within a range defined by any two aforementioned values. In some alternatives, the masking moiety comprises a phenolic hydroxyl group or PEG. In some alternatives, the phenolic hydroxyl group is bound to a hydroxyl on a xanthene moiety of fluorescein. In some alternatives, the masking moiety is bound to the target moiety by a cleavable moiety, which is optionally configured to be specifically cleavable in a tumor microenvironment. In some alternatives, the cleavable moiety, which is configured to be cleavable in a tumor microenvironment, is cleaved by a reactive oxygen species reaction, an acidic pH, hypoxia, or nitrosylation. In some alternatives, the cell is provided to the subject the cell is provided to the subject 1, 2, 3, 4, 5, 6, 7, 8, 9, 10, 11, 12, 15, 20, 24, 36, 48, 60 or 72 hours after administration of the composition, or any time within a range defined by any two aforementioned values. In some alternatives, the cell is provided to the subject 1, 2, 3, 4, 5, 6, 7, 8, 9, 10, 11, 12, 15, 20, 24, 36 or 48 hours before administration of the composition, or any time within a range defined by any two aforementioned values. Administration of the composition and the CAR T cell may be by intravenous administration. In some alternatives, the cell is provided to the subject within seconds or minutes, such as less than an hour, of providing the composition to the subject. In some alternatives, a boost of the cell and/or the composition is provided to the subject. In some alternatives, an additional cancer therapy is provided, such as a small molecule, e.g., a chemical compound, an antibody therapy, e.g., a humanized monoclonal antibody with or without conjugation to a radionuclide, toxin, or drug, surgery, and/or radiation. In some alternatives, the cancer is breast, ovarian, lung, pancreatic, prostate, melanoma, renal, pancreatic, glioblastoma, neuroblastoma, medulloblastoma, sarcoma or liver cancer. In some alternatives, the cell comprising the CAR or TCR is a T cell. In some alternatives, the CAR or TCR is on the surface of the cell or the T cell. In some alternatives, the cell is a precursor T cell. In some alternatives, the precursor T cell is a hematopoietic stem cell. In some alternatives, the cell is a CD8+ T cytotoxic lymphocyte cell selected from the group consisting of naïve CD8+ T cells, central memory CD8+ T cells, effector memory CD8+ T cells and bulk CD8+ T cells. In some alternatives, the cell is a CD4+ T helper lymphocyte cell that is selected from the group consisting of naïve CD4+ T cells, central memory CD4+ T cells, effector memory CD4+ T cells, and bulk CD4+ T cells. In some alternatives, the lipid intercalates in a lipid bilayer of a target cell, such as a cancer cell. In some alternatives, the target cell is a tumor cell. In some alternatives, the target cell is an immune cell. In some alternatives, the immune cell is a T cell or a B cell. In some alternatives, the target cell exists in a tumor microenvironment. In some alternatives, a boost of the cell and/or the composition is provided to the subject. In some alternatives, free or freely available target moiety, such as fluorescein is provided to the subject so as to quench the therapy being provided. In some alternatives, an additional cancer therapy is provided, such as a small molecule, e.g., a chemical compound, an antibody therapy, e.g., a humanized monoclonal antibody with or without conjugation to a radionuclide, toxin, or drug, surgery, and/or radiation. In some alternatives, the cancer is breast, ovarian, lung, pancreatic, prostate, melanoma, renal, pancreatic, glioblastoma, neuroblastoma, medulloblastoma, sarcoma or liver cancer. In some alternatives, the cancer is breast, ovarian, lung, pancreatic, prostate, melanoma, renal, pancreatic, glioblastoma, neuroblastoma, medulloblastoma, sarcoma, liver, colon, skin (including melanoma), bone or brain cancer. In some alternatives, the subject is selected to receipt additional cancer therapy, which can include cancer therapeutics or drugs for the treatment of cancer. In some alternatives, the drugs comprise Abiraterone, Alemtuzumab, Anastrozole, Aprepitant, Arsenic trioxide, Atezolizumab, Azacitidine, Bevacizumab, Bleomycin, Bortezomib, Cabazitaxel, Capecitabine, Carboplatin, Cetuximab, Chemotherapy drug combinations, Cisplatin, Crizotinib, Cyclophosphamide, Cytarabine, Denosumab, Docetaxel, Doxorubicin, Eribulin, Erlotinib, Etoposide, Everolimus, Exemestane, Filgrastim, Fluorouracil, Fulvestrant, Gemcitabine, Imatinib, Imiquimod, Ipilimumab, Ixabepilone, Lapatinib, Lenalidomide, Letrozole, Leuprolide, Mesna, Methotrexate, Nivolumab, Oxaliplatin, Paclitaxel, Palonosetron, Pembrolizumab, Pemetrexed, Prednisone, Radium-223, Rituximab, Sipuleucel-T, Sorafenib, Sunitinib, Talc Intrapleural, Tamoxifen, Temozolomide, Temsirolimus, Thalidomide, Trastuzumab, Vinorelbine or Zoledronic acid. In some alternatives, the masking moiety is removed when the composition is within an acidic environment. In some alternatives, the acidic environment comprises a pH of 4, 5, 6 or 6.5 or any pH in between a range defined by any two aforementioned values. In some alternatives, the masking moiety is removed by nitrosylation.

In some embodiments is provided a method comprising a) introducing, providing, or administering to a subject a composition that comprises an antibody or binding fragment thereof, which comprises a target moiety, b) introducing, providing, or administering to said subject a cell comprising a chimeric antigen receptor (CAR), such as a T cell, which is specific for the target moiety, and, c) optionally, measuring or evaluating the binding of the cell comprising the CAR to the antibody or fragment thereof, after steps a-c and/or d) optionally, measuring or evaluating the treatment, amelioration, or inhibition of said cancer after steps a-b, and/or e) optionally, identifying a subject in need of a therapy for cancer prior to steps a-b. In some embodiments, the antibody or binding fragment thereof comprising a target moiety is an antibody or binding fragment thereof specific to a cancer cell or a pathogenic cell. In some embodiments, the antibody or binding fragment thereof comprising the target moiety is specific to a tumor cell. Administration of the composition and the CAR T cell may be by intravenous administration. In some embodiments, the antibody or binding fragment thereof comprising the target moiety includes abagovomab, abituzumab, adecatumumab, afutuzumab, alacizumab pegol, alemtuzumab, altumomab pentetate, amatuximab, anatumomab mafenatox, anetumab ravtansine, apolizumab, arcitumomab, ascrinvacumab, aselizumab, atezolizumab, atlizumab, avelumab, bapineuzumab, bavituximab, bectumomab, belimumab, besilesomab, bevacizumab, bivatuzumab mertansine, blinatumomab, blontuvetmab, brentuximab, brontictuzumab, cantuzumab mertansine, cantuzumab ravansine, capromab pendetide, carlumab, carotuximab, catumaxomab, cBR96-doxorubicin immunoconjugate, cedelizumab, certolizumab pegol, cetuximab, cidfusituzumab, cidtuzumab, citatuzumab bogatox, cixutumumab, clivatuzumab tetraxetan, codrituzumab, coltuximab ravtansine, conatumumab, dacetuzumab, daclizumab, dalotuzumab, daratumumab, demcizumab, denintuzumab mafodotin, denosumab, depatuxizumab mafodotin, derlotuximab biotin, detumomab, dinutuximab, drozitumab, duligotumab, durvalumab, dusigitumab, duvortuxizumab, ecromeximab, eculizumab, edrecolomab, efalizumab, elgemtumab, elotuzumab, emactuzumab, emibetuzumab, enavatuzumab, enfortumab vedotin, enoblituzumab, enoticumab, ensituximab, epratuzumab, erlizumab, ertumaxomab, etaracizumab, farletuzumab, FBTA05, femzumab, ficlatuzumab, figitumumab, flanvotumab, fontolizumab, futuximab, galiximab, ganitumab, gemtuzumab ozogamicin, girentuximab, glembatumumab vedotin, ibritumomab, icrucumab, igovomab, IMAB362, imalumab, imgatuzumab, indatuximab ravtansine, indusatumab vedotin, intetumumab, inotuzumab ozogamicin, intetumumab, ipilimumab, iratumumab, isatuximab, labetuzumab, lambrolizumab, lexatumumab, lifastuzumab vedotin, lilotomab satetraxetan, lintuzumab, lorvotuzumab mertansine, lucatumumab, lumiliximab, lumretuzumab, mapatumumab, margetuximab, matuzumab, mepolizumab, milatuzumab, minretumomab, mirvetuximab soravtansine, mitumomab, mogamulizumab, moxetumomab pasudotox, nacolomab tafenatox, naptumomab estafenatox, narnatumab, natalizumab, necitumumab, nesvacumab, nimotuzumab, nivolumab, nofetumomab merpentan, obinutuzumab, ocaratuzumab, ocrelizumab, ofatumumab, olaratumab, omalizumab, onartuzumab, ontuxizumab, oportuzumab monatox, oregovomab, otlertuzumab, panitumumab, pankomab, parsatuzumab, pascolizumab, pasotuxizumab, patritumab, pecfusituzumab, pectuzumab, pembrolizumab, pemtumomab, pertuzumab, pexelizumab, pidilizumab, pinatuzumab vedotin, pintumomab, polatuzumab vedotin, pritumumab, racotumomab, radretumab, ramucirumab, ranibizumab, reslizumab, rilotumumab, rituximab, robatumumab, rovelizumab, ruplizumab, sacituzumab govitecan, samalizumab, satumomab pendetide, seribantumab, sibrotuzumab, SGN-CD19A, SGN-CD33A, simtuzumab, siplizumab, siltuximab, sofituzumab vedotin, solitomab, sontuzumab, tabalumab, tacatuzumab tetraxetan, tadocizumab, talizumab, tamtuvetmab, taplitumomab paptox, tarextumab, tenatumomab, teprotumumab, TGN1412, ticilimumab (tremelimumab), tigatuzumab, TNX-650, tocilizumab, toralizumab, tositumomab, tovetumab, trastuzumab, TRB S07, tremelimumab, tucotuzumab celmoleukin, tucusituzumab, ublituximab, ulocuplumab, urelumab, urtoxazumab, ustekinumab, vandortuzumab vedotin, vantictumab, vanucizumab, veltuzumab, vesencumab, visilizumab, volociximab, vorsetuzumab mafodotin, votumumab, zalutumamab, zanolimumab, or zatuximab, or a derivative, analogue, or binding fragment thereof.

In some embodiments, the antibody or binding fragment thereof, which comprises the target moiety, includes cosfroviximab, diridavumab, exbivirumab, felvizumab, foravirumab, larcaviximab, libivirumab, motavizumab, motovizumab, nolovizumab, numavizumab, palivizumab, porgaviximab, PRO 140, rafivirumab, ralivizumab, regavirumab, reslivizumab, resyvizumab, sevirumab, suvizumab, tuvirumab, or umavizumab or a derivative, analogue, or binding fragment thereof. In some embodiments, the antibody or binding fragment thereof includes, edobacomab, nebacumab, pagibaximab, panobacumab, raxibacumab, or tefibazumab or a derivative, analogue, or binding fragment thereof. In some embodiments, the antibody or binding fragment thereof includes actoxumab, bezlotoxumab, efungumab, obiltoxaximab, suvratoxumab, or urtoxazumab, or a derivative, analogue, or binding fragment thereof.

Methods

A method of treating, ameliorating, or inhibiting a cancer in a subject is described herein. The method comprises a) introducing, providing, or administering to a subject a composition that comprises a targeting peptide, which comprises a target moiety that is bound to a masking moiety and, optionally, by attachment through a spacer, b) introducing, providing, or administering to said subject a cell comprising a chimeric antigen receptor (CAR) or T cell receptor, which is specific for the target moiety once the masking moiety is removed from the target moiety, c) removing the masking moiety from the target moiety thereby allowing the target moiety to bind to and/or interact with the CAR present on the cell, and, d) optionally, measuring or evaluating the binding of the cell comprising the CAR to the targeting peptide, after steps a-c and/or e) optionally, measuring or evaluating the treatment, amelioration, or inhibition of said cancer after steps a-d, and/or f) optionally, identifying a subject in need of a therapy for cancer prior to steps a-c. In some alternatives, targeting peptide comprises hydrophobic amino acids. In some alternatives, the target moiety is a hapten, poly(his) tag, Strep-tag, FLAG-tag, V5-tag, Myc-tag, HA-tag, NE-tag, biotin, digoxigenin, dinotrophenol or fluorescein. In some alternatives, the targeting peptide comprises a spacer for the targeting moiety. In some alternatives, the spacer comprises a poly(carboxybetaine), peptide, Polyglycidols, polyethylene, Polyanhydrides, Polyphosphoesters, Polycaprolactone, Poly(ethylene oxide), PEG spacer, a Hapten (2x), (3x), (4x), or (5x) spacer, or an alkane chain. In some alternatives, the PEG spacer comprises 1, 2, 3, 4, 5, 6, 7, 8, 9, 10, 11, 12, 13, 14, 15, 16, 17, 18, 19, 20 or 21 PEG molecules, or any amount of PEG molecules that is within a range defined by any two aforementioned values. In some alternatives, the masking moiety comprises a phenolic hydroxyl group or PEG. In some alternatives, the phenolic hydroxyl group is bound to a hydroxyl on a xanthene moiety of fluorescein. In some alternatives, the masking moiety is bound to the target moiety by a cleavable moiety, which is optionally configured to be specifically cleavable in a tumor microenvironment. In some alternatives, the cleavable moiety, which is configured to be cleavable in a tumor microenvironment, is cleaved by a reactive oxygen species reaction, an acidic pH, hypoxia, or nitrosylation. In some alternatives, the cell is provided to the subject the cell is provided to the subject 1, 2, 3, 4, 5, 6, 7, 8, 9, 10, 11, 12, 15, 20, 24, 36, 48, 60 or 72 hours after administration of the composition, or any time within a range defined by any two aforementioned values. In some alternatives, the cell is provided to the subject 1, 2, 3, 4, 5, 6, 7, 8, 9, 10, 11, 12, 15, 20, 24, 36 or 48 hours before administration of the composition, or any time within a range defined by any two aforementioned values. In some alternatives, the cell is provided to the subject within seconds or minutes, such as less than an hour, of providing the composition to the subject. In some alternatives, a boost of the cell and/or the composition is provided to the subject. In some alternatives, an additional cancer therapy is provided, such as a small molecule, e.g., a chemical compound, an antibody therapy, e.g., a humanized monoclonal antibody with or without conjugation to a radionuclide, toxin, or drug, surgery, and/or radiation. In some alternatives, the cancer is breast, ovarian, lung, pancreatic, prostate, melanoma, renal, pancreatic, glioblastoma, neuroblastoma, medulloblastoma, sarcoma or liver cancer. In some alternatives, the cell comprising the CAR or TCR is a T cell. In some alternatives, the CAR or TCR is on the surface of the cell or the T cell. In some alternatives, the cell is a precursor T cell. In some alternatives, the precursor T cell is a hematopoietic stem cell. In some alternatives, the cell is a CD8+ T cytotoxic lymphocyte cell selected from the group consisting of naïve CD8+ T cells, central memory CD8+ T cells, effector memory CD8+ T cells and bulk CD8+ T cells. In some alternatives, the cell is a CD4+ T helper lymphocyte cell that is selected from the group consisting of naïve CD4+ T cells, central memory CD4+ T cells, effector memory CD4+ T cells, and bulk CD4+ T cells. In some alternatives, the targeting peptide intercalates in a lipid bilayer of a target cell, such as a cancer cell. In some alternatives, the target cell is a tumor cell. In some alternatives, the target cell is an immune cell. In some alternatives, the immune cell is a T cell or a B cell. In some alternatives, the target cell exists in a tumor microenvironment. In some alternatives, a boost of the cell and/or the composition is provided to the subject. In some alternatives, free or freely available target moiety, such as fluorescein is provided to the subject so as to quench the therapy being provided. In some alternatives, an additional cancer therapy is provided, such as a small molecule, e.g., a chemical compound, an antibody therapy, e.g., a humanized monoclonal antibody with or without conjugation to a radionuclide, toxin, or drug, surgery, and/or radiation. In some alternatives, the cancer is breast, ovarian, lung, pancreatic, prostate, melanoma, renal, pancreatic, glioblastoma, neuroblastoma, medulloblastoma, sarcoma or liver cancer. In some alternatives, the cancer is breast, ovarian, lung, pancreatic, prostate, melanoma, renal, pancreatic, glioblastoma, neuroblastoma, medulloblastoma, sarcoma, liver, colon, skin (including melanoma), bone or brain cancer. In some alternatives, the subject is selected to receipt additional cancer therapy, which can include cancer therapeutics or drugs for the treatment of cancer. In some alternatives, the drugs comprise Abiraterone, Alemtuzumab, Anastrozole, Aprepitant, Arsenic trioxide, Atezolizumab, Azacitidine, Bevacizumab, Bleomycin, Bortezomib, Cabazitaxel, Capecitabine, Carboplatin, Cetuximab, Chemotherapy drug combinations, Cisplatin, Crizotinib, Cyclophosphamide, Cytarabine, Denosumab, Docetaxel, Doxorubicin, Eribulin, Erlotinib, Etoposide, Everolimus, Exemestane, Filgrastim, Fluorouracil, Fulvestrant, Gemcitabine, Imatinib, Imiquimod, Ipilimumab, Ixabepilone, Lapatinib, Lenalidomide, Letrozole, Leuprolide, Mesna, Methotrexate, Nivolumab, Oxaliplatin, Paclitaxel, Palonosetron, Pembrolizumab, Pemetrexed, Prednisone, Radium-223, Rituximab, Sipuleucel-T, Sorafenib, Sunitinib, Talc Intrapleural, Tamoxifen, Temozolomide, Temsirolimus, Thalidomide, Trastuzumab, Vinorelbine or Zoledronic acid. In some alternatives, the masking moiety is removed when the composition is within an acidic environment. In some alternatives, the acidic environment comprises a pH of 4, 5, 6 or 6.5 or any pH in between a range defined by any two aforementioned values. In some alternatives, the masking moiety is removed by nitrosylation. Administration of the composition and the CAR T cell may be by intravenous administration.

In some embodiments is provided a method comprising a) introducing, providing, or administering to a subject a composition that comprises an antibody or binding fragment thereof, which comprises a target moiety, b) introducing, providing, or administering to said subject a cell comprising a chimeric antigen receptor (CAR), such as a T cell, which is specific for the target moiety, and, c) optionally, measuring or evaluating the binding of the cell comprising the CAR to the antibody or fragment thereof, after steps a-c and/or d) optionally, measuring or evaluating the treatment, amelioration, or inhibition of said cancer after steps a-b, and/or e) optionally, identifying a subject in need of a therapy for cancer prior to steps a-b. In some embodiments, the antibody or binding fragment thereof comprising a target moiety is an antibody or binding fragment thereof specific to a cancer cell or a pathogenic cell. In some embodiments, the antibody or binding fragment thereof comprising the target moiety is specific to a tumor cell. In some embodiments, the antibody or binding fragment thereof comprising the target moiety includes abagovomab, abituzumab, adecatumumab, afutuzumab, alacizumab pegol, alemtuzumab, altumomab pentetate, amatuximab, anatumomab mefanetox, anetumab ravtansine, apolizumab, arcitumomab, ascrinvacumab, aselizumab, atezolizumab, atlizumab, avelumab, bapineuzumab, bavituximab, bectumomab, belimumab, besilesomab, bevacizumab, bivatuzumab mertansine, blinatumomab, blontuvetmab, brentuximab, brontictuzumab, cantuzumab mertansine, cantuzumab ravansine, capromab pendetide, carlumab, carotuximab, catumaxomab, cBR96-doxorubicin immunoconjugate, cedelizumab, certolizumab pegol, cetuximab, cidfusituzumab, cidtuzumab, citatuzumab bogatox, cixutumumab, clivatuzumab tetraxetan, codrituzumab, coltuximab ravtansine, conatumumab, dacetuzumab, daclizumab, dalotuzumab, daratumumab, demcizumab, denintuzumab mafodotin, denosumab, depatuxizumab mafodotin, derlotuximab biotin, detumomab, dinutuximab, drozitumab, duligotumab, durvalumab, dusigitumab, duvortuxizumab, ecromeximab, eculizumab, edrecolomab, efalizumab, elgemtumab, elotuzumab, emactuzumab, emibetuzumab, enavatuzumab, enfortumab vedotin, enoblituzumab, enoticumab, ensituximab, epratuzumab, erlizumab, ertumaxomab, etaracizumab, farletuzumab, FBTA05, femzumab, ficlatuzumab, figitumumab, flanvotumab, fontolizumab, futuximab, galiximab, ganitumab, gemtuzumab ozogamicin, girentuximab, glembatumumab vedotin, ibritumomab, icrucumab, igovomab, IMAB362, imalumab, imgatuzumab, indatuximab ravtansine, indusatumab vedotin, intetumumab, inotuzumab ozogamicin, intetumumab, ipilimumab, iratumumab, isatuzimab, labetuzumab, lambrolizumab, lexatumumab, lifastuzumab vedotin, lilotomab satetraxetan, lintuzumab, lorvotuzumab mertansine, lucatumumab, lumiliximab, lumretuzumab, mapatumumab, margetuximab, matuzumab, mepolizumab, milatuzumab, minretumomab, mirvetuximab soravtansine, mitumomab, mogamulizumab, moxetumomab pasudotox, nacolomab tafenatox, naptumomab estafenatox, narnatumab, natalizumab, necitumumab, nesvacumab, nimotuzumab, nivolumab, nofetumomab merpentan, obinutuzumab, ocaratuzumab, ocrelizumab, ofatumumab, olaratumab, omalizumab, onartuzumab, ontuxizumab, oportuzumab monatox, oregovomab, otlertuzumab, panitumumab, pankomab, parsatuzumab, pascolizumab, pasotuxizumab, patritumab, pecfusituzumab, pectuzumab, pembrolizumab, pemtumomab, pertuzumab, pexelizumab, pidilizumab, pinatuzumab vedotin, pintumomab, polatuzumab vedotin, pritumumab, racotumomab, radretumab, ramucirumab, ranibizumab, reslizumab, rilotumumab, rituximab, robatumumab, rovelizumab, ruplizumab, sacituzumab govitecan, samalizumab, satumomab pendetide, seribantumab, sibrotuzumab, SGN-CD19A, SGN-CD33A, simtuzumab, siplizumab, siltuximab, sofituzumab vedotin, solitomab, sontuzumab, tabalumab, tacatuzumab tetraxetan, tadocizumab, talizumab, tamtuvetmab, taplitumomab paptox, tarextumab, tenatumomab, teprotumumab, TGN1412, ticilimumab (tremelimumab), tigatuzumab, TNX-650, tocilizumab, toralizumab, tositumomab, tovetumab, trastuzumab, TRB S07, tremelimumab, tucotuzumab celmoleukin, tucusituzumab, ublituximab, ulocuplumab, urelumab, urtoxazumab, ustekinumab, vandortuzumab vedotin, vantictumab, vanucizumab, veltuzumab, vesencumab, visilizumab, volociximab, vorsetuzumab mafodotin, votumumab, zalutumamab, zanolimumab, or zatuximab, or a derivative, analogue, or binding fragment thereof. Administration of the composition and the CAR T cell may be by intravenous administration.

In some embodiments, the antibody or binding fragment thereof, which comprises the target moiety, includes cosfroviximab, diridavumab, exbivirumab, felvizumab, foravirumab, larcaviximab, libivirumab, motavizumab, motovizumab, nolovizumab, numavizumab, palivizumab, porgaviximab, PRO 140, rafivirumab, ralivizumab, regavirumab, reslivizumab, resyvizumab, sevirumab, suvizumab, tuvirumab, or umavizumab or a derivative, analogue, or binding fragment thereof. In some embodiments, the antibody or binding fragment thereof includes, edobacomab, nebacumab, pagibaximab, panobacumab, raxibacumab, or tefibazumab or a derivative, analogue, or binding fragment thereof. In some embodiments, the antibody or binding fragment thereof includes actoxumab, bezlotoxumab, efungumab, obiltoxaximab, suvratoxumab, or urtoxazumab, or a derivative, analogue, or binding fragment thereof.

Alternative 1: CARS Designed for Binding a Target Moiety.

In some alternatives herein, the binding site of the chimeric antigen receptor (CAR) is designed so as to bind and/or interact with a target moiety of the FL-PLE. The targeting moiety may be a hapten, poly(his) tag, Strep-tag, FLAG-tag, V5-tag, Myc-tag, HA-tag, NE-tag, biotin, digoxigenin, dinotrophenol or fluorescein. The CAR comprises an antibody or antibody fragment, ScFv or a protein or portion thereof that is designed to recognize the target moiety. Designing proteins for interactions are known to those skilled in the art, and are desirably very specific, as proteins can interact with a large number of proteins or chemicals such as FL, for example, thus successful design should utilize selective binders. Thus, protein design algorithms can be used to distinguish between on target and off target binding. The protein can also be designed by focusing on electrostatic contributions, so as to increase the affinity for its binding partner, or target moiety. Screening of a variety of different CAR structures can be performed by contacting cells comprising CARs, which are specific for a target moiety, with a substrate or binding agent comprising said target moiety and evaluating the binding of the CARs to said substrate or binding agent. Additionally, a target cell or a target virus unto which the binding agent is specific can be added so that the formation of a complex comprising the cell, which comprises the CAR, bound to the binding agent by virtue of the interaction of the CAR and the target moiety, and a target cell or virus unto which the binding agent is specific for can be evaluated. In some alternatives, the scFv is specific for the FL-PLE. However, increasing the binding affinity of a CAR does not always increase the effects that one would expect for a high affinity binding CAR.

In some alternatives herein, the binding site of the chimeric antigen receptor (CAR) is designed so as to bind and/or interact with a target moiety of the targeting peptide. The targeting moiety may be a hapten, poly(his) tag, Strep-tag, FLAG-tag, V5-tag, Myc-tag, HA-tag, NE-tag, biotin, digoxigenin, dinitrophenol or fluorescein. The CAR comprises an antibody or antibody fragment, ScFv or a protein or portion thereof that is designed to recognize the target moiety. Designing proteins for interactions are known to those skilled in the art, and are desirably very specific, as proteins can interact with a large number of proteins or chemicals such as FL, for example, thus successful design should utilize selective binders. Thus, protein design algorithms can be used to distinguish between on target and off target binding. The protein can also be designed by focusing on electrostatic contributions, so as to increase the affinity for its binding partner, or target moiety. Screening of a variety of different CAR structures can be performed by contacting cells comprising CARs, which are specific for a target moiety, with a substrate or binding agent comprising said target moiety and evaluating the binding of the CARs to said substrate or binding agent. Additionally, a target cell or a target virus unto which the binding agent is specific can be added so that the formation of a complex comprising the cell, which comprises the CAR, bound to the binding agent by virtue of the interaction of the CAR and the target moiety, and a target cell or virus unto which the binding agent is specific for can be evaluated. In some alternatives, the scFv is specific for the FL-PLE. However, increasing the binding affinity of a CAR does not always increase the effects that one would expect for a high affinity binding CAR.

Alternative 2: Testing the Efficacy of the CARS in Targeting the PLE in Different Types of Mouse Models.

Also described herein, are the methods of treatment, inhibition, or amelioration of cancer in mouse models of cancer. Mice that can be used for these evaluations include mice with mutations in the MSH2 and/or MLH1 genes. These mice are susceptible to developing gastrointestinal cancer and tumors that are classified as adenomas, invasive adenocarcinomas and late stage carcinomas.

In order to test for the efficacy of the compositions and CAR T cells expressing CARs that are specific for the target moiety, several groups of mice are selected for the study: 1) Control mice; 2) Mice given the FL-PLE; 3) Mice given the CAR T cell; 4) Mice given the FL-PLE followed by the CAR T cell 1 hour after FL-PLE administration; 5) Mice given the FL-PLE followed by the CAR T cell 2 hours after FL-PLE administration; 6) Mice given the FL-PLE followed by the CAR T cell 4 hours after FL-PLE administration; 7) Mice given the FL-PLE followed by the CAR T cell 6 hours after FL-PLE administration; 8) Mice given the FL-PLE followed by the CAR T cell 12 hours after FL-PLE administration; 9) Mice given the FL-PLE followed by the CAR T cell 24 hours after FL-PLE administration; and 10) Mice given the FL-PLE followed by the CAR T cell 48 hours after FL-PLE administration. Administration of the composition and the CAR T cell may be by intravenous administration. Each group of the mice have mutations in the MSH2 and MLH1 genes and have early stage tumors as detected by diffusion weighted whole body imaging. Each group of mice have 5 males and 5 females aged 16 weeks. Experiments were also performed where tumors are engrafted at day 0 and days 5-7. FL-PLEs are injected for integration into cells and this is followed by T cells injected on day 7. FL-PLE's may then be redosed weekly or bi weekly.

Three weeks after the administration of the drugs, the tumors are again analyzed for size by diffusion weighted whole body imaging to review the sizes of the tumors in the mice. It is expected that the mice that were administered the FL-PLE followed by the CAR T cell will have an appreciable reduction and/or inhibition of tumor growth.

Alternative 3: Synthesis of FL-PLE

Figure 3:
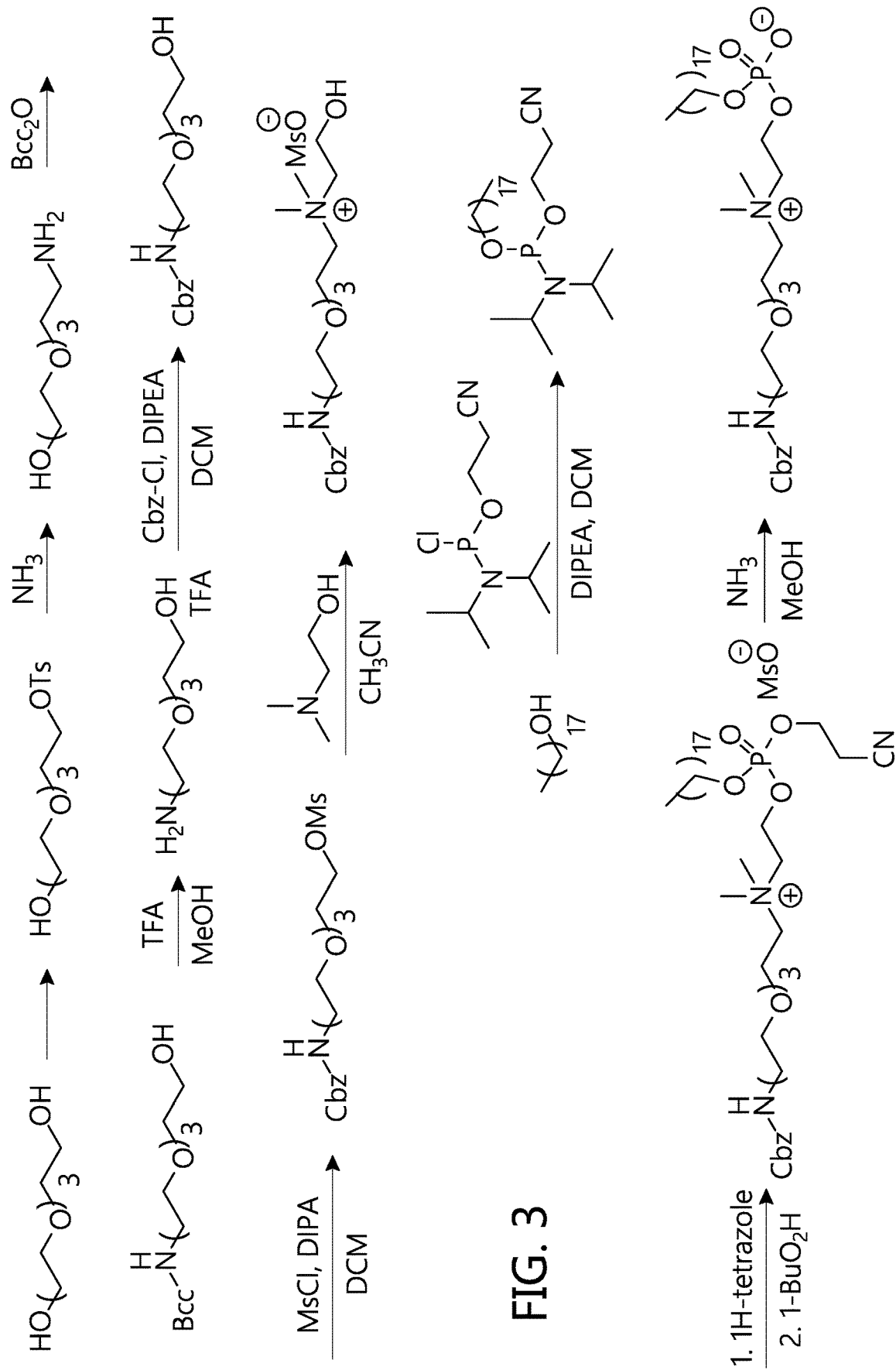
FIG. 3 shows the synthesis routes for FL-PLE.
Figure 3:
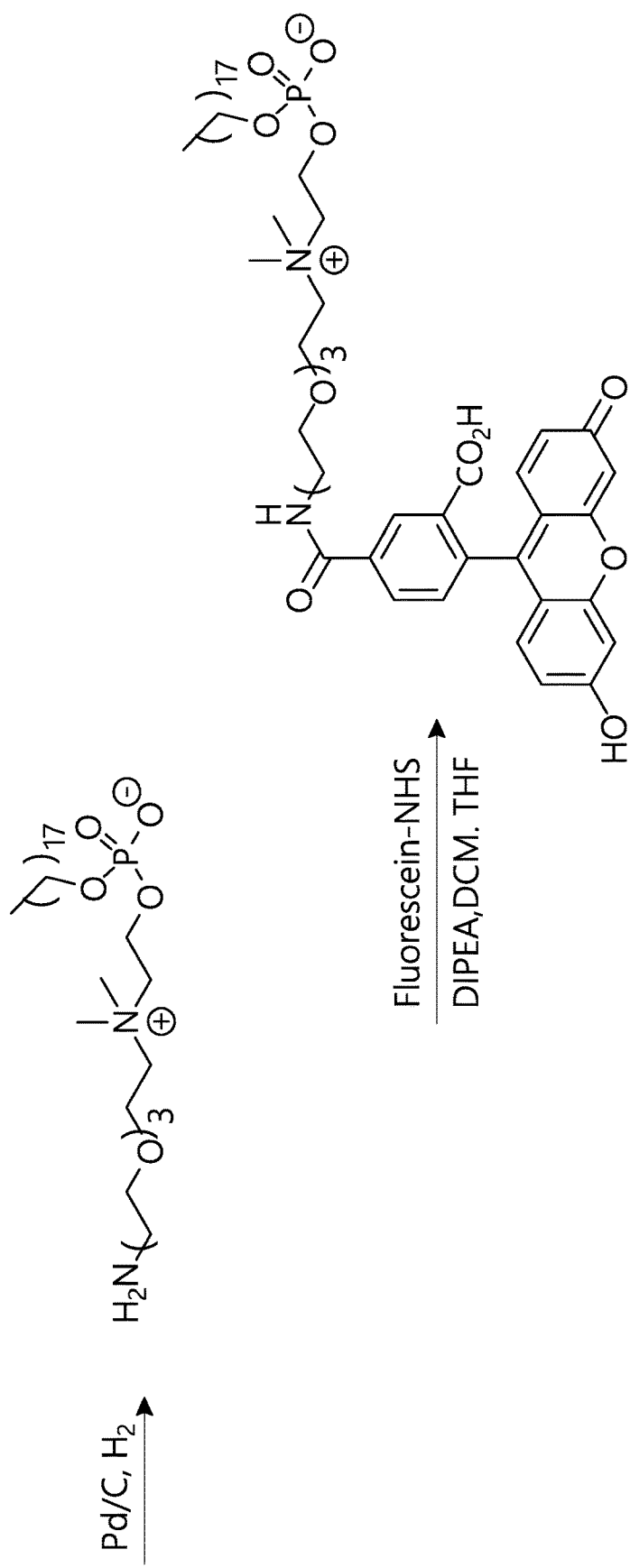
Figure 4:
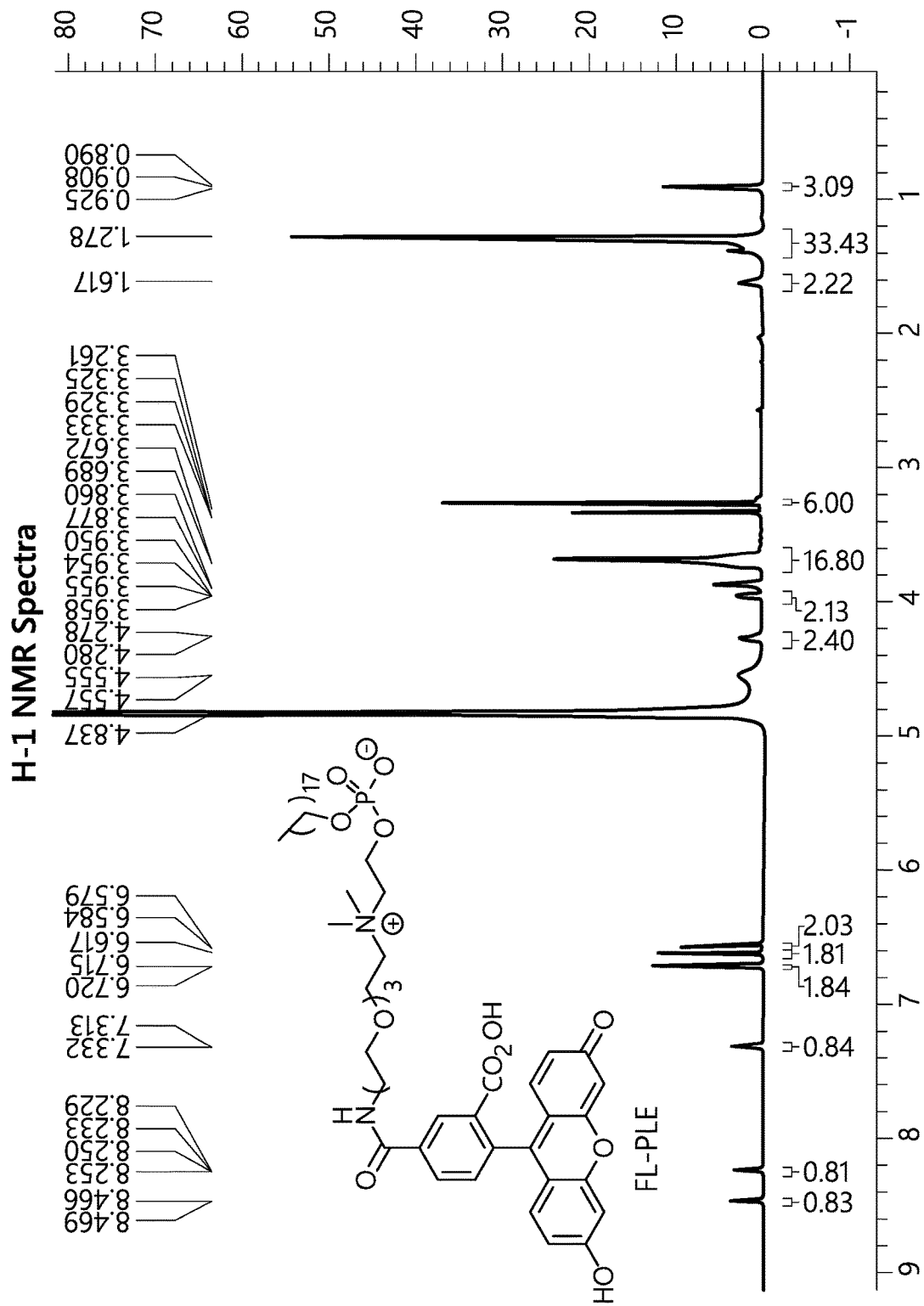
FIG. 4 shows the resulting NMR data in a 1D NMR spectra of the synthesized FL-PLE, which was subjected to NMR analysis. The 1D-spectra from the NMR identified the synthesized product as FL-PLE that was shown in the synthesis of FIG. 3.

Shown in FIG. 3 is the synthesis of a FL-PLE. The synthesized FL-PLE was subjected to an NMR analysis. A 1D NMR spectra was obtained with the FL-PLE sample in a buffer solution (FIG. 4). As shown, the 1D spectra of the sample of the synthesized FL-PLE indicated peaks for the specific groups on the molecule which were expected for the synthesized structure of the FL-PLE.

Alternative 4 Synthesis of ProFL-PLE

Figure 5:
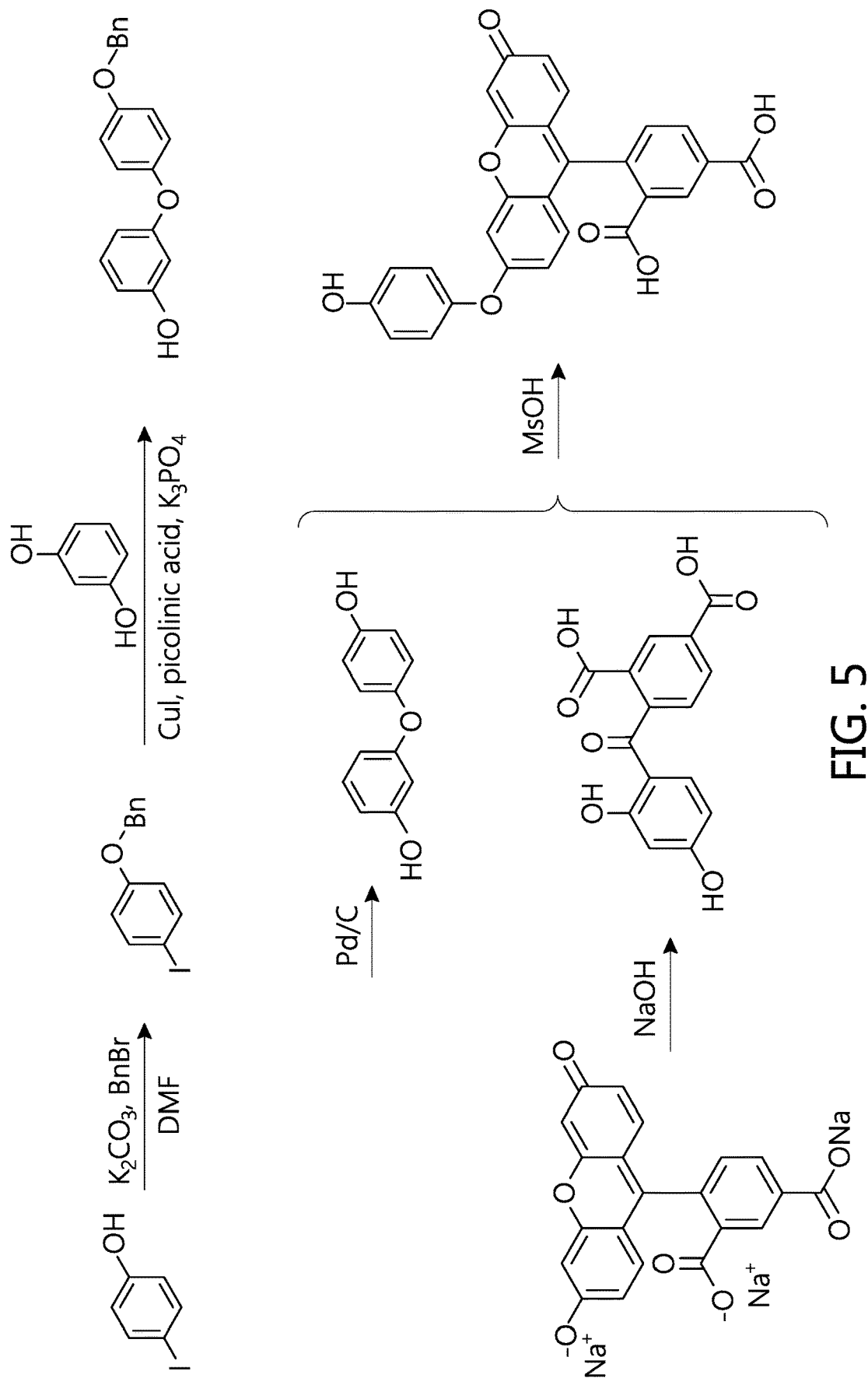
FIG. 5 shows Synthesis Routes for ProFL-PLE.
Figure 5:
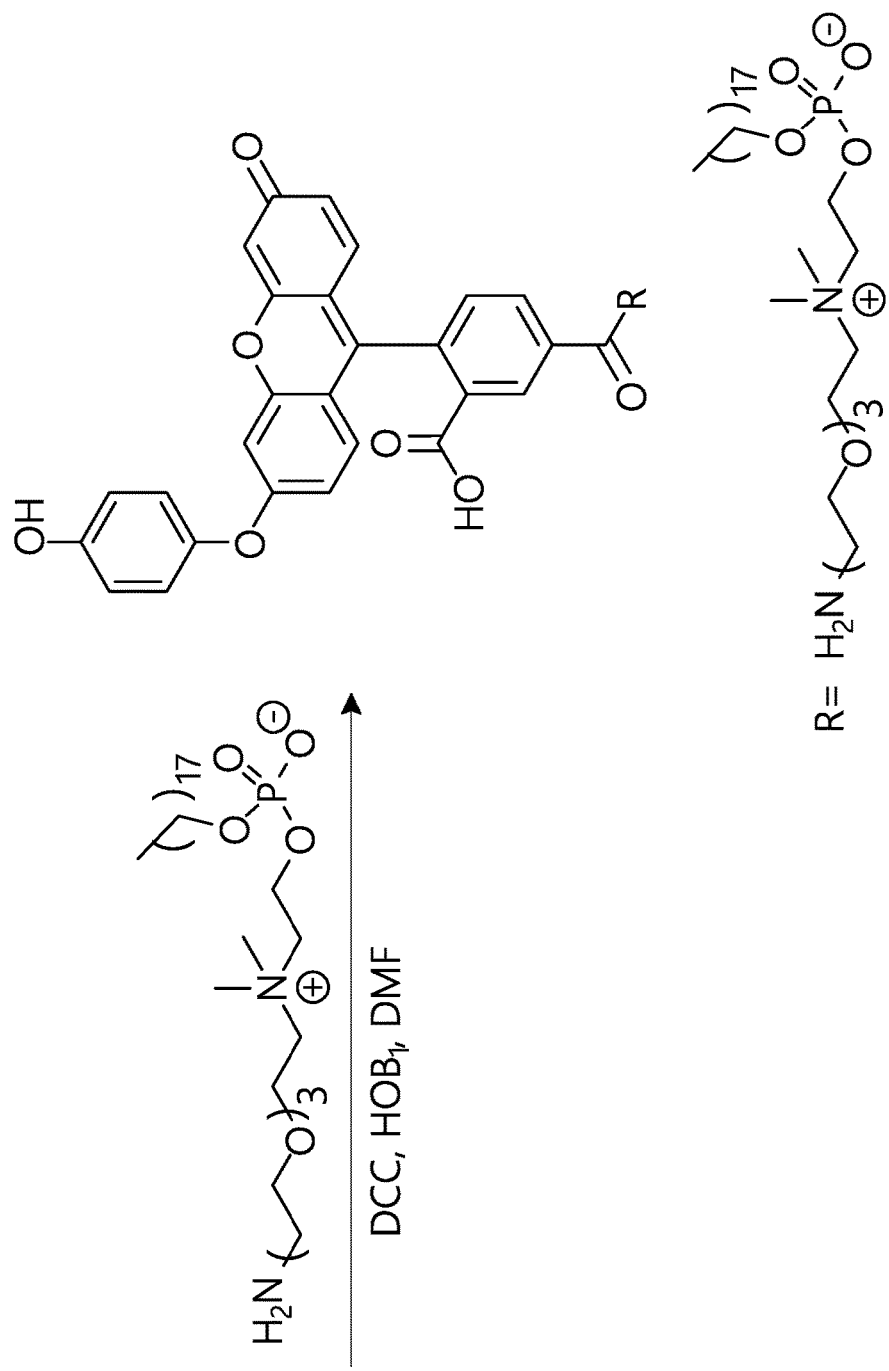
Figure 6:
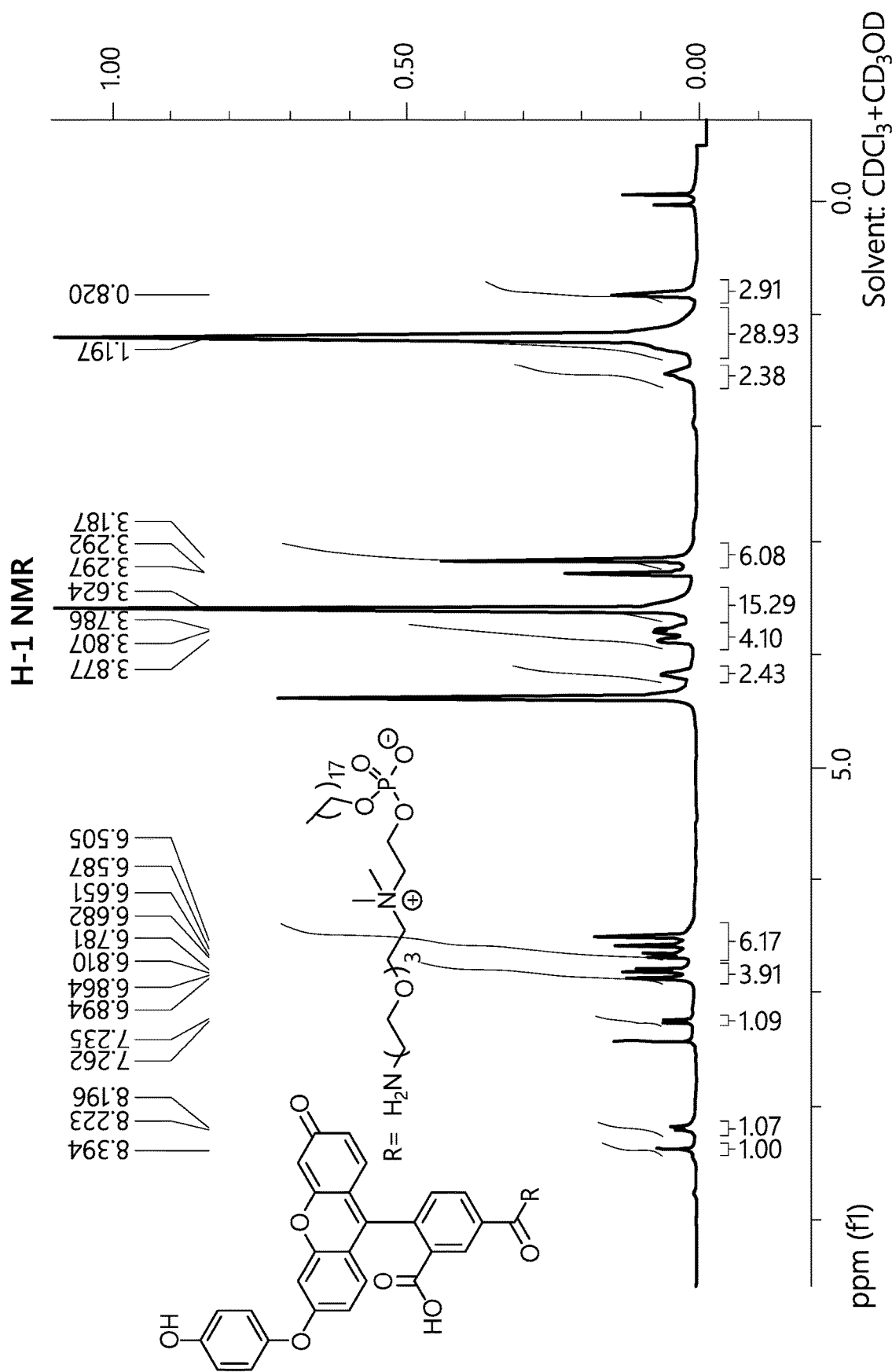
FIG. 6 shows the NMR of ProFL-PLE. The Synthesized ProFL-PLE was subjected to NMR analysis. Spectra from the NMR identify the synthesized product as ProFL-PLE that was shown in the synthesis of FIG. 5.

Shown in FIG. 5, is the synthesis scheme for ProFL-PLE. A 1D NMR spectra was obtained with the ProFL-PLE sample in a buffer solution (FIG. 6). As shown, the 1D spectra of the sample of the synthesized ProFL-PLE indicated peaks for the specific groups on the molecule which were expected for the synthesized structure of the ProFL-PLE.

Alternative 5: Tumor Targeting & Integration of FL-PLE

Figure 7C:
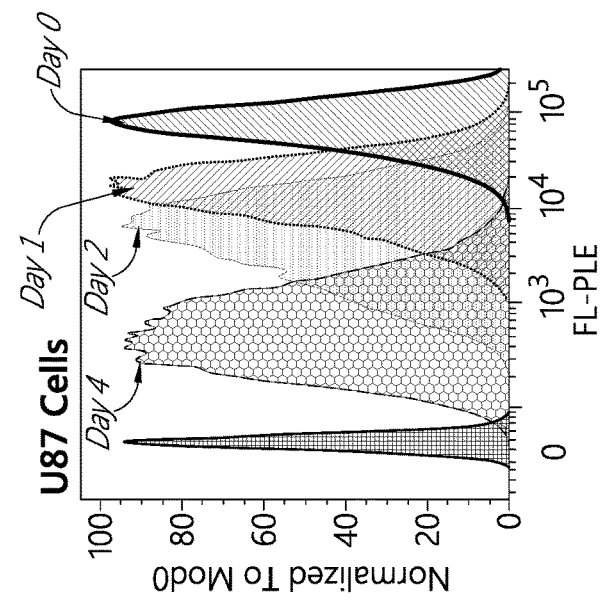
FIG. 7A-7E shows tumor targeting & integration of FL-PLE. (7A-7D) Cells were incubated with 5 µM FL-PLE overnight then cells were analyzed by flow or confocal microscope. The cells may also be incubated with 1 nM, 5 nM, 10 nM, 100 nM, 200 nM, 300 nM 400 nM, 500 nM, 600 nM, 700 nM, 800 nM, 1 µM, 5 µM, 10 µM, 15 µM, 20 µM or 25 µM FL-PLE overnight. The level of FL-PLE integration into the cell membrane was identified by the signal intensity emitted from the fluorescein moiety of the FL-PLE. (7A) Shows FL-PLE is able to integrate into multiple cancers: Be2 (neuroblastoma), U87 (glioblastoma), and daoy (medulloblastoma). (7B) U87 cells were incubated overnight in the presence of 0, 0.1, 1, or 5 µM FL-PLE and then subjected to flow analysis. These results demonstrate that FL-PLE integration into the cancer cell membrane is concentration dependent. (7C) U87 cells were incubated overnight in the presence of 5 µM FL-PLE, washed to remove residual FL-PLE, cultured in fresh (FL-PLE free) media for up to 4 days, and then subjected to flow analysis. Results demonstrate a multiday FL-PLE retention time. As shown, the blue and green stain is actually throughout the cells. Alternatively, the cells may be incubated with 1 nM, 5 nM, 10 nM, 100 nM, 200 nM, 300 nM 400 nM, 500 nM, 600 nM, 700 nM, 800 nM, 1 µM, 5 µM, 10 µM, 15 µM, 20 µM or 25 µM FL-PLE (7D) Confocal images show that FL-PLE integrates over the whole cell surface (U87 cells). The FL-PLE is shown in green and the nucleus is stained with DAPI which is shown in blue. (7E) After a glioblastoma (U87 cells) tumor was established in a group of mice by intracranial injection, the mice received an intravenous injection of FL-PLE. Mice were sacrificed and brains were harvested at various time points post FL-PLE injection. The fluorescent image of a brain harvested 2 days post FL-PLE injection demonstrates that FL-PLE preferentially targets and integrates into the tumor in an in vivo environment. As shown, the FL-PLE is in a targeted area as demonstrated by the circular area within the right quadrant of the brain shown in FIG. 7E.
Figure 7B:
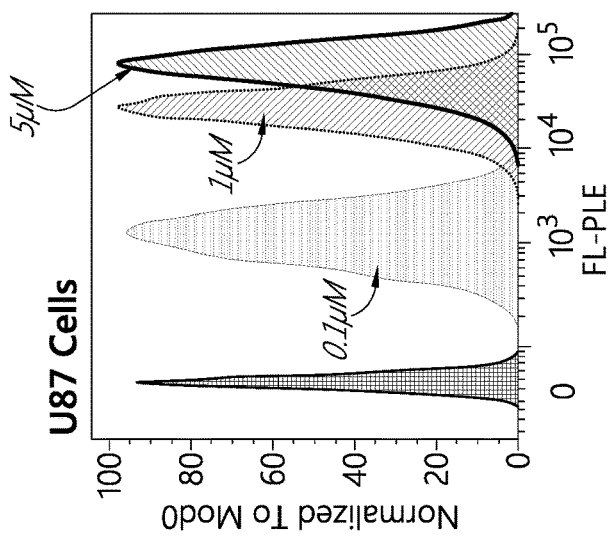
Figure 7A:
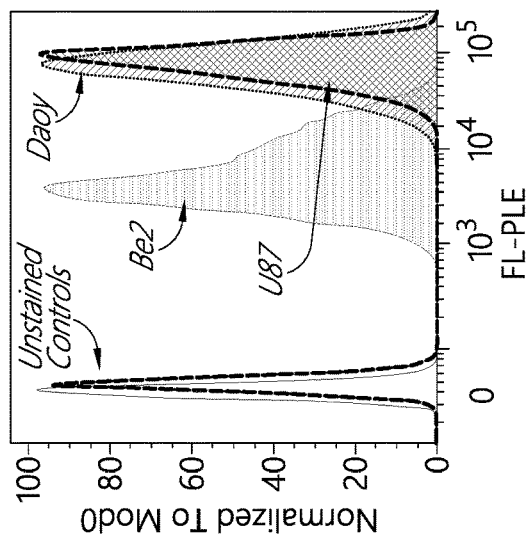
Figure 7D:
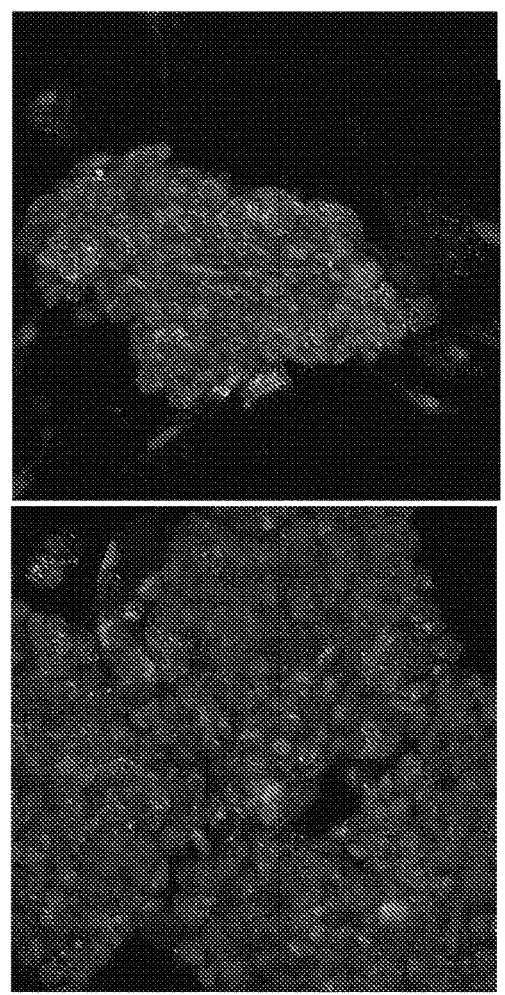
Figure 7E:
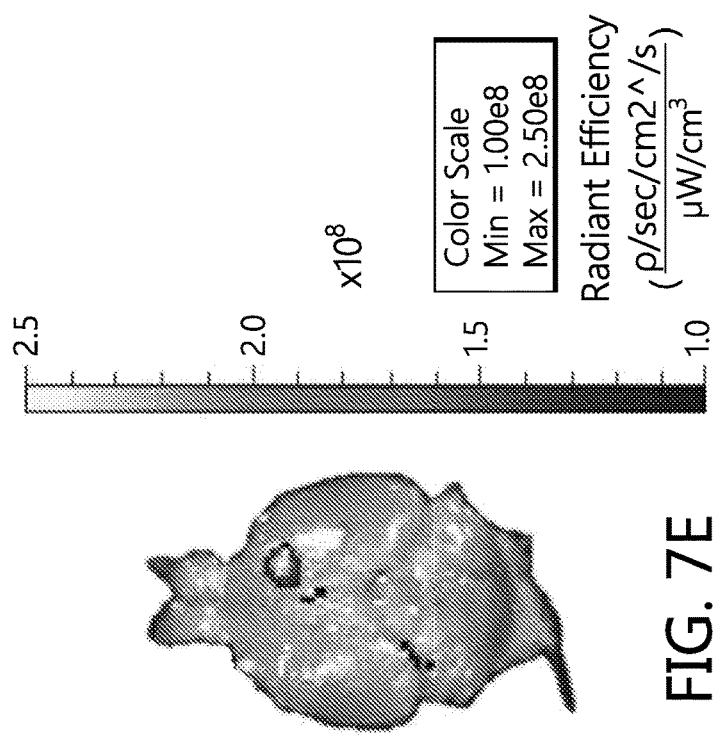

Cells were incubated with 5 µM (unless otherwise stated) FL-PLE overnight then cells were analyzed by flow or confocal microscope. The level of FL-PLE integration into the cell membrane was identified by the signal intensity emitted from the fluorescein moiety of the FL-PLE. FIG. 7A shows FL-PLE is able to integrate into multiple cancers: Be2 (neuroblastoma), U87 (glioblastoma), and daoy (medulloblastoma). In FIG. 7B, U87 cells were incubated overnight in the presence of 0, 0.1, 1, or 5 µM FL-PLE and then subjected to flow analysis. The results demonstrate that FL-PLE integration into the cancer cell membrane is concentration dependent. In FIG. 7C, U87 cells were incubated overnight in the presence of 5 µM FL-PLE, washed to remove residual FL-PLE, cultured in fresh (FL-PLE free) media for up to 4 days, and then subjected to flow analysis. Results demonstrate a multiday FL-PLE retention time. In FIG. 7D, confocal images show that FL-PLE integrates over the whole cell surface (U87 cells). The FL-PLE is shown in green and the nucleus is stained with DAPI, which is shown in blue. In FIG. 7E, after a glioblastoma (U87 cells) tumor was established in a group of mice by intracranial injection, the mice received an intravenous injection of FL-PLE. Mice were sacrificed and brains were harvested at various time points post FL-PLE injection. The fluorescent image of a brain harvested 2 days post FL-PLE injection demonstrates that FL-PLE preferentially targets and integrates into the tumor in an in vivo environment.

The use of the system led to the surprising effect of having the FL-PLE preferentially targeting the tumor and integrating into the cells that are within the tumor environment specifically.

Alternative 6: FL Moiety is Accessible for Binding

Figure 8:
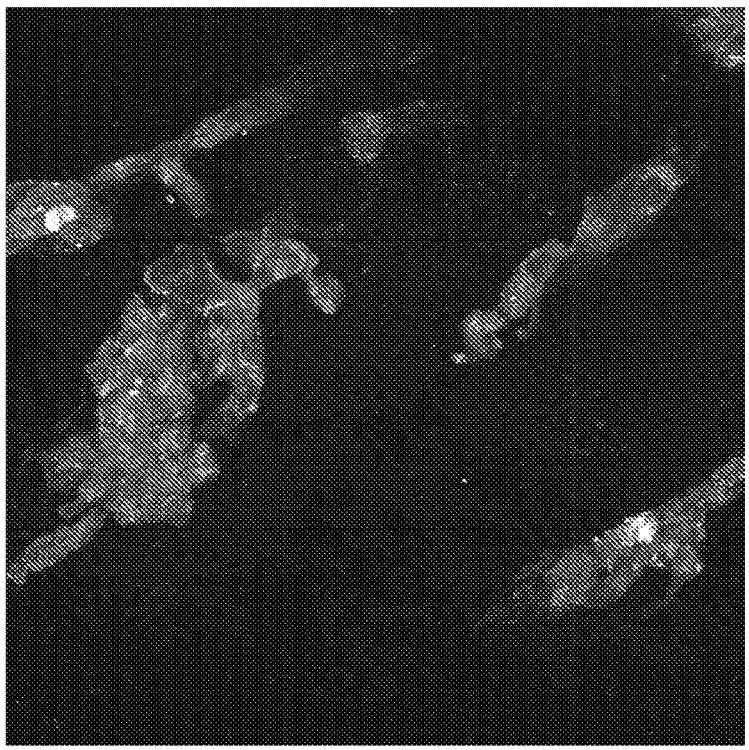
FIG. 8 shows that the FL moiety is accessible for binding. U87 cells were incubated with 5 µM FL-PLE overnight then imaged by confocal microscopy. Same as FIG. 7D except this time U87 cells (nucleus shown in blue, DAPI) with FL-PLE (green) integrated into the membrane were stained with an antifluorescein antibody conjugated with an Alex 647 fluorophore (grey). These images demonstrate that the FL moiety is accessible for binding.
Figure 8:
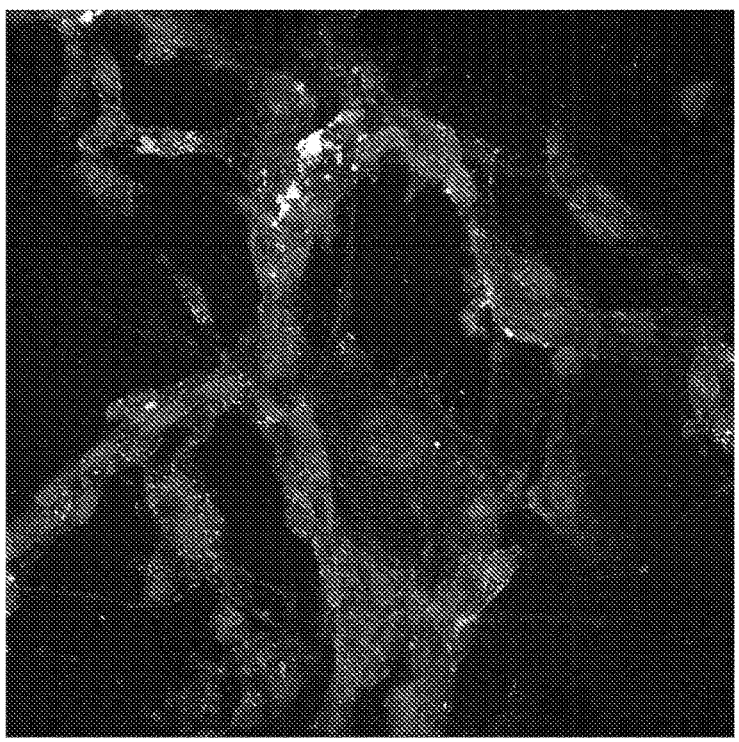

U87 cells were incubated with 5 mM FL-PLE overnight then imaged by confocal microscopy. Same as FIG. 7D except this time U87 cells (nucleus shown in blue, DAPI) with FL-PLE (green) integrated into the membrane were stained with an antifluorescein antibody conjugated with an Alex 647 fluorophore (grey). These images demonstrate that the FL moiety is accessible for binding. In FIG. 8, the use of the FL-PLE led to the surprising effect of having the FL-PLE integrate into the membrane demonstrating that it is accessible for CAR recognition, binding, and interaction. As shown, the lipids are able to target lipid rafts in cancer.

Alternative 7: CAR T Cell Recognition and Activation Through FL-PLE (In Vitro). K562 (Leukemia) Cells were Incubated with FL-PLE Overnight.

Figure 9A:
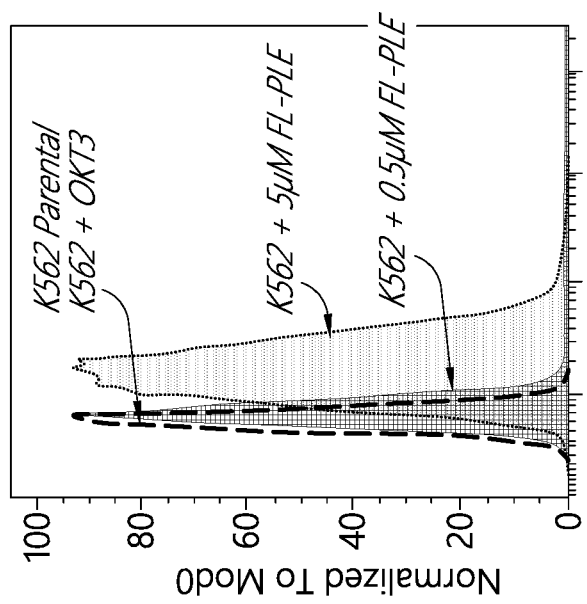
FIG. 9A-9C shows the results of CAR T cell recognition and activation through FL-PLE (in vitro). K562 (leukemia) cells were incubated with FL-PLE overnight. Cell integration of FL-PLE was analyzed by flow cytometry (9A). There is a clear shift from the control K562 parental with the K562 parental incubated with 5 mM FL-PLE whereas there is a very slight shift with K562 parental incubated with 0.5 mM FL-PLE. This slight shift corresponds to a difference in the amount of FL exposed on the surface of the cell for CAR T cell recognition. Also the K562+OKT3 cells (a cell line created to test the endogenous activation of T cells through the TCR) match the K562 parental exactly, as expected. These cells were used in a chromium release assay (9B) and a cytokine release assay (9C) to test the activation of CD8+ antiFL CAR T cells compared with a CD8+ mock T cells. From these experiments antiFL CAR T cells can recognize the FL moiety of the FL-PLE integrated into the plasma membrane and able to activate. The amount of the activation is dependent on the amount of FL exposed on the surface of the cell. As shown in 9B, in the K562 parental cells panel, the specific lysis was the same for the CD8+ mock cells and the CD8+ AntiFL CAR bearing cells. In the K562+OKT3 panel of FIG. 9B, the specific lysis was the same for the CD8+ mock cells and the CD8+ AntiFL CAR bearing cells. In the bottom panels of FIG. 9B, the CD8+ AntiFL CAR cells showed a higher percentage of specific lysis.

Cell integration of FL-PLE was analyzed by flow cytometry (FIG. 9A). There is a clear shift from the control K562 parental with the K562 parental incubated with 5 µM FL-PLE; whereas there is a very slight shift with K562 parental incubated with 0.5 µM FL-PLE. This slight shift corresponds to a difference in the amount of FL exposed on the surface of the cell for CAR T cell recognition. Also, the K562+OKT3 cells (a cell line created to test the endogenous activation of T cells through the TCR) match the K562 parental exactly, as expected. These cells were used in a chromium release assay (FIG. 9B) and a cytokine release assay (FIG. 9C) to test the activation of CD8+ antiFL CAR T cells compared with a CD8+ mock T cells. From these experiments, it was determined that antiFL CAR T cells recognize the FL moiety of the FL-PLE, which has integrated into the plasma membrane of target cells and activation occurred as a result of this binding and/or interaction event. The amount of the activation was dependent on the amount of FL exposed on the surface of the cell.

Alternative 8: CAR T Cell Recognition and Activation Through FL-PLE (In Vivo).

Figure 10:
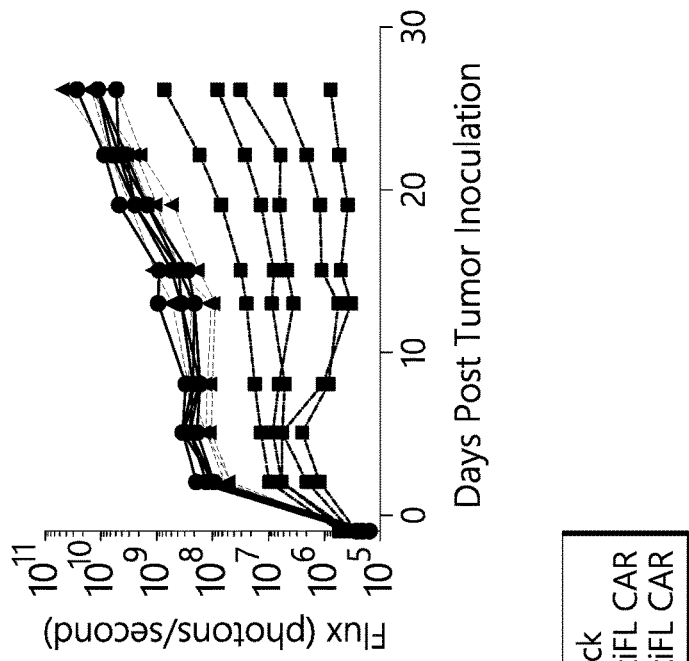
FIG. 10 shows the results of CAR T cell recognition and activation through FL-PLE (in vivo). Winn Assay: U87 cells harboring a green fluorescent protein and firefly luciferase fusion protein (GFP-ffLuc) were incubated with FL-PLE overnight. Note, the GFP-ffLuc allows for real-time monitoring of tumor progression via luminescent imaging. These cells were then mixed with CD8+ antiFL CAR T cells or CD8+ mock T cells at a 1:1 or 10:1 effector to target (E:T) ratio. Cell mixtures were injected into the brain of a mouse and tumor engraftment was monitored by luminescent flux over time. Here the antiFL CAR T cell is able to activate and slow down the engraftment of the tumor at a 10:1 (E:T). This demonstrates that the FL-PLE works as a target for CAR T-cell recognition in a living model.
Figure 10:
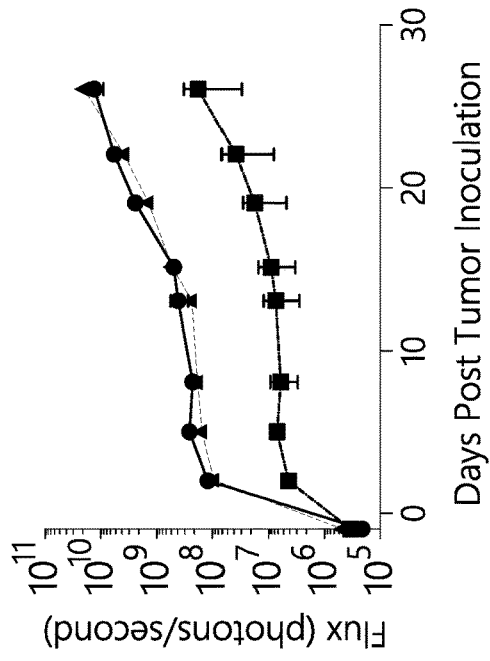
Figure 11:
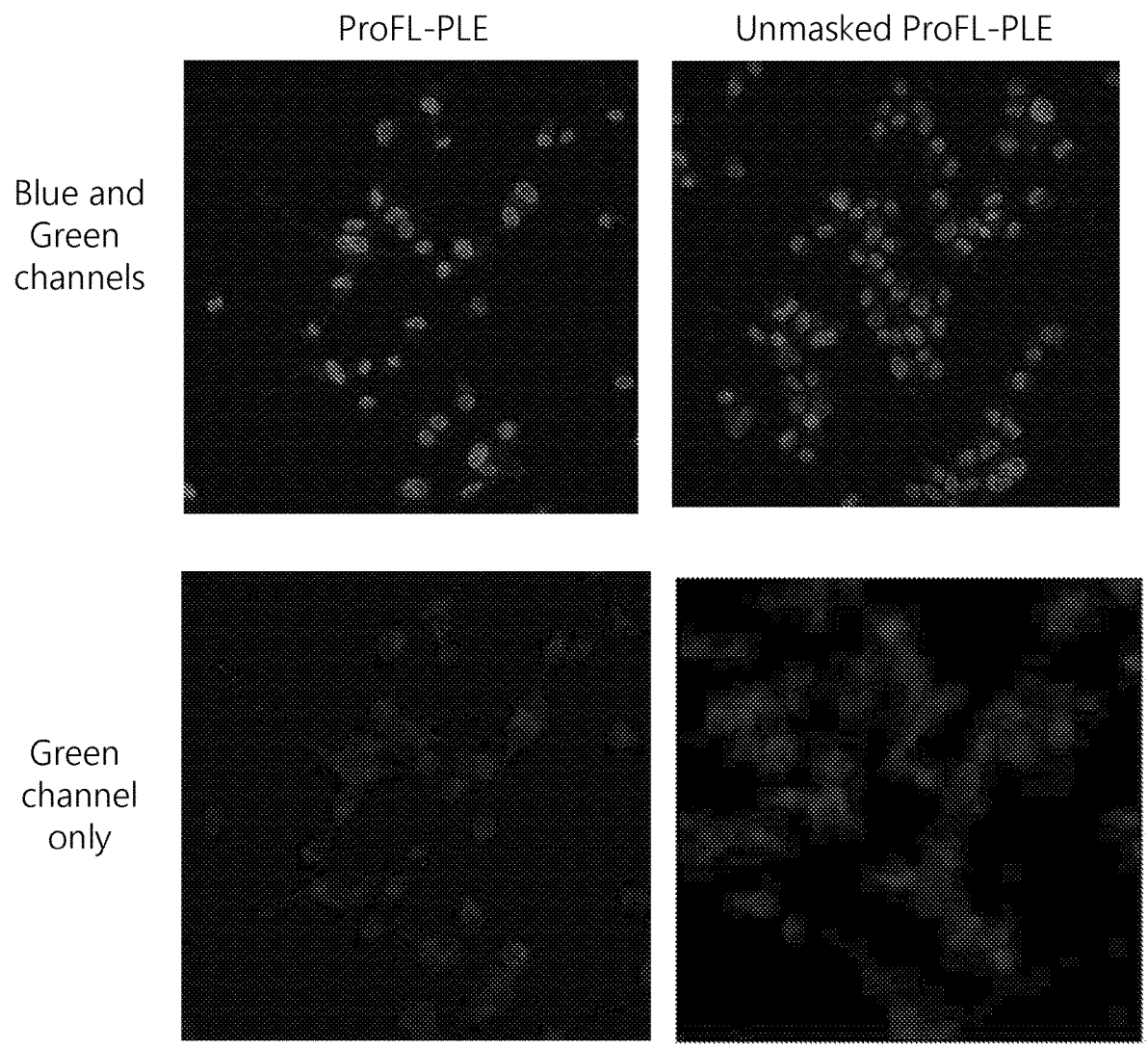
FIG. 11 shows ProFL-PLE integration into cells and unmasking. U87 cells were incubated with 5 µM ProFL-PLE overnight then imaged by confocal microscopy. The nucleus of the cells were stained with DAPI (blue). Same procedure as FIG. 5D. ProFL-PLE is not fluorescent due to the presence of the masking agent, a phenolic hydroxy group. When ProFL-PLE is introduced to a ROS environment, as modeled by the presence of H2O2, it is unmasked revealing the FL moiety. Therefore the unmasked ProFL-PLE has the capability to emit green fluorescence (green). Below is an image of ProFL-PLE integrated into the U87 cells with almost no green fluorescence. Cells that were exposed to ROS now emit green fluorescence, showing that ProFL-PLE can be unmasked and is integrated into the cell membrane.

U87 cells harboring a green fluorescent protein and firefly luciferase fusion protein (GFP-ffLuc) were incubated with FL-PLE overnight. Note, the GFP-ffLuc allows for real-time monitoring of tumor progression via luminescent imaging. These cells were then mixed with CD8+ antiFL CAR T cells or CD8+ mock T cells at a 1:1 or 10:1 effector to target (E:T) ratio. Cell mixtures were injected into the brain of a mouse and tumor engraftment was monitored by luminescent flux over time. Here the antiFL CAR T cell was able to activate and slow down the engraftment of the tumor at a 10:1 (E:T). This demonstrates that the FL-PLE works as a target for CAR T-cell recognition in a living model. (FIG. 10).

Alternative 9: ProFL-PLE Integration into Cells and Unmasking

U87 cells were incubated with 5 µM ProFL-PLE overnight then imaged by confocal microscopy. The nucleus of the cells were stained with DAPI (blue). The same procedure as shown in FIG. 5D was used. ProFL-PLE is not fluorescent due to the presence of the masking agent, a phenolic hydroxy group. When ProFL-PLE is introduced to a ROS environment, as modeled by the presence of $H_2O_2$, it is unmasked revealing the FL moiety. Therefore, the unmasked ProFL-PLE has the ability to emit green fluorescence (green). The image of ProFL-PLE integrated into the U87 cells shows almost no green fluorescence. Cells that were exposed to the ROS environment then emit green fluorescence, showing that ProFL-PLE was unmasked while being integrated into the cell membrane of the target cell. As shown, the use of the ProFL-PLE led to the surprising effect of having the ProFL-PLE integrate into the membrane of the target cell and evidence was found that this recognition moiety was accessible for CAR recognition, binding, and interaction. Also surprising was the unmasking of the lipid within a $H_2O_2$ rich environment for recognition by a CAR T cell providing evidence that the system would work in a tumor microenvironment.

Figure 12:
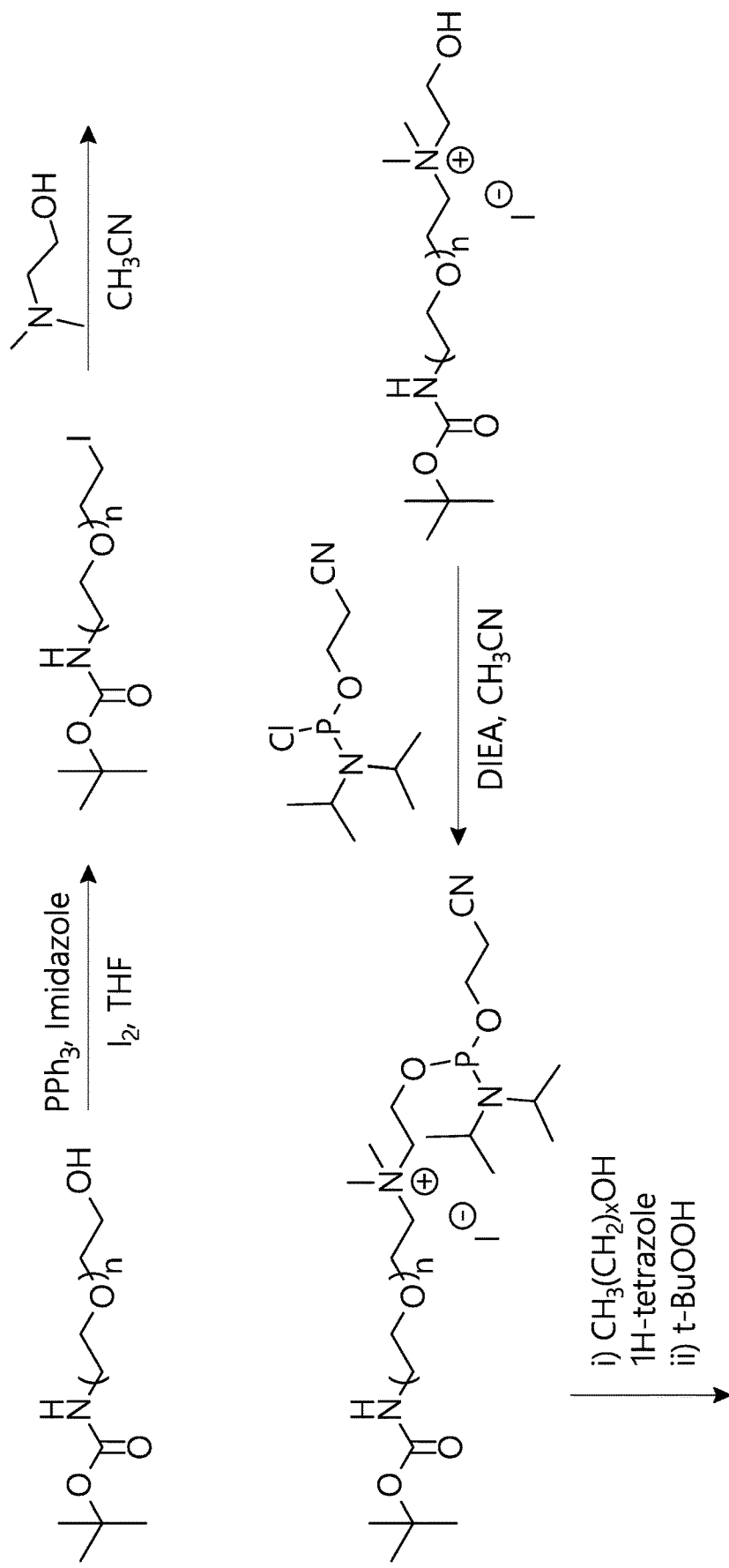
FIG. 12 shows an example of a construction scheme for the synthesis of fluorescein-PEG-phosphatidylcholine.
Figure 12:
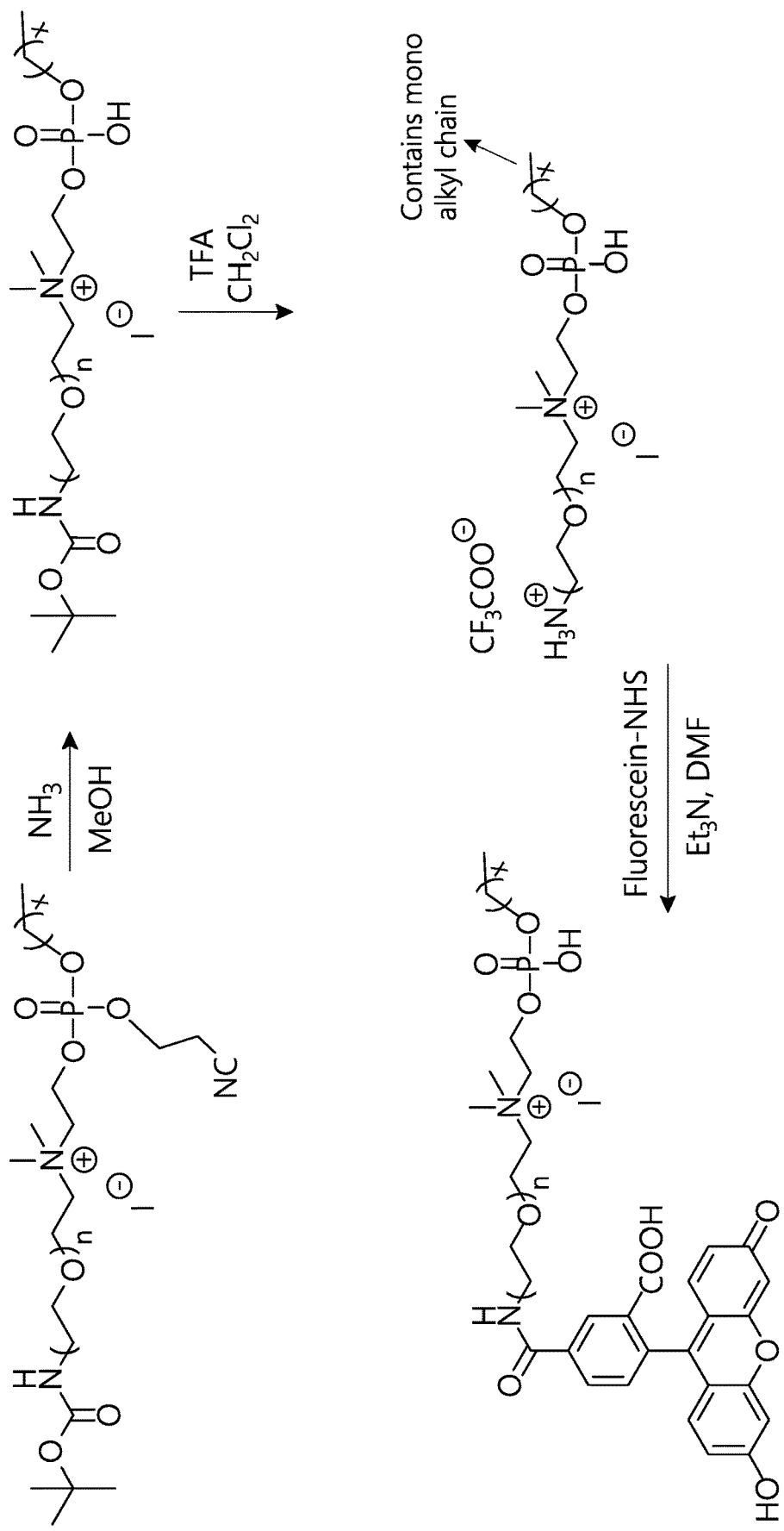

Alternative 10: Construction Scheme for the Synthesis of Fluorescein-PEG-Phosphatidylcholine Shown in FIG. 12 is an example of a construction scheme for the synthesis of fluorescein-PEG-phosphatidylcholine.

Alternative 11: Construction Scheme for the Synthesis of Fluorescein-PEG

Figure 13:
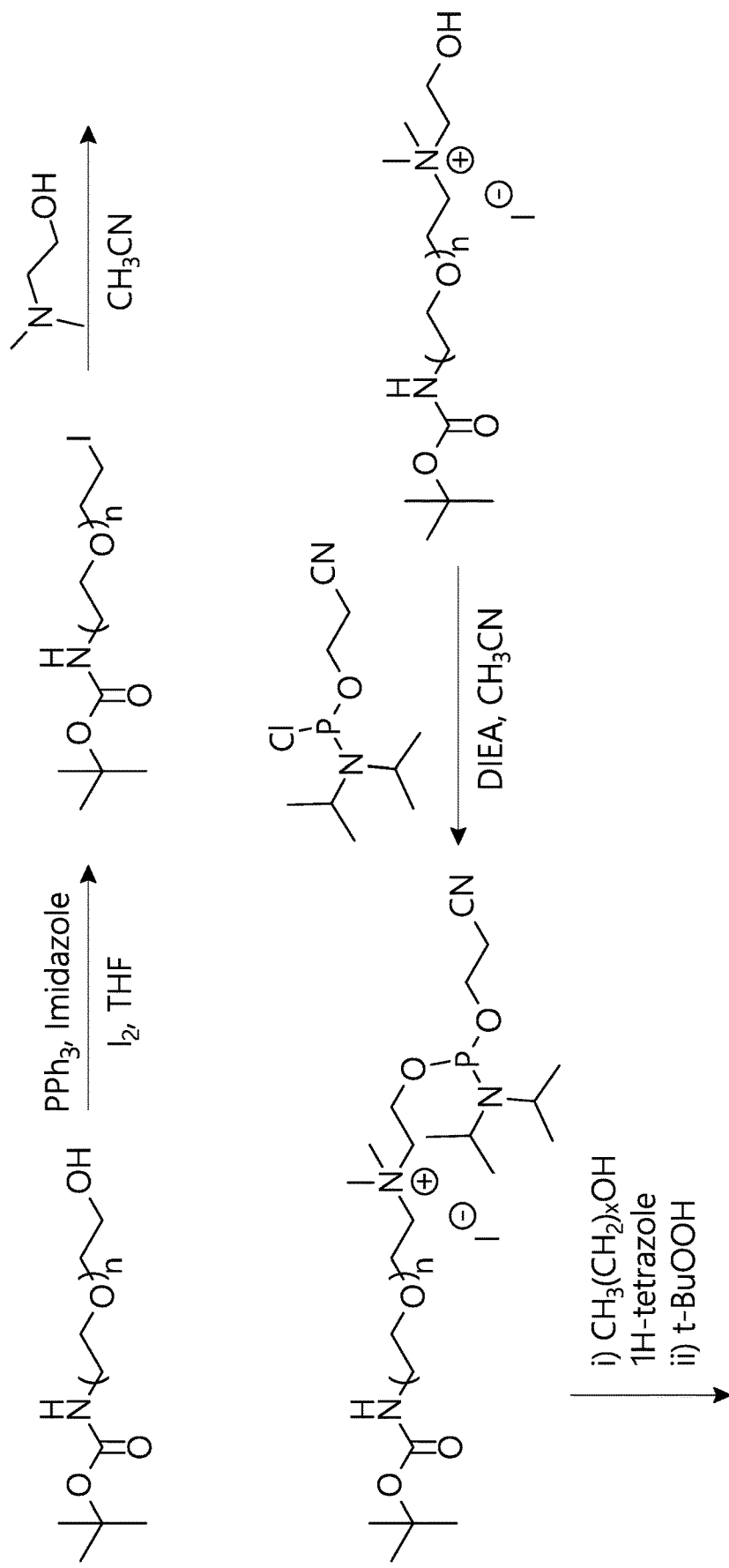
FIG. 13 shows an example of a construction scheme for the synthesis of fluorescein-PEG.
Figure 13:
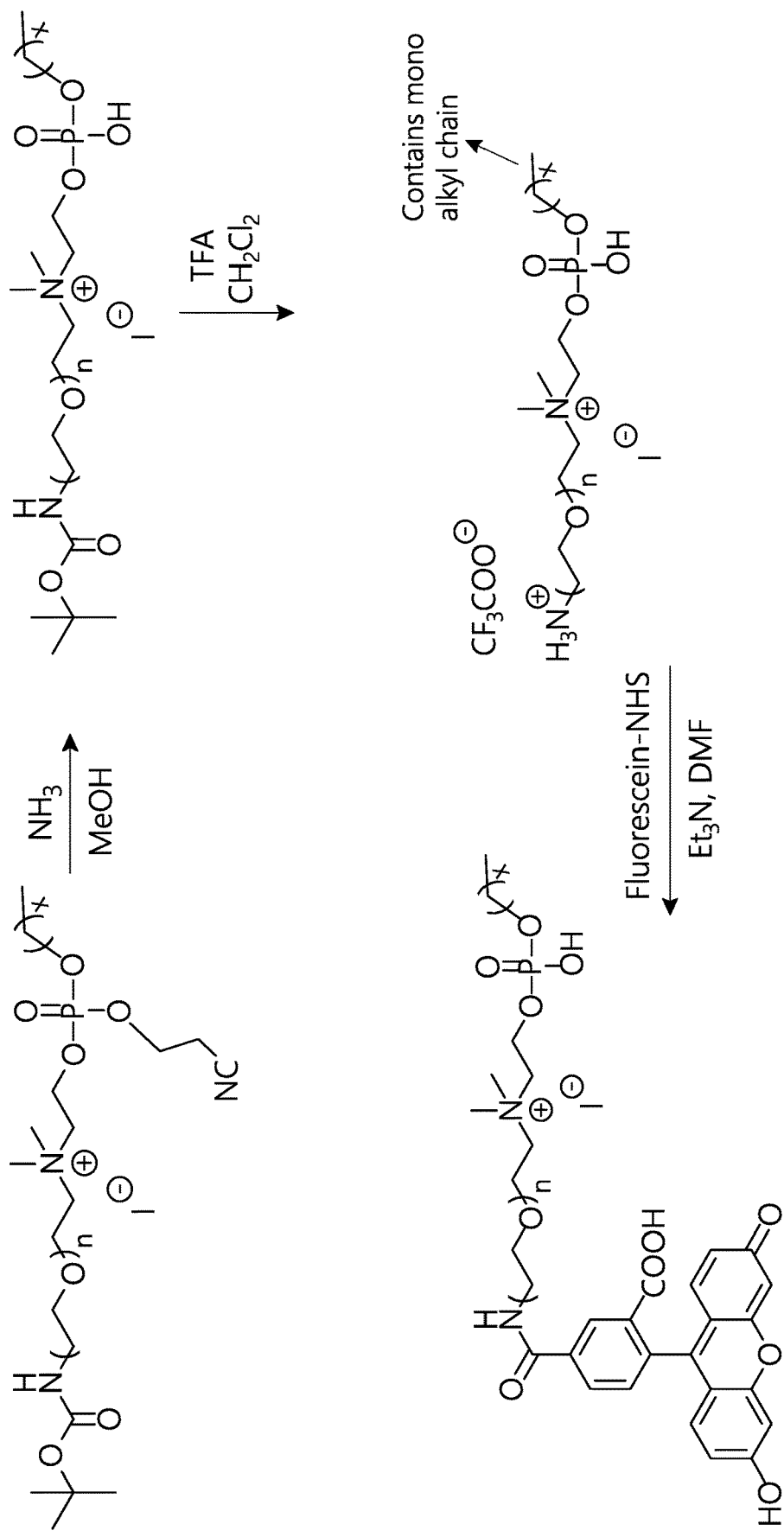

Shown in FIG. 13 is an example of a construction scheme for the synthesis of fluorescein-PEG.

Alternative 12: Construction Scheme for ProFL-NHS

Figure 14:
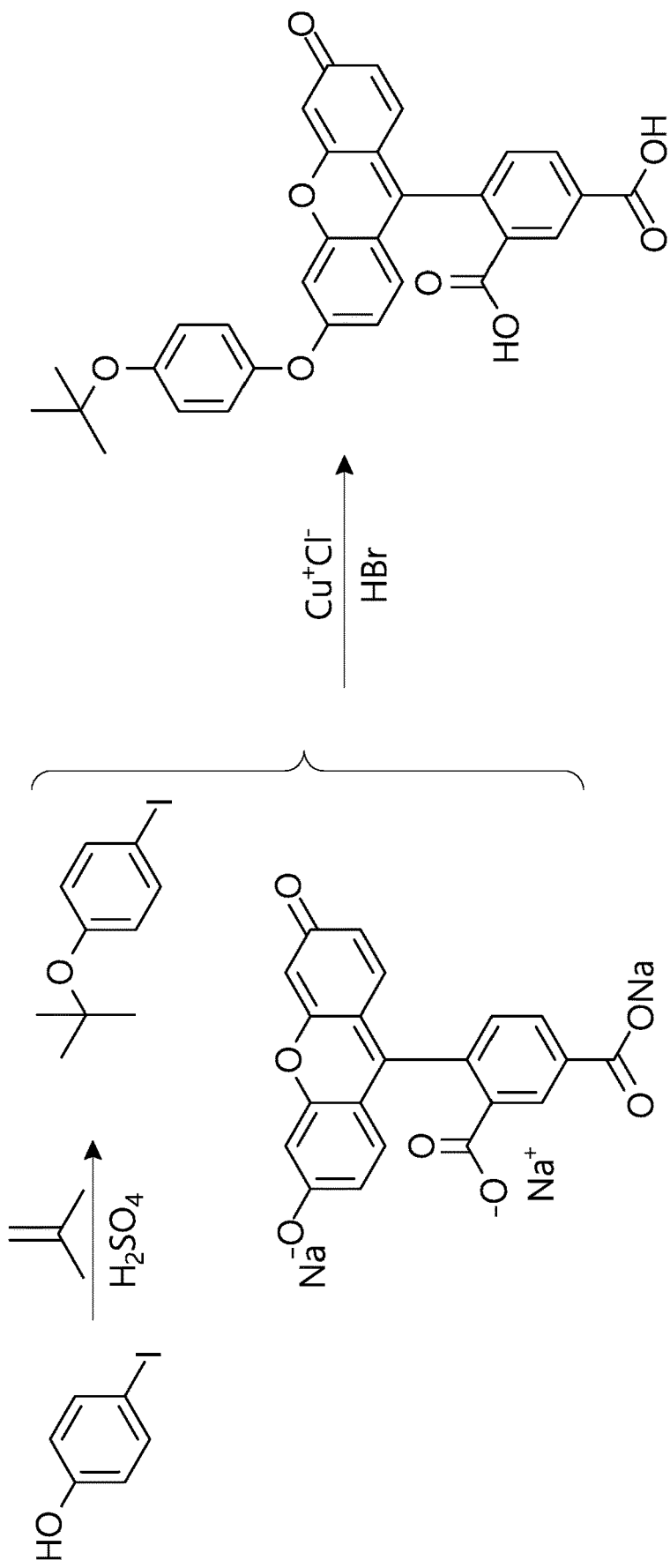
FIG. 14 shows the construction scheme for ProFL-NHS.
Figure 14:
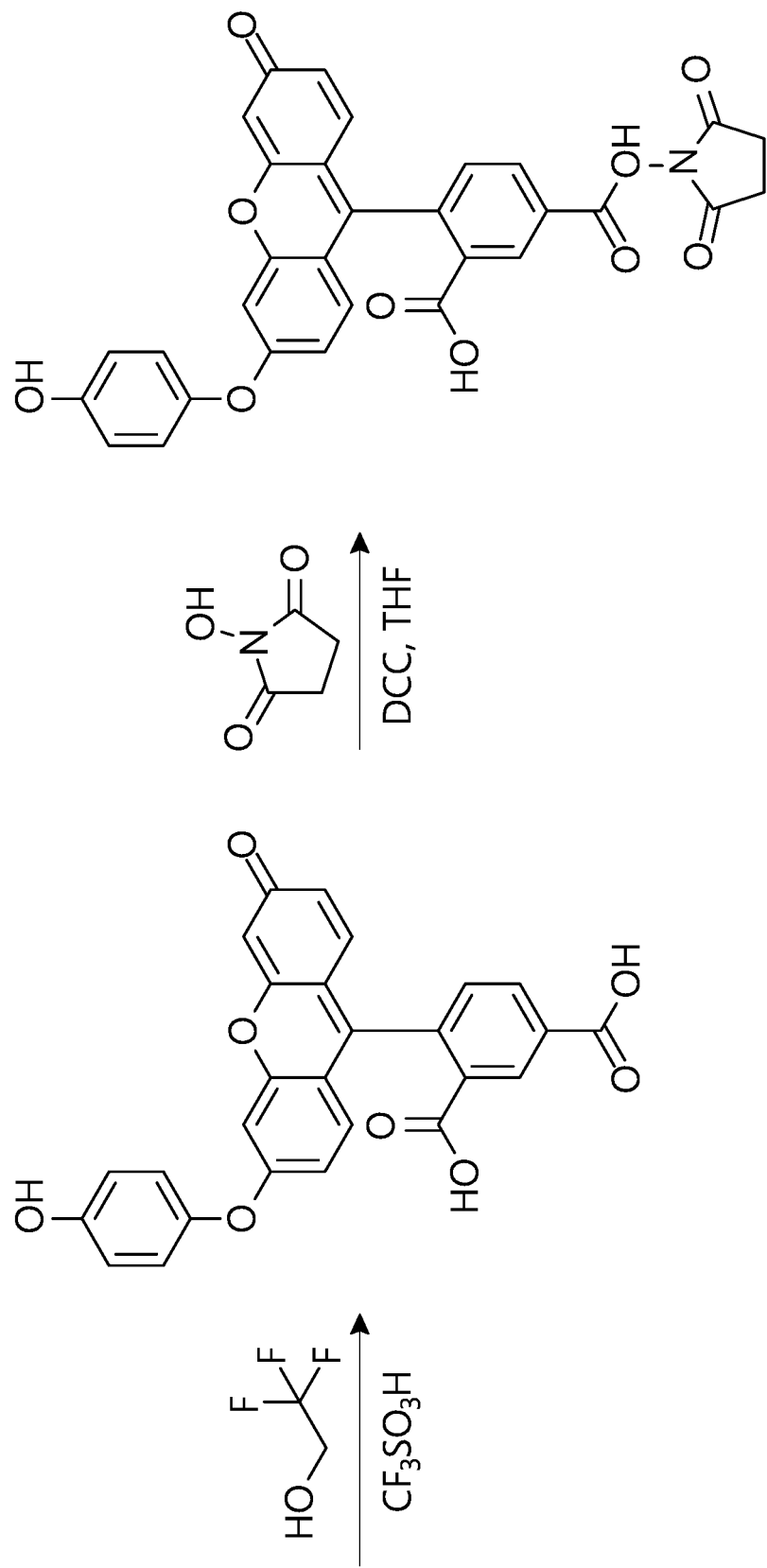
Figure 15:
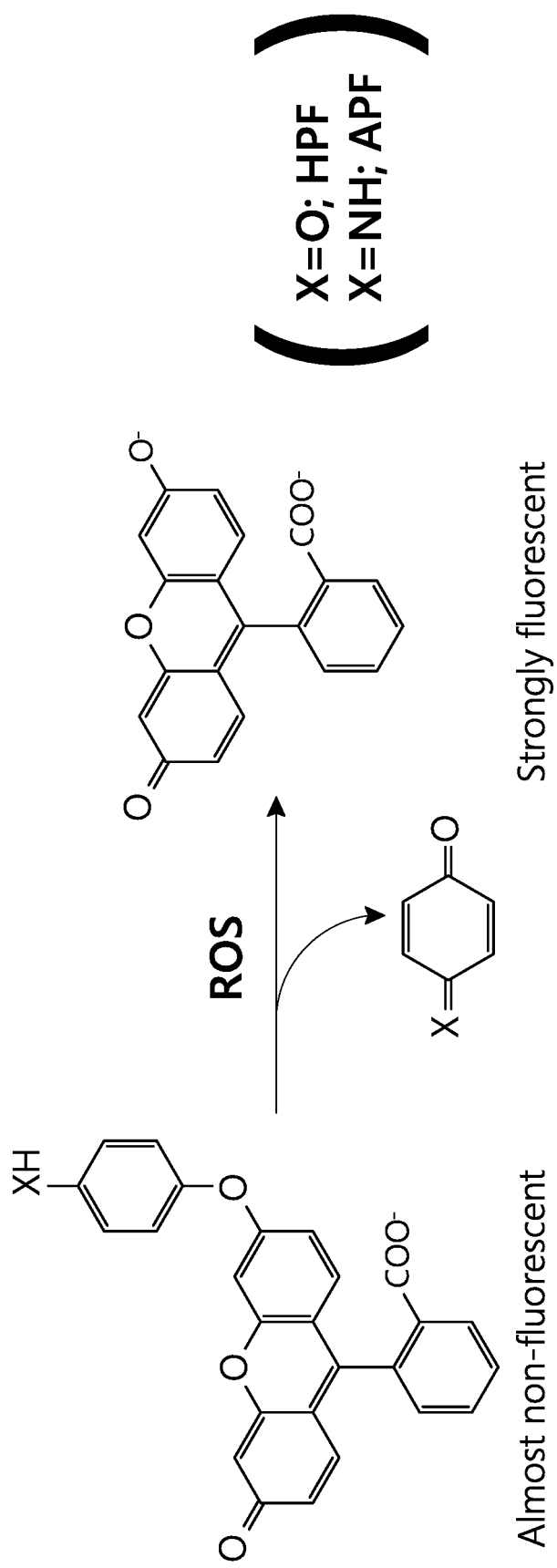
FIG. 15 shows a commercially available ROS detection system. As shown, a development of novel fluorescence probes can reliably detect reactive oxygen species and distinguish specific species. (Journal of Biological Chemistry 2003 278(5) 3170-3175, incorporated by reference in its entirety herein).

Shown in FIG. 14 is an example of a construction scheme for ProFL-NHS.

Alternative 13: Types of Lipids.

As described herein, there are many types of lipids that can be used for intercalating into the target cell. In some alternatives, the target cell is a cancer cell such as a tumor cell. In some alternatives, the target cell is an immune cell. In some alternatives, the target cell is in a tumor microenvironment. In some alternatives, the target cell is a tumor cell of a solid tumor. In some alternatives, the solid tumor is a cancerous tumor, wherein the tumor comprises a plurality of cancer cells. In some alternatives, the cancer is breast, ovarian, lung, pancreatic, prostate, melanoma, renal, pancreatic, glioblastoma, neuroblastoma, medulloblastoma, sarcoma, liver, colon, skin (including melanoma), bone or brain cancer. In some alternatives, the lipid is a glycerolipid, glycerophospholipid, sphingolipid, sterol lipids, prenol lipid, saccharolipid or a polyketide. In some alternatives, a complex comprising a chimeric antigen receptor (CAR) or a T cell receptor (TCR) is provided, wherein the CAR or TCR is joined to a lipid, wherein the lipid comprises a target moiety and the CAR is joined to said lipid through an interaction with said target moiety. In some alternatives, the lipid comprises a polar head group and a hydrophobic moiety. In some alternatives, the hydrophobic moiety is a hydrophobic carbon tail. In some alternatives the hydrophobic carbon tail is saturated or unsaturated. In some alternatives, the hydrophobic carbon tail comprises 10, 11, 12, 13, 14, 15, 16, 17, 18, 19, 20, 21, 22, 23, 24 or 25 carbons or any number of carbons in between a range set forth in any aforementioned value. In some alternatives, the hydrophobic moiety is a steroid or a cholesterol or comprises an aromatic ring. In some alternatives, the lipid comprises a glycerolipid, glycerophospholipid, sphingolipid, sterol lipid, prenol lipid, saccharolipid or polyketide. In some alternatives, the lipid is a phospholipid ether. In some alternatives, the lipid contains branched alkyl tails. In some alternatives, the lipid can be a sphingolipid. The sphingolipid can contain a backbone of sphingoid bases, such as a set of aliphatic amino alcohols that includes sphingosine. A sphingolipid with an R group consisting of a hydrogen atom only is a ceramide. Other common R groups include phosphocholine, yielding a sphingomyelin, and various sugar monomers or dimers, yielding cerebrosides and globosides, respectively. Cerebrosides and globosides are collectively known as glycosphingolipids. In some alternatives, the lipid is a glycosphingolipid. As provided herein, the lipid comprises a polar head group and a hydrophobic group. In some alternatives, the hydrophobic group comprises a fatty acid such as an aliphatic chain. The fatty acid can be saturated or unsaturated depending on the desired embodiments. In some alternatives, the hydrophobic group comprises an alkyl, alkenyl or alkynyl group. In some alternatives, the hydrophobic group comprises a terpenoid lipid such as a steroid or cholesterol or comprises an aromatic ring. In some alternatives, the hydrophobic group comprises an ether linkage, wherein the ether linkage is between the polar head group and the aliphatic chain. In some alternatives, the lipid is a phospholipid ether. In some alternatives, the polar head comprises a choline, a phosphatidylcholine, sphingomyelin, phosphoethanolamine group, an oligosaccharide residue, a sugar residue, phosphatidyl serine or phosphatidyl inositol. In some alternatives, the sugar is a glycerol. In some alternatives, the lipid is a single chain alkylphospholipid. In some alternatives, the lipids comprise a structure of synthetic alkylphospholipids such as edelfosine, perifosine or erucylphosphocholine. In some alternatives, the lipid is a lysophosphatidylcholine, edelfosine, erucylphosphocholine, D-21805 or perifosine. Such lipids are described for example, in van der Lui et al ("A new class of anticancer alkylphospholipids uses lipid rafts as membrane gateways to induce apoptosis in lymphoma cells" Mol Cancer Ther 2007; 6(8), 2007; incorporated by reference in its entirety). In some alternatives of the lipids described herein, a choline within the polar head group can be substituted with a piperidine moiety. In some alternatives, the lipid is an anticancer alkylphospholipid. Anticancer phospholipids are described e.g., in vander Lui et al. ("A new class of anti-cancer alkylphospholipids uses lipid rafts as membrane gateways to induce apoptosis in lymphoma cells" Mol Cancer Ther 2007; 6(8), 2007; incorporated by reference in its entirety).In some alternatives, the lipids provided herein are synthetic and structurally related antitumor agents that can act on cell membranes. These types of synthetic lipids are alkylphospholipids and are described by van Blitterswijk et al. ("Anticancer mechanisms and clinical application of alkylphopholipids" Biochimica et Biophysica Acta 1831 (2013)663-674; incorporated by reference in its entirety herein). Without being limiting the synthetic alkylphospholipids can include edelfosine, miltefosine, perifosine, erucylphosphocholine and/or Erufosine. In some alternatives, the lipid is edelfosine, miltefosine, perifosine, erucylphosphocholine or Erufosine. In some alternatives, the lipid is a stable analog of lysophosphatidylcholine. In some alternatives, the lipid is a thio-ether variant of edelfosine, 1-hexadecylthio-2-methoxymethyl-rac-glycero-3-phosphocholine. In some alternatives, the lipid is LysoPC, edelfosine, Ilmofosine, Miltefosine, Perifosine, Erucylphosphocholine, or Erufosine. In some alternatives herein, the polar-head group comprises phosphocholine, a piperidine moiety or a trimethylarseno-ethyl-phosphate moiety. In some alternatives, the lipid comprises a target moiety and the CAR is joined to said lipid through an interaction with said target moiety. In some alternatives, the lipid is a phospholipid ether. In some alternatives, the phospholipid ether comprises a polar-head group and a carbon alkyl chain. In some alternatives, the carbon alkyl chain comprises at least 8, 9, 10, 11, 12, 13, 14, 15, 16, 17, 18, 19, 20, 21 or 22 carbons or any number that is within a range defined by any two aforementioned values. In some alternatives, the carbon alkyl chain comprises 8-22 carbons, such as 8-12, 12-14, 14-16, or 16-22 carbons. In some alternatives herein, a complex is provided, wherein the complex comprises a lipid. In some alternatives, the lipid targets a cell, such as a cancer cell or a tumor cell, or a tumor. In some alternatives, the lipid comprises a polar head group. In some alternatives the polar head group comprises a choline, a phosphatidylcholine, sphingomyelin, phosphoethanolamine group, an oligosaccharide residue, a sugar residue, phosphatidyl serine or phosphatidyl inositol. In some alternatives, the polar head group comprises phosphocholine, a piperidine moiety or a trimethylarseno-ethyl-phosphate moiety. In some alternatives, the lipid is a phospholipid ether. In some alternatives, the sugar is a glycerol. In some alternatives, the polar head group of the lipid comprises glycerol. In some alternatives, the polar head group of the lipid comprises a phosphate group. In some alternatives, the polar head group of the lipid comprises choline. In some alternatives, the lipid is a phosphatidylethanolomine. In some alternatives, the lipid is a phosphatidylinositol. In some alternatives, the lipid comprises a sphingoid base backbone. In some alternatives, the lipid comprises a sterol lipid, such as cholesterol or its derivatives. In some alternatives, the lipid comprises saccharolipids. In some alternatives, the polar head group comprises choline, phosphate and/or glycerol. In some alternatives, the lipid is a glycolipid. In some alternatives, the lipid comprise a sugar. In some alternatives, the lipid is derived from sphingosine. In some alternatives, the lipid is a glycerol-glycolipid or a sphingo-glycolipid. In some alternatives, the lipid is an ether lipid with branched hydrophobic chains. In some alternatives, the polar head comprises a choline, a phosphatidylcholine, sphingomyelin, phosphoethanolamine group, an oligosaccharide residue, a sugar residue, phosphatidyl serine or phosphatidyl inositol. In some alternatives, the lipid further comprises a target moiety which interacts with the CAR or TCR.

The lipid can comprise a spacer that separates the target moiety from the lipid and is bound to the polar-head group of the lipid. The spacer of the lipid can comprise a poly (carboxybetaine), peptide, Polyglycidols, polyethylene, Polyanhydrides, Polyphosphoesters, Polycaprolactone, Poly (ethylene oxide), PEG spacer, a Hapten (2x), (3x), (4x), or (5x) spacer, or an alkane chain. In some alternatives, the hapten spacer comprises two haptens and is referred to as a hapten (2x) spacer. In some alternatives, the lipid comprises a hydrophobic group such as an alkane chain. In some alternatives, the alkane chain can comprise 2, 3, 4, 5, 6, 7, 8, 9, 10, 11, 12, 13, 14, 15, 16, 17, or 18 carbons, or any number of carbons in between a range defined by any two aforementioned values. In some alternatives, the PEG spacer comprises 1, 2, 3, 4, 5, 6, 7, 8, 9, 10, 11, 12, 13, 14, 15, 16, 17, 18, 19, 20 or 21 PEG molecules, or any amount of PEG molecules that is within a range defined by any two aforementioned values. In some alternatives, the spacer comprises at least two haptens, at least three haptens or at least four haptens. In some alternatives, the FL-PLE comprises multiple fluoresceins. In some alternatives, the FL-PLE comprises 1, 2, 3, 4 or 5 flourescein moieties.

Alternative 14: Types of Antibodies.

As described herein, various antibodies or binding fragments thereof, which comprise a target moiety, may be used for recognizing a target cell. In some alternatives, a target cell is a cancer cell or a pathogenic cell. In some embodiments, the target cell is a tumor cell. In some alternatives, the target cell is a tumor cell of a solid tumor. In some alternatives, the solid tumor is a cancerous tumor, wherein the tumor comprises a plurality of cancer cells. In some alternatives, the cancer is breast, ovarian, lung, pancreatic, prostate, melanoma, renal, pancreatic, glioblastoma, neuroblastoma, medulloblastoma, sarcoma, liver, colon, skin (including melanoma), bone or brain cancer. In some alternatives, the target cell is a virus or a bacteria. In some embodiments, the antibody is a full antibody or a binding fragment thereof that specifically binds to an antigen on a target cell. In some alternatives, the antigen is an angiopoietin, a transmembrane receptor, a cell adhesion molecule, a cluster of differentiation molecule, a ganglioside, a glycoprotein, a growth factor, an integrin, an interleukin, a Notch receptor, a transmembrane glycoprotein, a tumor necrosis factor, or a tyrosine kinase. In some embodiments, antigen is 5T4, B7-H3, carbonic anhydrase IX, carcinoembryonic antigen, CA-125, CD-3, CD-19, CD-20, CD-22, CD-30, CD-33, CD-38, CD-40, CD-51, CD-52, CD-56, CD-70, CD-74, CD-79b, CD-138, CD-221, CD-319, CD-326, cell adhesion molecule 5, CTLA-4, cytokeratin polypeptides, death receptor 2, DLL4, EGFL7, EGFR, endosialin, EpCAM, FAP, FR-alpha, fibronectin, frizzled receptors, GD2, GPNMB, HER-1, HER-2, HER-3, IGF-IR, IGLF2, LOXL2, mesothelin, MS4A1, mucin 5AC, MUC1, Nectin-4, neuropilin, N-glycolyl GM3, PSMA, SLAMF7, TAG-72, TRAIL, TYRP1, VEGF, or other cancer expressing antigens. In some alternatives, the antibody or binding fragment, which is conjugated with a target moiety, thereof may bind specifically to a viral antigen or a bacterial antigen, including, for example by binding to an antigen of a *Bacillus*, a *Candida*, a *Clostridium*, a cytomegalovirus, an Ebola virus, an *Escherichia*, a Gram-negative bacteria, a Gram-positive bacteria, a hepatitis virus, a herpes virus, an HIV, an influenza virus, a *Pseudomonas*, a *Staphylococcus*, or a syncytial virus. For example, an antibody or fragment thereof may bind to a core antigen of HBV or HCV.

In some alternatives, a complex comprising a chimeric antigen receptor (CAR) or a T cell receptor (TCR) is provided, wherein the CAR or TCR is joined to an antibody or binding fragment thereof, wherein the antibody or binding fragment thereof comprises a target moiety and the CAR is joined to said antibody or binding fragment thereof through an interaction with said target moiety. In some alternatives, the antibody or binding fragment thereof, which comprises a target moiety, comprises abagovomab, abituzumab, adecatumumab, afutuzumab, alacizumab pegol, alemtuzumab, altumomab pentetate, amatuximab, anatumomab mefanetox, anetumab ravtansine, apolizumab, arcitumomab, ascrinvacumab, aselizumab, atezolizumab, atlizumab, avelumab, bapineuzumab, bavituximab, bectumomab, belimumab, besilesomab, bevacizumab, bivatuzumab mertansine, blinatumomab, blontuvetmab, brentuximab, brontictuzumab, cantuzumab mertansine, cantuzumab ravansine, capromab pendetide, carlumab, caroximab, catumaxomab, cBR96-doxorubicin immunoconjugate, cedelizumab, certolizumab pegol, cetuximab, cidfusituzumab, cidtuzumab, citatuzumab bogatox, cixutumumab, clivatuzumab tetraxetan, codrituzumab, coltuximab ravtansine, conatumumab, dacetuzumab, daclizumab, dalotuzumab, daratumumab, demcizumab, denintuzumab mafodotin, denosumab, depatuxizumab mafodotin, derlotuximab biotin, detumomab, dinutuximab, drozitumab, duligotumab, durvalumab, dusigitumab, duvortuxizumab, ecromeximab, eculizumab, edrecolomab, efalizumab, elgemtumab, elotuzumab, emactuzumab, emibetuzumab, enavatuzumab, enfortumab vedotin, enoblituzumab, enoticumab, ensituximab, epratuzumab, erlizumab, ertumaxomab, etaracizumab, farletuzumab, FBTA05, femzumab, ficlatuzumab, figitumumab, flanvotumab, fontolizumab, futuximab, galiximab, ganitumab, gemtuzumab ozogamicin, girentuximab, glembatumumab vedotin, ibritumomab, icrucumab, igovomab, IMAB362, imalumab, imgatuzumab, indatuximab ravtansine, indusatumab vedotin, intetumumab, inotuzumab ozogamicin, intetumumab, ipilimumab, iratumumab, isatuzimab, labetuzumab, lambrolizumab, lexatumumab, lifastuzumab vedotin, lilotomab satetraxetan, lintuzumab, lorvotuzumab mertansine, lucatumumab, lumiliximab, lumretuzumab, mapatumumab, margetuximab, matuzumab, mepolizumab, milatuzumab, minretumomab, mirvetuximab soravtansine, mitumomab, mogamulizumab, moxetumomab pasudotox, nacolomab tafenatox, naptumomab estafenatox, narnatumab, natalizumab, necitumumab, nesvacumab, nimotuzumab, nivolumab, nofetumomab merpentan, obinutuzumab, ocaratuzumab, ocrelizumab, ofatumumab, olaratumab, omalizumab, onartuzumab, ontuxizumab, oportuzumab monatox, oregovomab, otlertuzumab, panitumumab, pankomab, parsatuzumab, pascolizumab, pasotuxizumab, patritumab, pecfusituzumab, pectuzumab, pembrolizumab, pemtumomab, pertuzumab, pexelizumab, pidilizumab, pinatuzumab vedotin, pintumomab, polatuzumab vedotin, pritumumab, racotumomab, radretumab, ramucirumab, ranibizumab, reslizumab, rilotumumab, rituximab, robatumumab, rovelizumab, ruplizumab, sacituzumab govitecan, samalizumab, satumomab pendetide, seribantumab, sibrotuzumab, SGN-CD19A, SGN-CD33A, simtuzumab, siplizumab, siltuximab, sofituzumab vedotin, solitomab, sontuzumab, tabalumab, tacatuzumab tetraxetan, tadocizumab, talizumab, tamtuvetmab, taplitumomab paptox, tarextumab, tenatumomab, teprotumumab, TGN1412, ticilimumab (tremelimumab), tigatuzumab, TNX-650, tocilizumab, toralizumab, tositumomab, tovetumab, trastuzumab, TRB S07, tremelimumab, tucotuzumab celmoleukin, tucusituzumab, ublituximab, ulocuplumab, urelumab, urtoxazumab, ustekinumab, vandortuzumab vedotin, vantictumab, vanucizumab, veltuzumab, vesencumab, visilizumab, volociximab, vorsetuzumab mafodotin, votumumab, zalutumamab, zanolimumab, zatuximab, cosfroviximab, diridavumab, exbivirumab, felvizumab, foravirumab, larcaviximab, libivirumab, motavizumab, motovizumab, nolovizumab, numavizumab, palivizumab, porgaviximab, PRO 140, rafivirumab, ralivizumab, regavirumab, reslivizumab, resyvizumab, sevirumab, suvizumab, tuvirumab, umavizumab, edobacomab, nebacumab, pagibaximab, panobacumab, raxibacumab, tefibazumab, actoxumab, bezlotoxumab, efungumab, obiltoxaximab, suvratoxumab, or urtoxazumab, or a derivative, analogue, or binding fragment thereof.

In some alternatives, the antibody or binding fragment thereof comprises a target moiety and the CAR is joined to said antibody or binding fragment thereof through an interaction with said target moiety. In some alternatives, the antibody or binding fragment thereof further comprises a target moiety, which interacts with the CAR or TCR.

Alternative 15: Kit

Some alternatives include a kit that comprises a pharmaceutical grade PLE-CTCT, which can be used with a CAR T cell product designed to be specific for a recognition moiety on said PLE-CEC in the tumor or cancer.

Some alternatives include a kit that comprises an antibody or binding fragment thereof labeled with a target moiety, which can be used with a CAR T cell product designed to be specific for a recognition moiety on said labeled antibody or binding fragment thereof.

In some alternatives, the antibody or binding fragment thereof, which comprises the target moiety, comprises abagovomab, abituzumab, adecatumumab, afutuzumab, alacizumab pegol, alemtuzumab, altumomab pentetate, amatuximab, anatumomab mefanetox, anetumab ravtansine, apolizumab, arcitumomab, ascrinvacumab, aselizumab, atezolizumab, atlizumab, avelumab, bapineuzumab, bavituximab, bectumomab, belimumab, besilesomab, bevacizumab, bivatuzumab mertansine, blinatumomab, blontuvetmab, brentuximab, brontictuzumab, cantuzumab mertansine, cantuzumab ravansine, capromab pendetide, carlumab, carotuximab, catumaxomab, cBR96-doxorubicin immunoconjugate, cedelizumab, certolizumab pegol, cetuximab, cidfusituzumab, cidtuzumab, citatuzumab bogatox, cixutumumab, clivatuzumab tetraxetan, codrituzumab, coltuximab ravtansine, conatumumab, dacetuzumab, daclizumab, dalotuzumab, daratumumab, demcizumab, denintuzumab mafodotin, denosumab, depatuxizumab mafodotin, derlotuximab biotin, detumomab, dinutuximab, drozitumab, duligotumab, durvalumab, dusigitumab, duvortuxizumab, ecromeximab, eculizumab, edrecolomab, efalizumab, elgemtumab, elotuzumab, emactuzumab, emibetuzumab, enavatuzumab, enfortumab vedotin, enoblituzumab, enoticumab, ensituximab, epratuzumab, erlizumab, ertumaxomab, etaracizumab, farletuzumab, FBTA05, femzumab, ficlatuzumab, figitumumab, flanvotumab, fontolizumab, futuximab, galiximab, ganitumab, gemtuzumab ozogamicin, girentuximab, glembatumumab vedotin, ibritumomab, icrucumab, igovomab, IMAB362, imalumab, imgatuzumab, indatuximab ravtansine, indusatumab vedotin, intetumumab, inotuzumab ozogamicin, intetumumab, ipilimumab, iratumumab, isatuzimab, labetuzumab, lambrolizumab, lexatumumab, lifastuzumab vedotin, lilotomab satetraxetan, lintuzumab, lorvotuzumab mertansine, lucatumumab, lumiliximab, lumretuzumab, mapatumumab, margetuximab, matuzumab, mepolizumab, milatuzumab, minretumomab, mirvetuximab soravtansine, mitumomab, mogamulizumab, moxetumomab pasudotox, nacolomab tafenatox, naptumomab estafenatox, narnatumab, natalizumab, necitumumab, nesvacumab, nimotuzumab, nivolumab, nofetumomab merpentan, obinutuzumab, ocaratuzumab, ocrelizumab, ofatumumab, olaratumab, omalizumab, onartuzumab, ontuxizumab, oportuzumab monatox, oregovomab, otlertuzumab, panitumumab, pankomab, parsatuzumab, pascolizumab, pasotuxizumab, patritumab, pecfusituzumab, pectuzumab, pembrolizumab, pemtumomab, pertuzumab, pexelizumab, pidilizumab, pinatuzumab vedotin, pintumomab, polatuzumab vedotin, pritumumab, racotumomab, radretumab, ramucirumab, ranibizumab, reslizumab, rilotumumab, rituximab, robatumumab, rovelizumab, ruplizumab, sacituzumab govitecan, samalizumab, satumomab pendetide, seribantumab, sibrotuzumab, SGN-CD19A, SGN-CD33A, simtuzumab, siplizumab, siltuximab, sofituzumab vedotin, solitomab, sontuzumab, tabalumab, tacatuzumab tetraxetan, tadocizumab, talizumab, tamtuvetmab, taplitumomab paptox, tarextumab, tenatumomab, teprotumumab, TGN1412, ticilimumab (tremelimumab), tigatuzumab, TNX-650, tocilizumab, toralizumab, tositumomab, tovetumab, trastuzumab, TRB S07, tremelimumab, tucotuzumab celmoleukin, tucusituzumab, ublituximab, ulocuplumab, urelumab, urtoxazumab, ustekinumab, vandortuzumab vedotin, vantictumab, vanucizumab, veltuzumab, vesencumab, visilizumab, volociximab, vorsetuzumab mafodotin, votumumab, zalutumamab, zanolimumab, zatuximab, cosfroviximab, diridavumab, exbivirumab, felvizumab, foravirumab, larcaviximab, libivirumab, motavizumab, motovizumab, nolovizumab, numavizumab, palivizumab, porgaviximab, PRO 140, rafivirumab, ralivizumab, regavirumab, reslivizumab, resyvizumab, sevirumab, suvizumab, tuvirumab, umavizumab, edobacomab, nebacumab, pagibaximab, panobacumab, raxibacumab, tefibazumab, actoxumab, bezlotoxumab, efungumab, obiltoxaximab, suvratoxumab, or urtoxazumab, or a derivative, analogue, or binding fragment thereof.

Additional Alternatives

In some alternatives, a complex comprising a chimeric antigen receptor (CAR) or a T cell receptor (TCR) is provided, wherein the CAR or TCR is joined to a lipid, wherein the lipid comprises a target moiety and the CAR is joined to said lipid through an interaction with said target moiety. In some alternatives, the lipid comprises a polar head group and a hydrophobic group. In some alternatives, the hydrophobic group is fatty acid such as an aliphatic chain. In some alternatives, the fatty acid is saturated or unsaturated. In some alternatives, the hydrophobic group comprises an alkyl, alkenyl or alkynyl group. In some alternatives, the hydrophobic group comprises a terpenoid lipid such as a steroid or cholesterol. In some alternatives, the hydrophobic group comprises an ether linkage, wherein the ether linkage is between the polar head group and the aliphatic chain. In some alternatives, the lipid is a phospholipid ether. In some alternatives, the polar head comprises a choline, a phosphatidylcholine, sphingomyelin, phosphoethanolamine group, an oligosaccharide residue, a sugar residue, phosphatidyl serine or phosphatidyl inositol. In some alternatives, the sugar is a glycerol. In some alternatives, the target moiety is a hapten, poly(his) tag, Strep-tag, FLAG-tag, V5-tag, Myc-tag, HA-tag, NE-tag, biotin, digoxigenin, dinotrophenol or fluorescein. In some alternatives, the hydrophobic group comprises a carbon alkyl chain, wherein the carbon alkyl chain comprises 8, 9, 10, 11, 12, 13, 14, 15, 16, 17, 18, 19, 20, 21 or 22 carbons or any number that is within a range defined by any two aforementioned values. In some alternatives, the carbon alkyl chain comprises 18 carbons. In some alternatives, the polar-head group comprises phosphocholine, a piperidine moiety or a trimethylarseno-ethyl-phosphate moiety. In some alternatives, the lipid further comprises a spacer that separates the target moiety from the polar head group. In some alternatives, the spacer comprises a PEG spacer, a hapten (2×), (3×), (4×), or (5×) spacer, or an alkane chain. In some alternatives, the PEG spacer comprises 1, 2, 3, 4, 5, 6, 7, 8, 9, 10, 11, 12, 13, 14, 15, 16, 17, 18, 19, 20 or 21 PEG molecules, or any amount of PEG molecules that is within a range defined by any two aforementioned values. In some alternatives, the CAR or TCR is expressed by a cell or a T cell. In some alternatives, the CAR or TCR is on the surface of a cell or a T cell. In some alternatives, the cell is a precursor T cell. In some alternatives, the precursor T cell is a hematopoietic stem cell. In some alternatives, the cell is a CD8+ T cytotoxic lymphocyte cell selected from the group consisting of naïve CD8+ T cells, central memory CD8+ T cells, effector memory CD8+ T cells and bulk CD8+ T cells. In some alternatives, the cell is a CD4+ T helper lymphocyte cell that is selected from the group consisting of naïve CD4+ T cells, central memory CD4+ T cells, effector memory CD4+ T cells, and bulk CD4+ T cells. In some alternatives, the lipid is intercalated in a lipid bilayer of a target cell, such as a cancer cell. In some alternatives, the target cell is a tumor cell. In some alternatives, the target cell is an immune cell. In some alternatives, the immune cell is a T cell or a B cell. In some alternatives, the target cell is in a tumor microenvironment. In some alternatives, the target cell is a tumor cell. In some alternatives, the target cell is an immune cell. In some alternatives, the immune cell is a T cell or a B cell. In some alternatives, the target cell is in a tumor microenvironment. In some alternatives, the target cell is a tumor cell of a solid tumor. In some alternatives, the solid tumor is a cancerous tumor, wherein the tumor is from a cancer. In some alternatives, the cancer is breast, ovarian, lung, pancreatic, prostate, melanoma, renal, pancreatic, glioblastoma, neuroblastoma, medulloblastoma, sarcoma, liver, colon, skin (including melanoma), bone or brain cancer. In some alternatives, the lipid is a glycerolipid, glycerophospholipid, sphingolipid, sterol lipids, prenol lipid, saccharolipid or a polyketide. In some alternatives, a complex comprising a chimeric antigen receptor (CAR) or a T cell receptor (TCR) is provided, wherein the CAR or TCR is joined to a lipid, wherein the lipid comprises a target moiety and the CAR is joined to said lipid through an interaction with said target moiety. In some alternatives, the lipid comprises a polar head group and a hydrophobic moiety. In some alternatives, the hydrophobic moiety is a hydrophobic carbon tail. In some alternatives the hydrophobic carbon tail is saturated or unsaturated. In some alternatives, the hydrophobic carbon tail comprises 10, 11, 12, 13, 14, 15, 16, 17, 18, 19, 20, 21, 22, 23, 24 or 25 carbons or any number of carbons in between a range set forth in any aforementioned value. In some alternatives, the hydrophobic moiety is a steroid or a cholesterol. In some alternatives, the lipid comprises a glycerolipid, glycerophospholipid, sphingolipid, sterol lipid, prenol lipid, saccharolipid or polyketide. In some alternatives, the lipid is a phospholipid ether. In some alternatives, the lipid contains branched alkyl tails. In some alternatives, the lipid can be a sphingolipid. The sphingolipid can contain a backbone of sphingoid bases, such as a set of aliphatic amino alcohols that includes sphingosine. A sphingolipid with an R group consisting of a hydrogen atom only is a ceramide. Other common R groups include phosphocholine, yielding a sphingomyelin, and various sugar monomers or dimers, yielding cerebrosides and globosides, respectively. Cerebrosides and globosides are collectively known as glycosphingolipids. In some alternatives, the lipid is a glycosphingolipid. As provided herein, the lipid comprises a polar head group and a hydrophobic group. In some alternatives, the hydrophobic group comprises a fatty acid such as an aliphatic chain. In some alternatives, the fatty acid is saturated or unsaturated. In some alternatives, the hydrophobic group comprises an alkyl, alkenyl or alkynyl group. In some alternatives, the hydrophobic group comprises a terpenoid lipid such as a steroid or cholesterol. In some alternatives, the hydrophobic group comprises an ether linkage, wherein the ether linkage is between the polar head group and the aliphatic chain. In some alternatives, the lipid is a phospholipid ether. In some alternatives, the polar head comprises a choline, a phosphatidylcholine, sphingomyelin, phosphoethanolamine group, an oligosaccharide residue, a sugar residue, phosphatidyl serine or phosphatidyl inositol. In some alternatives, the sugar is a glycerol. In some alternatives, the lipid is a single chain alkylphospholipid. In some alternatives, the lipids comprise a structure of synthetic alkylphospholipids such as edelfosine, perifosine or erucylphosphocholine. In some alternatives, the lipid is a lysophosphatidylcholine, edelfosine, erucylphosphocholine, D-21805 or perifosine. Such lipids are described for example, in van der Lui et al ("A new class of anticancer alkylphospholipids uses lipid rafts as membrane gateways to induce apoptosis in lymphoma cells" Mol Cancer Ther 2007; 6(8), 2007; incorporated by reference in its entirety). In some alternatives of the lipids described herein, a choline within the polar head group can be substituted with a piperidine moiety. In some alternatives, the lipid is an anticancer alkylphospholipid. Anticancer phospholipids are described by vander Lui et al. ("A new class of anticancer alkylphospholipids uses lipid rafts as membrane gateways to induce apoptosis in lymphoma cells" Mol Cancer Ther 2007; 6(8), 2007; incorporated by reference in its entirety). In some alternatives, the lipids provided herein are synthetic and structurally related antitumor agents that can act on cell membranes. These types of synthetic lipids are alkylphospholipids and are described by van Blitterswijk et al. ("Anticancer mechanisms and clinical application of alkylphopholipids" Biochimica et Biophysica Acta 1831 (2013)663-674; incorporated by reference in its entirety herein). Without being limiting the synthetic alkylphospholipids can include edelfosine, miltefosine, perifosine, erucylphosphocholine and/or Erufosine. In some alternatives, the lipid is edelfosine, miltefosine, perifosine, erucylphosphocholine or Erufosine. In some alternatives, the lipid is a stable analog of lysophosphatidylcholine. In some alternatives, the lipid is a thio-ether variant of edelfosine, 1-hexadecylthio-2-methoxymethyl-rac-glycero-3-phosphocholine. In some alternatives, the lipid is LysoPC, edelfosine, Ilmofosine, Miltefosine, Perifosine, Erucylphophocholine, or Erufosine. In some alternatives herein, the polar-head group comprises phosphocholine, a piperidine moiety or a trimethylarseno-ethyl-phosphate moiety. In some alternatives, the lipid comprises a target moiety and the CAR is joined to said lipid through an interaction with said target moiety. In some alternatives, the lipid comprises a polar-head group and a carbon alkyl chain. In some alternatives, the carbon alkyl chain comprises at least 8, 9, 10, 11, 12, 13, 14, 15, 16, 17, 18, 19, 20, 21 or 22 carbons or any number that is within a range defined by any two aforementioned values. In some alternatives, the carbon alkyl chain comprises 8-22 carbons, such as 8-12, 12-14, 14-16, or 16-22 carbons. In some alternatives, the lipid is a phospholipid ether. In some alternatives herein, a complex is provided, wherein the complex comprises a lipid. In some alternatives, the lipid targets a cell, such as a cancer cell or a tumor cell, or a tumor. In some alternatives, the lipid comprises a polar head group. In some alternatives the polar head group comprises a choline, a phosphatidylcholine, sphingomyelin, phosphoethanolamine group, an oligosaccharide residue, a sugar residue, phosphatidyl serine or phosphatidyl inositol. In some alternatives, the polar head group comprises phosphocholine, a piperidine moiety or a trimethylarseno-ethyl-phosphate moiety. In some alternatives, the lipid is a phospholipid ether. In some alternatives, the sugar is a glycerol. In some alternatives, the polar head group of the lipid comprises glycerol. In some alternatives, the polar head group of the lipid comprises a phosphate group. In some alternatives, the polar head group of the lipid comprises choline. In some alternatives, the lipid is a phosphatidylethanolomine. In some alternatives, the lipid is a phosphatidylinositol. In some alternatives, the lipid comprises a sphingoid base backbone. In some alternatives, the lipid comprises a sterol lipid, such as cholesterol or its derivatives. In some alternatives, the lipid comprises saccharolipids. In some alternatives, the polar head group comprises choline, phosphate and/or glycerol. In some alternatives, the lipid is a glycolipid. In some alternatives, the lipid comprise a sugar. In some alternatives, the lipid is derived from sphingosine. In some alternatives, the lipid is a glycerol-glycolipid or a sphingo-glycolipid. In some alternatives, the lipid is an ether lipid with branched hydrophobic chains. In some alternatives, the polar head comprises a choline, a phosphatidylcholine, sphingomyelin, phosphoethanolamine group, an oligosaccharide residue, a sugar residue, phosphatidyl serine or phosphatidyl inositol. In some alternatives, the lipid further comprises a target moiety which interacts with the CAR or TCR. In some alternatives, the cancer is kidney, uterine, colon, lung, liver, breast, renal, prostate, ovarian, skin (including melanoma), bone, and brain cancer, adenocarcinoma, pancreatic cancer, chronic myelogenous leukemia or leukemia. In some alternatives, the cancer is breast, ovarian, lung, pancreatic, prostate, melanoma, renal, pancreatic, glioblastoma, neuroblastoma, medulloblastoma, sarcoma or liver cancer. In some alternatives, the cancer is a neuroblastoma, glioblastoma, leukemia or medulloblastoma. In some alternatives, instead of a lipid, an antibody or binding fragment thereof, which comprises a target moiety, is used and such antibody or binding fragment thereof is abagovomab, abituzumab, adecatumumab, afutuzumab, alacizumab pegol, alemtuzumab, altumomab pentetate, amatuximab, anatumomab mefanetox, anetumab ravtansine, apolizumab, arcitumomab, ascrinvacumab, aselizumab, atezolizumab, atlizumab, avelumab, bapineuzumab, bavituximab, bectumomab, belimumab, besilesomab, bevacizumab, bivatuzumab mertansine, blinatumomab, blontuvetmab, brentuximab, brontictuzumab, cantuzumab mertansine, cantuzumab ravansine, capromab pendetide, carlumab, carotuximab, catumaxomab, cBR96-doxorubicin immunoconjugate, cedelizumab, certolizumab pegol, cetuximab, cidfusituzumab, cidtuzumab, citatuzumab bogatox, cixutumumab, clivatuzumab tetraxetan, codrituzumab, coltuximab ravtansine, conatumumab, dacetuzumab, daclizumab, dalotuzumab, daratumumab, demcizumab, denintuzumab mafodotin, denosumab, depatuxizumab mafodotin, derlotuximab biotin, detumomab, dinutuximab, drozitumab, duligotumab, durvalumab, dusigitumab, duvortuxizumab, ecromeximab, eculizumab, edrecolomab, efalizumab, elgemtumab, elotuzumab, emactuzumab, emibetuzumab, enavatuzumab, enfortumab vedotin, enoblituzumab, enoticumab, ensituximab, epratuzumab, erlizumab, ertumaxomab, etaracizumab, farletuzumab, FBTA05, femzumab, ficlatuzumab, figitumumab, flanvotumab, fontolizumab, futuximab, galiximab, ganitumab, gemtuzumab ozogamicin, girentuximab, glembatumumab vedotin, ibritumomab, icrucumab, igovomab, IMAB362, imalumab, imgatuzumab, indatuximab ravtansine, indusatumab vedotin, intetumumab, inotuzumab ozogamicin, intetumumab, ipilimumab, iratumumab, isatuximab, labetuzumab, lambrolizumab, lexatumumab, lifastuzumab vedotin, lilotomab satetraxetan, lintuzumab, lorvotuzumab mertansine, lucatumumab, lumiliximab, lumretuzumab, mapatumumab, margetuximab, matuzumab, mepolizumab, milatuzumab, minretumomab, mirvetuximab soravtansine, mitumomab, mogamulizumab, moxetumomab pasudotox, nacolomab tafenatox, naptumomab estafenatox, narnatumab, natalizumab, necitumumab, nesvacumab, nimotuzumab, nivolumab, nofetumomab merpentan, obinutuzumab, ocaratuzumab, ocrelizumab, ofatumumab, olaratumab, omalizumab, onartuzumab, ontuxizumab, oportuzumab monatox, oregovomab, otlertuzumab, panitumumab, pankomab, parsatuzumab, pascolizumab, pasotuxizumab, patritumab, pecfusituzumab, pectuzumab, pembrolizumab, pemtumomab, pertuzumab, pexelizumab, pidilizumab, pinatuzumab vedotin, pintumomab, polatuzumab vedotin, pritumumab, racotumomab, radretumab, ramucirumab, ranibizumab, reslizumab, rilotumumab, rituximab, robatumumab, rovelizumab, ruplizumab, sacituzumab govitecan, samalizumab, satumomab pendetide, seribantumab, sibrotuzumab, SGN-CD19A, SGN-CD33A, simtuzumab, siplizumab, siltuximab, sofituzumab vedotin, solitomab, sontuzumab, tabalumab, tacatuzumab tetraxetan, tadocizumab, talizumab, tamtuvetmab, taplitumomab paptox, tarextumab, tenatumomab, teprotumumab, TGN1412, ticilimumab (tremelimumab), tigatuzumab, TNX-650, tocilizumab, toralizumab, tositumomab, tovetumab, trastuzumab, TRB S07, tremelimumab, tucotuzumab celmoleukin, tucusituzumab, ublituximab, ulocuplumab, urelumab, urtoxazumab, ustekinumab, vandortuzumab vedotin, vantictumab, vanucizumab, veltuzumab, vesencumab, visilizumab, volociximab, vorsetuzumab mafodotin, votumumab, zalutumamab, zanolimumab, zatuximab, cosfroviximab, diridavumab, exbivirumab, felvizumab, foravirumab, larcaviximab, libivirumab, motavizumab, motovizumab, nolovizumab, numavizumab, palivizumab, porgaviximab, PRO 140, rafivirumab, ralivizumab, regavirumab, reslivizumab, resyvizumab, sevirumab, suvizumab, tuvirumab, umavizumab, edobacomab, nebacumab, pagibaximab, panobacumab, raxibacumab, or tefibazumab or a binding fragment thereof.

In some alternatives, a cell comprising a chimeric antigen receptor (CAR) or T cell receptor (TCR) is provided, wherein the CAR or TCR is bound to a lipid, wherein the lipid comprises a target moiety and the cell comprising the CAR is bound to the target moiety of the lipid. In some alternatives, the lipid comprises a polar head group and a hydrophobic group. In some alternatives, the hydrophobic group is a fatty acid such as an aliphatic chain. In some alternatives, the fatty acid is saturated or unsaturated. In some alternatives, the hydrophobic group comprises an alkyl, alkenyl or alkynyl group. In some alternatives, the hydrophobic group comprises a terpenoid lipid such as a steroid or cholesterol or an aromatic ring. In some alternatives, the hydrophobic group comprises an ether linkage, wherein the ether linkage is between the polar head group and the aliphatic chain. In some alternatives, the lipid is a phospholipid ether. In some alternatives, the polar head comprises a choline, a phosphatidylcholine, sphingomyelin, phosphoethanolamine group, an oligosaccharide residue, a sugar residue, phosphatidyl serine or phosphatidyl inositol. In some alternatives, the sugar is a glycerol. In some alternatives, the target moiety is a hapten, poly(his) tag, Strep-tag, FLAG-tag, V5-tag, Myc-tag, HA-tag, NE-tag, biotin, digoxigenin, dinotrophenol or fluorescein. In some alternatives, the hydrophobic group comprises a carbon alkyl chain, wherein the carbon alkyl chain comprises 8, 9, 10, 11, 12, 13, 14, 15, 16, 17, 18, 19, 20, 21 or 22 carbons or any number that is within a range defined by any two aforementioned values. In some alternatives, the carbon alkyl chain comprises 8-22 carbons, such as 8-12, 12-14, 14-16, or 16-22 carbons. In some alternatives, the polar-head group comprises phosphocholine, a piperidine moiety or a trimethylarseno-ethyl-phosphate moiety. In some alternatives, the lipid further comprises a spacer group that separates the target moiety from the polar head group. In some alternatives, the spacer comprises a PEG spacer, a hapten (2×) spacer, or an alkane chain. In some alternatives, the PEG spacer comprises 1, 2, 3, 4, 5, 6, 7, 8, 9, 10, 11, 12, 13, 14, 15, 16, 17, 18, 19, 20 or 21 PEG molecules, or any amount of PEG molecules that is within a range defined by any two aforementioned values. In some alternatives, the cell is a precursor T cell. In some alternatives, the precursor T cell is a hematopoietic stem cell. In some alternatives, the cell is a CD8+ T cytotoxic lymphocyte cell selected from the group consisting of naïve CD8+ T cells, central memory CD8+ T cells, effector memory CD8+ T cells and bulk CD8+ T cells. In some alternatives, the cell is a CD4+ T helper lymphocyte cell that is selected from the group consisting of naïve CD4+ T cells, central memory CD4+ T cells, effector memory CD4+ T cells, and bulk CD4+ T cells. In some alternatives, the lipid is intercalated in a lipid bilayer of a target cell, such as a cancer cell. In some alternatives, the target cell is a tumor cell. In some alternatives, the target cell is an immune cell. In some alternatives, the immune cell is a T cell or a B cell. In some alternatives, the target cell is in a tumor microenvironment. In some alternatives, the target cell is a tumor cell. In some alternatives, the target cell is an immune cell. In some alternatives, the immune cell is a T cell or a B cell. In some alternatives, the target cell is in a tumor microenvironment. In some alternatives, the target cell is a tumor cell of a solid tumor. In some alternatives, the solid tumor is a cancerous tumor, wherein the tumor is from a cancer. In some alternatives, the cancer is breast, ovarian, lung, pancreatic, prostate, melanoma, renal, pancreatic, glioblastoma, neuroblastoma, medulloblastoma, sarcoma, liver, colon, skin (including melanoma), bone or brain cancer. In some alternatives, the lipid is a glycerolipid, glycerophospholipid, sphingolipid, sterol lipids, prenol lipid, saccharolipid or a polyketide. In some alternatives, a complex comprising a chimeric antigen receptor (CAR) or a T cell receptor (TCR) is provided, wherein the CAR or TCR is joined to a lipid, wherein the lipid comprises a target moiety and the CAR is joined to said lipid through an interaction with said target moiety. In some alternatives, the lipid comprises a polar head group and a hydrophobic moiety. In some alternatives, the hydrophobic moiety is a hydrophobic carbon tail. In some alternatives the hydrophobic carbon tail is saturated or unsaturated. In some alternatives, the hydrophobic carbon tail comprises 10, 11, 12, 13, 14, 15, 16, 17, 18, 19, 20, 21, 22, 23, 24 or 25 carbons or any number of carbons in between a range set forth in any aforementioned value. In some alternatives, the hydrophobic moiety is a steroid or a cholesterol or comprises an aromatic ring. In some alternatives, the lipid comprises a glycerolipid, glycerophospholipid, sphingolipid, sterol lipid, prenol lipid, saccharolipid or polyketide. In some alternatives, the lipid is a phospholipid ether. In some alternatives, the lipid contains branched alkyl tails. In some alternatives, the lipid can be a sphingolipid. The sphingolipid can contain a backbone of sphingoid bases, such as a set of aliphatic amino alcohols that includes sphingosine. A sphingolipid with an R group consisting of a hydrogen atom only is a ceramide. Other common R groups include phosphocholine, yielding a sphingomyelin, and various sugar monomers or dimers, yielding cerebrosides and globosides, respectively. Cerebrosides and globosides are collectively known as glycosphingolipids. In some alternatives, the lipid is a glycosphingolipid. As provided herein, the lipid comprises a polar head group and a hydrophobic group. In some alternatives, the hydrophobic group comprises a fatty acid such as an aliphatic chain. The fatty acid can be saturated or unsaturated depending on the desired embodiments. In some alternatives, the hydrophobic group comprises an alkyl, alkenyl or alkynyl group. In some alternatives, the hydrophobic group comprises a terpenoid lipid such as a steroid or cholesterol. In some alternatives, the hydrophobic group comprises an ether linkage, wherein the ether linkage is between the polar head group and the aliphatic chain. In some alternatives, the lipid is a phospholipid ether. In some alternatives, the polar head comprises a choline, a phosphatidylcholine, sphingomyelin, phosphoethanolamine group, an oligosaccharide residue, a sugar residue, phosphatidyl serine or phosphatidyl inositol. In some alternatives, the sugar is a glycerol. In some alternatives, the lipid is a single chain alkylphospholipid. In some alternatives, the lipids comprise a structure of synthetic alkylphospholipids such as edelfosine, perifosine or erucylphosphocholine. In some alternatives, the lipid is a lysophosphatidylcholine, edelfosine, erucylphosphocholine, D-21805 or perifosine. Such lipids are described for example, in van der Lui et al ("A new class of anticancer alkylphospholipids uses lipid rafts as membrane gateways to induce apoptosis in lymphoma cells" Mol Cancer Ther 2007; 6(8), 2007; incorporated by reference in its entirety). In some alternatives of the lipids described herein, a choline within the polar head group can be substituted with a piperidine moiety. In some alternatives, the lipid is an anticancer alkylphospholipid. Anticancer phospholipids are described by vander Lui et al. ("A new class of anticancer alkylphospholipids uses lipid rafts as membrane gateways to induce apoptosis in lymphoma cells" Mol Cancer Ther 2007; 6(8), 2007; incorporated by reference in its entirety). In some alternatives, the lipids provided herein are synthetic and structurally related antitumor agents that can act on cell membranes. These types of synthetic lipids are alkylphospholipids and are described by van Blitterswijk et al. ("Anticancer mechanisms and clinical application of alkylphopholipids" Biochimica et Biophysica Acta 1831 (2013)663-674; incorporated by reference in its entirety herein). Without being limiting the synthetic alkylphospholipids can include edelfosine, miltefosine, perifosine, erucylphosphocholine and/or Erufosine. In some alternatives, the lipid is edelfosine, miltefosine, perifosine, erucylphosphocholine or Erufosine. In some alternatives, the lipid is a stable analog of lysophosphatidylcholine. In some alternatives, the lipid is a thio-ether variant of edelfosine, 1-hexadecylthio-2-methoxymethyl-rac-glycero-3-phosphocholine. In some alternatives, the lipid is LysoPC, edelfosine, Ilmofosine, Miltefosine, Perifosine, Erucylphophocholine, or Erufosine. In some alternatives herein, the polar-head group comprises phosphocholine, a piperidine moiety or a trimethylarseno-ethyl-phosphate moiety. In some alternatives, the lipid comprises a target moiety and the CAR is joined to said lipid through an interaction with said target moiety. In some alternatives, the lipid comprises a polar-head group and a carbon alkyl chain. In some alternatives, the carbon alkyl chain comprises at least 8, 9, 10, 11, 12, 13, 14, 15, 16, 17, 18, 19, 20, 21 or 22 carbons or any number that is within a range defined by any two aforementioned values. In some alternatives, the carbon alkyl chain comprises 8-22 carbons, such as 8-12, 12-14, 14-16, or 16-22 carbons. In some alternatives, the lipid is a phospholipid ether. In some alternatives herein, a complex is provided, wherein the complex comprises a lipid. In some alternatives, the lipid targets a cell, such as a cancer cell or a tumor cell, or a tumor. In some alternatives, the lipid comprises a polar head group. In some alternatives the polar head group comprises a choline, a phosphatidylcholine, sphingomyelin, phosphoethanolamine group, an oligosaccharide residue, a sugar residue, phosphatidyl serine or phosphatidyl inositol. In some alternatives, the polar head group comprises phosphocholine, a piperidine moiety or a trimethylarseno-ethyl-phosphate moiety. In some alternatives, the lipid is a phospholipid ether. In some alternatives, the sugar is a glycerol. In some alternatives, the polar head group of the lipid comprises glycerol. In some alternatives, the polar head group of the lipid comprises a phosphate group. In some alternatives, the polar head group of the lipid comprises choline. In some alternatives, the lipid is a phosphatidyletanolomine. In some alternatives, the lipid is a phosphatidylinositol. In some alternatives, the lipid comprises a sphingoid base backbone. In some alternatives, the lipid comprises a sterol lipid, such as cholesterol or its derivatives. In some alternatives, the lipid comprises saccharolipids. In some alternatives, the polar head group comprises choline, phosphate and/or glycerol. In some alternatives, the lipid is a glycolipid. In some alternatives, the lipid comprises a sugar. In some alternatives, the lipid is derived from a sphingosine. In some alternatives, the lipid is a glycerol-glycolipid or a sphingo-glycolipid. In some alternatives, the lipid is an ether lipid with branched hydrophobic chains. In some alternatives, the polar head comprises a choline, a phosphatidylcholine, sphingomyelin, phosphoethanolamine group, an oligosaccharide residue, a sugar residue, phosphatidyl serine or phosphatidyl inositol. In some alternatives, the lipid further comprises a target moiety which interacts with the CAR or TCR. In some alternatives, the cancer is kidney, uterine, colon, lung, liver, breast, renal, prostate, ovarian, skin (including melanoma), bone cancer, brain cancer, adenocarcinoma, pancreatic cancer, chronic myelogenous leukemia or leukemia. In some alternatives, the cancer is breast, ovarian, lung, pancreatic, prostate, melanoma, renal, pancreatic, glioblastoma, neuroblastoma, medulloblastoma, sarcoma or liver cancer. In some alternatives, an antibody or binding fragment thereof conjugated to a target moiety is used and said antibody or binding fragment thereof can include abagovomab, abituzumab, adecatumumab, afutuzumab, alacizumab pegol, alemtuzumab, altumomab pentetate, amatuximab, anatumomab mefanetox, anetumab ravtansine, apolizumab, arcitumomab, ascrinvacumab, aselizumab, atezolizumab, atlizumab, avelumab, bapineuzumab, bavituximab, bectumomab, belimumab, besilesomab, bevacizumab, bivatuzumab mertansine, blinatumomab, blontuvetmab, brentuximab, brontictuzumab, cantuzumab mertansine, cantuzumab ravansine, capromab pendetide, carlumab, carotuximab, catumaxomab, cBR96-doxorubicin immunoconjugate, cedelizumab, certolizumab pegol, cetuximab, cidfusituzumab, cidtuzumab, citatuzumab bogatox, cixutumumab, clivatuzumab tetraxetan, codrituzumab, coltuximab ravtansine, conatumumab, dacetuzumab, daclizumab, dalotuzumab, daratumumab, demcizumab, denintuzumab mafodotin, denosumab, depatuxizumab mafodotin, derlotuximab biotin, detumomab, dinutuximab, drozitumab, duligotumab, durvalumab, dusigitumab, duvortuxizumab, ecromeximab, eculizumab, edrecolomab, efalizumab, elgemtumab, elotuzumab, emactuzumab, emibetuzumab, enavatuzumab, enfortumab vedotin, enoblituzumab, enoticumab, ensituximab, epratuzumab, erlizumab, ertumaxomab, etaracizumab, farletuzumab, FBTA05, femzumab, ficlatuzumab, figitumumab, flanvotumab, fontolizumab, futuximab, galiximab, ganitumab, gemtuzumab ozogamicin, girentuximab, glembatumumab vedotin, ibritumomab, icrucumab, igovomab, IMAB362, imalumab, imgatuzumab, indatuximab ravtansine, indusatumab vedotin, intetumumab, inotuzumab ozogamicin, inetumumab, ipilimumab, iratumumab, isatuximab, labetuzumab, lambrolizumab, lexatumumab, lifastuzumab vedotin, lilotomab satetraxetan, lintuzumab, lorvotuzumab mertansine, lucatumumab, lumiliximab, lumretuzumab, mapatumumab, margetuximab, matuzumab, mepolizumab, milatuzumab, minretumomab, mirvetuximab soravtansine, mitumomab, mogamulizumab, moxetumomab pasudotox, nacolomab tafenatox, naptumomab estafenatox, narnatumab, natalizumab, necitumumab, nesvacumab, nimotuzumab, nivolumab, nofetumomab merpentan, obinutuzumab, ocaratuzumab, ocrelizumab, ofatumumab, olaratumab, omalizumab, onartuzumab, ontuxizumab, oportuzumab monatox, oregovomab, otlertuzumab, panitumumab, pankomab, parsatuzumab, pascolizumab, pasotuxizumab, patritumab, pecfusituzumab, pectuzumab, pembrolizumab, pemtumomab, pertuzumab, pexelizumab, pidilizumab, pinatuzumab vedotin, pintumomab, polatuzumab vedotin, pritumumab, racotumomab, radretumab, ramucirumab, ranibizumab, reslizumab, rilotumumab, rituximab, robatumumab, rovelizumab, ruplizumab, sacituzumab govitecan, samalizumab, satumomab pendetide, seribantumab, sibrotuzumab, SGN-CD19A, SGN-CD33A, simtuzumab, siplizumab, siltuximab, sofituzumab vedotin, solitomab, sontuzumab, tabalumab, tacatuzumab tetraxetan, tadocizumab, talizumab, tamtuvetmab, taplitumomab paptox, tarextumab, tenatumomab, teprotumumab, TGN1412, ticilimumab (tremelimumab), tigatuzumab, TNX-650, tocilizumab, toralizumab, tositumomab, tovetumab, trastuzumab, TRB S07, tremelimumab, tucotuzumab celmoleukin, tucusituzumab, ublituximab, ulocuplumab, urelumab, urtoxazumab, ustekinumab, vandortuzumab vedotin, vantictumab, vanucizumab, veltuzumab, vesencumab, visilizumab, volociximab, vorsetuzumab mafodotin, votumumab, zalutumamab, zanolimumab, zatuximab, cosfroviximab, diridavumab, exbivirumab, felvizumab, foravirumab, larcaviximab, libivirumab, motavizumab, motovizumab, nolovizumab, numavizumab, palivizumab, porgaviximab, PRO 140, rafivirumab, raliviзумаб, regavirumab, reslivizumab, resyvizumab, sevirumab, suvizumab, tuvirumab, umavizumab, edobacomab, nebacumab, pagibaximab, panobacumab, raxibacumab, or tefibazumab or a binding fragment thereof. In some alternatives, the CAR comprises an scFv.

In some alternatives, a method of treating, ameliorating, or inhibiting a cancer in a subject is provided, the method comprising: a) introducing, providing, or administering to a subject a composition that comprises a lipid, which comprises a target moiety that is bound to a masking moiety and, optionally, by attachment through a spacer, b) introducing, providing, or administering to said subject a cell comprising a chimeric antigen receptor (CAR) or T cell receptor (TCR), which is specific for the target moiety once the masking moiety is removed from the target moiety, c) removing the masking moiety from the target moiety thereby allowing the target moiety to bind to the CAR present on the cell, and, d) optionally, measuring or evaluating the binding of the cell comprising the CAR to the lipid, after steps a-c and/or e) optionally, measuring or evaluating the treatment, amelioration, or inhibition of said cancer after steps a-d, and/or f) optionally, identifying a subject in need of a therapy for cancer prior to steps a-c. In some alternatives, the lipid targets a cell, such as a cancer cell or a tumor cell, or a tumor. In some alternatives, the lipid comprises a polar head group and a hydrophobic group. In some alternatives, the hydrophobic group is fatty acid such as an aliphatic chain. In some alternatives, the fatty acid is saturated or unsaturated. In some alternatives, the hydrophobic group comprises an alkyl, alkenyl or alkynyl group. In some alternatives, the hydrophobic group comprises a terpenoid lipid such as a steroid or cholesterol. In some alternatives, the hydrophobic group comprises an ether linkage, wherein the ether linkage is between the polar head group and the aliphatic chain. In some alternatives, the lipid is a phospholipid ether. In some alternatives, the polar head comprises a choline, a phosphatidylcholine, sphingomyelin, phosphoethanolamine group, an oligosaccharide residue, a sugar residue, phosphatidyl serine or phosphatidyl inositol. In some alternatives, the sugar is a glycerol. In some alternatives, the target moiety is a hapten, poly(his) tag, Strep-tag, FLAG-tag, V5-tag, Myc-tag, HA-tag, NE-tag, biotin, digoxigenin, dinotrophenol or fluorescein. In some alternatives, the hydrophobic group comprises a carbon alkyl chain. In some alternatives, the carbon alkyl chain comprises 8, 9, 10, 11, 12, 13, 14, 15, 16, 17, 18, 19, 20, 21 or 22 carbons or any number that is within a range defined by any two aforementioned values. In some alternatives, the carbon alkyl chain comprises 8-22 carbons, such as 8-12, 12-14, 14-16, or 16-22 carbons. In some alternatives, the polar-head group comprises phosphocholine, a piperidine moiety or a trimethylarseno-ethyl-phosphate moiety. In some alternatives, the spacer comprises a PEG spacer, a hapten (2×) spacer, or an alkane chain. In some alternatives, the PEG spacer comprises 1, 2, 3, 4, 5, 6, 7, 8, 9, 10, 11, 12, 13, 14, 15, 16, 17, 18, 19, 20 or 21 PEG molecules, or any amount of PEG molecules that is within a range defined by any two aforementioned values. In some alternatives, the masking moiety comprises a phenolic hydroxyl group or PEG. In some alternatives, the phenolic hydroxyl group is bound to a hydroxyl on a xanthene moiety of fluorescein. In some alternatives, the masking moiety is bound to the target moiety by a cleavable moiety, which is optionally configured to be specifically cleavable in a tumor microenvironment. In some alternatives, the cleavable moiety, which is configured to be cleavable in a tumor microenvironment, is cleaved by a reactive oxygen species reaction, an acidic pH, hypoxia, or nitrosylation. In some alternatives, the masking moiety is removed when the composition is within an acidic environment. In some alternatives, the acidic environment comprises a pH of 4, 5, 6 or 6.5 or any pH in between a range defined by any two aforementioned values. In some alternatives, the masking moiety is removed by nitrosylation. In some alternatives, the cell is provided to the subject the cell is provided to the subject 1, 2, 3, 4, 5, 6, 7, 8, 9, 10, 11, 12, 15, 20, 24, 36, 48, 60 or 72 hours after administration of the composition, or any time within a range defined by any two aforementioned values. In some alternatives, the cell is provided to the subject 1, 2, 3, 4, 5, 6, 7, 8, 9, 10, 11, 12, 15, 20, 24, 36 or 48 hours before administration of the composition, or any time within a range defined by any two aforementioned values. In some alternatives, the cell is provided to the subject within seconds or minutes, such as less than an hour, of providing the composition to the subject. In some alternatives, a boost of the cell and/or the composition is provided to the subject. In some alternatives, an additional cancer therapy is provided, such as a small molecule, e.g., a chemical compound, an antibody therapy, e.g., a humanized monoclonal antibody with or without conjugation to a radionuclide, toxin, or drug, surgery, and/or radiation. In some alternatives, the cancer is breast, ovarian, lung, pancreatic, prostate, melanoma, renal, pancreatic, glioblastoma, neuroblastoma, medulloblastoma, sarcoma or liver cancer. In some alternatives, the cell comprising the CAR or TCR is a T cell. In some alternatives, the CAR or TCR is on the surface of the cell or the T cell. In some alternatives, the cell is a precursor T cell. In some alternatives, the precursor T cell is a hematopoietic stem cell. In some alternatives, the cell is a CD8+ T cytotoxic lymphocyte cell selected from the group consisting of naïve CD8+ T cells, central memory CD8+ T cells, effector memory CD8+ T cells and bulk CD8+ T cells. In some alternatives, the cell is a CD4+ T helper lymphocyte cell that is selected from the group consisting of naïve CD4+ T cells, central memory CD4+ T cells, effector memory CD4+ T cells, and bulk CD4+ T cells. In some alternatives, the lipid intercalates in a lipid bilayer of a target cell, such as a cancer cell. In some alternatives, the target cell is a tumor cell. In some alternatives, the target cell is an immune cell. In some alternatives, the target cell is a tumor cell. In some alternatives, the target cell is an immune cell. In some alternatives, the immune cell is a T cell or a B cell. In some alternatives, the target cell is in a tumor microenvironment. In some alternatives, the target cell is a tumor cell of a solid tumor. In some alternatives, the solid tumor is a cancerous tumor, wherein the tumor is from a cancer. In some alternatives, the cancer is breast, ovarian, lung, pancreatic, prostate, melanoma, renal, pancreatic, glioblastoma, neuroblastoma, medulloblastoma, sarcoma, liver, colon, skin (including melanoma), bone or brain cancer. In some alternatives, the lipid is a glycerolipid, glycerophospholipid, sphingolipid, sterol lipids, prenol lipid, saccharolipid or a polyketide. In some alternatives, a complex comprising a chimeric antigen receptor (CAR) or a T cell receptor (TCR) is provided, wherein the CAR or TCR is joined to a lipid, wherein the lipid comprises a target moiety and the CAR is joined to said lipid through an interaction with said target moiety. In some alternatives, the lipid comprises a polar head group and a hydrophobic moiety. In some alternatives, the hydrophobic moiety is a hydrophobic carbon tail. In some alternatives the hydrophobic carbon tail is saturated or unsaturated. In some alternatives, the hydrophobic carbon tail comprises 10, 11, 12, 13, 14, 15, 16, 17, 18, 19, 20, 21, 22, 23, 24 or 25 carbons or any number of carbons in between a range set forth in any aforementioned value. In some alternatives, the hydrophobic moiety is a steroid or a cholesterol or comprises an aromatic ring. In some alternatives, the lipid comprises a glycerolipid, glycerophospholipid, sphingolipid, sterol lipid, prenol lipid, saccharolipid or polyketide. In some alternatives, the lipid is a phospholipid ether. In some alternatives, the lipid contains branched alkyl tails. In some alternatives, the lipid can be a sphingolipid. The sphingolipid can contain a backbone of sphingoid bases, such as a set of aliphatic amino alcohols that includes sphingosine. A sphingolipid with an R group consisting of a hydrogen atom only is a ceramide. Other common R groups include phosphocholine, yielding a sphingomyelin, and various sugar monomers or dimers, yielding cerebrosides and globosides, respectively. Cerebrosides and globosides are collectively known as glycosphingolipids. In some alternatives, the lipid is a glycosphingolipid. As provided herein, the lipid comprises a polar head group and a hydrophobic group. In some alternatives, the hydrophobic group comprises a fatty acid such as an aliphatic chain. The fatty acid is saturated or unsaturated depending on the desired embodiments. In some alternatives, the hydrophobic group comprises an alkyl, alkenyl or alkynyl group. In some alternatives, the hydrophobic group comprises a terpenoid lipid such as a steroid or cholesterol or an aromatic ring. In some alternatives, the hydrophobic group comprises an ether linkage, wherein the ether linkage is between the polar head group and the aliphatic chain. In some alternatives, the lipid is a phospholipid ether. In some alternatives, the polar head group comprises a choline, a phosphatidylcholine, sphingomyelin, phosphoethanolamine group, an oligosaccharide residue, a sugar residue, phosphatidyl serine or phosphatidyl inositol. In some alternatives, the sugar is a glycerol. In some alternatives, the lipid is a single chain alkylphospholipid. In some alternatives, the lipids comprise a structure of synthetic alkylphospholipids such as edelfosine, perifosine or erucylphosphocholine. In some alternatives, the lipid is a lysophosphatidylcholine, edelfosine, erucylphosphocholine, D-21805 or perifosine. Such lipids are described for example, in van der Lui et al ("A new class of anticancer alkylphospholipids uses lipid rafts as membrane gateways to induce apoptosis in lymphoma cells" Mol Cancer Ther 2007; 6(8), 2007; incorporated by reference in its entirety). In some alternatives of the lipids described herein, a choline within the polar head group can be substituted with a piperidine moiety. In some alternatives, the lipid is an anticancer alkylphospholipid. Anticancer phospholipids are described by vander Lui et al. ("A new class of anticancer alkylphospholipids uses lipid rafts as membrane gateways to induce apoptosis in lymphoma cells" Mol Cancer Ther 2007; 6(8), 2007; incorporated by reference in its entirety). In some alternatives, the lipids provided herein are synthetic and structurally related antitumor agents that can act on cell membranes. These types of synthetic lipids are alkylphospholipids and are described by van Blitterswijk et al. ("Anticancer mechanisms and clinical application of alkylphopholipids" Biochimica et Biophysica Acta 1831 (2013)663-674; incorporated by reference in its entirety herein). Without being limiting the synthetic alkylphospholipids can include edelfosine, miltefosine, perifosine, erucylphosphocholine and Erufosine. In some alternatives, the lipid is edelfosine, miltefosine, perifosine, erucylphosphocholine or Erufosine. In some alternatives, the lipid is a stable analog of lysophosphatidylcholine. In some alternatives, the lipid is a thio-ether variant of edelfosine, 1-hexadecylthio-2-methoxymethyl-rac-glycero-3-phosphocholine. In some alternatives, the lipid is LysoPC, edelfosine, Ilmofosine, Miltefosine, Perifosine, Erucylphosphocholine, or Erufosine. In some alternatives herein, the polar-head group comprises phosphocholine, a piperidine moiety or a trimethylarseno-ethyl-phosphate moiety. In some alternatives, the lipid comprises a target moiety and the CAR is joined to said lipid through an interaction with said target moiety. In some alternatives, the lipid comprises a polar-head group and a carbon alkyl chain. In some alternatives, the carbon alkyl chain comprises at least 8, 9, 10, 11, 12, 13, 14, 15, 16, 17, 18, 19, 20, 21 or 22 carbons or any number that is within a range defined by any two aforementioned values. In some alternatives, the carbon alkyl chain comprises 8-22 carbons, such as 8-12, 12-14, 14-16, or 16-22 carbons. In some alternatives herein, a complex is provided, wherein the complex comprises a lipid. In some alternatives, the lipid targets a cell, such as a cancer cell or a tumor cell, or a tumor. In some alternatives, the lipid comprises a polar head group. In some alternatives, the lipid is a phospholipid ether. In some alternatives the polar head group comprises a choline, a phosphatidylcholine, sphingomyelin, phosphoethanolamine group, an oligosaccharide residue, a sugar residue, phosphatidyl serine or phosphatidyl inositol. In some alternatives, the polar head group comprises phosphocholine, a piperidine moiety or a trimethylarseno-ethyl-phosphate moiety. In some alternatives, the lipid is a phospholipid ether. In some alternatives, the sugar is a glycerol. In some alternatives, the polar head group of the lipid comprises glycerol. In some alternatives, the polar head group of the lipid comprises a phosphate group. In some alternatives, the polar head group of the lipid comprises choline. In some alternatives, the lipid is a phosphatidylethanolomine. In some alternatives, the lipid is a phosphatidylinositol. In some alternatives, the lipid comprises a sphingoid base backbone. In some alternatives, the lipid comprises a sterol lipid, such as cholesterol or its derivatives. In some alternatives, the lipid comprises saccharolipids. In some alternatives, the polar head group comprises choline, phosphate and/or glycerol. In some alternatives, the lipid is a glycolipid. In some alternatives, the lipid comprises a sugar. In some alternatives, the lipid is derived from sphingosine. In some alternatives, the lipid is a glycerolglycolipid or a sphingo-glycolipid. In some alternatives, the lipid is an ether lipid with branched hydrophobic chains. In some alternatives, the polar head comprises a choline, a phosphatidylcholine, sphingomyelin, phosphoethanolamine group, an oligosaccharide residue, a sugar residue, phosphatidyl serine or phosphatidyl inositol. In some alternatives, the lipid further comprises a target moiety which interacts with the CAR or TCR. In some alternatives, the cancer is kidney, uterine, colon, lung, liver, breast, renal, prostate, ovarian, skin (including melanoma), bone, and brain cancer, adenocarcinoma, pancreatic cancer, chronic myelogenous leukemia or leukemia. In some alternatives, the cancer is breast, ovarian, lung, pancreatic, prostate, melanoma, renal, pancreatic, glioblastoma, neuroblastoma, medulloblastoma, sarcoma or liver cancer. In some alternatives, a method of treating, ameliorating, or inhibiting a cancer in a subject is provided. In some alternatives, the cancer is breast, ovarian, lung, pancreatic, prostate, melanoma, renal, pancreatic, glioblastoma, neuroblastoma, medulloblastoma, sarcoma, liver, colon, skin (including melanoma), bone or brain cancer. In some alternatives, the subject is selected to receipt additional cancer therapy which can include cancer therapeutics or drugs for the treatment of cancer. In some alternatives, the drugs comprise Abiraterone, Alemtuzumab, Anastrozole, Aprepitant, Arsenic trioxide, Atezolizumab, Azacitidine, Bevacizumab, Bleomycin, Bortezomib, Cabazitaxel, Capecitabine, Carboplatin, Cetuximab, Chemotherapy drug combinations, Cisplatin, Crizotinib, Cyclophosphamide, Cytarabine, Denosumab, Docetaxel, Doxorubicin, Eribulin, Erlotinib, Etoposide, Everolimus, Exemestane, Filgrastim, Fluorouracil, Fulvestrant, Gemcitabine, Imatinib, Imiquimod, Ipilimumab, Ixabepilone, Lapatinib, Lenalidomide, Letrozole, Leuprolide, Mesna, Methotrexate, Nivolumab, Oxaliplatin, Paclitaxel, Palonosetron, Pembrolizumab, Pemetrexed, Prednisone, Radium-223, Rituximab, Sipuleucel-T, Sorafenib, Sunitinib, Talc Intrapleural, Tamoxifen, Temozolomide, Temsirolimus, Thalidomide, Trastuzumab, Vinorelbine or Zoledronic acid. In some alternatives, an antibody or binding fragment thereof is used and said antibody or binding fragment thereof can be abagovomab, abituximab, adecatumumab, afutuzumab, alacizumab pegol, alemtuzumab, altumomab pentetate, amatuximab, anatumomab mefanetox, anetumab ravtansine, apolizumab, arcitumomab, ascrinvacumab, aselizumab, atezolizumab, atlizumab, avelumab, bapineuzumab, bavituximab, bectumomab, belimumab, besilesomab, bevacizumab, bivatuzumab mertansine, blinatumomab, blontuvetmab, brentuximab, brontictuzumab, cantuzumab mertansine, cantuzumab ravansine, capromab pendetide, carlumab, carotuximab, catumaxomab, cBR96-doxorubicin immunoconjugate, cedelizumab, certolizumab pegol, cetuximab, cidfusituzumab, cidtuzumab, citatuzumab bogatox, cixutumumab, clivatuzumab tetraxetan, codrituzumab, coltuximab ravtansine, conatumumab, dacetuzumab, daclizumab, dalotuzumab, daratumumab, demcizumab, denintuzumab mafodotin, denosumab, depatuxizumab mafodotin, derlotuximab biotin, detumomab, dinutuximab, drozitumab, duligotumab, durvalumab, dusigitumab, duvortuxizumab, ecromeximab, eculizumab, edrecolomab, efalizumab, elgemtumab, elotuzumab, emactuzumab, emibetuzumab, enavatuzumab, enfortumab vedotin, enoblituzumab, enoticumab, ensituximab, epratuzumab, erlizumab, ertumaxomab, etaracizumab, farletuzumab, FBTA05, femzumab, ficlatuzumab, figitumumab, flanvotumab, fontolizumab, futuximab, galiximab, ganitumab, gemtuzumab ozogamicin, girentuximab, glembatumumab vedotin, ibritumomab, icrucumab, igovomab, IMAB362, imalumab, imgatuzumab, indatuximab ravtansine, indusatumab vedotin, intetumumab, inotuzumab ozogamicin, intetumumab, ipilimumab, iratumumab, isatuximab, labetuzumab, lambrolizumab, lexatumumab, lifastuzumab vedotin, lilotomab satetraxetan, lintuzumab, lorvotuzumab mertansine, lucatumumab, lumiliximab, lumretuzumab, mapatumumab, margetuximab, matuzumab, mepolizumab, milatuzumab, minretumomab, mirvetuximab soravtansine, mitumomab, mogamulizumab, moxetumomab pasudotox, nacolomab tafenatox, naptumomab estafenatox, narnatumab, natalizumab, necitumumab, nesvacumab, nimotuzumab, nivolumab, nofetumomab merpentan, obinutuzumab, ocaratuzumab, ocrelizumab, ofatumumab, olaratumab, omalizumab, onartuzumab, ontuxizumab, oportuzumab monatox, oregovomab, otlertuzumab, panitumumab, pankomab, parsatuzumab, pascolizumab, pasotuxizumab, patritumab, pecfusituzumab, pectuzumab, pembrolizumab, pemtumomab, pertuzumab, pexelizumab, pidilizumab, pinatuzumab vedotin, pintumomab, polatuzumab vedotin, pritumumab, racotumomab, radretumab, ramucirumab, ranibizumab, reslizumab, rilotumumab, rituximab, robatumumab, rovelizumab, ruplizumab, sacituzumab govitecan, samalizumab, satumomab pendetide, seribantumab, sibrotuzumab, SGN-CD19A, SGN-CD33A, simtuzumab, siplizumab, siltuximab, sofituzumab vedotin, solitomab, sontuzumab, tabalumab, tacatuzumab tetraxetan, tadocizumab, talizumab, tamtuvetmab, taplitumomab paptox, tarextumab, tenatumomab, teprotumumab, TGN1412, ticilimumab (tremelimumab), tigatuzumab, TNX-650, tocilizumab, toralizumab, tositumomab, tovetumab, trastuzumab, TRB S07, tremelimumab, tucotuzumab celmoleukin, tucusituzumab, ublituximab, ulocuplumab, urelumab, urtoxazumab, ustekinumab, vandortuzumab vedotin, vantictumab, vanucizumab, veltuzumab, vesencumab, visilizumab, volociximab, vorsetuzumab mafodotin, votumumab, zalutumamab, zanolimumab, zatuximab, cosfroviximab, diridavumab, exbivirumab, felvizumab, foravirumab, larcaviximab, libivirumab, motavizumab, motovizumab, nolovizumab, numavizumab, palivizumab, porgaviximab, PRO 140, rafivirumab, ralivizumab, regavirumab, reslivizumab, resyvizumab, sevirumab, suvizumab, tuvirumab, umavizumab, edobacomab, nebacumab, pagibaximab, panobacumab, raxibacumab, or tefibazumab or a binding fragment thereof. In some alternatives, the CAR comprises an scFv. Administration of the composition and the CAR T cell may be by intravenous administration.

In some alternatives, a composition is provided, wherein the composition comprises a lipid, wherein the lipid comprises a target moiety that is bound to a masking moiety. In some alternatives, the target is bound to the masking moiety through a spacer. In some alternatives, the masking moiety is removed when the composition is in a tumor microenvironment. In some alternatives, the masking moiety is removed when the composition is in a ROS rich tumor environment. In some alternatives, the masking moiety is removed when the composition is within an acidic environment. In some alternatives, the acidic environment comprises a pH of 4, 5, 6 or 6.5 or any pH in between a range defined by any two aforementioned values. In some alternatives, the masking moiety is removed by nitrosylation. In some alternatives, the lipid targets a cell, such as a cancer cell or a tumor cell, or a tumor.

In some alternatives, a method of treating, ameliorating, or inhibiting a cancer in a subject is provided, wherein the method comprises a) introducing, providing, or administering to a subject the composition of any one of the alternatives herein, wherein the composition comprises a lipid, which comprises a target moiety that is bound to a masking moiety and, optionally, by attachment through a spacer, b) introducing, providing, or administering to said subject a cell comprising a chimeric antigen receptor (CAR) or T cell receptor (TCR), which is specific for the target moiety once the masking moiety is removed from the target moiety, c) removing the masking moiety from the target moiety thereby allowing the target moiety to bind to the CAR present on the cell, and, d) optionally, measuring or evaluating the binding of the cell comprising the CAR to the lipid, after steps a-c and/or e) optionally, measuring or evaluating the treatment, amelioration, or inhibition of said cancer after steps a-d, and/or f) optionally, identifying a subject in need of a therapy for cancer prior to steps a-c. In some alternatives, the lipid targets a cell, such as a cancer cell or a tumor cell, or a tumor. In some alternatives, the lipid comprises a polar head group and a hydrophobic group. In some alternatives, the hydrophobic group is fatty acid such as a aliphatic chain. In some alternatives, the fatty acid is saturated or unsaturated. In some alternatives, the hydrophobic group comprises an alkyl, alkenyl or alkynyl group. In some alternatives, the hydrophobic group comprises a terpenoid lipid such as a steroid or cholesterol. In some alternatives, the hydrophobic group comprises an ether linkage, wherein the ether linkage is between the polar head group and the aliphatic chain. In some alternatives, the lipid is a phospholipid ether. In some alternatives, the polar head comprises a choline, a phosphatidylcholine, sphingomyelin, phosphoethanolamine group, an oligosaccharide residue, a sugar residue, phosphatidyl serine or phosphatidyl inositol. In some alternatives, the sugar is a glycerol. In some alternatives, the target moiety is a hapten, poly(his) tag, Strep-tag, FLAG-tag, V5-tag, Myc-tag, HA-tag, NE-tag, biotin, digoxigenin, dinitrophenol or fluorescein. In some alternatives, the hydrophobic group comprises a carbon alkyl chain. In some alternatives, the carbon alkyl chain comprises 8, 9, 10, 11, 12, 13, 14, 15, 16, 17, 18, 19, 20, 21 or 22 carbons or any number that is within a range defined by any two aforementioned values. In some alternatives, the carbon alkyl chain comprises 8-22 carbons, such as 8-12, 12-14, 14-16, or 16-22 carbons. In some alternatives, the polar-head group comprises phosphocholine, a piperidine moiety or a trimethylarseno-ethyl-phosphate moiety. In some alternatives, the spacer comprises a PEG spacer, a hapten (2×) spacer, or an alkane chain. In some alternatives, the PEG spacer comprises 1, 2, 3, 4, 5, 6, 7, 8, 9, 10, 11, 12, 13, 14, 15, 16, 17, 18, 19, 20 or 21 PEG molecules, or any amount of PEG molecules that is within a range defined by any two aforementioned values. In some alternatives, the masking moiety comprises a phenolic hydroxyl group or PEG. In some alternatives, the phenolic hydroxyl group is bound to a hydroxyl on a xanthene moiety of fluorescein. In some alternatives, the masking moiety is bound to the target moiety by a cleavable moiety, which is optionally configured to be specifically cleavable in a tumor microenvironment. In some alternatives, the masking moiety is removed when the composition is within an acidic environment. In some alternatives, the acidic environment comprises a pH of 4, 5, 6 or 6.5 or any pH in between a range defined by any two aforementioned values. In some alternatives, the masking moiety is removed by nitrosylation. In some alternatives, the cleavable moiety, which is configured to be cleavable in a tumor microenvironment, is cleaved by a reactive oxygen species reaction, an acidic pH, hypoxia, or nitrosylation. In some alternatives, the cell is provided to the subject the cell is provided to the subject 1, 2, 3, 4, 5, 6, 7, 8, 9, 10, 11, 12, 15, 20, 24, 36, 48, 60 or 72 hours after administration of the composition, or any time within a range defined by any two aforementioned values. In some alternatives, the cell is provided to the subject 1, 2, 3, 4, 5, 6, 7, 8, 9, 10, 11, 12, 15, 20, 24, 36 or 48 hours before administration of the composition, or any time within a range defined by any two aforementioned values. In some alternatives, the cell is provided to the subject within seconds or minutes, such as less than an hour, of providing the composition to the subject. In some alternatives, a boost of the cell and/or the composition is provided to the subject. In some alternatives, an additional cancer therapy is provided, such as a small molecule, e.g., a chemical compound, an antibody therapy, e.g., a humanized monoclonal antibody with or without conjugation to a radionuclide, toxin, or drug, surgery, and/or radiation. In some alternatives, the cancer is breast, ovarian, lung, pancreatic, prostate, melanoma, renal, pancreatic, glioblastoma, neuroblastoma, medulloblastoma, sarcoma or liver cancer. In some alternatives, the cell comprising the CAR or TCR is a T cell. In some alternatives, the CAR or TCR is on the surface of the cell or the T cell. In some alternatives, the cell is a precursor T cell. In some alternatives, the precursor T cell is a hematopoietic stem cell. In some alternatives, the cell is a CD8+ T cytotoxic lymphocyte cell selected from the group consisting of naïve CD8+ T cells, central memory CD8+ T cells, effector memory CD8+ T cells and bulk CD8+ T cells. In some alternatives, the cell is a CD4+ T helper lymphocyte cell that is selected from the group consisting of naïve CD4+ T cells, central memory CD4+ T cells, effector memory CD4+ T cells, and bulk CD4+ T cells. In some alternatives, the lipid intercalates in a lipid bilayer of a target cell, such as a cancer cell. In some alternatives, the target cell is a tumor cell. In some alternatives, the target cell is an immune cell. In some alternatives, the target cell is a tumor cell. In some alternatives, the target cell is an immune cell. In some alternatives, the immune cell is a T cell or a B cell. In some alternatives, the target cell is in a tumor microenvironment. In some alternatives, the target cell is a tumor cell of a solid tumor. In some alternatives, the solid tumor is a cancerous tumor, wherein the tumor is from a cancer. In some alternatives, the cancer is breast, ovarian, lung, pancreatic, prostate, melanoma, renal, pancreatic, glioblastoma, neuroblastoma, medulloblastoma, sarcoma, liver, colon, skin (including melanoma), bone or brain cancer. In some alternatives, the lipid is a glycerolipid, glycerophospholipid, sphingolipid, sterol lipids, prenol lipid, saccharolipid or a polyketide. In some alternatives, a complex comprising a chimeric antigen receptor (CAR) or a T cell receptor (TCR) is provided, wherein the CAR or TCR is joined to a lipid, wherein the lipid comprises a target moiety and the CAR is joined to said lipid through an interaction with said target moiety. In some alternatives, the lipid comprises a polar head group and a hydrophobic moiety. In some alternatives, the hydrophobic moiety is a hydrophobic carbon tail. In some alternatives the hydrophobic carbon tail is saturated or unsaturated. In some alternatives, the hydrophobic carbon tail comprises 10, 11, 12, 13, 14, 15, 16, 17, 18, 19, 20, 21, 22, 23, 24 or 25 carbons or any number of carbons in between a range set forth in any aforementioned value. In some alternatives, the hydrophobic moiety is a steroid or a cholesterol or comprises an aromatic ring. In some alternatives, the lipid comprises a glycerolipid, glycerophospholipid, sphingolipid, sterol lipid, prenol lipid, saccharolipid or polyketide. In some alternatives, the lipid is a phospholipid ether. In some alternatives, the lipid contains branched alkyl tails. In some alternatives, the lipid can be a sphingolipid. The sphingolipid can contain a backbone of sphingoid bases, such as a set of aliphatic amino alcohols that includes sphingosine. A sphingolipid with an R group consisting of a hydrogen atom only is a ceramide. Other common R groups include phosphocholine, yielding a sphingomyelin, and various sugar monomers or dimers, yielding cerebrosides and globosides, respectively. Cerebrosides and globosides are collectively known as glycosphingolipids. In some alternatives, the lipid is a glycosphingolipid. As provided herein, the lipid comprises a polar head group and a hydrophobic group. In some alternatives, the hydrophobic group comprises a fatty acid such as an aliphatic chain. The fatty acid is saturated or unsaturated depending on the desired embodiments. In some alternatives, the hydrophobic group comprises an alkyl, alkenyl or alkynyl group. In some alternatives, the hydrophobic group comprises a terpenoid lipid such as a steroid or cholesterol or an aromatic ring. In some alternatives, the hydrophobic group comprises an ether linkage, wherein the ether linkage is between the polar head group and the aliphatic chain. In some alternatives, the lipid is a phospholipid ether. In some alternatives, the polar head comprises a choline, a phosphatidylcholine, sphingomyelin, phosphoethanolamine group, an oligosaccharide residue, a sugar residue, phosphatidyl serine or phosphatidyl inositol. In some alternatives, the sugar is a glycerol. In some alternatives, the lipid is a single chain alkylphospholipid. In some alternatives, the lipids comprise a structure of synthetic alkylphospholipids such as edelfosine, perifosine or erucylphosphocholine. In some alternatives, the lipid is a lysophosphatidylcholine, edelfosine, erucylphosphocholine, D-21805 or perifosine. Such lipids are described for example, in van der Lui et al ("A new class of anticancer alkylphospholipids uses lipid rafts as membrane gateways to induce apoptosis in lymphoma cells" Mol Cancer Ther 2007; 6(8), 2007; incorporated by reference in its entirety). In some alternatives of the lipids described herein, a choline within the polar head group can be substituted with a piperidine moiety. In some alternatives, the lipid is an anticancer alkylphospholipid. Anticancer phospholipids are described by vander Lui et al. ("A new class of anticancer alkylphospholipids uses lipid rafts as membrane gateways to induce apoptosis in lymphoma cells" Mol Cancer Ther 2007; 6(8), 2007; incorporated by reference in its entirety).In some alternatives, the lipids provided herein are synthetic and structurally related antitumor agents that can act on cell membranes. These types of synthetic lipids are alkylphospholipids and are described by van Blitterswijk et al. ("Anticancer mechanisms and clinical application of alkylphopholipids" Biochimica et Biophysica Acta 1831 (2013)663-674; incorporated by reference in its entirety herein). Without being limiting the synthetic alkylphospholipids can include edelfosine, miltefosine, perifosine, erucylphosphocholine and Erufosine. In some alternatives, the lipid is edelfosine, miltefosine, perifosine, erucylphosphocholine or Erufosine. In some alternatives, the lipid is a stable analog of lysophosphatidylcholine. In some alternatives, the lipid is a thio-ether variant of edelfosine, 1-hexadecylthio-2-methoxymethyl-rac-glycero-3-phosphocholine. In some alternatives, the lipid is LysoPC, edelfosine, Ilmofosine, Miltefosine, Perifosine, Erucylphophocholine, or Erufosine. In some alternatives herein, the polar-head group comprises phosphocholine, a piperidine moiety or a trimethylarseno-ethyl-phosphate moiety. In some alternatives, the lipid comprises a target moiety and the CAR is joined to said lipid through an interaction with said target moiety. In some alternatives, the lipid comprises a polar-head group and a carbon alkyl chain. In some alternatives, the carbon alkyl chain comprises at least 8, 9, 10, 11, 12, 13, 14, 15, 16, 17, 18, 19, 20, 21 or 22 carbons or any number that is within a range defined by any two aforementioned values. In some alternatives, the carbon alkyl chain comprises 8-22 carbons, such as 8-12, 12-14, 14-16, or 16-22 carbons. In some alternatives herein, a complex is provided, wherein the complex comprises a lipid. In some alternatives, the lipid targets a cell, such as a cancer cell or a tumor cell, or a tumor. In some alternatives, the lipid comprises a polar head group. In some alternatives, the lipid is a phospholipid ether. In some alternatives the polar head group comprises a choline, a phosphatidylcholine, sphingomyelin, phosphoethanolamine group, an oligosaccharide residue, a sugar residue, phosphatidyl serine or phosphatidyl inositol. In some alternatives, the polar head group comprises phosphocholine, a piperidine moiety or a trimethylarseno-ethyl-phosphate moiety. In some alternatives, the lipid is a phospholipid ether. In some alternatives, the sugar is a glycerol. In some alternatives, the polar head group of the lipid comprises glycerol. In some alternatives, the polar head group of the lipid comprises a phosphate group. In some alternatives, the polar head group of the lipid comprises choline. In some alternatives, the lipid is a phosphatidylethanolomine. In some alternatives, the lipid is a phosphatidylinositol. In some alternatives, the lipid comprises a sphingoid base backbone. In some alternatives, the lipid comprises a sterol lipid, such as cholesterol or its derivatives. In some alternatives, the lipid comprises saccharolipids. In some alternatives, the polar head group comprises choline, phosphate and/or glycerol. In some alternatives, the lipid is a glycolipid. In some alternatives, the lipid comprises a sugar. In some alternatives, the lipid is derived from sphingosine. In some alternatives, the lipid is a glycerolglycolipid or a sphingo-glycolipid. In some alternatives, the lipid is an ether lipid with branched hydrophobic chains. In some alternatives, the polar head comprises a choline, a phosphatidylcholine, sphingomyelin, phosphoethanolamine group, an oligosaccharide residue, a sugar residue, phosphatidyl serine or phosphatidyl inositol. In some alternatives, the lipid further comprises a target moiety which interacts with the CAR or TCR. In some alternatives, the cancer is kidney, uterine, colon, lung, liver, breast, renal, prostate, ovarian, skin (including melanoma), bone, and brain cancer, adenocarcinoma, pancreatic cancer, chronic myelogenous leukemia or leukemia. In some alternatives, the cancer is breast, ovarian, lung, pancreatic, prostate, melanoma, renal, pancreatic, glioblastoma, neuroblastoma, medulloblastoma, sarcoma or liver cancer. In some alternatives, a method of treating, ameliorating, or inhibiting a cancer in a subject is provided. In some alternatives, the cancer is breast, ovarian, lung, pancreatic, prostate, melanoma, renal, pancreatic, glioblastoma, neuroblastoma, medulloblastoma, sarcoma, liver, colon, skin (including melanoma), bone or brain cancer. In some alternatives, the subject is selected to receipt additional cancer therapy which can include cancer therapeutics or drugs for the treatment of cancer. In some alternatives, the drugs comprise Abiraterone, Alemtuzumab, Anastrozole, Aprepitant, Arsenic trioxide, Atezolizumab, Azacitidine, Bevacizumab, Bleomycin, Bortezomib, Cabazitaxel, Capecitabine, Carboplatin, Cetuximab, Chemotherapy drug combinations, Cisplatin, Crizotinib, Cyclophosphamide, Cytarabine, Denosumab, Docetaxel, Doxorubicin, Eribulin, Erlotinib, Etoposide, Everolimus, Exemestane, Filgrastim, Fluorouracil, Fulvestrant, Gemcitabine, Imatinib, Imiquimod, Ipilimumab, Ixabepilone, Lapatinib, Lenalidomide, Letrozole, Leuprolide, Mesna, Methotrexate, Nivolumab, Oxaliplatin, Paclitaxel, Palonosetron, Pembrolizumab, Pemetrexed, Prednisone, Radium-223, Rituximab, Sipuleucel-T, Sorafenib, Sunitinib, Talc Intrapleural, Tamoxifen, Temozolomide, Temsirolimus, Thalidomide, Trastuzumab, Vinorelbine or Zoledronic acid. In some alternatives, an antibody or binding fragment thereof, which comprises a target moiety, is used and said antibody or binding fragment thereof comprises abagovomab, abituzumab, adecatumumab, afutuzumab, alacizumab pegol, alemtuzumab, altumomab pentetate, amatuximab, anatumomab mefanetox, anetumab ravtansine, apolizumab, arcitumomab, ascrinvacumab, aselizumab, atezolizumab, atlizumab, avelumab, bapineuzumab, bavituximab, bectumomab, belimumab, besilesomab, bevacizumab, bivatuzumab mertansine, blinatumomab, blontuvetmab, brentuximab, brontictuzumab, cantuzumab mertansine, cantuzumab ravansine, capromab pendetide, carlumab, carotuximab, catumaxomab, cBR96-doxorubicin immunoconjugate, cedelizumab, certolizumab pegol, cetuximab, cidfusituzumab, cidtuzumab, citatuzumab bogatox, cixutumumab, clivatuzumab tetraxetan, codrituzumab, coltuximab ravtansine, conatumumab, dacetuzumab, daclizumab, dalotuzumab, daratumumab, demcizumab, denintuzumab mafodotin, denosumab, depatuxizumab mafodotin, derlotuximab biotin, detumomab, dinutuximab, drozitumab, duligotumab, durvalumab, dusigitumab, duvortuxizumab, ecromeximab, eculizumab, edrecolomab, efalizumab, elgemtumab, elotuzumab, emactuzumab, emibetuzumab, enavatuzumab, enfortumab vedotin, enoblituzumab, enoticumab, ensituximab, epratuzumab, erlizumab, ertumaxomab, etaracizumab, farletuzumab, FBTA05, femzumab, ficlatuzumab, figitumumab, flanvotumab, fontolizumab, futuximab, galiximab, ganitumab, gemtuzumab ozogamicin, girentuximab, glembatumumab vedotin, ibritumomab, icrucumab, igovomab, IMAB362, imalumab, imgatuzumab, indatuximab ravtansine, indusatumab vedotin, intetumumab, inotuzumab ozogamicin, intetumumab, ipilimumab, iratumumab, isatuzimab, labetuzumab, lambrolizumab, lexatumumab, lifastuzumab vedotin, lilotomab satetraxetan, lintuzumab, lorvotuzumab mertansine, lucatumumab, lumiliximab, lumretuzumab, mapatumumab, margetuximab, matuzumab, mepolizumab, milatuzumab, minretumomab, mirvetuximab soravtansine, mitumomab, mogamulizumab, moxetumomab pasudotox, nacolomab tafenatox, naptumomab estafenatox, narnatumab, natalizumab, necitumumab, nesvacumab, nimotuzumab, nivolumab, nofetumomab merpentan, obinutuzumab, ocaratuzumab, ocrelizumab, ofatumumab, olaratumab, omalizumab, onartuzumab, ontuxizumab, oportuzumab monatox, oregovomab, otlertuzumab, panitumumab, pankomab, parsatuzumab, pascolizumab, pasotuxizumab, patritumab, pecfusituzumab, pectuzumab, pembrolizumab, pemtumomab, pertuzumab, pexelizumab, pidilizumab, pinatuzumab vedotin, pintumomab, polatuzumab vedotin, pritumumab, racotumomab, radretumab, ramucirumab, ranibizumab, reslizumab, rilotumumab, rituximab, robatumumab, rovelizumab, ruplizumab, sacituzumab govitecan, samalizumab, satumomab pendetide, seribantumab, sibrotuzumab, SGN-CD19A, SGN-CD33A, simtuzumab, siplizumab, siltuximab, sofituzumab vedotin, solitomab, sontuzumab, tabalumab, tacatuzumab tetraxetan, tadocizumab, talizumab, tamtuvetmab, taplitumomab paptox, tarextumab, tenatumomab, teprotumumab, TGN1412, ticilimumab (tremelimumab), tigatuzumab, TNX-650, tocilizumab, toralizumab, tositumomab, tovetumab, trastuzumab, TRB S07, tremelimumab, tucotuzumab celmoleukin, tucusituzumab, ublituximab, ulocuplumab, urelumab, urtoxazumab, ustekinumab, vandortuzumab vedotin, vantictumab, vanucizumab, veltuzumab, vesencumab, visilizumab, volociximab, vorsetuzumab mafodotin, votumumab, zalutumamab, zanolimumab, zatuximab, cosfroviximab, diridavumab, exbivirumab, felvizumab, foravirumab, larcaviximab, libivirumab, motavizumab, motovizumab, nolovizumab, numavizumab, palivizumab, porgaviximab, PRO 140, rafivirumab, ralivizumab, regavirumab, reslivizumab, resyvizumab, sevirumab, suvizumab, tuvirumab, umavizumab, edobacomab, nebacumab, pagibaximab, panobacumab, raxibacumab, or tefibazumab or a binding fragment thereof. In some alternatives, the CAR comprises an scFv. Administration of the composition and the CAR T cell may be by intravenous administration.

It is understood that the examples and alternatives described herein are for illustrative purposes only and that various modifications or changes in light thereof will be suggested to persons skilled in the art and are to be included within the spirit and purview of this application and scope of any appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to alternatives containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

Any of the features of an embodiment of the first through ninth aspects is applicable to all aspects and embodiments identified herein. Moreover, any of the features of an embodiment of the first through ninth aspects is independently combinable, partly or wholly with other embodiments described herein in any way, e.g., one, two, or three or more embodiments may be combinable in whole or in part. Further, any of the features of an embodiment of the first through ninth aspects may be made optional to other aspects or embodiments.

What is claimed is:

1. A method of forming a complex between an effector cell and a target cell, the method comprising:
   (a) contacting the target cell with a compound comprising a phospholipid, wherein the phospholipid comprises a hydrophobic group, a polar head group, and a target moiety, thereby obtaining a target cell comprising the target moiety; and
   (b) contacting the target cell comprising the target moiety with the effector cell, wherein the effector cell comprises a chimeric antigen receptor (CAR), wherein the CAR specifically binds to the target moiety.

2. The method of claim 1, wherein the compound further comprises a masking moiety, wherein the masking moiety is linked to the target moiety via a cleavable moiety.

3. The method of claim 2, wherein the cleavable moiety is configured to be cleavable by a reactive oxygen species (ROS) or by an acidic environment.

4. The method of claim 1, wherein the hydrophobic group comprises a fatty acid.

5. The method of claim 1, wherein the hydrophobic group comprises a $C_{8-22}$ alkyl group.

6. The method of claim 1, wherein the hydrophobic group comprises a terpenoid lipid.

7. The method of claim 1, wherein the phospholipid comprises an ether linkage, wherein the ether linkage is between the polar head group and the hydrophobic group.

8. The method of claim 7, wherein the phospholipid is a phospholipid ether (PLE).

9. The method of claim 1, wherein the polar head comprises a group selected from phosphatidylcholine, sphingomyelin, phosphoethanolamine, phosphatidyl serine, phosphatidyl inositol, phosphocholine, or a trimethylarsenoethyl-phosphate.

10. The method of claim 1, wherein the phospholipid further comprises a spacer between the target moiety and the polar head group, wherein the spacer is selected from the group consisting of poly(carboxybetaine), peptide, polyglycidol, polyethylene, polyanhydride, polyphosphoester, polycaprolactone, polyethylene glycol (PEG), and an alkane chain.

11. The method of claim 10, wherein the PEG spacer comprises from 1 to 21 PEG subunits.

12. The method of claim 1, wherein the effector cell is a T cell.

13. The method of claim 1, wherein the effector cell is selected from a precursor T cell, a hematopoietic stem cell, a CD8+ T cell, or a CD4+ T cell, a tumor cell, an immune cell, a T cell, or a B cell.

14. The method of claim 1, wherein the target cell is a cancer cell.

15. The method of claim 14, wherein the cancer cell is selected from a breast cancer cell, an ovarian cancer cell, a lung cancer cell, a pancreatic cancer cell, a prostate cancer cell, a melanoma cell, a renal cancer cell, a glioblastoma cell, a neuroblastoma cell, a medulloblastoma cell, a sarcoma cell, or a liver cancer cell.

16. The method of claim 1, wherein the compound has the following structure:

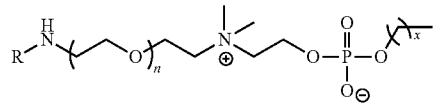

wherein:
R is the target moiety;
n is 0 to 21; and
x is 8 to 22.

17. The method of claim 1, wherein the target cell is in vivo.

18. The method of claim 1, wherein the target cell is human.

19. The method of claim 16, wherein:
the target cell is a neuroblastoma cell, a glioblastoma cell, a medulloblastoma cell, or a leukemia cell; and
the effector cell is a T cell.

20. A method of forming a complex between an effector cell and a target cell, the method comprising:
   (a) contacting the target cell with a compound comprising a phospholipid, wherein the phospholipid comprises a target moiety, thereby obtaining a target cell comprising the target moiety, wherein the target cell is a non-solid tumor cell, and wherein the compound has the following structure:

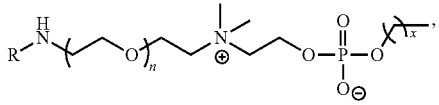

wherein:
R is the target moiety,
n is 0 to 21, and
x is 8 to 22; and
   (b) contacting the target cell comprising the target moiety with the effector cell, wherein the effector cell comprises a T cell, wherein the effector cell comprises a chimeric antigen receptor (CAR), and wherein the CAR specifically binds to the target moiety.

* * * * *

UNITED STATES PATENT AND TRADEMARK OFFICE
CERTIFICATE OF CORRECTION

| | | |
|---|---|---|
| PATENT NO. | : 11,649,288 B2 | Page 1 of 16 |
| APPLICATION NO. | : 16/480833 | |
| DATED | : May 16, 2023 | |
| INVENTOR(S) | : Jensen et al. | |

It is certified that error appears in the above-identified patent and that said Letters Patent is hereby corrected as shown below:

On the Title Page

Page 2, Column 1 (item (56) U.S. Patent Documents), Line 29, delete "Sadelain" and insert -- Sadelain et al. --.

Page 2, Column 1 (item (56) U.S. Patent Documents), Line 42, delete "Elsenbach et al." and insert -- Eisenbach et al. --.

Page 2, Column 1 (item (56) U.S. Patent Documents), Line 52, delete "Zhang" and insert -- Zhang et al. --.

Page 2, Column 2 (item (56) U.S. Patent Documents), Line 5, delete "Riddell" and insert -- Riddell et al. --.

Page 3, Column 1 (item (56) U.S. Patent Documents), Line 14, delete "Karlsson-Parra" and insert -- Karlsson-Parra et al. --.

Page 4, Column 2 (item (56) Other Publications), Line 10, delete "Ceil" and insert -- Cell --.

Page 5, Column 2 (item (56) Other Publications), Line 56, delete "Ceils" and insert -- Cells --.

Page 6, Column 2 (item (56) Other Publications), Line 11, delete "Wiezmann" and insert -- Weizmann --.

Page 6, Column 2 (item (56) Other Publications), Line 16, delete "immunoglobuling" and insert -- immunoglobulin --.

Page 7, Column 1 (item (56) Other Publications), Line 5, delete "fiuorescein" and insert -- fluorescein --.

Signed and Sealed this
Nineteenth Day of September, 2023

*Katherine Kelly Vidal*

Katherine Kelly Vidal
*Director of the United States Patent and Trademark Office*

CERTIFICATE OF CORRECTION (continued)
U.S. Pat. No. 11,649,288 B2

Page 7, Column 1 (item (56) Other Publications), Line 17, delete "ftagments" and insert -- fragments --.

Page 10, Column 1 (item (56) Other Publications), Line 28, delete "Expresslng" and insert -- Expressing --.

Page 10, Column 1 (item (56) Other Publications), Line 41, delete "anay" and insert -- array --.

Page 10, Column 1 (item (56) Other Publications), Line 57, delete "5164-" and insert -- 5154- --.

Page 10, Column 2 (item (56) Other Publications), Line 21, delete "Celis" and insert -- Cells --.

Page 10, Column 2 (item (56) Other Publications), Line 28, delete "alkylphopholipids," and insert -- alkylphospholipids, --.

Page 10, Column 2 (item (56) Other Publications), Line 39, delete "affinitis" and insert -- affinities --.

Page 10, Column 2 (item (56) Other Publications), Line 49, delete "lmmunother." and insert -- Immunother. --.

In the Specification

Column 1, Line 15, after "entireties" insert -- . --.

Column 1, Line 41, delete "CD3" and insert -- CD3ζ --.

Column 2, Line 59, delete "Pragman." and insert -- Pragman, --.

Column 3, Line 18, delete "Dimetachlor," and insert -- Dimetolachlor, --.

Column 3, Line 37, delete "O,O-dimetyl" and insert -- O,O-dimethyl --.

Column 3, Line 51, delete "R4-CH2COOH" and insert -- R4=CH2COOH --.

Column 4, Line 30, delete "Flourescein" and insert -- Fluorescein --.

Column 6, Line 29, delete "Galic" and insert -- Gallic --.

Column 6, Line 42, delete "Terbuthiuron," and insert -- Tebuthiuron, --.

Column 6, Line 47, delete "ethalfluaralin," and insert -- ethalfluralin, --.

Column 6, Line 62, delete "Benzphenanthrene," and insert -- Benzophenanthrene, --.

Column 8, Line 12, delete "—OCH2CH—CH2" and insert -- —OCH2CH=CH2 --.

CERTIFICATE OF CORRECTION (continued)  Page 3 of 16
U.S. Pat. No. 11,649,288 B2

Column 9, Line 8, delete "Aeromatic" and insert -- Aromatic --.

Column 9, Line 9, delete "Aeromatic" and insert -- Aromatic --.

Column 9, Line 10, delete "Aeromatic" and insert -- Aromatic --.

Column 9, Line 10, delete "Aeromatic" and insert -- Aromatic --.

Column 9, Line 16, delete "mehtoxy" and insert -- methoxy --.

Column 9, Line 17, delete "mehtoxyphenyl)" and insert -- methoxyphenyl) --.

Column 10, Line 51-52, delete "isoropylammeline," and insert -- isopropylammeline, --.

Column 11, Line 37, delete "-N-" and insert -- -N'- --.

Column 12, Line 20, delete "geninstein," and insert -- genistein, --.

Column 12, Line 24, delete "R1=OHR2=NHCH2CH3R3=NHCH2CH3," and insert
-- R1=OH R2=NHCH2CH3 R3=NHCH2CH3, --.

Column 13, Line 34, delete "R3==N(—>O)" and insert -- R3=N(—>O) --.

Column 13, Line 42-43, delete "Nitorphenyl" and insert -- Nitrophenyl --.

Column 13, Line 46, delete "Carbophenthion," and insert -- Carbophenothion, --.

Column 14, Line 53-54, delete "PGFlalpha," and insert -- PGF1alpha, --.

Column 14, Line 54, delete "6-keto-PGFlalpha," and insert -- 6-keto-PGF1alpha, --.

Column 15, Line 4, delete "2-[2-Chloro-(2-6'-diethyl)acetanilido]butanoic" and insert -- 2-[2-Chloro-
(2'-6'-diethyl)acetanilido]butanoic --.

Column 15, Line 27, delete "lycopersicin," and insert -- lycopersicine, --.

Column 16, Line 64, delete "Anit-Fumonisin" and insert -- Anti-Fumonisin --.

Column 18, Line 16, delete "Antoboides" and insert -- Antibodies --.

Column 19, Line 3, delete "Simizine" and insert -- Simazine --.

Column 22, Line 14, delete "Pragman." and insert -- Pragman, --.

Column 22, Line 40, delete "Dimetachlor," and insert -- Dimetolachlor, --.

CERTIFICATE OF CORRECTION (continued)
U.S. Pat. No. 11,649,288 B2

Column 22, Line 59, delete "O,O-dimetyl" and insert -- O,O-dimethyl --.

Column 23, Line 6, delete "R4-CH2COOH" and insert -- R4=CH2COOH --.

Column 23, Line 52, delete "Flourescein" and insert -- Fluorescein --.

Column 25, Line 51, delete "Galic" and insert -- Gallic --.

Column 25, Line 64, delete "Terbuthiuron," and insert -- Tebuthiuron, --.

Column 26, Line 2, delete "ethalfluaralin," and insert -- ethalfluralin, --.

Column 26, Line 17, delete "Benzphenanthrene," and insert -- Benzophenanthrene, --.

Column 27, Line 34, delete "—OCH2CH—CH2" and insert -- —OCH2CH=CH2 --.

Column 28, Line 29-30, delete "Aeromatic" and insert -- Aromatic --.

Column 28, Line 30, delete "Aeromatic" and insert -- Aromatic --.

Column 28, Line 31, delete "Aeromatic" and insert -- Aromatic --.

Column 28, Line 32, delete "Aeromatic" and insert -- Aromatic --.

Column 28, Line 38, delete "mehtoxy" and insert -- methoxy --.

Column 28, Line 38, delete "mehtoxyphenyl)" and insert -- methoxyphenyl) --.

Column 30, Line 5-6, delete "isoropylammeline," and insert -- isopropylammeline, --.

Column 30, Line 38-40, delete "3,4,5,3,4,5′-hexabromobiphenyl, 2,4,5,2,4,5′-hexabromobiphenyl," and insert -- 3,4,5,3′,4′,5′-hexabromobiphenyl, 2,4,5,2′,4′,5′-hexabromobiphenyl, --.

Column 31, Line 41, delete "geninstein," and insert -- genistein, --.

Column 31, Line 45, delete "R1=OHR2=NHCH2CH3R3=NHCH2CH3," and insert -- R1=OH R2=NHCH2CH3 R3=NHCH2CH3, --.

Column 32, Line 23, delete "α,α" and insert -- α,α,α --.

Column 32, Line 55, delete "R3==N(—>O)" and insert -- R3=N(—>O) --.

Column 32, Line 63-64, delete "Nitorphenyl" and insert -- Nitrophenyl --.

Column 32, Line 67, delete "Carbophenthion," and insert -- Carbophenothion, --.

CERTIFICATE OF CORRECTION (continued)
U.S. Pat. No. 11,649,288 B2

Column 34, Line 7-8, delete "PGFlalpha," and insert -- PGF1alpha, --.

Column 34, Line 8, delete "6-keto-PGFlalpha," and insert -- 6-keto-PGF1alpha, --.

Column 34, Line 48, delete "lycopersicin," and insert -- lycopersicine, --.

Column 36, Line 18, delete "Anit-Fumonisin" and insert -- Anti-Fumonisin --.

Column 37, Line 37, delete "Antoboides" and insert -- Antibodies --.

Column 38, Line 23, delete "6(38)," and insert -- 6G8), --.

Column 38, Line 24, delete "Simizine" and insert -- Simazine --.

Column 41, Line 41, delete "Pragman." and insert -- Pragman, --.

Column 41, Line 67, delete "Dimetachlor," and insert -- Dimetolachlor, --.

Column 42, Line 19, delete "O,O-dimetyl" and insert -- O,O-dimethyl --.

Column 42, Line 33, delete "R4-CH2COOH" and insert -- R4=CH2COOH --.

Column 43, Line 12, delete "Flourescein" and insert -- Fluorescein --.

Column 45, Line 11, delete "Galic" and insert -- Gallic --.

Column 45, Line 24, delete "Terbuthiuron," and insert -- Tebuthiuron, --.

Column 45, Line 29, delete "ethalfluaralin," and insert -- ethalfluralin, --.

Column 45, Line 44, delete "Benzphenanthrene," and insert -- Benzophenanthrene, --.

Column 46, Line 61, delete "—OCH2CH—CH2" and insert -- —OCH2CH=CH2 --.

Column 47, Line 57, delete "Aeromatic" and insert -- Aromatic --.

Column 47, Line 58, delete "Aeromatic" and insert -- Aromatic --.

Column 47, Line 59, delete "Aeromatic" and insert -- Aromatic --.

Column 47, Line 59, delete "Aeromatic" and insert -- Aromatic --.

Column 47, Line 65, delete "mehtoxy" and insert -- methoxy --.

Column 47, Line 66, delete "mehtoxyphenyl)" and insert -- methoxyphenyl) --.

CERTIFICATE OF CORRECTION (continued)
U.S. Pat. No. 11,649,288 B2

Column 48, Line 9, delete "n=3X=CH2)," and insert -- n=3 X=CH2), --.

Column 49, Line 33-34, delete "isoropylammeline," and insert -- isopropylammeline, --.

Column 51, Line 2, delete "geninstein," and insert -- genistein, --.

Column 51, Line 6, delete "R1=OHR2=NHCH2CH3R3=NHCH2CH3," and insert -- R1=OH R2=NHCH2CH3 R3=NHCH2CH3, --.

Column 51, Line 64, delete "Aflatoxin M," and insert -- Aflatoxin M1, --.

Column 52, Line 16, delete "R3==N(—>O)" and insert -- R3=N(—>O) --.

Column 52, Line 24-25, delete "Nitorphenyl" and insert -- Nitrophenyl --.

Column 52, Line 28, delete "Carbophenthion," and insert -- Carbophenothion, --.

Column 53, Line 35-36, delete "PGFlalpha," and insert -- PGF1alpha, --.

Column 53, Line 36, delete "6-keto-PGFlalpha," and insert -- 6-keto-PGF1alpha, --.

Column 54, Line 9, delete "lycopersicin," and insert -- lycopersicine, --.

Column 55, Line 46, delete "Anit-Fumonisin" and insert -- Anti-Fumonisin --.

Column 56, Line 65, delete "Antoboides" and insert -- Antibodies --.

Column 57, Line 52, delete "Simizine" and insert -- Simazine --.

Column 61, Line 27, delete "Pragman." and insert -- Pragman, --.

Column 61, Line 53, delete "Dimetachlor," and insert -- Dimetolachlor, --.

Column 62, Line 5, delete "O,O-dimetyl" and insert -- O,O-dimethyl --.

Column 62, Line 19, delete "R4-CH2COOH" and insert -- R4=CH2COOH --.

Column 62, Line 65, delete "Flourescein" and insert -- Fluorescein --.

Column 64, Line 64, delete "Galic" and insert -- Gallic --.

Column 65, Line 10, delete "Terbuthiuron," and insert -- Tebuthiuron, --.

Column 65, Line 15, delete "ethalfluaralin," and insert -- ethalfluralin, --.

Column 65, Line 30, delete "Benzphenanthrene," and insert -- Benzophenanthrene, --.

CERTIFICATE OF CORRECTION (continued)
U.S. Pat. No. 11,649,288 B2

Column 66, Line 40, delete "2',6-diethylacetanilide," and insert -- 2',6'-diethylacetanilide, --.

Column 66, Line 47, delete "—OCH2CH—CH2" and insert -- —OCH2CH=CH2 --.

Column 67, Line 43, delete "Aeromatic" and insert -- Aromatic --.

Column 67, Line 44, delete "Aeromatic" and insert -- Aromatic --.

Column 67, Line 45, delete "Aeromatic" and insert -- Aromatic --.

Column 67, Line 45, delete "Aeromatic" and insert -- Aromatic --.

Column 67, Line 51, delete "mehtoxy" and insert -- methoxy --.

Column 67, Line 52, delete "mehtoxyphenyl)" and insert -- methoxyphenyl) --.

Column 67, Line 64, delete "1-hexachloro" and insert -- 10-hexachloro --.

Column 69, Line 18-19, delete "isoropylammeline," and insert -- isopropylammeline, --.

Column 70, Line 54, delete "geninstein," and insert -- genistein, --.

Column 70, Line 58, delete "R1=OHR2=NHCH2CH3R3=NHCH2CH3," and insert -- R1=OH R2=NHCH2CH3 R3=NHCH2CH3, --.

Column 72, Line 1, delete "R3==N(—>O)" and insert -- R3=N(—>O) --.

Column 72, Line 9-10, delete "Nitorphenyl" and insert -- Nitrophenyl --.

Column 72, Line 13, delete "Carbophenthion," and insert -- Carbophenothion, --.

Column 73, Line 20-21, delete "PGFlalpha," and insert -- PGF1alpha, --.

Column 73, Line 21, delete "6-keto-PGFlalpha," and insert -- 6-keto-PGF1alpha, --.

Column 73, Line 61, delete "lycopersicin," and insert -- lycopersicine, --.

Column 75, Line 31, delete "Anit-Fumonisin" and insert -- Anti-Fumonisin --.

Column 76, Line 50, delete "Antoboides" and insert -- Antibodies --.

Column 77, Line 3, delete "Abl" and insert -- Ab1 --.

Column 77, Line 3, delete "Abl" and insert -- Ab1 --.

Column 77, Line 37, delete "Simizine" and insert -- Simazine --.

Column 77, Line 50, delete "(SA5A0.1)," and insert -- (SA5A1.1), --.

Column 79, Line 65, delete "zalutumamab," and insert -- zalutumumab, --.

Column 80, Line 46, delete "3-Ketocyclobarbital," and insert -- 3'-Ketocyclobarbital, --.

Column 80, Line 54, delete "Pragman." and insert -- Pragman, --.

Column 81, Line 13, delete "Dimetachlor," and insert -- Dimetolachlor, --.

Column 81, Line 32, delete "O,O-dimetyl" and insert -- O,O-dimethyl --.

Column 81, Line 46, delete "R4-CH2COOH" and insert -- R4=CH2COOH --.

Column 82, Line 25, delete "Flourescein" and insert -- Fluorescein --.

Column 84, Line 25, delete "Galic" and insert -- Gallic --.

Column 84, Line 38, delete "Terbuthiuron," and insert -- Tebuthiuron, --.

Column 84, Line 43, delete "ethalfluaralin," and insert -- ethalfluralin, --.

Column 84, Line 58, delete "Benzphenanthrene," and insert -- Benzophenanthrene, --.

Column 86, Line 8, delete "—OCH2CH—CH2" and insert -- —OCH2CH=CH2 --.

Column 87, Line 4, delete "Aeromatic" and insert -- Aromatic --.

Column 87, Line 5, delete "Aeromatic" and insert -- Aromatic --.

Column 87, Line 6, delete "Aeromatic" and insert -- Aromatic --.

Column 87, Line 6, delete "Aeromatic" and insert -- Aromatic --.

Column 87, Line 12, delete "mehtoxy" and insert -- methoxy --.

Column 87, Line 13, delete "mehtoxyphenyl)" and insert -- methoxyphenyl) --.

Column 88, Line 47-48, delete "isoropylammeline," and insert -- isopropylammeline, --.

Column 90, Line 16, delete "geninstein," and insert -- genistein, --.

Column 90, Line 20, delete "R1=OHR2=NHCH2CH3R3=NHCH2CH3," and insert -- R1=OH R2=NHCH2CH3 R3=NHCH2CH3, --.

Column 91, Line 30, delete "R3==N(—>O)" and insert -- R3=N(—>O) --.

CERTIFICATE OF CORRECTION (continued)
U.S. Pat. No. 11,649,288 B2

Column 91, Line 38-39, delete "Nitorphenyl" and insert -- Nitrophenyl --.

Column 91, Line 42, delete "Carbophenthion," and insert -- Carbophenothion, --.

Column 92, Line 49-50, delete "PGFlalpha," and insert -- PGF1alpha, --.

Column 92, Line 50, delete "6-keto-PGFlalpha," and insert -- 6-keto-PGF1alpha, --.

Column 93, Line 23, delete "lycopersicin," and insert -- lycopersicine, --.

Column 94, Line 60, delete "Anit-Fumonisin" and insert -- Anti-Fumonisin --.

Column 96, Line 12, delete "Antoboides" and insert -- Antibodies --.

Column 96, Line 66, delete "Simizine" and insert -- Simazine --.

Column 97, Line 12, delete "(SA5A0.1)," and insert -- (SA5A1.1), --.

Column 99, Line 2, delete "Pragman." and insert -- Pragman, --.

Column 99, Line 28, delete "Dimetachlor," and insert -- Dimetolachlor, --.

Column 99, Line 47, delete "O,O-dimetyl" and insert -- O,O-dimethyl --.

Column 99, Line 61, delete "R4-CH2COOH" and insert -- R4=CH2COOH --.

Column 100, Line 40, delete "Flourescein" and insert -- Fluorescein --.

Column 102, Line 40, delete "Galic" and insert -- Gallic --.

Column 102, Line 53, delete "Terbuthiuron," and insert -- Tebuthiuron, --.

Column 102, Line 58, delete "ethalfluaralin," and insert -- ethalfluralin, --.

Column 103, Line 6, delete "Benzphenanthrene," and insert -- Benzophenanthrene, --.

Column 104, Line 23, delete "—OCH2CH—CH2" and insert -- —OCH2CH=CH2 --.

Column 105, Line 19, delete "Aeromatic" and insert -- Aromatic --.

Column 105, Line 20, delete "Aeromatic" and insert -- Aromatic --.

Column 105, Line 21, delete "Aeromatic" and insert -- Aromatic --.

Column 105, Line 21, delete "Aeromatic" and insert -- Aromatic --.

CERTIFICATE OF CORRECTION (continued)
U.S. Pat. No. 11,649,288 B2

Column 105, Line 27, delete "mehtoxy" and insert -- methoxy --.

Column 105, Line 28, delete "mehtoxyphenyl)" and insert -- methoxyphenyl) --.

Column 106, Line 62-63, delete "isoropylammeline," and insert -- isopropylammeline, --.

Column 108, Line 31, delete "geninstein," and insert -- genistein, --.

Column 108, Line 35, delete "R1=OHR2=NHCH2CH3R3=NHCH2CH3," and insert -- R1=OH R2=NHCH2CH3 R3=NHCH2CH3, --.

Column 109, Line 45, delete "R3==N(—>O)" and insert -- R3=N(—>O) --.

Column 109, Line 53-54, delete "Nitorphenyl" and insert -- Nitrophenyl --.

Column 109, Line 57, delete "Carbophenthion," and insert -- Carbophenothion, --.

Column 110, Line 64-65, delete "PGFlalpha," and insert -- PGF1alpha, --.

Column 110, Line 65, delete "6-keto-PGFlalpha," and insert -- 6-keto-PGF1alpha, --.

Column 111, Line 38, delete "lycopersicin," and insert -- lycopersicine, --.

Column 113, Line 8, delete "Anit-Fumonisin" and insert -- Anti-Fumonisin --.

Column 114, Line 27, delete "Antoboides" and insert -- Antibodies --.

Column 115, Line 14, delete "Simizine" and insert -- Simazine --.

Column 115, Line 27, delete "(SA5A0.1)," and insert -- (SA5A1.1), --.

Column 116, Line 21-22, delete "dinotrophenol" and insert -- dinitrophenol --.

Column 118, Line 4, delete "zalutumamab," and insert -- zalutumumab, --.

Column 118, Line 61, delete "Pragman." and insert -- Pragman, --.

Column 119, Line 20, delete "Dimetachlor," and insert -- Dimetolachlor, --.

Column 119, Line 39, delete "O,O-dimetyl" and insert -- O,O-dimethyl --.

Column 119, Line 53, delete "R4-CH2COOH" and insert -- R4=CH2COOH --.

Column 120, Line 32, delete "Flourescein" and insert -- Fluorescein --.

Column 122, Line 32, delete "Galic" and insert -- Gallic --.

Column 122, Line 45, delete "Terbuthiuron," and insert -- Tebuthiuron, --.

Column 122, Line 50, delete "ethalfluaralin," and insert -- ethalfluralin, --.

Column 122, Line 65, delete "Benzphenanthrene," and insert -- Benzophenanthrene, --.

Column 124, Line 15, delete "—OCH2CH—CH2" and insert -- —OCH2CH=CH2 --.

Column 125, Line 11, delete "Aeromatic" and insert -- Aromatic --.

Column 125, Line 12, delete "Aeromatic" and insert -- Aromatic --.

Column 125, Line 13, delete "Aeromatic" and insert -- Aromatic --.

Column 125, Line 13, delete "Aeromatic" and insert -- Aromatic --.

Column 125, Line 19, delete "mehtoxy" and insert -- methoxy --.

Column 125, Line 20, delete "mehtoxyphenyl)" and insert -- methoxyphenyl) --.

Column 126, Line 54-55, delete "isoropylammeline," and insert -- isopropylammeline, --.

Column 128, Line 23, delete "geninstein," and insert -- genistein, --.

Column 128, Line 27, delete "R1=OHR2=NHCH2CH3R3=NHCH2CH3," and insert -- R1=OH R2=NHCH2CH3 R3=NHCH2CH3, --.

Column 129, Line 37, delete "R3==N(—>O)" and insert -- R3=N(—>O) --.

Column 129, Line 45-46, delete "Nitorphenyl" and insert -- Nitrophenyl --.

Column 129, Line 49, delete "Carbophenthion," and insert -- Carbophenothion, --.

Column 130, Line 56-57, delete "PGFlalpha," and insert -- PGF1alpha, --.

Column 130, Line 57, delete "6-keto-PGFlalpha," and insert -- 6-keto-PGF1alpha, --.

Column 131, Line 30, delete "lycopersicin," and insert -- lycopersicine, --.

Column 132, Line 67, delete "Anit-Fumonisin" and insert -- Anti-Fumonisin --.

Column 134, Line 19, delete "Antoboides" and insert -- Antibodies --.

Column 135, Line 6, delete "Simizine" and insert -- Simazine --.

Column 135, Line 19, delete "(SA5A0.1)," and insert -- (SA5A1.1), --.

CERTIFICATE OF CORRECTION (continued)
U.S. Pat. No. 11,649,288 B2

Column 136, Line 12, delete "dinotrophenol" and insert -- dinitrophenol --.

Column 137, Line 56, delete "zalutumamab," and insert -- zalutumumab, --.

Column 138, Line 45, delete "Pragman." and insert -- Pragman, --.

Column 139, Line 4, delete "Dimetachlor," and insert -- Dimetolachlor, --.

Column 139, Line 23, delete "O,O-dimetyl" and insert -- O,O-dimethyl --.

Column 139, Line 37, delete "R4-CH2COOH" and insert -- R4=CH2COOH --.

Column 140, Line 15, delete "Flourescein" and insert -- Fluorescein --.

Column 142, Line 15, delete "Galic" and insert -- Gallic --.

Column 142, Line 28, delete "Terbuthiuron," and insert -- Tebuthiuron, --.

Column 142, Line 33, delete "ethalfluaralin," and insert -- ethalfluralin, --.

Column 142, Line 48, delete "Benzphenanthrene," and insert -- Benzophenanthrene, --.

Column 143, Line 65, delete "—OCH2CH—CH2" and insert -- —OCH2CH=CH2 --.

Column 144, Line 61, delete "Aeromatic" and insert -- Aromatic --.

Column 144, Line 62, delete "Aeromatic" and insert -- Aromatic --.

Column 144, Line 63, delete "Aeromatic" and insert -- Aromatic --.

Column 144, Line 63, delete "Aeromatic" and insert -- Aromatic --.

Column 145, Line 2, delete "mehtoxy" and insert -- methoxy --.

Column 145, Line 3, delete "mehtoxyphenyl)" and insert -- methoxyphenyl) --.

Column 146, Line 37-38, delete "isoropylammeline," and insert -- isopropylammeline, --.

Column 148, Line 6, delete "geninstein," and insert -- genistein, --.

Column 148, Line 10, delete "R1=OHR2=NHCH2CH3R3=NHCH2CH3," and insert -- R1=OH R2=NHCH2CH3 R3=NHCH2CH3, --.

Column 149, Line 20, delete "R3==N(—>O)" and insert -- R3=N(—>O) --.

Column 149, Line 28-29, delete "Nitorphenyl" and insert -- Nitrophenyl --.

Column 149, Line 32, delete "Carbophenthion," and insert -- Carbophenothion, --.

Column 150, Line 39-40, delete "PGFlalpha," and insert -- PGF1alpha, --.

Column 150, Line 40, delete "6-keto-PGFlalpha," and insert -- 6-keto-PGF1alpha, --.

Column 151, Line 13, delete "lycopersicin," and insert -- lycopersicine, --.

Column 152, Line 50, delete "Anit-Fumonisin" and insert -- Anti-Fumonisin --.

Column 154, Line 2, delete "Antoboides" and insert -- Antibodies --.

Column 154, Line 56, delete "Simizine" and insert -- Simazine --.

Column 155, Line 2, delete "(SA5A0.1)," and insert -- (SA5A1.1), --.

Column 156, Line 30, delete "FIG. 7A-7E" and insert -- FIGS. 7A-7E --.

Figure 9B:
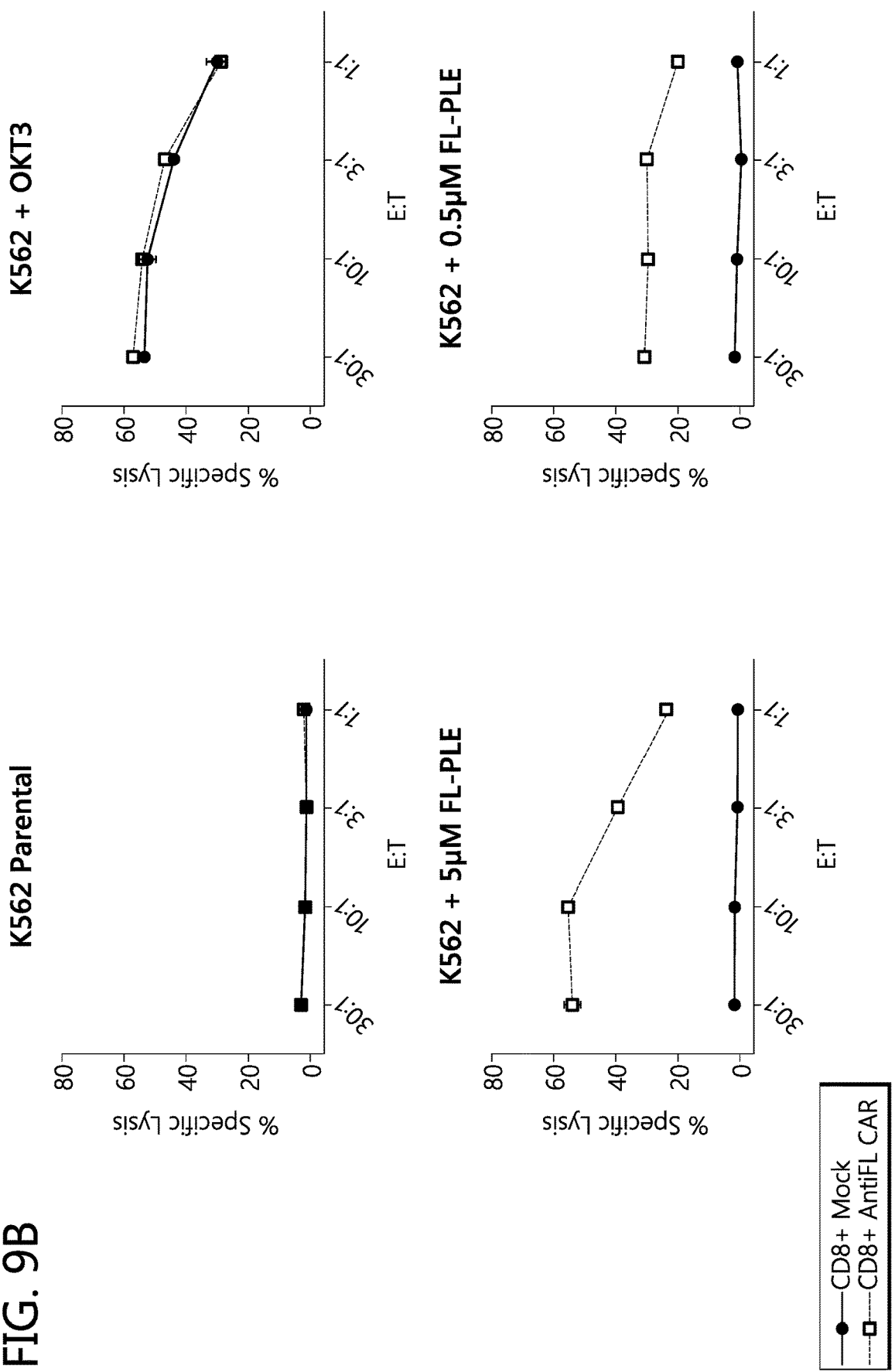
Figure 9C:
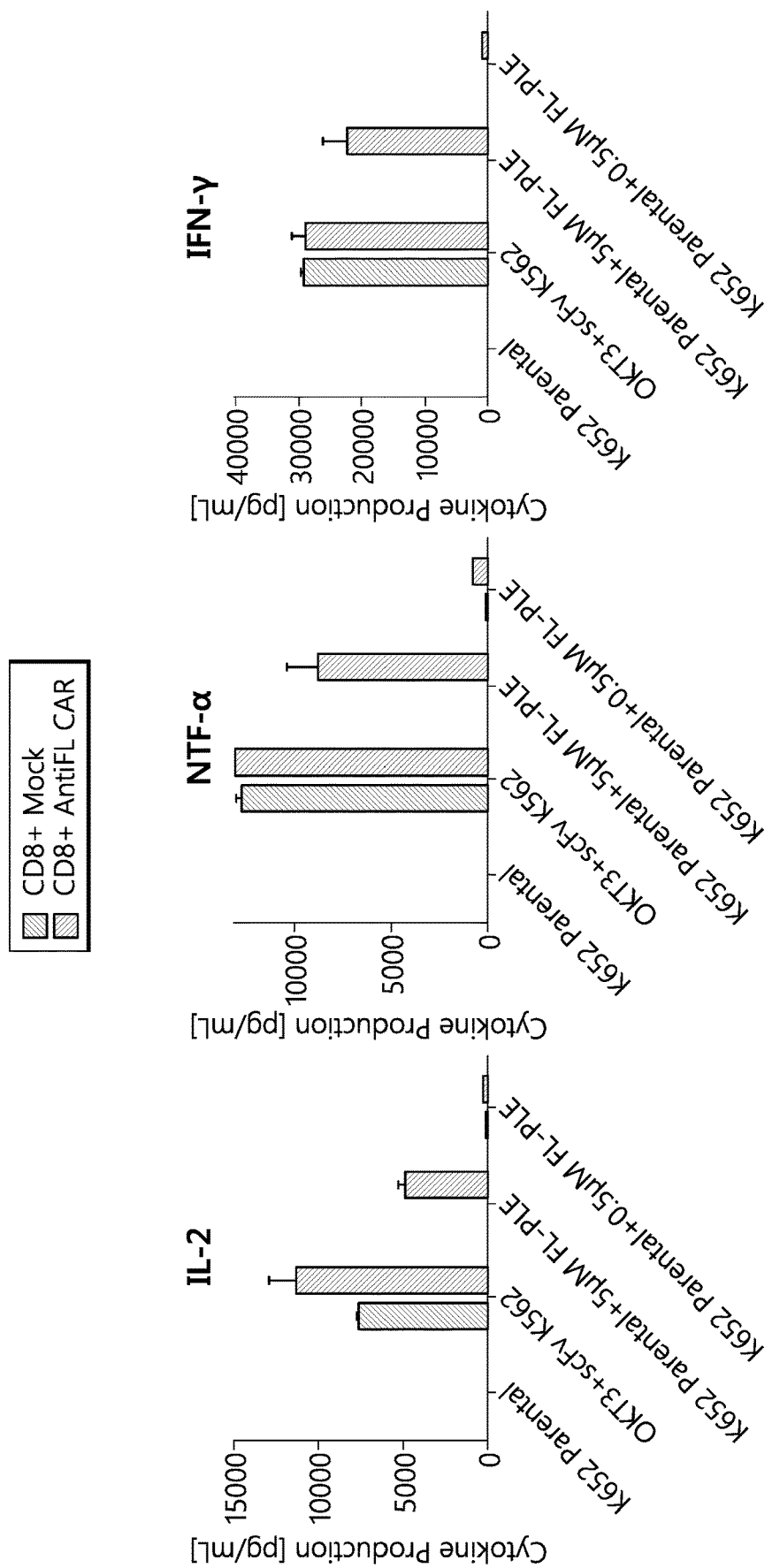

Column 157, Line 10, delete "FIG. 9A-9C" and insert -- FIGS. 9A-9C --.

Column 157, Line 36, delete "11-2," and insert -- IL-2, --.

Column 160, Line 23, delete "zalutumamab," and insert -- zalutumumab, --.

Column 162, Line 25, delete "zalutumamab," and insert -- zalutumumab, --.

Column 164, Line 19, delete "derivitives" and insert -- derivatives --.

Column 165, Line 51, delete "alkylphopholipids" and insert -- alkylphospholipids" --.

Column 165, Line 62-63, delete "Erucylphophocholine," and insert -- Erucylphosphocholine, --.

Column 166, Line 46-47, delete "N-actyl-n-galactosamine." and insert -- N-acetyl-n-galactosamine. --.

Column 166, Line 53-54, delete "phosphatidylethanolomine." and insert -- phosphatidylethanolamine. --.

Column 168, Line 49, delete "zalutumamab," and insert -- zalutumumab, --.

Column 170, Line 1, delete "zalutumamab," and insert -- zalutumumab, --.

Column 172, Line 11, delete "dinotrophenol" and insert -- dinitrophenol --.

Column 173, Line 42, delete "Pragman." and insert -- Pragman, --.

Column 174, Line 1, delete "Dimetachlor," and insert -- Dimetolachlor, --.

Column 174, Line 20, delete "O,O-dimetyl" and insert -- O,O-dimethyl --.

Column 174, Line 34, delete "R4-CH2COOH" and insert -- R4=CH2COOH --.

Column 175, Line 13, delete "Flourescein" and insert -- Fluorescein --.

Column 177, Line 13, delete "Galic" and insert -- Gallic --.

Column 177, Line 26, delete "Terbuthiuron," and insert -- Tebuthiuron, --.

Column 177, Line 31, delete "ethalfluaralin," and insert -- ethalfluralin, --.

Column 177, Line 46, delete "Benzphenanthrene," and insert -- Benzophenanthrene, --.

Column 178, Line 63, delete "—OCH2CH—CH2" and insert -- —OCH2CH=CH2 --.

Column 179, Line 58-59, delete "Aeromatic" and insert -- Aromatic --.

Column 179, Line 59, delete "Aeromatic" and insert -- Aromatic --.

Column 179, Line 60, delete "Aeromatic" and insert -- Aromatic --.

Column 179, Line 61, delete "Aeromatic" and insert -- Aromatic --.

Column 179, Line 67, delete "mehtoxy" and insert -- methoxy --.

Column 179, Line 67, delete "mehtoxyphenyl)" and insert -- methoxyphenyl) --.

Column 181, Line 34-35, delete "isoropylammeline," and insert -- isopropylammeline, --.

Column 183, Line 3, delete "geninstein," and insert -- genistein, --.

Column 183, Line 7, delete "R1=OHR2=NHCH2CH3R3=NHCH2CH3," and insert -- R1=OH R2=NHCH2CH3 R3=NHCH2CH3, --.

Column 184, Line 17, delete "R3==N(—>O)" and insert -- R3=N(—>O) --.

Column 184, Line 25-26, delete "Nitorphenyl" and insert -- Nitrophenyl --.

Column 184, Line 29, delete "Carbophenthion," and insert -- Carbophenothion, --.

Column 185, Line 36-37, delete "PGFlalpha," and insert -- PGF1alpha, --.

Column 185, Line 37, delete "6-keto-PGFlalpha," and insert -- 6-keto-PGF1alpha, --.

CERTIFICATE OF CORRECTION (continued)
U.S. Pat. No. 11,649,288 B2

Column 186, Line 10, delete "lycopersicin," and insert -- lycopersicine, --.

Column 187, Line 47, delete "Anit-Fumonisin" and insert -- Anti-Fumonisin --.

Column 188, Line 66, delete "Antoboides" and insert -- Antibodies --.

Column 189, Line 53, delete "Simizine" and insert -- Simazine --.

Column 189, Line 66, delete "(SA5A0.1)," and insert -- (SA5A1.1), --.

Column 195, Line 3, delete "dinotrophenol" and insert -- dinitrophenol --.

Column 197, Line 22, delete "dinotrophenol" and insert -- dinitrophenol --.

Column 199, Line 28, delete "dinotrophenol" and insert -- dinitrophenol --.

Column 202, Line 16, delete "zalutumamab," and insert -- zalutumumab, --.

Column 202, Line 57, delete "dinotrophenol" and insert -- dinitrophenol --.

Column 205, Line 36, delete "zalutumamab," and insert -- zalutumumab, --.

Column 205, Line 62, delete "dinotrophenol" and insert -- dinitrophenol --.

Column 210, Line 40, delete "alkylphopholipids" and insert -- alkylphospholipids" --.

Column 210, Line 51-52, delete "Erucylphophocholine," and insert -- Erucylphosphocholine, --.

Column 211, Line 15, delete "phosphatidylethanolomine." and insert -- phosphatidylethanolamine. --.

Column 211, Line 54, delete "Flourescein" and insert -- Fluorescein --.

Column 213, Line 34, delete "zalutumamab," and insert -- zalutumumab, --.

Column 214, Line 57, delete "zalutumamab," and insert -- zalutumumab, --.

Column 215, Line 25, delete "dinotrophenol" and insert -- dinitrophenol --.

Column 217, Line 5, delete "alkylphopholipids" and insert -- alkylphospholipids" --.

Column 217, Line 16-17, delete "Erucylphophocholine," and insert -- Erucylphosphocholine, --.

Column 217, Line 47, delete "phosphatidylethanolomine." and insert -- phosphatidylethanolamine. --.

Column 219, Line 4, delete "zalutumamab," and insert -- zalutumumab, --.

CERTIFICATE OF CORRECTION (continued)
U.S. Pat. No. 11,649,288 B2

Column 219, Line 36, delete "dinotrophenol" and insert -- dinitrophenol --.

Column 221, Line 14-15, delete "alkylphopholipids" and insert -- alkylphospholipids" --.

Column 221, Line 26, delete "Erucylphophocholine," and insert -- Erucylphosphocholine, --.

Column 221, Line 56-57, delete "phosphatidylethanolomine." and insert -- phosphatidylethanolamine. --.

Column 223, Line 12, delete "zalutumamab," and insert -- zalutumumab, --.

Column 223, Line 58, delete "dinotrophenol." and insert -- dinitrophenol. --.

Column 226, Line 4, delete "alkylphopholipids" and insert -- alkylphospholipids" --.

Column 226, Line 15-16, delete "Erucylphophocholine," and insert -- Erucylphosphocholine, --.

Column 226, Line 45-46, delete "phosphatidylethanolomine." and insert -- phosphatidylethanolamine. --.

Column 228, Line 23, delete "zalutumamab," and insert -- zalutumumab, --.

Column 231, Line 35, delete "alkylphopholipids" and insert -- alkylphospholipids" --.

Column 231, Line 46-47, delete "Erucylphophocholine," and insert -- Erucylphosphocholine, --.

Column 232, Line 9-10, delete "phosphatidylethanolomine." and insert -- phosphatidylethanolamine. --.

Column 233, Line 56, delete "zalutumamab," and insert -- zalutumumab, --.

In the Claims

Column 236, Line 3, In Claim 13, after "cell," delete "a tumor cell,".